United States Patent
Franz et al.

(10) Patent No.: US 11,746,103 B2
(45) Date of Patent: Sep. 5, 2023

(54) ALK-5 INHIBITORS AND USES THEREOF

(71) Applicant: Sumitomo Pharma Oncology, Inc., Marlborough, MA (US)

(72) Inventors: Bettina Franz, South Jordan, UT (US); Adam Siddiqui-Jain, South Jordan, UT (US); Steven L. Warner, Sandy, UT (US); Siva Reddy Basireddy, Telangana (IN); Srinivas Padakanti, Telangana (IN); Naresh Kumar, Telangana (IN)

(73) Assignee: Sumitomo Pharma Oncology, Inc., Marlborough, MA (US)

( * ) Notice: Subject to any disclaimer, the term of this patent is extended or adjusted under 35 U.S.C. 154(b) by 0 days.

(21) Appl. No.: 17/733,650

(22) Filed: Apr. 29, 2022

(65) Prior Publication Data

US 2022/0315563 A1   Oct. 6, 2022

Related U.S. Application Data

(63) Continuation of application No. PCT/US2021/072858, filed on Dec. 10, 2021.

(60) Provisional application No. 63/166,621, filed on Mar. 26, 2021, provisional application No. 63/123,894, filed on Dec. 10, 2020.

(51) Int. Cl.

| | | |
|---|---|---|
| C07D 401/14 | (2006.01) | |
| C07D 403/12 | (2006.01) | |
| C07D 403/14 | (2006.01) | |
| C07D 405/14 | (2006.01) | |
| C07D 413/14 | (2006.01) | |
| A61P 35/00 | (2006.01) | |
| C07D 471/08 | (2006.01) | |

(52) U.S. Cl.
CPC .......... C07D 403/14 (2013.01); A61P 35/00 (2018.01); C07D 401/14 (2013.01); C07D 403/12 (2013.01); C07D 405/14 (2013.01); C07D 413/14 (2013.01); C07D 471/08 (2013.01)

(58) Field of Classification Search
CPC .. C07D 401/14; C07D 403/12; C07D 403/14; C07D 405/14; C07D 413/14
See application file for complete search history.

(56) References Cited

U.S. PATENT DOCUMENTS

| | | | |
|---|---|---|---|
| 2,779,780 | A | 1/1957 | Middleton et al. |
| 5,621,002 | A | 4/1997 | Bosslet et al. |
| 5,861,510 | A | 1/1999 | Piscopio et al. |
| 5,863,949 | A | 1/1999 | Robinson et al. |
| 7,332,582 | B2 | 2/2008 | Hardy et al. |
| 7,488,802 | B2 | 2/2009 | Collins et al. |
| 7,632,947 | B2 | 12/2009 | Jeong et al. |
| 7,695,715 | B2 | 4/2010 | Hardy et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,217,149 | B2 | 7/2012 | Irving et al. |
| 8,354,509 | B2 | 1/2013 | Carven et al. |
| 8,460,927 | B2 | 6/2013 | Chen |
| 8,552,154 | B2 | 10/2013 | Freeman et al. |
| 8,552,156 | B2 | 10/2013 | Takayanagi et al. |
| 8,686,119 | B2 | 4/2014 | Rotem-Yehudar et al. |
| 8,735,553 | B1 | 5/2014 | Li et al. |
| 8,779,108 | B2 | 7/2014 | Queva et al. |
| 8,841,418 | B2 | 9/2014 | Karsunky et al. |
| 8,907,053 | B2 | 12/2014 | Sasikumar et al. |

(Continued)

FOREIGN PATENT DOCUMENTS

| | | |
|---|---|---|
| CN | 109665968 | 4/2019 |
| EP | 523533 A1 | 1/1993 |

(Continued)

OTHER PUBLICATIONS

Blobe, G. C., et al., "Role of Transforming Growth Factor beta in Human Disease", N Engl J Med (342), pp. 1350-1358 (2000).

(Continued)

*Primary Examiner* — Brian E McDowell
(74) *Attorney, Agent, or Firm* — Hamilton, Brook, Smith & Reynolds, P.C.

(57) ABSTRACT

Provided herein are compounds (e.g., compounds of Formulae (I), (II), (III) and (IV), or of Table 1 or Table 4), and pharmaceutically acceptable salts thereof, pharmaceutical compositions thereof, and kits comprising the same. The compounds provided herein are activin receptor-like kinase (e.g., ALK-5) inhibitors and are, therefore, useful, for example, for treating and/or preventing diseases (e.g., proliferative diseases, such as cancer) in a subject, inhibiting tumor growth in a subject, or inhibiting the activity of an activin receptor-like kinase (e.g., ALK-5) in vitro or in vivo. Also provided herein are methods and synthetic intermediates useful in the preparation of compounds described herein.

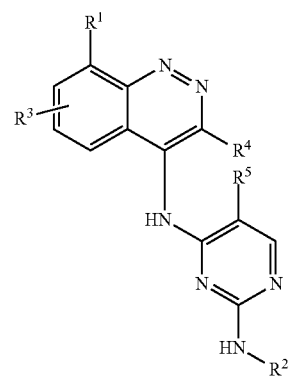

(I)

27 Claims, 55 Drawing Sheets
(46 of 55 Drawing Sheet(s) Filed in Color)

(56) References Cited

U.S. PATENT DOCUMENTS

| | | |
|---|---|---|
| 8,927,697 B2 | 1/2015 | Davis et al. |
| 8,993,731 B2 | 3/2015 | Tyson |
| 9,102,727 B2 | 8/2015 | Freeman et al. |
| 9,163,087 B2 | 10/2015 | Kuchroo et al. |
| 9,175,082 B2 | 11/2015 | Zhou et al. |
| 9,205,148 B2 | 12/2015 | Langermann et al. |
| 9,244,059 B2 | 1/2016 | Triebel et al. |
| 9,505,839 B2 | 11/2016 | Longberg et al. |
| 2004/0106616 A1 | 6/2004 | Bakthavatchalam et al. |
| 2006/0089354 A1 | 4/2006 | Bakthavatchalam et al. |
| 2007/0191374 A1 | 8/2007 | Hodgetts |
| 2008/0004273 A1 | 1/2008 | Bebbington et al. |
| 2009/0312543 A1 | 12/2009 | Bebbington et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2015/0353495 A1 | 12/2015 | Bauer et al. |
| 2016/0108123 A1 | 4/2016 | Freeman et al. |
| 2020/0165256 A1 | 5/2020 | Woll et al. |

FOREIGN PATENT DOCUMENTS

| | | |
|---|---|---|
| EP | 0606046 A1 | 7/1994 |
| EP | 780386 A1 | 6/1997 |
| EP | 0818442 A2 | 1/1998 |
| EP | 0931788 | 7/1999 |
| EP | 0949244 A2 | 10/1999 |
| EP | 1004578 A2 | 5/2000 |
| EP | 3059591 A1 | 8/2016 |
| EP | 3590933 A1 | 1/2020 |
| EP | 1951684 | 2/2021 |
| GB | 9912961.1 | 6/1999 |
| WO | WO 1990/05719 A1 | 5/1990 |
| WO | WO 1996/27583 A1 | 9/1996 |
| WO | WO 1996/33172 A1 | 10/1996 |
| WO | WO 1998/03516 A1 | 1/1998 |
| WO | WO 1998/07697 A1 | 2/1998 |
| WO | WO 1998/30566 A1 | 7/1998 |
| WO | WO 1998/33768 A1 | 8/1998 |
| WO | WO 1998/34915 A1 | 8/1998 |
| WO | WO 1998/34918 A1 | 8/1998 |
| WO | WO 99/07675 | 2/1999 |
| WO | WO 1999/29667 A1 | 6/1999 |
| WO | WO 1999/52889 A1 | 10/1999 |
| WO | WO 1999/52910 A1 | 10/1999 |
| WO | WO 2000/035436 A3 | 6/2000 |
| WO | WO 2002/006213 A3 | 1/2002 |
| WO | WO 2002/059112 A2 | 8/2002 |
| WO | WO 2002/059112 A3 | 8/2002 |
| WO | WO 2002/066470 A1 | 8/2002 |
| WO | WO 2003/018021 A1 | 3/2003 |
| WO | WO 2003/062209 A2 | 7/2003 |
| WO | WO 2003/064383 A2 | 8/2003 |
| WO | WO 2003/076424 A1 | 9/2003 |
| WO | WO 2003/077914 A1 | 9/2003 |
| WO | WO 2004/055003 A1 | 7/2004 |
| WO | WO 2004/055004 | 7/2004 |
| WO | WO 2005/037285 A1 | 4/2005 |
| WO | WO 2005/070891 A2 | 8/2005 |
| WO | WO 2006/076644 A2 | 7/2006 |
| WO | WO 2006/076644 A3 | 7/2006 |
| WO | WO 2006/121168 A1 | 11/2006 |
| WO | WO 2007/014011 A2 | 2/2007 |
| WO | WO 2007/067444 A1 | 6/2007 |
| WO | WO 2007/084786 A1 | 7/2007 |
| WO | WO 2008/132601 A1 | 11/2008 |
| WO | WO 2009/036082 A2 | 3/2009 |
| WO | WO 2009/044273 A2 | 4/2009 |
| WO | WO 2009/055730 A1 | 4/2009 |
| WO | WO 2009/114335 A2 | 9/2009 |
| WO | WO 2010/019570 A2 | 2/2010 |
| WO | WO 2010/026122 A1 | 3/2010 |
| WO | WO 2010/027827 A2 | 3/2010 |
| WO | WO 2010/143168 A2 | 12/2010 |
| WO | WO 2010/143169 A2 | 12/2010 |
| WO | WO 2010/143170 A2 | 12/2010 |
| WO | WO 2010/144468 A1 | 12/2010 |
| WO | WO 2011/039735 A2 | 4/2011 |
| WO | WO 2011/039735 A3 | 4/2011 |
| WO | WO 2011/066342 A2 | 6/2011 |
| WO | WO 2011/115677 A1 | 9/2011 |
| WO | WO 2011/159297 A1 | 12/2011 |
| WO | WO 2012/145493 A1 | 10/2012 |
| WO | WO 2013/079174 A1 | 6/2013 |
| WO | WO 2013/086397 A1 | 6/2013 |
| WO | WO 2014/022758 A1 | 2/2014 |
| WO | WO 2014/055897 A2 | 4/2014 |
| WO | WO 2014/059185 A1 | 4/2014 |
| WO | WO 2014/100079 A1 | 6/2014 |
| WO | WO 2014/134341 A1 | 9/2014 |
| WO | WO 2014/138484 A1 | 9/2014 |
| WO | WO 2014/140180 A1 | 9/2014 |
| WO | WO 2014/179664 A2 | 11/2014 |
| WO | WO 2014/194302 A2 | 12/2014 |
| WO | WO 2014/209804 A1 | 12/2014 |
| WO | WO 2015/001518 | 1/2015 |
| WO | WO 2015/061668 A1 | 4/2015 |
| WO | WO 2015/081158 A1 | 6/2015 |
| WO | WO 2015/085847 A1 | 6/2015 |
| WO | WO 2015/109124 A1 | 7/2015 |
| WO | WO 2015/112800 A1 | 7/2015 |
| WO | WO 2015/112805 A1 | 7/2015 |
| WO | WO 2015/116539 A1 | 8/2015 |
| WO | WO 2015/161016 A1 | 10/2015 |
| WO | WO 2015/181342 A1 | 12/2015 |
| WO | WO 2015/195163 A1 | 12/2015 |
| WO | WO 2015/200119 A1 | 12/2015 |
| WO | WO 2016/000619 A1 | 1/2016 |
| WO | WO 2016/012965 A2 | 1/2016 |
| WO | WO 2016/028672 A1 | 2/2016 |
| WO | WO 2016/071448 A1 | 5/2016 |
| WO | WO 2016/092419 A1 | 6/2016 |
| WO | WO 2016/111947 A2 | 7/2016 |
| WO | WO 2016/144803 A2 | 9/2016 |
| WO | WO 2016/161270 A1 | 10/2016 |
| WO | WO 2019/089577 A1 | 5/2019 |
| WO | WO 2019/241787 A1 | 12/2019 |
| WO | WO 2021/026101 A1 | 2/2021 |
| WO | WO 2022/126133 A1 | 6/2022 |
| WO | 2022204721 A1 | 9/2022 |

OTHER PUBLICATIONS

International Search Report and the Written Opinion for PCT/US2022/071345, dated Jun. 7, 2022, 16 pages.

Accornero, F., et al., "Genetic Analysis of Connective Tissue Growth Factor as an Effector of Transforming Growth Factor β Signaling and Cardiac Remodeling", Molecular and Cellular Biology, 35(12):2154-2164 (2015).

Akhurst, R. J. and Hata, A., "Targeting the TGFβ Signalling Pathway in Disease", Nature Reviews, 11:790-811 (2012).

Ballester, B., et al., "Idiopathic Pulmonary Fibrosis and Lung Cancer: Mechanisms and Molecular Targets", Int. J. Mol. Sci., 20:593-28 pages (2019).

Benayoun, B.A., et al., "Functional exploration of the adult ovarian granulosa cell tumor-associated somatic FOXL2 mutation p.Cys134Trp (c.402C>G).", PLoSOne, 5:e8789, 10 pages (2010).

Bhola, N.E., et al., "TGF-β Inhibition Enhances Chemotherapy Action Against Triple Negative Breast Cacner", The Journal of Clinical Investigation, 123(3): 1348-1358 (2013).

Bonniaud, P., et al., "Progressive Transforming Growth Factor β1-Induced Lung Fibrosis is Blocked by an Orally Active ALK5 Kinase Inhibitor", Am. J. of Respiratory and Critical Care Medicine, 171:879-898 (2005).

Brunetto, A.T., et al., "First-in-human, Phamacokinetic and Pharmacodynamic Phase I Study of Resminostat, and Oral Histone Deacetylase Inhibitor, in Patients with Advanced Solid Tumors", Clin Cancer Res., 19(19):5494-5504 (2013).

Buggy, J.J., et al., "CRA-024781: A Novel Synthetic Inhibitor of Histone Deacetylase Enzymes with Antitumor Activity in vitro and in vivo", Mol Cancer Ther, 5(5):1309-1317 (2006).

(56) References Cited

OTHER PUBLICATIONS

Bujak, M. and Frangogiannis, N.G., "The Role of TGF-β Signaling in Myocardial Infarction and Cardiac Remodeling", Cardiovascular Research 74:184-195 (2007).
Cho, M.E. and Kopp, J.B., "Pirfenidone: An Anti-Fibrotic and Cytoprotective Agent as Therapy for Progressive Kidney Disease", Expert Opin Investig Drugs, 19(2):275-283 (2010).
Clarkin, C.E., et al., "Activin Receptor-Like Kinase 5 Inhibition Reverses Impairment of Endothelial Cell Viability by Endogenous Islet Mesenchymal Stromal Cells", Stem Cells, 31:547-559 (2013).
Cox, T.R. and Erler, J.T., "Molecular Pathways: Connecting Fibrosis and Solid Tumor Metastasis", Clin. Cancer Res, 20(14):3637-3643 (2014).
De Reyniès, A., et al., "Large-Scale Pan-Cancer Analysis Reveals Broad Prognostic Association Between TFG-β Ligands, not Hedgegog, and GL11/2 Expression in Tumors", Nature, Scientific Reports, 10:14491, 8 pages (2020).
De Streel, G. and Lucas, S., "Targeting Immunosuppression by TGF-β1 for Cancer Immunotherapy", Biochemical Pharmacology, 192:114697, 11 pages (2021).
Dobaczewski, M., et al., "Tranforming Growth Factor (TG)-β Signaling in Cardiac Remodeling", Journal of Molecular and Cellular Cardiology, 51:600-606 (2011).
Edmondson, S.D., et al., "Fluoroolefins as Amide Bond Mimics in Dipeptidyl Peptidase IV Inhibitors", Bioorganic & Medicinal Chemistry Letters, 18(3):2409-2413 (2008).
Ember, S.W.J., et al., "Acetyl-Lysine Binding Site of Bromodomain-Containing Protein 4 (BRD$) Interacts with Diverse Kinase Inhibitors", ACS Chemical Biology,9(5):1160-1171 (2014).
Filippakopoulos, P., et al., "Selective Inhibition of BET Bromodomains", Nature, 468(7327):1067-1073 (2010).
Fish, P.V., et al., "Identification of a Chemical Probe for Bromo and Extra C-Terminal Bromodomain Inhibition through Optimization of a Fragment-Derived Hit", J. Med Chem, 55:9831-9837 (2012).
Galunisertib definition, downloaded on Feb. 21, 2020 from Wikipedia, URL: https://en.wikipedia.org/wiki/Galunisertib —2 pages.
Ghahremanifard, P., et al.,"TGF-β Mediated Immune Evasion in Cancer—Spotlight on Cancer-Associated Fibroblasts", Cancers, 12:3650, 11 pages (2020).
Giles, F., et al., "A Phase I Study of Intravenous LBH589, a Novel Cinnamic Hydroxamic Acid Analogue Histone Deacetylase Inhibitor, in Patients with Refractory Hematologic Malignancies", Clinical Cancer Research, 12(16):4628-4635 (2006).
Goggins, M., et al., "Progress in Cancer Genetics: Lessons from Pancreatic Cancer", Annals of Oncology, 10(Suppl 4):S4-S8 (1999).
Göttlicher, M., et al., "Valprioic Acid Defines a Novel Class of HDAC Inhibitors Inducing Differentiation of Transformed Cells", The EMBO Journal, 20(24):6969-6978 (2001).
Hallberg, B. and Palmer, R.H., "The Role of the ALK Receptor in Cancer Biology", Annuls of Oncology, 27(Suppl 3):12 pages (2016).
Hamid, O., et al., "Safety and Tumor Responses with Lambrolizumab (Anti PD-1) in Melanoma", The New England Journal of Medicine, 369(2):134-144 (2013).
Hao, Y., et al., "TGF-β-Mediated Epithelial-Mesenchymal Transition and Cancer Metastasis", International Journal of Molecular Sciences, 20(2767):34 pages (2019).
Herbetz, S., et al., "Clinical Development of Galunisertib (LY2157299 monohydrate), a Small Molecule Inhibitor of Transforming Growth Factor-Beta Signaling Pathway", Drug Design, Development and Therapy, 9:4479-4499 (2015).
Hinz, S., et al., "Foxp3 Expression in Pancreatic Carcinoma Cells as a Novel Mechanism of Immune Evastion in Cancer", Cancer Res, 67(17):8344-8350 (2007).
Homgaard, R.B., et al., "Targeting the TGFβ Pathway with Galunisertib, a TGFβR1 Small Molecule Inhibitor, Promotes Anti-Tumor Immunity Leading to Durable, Complete Responses, as Monotherapy and in Combination with Checkpoint Blockade", Journal of ImmunoTherapy of Cancer, 6:47-15 pages (2018).
Huang, J.J.and Blobe, G.C., "Dichotomous Roles of TGF-β in Human Cancer", Biochem Soc Trans, 44(5):1441-1454 (2016).

Inman, G.J., et al., "SB-431542 is a Potent and Specific Inhibitor of Transforming Growth Factor-β Superfamily Type I Activin Receptor-Like Kinase (ALK) Receptors ALK4, ALK5, and ALK7", Molecular Pharmacology, 62:65-74 (2002).
Jamieson, S., et al., "The FOXL2 C134W Mutation is Characteristic of Adult Granulosa Cell Tumors of the Ovary", Modem Pathology, 23:1477-1485 (2010).
Kahn, R. and Sheppard, R., "Fibrosis in Heart Disease: Understanding the Role of Transforming Growth Factor-β₁ in Cardiomyopathy, Valvular Disease and Arrhythmia", Immunology, 118:10-24 (2006).
Katsuno, Y. and Derynck, R., "Epithelial Plasticity, Epithelial-Mesenchymal Transition, and the TGF-β Family", Developmental Cell, 56:726-746 (2021).
Knüppel, L., et al., "A Novel Antifibrotic Mechanism of Nintedanib and Pirfenidone Inhibition of Collagen Fibril Assembly", Am J Respiratory Cell and Mol Biol, 57:77-90 (2017).
Knutson, S.K., et al., "Synergistic Anti-Tumor Activity of EZH2 Inhibitors and Glucocorticoid Receptor Agonists in Models of Germinal Center Non-Hodgkin Lymphomas", Knutson, S., et al., PLoS One, DOI:10.1371/journal.pone.0111840; 22 pages (2014).
Köbel, M., et al., "Adult-Type Granulosa Cell Tumors and FOXL2 Mutation", Cancer Res, 69(24):9160-9162 (2009).
Laping, N.J., et al., "Inhibition of Transforming Growth Factor (TGF)-β1-Induced Extracellular Matrix with a Novel Inhibitor of the TGF-β Type 1 Receptor Kinase Activity: SB-431542", Molecular Pharmacology, 62:58-64 (2002).
Leslie, K.O., "Idiopathic Pulmonary Fibrosis May Be a Disease of Recurrent, Tractional Injury to the Periphery of the Aging Lung", Arch Pathol Lab Med., 136:591-600 (2012).
Liu, L., et al., "Smad2 and Smad3 have Differential Sensitivity in Relaying TGFβ Signaling and Inversely Regulate Early Lineage Specification", Nature, Scientific Reports, 6:14 pages (2016).
Monsivais, D., et al., "Activin-like Kinase 5 (ALK5) Inactivation in the Mouse Uterus Results in Metastatic Endometrial Carcinoma", PNAS, 116(9):3883-3892 (2019).
Moore, B.B. and Moore, T.A., "Vimses in Idiopathic Pulmonary Fibrosis, Etiology and Exacerbatopm", Ann Am Thorac Soc., 12(Supplmnt 2):S186-S192 (2015).
Mori, Y., et al., "Selective Inhibition of Activin Receptor-Like Kinase 5 Signaling Blocks Profibrotic Transforming Growth Factor β Responses in Skin Fibroblasts", Arthritis & Rheumatism, 50(12):4008-4021 (2004).
Newsted, D., et al., "Blockade of TGF-β Signaling with Novel Synthetic Antibodies Limits Immune Exclusion and Improves Chemotherapy Response in Metastatic Ovarian Cancer Models", OncoImmunology, 8(2):e1539613, 14 pages (2019).
Noel, J.K., et al., "Abstract C244: Development of the BET Bromodomain Inhibitor OTX015", Molecular Cancer Therapeutics, 12(11 Supplement): 1 page (2013).
Notification of Transmittal of The International Search Report and The Written Opinion of the International Searching Authority, or the Declaration for International Application No. PCT/US2021/72858 "ALK-5 Inhibitors and Uses Thereof", dated Apr. 11, 2022.
Paruch, K., et al., "Discovery of Dinaciclib (SCH 727965): A Potent Selective Inhibitor of Cyclin-Dependent Kinases", ACS Med. Chem. Lett., 17;1(5):204-208 (2010).
Parry, D., et al., "Dinaciclib (SCH 727965), a Novel and Potent Cyclin-Dependent Kinase Inhibitor", Mol. Cancer Ther. Mol. Cancer Ther. Aug. 2010;9(8):2344-53, 9(8):2344-53 (2010).
Picaud, S., et al., "PFI-1, a Highly Selective Protein Interaction Inhibitor, Targeting BET Bromodomains", Cancer Res, 73(11):3336-3346 (2013).
Piekarz, R.L., et al., "Inhibitor of Histone Deacetylation, Depsipeptide (FR901228), in the Treatment of Peripheral and Cutaneous T-Cell Lymphoma: a Case Report", Blood, 98(9):2865-2866 (2001).
Plumb, J. A., et al., "Phamacodymanic Response and Inhibition of Growth of Human Tumor Xenografts by the Novel Histone Deacetylase Inhibitor PXD101", Mol. Cancer Ther, 2(8):721-728 (2003).
Radisky, D.C., et al., "Fibrosis and Cancer: Do Myofibroblasts Come Also from Epithelial Cells Via EMT?", Journal of Cellular Biochemistry, 101:830-839 (2007).

(56) References Cited

OTHER PUBLICATIONS

Richon, V.M., et al, "A Class of Hybrid Polar Inducers of Transformed Cell Differentiation Inghibits Histone Deacetylases", PNAS, 95( ):3003-3007 (1998).
Rosario, R., et al., "The Transcriptional Targets of Mutant FOXL2 in Granulosa Cell Tumors", PLOSone, 7(9):e46270 (2012).
Rosenblatt, J , et al., "PD-1 Blockade by CT-011, anti PD-1 Antibody, Enhances Ex-vivo Tcell Responses to Autologous Dendritic/Myeloma Fusion Vaccine", J. Immunother, 34(5):409-418 (2011).
Rybinski, R., et al., "The Wound Healing, Chronic Fibrosis, and Cancer Progression Triad", Physiol Genomics, 46:223-244 (2014).
Saito, A., et al., "A Synthetic Inhibitor of Histone Deacetylase, MS-27-275, with Marked in vivo Antitumor Activity Against Human Tumors", PNAS, 96(8):4592-4597 (1999).
Seal, J., et al., "Identification of a Novel Series of BET Family Bromodomain Inhibitors: Binding Mode and Profile of I-BET151 (GSK1210151A", Bioorg & Med Chemistry Letters, 22:2968-2972 (2012).
Shah, S.P., et al., "Mutation of FOSL2 in Granulosa-Cell Tumors of the Ovary", The New England Journal of Medicine, 3 60:2719-2729 (2009).
TGF beta Signaling Pathway, downloaded on Apr. 8, 2021, URL:https://en.wikipedia org/wiki/TGF_beta_Signaling_ pathway, 7 pages.
Toogood, Pl.L., et al., "Discovery of a Potent and Selective Inhibitor of Cyclin-Dependent Kinase 4/6", J. Med. Chem., 48(7):2388-406 (2005).
Tojo, M., et al., "The ALK-5 Inhibitor A-83-01 Inhibits Smad Signaling and Epithelial-to-Mesenchymal Transition by Transforming Growth Factor-β", Cancer Sci, 96:791-800 (2005).
Truty, M. J., and Urrutia, R., "Basics of TGF-β and Pancreatic Cancer", Pancreatology, 7:423-435 (2007).
Venugopal, B., et al., "A Phase I Study of Quisinostat (JNJ-26481585), an Oral Hydroxamate Histone Deacetylse Inhibitor with Evidence of Target Modulation and Antitumor Activity, in Patients with Advanced Solid Tumors", Clin Cancer Res, 19(15):4262-4272 (2013).
Vishnubalaji, R. and Alajez, N.M., "Epigenetic Regulation of Triple Negative Breast Cancer (TNBC) by TGF-β Signaling", Nature Scientific Reports, 11:15410, 13 pages (2021).
Walczak, A., et al., "The Role of the ER-Induced UPR Pathway and the Efficacy of Its Inhibitors and Inducers in the Inhibition of Tumor Progression", Hidawi, Oxidative Medicine and Cellular Longevity, 2019: article ID 5729710, 15 pages (2019).
Wang, G., et al., "The Pan-Cancer Landscape of Crosstalk Between Epithelial-Mesenchymal Transition and Immune Evasion Relevant to Prognosis and Immunotherapy Response", npj Precision Oncology, 5:56, 10 pages (2021).
Weiss, A. and Attisano, L., "The TGFbeta Superfamily Signaling Pathway", Wires Developmental Biology, 2(1):47-63 (2013).
Wyatt, P.F., et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design", J. Med. Chem., 51(16):4986-99 (2008).
Zhao, Y., et al., "The Making of I-BET762, a BET Bromodomain Inhibitor Now in Clinical Development", J Med. Chem., 56:7498-7500 (2013).
Zhu, Y.X., et al., "RNAi Screen of the Druggable Genome Identifies Modulators of Proteasome Inhibitor Sensitivity in Myeloma, Including CDKS", Blood , 117 (14): 3847-3857 (2011)

Group 3 -EX-11 75mpk

Group 4 -EX-11 150mpk

Group 7 - EX-11

Group 8 – aPD-1 + EX-11 (150 mg/kg)

ALK-5 INHIBITORS AND USES THEREOF

RELATED APPLICATIONS

This application is a continuation of International Application No. PCT/US2021/072858, which designated the United States, was filed on Dec. 10, 2021, published in English, and claims the benefit of U.S. Provisional Application No. 63/123,894, filed on Dec. 10, 2020, and U.S. Provisional Application No. 63/166,621, filed on Mar. 26, 2021. The entire teachings of these applications are incorporated herein by reference.

BACKGROUND

Activin receptor-like kinase 5 (ALK-5) (also known as TGF-β receptor type 1 (TGFβR1)) is a therapeutic target, e.g., in proliferative diseases such as cancer because of its suggested roles in promoting tumor growth, survival, and metastasis. ALK-5 is a member of the TGF-β superfamily of receptors that has been suggested to regulate a wide array of cellular processes. Modulating TGF-β signaling is important to controlling cellular processes implicated in cellular proliferation. See, for example, Akhurst, R. J. and Hata, A., "Targeting the TGF-β Signalling Pathway in Disease", *Nat. Rev. Drug Disc.*, 11 pp 790-811 (2012) and Hallberg and Palmer, "The role of the ALK receptor in cancer biology", *Annals of Oncology*, 2016, 27, iii4.

Generally during TGF-β signaling, a type I receptor is brought together with a type II receptor, both of which are serine/threonine kinases. To date there are seven (7) known type I receptors: activin receptor-like kinases 1 through 7 (ALK-1 through ALK-7). In some instances, TGF-β signals through a combination of TOR-II (a type II receptor) and ALK-5. Upon activation, the type I receptors transduce signals through various proteins, for example, activated type I receptors phosphorylate members of the receptor-regulated subfamily of SMADs, which allows them to complex with mediator SMADs. The resulting activated SMAD complexes accumulate in the nucleus, where they play a role in the transcription of target genes. Blocking this TGF-β signaling pathway through ALK inhibition (in particular, ALK-5 inhibition) is an attractive target for therapy due to the complex roles the pathway plays in cell proliferation, differentiation, adhesion, migration, and apoptosis. It has been noted that in proliferative and fibrotic diseases, cellular mutations occur wherein the normal proliferative suppression function of TGF-β signaling is conferred, thus allowing uncontrolled proliferation of the cells, see, e.g., Blobe, G. C., et al., "Role of Transforming Growth Factor β in Human Disease", N Engl J Med (342), pp 1350-1358 (2000); Ballester, B. et al, "Idiopathic Pulmonary Fibrosis and Lung cancer: Mechanisms and Molecular Targets", Int. J. of Molecular Sciences 20(593), doi:10.3390/ijms20030593 (2019), and Huang, J. J. and Blobe, G. C., "Dichotomous Roles of TGF-β in Human Cancer", Biochem Soc. Trans 342(2016); 1441-1454 (https://doi.org/10.1042/BST20160065).

TGF-β is an important pathway in cancer that facilitates tumor growth and immune evasion, as well as playing a role in other cancer process such as metastasis and angiogenesis. Upregulation of the components of the TGF-β pathway, including the ligand and receptors, is observed in many types of cancer and is often associated with poor outcomes (de Reyniès, A., Javelaud, D., Elarouci, N. et al., *Sci Rep* 10, 14491 (2020). https://doi.org/10.1038/s41598-020-71559-w). Aberrant TGF-β signaling has been shown to be involved in the development of multiple cancer types, including triple negative breast cancer (Bhola, Neil E., et al "TGF-β inhibition enhances chemotherapy action against triple-negative breast cancer." *The Journal of clinical investigation* 123.3 (2013) https://doi.org/10.1172/JCI65416; Vishnubalaji, Radhakrishnan, and Nehad M. Alajez. "Epigenetic regulation of triple negative breast cancer (TNBC) by TGF-β signaling." *Scientific Reports* 11.1 (2021) https://doi.org/10.1038/s41598-021-94514-9), pancreatic cancer (Goggins, Michael, et al. "Progress in cancer genetics: lessons from pancreatic cancer." *Annals of oncology* 10 (1999) https://doi.org/10.1093/annonc/10.suppl_4.S4), Truty, Mark J., and Raul Urrutia. "Basics of TGF-β and pancreatic cancer." *Pancreatology* 7.5-6 (2007) https://doi.org/10.1159/000108959), and ovarian cancer (Monsivais, Diana, et al. "Activin-like kinase 5 (ALK5) inactivation in the mouse uterus results in metastatic endometrial carcinoma." *Proceedings of the National Academy of Sciences* 116.9 (2019) https://doi.org/10.1073/pnas.1806838116, Newsted, Daniel, et al. "Blockade of TGF-β) signaling with novel synthetic antibodies limits immune exclusion and improves chemotherapy response in metastatic ovarian cancer models." *Oncoimmunology* 8.2 (2019) https://doi.org/10.1080/2162402X.2018.1539613).

Signaling though this pathway begins with the liberation of the latent ligand (TGF-β) and binding specific serine/threonine residues on a specific receptor (TGF-β R2), which then binds to and phosphorylates a second receptor (TGF-β R1, also named ALK5). This complex in turn phosphorylates and activates members of the SMAD family of proteins, which translocate to the nucleus and regulate the expression of target genes of this TGF-β pathway (Weiss, Alexander, and Liliana Attisano. "The TGFbeta superfamily signaling pathway." *Wiley Interdisciplinary Reviews: Developmental Biology* 2.1 (2013) https://doi.org/10.1002/wdev.86).

Activation of the TGF-β pathway can lead to immune evasion of tumor cells through epithelial-to-mesenchymal transition (EMT) (Wang, G., Xu, D., Zhang, Z. et al. The pan-cancer landscape of crosstalk between epithelial-mesenchymal transition and immune evasion relevant to prognosis and immunotherapy response. *npj Precis. Onc.* 5, 56 (2021). https://doi.org/10.1038/s41698-021-00200-4). It can also lead to immunosuppression through direct suppressive effects on innate and adaptive immune cells, as well as stimulation of suppressive Tregs and MDSCs (de Streel, Gregoire, and Sophie Lucas. "Targeting immunosuppression by TGF-β1 for cancer immunotherapy." Biochemical Pharmacology (2021) https://doi.org/10.1016/j.bcp.2021.114697). TGF-β additionally potently regulates the tumor microenvironment by altering levels of ECM proteins and signaling molecules, leading to immune cell exclusion (Ghahremanifard, P.; Chanda, A.; Bonni, S.; Bose, P. TGF-β Mediated Immune Evasion in Cancer—Spotlight on Cancer-Associated Fibroblasts. Cancers 2020, 12, 3650. https://doi.org/10.3390/cancers12123650).

Granulosa cell tumors (GCTs) of the ovary represent ~5% of malignant ovarian cancers and it has recently been reported that 95-97% of adult granulosa cell tumors carry a unique somatic mutation 402C>C in the FOXL2 gene (Jamieson, S., Butzow, R., Andersson, N. et al. The FOXL2 C134W mutation is characteristic of adult granulosa cell tumors of the ovary. *Mod Pathol* 23, 1477-1485 (2010). https://doi.org/10.1038/modpathol.2010.145). The 402C>G mutation results in an amino acid substitution of tryptophan for cysteine (C134W) (Shah S P, Kobel M, Senz J, Morin R D, Clarke B A, et al. (2009) Mutation of FOXL2 in granulosa-cell tumors of the ovary. N Engl J Med 360: 2719-2729) which is located in the second wing on the surface of the forkhead domain. Computer modelling suggests this alteration does not disrupt the folding of the FOX 2 forkhead domain or its interactions with DNA. In addition, it has been shown that mutation does not affect the localisation of the FOXL2 protein (Benayoun B A, Caburet S, Dipietromaria A, Georges A, D'Haene B, et al. (2010) Functional exploration of the adult ovarian granulosa cell tumor-associated somatic FOXL2 mutation p.Cys134Trp (c.402C>G) PoS one 5: e8789). Therefore, it is believed that the pathogenicity of mutant FOXL2 occurs through changes to its interactions with other proteins. Such candidate proteins include the SMAD transcription factors and the effectors of TG-β and BIP family signalling (Kobel M, Gilks C B, Huntsman D G (2009) Adult-type granulosa cell tumors and FOXL2 mutation Cancer Res 69: 9160-9162) In addition, many of the transcriptional targets of mutant FOXL2 are known TGF-β signalling genes. Therefore, deregulation of this key antiproliferative pathway is one-way mutant FOXL2 contribute to the pathogenesis of adult-type GCTs (Rosario R, Araki H, Print C G, Shelling A N (2012) The transcriptional targets of mutant FOXL2 in granulosa cell tumors. PloS one; https://doi.org/10.1371/journal.pone.0046270).

Activin receptor-like kinases have been implicated as an important therapeutic target in proliferative diseases such as cancer because of their roles in promoting tumor growth, survival, and metastasis. For example, many small molecule ALK-5 inhibitors have been shown to have anti-proliferative activity in a variety of cancer and tumor types. Small molecule SB-431542 was developed as an ALK-5 inhibitor and was found to inhibit other activin receptor-like kinases, ALK-4 and ALK-7. See, e.g., Inman et al., "SB-431542 is a Potent and Specific Inhibitor of Transforming Growth Factor-β Superfamily Type I Activin Receptor-Like Kinase (ALK) Receptors ALK4, ALK5, and ALK7", Molecular Pharmacology, 2002, 62, 65. Additionally, small molecule ALK-4, ALK-5, and ALK-7 inhibitor A-83-01 was developed, and was found to inhibit SMAD signaling and epithelial-to-mesenchymal transition (EMT), suggesting that such inhibitors are useful for treating a variety of advanced-stage cancers. See, e.g., Tojo et al. "The ALK-5 inhibitor A-83-01 inhibits SMAD signaling and epithelial-to-mesenchymal transition by transforming growth factor-β", Cancer Sci., 2005, 96, 791. In the same manner, the role of ALK-5 in TGF-β signaling may play a role in the production of cancer-associated fibroblasts and other fibrotic conditions. See for example, Blobe, G. C., et al., "Role of Transforming Growth Factor β in Human Disease", N Engl J Med (342), pp 1350-1358 (2000); Ballester, B. et al, "Idiopathic Pulmonary Fibrosis and Lung cancer: Mechanisms and Molecular Targets", Int. J. of Molecular Sciences 20(593), doi: 10.3390/ijms20030593 (2019), Liu, L et al., "Smad2 and Smad3 Have Differential Sensitivity in Relaying TGFb Signaling and Inversely Regulate Early Linage Specification", Scientific Reports [6:21602/DOI: 10.1038/srep21602], February 2015-14 pages, Huang, J. J. and Blobe, G. C., "Dichotomous Roles of TGF-β in Human Cancer", Biochem Soc. Trans 342(2016); 1441-1454 (https://doi.org/10.1042/BST20160065), Akhurst, R. J. and Hata, A., "Targeting the TGF-β Signalling Pathway in Disease", Nat. Rev. Drug Disc., 11 pp 790-811 (2012), Leslie, K. O., "Idiopathic Pulmonary Fibrosis May Be a Disease of Recurrent, Tractional Injury to the Periphery of the Aging Lung—A Unifying Hypothesis Regarding Etiology and Pathogenesis" Arch Pathol Lab Med (136) [[591-600 (2012), Knuppel, L. et al., "A Novel Antifibrotic Mechanism of Nintedanib and Pirfenidone—Inhibition of Collagen Fibril Assembly", Am. J. of Resp. Cell and Mole. Bio. 1 (57), pp 77-90 (2017), Laping, N. J. et al., "Inhibition of TGF-b1-Induced Extracellular Matrix", Mol. Pharmacol. Vol 62, No1, pp 580-64 (2002), Moore, B. B. and Moore, T. A., Viruses in Idiopathic Pulmonary Fibrosis—Etiology and Exacerbation, Ann Am Thorac. Soc., Vol 12 (Suppl 2) pp S186-S192 (2015)-[DOI: 10.1513/AnnalsATS.201502-088AW], Cho, M. E. and Kopp, J. B., "Pirfenidone: an Anti-Fibrotic and Cytoprotective Agent as Therapy for Progressive Kidney Disease", Expert Opin. Investig. Drugs, 19(2), pp 275-283 (2010) [DOI:10.1517/13543780903501539], and B. Rybinski et al., "The Wound Healing, Chronic Fibrosis, and Cancer Progression Triad, Physiol Genomics. 46(7); 2014, 223-244 PMID:24520152.

Galunisertib, a small molecule ALK-5 inhibitor, was found to inhibit tumor growth in a breast cancer model. Galunisertib in combination with a PD-L1 inhibitor showed tumor growth inhibition and regression in a colon carcinoma model, signaling synergy between ALK-5 inhibition and PD-1/PD-L1 inhibition. See, e.g., Holmgaard et al., "Targeting the TGFβ pathway with galunisertib, a TGFβRI small molecule inhibitor, promotes anti-tumor immunity leading to durable, complete responses, as monotherapy and in combination with checkpoint blockade", Journal for ImmunoTherapy of Cancer, 2018, 6, 47. In addition, galunisertib has been under investigation for use in treating various other cancers, including glioblastoma, pancreatic carcinoma, hepatocellular carcinoma (HCC), and myelodysplastic syndromes, sometimes in combination with a PD-1/PD-L1 inhibitor. See, e.g., Herbertz et al., "Clinical development of galunisertib (LY2 IS7299 monohydrate), a small molecule inhibitor of transforming growth factor-beta signaling pathway", Drug Design, Development, and Therapy, 2015, 9, 4479.

Another small molecule ALK-5 inhibitor, TEW-7197, also known as vactosertib, has also been under investigation for treating cancers such as melanoma, prostate cancer, breast cancer, HCC, and glioblastoma.

ALK inhibitors, especially ALK-5 inhibitors, are promising therapeutics for a variety of indications that are still being explored. For example, studies have shown that TGFβR1/ALK-5 mutants can induce Foxp3 expression, which has been found to play a key role in the immune resistance of different tumor types, including pancreatic carcinoma. See, e.g., Hinz et al. "Foxp3 Expression in Pancreatic Carcinoma Cells as Novel Mechanism of Immune Evasion in Cancer", Cancer Res. 2007, 67, 8344. Therefore, cancers that have traditionally been resistant to apoptosis via chemo- and/or radiation-based therapies may respond when combined with ALK-5 inhibition.

Research has also shown that ALK-5 inhibitors are also useful for treating proliferative diseases other than cancer, including systemic sclerosis and other fibrotic conditions in a subject, including fibrotic conditions associated with cancer, see for example, those conditions described in Mori et al. "Activin Receptor-Like Kinase 5 Signaling Blocks Profibrotic Transforming Growth Factor β Responses in Skin Fibroblasts", Arthritis & Rheumatism, 2004, 8, 4008, Akhurst, R. J. and Hata, A., "Targeting the TGF-β Signalling Pathway in Disease", Nat. Rev. Drug Disc., 11 pp 790-811 (2012), and Cox, T. R and Erler, J. T., "Molecular Pathways Connecting Fibrosis and Solid Tumor Metastasis", Clin Cancer Res., 2014, 20(14), pp 3637-3643.

Increased levels of ALK-5 have also been implicated in cardiac pathologies and cardiovascular disease, including not only cardiac remodeling and fibrosis, e.g., following myocardial infarction, and cardiac hypertrophy, but also dilated, ischemic and hypertrophic cardiomyopathies, valvular disease and arrhythmia, such as atrial fibrillation. Khan, R. and Sheppard, R. "Fibrosis in heart disease: understanding the role of transforming growth factor-$\beta_1$ in cardiomyopathy, valvular disease and arrhythmia", *Immunology* 2006, 118:10-24; Bujak, M. and Frangogiannis, N. G., "The role of TGF-β in myocardial infarction and cardiac remodeling," *Cardiovascular Research* 74 (2007), 184-195; Dobaczewski, M., et al., "Transforming Growth Factor (TGF)-β signaling in cardiac remodeling", *J. Mol. Cell Cardiol.*, 2011, 51(4):600-606; and Accornero, F., et al., "Genetic Analysis of Connective Tissue Growth Factor as an Effector of Transforming Growth Factor R Signaling and Cardiac Remodeling", Molecular and Cellular Biology 2015, 35(12): 2154-2164.

Despite the progress made, additional compounds are needed to progress research and medical care of patients with proliferative diseases such as tumors and cancer, and fibrotic diseases, both those associated with proliferative diseases and those that are not associated with proliferative diseases.

SUMMARY OF THE INVENTION

Provided herein are inhibitors of activin receptor-like kinases (e.g., ALK-5), including compounds of any of the formulae herein, pharmaceutical compositions and kits comprising the same, and methods of using the same (e.g., for the treatment and/or prevention of diseases in a subject). Also provided herein are methods of preparing the compounds and pharmaceutical compositions described herein.

In some embodiments, there are provided compounds of Formula (I):

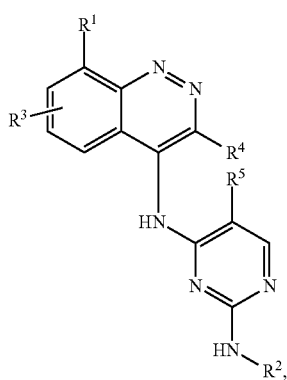

(I)

or a pharmaceutically acceptable salt thereof, wherein $R^1$, $R^2$, $R^3$, $R^4$, and $R^5$ are as defined herein. In some embodiments, there are provided compounds of Formula (II), as defined herein. In some embodiments, there are provided compounds of Formula (III), as defined herein. In some embodiments, there are provided compounds of Formula (IV), as defined herein. In some embodiments, there are provided compounds presented in Table 1.

The compounds provided herein are activin receptor-like kinase (e.g., ALK-5) inhibitors useful for treating and/or preventing diseases (e.g., that involve regulating or targeting the TGFβ signaling pathway, for example, as it pertains to treatment, amelioration, or prevention of fibrotic, inflammatory, and/or proliferative diseases (e.g., cancer, pulmonary fibrosis and cardiac diseases associated with TGFβ1 signaling)). See, for example, the relationship of these diseases and conditions and role of various signaling pathways that may be implicated in treatments that are described in, for example, Akhurst, R. J. and Hata, A., "Targeting the TGF-β Signalling Pathway in Disease", *Nat. Rev. Drug Disc.*, 11 pp 790-811 (2012), Cox, T. R and Erler, J. T., "Molecular Pathways Connecting Fibrosis and Solid Tumor Methastasis", *Clin Cancer Res.*, 2014, 20(14), pp 3637-3643, Radisky, D. C., et al., "Fibrosis and Cancer: Do Myofibroblasts Come Also From Epithelial Cells via EMT?", *J. Cell Biochem.*, 2101(4), pp 830-839 [DOI: 10.1002/jcb.21186], and the role of viral complications in IPF, for example, as described in Moore, B. B. and Moore, T. A., Viruses in Idiopathic Pulmonary Fibrosis—Etiology and Exacerbation, *Ann Am Thorac. Soc., Vol* 12 (Suppl 2) pp S186-S192 (2015)-[DOI: 10.1513/AnnalsATS.201502-088AW], and the role of TGF signaling in cardiac remodeling described, for example, in Dobaczewski, M., et al., "Transforming Growth Factor (TGF)-μ signaling in cardiac remodeling", *J. Mol. Cell Cardiol.*, 2011, 51(4):600-606.

In certain embodiments, the compounds provided herein are selective ALK-5 inhibitors, i.e., selective for ALK-5 over other kinases (e.g., over other activin receptor-like kinases). In certain embodiments, for example, a compound of Formula (I) is selected from the compounds recited in Table 1 (infra), and pharmaceutically acceptable salts thereof.

In the various aspects and embodiments disclosed herein, express reference to a compound of Formula (I) is understood to alternatively refer to a compound of any disclosed subgenus thereof, for example, a compound of Formula (I) includes compounds of Formula (II) (infra), Formula (III) (infra), Formula (IV) (infra), or a compound of Table 1 (infra), Table 4 (infra), or any of the specific compounds disclosed herein.

In some aspects, provided is a compound, or t a pharmaceutically acceptable salt thereof, which is:
N4-(7-fluoro-8-methylcinnolin-4-yl)-N2-(4-(4-methylpiperazin-1-yl)phenyl)pyrimidine-2,4-diamine;
N4-(7-fluoro-8-methylcinnolin-4-yl)-N2-(4-(piperazin-1-yl)phenyl)pyrimidine-2,4-diamine;
N2-(2-fluoro-5-(piperazin-1-ylmethyl)phenyl)-N4-(8-methylcinnolin-4-yl)pyrimidine-2,4-diamine;
N4-(8-methylcinnolin-4-yl)-N2-(3-((4-methylpiperazin-1-yl)methyl)phenyl)pyrimidine-2,4-diamine;
N4-(8-methylcinnolin-4-yl)-N2-(4-(piperidin-4-ylmethyl)phenyl)pyrimidine-2,4-diamine;
N2-(3-fluoro-5-(piperazin-1-ylmethyl)phenyl)-N4-(8-methylcinnolin-4-yl)pyrimidine-2,4-diamine;
N4-(6-fluoro-8-methylcinnolin-4-yl)-N2-(4-(4-methylpiperazin-1-yl)phenyl)pyrimidine-2,4-diamine;
N2-(3-fluoro-4-(piperazin-1-yl)phenyl)-N4-(8-methylcinnolin-4-yl)pyrimidine-2,4-diamine;
5-fluoro-N4-(8-methylcinnolin-4-yl)-N2-(4-(piperazin-1-yl)phenyl)pyrimidine-2,4-diamine;
N4-(8-methylcinnolin-4-yl)-N2-(4-morpholinophenyl)pyrimidine-2,4-diamine;
N4-(8-methylcinnolin-4-yl)-N2-(3-morpholinophenyl)pyrimidine-2,4;
N2-(3-chloro-4-morpholinophenyl)-N4-(8-methylcinnolin-4-yl)pyrimidine-2,4-diamine;
N2-(3-fluoro-4-morpholinophenyl)-N4-(8-methylcinnolin-4-yl)pyrimidine-2,4-diamine;
N4-(6-fluoro-8-methylcinnolin-4-yl)-N2-(4-(piperazin-1-yl)phenyl)pyrimidine-2,4-diamine;
N2-(2-fluoro-5-(piperidin-4-ylmethyl)phenyl)-N4-(8-methylcinnolin-4-yl)pyrimidine-2,4-diamine;

N4-(8-methylcinnolin-4-yl)-N2-(4-(4-(2,2,2-trifluoroethyl)piperazin-1-yl)phenyl)pyrimidine-2,4-diamine;
N4-(8-methylcinnolin-4-yl)-N2-(4-(piperazin-1-ylmethyl)phenyl)pyrimidine-2,4-diamine;
N2-(2-fluoro-4-(4-methylpiperazin-1-yl)phenyl)-N4-(8-methylcinnolin-4-yl)pyrimidine-2,4-diamine;
N2-(2-fluoro-4-(piperazin-1-yl)phenyl)-N4-(8-methylcinnolin-4-yl)pyrimidine-2,4-diamine;
N4-(8-methylcinnolin-4-yl)-N2-(6-(4-methylpiperazin-1-yl)pyridin-3-yl)pyrimidine-2,4-diamine;
N4-(5-fluoro-8-methylcinnolin-4-yl)-N2-(4-(4-methylpiperazin-1-yl)phenyl)pyrimidine-2,4-diamine;
N4-(8-methylcinnolin-4-yl)-N2-(4-(morpholinomethyl)phenyl)pyrimidine-2,4-diamine;
N4-(8-methylcinnolin-4-yl)-N2-(4-((4-methylpiperazin-1-yl)methyl)phenyl)pyrimidine-2,4-diamine;
N2-(4-(8-methyl-3,8-diazabicyclo[3.2.1]octan-3-yl)phenyl)-N4-(8-methylcinnolin-4-yl)pyrimidine-2,4-diamine;
N4-(8-methylcinnolin-4-yl)-N2-(4-((4-methylpiperazin-1-yl)methyl)-3-(trifluoromethyl)phenyl)pyrimidine-2,4-diamine;
N2-(4-chlorophenyl)-N4-(8-methylcinnolin-4-yl)pyrimidine-2,4-diamine;
N4-(8-methylcinnolin-4-yl)-N2-(3-(piperazin-1-ylmethyl)phenyl)pyrimidine-2,4-diamine;
5-fluoro-N4-(8-methylcinnolin-4-yl)-N2-(4-(4-methylpiperazin-1-yl)phenyl)pyrimidine-2,4-diamine;
N4-(8-methylcinnolin-4-yl)-N2-(4-(4-methylpiperazin-1-yl)phenyl)pyrimidine-2,4-diamine;
N2-(3-chloro-4-(4-methylpiperazin-1-yl)phenyl)-N4-(8-methylcinnolin-4-yl)pyrimidine-2,4-diamine;
3-((4-((8-methylcinnolin-4-yl)amino)pyrimidin-2-yl)amino)benzenesulfonamide;
N4-(8-methylcinnolin-4-yl)-N2-(3-(piperidin-4-yl)phenyl)pyrimidine-2,4-diamine;
2-(4-(4-((4-((8-methylcinnolin-4-yl)amino)pyrimidin-2-yl)amino)phenyl)piperazin-1-yl)ethan-1-ol;
N2-(4-fluoro-3-morpholinophenyl)-N4-(8-methylcinnolin-4-yl)pyrimidine-2,4-diamine;
N4-(8-methylcinnolin-4-yl)-N2-(3-morpholino-5-(trifluoromethyl)phenyl)pyrimidine-2,4-diamine;
N4-(7-fluoro-8-methylcinnolin-4-yl)-N2-(3-morpholinophenyl)pyrimidine-2,4-diamine;
N4-(7-fluoro-8-methylcinnolin-4-yl)-N2-(4-morpholinophenyl)pyrimidine-2,4-diamine;
N2-(3-fluoro-5-((4-methylpiperazin-1-yl)methyl)phenyl)-N4-(8-methylcinnolin-4-yl)pyrimidine-2,4-diamine;
N2-(3-fluoro-5-((1-methylpiperidin-4-yl)methyl)phenyl)-N4-(8-methylcinnolin-4-yl)pyrimidine-2,4-diamine;
N2-(3-fluoro-5-morpholinophenyl)-N4-(8-methylcinnolin-4-yl)pyrimidine-2,4-diamine;
N2-(4-(5-methyl-2,5-diazabicyclo[2.2.1]heptan-2-yl)phenyl)-N4-(8-methylcinnolin-4-yl)pyrimidine-2,4-diamine;
N4-(8-methylcinnolin-4-yl)-N2-(4-(tetrahydro-2H-pyran-4-yl)phenyl)pyrimidine-2,4-diamine;
N4-(8-methylcinnolin-4-yl)-N2-(3-(morpholinomethyl)phenyl)pyrimidine-2,4-diamine;
N4-(8-methylcinnolin-4-yl)-N2-(4-(piperazin-1-yl)phenyl)pyrimidine-2,4-diamine;
N4-(8-chlorocinnolin-4-yl)-N2-(4-(4-methylpiperazin-1-yl)phenyl)pyrimidine-2,4-diamine;
N4-(8-chlorocinnolin-4-yl)-N2-(4-(piperazin-1-yl)phenyl)pyrimidine-2,4-diamine;
N4-(3,8-dimethylcinnolin-4-yl)-N2-(3-morpholinophenyl)pyrimidine-2,4-diamine;
N4-(3,8-dimethylcinnolin-4-yl)-N2-(4-morpholinophenyl)pyrimidine-2,4-diamine;
N2-(3-fluoro-4-(4-methylpiperazin-1-yl)phenyl)-N4-(8-methylcinnolin-4-yl)pyrimidine-2,4-diamine;
N2-(4-(tert-butyl)phenyl)-N4-(8-methylcinnolin-4-yl)pyrimidine-2,4-diamine;
N4-(8-methylcinnolin-4-yl)-N2-(4-(piperidin-1-yl)phenyl)pyrimidine-2,4-diamine;
N4-(8-cyclopropylcinnolin-4-yl)-N2-(3-morpholinophenyl)pyrimidine-2,4-diamine;
N4-(8-cyclopropylcinnolin-4-yl)-N2-(4-morpholinophenyl)pyrimidine-2,4-diamine; or
N2-(4-cyclohexylphenyl)-N4-(8-methylcinnolin-4-yl)pyrimidine-2,4-diamine.

In another aspect, provided herein are pharmaceutical compositions comprising a compound of Formula (I), or a pharmaceutically acceptable salt thereof, and one or more pharmaceutically acceptable carriers or excipients. In certain embodiments, a pharmaceutical composition provided herein comprises a therapeutically and/or prophylactically effective amount of a compound of Formula (I), or a pharmaceutically acceptable salt thereof. The pharmaceutical compositions described herein may be useful for treating and/or preventing a disease (e.g., an inflammatory, fibrotic, or proliferative disease, e.g., cancer or a combination of two or more of the foregoing, as described further herein) in a subject. The pharmaceutical compositions provided herein may further comprise one or more additional therapeutic agents (e.g., anti-proliferative agents, e.g., anti-cancer agents).

In another aspect, provided herein are methods of treating and/or preventing a disease in a subject (e.g., a subject in need thereof), the methods comprising administering to the subject a therapeutically and/or prophylactically effective amount of a compound of Formula (I) (II), (III), or (IV), or Table 1 or Table 4, or a pharmaceutically acceptable salt of any of said compounds, or a pharmaceutical composition thereof. For example, provided herein are methods for treating a disease, for example, an inflammatory, fibrotic, or proliferative disease (e.g., cancer) in a subject, the methods comprising administering to the subject a therapeutically effective amount of a compound of Formula (I), or a pharmaceutically acceptable salt thereof, or a pharmaceutical composition comprising a compound of Formula (I), or a pharmaceutically acceptable salt thereof, for example, a compound of Formula (II), Formula (III), Formula (IV), Table 1, or Table 4, or any of the specific compounds disclosed herein, or a pharmaceutically acceptable salt of any of said compounds, or a pharmaceutical composition thereof.

In certain embodiments, the proliferative disease is cancer. In certain embodiments, the proliferative disease is a solid tumor cancer. In some embodiments, the proliferative disease is a hematological cancer. In some embodiments, the cancer is associated with the activity (e.g., aberrant or increased activity) of an activin receptor-like kinase (e.g., ALK-5) in a subject or cell. In some embodiments, the cancer has associated with it a TGFβ signaling pathway that is critical in the progress of the disease and which can be amelioriated by Alk-5 inhibition. In some embodiments, the cancer has associated with it a FOXL2 mutation, for example, a tumor-associated somatic FOXL2 mutation p.Cys134Trp (c.402C>G). In some embodiments, the FOXL2 mutation affects one or more transcriptional targets which are TGF-β signalling genes.

In certain embodiments, the cancer is lung cancer (e.g., non-small cell lung cancer (NSCLC)), brain cancer (e.g., neuroblastoma, glioblastoma), thyroid cancer (e.g., anaplastic thyroid cancer (ATC)), breast cancer, colorectal cancer (e.g., colon carcinoma), liver cancer (e.g., hepatocellular carcinoma (HCC)), pancreatic cancer (e.g., pancreatic carcinoma), skin cancer (e.g., melanoma), prostate cancer, or a hematological cancer (e.g., anaplastic large cell lymphoma (ALCL), myelodysplastic syndrome (MDS)). In certain embodiments, the cancer is myelofibrosis (MF).

In some embodiments, the proliferative disease is cancer, for example, anaplastic astrocytoma, pancreatic cancer, for example, pancreatic ductal adenocarcinoma and associated CAF, metastatic melanoma, colorectal cancer, breast cancer, prostate cancer, renal cancer, hepatocellular cancer, ovarian cancer, HPV-associated cancers (e.g., cervical cancer, oropharyngeal cancer, anal cancer, vulvar/vaginal cancer, and penile cancer), multiple myeloma, myelodysplastic syndrome, or myelofibrosis. In some embodiments, the cancer is treated by targeting a tumor stromal cell (e.g., in a tumor microenvironment), such as a cancer-associated fibroblast (CAF), stellate cell or myofibroblast, and/or a tumor-associated immune cell (e.g., in the tumor-immune microenvironment), for example, to thereby modulate the tumor-stroma microenvironment and/or the tumor-immune microenvironment.

In some embodiments the disease is a fibrotic condition, for example, idiopathic pulmonary fibrosis, liver fibrosis, liver cirrhosis, nonalcoholic steatohepatitis, Peyronie's, cystic fibrosis, beta thalassemia, actinic keratosis, hypertension, general inflammatory disorders, dry eye, ulcers, corneal fibrosis, wet age-related macular degeneration, psoriasis, wound closure, chronic kidney disease, renal fibrosis, systemic sclerosis, and chronic Chagas' heart disease. In some embodiments, the fibrotic condition is cardiac fibrosis or an associated condition, for example, valvular disease, arrhythmia (e.g., atrial fibrillation), myocardial remodeling (e.g., after infarction), cardiomyopathy (e.g., dilated, ischaemic or hypertrophic cardiomyopathy), restenosis (e.g., in-stent restenosis, post-angioplasty restenosis). In some embodiments, the fibrotic condition is Dupuytren's contracture. In some embodiments, the fibrotic condition is, for example, acute exacerbation of idiopathic pulmonary fibrosis or familial pulmonary fibrosis, vascular fibrosis, kidney fibrosis (renal fibrosis), skin fibrosis (cutaneous fibrosis or endometrial fibrosis, e.g., keloids, scleroderma, or nephrogenic systemic fibrosis), gastrointestinal fibrosis (e.g., Crohn's disease), bone marrow fibrosis (myelofibrosis), athrofibrosis (e.g., of the knee, the shoulder or another joint), Dupuytren's contracture, mediastinal fibrosis, retroperitoneal fibrosis, systemic sclerosis, or autoimmune hepatitis. In some embodiments, the fibrotic condition is cancer-associated fibrosis; lung fibrosis, commonly known as "scarring of the lungs" (e.g., pulmonary fibrosis, for example, acute exacerbation of idiopathic pulmonary fibrosis or familial pulmonary fibrosis). In some embodiments, the fibrotic conditions is lung fibrosis, for example, pulmonary fibrosis, such as idiopathic pulmonary fibrosis, acute exacerbation of idiopathic pulmonary fibrosis or familial pulmonary fibrosis. In an embodiment, the liver fibrosis is hepatic fibrosis, e.g., keloids, scleroderma, nephrogenic systemic fibrosis, bile duct fibrosis (biliary fibrosis), or liver cirrhosis, for example, primary biliary cholangitis (biliary cirrhosis) or primary sclerosing cholangitis.

Also provided herein are methods of inhibiting tumor growth in a subject (e.g., a subject in need thereof), the methods comprising administering to the subject a therapeutically effective amount of a compound of Formula (I), or a pharmaceutically acceptable salt thereof, or a pharmaceutical composition thereof.

Also provided herein are methods of treating cachexia in a subject (e.g., a subject in need thereof), the methods comprising administering to the subject a therapeutically effective amount of a compound of Formula (I), or a pharmaceutically acceptable salt thereof, or a pharmaceutical composition thereof.

Also provided herein are methods for promoting infiltration in a tumor-immune microenvironment in a subject in need thereof, comprising administering to the subject a therapeutically effective amount of a compound of Formula (I), or a pharmaceutically acceptable salt thereof, or a pharmaceutical composition thereof.

Also provided herein are methods for inhibiting epithelial-to-mesenchymal transition in a tumor (e.g., in a subject in need thereof), comprising contacting the tumor with (e.g., an effective amount of) a compound of Formula (I), or a pharmaceutically acceptable salt thereof, or a pharmaceutical composition thereof. In some embodiments, the tumor is in a subject in need thereof and the method comprises administering to the subject a therapeutically effective amount of a compound of Formula (I), or a pharmaceutically acceptable salt thereof, or a pharmaceutical composition thereof.

Also provided herein are methods for modulating (e.g., promoting, upregulating) the antigen presentation pathway in a tumor (e.g., in a subject in need thereof), comprising contacting the tumor with (e.g., an effective amount of) a compound of Formula (I), or a pharmaceutically acceptable salt thereof, or a pharmaceutical composition thereof. In some embodiments, the tumor is in a subject in need thereof and the method comprises administering to the subject a therapeutically effective amount of a compound of Formula (I), or a pharmaceutically acceptable salt thereof, or a pharmaceutical composition thereof.

Also provided herein are methods of modulating the tumor-immune microenvironment in a subject, the methods comprising administering to the subject a therapeutically effective amount of a compound of Formula (I), or a pharmaceutically acceptable salt thereof, or a pharmaceutical composition thereof.

Also provided herein are methods increasing tumor vasculature or blood flow to a tumor or both in a subject, the methods comprising administering to the subject a therapeutically effective amount of a compound of Formula (I), or a pharmaceutically acceptable salt thereof, or a pharmaceutical composition thereof.

Also provided herein are methods of inhibiting metastasis of a cancer in a subject, the methods comprising administering to the subject a therapeutically effective amount of a compound of Formula (I), or a pharmaceutically acceptable salt thereof, or a pharmaceutical composition thereof.

Also provided herein are methods for inhibiting activin receptor-like kinase (e.g., ALK-5) activity in vivo or in vitro, the methods comprising contacting the activin receptor-like kinase (e.g., ALK-5) with a compound of Formula (I) (II), (III), or (IV), or of Table 1 or Table 4), or a pharmaceutically acceptable salt thereof, or a pharmaceutical composition thereof. In certain embodiments, inhibiting occurs in vivo in a subject. In certain embodiments, inhibiting occurs in vitro (e.g., in a cell line or biological sample). In certain embodiments, the inhibition is selective ALK-5 inhibition.

In another aspect, provided herein are compounds of Formula (I) (II), (III), or (IV), or Table 1 or Table 4, or a pharmaceutically acceptable salt of any of the foregoing, or pharmaceutical compositions of any of the foregoing, for a use described herein, including, but not limited to, treating and/or preventing a disease (e.g., an inflammatory disease, a fibrotic disease (e.g., a cardiac fibrosis or hypertrophic condition), or a proliferative disease, e.g., cancer, or two or more of the foregoing in combination) in a subject, inhibiting tumor growth in a subject, or inhibiting activin receptor-like kinase (e.g., ALK-5) activity in vitro or in vivo. In yet another aspect, provided herein are uses of compounds of Formula (I) (II), (III), or (IV), or Table 1 or Table 4, or a pharmaceutically acceptable salt of any of the foregoing, or pharmaceutical compositions of any of the foregoing, for the preparation of medicaments, for example, for treating and/or preventing a disease (e.g., an inflammatory disease, a fibrotic disease (e.g., a cardiac fibrosis or hypertrophic condition), or a proliferative disease, e.g., cancer, or two or more of the foregoing in combination) in a subject, inhibiting tumor growth in a subject, or inhibiting ALK-5 activity in a subject.

In some embodiments, the methods and uses provided herein further comprise administering one or more additional therapeutic agents (e.g., anti-cancer agents or immunotherapies or other agents described herein) to the subject. In certain embodiments, a PD-1 or PD-L1 inhibitor is administered in combination with a compound or pharmaceutical composition provided herein. The methods provided herein may also or alternatively further comprise treating a subject with radiation therapy or surgery.

Also provided herein are methods for enhancing the activity of one or more therapeutic agents for treating cancer (e.g., an anti-cancer agent and/or immunotherapy) in a subject (e.g., a subject in need thereof, such as a subject having cancer and/or receiving the one or more therapeutic agents), comprising administering to the subject a therapeutically effective amount of a compound of Formula (I) (II), (III), or (IV), or Table 1 or Table 4), or a pharmaceutically acceptable salt thereof, or a pharmaceutical composition thereof.

In another aspect, provided herein are kits comprising a compound of Formula (I), or a pharmaceutically acceptable salt thereof, or pharmaceutical composition thereof. The kits described herein may include a single dose or multiple doses of the compound, or a pharmaceutically acceptable salt thereof, or pharmaceutical composition thereof. The provided kits may be useful in a method of the invention (e.g., a method of treating and/or preventing a disease in a subject). A kit of the invention may further include instructions for using the kit (e.g., instructions for using the compound, or a pharmaceutically acceptable salt thereof, or a composition thereof included in the kit).

Also provided herein are methods of preparing compounds of the invention, for example, compounds of Formula (I) (II), (III), or (IV), or Table 1 or Table 4, and pharmaceutically acceptable salts thereof. Synthetic intermediates useful in the preparation of such compounds, and pharmaceutically acceptable salts thereof, as well as preparations of the synthetic intermediates are also provided herein.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying Figures, which are incorporated in and constitute a part of this specification, and may illustrate several embodiments of the invention and together with the description, may provide non-limiting examples of the invention.

DETAILED DESCRIPTION

Figure 1:
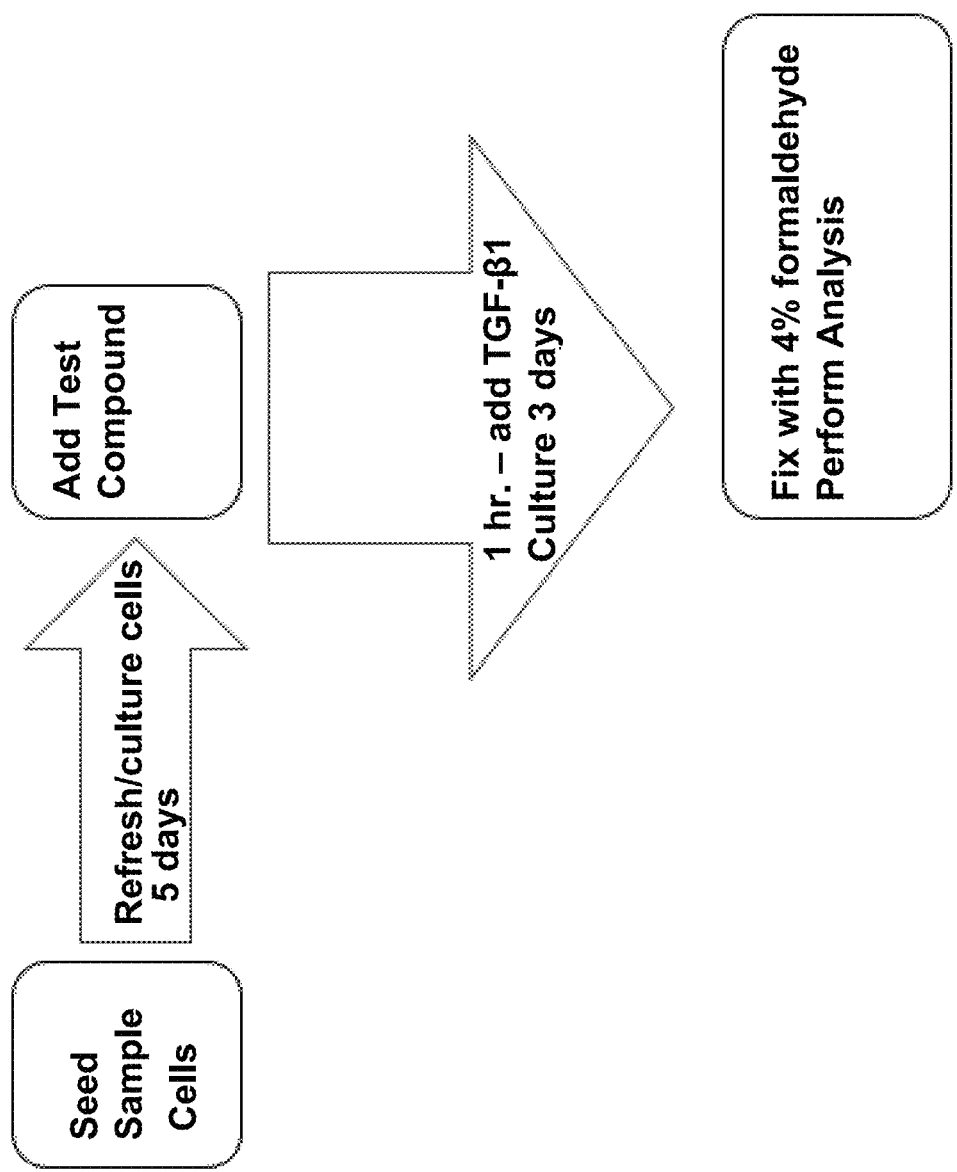
FIG. 1 shows a graphic illustration of Fibroblast Assay described in Example A.

Provided herein are compounds (e.g., compounds of Formula (I) (II), (III), or (IV), or of Table 1 or Table 4, or any of the compounds specifically exemplified herein, "the exemplified compounds"), and pharmaceutically acceptable salts thereof, pharmaceutical compositions of the foregoing, and kits comprising the same. The compounds provided herein are activin receptor-like kinase (e.g., ALK-5) inhibitors and are therefore useful, for example, for treating and/or preventing diseases (e.g., proliferative diseases, e.g., cancer) in a subject, for inhibiting tumor growth in a subject, or for inhibiting the activity of an activin receptor-like kinase (e.g., ALK-5) in vitro or in vivo. In certain embodiments, the compounds provided herein are ALK-5 inhibitors (e.g., selective ALK-5 inhibitors). Also provided herein are methods and synthetic intermediates useful in the preparation of compounds described herein.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). Additionally, encompassed are compounds as individual isomers substantially free of other isomers, and alternatively, as mixtures of various isomers.

Unless otherwise stated, structures depicted herein are also meant to include compounds that differ only in the enrichment of the compound with one or more isotopes, for example, compounds having the present structures except selected positions occupied by hydrogen are enriched with deuterium or tritium, selected positions occupied by F are enriched by $^{19}$F, or selected positions occupied by C are enriched by $^{13}$C or $^{14}$C. Examples of isotopes that can be incorporated into compounds described herein include isotopes of hydrogen, carbon, nitrogen, oxygen, phosphorous, fluorine, chlorine and iodine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I and $^{125}$I, respectively. It will be appreciated that numerous other isotopic enrichments may be made and be within the scope of the present invention and are within the scope of the disclosure. Such compounds are useful, for example, as therapeutics or as analytical tools or probes in biological assays.

For example, the present disclosure contemplates compounds in which radioactive isotopes, such as $^3$H and $^{14}$C, and/or compounds in which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies.

Further, substitution with heavier isotopes, particularly deuterium (i.e., $^2$H or D) may afford certain therapeutic advantages resulting from greater metabolic stability, for example, increased in vivo half-life or reduced dosage requirements or an improvement in therapeutic index. It is understood that deuterium in this context is regarded as a substituent of a compound disclosed herein. The concentration of such a heavier isotope, specifically deuterium, may be defined by the isotopic enrichment factor. The term "isotopic enrichment factor," as used herein, means the ratio between the isotopic abundance and the natural abundance of a specified isotope. If a substituent in a compound of this present disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically labeled compounds can generally be prepared by conventional techniques known to those skilled in the art or by processes disclosed in the schemes or in the examples and preparations described below (or analogous processes to those described hereinbelow), by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group. In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, iso-propyl), butyl ($C_4$) (e.g., n-butyl, tert-butyl, sec-butyl, iso-butyl), pentyl (C) (e.g., n-pentyl, 3-pentanyl, amyl, neopentyl, 3-methyl-2-butanyl, tertiary amyl), and hexyl ($C_6$) (e.g., n-hexyl and all branched alkyls comprising 6 carbon atoms), and the like. When an alkyl group is defined as being "substituted" herein, in conjunction with any limitations presented at the point of definition herein, and unless otherwise specified, a "substituted alkyl" indicates that one or more positions on the carbon backbone of the alkyl group normally occupied by a proton is replaced with another substituent (e.g., a methyl group which is optionally substituted by one or more halogen includes —F, —Cl, and/or —Br and, for example, when substituted with F, includes —$CH_2F$, —$CHF_2$, and —$CF_3$).

The term "carbocyclyl", "carbocycle" or "carbocyclic" refers to a non-aromatic cyclic hydrocarbon substituent (meaning the defining ring contains no heteroatoms), where the defining ring has from 3 to 10 ring carbon atoms ("$C_{3-10}$ carbocycle") in a monocyclic, bicyclic, bridged, or spirocyclic configuration. While carbocycles are non-aromatic, they may contain one or more double bonds located within the ring such that they aren't conjugated. In some embodiments one or more of the ring carbon atoms may be oxidized (e.g., a cycloketone). In some embodiments, a carbocycle group (moiety) has 3 to 10 ring carbon atoms ("$C_{3-10}$ carbocycle"). In some embodiments, a carbocycle group has 3 to 8 ring carbon atoms ("$C_{3-8}$ carbocycle"). In some embodiments, a carbocycle group has 3 to 7 ring carbon atoms ("$C_{3-7}$ carbocycle"). In some embodiments, a carbocycle group has 3 to 6 ring carbon atoms ("$C_{3-6}$ carbocycle"). In some embodiments, a carbocycle group has 4 to 6 ring carbon atoms ("$C_{4-6}$ carbocycle"). Examples of $C_{3-6}$ carbocycle groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. In some embodiments, the carbocycle group is a cyclopropyl ($C_3$). As the foregoing examples illustrate, in certain embodiments, the carbocycle group is either monocyclic ("monocyclic carbocycle") or polycyclic (e.g., containing a fused, bridged or spiro ring system such as a bicyclic system ("bicyclic carbocycle") or tricyclic system ("tricyclic carbocycle")) and can be saturated or can contain one or more carbon-carbon double or triple bonds. In some embodiments, a carbocycle is saturated. In some embodiments, the carbocycle group is a bicyclic carbocycle, for example, a spiro ring preferably comprising from 6 to 9 carbon atoms. It will be understood that the minimum number of carbon atoms in a bicyclic carbocycle is four, and the minimum number of carbon atoms in a spirocyclic carbocycle is five. Thus, it will be understood that recitation of a monocyclic, bicyclic or spirocyclic $C_3$-$C_{10}$ carbocycle refers to a monocyclic $C_3$-$C_{10}$ carbocyclyl, bicyclic $C_4$-$C_{10}$ carbocyclyl or spirocyclic $C_5$-$C_{10}$ carbocyclyl. In some embodiments of a spirocyclic carbocyclyl, the carbocycle is preferably a $C_{5-10}$ spirocyclic carbocyclyl, e.g., $C_{6-9}$ spirocyclic carbocyclyl.

The term "hydroxy" or "hydroxyl" refers to —OH.

The term "heterocyclyl", "heterocycle" or "heterocyclic" refers to a non-aromatic substituent defined by a ring of 3- to 10-members comprising carbon atoms and at least 1, up to 3 (e.g., 1 or 2), heteroatoms which are the same, or independently selected from, N, S, and O (e.g., N and O), selected to be bonded such that they form a stable chemical entity ("$C_{3-10}$ heterocycle"). The heterocycle ring may be saturated or may contain one or more sites of unsaturation so long as the bonding pattern does not provide aromatic delocalization. Heterocycle cores can either be monocyclic ("monocyclic heterocycle") or polycyclic (e.g., a fused, bridged or spiro ring system such as a bicyclic system ("bicyclic heterocycle") or tricyclic system ("tricyclic heterocycle")) so long as at least one cyclic moiety defined by ring members contains a heteroatom, and polycyclic heterocycle substituents can, but need not, include one or more heteroatoms in multiple rings. Examples of heterocycle groups include, without limitation, azetidinyl, oxetanyl, piperidinyl, piperazinyl, pyrrolyl, pyrrolidinyl, imidazolidinyl, imidazolinyl, morpholinyl, tetrahydrofuranyl, tetrahydrothiophenyl, tetrahydrothiopyranyl, tetrahydropyranyl, diazabicyclooctanyl, diazabicycloheptanyl, oxanyl, 1,4-dioxanyl, 1,4-oxathianyl, hexahydropyrimidinyl, 3-azabicyclo[3.1.0]hexanyl, azepanyl, 3-azabicyclo[3.2.2]nonanyl, decahydroisoquinolinyl, 2-azaspiro[3.3]heptanyl, 2-oxa-6-azaspiro[3.3]heptanyl, 2,6-diazaspiro[3.3]heptanyl, 8-aza-bicyclo[3.2.1]octanyl, 3,8-diazabicyclo[3.2.1]octanyl, 3-oxa-8-aza-bicyclo[3.2.1]octanyl, 8-oxa-3-aza-bicyclo[3.2.1]octanyl, 2-oxa-5-aza-bicyclo[2.2.1]heptanyl, 2,5-diaza-bicyclo

[2.2.1]heptanyl, 1,4-dioxa-8-aza-spiro[4.5]decanyl, 3-oxa-1,8-diazaspiro[4.5]decanyl, octahydropyrrolo[3,2-b]pyrrolyl, and the like. As the foregoing examples illustrate, in certain embodiments, the heterocycle group is either monocyclic ("monocyclic heterocycle") or polycyclic (e.g., containing a fused, bridged or spiro ring system such as a bicyclic system ("bicyclic heterocycle") or tricyclic system ("tricyclic heterocycle")) and can be saturated or can contain one or more carbon-carbon double or triple bonds. In some embodiments, a heterocycle is saturated. In some embodiments, the heterocycle group is a monocyclic or bicyclic heterocycle (e.g., saturated heterocycle), preferably comprising from 6 to 9 carbon atoms.

Unless otherwise specified, each instance of heterocycle is independently unsubstituted (an "unsubstituted heterocycle") or substituted (a "substituted heterocycle") with one or more substituents. Substituents bonded to "substituted heterocycle" cores can be bonded via any of the ring member atoms that provide a stable bonding arrangement. In certain embodiments, the heterocycle group is an unsubstituted 3-10 membered heterocycle. In certain embodiments, the heterocycle group is a substituted 3-10 membered heterocycle. In some embodiments it is preferred to select heterocycle substituents which are 6-membered ring systems. In some embodiments, it is preferred to select heterocycle substituents which are 10-membered spirocycle substituents. It will be understood that the minimum number of ring atoms in a bicyclic heterocycle is four, and the minimum number of ring atoms in a spirocyclic heterocycle is five. Thus, it will be understood that recitation of a monocyclic, bicyclic or spirocyclic $C_3$-$C_{10}$ heterocycle refers to a monocyclic $C_3$-$C_{10}$ heterocyclyl, bicyclic $C_4$-$C_{10}$ heterocyclyl or spirocyclic $C_5$-$C_{10}$ heterocyclyl. In some embodiments of a spirocyclic heterocyclyl, the heterocyclyl is preferably a $C_{5-10}$ spirocyclic heterocyclyl, e.g., $C_{6-9}$ spirocyclic heterocyclyl.

The term "aryl" refers to an aromatic moiety of up to 10 carbon atoms defining the aromatic ring system. Such substituents are bonded to a substrate via any ring carbon atom providing a stable structure. As defined or limited at the point of use, these moieties may comprise monocyclic or bicyclic structures (e.g., fused rings). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, as defined or illustrated at the point of use herein, an aryl moiety includes substituents on the aryl ring, as defined above, which are bonded to form a fused carbocyclic structure with the aryl moiety, the size of the carbocyclic ring in the fused structure being defined at the point of use. If an aryl moiety is defined herein as substituted, it means the specified substituents may replace one or more protons bonded to a carbon atom defining the aryl ring in a manner the provides a stable species. In some embodiments, aryl moieties are 6-membered aryl rings.

The term "heteroaryl" refers to an aromatic moiety of at least 6 atoms defining the aromatic ring system wherein one or more of the atoms defining said aromatic ring system are selected from N or S. Heteroaryl substituents may be bonded to the substrate via any atom in the heteroaryl ring that affords a stable bond. In some embodiments, a heteroaryl group has 6 ring carbon atoms ("$C_6$ heteroaryl"; e.g., pyridinyl, such as pyridine-2-yl, pyridine-3-yl, pyridine-4-yl). Other examples of heteroaryl include, but are not limited to pyrrolyl, pyridyl, pyrazolyl, indolyl, indolinyl, isoindolinyl, indazolyl, thienyl, furanyl, benzofuranyl, dihydrobenzofuranyl, dihydroisobenzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, tetrahydroquinolinyl, benzofuranyl, benzopyranyl, benzothiophenyl, benzoimidazolyl, benzoxazolyl, 1H-benzo[d][1,2,3]triazolyl, and the like. Heteroaryl substituents may optionally be substituted as defined at the point of use herein.

The term "optionally substituted" used in substituent definitions herein indicates that the defined moiety may be present without any substituents or may be present in a form having one or more bonding positions therein normally occupied by a proton being replaced (i.e., substituted) with one or more of the specified optional substituents. In all embodiments, when optional substituents are present, they are present in an amount and a bonding configuration that provides stable compounds, e.g., a compound which does not spontaneously undergo transformation such as by rearrangement, cyclization, elimination, or other reaction, however, it does contemplate arrangements which provide tautomers or other like bonding arrangements. Unless otherwise indicated, a "substituted" moiety has a substituent at one or more substitutable positions of the moiety, and when more than one position in any given structure is substituted, the substituent is independently selected from the stated allowable substituents. Unless defined differently at the point of use, the term "substituted" is contemplated to include substitution with all permissible substituents of organic compounds, and includes any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In some embodiments, where a trivalent nitrogen can be quaternized or where a quaternary nitrogen can be deprotonated to a trivalent form, a representation of either form contemplates the transformation between the two forms and such representation is not intended to be limited in any manner by the exemplary substituents described herein. For example, a nitrogen atom(s) in a compound described herein may be independently converted to its (their) N-oxide(s) by treatment with an oxidizing agent (e.g., mCPBA and/or hydrogen peroxide) to afford other compounds also contemplated by the disclosure. Thus, shown and claimed nitrogen atoms are considered to cover both the shown nitrogen and its N-oxide (N→O) derivative.

As used herein, unless specified differently at the point of definition, the term "halo" or "halogen" refers to fluorine (fluoro, —F), chlorine (chloro, —Cl), bromine (bromo, —Br), or iodine (iodo, —I) unless the term is more limited at the point of use herein.

The term "sulfonamide" refers to —SO$_2$R'R", wherein R' and R" are the same or different, and are each independently selected from hydrogen, alkyl or carbocyclyl. In some embodiments, R' and R" are each independently selected from hydrogen, $C_1$-$C_5$ alkyl or $C_3$-$C_5$ cycloalkyl. In some embodiments, sulfonamide is —SO$_2$NH$_2$.

When any variable occurs more than one time in any constituent or formula for a compound, its definition at each occurrence is independent of its definition at every other occurrence. Thus, for example, if a group is shown to be substituted with 0-3 substituents, then said group may be unsubstituted or substituted with up to three substituents, and each substituent is selected independently from the other substituent(s).

When a bond to a substituent is shown to cross a bond connecting two atoms in a ring (as the bond to $R^3$ in Formula I, for example) or to cross a circle denoting a ring, then such substituent may be bonded to any substitutable atom in the ring. Further, when the ring the bond to the substituent crosses into is polycyclic, the substituent may be bonded to any substitutable atom of the ring or ring system the bond to the substituent crosses into. When a substituent is listed without indicating the atom to which such substituent is bonded to the rest of the compound of a given formula, then such substituent may be bonded via any atom in such substituent.

Combinations of substituents and/or variables are permissible only if such combinations result in stable compounds.

Compounds may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemic mixtures, individual isomers (e.g., diastereomers, enantiomers, geometrical isomers, conformational isomers (including rotamers and atropisomers), tautomers) and intermediate mixtures, with all possible isomers and mixtures thereof being included in the present disclosure.

As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. "Racemate" or "racemic" is used to designate a racemic mixture where appropriate. When designating the stereochemistry for the compounds of the present disclosure, a single stereoisomer with known relative and absolute configuration of the two chiral centers is designated using the conventional RS system (e.g., (1S,2S)); a single stereoisomer with known relative configuration but unknown absolute configuration is designated with stars (e.g., (1R*,2R*)); and a racemate with two letters (e.g., (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Geometric isomers may occur when a compound contains a double bond or some other feature that gives the molecule a certain amount of structural rigidity. If the compound contains a double bond, the double bond may be E- or Z-configuration. If the compound contains a disubstituted cycloalkyl, the cycloalkyl substituent may have a cis- or trans-configuration.

Conformational isomers (or conformers) are isomers that can differ by rotations about one or more bonds. Rotamers are conformers that differ by rotation about only a single bond.

The term "atropisomer," as used herein, refers to a structural isomer based on axial or planar chirality resulting from restricted rotation in the molecule.

Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® columns available from DAICEL Corp. or other equivalent columns, using the appropriate solvent or mixture of solvents to achieve suitable separation).

Compounds, e.g., compounds disclosed herein, can be isolated in optically active or racemic forms. Optically active forms may be prepared by resolution of racemic forms or by synthesis from optically active starting materials. All processes used to prepare compounds and intermediates disclosed herein are considered to be part of the present disclosure. When enantiomeric or diastereomeric products are prepared, they may be separated by conventional methods, for example, by chromatography or fractional crystallization.

In certain embodiments, certain features of compound substituents may be protected with a protecting group known to the ordinarily skilled practitioner, for example, those described in detail in *Protecting Groups in Organic Synthesis*, T. W. Greene and P. G. M. Wuts, 3$^{rd}$ edition, John Wiley & Sons, 1999, incorporated herein by reference. All such transformations are contemplated by representation of the unprotected form of the compound.

As used herein, the term "salt" refers to any and all salt forms that compounds disclosed herein can be prepared as, and encompasses pharmaceutically acceptable salts. Pharmaceutically acceptable salts are preferred. However, other salts may be useful, e.g., in isolation or purification steps which may be employed during preparation, and thus, are contemplated to be within the scope of the present disclosure. In general, salts of a compound described herein will be those that provide a composition suitable for administration to a human or animal subject via any suitable route of administration of a pharmaceutical composition.

The phrase "pharmaceutically acceptable" means that the substance or composition the phrase modifies must be, within the scope of sound medical judgment, suitable for use in contact with the tissues of humans and lower animals without undue toxicity, irritation, allergic response and the like, and are commensurate with a reasonable benefit/risk ratio. If a substance is part of a composition or formulation, the substance must also be compatible chemically and/or toxicologically with the other ingredients in the composition or formulation.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference, and for example, lists of suitable salts are found in Allen, L. V., Jr., ed., Remington: The Science and Practice of Pharmacy, 22nd Edition, Pharmaceutical Press, London, UK (2012). Pharmaceutically acceptable salts of the compounds described herein include those derived from suitable inorganic and organic acids and inorganic and organic bases.

Pharmaceutically acceptable acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art, such as ion-exchange. Other pharmaceutically acceptable acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable base addition salts are formed from inorganic and organic bases. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations (e.g., primary, secondary, tertiary, quaternary amine cations), for example, formed using counterions such as halide, hydroxide, carboxylate, sulfate, phosphate, nitrate, lower alkyl sulfonate, and aryl sulfonate. Examples of organic amines from which base addition salts can be derived include, but are not limited to, isopropylamine, benzathine, cholinate, diethanolamine, diethylamine, lysine, meglumine, piperazine and tromethamine.

A salt (e.g., pharmaceutically acceptable salt) of a compound described herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

It will be understood that when the compound described herein contains more than one basic moiety or more than one acidic moiety, each such moiety can independently be involved in forming an acid addition salt form or base addition salt form, with all possible salt forms being included in this disclosure. Further, when two or more moieties of a compound are in salt form, the anions or cations forming the two or more salt forms can be the same or different. Typically, the anions or cations forming the two or more salt forms are the same. Typical molar ratios of an anion or cation in a salt of a compound of the present disclosure to a compound described herein are 3:1, 2:1, 1:1, 2:1, 3:1, 4:1 and 5:1. In some embodiments, the molar ratio of an anion or cation (e.g., anion) in a salt of a compound described herein to the compound is 1:1.

Lists of suitable salts are found in Allen, L. V., Jr., ed., Remington: The Science and Practice of Pharmacy, 22nd Edition, Pharmaceutical Press, London, UK (2012), the relevant disclosure of which is hereby incorporated by reference in its entirety.

Compounds described herein are also provided, and can be administered, as a free base.

The term "solvate" means a physical association of a compound of the present disclosure with one or more solvent molecules, whether organic or inorganic. This physical association includes hydrogen bonding. In certain instances, the solvate will be capable of isolation, for example, when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution phase and solid phase solvates. Examples of solvates include, but are not limited to, hydrates, ethanolates, methanolates, and isopropanolates. Methods of solvation are generally known in the art.

A "pharmaceutically acceptable carrier" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like, and combinations thereof, as would be known to those skilled in the art (see, for example, Allen, L. V., Jr. et al., Remington: The Science and Practice of Pharmacy (2 Volumes), 22nd Edition, Pharmaceutical Press (2012).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

As used herein, a subject (e.g., a human) is "in need of" a treatment if such subject would benefit biologically, medically or in quality of life from such treatment.

The term "administer," "administering," or "administration" refers to implanting, absorbing, ingesting, injecting, inhaling, or otherwise introducing the referenced material (e.g., compound described herein, or a pharmaceutically acceptable salt thereof, or a composition thereof), in or on a subject.

The terms "treatment," "treat," and "treating" refer to administration of a medication or medical care to a subject, such as a human, having a disease or condition of interest, e.g., a cancer, and includes: (i) preventing the disease or condition from occurring in a subject, in particular, when such subject is predisposed to the condition but has not yet been diagnosed as having it; (ii) inhibiting the disease or condition, e.g., arresting its development; (iii) relieving the disease or condition, e.g., causing regression of the disease or condition; and/or (iv) relieving the symptoms resulting from the disease or condition (e.g., pain, weight loss, cough, fatigue, weakness, etc.). Treating thus includes reversing, alleviating, delaying the onset of, and/or inhibiting the progress of a disease (e.g., a disease described herein). In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms. Treatment may also be continued after symptoms have resolved, for example, to delay or prevent recurrence.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. Alternatively, an effective amount is a prophylactically effective amount. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition, for example, an amount sufficient to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating in any disease or condition described.

A "prophylactically effective amount" of a compound described herein is an amount sufficient to prevent a condition, or one or more symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, "inhibition", "inhibiting", "inhibit" and "inhibitor", and the like, refer to the ability of a compound to reduce, slow, halt, or prevent the activity of a biological process (e.g., the activity of an activin receptor-like kinase (e.g., ALK-5) in a subject or cell) or change thereby the progress of a disease by, for example, altering a signaling pathway, for example, altering TGF-β1 signaling.

In certain embodiments, a compound described herein is a "selective inhibitor" and "selectively inhibits" one protein kinase over one or more other kinases. In certain embodiments, the compounds described herein are selective ALK-5 inhibitors, i.e., selective for ALK-5 over one or more other kinases (e.g., over other activin receptor-like kinases). The selectivity of a compound described herein in inhibiting the activity of ALK-5 over a different kinase (e.g., a different activin receptor-like kinase) may be measured by the quotient of the $IC_{50}$ value of the compound in inhibiting the activity of the different kinase over the $IC_{50}$ value of the compound in inhibiting the activity of ALK-5. The selectivity of a compound described herein for ALK-5 over a different kinase (e.g., a different activin receptor-like kinase) may also be measured by the quotient of the $K_d$ value of an adduct of the compound and the different kinase over the $K_d$ value of an adduct of the compound and ALK-5. Selective inhibition includes, for example, $IC_{50}$ inhibition for ALK-5 which is at least 2-fold, at least 3-fold, at least 5-fold, at least 10-fold, at least 30-fold, at least 50-fold, at least 100-fold or greater than 100-fold of the $IC_{50}$ observed for ALK-2 under the same testing conditions.

The term "solid tumor," as used herein, refers to malignancies/cancers formed of abnormal masses of tissue that usually do not contain cysts or liquid areas. Solid tumors are named/classified according to the tissue/cells of origin. Examples include, but are not limited to, sarcomas and carcinomas.

The term "leukemia," as used herein, refers to hematologic or blood cell malignancies/cancers that begin in blood-forming tissue, such as the bone marrow. Examples include, but are not limited to, chronic leukemia, acute leukemia, acute myeloid leukemia (AML), chronic myeloid leukemia (CML), acute lymphocytic leukemia (ALL), acute lymphoblastic leukemia (e.g., B-cell, T-cell) and chronic lymphocytic leukemia (CLL). The term "lymphoma," as used herein, refers to lymphatic cell malignancies/cancers that begin in the cells of the immune system. Examples include, but are not limited to, Hodgkin's lymphoma, non-Hodgkin's lymphoma and multiple myeloma.

Compounds of the Disclosure

As will be appreciated by one of skill in the art, reference herein to "compounds of the disclosure," "compounds described herein," and the like refers to a compound of any structural formula depicted herein (e.g., a compound of Formula I, a subformula of a compound of Formula I), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs and/or solvates, such as hydrates) thereof. When a moiety is present that is capable of forming a salt, then salts are included as well, in particular, pharmaceutically acceptable salts. Compounds of the present disclosure can also be provided as amorphous solids or crystalline solids. Lyophilization can be employed to provide the compounds of the present disclosure as a solid. Such solid forms are also included in these terms. For example, a description using the structural representation of a free base form of a compound of the disclosure contemplates hydrates, solvates, polymorphs, co-crystals, salts, tautomers, stereoisomers, and isotopically labeled derivatives of the compounds. For example, a structural representation of a free base form of a compound of the disclosure contemplates all salt forms (e.g., pharmaceutically acceptable salt forms) of the compound. For example, a structural representation lacking stereochemical designation of a compound of the disclosure having asymmetric carbon centers contemplates all isomers, including isolation of one or more particular isomers in all levels of enantiomeric or diastereomeric purity. For example, a structural representation of a compound of the disclosure having keto/enol tautomeric forms in one particular tautomeric form contemplates all tautomeric forms of the compound.

In a first embodiment, provided are compounds of Formula (I):

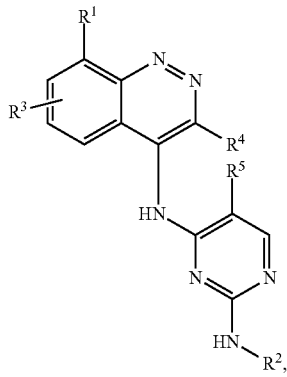

or a pharmaceutically acceptable salt thereof, wherein:
$R^1$ is a $C_1$-$C_5$ alkyl or $C_3$-$C_5$ carbocycle, or a halogen;
$R^3$ is —H, —F or —Cl;
$R^4$ is —H or a halogen, or a $C_1$-$C_3$ alkyl or cyclopropyl, each of which is optionally substituted with one or more —F;
$R^5$ is —H or —F, or a $C_1$-$C_3$ alkyl or cyclopropyl, each of which is optionally substituted with one or more —F; and
$R^2$ is an aryl of at least 6 carbon atoms or nitrogen-containing heteroaryl of at least 6 atoms, each of which is optionally substituted with:
(i) one or more halogens;
(ii) a moiety which is $C_1$-$C_6$ alkyl or $C_3$-$C_6$ carbocycle optionally substituted with a hydroxyl or one or more halogen; and wherein, when selected to be an alkyl larger than $C_3$ or a carbocycle larger than cyclopropyl, said moiety is present at a position on the aryl or heteroaryl of $R^2$ which is meta- or para- to the amino bond to said aryl;
(iii) a sulfonamide;
(iv) a monocyclic, bicyclic, or spirocyclic carbocycle which is optionally substituted with one or more linear, branched, or cyclic alkyl moieties of up to 6 carbon atoms which are optionally substituted with hydroxy or one or more halogen, and wherein, when present, said carbocycle is at a position on the aryl or heteroaryl of $R^2$ which is meta- or para- to the amino bond to the aryl or heteroaryl of $R^2$;
(v) a monocyclic, bicyclic or spirocyclic heterocycle which may contain up to 3 heteroatoms which are selected independently from N and O and which is optionally and independently substituted with one or more $C_1$-$C_6$ alkyl or $C_3$-$C_6$ carbocycle which are optionally substituted with hydroxy or one or more halogen, and wherein, when present, said heterocycle is at a position on the aryl of $R^2$ which is meta- or para- to the amino bond to the aryl or heteroaryl of $R^2$;
(vi) a moiety of the formula:

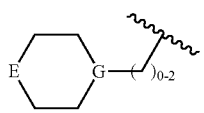

wherein,
G is >N— or >C(H)—; and
E is —O— or >C(H)—$R^{13}$, wherein $R^{13}$ is —H or a $C_1$-$C_6$ alkyl or $C_3$-$C_6$ carbocycle, each of which is optionally substituted with hydroxy or one or more halogen; or
(vii) a moiety of the formula:

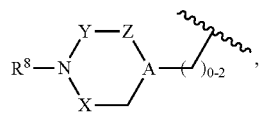

wherein:
$R^8$ is —H or a $C_1$-$C_6$ alkyl or $C_3$-$C_6$ carbocycle which is optionally substituted with hydroxyl or one or more halogen;
A is >N— or >C(H)—; and
X, Y and Z are defined as follows:
Z is >$CH_2$ and X and Y are independently >$CH_2$ or >$C(CH_3)_2$, or both X and Y are >CH— and are bonded together through a methylene or ethylene bridge; or Y is >$CH_2$ or >$C(CH_3)_2$, and X and Z are both >CH— and are bonded together through a methylene or ethylene bridge In some embodiments, $R^1$ is $C_1$-$C_5$ alkyl or $C_3$-$C_5$ carbocycle.
In some embodiments, $R^1$ is $C_1$-$C_5$ alkyl.
In some embodiments, $R^1$ is —$CH_3$.
In some embodiments, $R^1$ is $C_3$-$C_5$ carbocycle.
In some embodiments, $R^1$ is cyclopropyl.
In some embodiments, $R^1$ is a halogen (e.g., —Cl or —F).
In some embodiments, $R^1$ is —Cl.
In some embodiments, $R^3$ is —F or —Cl.
In some embodiments, $R^3$ is —H.
In some embodiments, $R^3$ is —F.
In some embodiments, $R^3$ is —Cl.
In some embodiments, $R^4$ is halogen.
In some embodiments, $R^4$ is —Cl.
In some embodiments, $R^4$ is —F.
In some embodiments, $R^4$ is a $C_1$-$C_3$ alkyl or cyclopropyl, each of which is optionally substituted with one or more —F.
In some embodiments, $R^4$ is cyclopropyl which is optionally substituted with one or more —F.
In some embodiments, $R^4$ is $C_1$-$C_3$ alkyl which is optionally substituted with one or more —F.
In some embodiments, $R^4$ is —$CF_3$.
In some embodiments, $R^4$ is —$CH_3$.
In some embodiments, $R^4$ is —H.
In some embodiments, $R^5$ is $C_1$-$C_3$ alkyl or cyclopropyl, each of which is optionally substituted with one or more —F.
In some embodiments, $R^5$ is —$CH_3$.
In some embodiments, $R^5$ is —$CF_3$.
In some embodiments, $R^5$ is —H.
In some embodiments, $R^5$ is —F.
In some embodiments $R^2$ is a moiety of the formula AA:

Formula AA

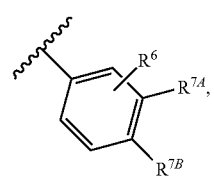

wherein,

R$^6$ is —H, —F, —Cl, or a C$_1$-C$_3$ alkyl or cyclopropyl which is optionally and independently substituted with one or more halogen;

one of R$^{7A}$ and R$^{7B}$ is —H, and the other is:
(i) a halogen;
(ii) —SO$_2$NR$^{7F}{}_2$, wherein each R$^{7F}$ is independently —H or a linear or branched alkyl of up to 4 carbon atoms;
(iii) a C$_1$-C$_6$ alkyl or C$_3$-C$_6$ carbocycle which is optionally substituted with one or more halogen;
(iv) a moiety of the formula:

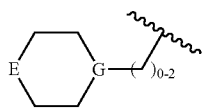

wherein,
G is >N— or >C(H)—; and
E is —O— or >C(H)—R$^{13}$, wherein R$^{13}$ is —H or a C$_1$-C$_6$ alkyl or C$_3$-C$_6$ carbocycle, each of which is optionally substituted with hydroxy or one or more halogen; or (v) a moiety of the formula:

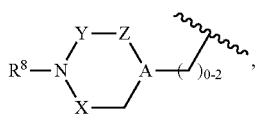

wherein
R$^8$ is —H or a C$_1$-C$_6$ alkyl or C$_3$-C$_6$ carbocycle which is optionally substituted with hydroxyl or one or more halogen;
A is >N— or >C(H)—; and
X, Y and Z are defined as follows:
Z is >CH$_2$ and X and Y are independently >CH$_2$ or >C(CH$_3$)$_2$, or both X and Y are >CH— and are bonded together through a methylene or ethylene bridge; or
Y is >CH$_2$ or >C(CH$_3$)$_2$, and X and Z are both >CH— and are bonded together through a methylene or ethylene bridge.

In some embodiments where R$^2$ is a moiety of Formula AA, R$^1$ is C$_1$-C$_5$ alkyl.

In some embodiments where R$^2$ is a moiety of Formula AA, R$^1$ is C$_3$-C$_5$ carbocycle.

In some embodiments where R$^2$ is a moiety of Formula AA, R$^1$ is —CH$_3$.

In some embodiments where R$^2$ is a moiety of Formula AA, R$^1$ is cyclopropyl.

In some embodiments where R$^2$ is a moiety of Formula AA, R$^1$ is halogen.

In some embodiments where R$^2$ is a moiety of Formula AA, R$^1$ is —Cl.

In some embodiments where R$^2$ is a moiety of Formula AA, R$^3$ is —H.

In some embodiments where R$^2$ is a moiety of Formula AA, R$^3$ is —F.

In some embodiments where R$^2$ is a moiety of Formula AA, R$^4$ is —H.

In some embodiments where R$^2$ is a moiety of Formula AA, R$^4$ is a C$_1$-C$_3$ alkyl which is optionally substituted with one or more —F.

In some embodiments where R$^2$ is a moiety of Formula AA, R$^4$ is —CF$_3$.

In some embodiments where R$^2$ is a moiety of Formula AA, R$^4$ is —CH$_3$.

In some embodiments where R$^2$ is a moiety of Formula AA, R$^4$ is a halogen.

In some embodiments where R$^2$ is a moiety of Formula AA, R$^4$ is —Cl.

In some embodiments where R$^2$ is a moiety of Formula AA, R$^4$ is —F.

In some embodiments where R$^2$ is a moiety of Formula AA, R$^5$ is —CH$_3$.

In some embodiments where R$^2$ is a moiety of Formula AA, R$^5$ is —CF$_3$.

In some embodiments where R$^2$ is a moiety of Formula AA, R$^5$ is —H.

In some embodiments where R$^2$ is a moiety of Formula AA, R$^5$ is —F.

In some embodiments where R$^2$ is a moiety of Formula AA, R$^6$ is C$_1$-C$_3$ alkyl which is optionally substituted with one or more halogen.

In some embodiments where R$^2$ is a moiety of Formula AA, R$^6$ is —CH$_3$.

In some embodiments where R$^2$ is a moiety of Formula AA, R$^6$ is —CF$_3$.

In some embodiments where R$^2$ is a moiety of Formula AA, one of R$^{7A}$ and R$^{7B}$ is —H and the other is halogen.

In some embodiments where R$^2$ is a moiety of Formula AA, one of R$^{7A}$ and R$^{7B}$ is —H and the other is —F or —Cl.

In some embodiments where R$^2$ is a moiety of Formula AA, one of R$^{7A}$ and R$^{7B}$ is —H and the other is C$_1$-C$_6$ alkyl or C$_3$-C$_6$ carbocycle each of which is optionally substituted with one or more halogen.

In some embodiments where R$^2$ is a moiety of Formula AA, one of R$^{7A}$ and R$^{7B}$ is —H, and the other is:
(i) a moiety of the following structure:

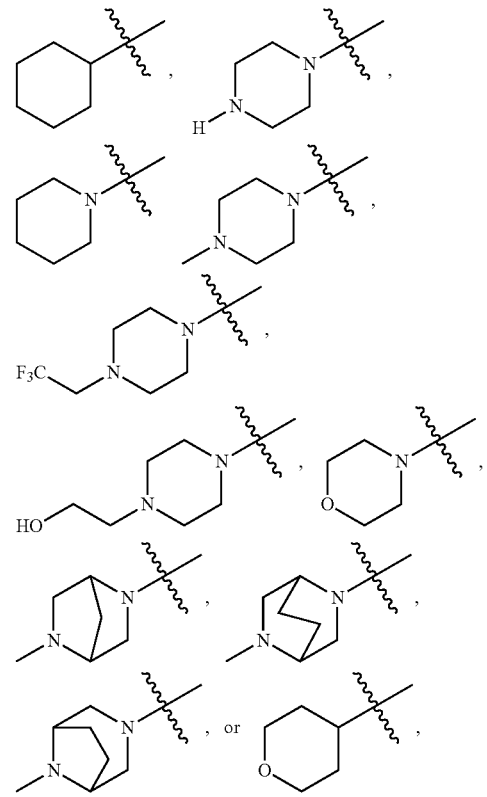

each of which is optionally substituted on one or more carbon atoms thereof with a halogen or $C_1$-$C_4$ alkyl or $C_3$-$C_4$ carbocycle which is optionally substituted with hydroxy or one or more halogen; or
(ii) —$SO_2N(R^{7F})_2$.

In some embodiments where $R^2$ is a moiety of Formula AA, $R^{7A}$ is —H.

In some embodiments where $R^2$ is a moiety of Formula AA, $R^{7B}$ is —H.

In some embodiments where $R^2$ is a moiety of Formula AA, $R^3$ is —F, $R^4$ is —H or —$CH_3$, $R^5$ is —H, and $R^6$ is —H.

In some embodiments where $R^2$ is a moiety of Formula AA, $R^4$ is —H, —Cl, —F, —$CF_3$, or —$CH_3$, $R^5$ is —H, —$CH_3$, —$CF_3$, —Cl, or —F, and $R^6$ is —H, —F, —Cl, —$CH_3$, or —$CF_3$.

In some embodiments where $R^2$ is a moiety of Formula AA, $R^4$ is —H or —$CH_3$, $R^5$ is —H or —F, and $R^6$ is —H, —F, —Cl, or —$CF_3$.

In some embodiments, $R^2$ is a heteroaryl moiety of Formula AB, AC, or AD:

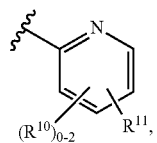

Formula AB

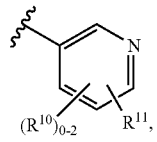

Formula AC

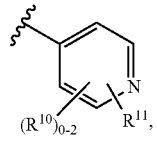

Formula AD wherein:
each $R^{10}$ is independently —H, —F, —Cl, or a $C_1$-$C_3$ alkyl or cyclopropyl, each of which is optionally substituted with one or more halogen; and
$R^{11}$ is bonded in a position that is meta or para to the amino bond to said heteroaryl moiety and is:
(i) —$SO_2N(R^{10F})_2$, wherein each $R^{10F}$ is independently —H or a $C_1$-$C_4$ alkyl;
(ii) a $C_1$-$C_6$ alkyl or $C_3$-$C_6$ carbocycle, each of which is optionally substituted with one or more halogen;
(iii) a moiety of the formula:

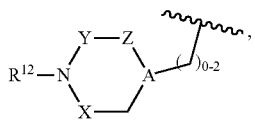

wherein:
$R^{12}$ is —H or a $C_1$-$C_6$ alkyl or $C_3$-$C_6$ carbocycle, each of which is optionally substituted with hydroxy or one or more halogen;
A is >N— or >C(H)—; and
X, Y and Z are defined as follows:
Z is >$CH_2$ and X and Y are independently >$CH_2$ or >$C(CH_3)_2$, or X and Y are both >CH— and are bonded together through a methylene or ethylene bridge; or Y is >$CH_2$ or >$C(CH_3)_2$, and X and Z are both >CH— and are bonded together through a methylene or ethylene bridge; or
(iv) a moiety of the formula:

wherein:
G is >N— or >C(H)—; and
E is —O— or >C(H)—$R^{13}$, wherein $R^{13}$ is —H or a $C_1$-$C_6$ alkyl or $C_3$-$C_6$ carbocycle, each of which is optionally substituted with hydroxy or one or more halogen.

In some embodiments where $R^2$ is selected to be a heteroaryl moiety of Formula AB, AC, or AD, $R^{11}$ is:
(i) a moiety of the following structure:

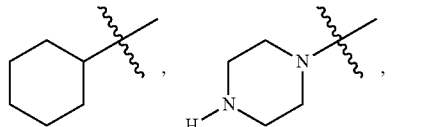

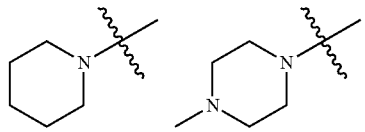

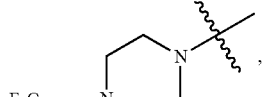

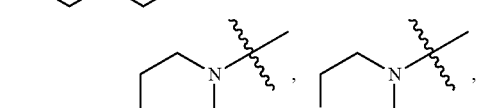

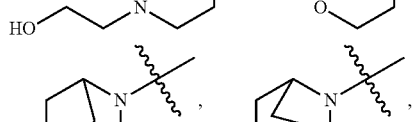

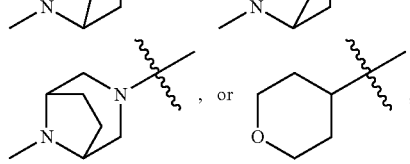

each of which is optionally substituted on one or more carbon atoms thereof with a halogen or with a moiety which is $C_1$-$C_4$ alkyl or $C_3$-$C_4$ carbocycle, each of which is optionally substituted on one or more carbon atoms thereof with: a halogen; or with a moiety which is $C_1$-$C_4$ alkyl or $C_3$-$C_4$ carbocycle, each of which is optionally substituted with hydroxyl or one or more halogen; or
(ii) —$SO_2N(R^{10F})_2$.

In some embodiments where $R^2$ is selected to be a heteroaryl moiety of Formula AB, AC, or AD, $R^1$ is $C_1$-$C_5$ alkyl.

In some embodiments where $R^2$ is selected to be a heteroaryl moiety of Formula AB, AC, or AD, $R^1$ is $C_3$-$C_5$ carbocycle.

In some embodiments where $R^2$ is selected to be a heteroaryl moiety of Formula AB, AC, or AD, $R^1$ is —$CH_3$.

In some embodiments where $R^2$ is selected to be a heteroaryl moiety of Formula AB, AC, or AD, $R^1$ is —$CF_3$.

In some embodiments where $R^2$ is selected to be a heteroaryl moiety of Formula AB, AC, or AD, $R^1$ is cyclopropyl.

In some embodiments where $R^2$ is selected to be a heteroaryl moiety of Formula AB, AC, or AD, $R^1$ is halogen.

In some embodiments where $R^2$ is selected to be a heteroaryl moiety of Formula AB, AC, or AD, $R^1$ is —Cl.

In some embodiments where $R^2$ is selected to be a heteroaryl moiety of Formula AB, AC, or AD, $R^3$ is —H.

In some embodiments where $R^2$ is selected to be a heteroaryl moiety of Formula AB, AC, or AD, $R^3$ is —H or —F.

In some embodiments where $R^2$ is selected to be a heteroaryl moiety of Formula AB, AC, or AD, $R^3$ is —F.

In some embodiments where $R^2$ is selected to be a heteroaryl moiety of Formula AB, AC, or AD, $R^4$ is —H, —Cl or —$CH_3$.

In some embodiments where $R^2$ is selected to be a heteroaryl moiety of Formula AB, AC, or AD, $R^4$ is —H.

In some embodiments where $R^2$ is selected to be a heteroaryl moiety of Formula AB, AC, or AD, $R^4$ is $C_1$-$C_3$ alkyl which is optionally substituted at one or more positions with one or more halogen In some embodiments where $R^2$ is selected to be a heteroaryl moiety of Formula AB, AC, or AD, $R^4$ is —$CF_3$.

In some embodiments where $R^2$ is selected to be a heteroaryl moiety of Formula AB, AC, or AD, $R^4$ is —$CH_3$.

In some embodiments where $R^2$ is selected to be a heteroaryl moiety of Formula AB, AC, or AD, $R^4$ is a halogen.

In some embodiments where $R^2$ is selected to be a heteroaryl moiety of Formula AB, AC, or AD, $R^4$ is —Cl.

In some embodiments where $R^2$ is selected to be a heteroaryl moiety of Formula AB, AC, or AD, $R^4$ is —F.

In some embodiments where $R^2$ is selected to be a heteroaryl moiety of Formula AB, AC, or AD, $R^5$ is —$CH_3$.

In some embodiments where $R^2$ is selected to be a heteroaryl moiety of Formula AB, AC, or AD, $R^5$ is —$CF_3$.

In some embodiments where $R^2$ is selected to be a heteroaryl moiety of Formula AB, AC, or AD, $R^5$ is —H or —F.

In some embodiments where $R^2$ is selected to be a heteroaryl moiety of Formula AB, AC, or AD, $R^5$ is —H.

In some embodiments where $R^2$ is selected to be a heteroaryl moiety of Formula AB, AC, or AD, $R^5$ is —F.

In some embodiments where $R^2$ is selected to be a heteroaryl moiety of Formula AB, AC, or AD, each $R^{10}$ is independently $C_1$-$C_3$ alkyl or cyclopropyl, each of which is optionally and independently substituted with one or more halogen.

In some embodiments where $R^2$ is selected to be a heteroaryl moiety of Formula AB, AC, or AD, each $R^{10}$ is independently $C_1$-$C_3$ alkyl which is optionally and independently substituted with one or more halogen.

In some embodiments where $R^2$ is selected to be a heteroaryl moiety of Formula AB, AC, or AD, each $R^{10}$ is independently —H, —$CH_3$, —$CF_3$, —Cl, or —F.

In some embodiments where $R^2$ is selected to be a heteroaryl moiety of Formula AB, AC, or AD, each $R^{10}$ is —$CH_3$.

In some embodiments where $R^2$ is selected to be a heteroaryl moiety of Formula AB, AC, or AD, each $R^{10}$ is —$CF_3$.

In some embodiments where $R^2$ is selected to be a heteroaryl moiety of Formula AB, AC, or AD, each $R^{10}$ is —H.

In some embodiments where $R^2$ is selected to be a heteroaryl moiety of Formula AB, AC, or AD, each $R^{10}$ is —F.

In some embodiments where $R^2$ is selected to be a heteroaryl moiety of Formula AB, AC, or AD, $R^{10}$ is —Cl.

In some embodiments where $R^2$ is selected to be a heteroaryl moiety of Formula AB, AC, or AD, $R^{10}$ is cyclopropyl which is optionally substituted at one or more carbon positions with halogen.

In an aspect, provided herein is a compound of Formula (II):

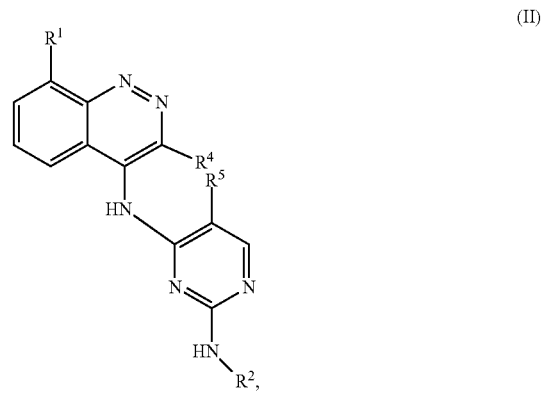

or a pharmaceutically acceptable salt thereof, wherein:
$R^1$ is cyclopropyl, —$CH_3$ or —Cl (e.g., —$CH_3$ or —Cl);
$R^4$ is —H or —$CH_3$;
$R^5$ is —H or —F; and
$R^2$ is:
a) a moiety of the formula:

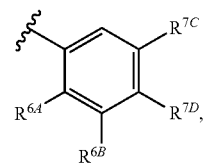

wherein,
one of $R^{6A}$ and $R^{6B}$ is —H and the other is —H, —F, —Cl, —$CH_3$, or $CF_3$;
one of $R^{7C}$ and $R^{7D}$ is —H and the other is:
(i) —F;
(ii) —Cl;
(iii) —$SO_2NH_2$;
(iv) cyclohexyl;
(v) t-butyl; or
(vi) a moiety of the formula:

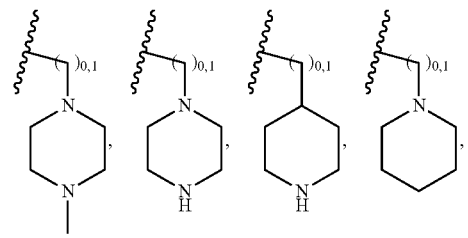

-continued

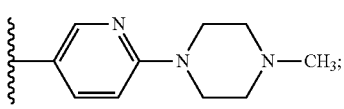

b) a moiety of the formula:

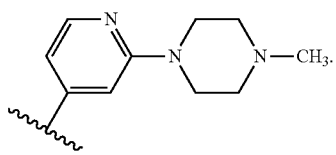 [SMILES: *c1ccnc(N2CCN(C)CC2)c1]

or
c) a moiety of the formula:

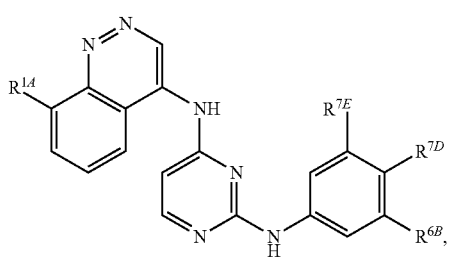

In some embodiments, the compound of Formula (I) is a compound of Formula (III):

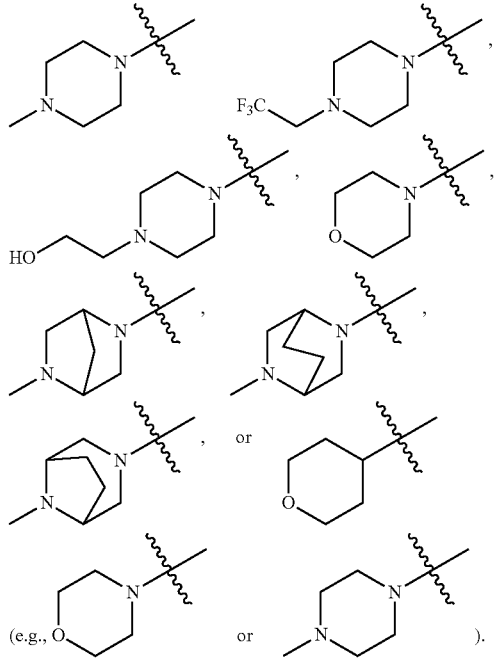
(III)

or a pharmaceutically acceptable salt thereof, wherein:
R$^{1A}$ is methyl or cyclopropyl;
R$^{6B}$ is —H, —F, or —Cl; and
one of R$^{7D}$ and R$^{7E}$ is —H and the other is a heterocycle of the formula:

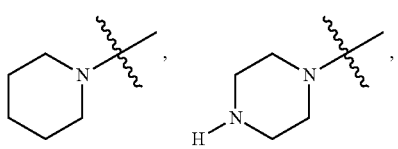

-continued

In some embodiments of the compound of Formula (III), R$^{7D}$ is one of the following:

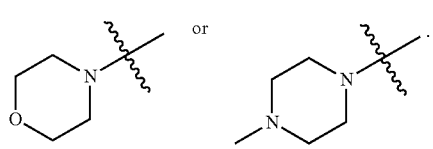

In some embodiments of the compound of Formula (III), R$^{7E}$ is one of the following:

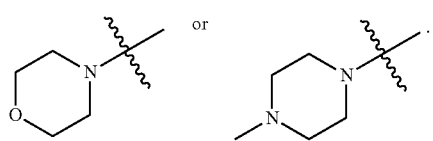

In some embodiments, the compound has the following structure:

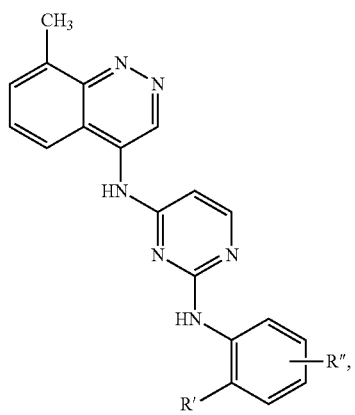

or a pharmaceutically acceptable salt thereof, wherein R' is H or F; and R" is at a position meta or para to the amino bond, and is morpholino or piperazinyl optionally N-substituted with —CH$_3$, —CH$_2$CF$_3$, or —CH$_2$CH$_2$OH.

In some embodiments, the compound is of Formula (IV):

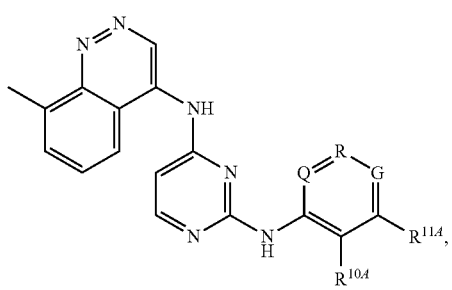
(IV)

or a pharmaceutically acceptable salt thereof, wherein:
one of Q, R, or G is =N—, and
when Q is not selected to be N, it is C—$R^{10A}$,
when R is not selected to be N, it is C—$R^{11A}$,
when G is not selected to be N, it is C—$R^{11A}$, and
wherein:
$R^{10A}$ is selected independently for each occurrence from —H, —F, —Cl, or a $C_1$-$C_3$ alkyl or cyclopropyl, each of which is optionally substituted with one or more halogen;
$R^{11A}$ is selected independently for each occurrence from:
(i) —H;
(ii) —F or —Cl;
(iii) a $C_1$-$C_3$ alkyl or cyclopropyl, each of which is optionally substituted with one or more halogen;
(iv) —$SO_2N(R^{10F})_2$, wherein each $R^{10F}$ is independently —H or a $C_1$-$C_4$ alkyl;
(v) a $C_1$-$C_6$ alkyl or $C_3$-$C_6$ carbocycle;
(vi) a moiety of the formula:

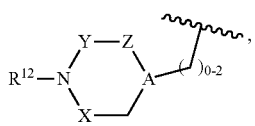

wherein:
$R^{12}$ is —H or a $C_1$-$C_6$ alkyl or $C_3$-$C_6$ carbocycle which is optionally substituted with hydroxy or one or more halogen;
A is >N— or >C(H)—; and
X, Y and Z are defined as follows:
Z is >$CH_2$ and X and Y are independently >$CH_2$ or >$C(CH_3)_2$, or X and Y are both >CH— and are bonded together through a methylene or ethylene bridge; or
Y is >$CH_2$ or >$C(CH_3)_2$, and X and Z are both >CH— and are bonded together through a methylene or ethylene bridge; or
(vii) a moiety of the formula:

wherein:
G is >N— or >C(H)—; and
E is —O— or >C(H)—$R^{13}$, wherein $R^{13}$ is —H or a $C_1$-$C_6$ alkyl or $C_3$-$C_6$ carbocycle which is optionally substituted with hydroxy or one or more halogen, provided that one of $R^{11A}$ present is not —H, —F, —Cl, or a $C_1$-$C_3$ alkyl or $C_3$ carbocycle which is optionally substituted at one or more positions with a halogen.

In certain embodiments, for example, a compound of any of Formula (I), (II), (III), or (IV), is selected from the compounds recited in Table 1 (infra), for example, the exemplary compounds Ex-10, Ex-11, Ex-12, Ex-13, Ex-33, Ex-34, Ex-57, or Ex-58, or any of these in the form of a pharmaceutically acceptable salt.

In the various aspects and embodiments disclosed herein, express reference to exemplified compounds or the generic formula is understood to alternatively refer to a compound of any disclosed subgenus thereof.

In certain embodiments, a compound of Formula (I) is of the following formula:

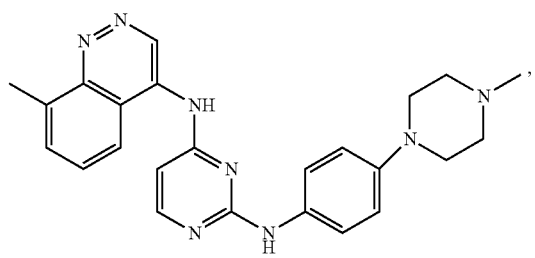

or a pharmaceutically acceptable salt thereof.

In certain embodiments, a compound of Formula (I) is of the following formula:

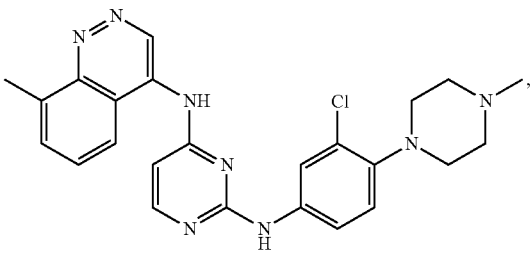

or a pharmaceutically acceptable salt thereof.

In certain embodiments, a compound of Formula (I) is of the following formula:

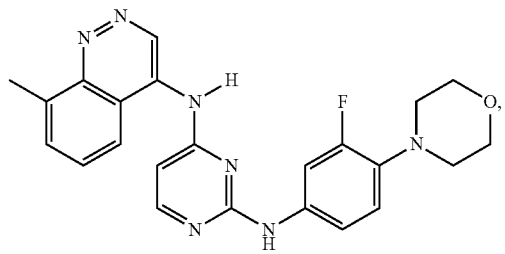 [SMILES: Cc1cccc2c(Nc3ccnc(Nc4ccc(N5CCOCC5)c(F)c4)n3)cnnc12]

or a pharmaceutically acceptable salt thereof.

In certain embodiments, a compound of Formula (I) is of the following formula:

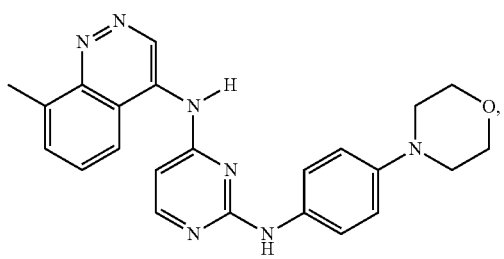 [SMILES: Cc1cccc2c(Nc3ccnc(Nc4ccc(N5CCOCC5)cc4)n3)cnnc12]

or a pharmaceutically acceptable salt thereof.

In certain embodiments, a compound of Formula (I) is of the following formula:

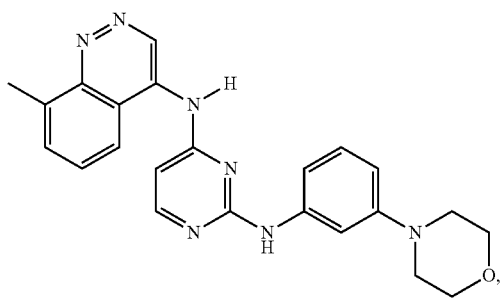 [SMILES: Cc1cccc2c(Nc3ccnc(Nc4cccc(N5CCOCC5)c4)n3)cnnc12]

or a pharmaceutically acceptable salt thereof.

In certain embodiments, a compound of Formula (I) is of the following formula:

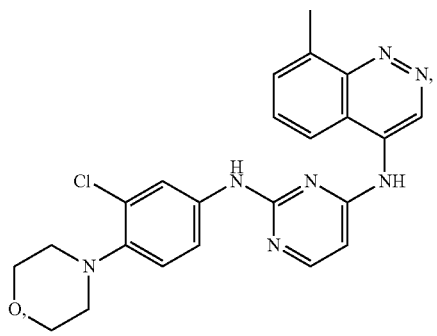 [SMILES: Cc1cccc2c(Nc3ccnc(Nc4ccc(N5CCOCC5)c(Cl)c4)n3)cnnc12]

or a pharmaceutically acceptable salt thereof.

In certain embodiments, a compound of Formula (I) is of the following formula:

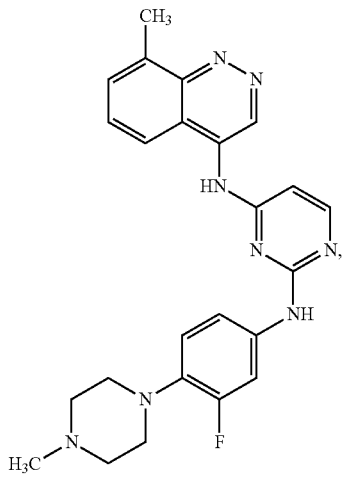 [SMILES: Cc1cccc2c(Nc3ccnc(Nc4ccc(N5CCN(C)CC5)c(F)c4)n3)cnnc12]

or a pharmaceutically acceptable salt thereof.

In certain embodiments, a compound of Formula (I) is of the following formula:

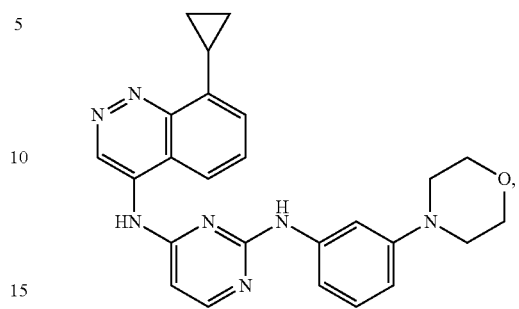

or a pharmaceutically acceptable salt thereof.

In certain embodiments, a compound of Formula (I) is of the following formula:

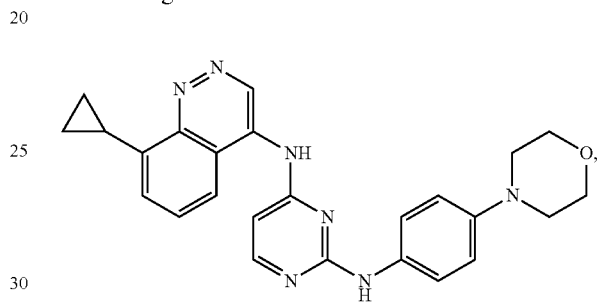

or a pharmaceutically acceptable salt thereof.

In a second embodiment, provided are compounds of Formula (I), or a pharmaceutically acceptable salt thereof, wherein:

$R^1$ is a $C_1$-$C_5$ alkyl or $C_3$-$C_5$ carbocycle, or a halogen;

$R^2$ is an aryl of at least 6 carbon atoms or nitrogen-containing heteroaryl of at least 6 atoms, optionally substituted with one or more of:

(i) one or more halogens;

(ii) a $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$;

(iii) a sulfonamide;

(iv) a monocyclic, bicyclic, or spiro-cyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$; or (v) a monocyclic, bicyclic or spiro-cyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of $R^2$ which is meta- or para- to the amino bond to said aryl;

$R^3$ is —H, —F or —Cl;

$R^4$ is —H or a halogen, or a $C_1$-$C_3$ alkyl or cyclopropyl optionally substituted with one or more —F; and $R^5$ is —H or —F, or a $C_1$-$C_3$ alkyl or cyclopropyl optionally substituted with one or more —F. In some embodiments, $R^1$ is a $C_1$-$C_5$ alkyl or $C_3$-$C_5$ carbocycle.

In some embodiments, $R^1$ is —$CH_3$.

In some embodiments, $R^1$ is cyclopropyl.

In some embodiments, $R^1$ is halo.

In some embodiments, $R^1$ is —Cl or —F.

In some embodiments, $R^2$ is a phenyl or pyridinyl optionally substituted with one or more of:
(i) one or more halogens;
(ii) a $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$;
(iii) a sulfonamide;
(iv) a monocyclic, bicyclic, or spiro-cyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$; or
(v) a monocyclic, bicyclic or spiro-cyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of $R^2$ which is meta- or para- to the amino bond to said aryl.

In some embodiments, $R^2$ is a phenyl or pyridinyl substituted with one or more of:
(i) one or more halogens;
(ii) a $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$;
(iii) a sulfonamide;
(iv) a monocyclic, bicyclic, or spiro-cyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$; or
(v) a monocyclic, bicyclic or spiro-cyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of $R^2$ which is meta- or para- to the amino bond to said aryl.

In some embodiments, $R^2$ is substituted with one or more halogens.

In some embodiments, $R^2$ is substituted with a sulfonamide.

In some embodiments, $R^2$ is substituted with $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$.

In some embodiments, $R^2$ is substituted with a monocyclic, bicyclic, or spiro-cyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$.

In some embodiments, $R^2$ is substituted with a monocyclic, bicyclic or spiro-cyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of $R^2$ which is meta- or para- to the amino bond to said aryl.

In some embodiments, the heterocycle is a piperazinyl, morpholinyl, piperidinyl, diazabicyclooctanyl, diazabicycloheptanyl, or oxanyl, which is optionally and independently substituted with one or more $C_1$-$C_6$ alkyl which are optionally substituted with hydroxy or one or more halogen.

In some embodiments, the heterocycle is

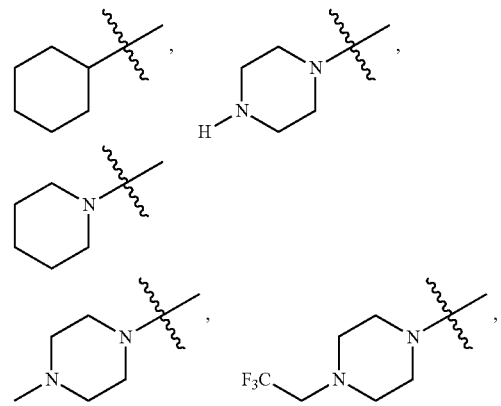

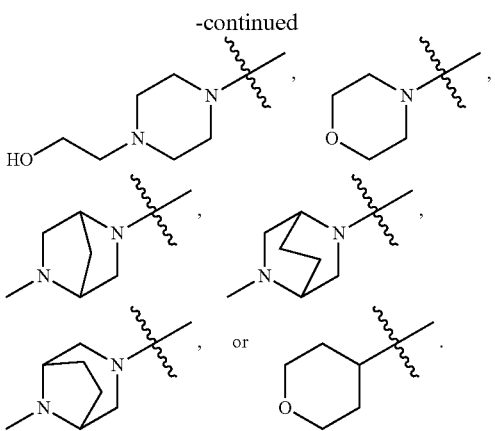

In some embodiments, the carbocycle or heterocycle attached to the aryl or heteroaryl of $R^2$ is attached to the aryl or heteroaryl of $R^2$ by a single bond or a methylene linker.

In some embodiments, the carbocycle or heterocycle attached to the aryl or heteroaryl of $R^2$ is attached to the aryl or heteroaryl of $R^2$ by a single bond.

In some embodiments, the carbocycle or heterocycle attached to the aryl or heteroaryl of $R^2$ is attached to the aryl or heteroaryl of $R^2$ at a position on $R^2$ which is meta- to the amino bond attached to $R^2$.

In some embodiments, the carbocycle or heterocycle attached to the aryl or heteroaryl of $R^2$ is attached to the aryl or heteroaryl of $R^2$ at a position on $R^2$ which is para- to the amino bond attached to $R^2$.

In some embodiments, $R^2$ is:

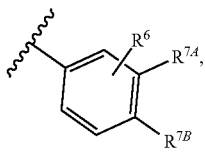

wherein:
$R^6$ is —H, —F, —Cl, or a $C_1$-$C_3$ alkyl or cyclopropyl which is optionally and independently substituted with one or more halogen;
one of $R^{7A}$ and $R^{7B}$ is —H, and the other is:
  (vi) a halogen;
  (vii) —$SO_2NR^{7F}_2$, wherein each $R^{7F}$ is independently —H or a linear or branched alkyl of up to 4 carbon atoms;
  (viii) a $C_1$-$C_6$ alkyl which is optionally substituted with one or more halogen; or (ix)

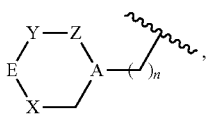

wherein:
A is >N— or >C(H)—;
E is —O—, >N($R^8$), or >C(H)—$R^{13}$
$R^8$ is —H or a $C_1$-$C_6$ alkyl or $C_3$-$C_6$ carbocycle which is optionally substituted with hydroxyl or one or more halogen;

$R^{13}$ is —H or a $C_1$-$C_6$ alkyl or $C_3$-$C_6$ carbocycle which is optionally substituted with hydroxy or one or more halogen; and
n is 0, 1, or 2, and
when E is >N($R^8$), X, Y, and Z are defined as follows:
  Z is >$CH_2$ and X and Y are independently >$CH_2$ or >C($CH_3$)$_2$, or both X and Y are >CH— and are bonded together through a methylene or ethylene bridge; or
  Y is >$CH_2$ or >C($CH_3$)$_2$, and X and Z are both >CH— and are bonded together through a methylene or ethylene bridge, and
when E is —O— or >C(H)—$R^{13}$, X, Y, and Z are >$CH_2$.

In some embodiments, $R^6$ is —H, —F, —Cl, —$CH_3$, or —$CF_3$.

In some embodiments, n is 0 or 1.
In some embodiments, n is 0.
In some embodiments, one of $R^{7A}$ and $R^{7B}$ is —H, and the other is:

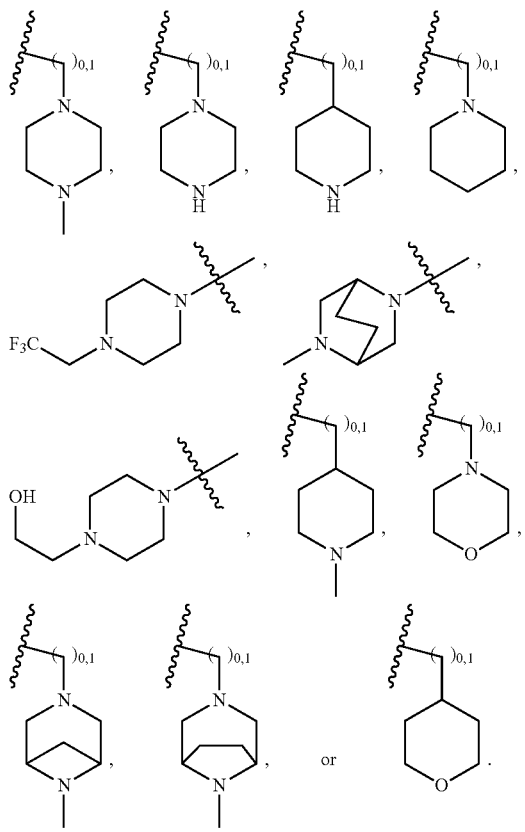

In some embodiments, $R^3$ is —H.
In some embodiments, $R^3$ is —F or —Cl.
In some embodiments, $R^3$ is —F.
In some embodiments, $R^3$ is —Cl.
In some embodiments, $R^4$ is a $C_1$-$C_3$ alkyl or cyclopropyl optionally substituted with one or more —F.
In some embodiments, $R^4$ is halogen.
In some embodiments, $R^4$ is —$CF_3$.
In some embodiments, $R^4$ is —$CH_3$.
In some embodiments, $R^4$ is —H.
In some embodiments, $R^4$ is —Cl.

In some embodiments, $R^4$ is —F.

In some embodiments, $R^5$ is a $C_1$-$C_3$ alkyl or cyclopropyl optionally substituted with one or more —F.

In some embodiments, $R^5$ is —H.

In some embodiments, $R^5$ is —CH$_3$.

In some embodiments, $R^5$ is —CF$_3$.

In some embodiments, $R^5$ is —F or —Cl.

In some embodiments, the compound of Formula (I) is a compound of Formula (II), or a pharmaceutically acceptable salt thereof, wherein:

$R^1$ is —CH$_3$ or —Cl;

$R^2$ is:

a) 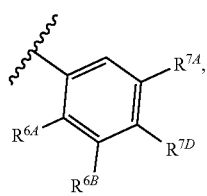

wherein:

one of $R^{6A}$ and $R^{6B}$ is —H, and the other is —H, —F, —Cl, —CH$_3$, or CF$_3$;

one of $R^{7C}$ and $R^{7D}$ is —H, and the other is:

(i) —F;

(ii) —Cl;

(iii) —SO$_2$NH$_2$;

(iv) cyclohexyl;

(v) t-butyl; or (vi)

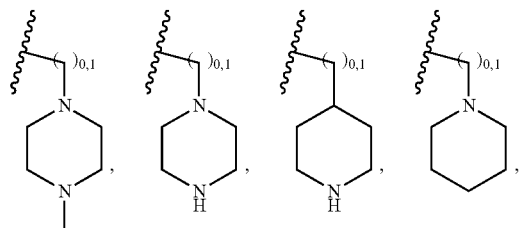

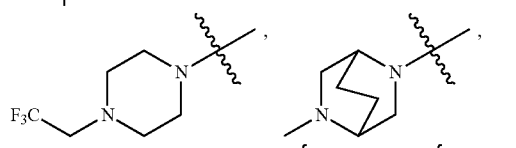

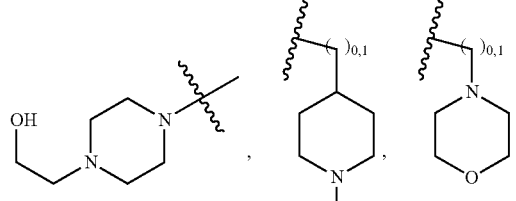

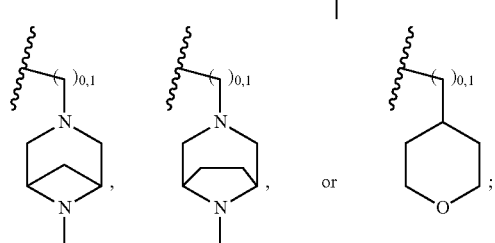

b) 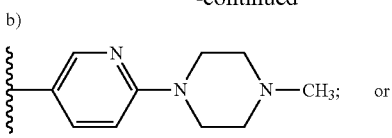

c) 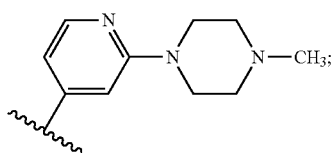

$R^4$ is —H or —CH$_3$; and $R^5$ is —H or —F.

In some embodiments, the compound of Formula (I) is a compound of Formula (III), or a pharmaceutically acceptable salt thereof, wherein:

$R^{1A}$ is methyl or cyclopropyl;

$R^{6B}$ is —H, —F, or —Cl; and one of $R^{7D}$ and $R^{7E}$ is —H, and the other is a heterocycle of the formula:

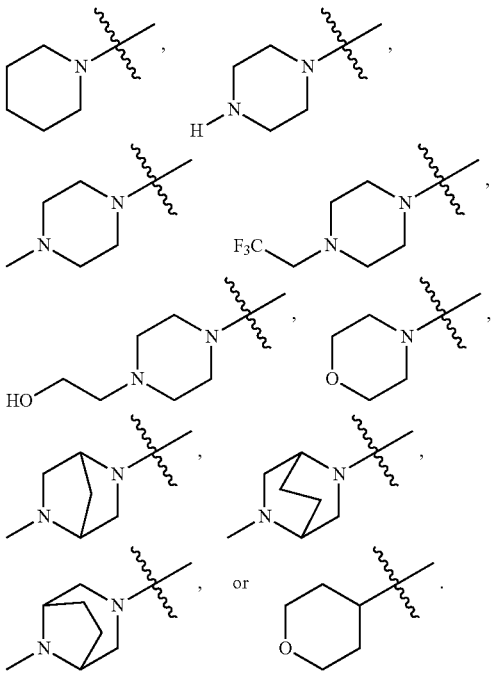

In some embodiments, one of $R^{7D}$ and $R^{7E}$ is —H, and the other is a heterocycle of the formula:

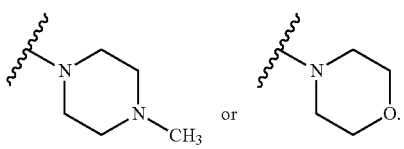

In certain embodiments, for example, a compound of any of Formulae (I), (II), (III) and (IV) is selected from a compound in Table 1 or Table 4, or a pharmaceutically acceptable salt thereof.

In an aspect, provided herein are compounds of Formula Int-A5:

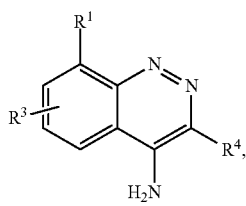

Int-A5 or a salt thereof, wherein $R^1$, $R^3$, and $R^4$ are as defined herein. In some embodiments, is methyl or chloro. In some embodiments, $R^1$ is methyl. In some embodiments, $R^1$ is chloro. In some embodiments, $R^3$ is meta to $R^1$ and is —H, —Cl, or —F. In some embodiments, $R^4$ is —H, —CH$_3$ or —F.

Also provided herein is a process for preparing Int-A5, or a salt thereof, comprising:
(a) providing a compound of Formula IntA-4:

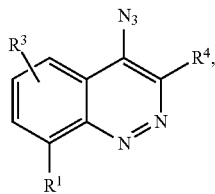

Int-A4 and reducing the azide functional group to an amino functional group using a palladium-catalyzed reduction, wherein:
$R^1$ is a $C_1$-$C_5$ alkyl or $C_3$-$C_5$ carbocycle, or a halogen;
$R^3$ is —H, —F, or —Cl; and
$R^4$ is —H, a halogen, or a $C_1$-$C_3$ alkyl or $C_3$ carbocycle optionally substituted with one or more —F. In some embodiments, the process further comprises a process for preparing the compound of Formula Int-A4 by treating the compound of Formula Int-A3:

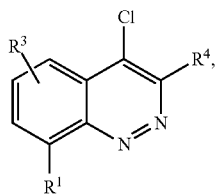

Int-A3 with sodium azide, wherein $R^1$, $R^3$ and $R^4$ are as defined for the compound of Formula Int-A4. In some embodiments, the process further comprises a process for preparing the compound of Formula Int-A3 by treating the compound of Formula Int-A2:

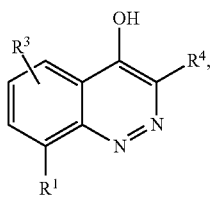

Int-A2 with phosphorousoxytrichloride, wherein $R^1$, $R^3$ and $R^4$ are as defined for the compound of Formula Int-A4. In some embodiments, the process further comprises a process for preparing the compound of Formula Int-A2 by treating a compound of Formula Int-A1:

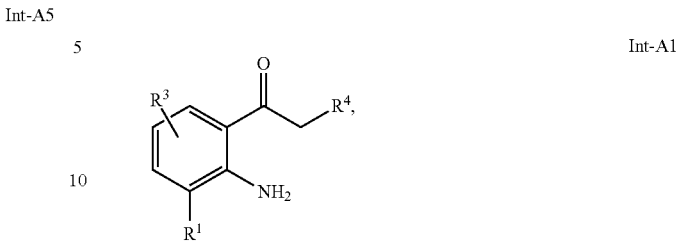

Int-A1 or a salt thereof, with sodium nitrite in an acid solution, wherein $R^1$, $R^3$ and $R^4$ are as defined for the compound of Formula Int-A4.

In one embodiment, the compound of formula Int-A5 is prepared by sodium nitrite-driven cyclization of 1-amino-2-alkylketo-aryl compound Int-A1 to provide a compound of Formula Int-A2, which is subsequently converted to its chloro analog by treatment with POCl$_3$ to provide the chlorocinnoline compound of formula Int-A3, which is subsequently converted to the corresponding azide of formula Int-A4 by treatment with sodium azide. Palladium metal-catalyzed reduction of the compound of formula Int-A4 provides the compound of formula Int-A5.

In another aspect, provided herein is a process for providing a compound of Formula Int-A5, comprising:

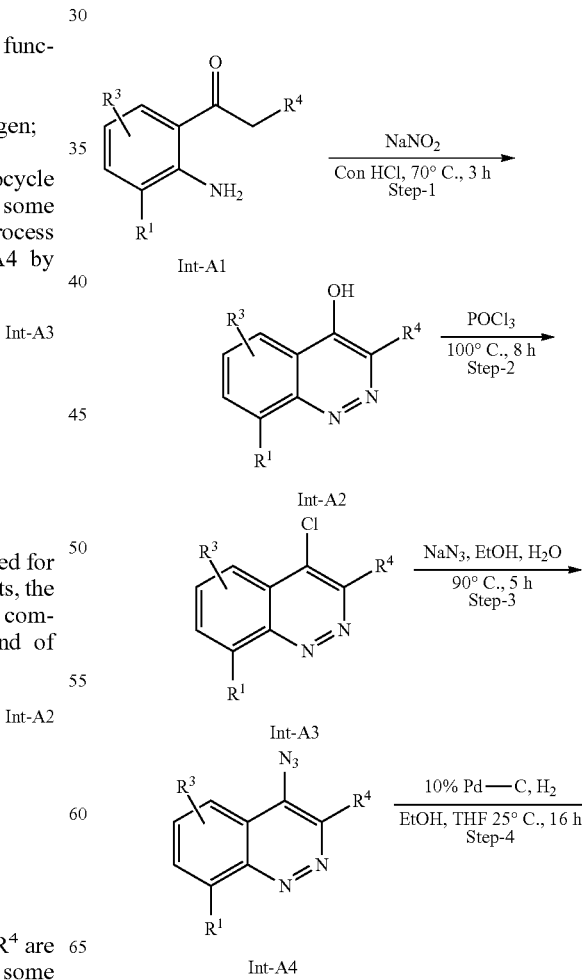

-continued

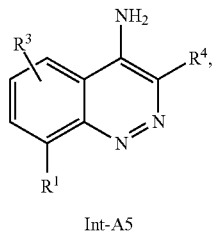

Int-A5 wherein $R^1$, $R^3$, and $R^4$ are defined herein.

In an aspect, provided herein are compounds of Formula Int-B2:

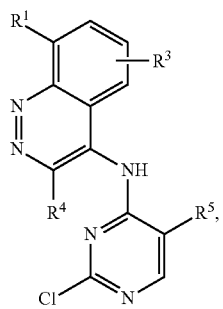

Int-B2 or a salt thereof, wherein $R^1$, $R^3$, $R^4$, and $R^5$ are defined herein. In some embodiments, $R^1$ is methyl or chloro. In some embodiments, $R^3$ is meta to $R^1$ and is —H, —Cl, or —F. In some embodiments, $R^4$ is —H, —CH$_3$ or —F. In some embodiments, $R^5$ is —H, —CH$_3$ or —F.

Also provided herein is a process for preparing a compound of Int-B2, or a salt thereof, comprising:

(a) providing a compound of Formula IntB-1:

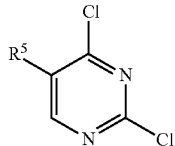

Int-B1, and reacting it with a compound of Formula Int-A5:

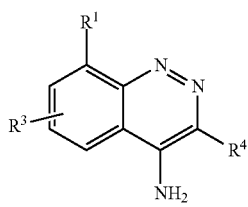

Int-A5, in the presence of a palladium coupling catalyst, wherein:

$R^1$ is a $C_1$-$C_5$ alkyl or $C_3$-$C_5$ carbocycle, or a halogen;
$R^3$ is —H, —F, or —Cl;
$R^4$ is —H, a halogen, or a $C_1$-$C_3$ alkyl or cyclopropyl, optionally substituted with one or more —F; and
$R^5$ is —H, —F, or a $C_1$-$C_3$ alkyl or cyclopropyl, optionally substituted with one or more —F.

Accordingly, in one embodiment, compounds of formula Int-B2 are prepared by palladium-catalyzed coupling of chloropyrimidine compound Int-B1 with amino-cinnoline compound Int-A5, wherein $R^1$, $R^3$, $R^4$, and $R^5$ are defined herein.

In an aspect, provided herein is a process for providing compounds of Formula Int-B2:

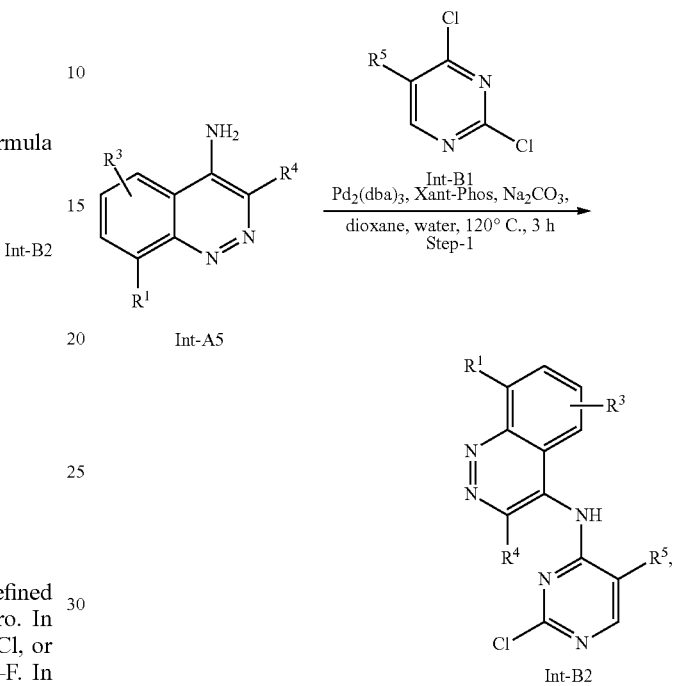

wherein $R^1$, $R^3$, $R^4$, and $R^5$ are defined herein.

Preparation of other exemplified compounds is provided herein below.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Pharmaceutical Compositions, Combinations, Kits, and Administration

Provided herein are pharmaceutical compositions comprising a compound of Formula (I), or a pharmaceutically acceptable salt thereof, and a pharmaceutically acceptable carrier or excipient. In certain embodiments, a pharmaceutical composition provided herein comprises a therapeutically and/or prophylactically effective amount of a compound of Formula (I), or a pharmaceutically acceptable salt thereof. In certain embodiments, the pharmaceutical composition comprises a therapeutically effective amount of a compound of Formula (I), or a pharmaceutically acceptable salt thereof. The pharmaceutical compositions provided herein may further comprise one or more additional therapeutic agents (e.g., anti-proliferative agents, e.g., anti-cancer agents).

Pharmaceutical compositions described herein can be prepared by any method known in the art of pharmacology. In general, such preparatory methods include bringing a compound described herein (i.e., the "active ingredient") into association with a carrier or excipient, and/or one or more other accessory ingredients, and then, if necessary and/or desirable, shaping, and/or packaging the product into a desired single- or multi-dose unit. In some embodiments, pharmaceutical compositions are adapted for oral administration.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient (e.g., the compound of Formula (I) or pharmaceutically acceptable salt thereof), the pharmaceutically acceptable carrier or excipient, and/or any additional ingredients in a pharmaceutical composition described herein will vary, depending, for example, upon the identity, size, and/or condition of the subject treated and upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Examples of diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Examples of granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Examples of surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Examples of binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Examples of preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Examples of antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Examples of chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Examples of antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Examples of antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Examples of alcohol preservatives include ethanol, polyethylene glycol, phenol, phenolic compounds, bisphenol, chlorobutanol, hydroxybenzoate, and phenylethyl alcohol.

Examples of acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Examples of buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Examples of lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Examples of natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms, for example, for oral and parenteral administration, include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the active ingredient is mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents, such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein.

A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

A therapeutic agent (e.g., a compound of the disclosure) described herein, or a composition thereof, can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), ophthalmic, mucosal, nasal, bucal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors, such as the nature of the agent (e.g., its stability in the environment of the gastrointestinal tract), and/or the condition of the subject (e.g., whether the subject is able to tolerate oral administration). In some embodiments, a pharmaceutical composition is formulated for oral administration.

In certain instances, it may be advantageous to administer a compound of the present disclosure (e.g., a compound of Formula I, or a subformula thereof, or a pharmaceutically acceptable salt thereof) in combination with one or more additional therapeutic agent(s). For example, it may be advantageous to administer a compound of the present disclosure (e.g., a compound of Formula I, or a subformula thereof, or a pharmaceutically acceptable salt thereof) in combination with one or more additional therapeutic agents, e.g., independently selected from an anti-cancer agent (e.g., chemotherapeutic agent), immunotherapy (e.g., an immune checkpoint inhibitor), anti-allergic agent, anti-emetic, pain reliever, immunomodulator and cytoprotective agent, to treat cancer.

Compositions for use in combination therapies will either be formulated together as a pharmaceutical combination, or provided for separate administration (e.g., associated in a kit). Accordingly, provided herein is a pharmaceutical combination comprising a compound of the present disclosure (e.g., a compound of Formula I, or a subformula thereof, or a pharmaceutically acceptable salt thereof) (e.g., a therapeutically effective amount of a compound of the present disclosure), and one or more other therapeutic agents (e.g., a therapeutically effective amount of one or more other therapeutic agents). A pharmaceutical combination can further comprise one or more pharmaceutically acceptable carriers or excipients, such as one or more of the pharmaceutically acceptable carriers or excipients described herein. Additional therapeutic agents for the pharmaceutical combinations and kits described herein include any of the therapeutic agents identified herein, particularly with respect to combination therapies, discussed below.

Therapeutic agents, such as the compounds and compositions described herein, are typically formulated in dosage unit form for ease of administration and uniformity of dosage. It will be understood, however, that the total daily usage of such forms will be decided by a physician within the scope of sound medical judgment. The specific therapeutically effective dose level for any particular subject or organism will depend upon a variety of factors including, for example, the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a therapeutic agent in a composition required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses may include different or substantially the same amounts of a therapeutic agent, such as a compound described herein. In certain embodiments, when multiple doses are administered to a subject or applied to a tissue or cell, the frequency of administering the multiple doses to the subject or applying the multiple doses to the tissue or cell is three doses per day, two doses per day (e.g. BID), one dose per day (e.g., QD), one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses, a unit dosage form) includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose includes independently between 1 mg and 3 mg, inclusive, of a compound described herein. In certain embodiments, a dose includes independently between 3 mg and 10 mg, inclusive, of a compound described herein. In certain embodiments, a dose includes independently between 10 mg and 30 mg, inclusive, of a compound described herein. In certain embodiments, a dose includes independently between 30 mg and 100 mg, inclusive, of a compound described herein. In certain embodiments, a dose includes independently between 10 mg and 250 mg, inclusive, of a compound described herein. In certain embodiments, a dose includes independently between 10 mg and 100 mg (e.g., about 45 mg, about 75 mg, about 90 mg), inclusive, of a compound described herein.

For example, the pharmaceutical compositions or combinations described herein can be in a unit dosage form containing from about 1 to about 1000 mg of active ingredient(s) (e.g., for a subject of from about 50 to about 70 kg), or from about 1 to about 500 mg, from about 1 to about 250 mg, from about 1 to about 150 mg, from about 0.5 to about 100 mg, or from about 1 to about 50 mg of active ingredient(s) (e.g., for a subject of from about 50 to about 70 kg). The therapeutically effective dosage of a compound, pharmaceutical composition or pharmaceutical combination is dependent on the species of the subject, the body weight, age and individual condition of the subject, and the disease, disorder or condition or the severity thereof being treated. A physician, clinician or veterinarian of ordinary skill can readily determine the therapeutically effective amount of each of the active ingredients necessary to prevent or treat the progress of the disease, disorder or condition.

Compositions can also be formulated so as to deliver a particular dose to a subject. A dose may range, depending on the route of administration, among other things, between about 0.1 mg/kg to about 500 mg/kg subject mass, or between about 1 mg/kg to about 100 mg/kg subject mass. In some embodiments, the dosage is expected to be in the range of 1 mg/Kg subject mass and 150 mg/Kg subject mass, for example, at least about 1 mg/Kg, at least about 10 mg/Kg, at least about 20 mg/Kg, at least about 30 mg/Kg, at least about 40 mg/Kg, at least about 50 mg/Kg, at least about 60 mg/Kg, at least about 70 mg/Kg, at least about 80 mg/Kg, at least about 90 mg/Kg, at least about 100 mg/Kg, at least about 110 mg/Kg, at least about 120 mg/Kg, at least about 130 mg/Kg, at least about 140 mg/Kg, or about 150 mg/Kg.

In some embodiments, dose ranges described herein provide guidance for the administration of provided pharmaceutical compositions to an adult. The amount to be administered to, for example, a child or an adolescent, can be determined by a medical practitioner or person skilled in the art and can be lower or the same as that administered to an adult.

Also encompassed by the disclosure are kits (e.g., pharmaceutical packs). The kits provided may comprise a compound of the disclosure, or pharmaceutical composition thereof, and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound contained in the kit. In some embodiments, the pharmaceutical composition or compound described herein provided in the first container and the second container are combined to form a unit dosage form.

Thus, in one aspect, provided are kits including a first container comprising a compound of the disclosure, or a pharmaceutical composition thereof. In certain embodiments, the kits are useful in one or more of the methods described herein, for example, for treating a disease (e.g., a proliferative disease such as cancer) in a subject in need thereof. In certain embodiments, the kits are useful for preventing a disease in a subject in need thereof. In certain embodiments, the kits are useful for reducing the risk of developing a disease in a subject in need thereof.

A kit described herein may include one or more additional therapeutic agents described herein as a separate composition or in a combination comprising a compound of the disclosure, or pharmaceutical composition thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information.

In the combinations and/or kits described herein, the compound of the present disclosure and the other therapeutic agent may be manufactured and/or formulated by the same or different manufacturers. Moreover, the compound of the present disclosure and the other therapeutic agent may be brought together into a combination therapy: (i) prior to release of the combination product to physicians (e.g., in the case of a kit comprising the compound of the present disclosure and the other therapeutic agent); (ii) by the physician (or under the guidance of a physician) shortly before administration; (iii) in the patient themselves, e.g., during sequential administration of the compound of the present disclosure and the other therapeutic agent.

A pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In some embodiments, the concentration of one or more therapeutic agents provided in a pharmaceutical composition is less than 100%, 90%, 80%, 70%, 60%, 50%, 40%, 30%, 20%, 19%, 18%, 17%, 16%, 15%, 14%, 13%, %12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more therapeutic agents provided in a pharmaceutical composition is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more therapeutic agents provided in a pharmaceutical composition is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% w/w, w/v or v/v.

In some embodiments, the concentration of one or more therapeutic agents provided in a pharmaceutical composition is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

Methods of Treatment and Uses

As shown herein, compounds of the disclosure are activin receptor-like kinase (e.g., ALK-5) inhibitors. In some embodiments, the compounds provided herein are useful for treating and/or preventing diseases (e.g., fibrotic diseases, for example IPF or cardiac fibrosis or a cardiac disease associated with TGFβ signaling, and proliferative diseases, e.g., a cancer) in a subject (e.g., a subject in need thereof), inhibiting tumor growth in a subject (e.g., a subject in need thereof), or inhibiting the activity of an activin receptor-like kinase (e.g., ALK-5) in vitro or in vivo. In some embodiments, the compounds of the disclosure are useful in moderating, preventing, or providing treatment for conditions and/or diseases the progress of which is driven by, or utilizes the TGFβ-signalling for disease progression, as described in detail herein.

Provided herein are methods of treating and/or preventing (e.g., treating) a disease, disorder or condition described herein (e.g., a fibrotic disease which is present by itself or comorbid with an infectious, inflammatory or proliferative disease (either benign or malignant), or a proliferative disease, e.g., cancer) in a subject (e.g., a subject in need thereof), the methods comprising administering to the subject a therapeutically and/or prophylactically effective amount (e.g., therapeutically effective amount) of a compound of Formula (I), or a pharmaceutically acceptable salt thereof, or a pharmaceutical composition thereof. Also provided herein are compounds of Formula (I), or a pharmaceutically acceptable salts thereof, and pharmaceutical compositions thereof, for use in treating and/or preventing a disease, disorder or condition described herein (e.g., a fibrotic disease which is present by itself or comorbid with an infectious, inflammatory or proliferative disease (either benign or malignant), or a proliferative disease, e.g., cancer). Also provided herein are uses of compounds of Formula (I), or a pharmaceutically acceptable salt thereof, and pharmaceutical compositions thereof, for the manufacture of a medicament for treating and/or preventing a disease, disorder or condition described herein (e.g., a fibrotic disease which is present by itself or comorbid with an infectious, inflammatory or proliferative disease (either benign or malignant), or a proliferative disease, e.g., cancer). In certain embodiments, the disease, disorder or condition is a disease, disorder or condition associated with activin receptor-like kinase (e.g., ALK-5) activity, e.g., in a subject or cell. In certain embodiments, the activity is aberrant (e.g., increased) activin receptor-like kinase (e.g., ALK-5) activity.

In certain embodiments, the disease, disorder or condition is a proliferative disease. Provided herein are methods for treating a proliferative disease (e.g., cancer) in a subject (e.g., a subject in need thereof), the methods comprising administering to the subject a therapeutically effective amount of a compound of Formula (I), or a pharmaceutically acceptable salt thereof, or a pharmaceutical composition thereof. Also provided herein are compounds of Formula (I), or a pharmaceutically acceptable salt thereof, and pharmaceutical compositions thereof, for use in treating a proliferative disease (e.g., cancer). Also provided herein are uses of compounds of Formula (I), or a pharmaceutically acceptable salt thereof, and pharmaceutical compositions thereof, for the manufacture of a medicament for treating a proliferative disease (e.g., a proliferative disease, e.g., cancer). In certain embodiments, the proliferative disease is associated with activin receptor-like kinase (e.g., ALK-5) activity, e.g., in a subject or cell. In certain embodiments, the activity is aberrant or increased activin receptor-like kinase (e.g., ALK-5) activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending, for example, on the following characteristics: degree of cellular differentiation (including morphology and functionality), rate of growth, local invasion, and metastasis.

A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Examples of benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma.

In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located.

In certain embodiments, the disease, disorder or condition to be treated is cancer. Provided herein are methods for treating cancer in a subject (e.g., a subject in need thereof), the methods comprising administering to the subject a therapeutically effective amount of a compound of the disclosure (e.g., one or more of the exemplified compounds), or a pharmaceutically acceptable salt thereof, or a pharmaceutical composition thereof. In some embodiments, the compound is a compound of Formula (I) (II), (III), or (IV), or Table 1 or Table 4, for example, compound Ex-10, Ex-11, Ex-12, Ex-13, Ex-33, Ex-34, Ex-57, or Ex-58 or a pharmaceutically acceptable salt thereof. Also provided herein are compounds of Formula (I) (II), (III), or (IV), or Table 1 or Table 4, or a pharmaceutically acceptable salt thereof, and pharmaceutical compositions thereof, for example, compound Ex-10, Ex-11, Ex-12, Ex-13, Ex-33, Ex-34, Ex-57, or Ex-58, or a pharmaceutically acceptable salt thereof, for use in treating cancer. Also provided herein are uses of compounds of Formula (I) (II), (III), or (IV), or Table 1 or Table 4, or a pharmaceutically acceptable salt thereof, and pharmaceutical compositions thereof, for the manufacture of a medicament for treating cancer.

In certain embodiments, cancer is associated with the activity of an activin receptor-like kinase (e.g., ALK-5) in a subject or cell. In certain embodiments, the cancer is associated with the activity of ALK-5 in a subject or cell. In certain embodiments, the activity is increased (e.g., aberrant) activin receptor-like kinase (e.g., ALK-5) activity.

In certain embodiments, the cancer expresses or has mutant forkhead box L2 (FOXL2) and/or FOXL2 (e.g., FOXL2$^{C134W}$). FOXL2$^{C134W}$ is characteristic of approximately 97% of AGCT, a rare ovarian cancer subtype (>5%).

An example of a cancer that expresses or has mutant FOXL2 is ovarian cancer (e.g., AGCT). Other sex cord stromal tumors, such as JGCT, thecoma, SLCT, male AGCT, and gynandroblastoma, are other examples of cancers that express or have mutant FOXL2 and/or FOXL2.

In some embodiments, provided herein is a method for treating a cancer (e.g., ovarian cancer, such as adult granulosa cell tumor), comprising determining whether a subject carries a FOXL2 mutation (e.g., FOXL2$^{C134W}$); and treating the subject with a therapeutically effective amount of a compound of the disclosure, for example, a compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing, or a composition thereof, if the subject is identified as having the FOXL2 mutation.

In some embodiments, the cancer has FOXL2 driven tumor growth.

In some embodiments, the cancer is associated with an elevated level of pSmad2 and/or aVP6 and/or alpha smooth muscle actin (α-SMA). In some embodiments, the cancer is associated with an elevated level of phosphorylated SMAD 2 (pSMAD2) or alpha smooth muscle actin (α-SMA).

In addition to FOXL2 mutants (e.g., FOXL2$^{C134W}$), pSMAD2, αVβ6, and α-SMA, other biomarkers that may be predictive (e.g., and used as a patient selection criterion) and/or indicative (e.g., and used during and/or after treatment to assess some aspect of the treatment) of efficacy of a treatment disclosed herein include CD31 (e.g., an elevated level of CD31), CD45 (e.g., an elevated level of CD45), and/or HLA (e.g., a low level of HLA).

In some embodiments, the cancer exhibits an excluded or desert phenotype.

The term "cancer" refers to a class of diseases characterized by the development of abnormal cells that proliferate uncontrollably and have the ability to infiltrate and destroy normal body tissues. In certain embodiments, the cancer is a solid tumor. In certain embodiments, the cancer is a hematological cancer.

A wide variety of cancers, including solid tumors, leukemias, lymphomas, and myelomas are amenable to the methods disclosed herein. In some embodiments, the cancer is a solid tumor cancer. In some embodiments, the cancer comprises a solid tumor (e.g., a colorectal, breast, prostate, lung, pancreatic, renal or ovarian tumor). Accordingly, in some embodiments, the cancer is a solid tumor cancer. In some embodiments, the cancer is selected from one or more of a cancer of the pulmonary system, a brain cancer, a cancer of the gastrointestinal tract, a skin cancer, a genitourinary cancer, head and neck cancer, a sarcoma, a carcinoma, and a neuroendocrine cancer. In various embodiments, the solid tumor cancer is breast cancer, bladder cancer, endometrial cancer, esophageal cancer, liver cancer, pancreatic cancer, lung cancer, cervical cancer, colon cancer, colorectal cancer, gastric cancer, kidney cancer, ovarian cancer, prostate cancer, testicular cancer, uterine cancer, a viral-induced cancer, melanoma or sarcoma. In some embodiments, the cancer is bladder cancer. In some embodiments, the cancer is lung cancer (e.g., non-small cell lung cancer). In other embodiments, the cancer is liver cancer. In some embodiments, the cancer is a sarcoma, bladder cancer or renal cancer. In some embodiments, the cancer is gastric cancer. In some embodiments, the cancer is breast cancer. In some embodiments, the cancer is ovarian cancer. In some embodiments, the cancer is pancreatic cancer. In some embodiments, the cancer is mesothelioma. In some embodiments, the cancer is prostate cancer (e.g., castration-resistant prostate cancer, castration-sensitive prostate cancer). In other embodiments, the cancer is bladder cancer, pancreatic cancer, colorectal cancer, glioblastoma, kidney cancer, non-small cell lung carcinoma, prostate cancer, sarcoma, skin cancer, thyroid cancer, testicular cancer or vulvar cancer. In some embodiments, the cancer is endometrial cancer, pancreatic cancer, testicular cancer, renal cancer, melanoma, colorectal cancer, thyroid cancer, bladder cancer, pancreatic cancer, vulvar cancer, sarcoma, prostate cancer, lung cancer or anal cancer. In some embodiments, the cancer is a sarcoma. In some embodiments, the cancer is a renal cell carcinoma. In particular embodiments, the cancer is ovarian granulosa cell tumor (e.g., adult granulosa cell tumor (AGCT), pediatric granulosa cell tumor).

In some embodiments, the cancer is a non-solid tumor cancer. In some embodiments, the cancer is a hematologic cancer. Hematologic cancers that can be treated according to the methods described herein include leukemias (e.g., acute leukemias, chronic leukemias), lymphomas (e.g., B-cell lymphoma, T-cell lymphoma) and multiple myeloma. In some embodiments, the hematologic cancer is selected from multiple myeloma, myelodysplastic syndrome (MDS), acute myeloid leukemia (AIL), acute lymphoblastic leukemia (ALL), acute lymphocytic leukemia, lymphocytic lymphoma, mycosis fungoides, chronic lymphogenous leukemia, chronic lymphocytic leukemia (CLL), mantle cell lymphoma, diffuse large B-cell lymphoma, follicular lymphoma, Hodgkin's lymphoma, non-Hodgkin's lymphoma or myelofibrosis.

Examples of cancer treatable according to the methods described herein include, but are not limited to, adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, lung cancer (e.g., large cell lung cancer, such as squamous cell carcinoma, non-small cell lung), oat cell, papillary, scirrhous, bronchiolar, bronchogenic, squamous cell, and transitional cell). Additional examples of cancer treatable according to the methods described herein include, but are not limited to, histiocytic disorders; leukemia; histiocytosis malignant; Hodgkin's disease; hypereosinophilia; immunoproliferative small; non-Hodgkin's lymphoma; plasmacytoma; reticuloendotheliosis; melanoma; chondroblastoma; chondroma; chondrosarcoma; dermatofibrosarcoma protuberans, fibrotic cancer (myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans) and hepatocellular carcinoma); fibroma; fibrosarcoma; giant cell tumors; histiocytoma; lipoma; liposarcoma; mesothelioma; myxoma; myxosarcoma; osteoma; osteosarcoma; pediatric malignancy, chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatocellular cancer, hepatoma; hidradenoma; islet cell tumor; Leydig cell tumor; papilloma; sertoli cell tumor; theca cell tumor; leiomyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. Yet more examples of cancer treatable according to the methods described herein include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; neurofibromatosis; and cervical dysplasia.

Further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Cancer of the anal region; Anal Cancer; Appendix Cancer; Astrocytomas, Childhood; Atypical Teratoid/Rhabdoid Tumor, Childhood, Central Nervous System (CNS); Neoplasms of the CNS (e.g., primary CNS lymphoma, spinal axis tumors, medulloblastoma, brain stem gliomas or pituitary adenomas), Barrett's esophagus (e.g., pre-malignant syndrome), and mycoses fungoides, Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Cancer of the Endocrine system (e.g., cancer of the thyroid, pancreas, parathyroid or adrenal glands), Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Gynecologic Tumors ((e.g., uterine sarcomas, carcinoma of the fallopian tubes, carcinoma of the endometrium, carcinoma of the cervix, carcinoma of the vagina or carcinoma of the vulva), Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Cutaneous or Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis (e.g., renal cell carcinoma, carcinoma of the renal pelvis), benign prostatic hypertrophy, parathyroid cancer, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some embodiments, the cancer is a pre-metastatic cancer. In some embodiments, the cancer is a metastatic cancer.

In certain embodiments, the cancer is a hematological cancer (e.g., leukemia (e.g., acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)); lymphoma (e.g., Hodgkin lymphoma (HL) (e.g., B-cell HL, T-cell HL)), non-Hodgkin lymphoma (NHL) (e.g., B-cell NHL such as diffuse large cell lymphoma (DLCL) (e.g., diffuse large B-cell lymphoma)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomads, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome)), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); heavy chain disease (e.g., alpha chain disease, gamma chain disease, mu chain disease); a myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); multiple myeloma (MM); plasma cell neoplasia; familiar hypereosinophilia; inflammatory myofibroblastic tumors; immunocytic amyloidosis). In certain embodiments, the cancer is leukemia. In certain embodiments, the cancer is acute lymphoblastic leukemia (ALL). In certain embodiments, the cancer is early T-cell precursor (ETP)-acute lymphoblastic leukemia (ALL).

In certain embodiments, the cancer is anaplastic astrocytoma, pancreatic cancer, skin cancer, melanoma, metastatic melanoma, colorectal cancer, breast cancer, prostate cancer, renal cancer, hepatocellular cancer, ovarian cancer, HPV-associated cancer (e.g., cervical cancer, oropharyngeal cancer, anal cancer, vulvar/vaginal cancer, and penile cancer), multiple myeloma, myelodysplastic syndrome, or myelofibrosis.

In certain embodiments, the cancer is liver cancer (e.g., hepatocellular cancer (HCC) (e.g., hepatocellular carcinoma, hepatoblastoma, hepatocellular adenoma), malignant hepatoma, hemangiomas, biliary cancer (e.g., cholangiocarcinoma)). In some embodiments where the cancer is liver cancer it is hepatocellular carcinoma (HCC). In some embodiments, the cancer is lung cancer (e.g., non-small cell lung cancer (NSCLC)). In some embodiments, the cancer is brain cancer (e.g., neuroblastoma, glioblastoma). In some embodiments wherein the cancer is a brain cancer, it is an anaplastic astrocytoma. In some embodiments, the cancer is thyroid cancer (e.g., anaplastic thyroid cancer (ATC)). In some embodiments, the cancer is breast cancer. In some embodiments the cancer is renal cancer. In some embodiments, the cancer is ovarian cancer. In some embodiments, the cancer is an HPV-associated cancer, for example, HPV-associated cervical cancer, HPV-associated oropharyngeal cancer, HPV-associated anal cancer, HPV-associated vulvar/ vaginal cancer, and HPV-associated penile cancer. In some embodiments the cancer is colorectal cancer (e.g., colon carcinoma). In some embodiments the cancer is pancreatic cancer (e.g., pancreatic carcinoma). In some embodiments wherein the cancer is a pancreatic cancer, it is pancreatic ductal adenocarcinoma and associated fibrosis CAF. In some embodiments, the cancer is skin cancer. In some embodiments wherein the cancer is a skin cancer, it is metastatic melanoma. In some embodiments, the cancer is prostate cancer.

In some embodiments, the proliferative disease is a hematological cancer (e.g., anaplastic large cell lymphoma (ALCL), myelodysplastic syndrome, multiple myeloma, and myelofibrosis).

In certain embodiments, the cancer is musculoskeletal cancer (e.g., bone cancer (e.g., osteosarcoma, osteoid osteoma, malignant fibrous histiocytoma, Ewing's sarcoma, chordoma, malignant giant cell tumor chordoma, chondrosarcoma osteochondroma, benign chondroma, chondroblastoma chondromyxofibroma, myelodysplastic syndrome (MDS)), muscle cancer (e.g., rhabdomyosarcoma, rhabdomyoma), connective tissue cancer, synovioma).

In certain embodiments, the cancer is a nervous system cancer (e.g., brain cancer (e.g., astrocytoma, medulloblastoma, glioma (e.g., astrocytoma, oligodendroglioma), glioblastomas, glioblastoma multiform, medulloblastoma, ependymoma, germinoma (i.e., pinealoma), oligodendroglioma, schwannoma, retinoblastoma, congenital tumors, craniopharyngioma), spinal cord cancer, neurofibroma (e.g., neurofibromatosis (NF) type 1 or type 2, schwannomatosis), neuroblastoma, primitive neuroectodermal tumors (PNT), meningeal cancer (e.g., meningioma, meningiosarcoma, gliomatosis), skull cancer, acoustic neuroma, ependymoma, hemangioblastoma, ocular cancer (e.g., intraocular melanoma, retinoblastoma)). In certain embodiments, the disease to be treated is a brain tumor. In certain embodiments, the disease is pleomorphic xenoanthrocytoma (PXA). In certain embodiments, the disease is pediatric pleomorphic xenoanthrocytoma (PXA).

In certain embodiments, the cancer is selected from endocrine/exocrine cancers (e.g., thyroid cancer (e.g., papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma), pancreatic cancer (e.g., pancreatic andenocarcinoma, intraductal papillary mucinous neoplasm (IPMN), Islet cell tumors, ductal adenocarcinoma, insulinoma, glucagonoma, vipoma), adrenal gland cancer, neuroendocrine cancer (e.g., gastroenteropancreatic neuroendoctrine tumor (GEP-NET), carcinoid tumor), sebaceous gland carcinoma, sweat gland carcinoma). In certain embodiments, the cancer is sweat gland cancer (e.g., sweat gland carcinoma).

In certain embodiments, the cancer is head and neck cancer (e.g., squamous cell carcinoma of the head and neck (SCCHN), adenoid cystic carcinoma).

In certain embodiments, the cancer is oral cancer (e.g., buccal cavity cancer, lip cancer, tongue cancer, mouth cancer, pharynx cancer, hypopharynx cancer (e.g., hypopharyngeal carcinoma), throat cancer (e.g., laryngeal cancer, pharyngeal cancer, nasopharyngeal cancer, oropharyngeal cancer), salivary gland cancer).

In certain embodiments, the cancer is esophageal cancer (e.g., esophageal squamous cell carcinoma, esophageal adenocarcinoma, Barrett's adenocarcinoma, esophageal leiomyosarcoma).

In certain embodiments, the cancer is gastrointestinal cancer (e.g., anal cancer, colorectal cancer (e.g., colon cancer, rectal cancer, colorectal adenocarcinoma), gall bladder cancer, gastric cancer (e.g., stomach cancer (e.g., stomach adenocarcinoma)), gastrointestinal stromal tumor (GIST), small bowel cancer (e.g., appendix cancer, small bowel carcinoma, e.g., small bowel adenocarcinoma), small intestine cancer, large bowel cancer, large intestine cancer).

In certain embodiments, the cancer is cardiovascular cancer (e.g., primary cardiac tumors, angiosarcoma (e.g., lymphangiosarcoma, lymphangioendotheliosarcoma, hemangiosarcoma), endotheliosarcoma (e.g., Kaposi's sarcoma, multiple idiopathic hemorrhagic sarcoma), cardiac myxoma, cardiac rhabdomyoma).

In certain embodiments, the cancer is lung cancer (e.g., bronchus cancer (e.g., bronchogenic carcinoma, bronchial adenoma), alveolar carcinoma, mesothelioma, small cell lung cancer (SCLC), non-small cell lung cancer (NSCLC), lung adenocarcinoma, chondromatous hamartoma, papillary adenocarcinoma).

In certain embodiments, the cancer is a genitourinary cancer (e.g., bladder cancer (e.g., urothelial carcinoma), urethral cancer, kidney cancer (e.g., nephroblastoma a.k.a. Wilms' tumor, renal cell carcinoma), testicular cancer (e.g., seminoma, testicular embryonal carcinoma), germ cell cancer, prostate cancer (e.g., prostate adenocarcinoma), penile cancer (e.g., Paget's disease of the penis and scrotum)).

In certain embodiments, the cancer is a gynecological cancer (e.g., breast cancer (e.g., adenocarcinoma of the breast, papillary carcinoma of the breast, mammary cancer, medullary carcinoma of the breast, triple negative breast cancer, HER-2 positive breast cancer, HER2– negative breast cancer), endometrial cancer (e.g., uterine cancer (e.g., uterine sarcoma, choriocarcinoma), endometrial carcinoma), cervical cancer (e.g., cervical adenocarcinoma), ovarian cancer (e.g., cystadenocarcinoma, ovarian embryonal carcinoma, ovarian adenocarcinoma), germ cell cancer, vulvar cancer (e.g., Paget's disease of the vulva) vaginal cancer, fallopian tube cancer).

In certain embodiments, the cancer is skin cancer (e.g., squamous cell carcinoma (SCC), keratoacanthoma (KA), melanoma, basal cell carcinoma (BCC), dermatofribroma).

In certain embodiments, the cancer is a soft tissue cancer (e.g., intraepithelial neoplasms, epithelial carcinomas, epithelial sarcomas, adenocarcinomas, adenomas, fibrosarcomas, fibromas, liposarcomas, lipomas, myxomas, teratomas).

Myeloproliferative neoplasms are also treatable according to the methods described herein. Non-limiting examples of myeloproliferative neoplasms include myelofibrosis, polycythemia vera and essential thrombocythemia.

In certain embodiments, the cancer is a rare cancer. The term "rare cancer" refers to cancers that occur in a relatively small number of patients.

In certain embodiments, the cancer is lung cancer (e.g., non-small cell lung cancer (NSCLC)), brain cancer (e.g., neuroblastoma, glioblastoma), thyroid cancer (e.g., anaplastic thyroid cancer (ATC)), breast cancer, colorectal cancer (e.g., colon carcinoma), liver cancer (e.g., hepatocellular carcinoma (HCC)), pancreatic cancer (e.g., pancreatic carcinoma), skin cancer (e.g., melanoma), prostate cancer, or a hematological cancer (e.g., anaplastic large cell lymphoma (ALCL), myelodysplastic syndrome). In some embodiments, the cancer is ovarian cancer (e.g., ovarian granulosa cell tumor), gastric cancer, or mesothelioma. In some embodiments, it is preferred to treat cancers which are driven by, or utilize TGF-b signaling for disease progression with one or more compounds of the disclosure, for example, compounds of Formula (I) (II), (III), or (IV), or Table 1 or Table 4, for example, exemplified compounds Ex-10, Ex-11, Ex-12, Ex-13, Ex-33, Ex-34, Ex-57, or Ex-58, or a pharmaceutically acceptable salt thereof. In other embodiments, it is preferred to treat cancers which are driven by, or utilize TGF-b signaling for disease progression and/or are related to mutation of the FOXL2 gene, with one or more compounds of the disclosure, for example, compounds of Formula (I) (II), (III), or (IV), or Table 1 or Table 4, for example, exemplified compounds Ex-10, Ex-11, Ex-12, Ex-13, Ex-33, Ex-34, Ex-57, or Ex-58, or a pharmaceutically acceptable salt thereof.

In some embodiments, the cancer described herein (e.g., solid tumor cancer) exhibits an excluded or desert phenotype. In some embodiments, the cancer (e.g., solid tumor cancer) exhibits an excluded phenotype. In some embodiments, the cancer (e.g., solid tumor cancer) exhibits a desert phenotype.

In some embodiments, provided herein is a method for treating a fibrotic condition. In some embodiments the fibrotic condition is associated with a proliferative disease. In some embodiments, the fibrotic condition is present without a comorbidity. In some embodiments, the fibrotic condition is idiopathic pulmonary fibrosis, liver fibrosis, liver cirrhosis, nonalcoholic steatohepatitis, Peyronie's, cystic fibrosis, beta thalassemia, actinic keratosis, hypertension, general inflammatory disorders, dry eye, ulcers, corneal fibrosis, wet age-related macular degeneration, psoriasis, wound closure, chronic kidney disease, renal fibrosis, systemic sclerosis, or chronic Chagas' heart disease. In some embodiments, the fibrotic condition is cardiac fibrosis or a condition associated with cardiac fibrosis (e.g., valvular disease, arrhythmia (e.g., atrial fibrillation), myocardial remodeling (e.g., after infarction), cardiomyopathy (e.g., dilated, ischemic or hypertrophic cardiomyopathy), restenosis (e.g., in-stent restenosis, post-angioplasty restenosis)). In some embodiments, the fibrotic condition is Dupuytren's contracture. In some embodiments, the fibrotic condition is desmoid tumors (fibromatosis).

As used herein, the terms "fibrosis", "fibrotic disease," "fibrotic condition," "fibrotic lesion" and "fibrotic disease and/or condition" (collectively herein, fibrosis) refer to disease or condition in a subject involving the formation of excess fibrous connective tissue in an organ or tissue. The occurrence of fibrosis may be concomitant with another disease state or condition, for example, inflammation, cancer, viral or bacterial infection or the like.

The formation of excess fibrous connective tissue leading to a fibrosis is believed to occur in an organ or tissue in a reparative or reactive process. This can be a reactive, benign, or pathological state. Physiologically, fibrosis acts to deposit connective tissue, which can interfere with, or totally inhibit the normal architecture and function of the underlying organ or tissue. For example, pulmonary fibrosis is a respiratory disease in which scars are formed in the lung tissues, leading to serious breathing problems. Scar formation typically involves the accumulation of excess fibrous connective tissue, and often leads to thickening of the walls and causes reduced oxygen supply in the blood. Reduced oxygen supply in the blood, in turn, can lead to heart failure, and even death. The replacement of normal lung with scar tissue causes irreversible decrease in oxygen diffusion capacity. Some types of pulmonary fibrosis are believed to be perpetuated by aberrant wound healing, rather than chronic inflammation. Once the scarring has developed, it is often permanent. Idiopathic pulmonary fibrosis (IPF) is a type of pulmonary fibrosis which is a fatal lung disease with an unknown etiology, but can be present with inflammation, cancer, and/or viral infection.

In general, a fibrosis progresses in three stages (illustrated for pulmonary fibrosis, but common across many fibrotic conditions): the injury stage ("Stage 1"), the epithelial-fibroblastic interaction stage ("Stage 2"), and the aberrant repair and fibrosis stage ("Stage 3"). In Stage 1, generally, the epithelium is damaged, and one or more of the following events can occur: epithelial damage, endothelial damage, for example, in pulmonary fibrosis, destruction of an alveolar capillary basilar membrane, vascular leak, platelet activation, and fibrin clot activation. In Stage 2, generally, fibroblasts begin to interact with the damaged epithelium, and one or more of the following events can occur: release of profibrotic cytokines, (myo)fibroblast recruitment, proliferation, and differentiation, provisional matrix formation, angiogenesis, and defective re-epithelialisation. In Stage 3, generally, the epithelial damage is aberrantly repaired resulting in fibrosis, and one or more of the following events can occur: exaggerated extracellular matrix (ECM) accumulation, lack of matrix degradation, for example, in pulmonary fibrosis, progressive lung remodeling and honeycomb changes (in pulmonary fibrosis, the lung tissue comes to resemble a honeycomb).

Although the occurrence of fibrosis concomitant with other disease conditions is not uncommon, for example, the presence of a cancer concomitant with fibrosis, viral infection concomitant with fibrosis or chronic inflammation concomitant with fibrosis, the etiology of fibrosis disease is not well understood and occurs also in the absence of other disease states. However, it is believed that similar mechanisms and signaling pathways are present in both fibrosis conditions and many of the concomitant diseases (including cancers, infections and general inflammation) effecting organs or tissues in which fibrotic disease is also present, for example, the presence of IPF with lung cancer. Accordingly, it is believed that fibrosis along with many diseases with which it is often present progress via the TGFβ protein and the signaling cascade implicated by overexpression of it, see for example, Ballester, B; et al., Idiopathic Pulmonary Fibrosis and lung Cancer: Mechanisms and Molecular targets, Int. J. Mol. Sci. 2019, 20, 593; doi:10.3390/ijms20030593.

Accordingly, in some embodiments, a compound described herein can be used to treat (e.g., provide therapy for, reverse the course of), ameliorate (e.g., reduce symptoms associated with), prevent (e.g., prophylactically treat) or manage (e.g., slow or halt progression) of a fibrotic disease (collectively herein, "treatment of a fibrotic disease" or "treatment of a fibrosis"). In some embodiments, the fibrosis to be treated is present without any concomitant disease. In some embodiments, the fibrosis to be treated is present with an infection, for example, a viral or bacterial infection. In some embodiments, the fibrosis to be treated is present with an inflammatory condition. In some embodiments, the inflammatory condition present is each and several of those described in detail herein. In some embodiments, treatment comprises identifying a patient who has fibrosis, with or without a concomitant comorbid, causative, or exacerbating condition, or who is at risk of developing a fibrosis, with or without a concomitant comorbid, causative, or exacerbating condition, and administering thereto a therapeutically effective amount of a compound described herein, for example, one or more ALK-5 inhibitor compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof.

In some embodiments, the fibrosis to be treated is present with a cancer. In some embodiments, the fibrosis is comorbid with the cancerous condition. In some embodiments, the cancer is a cause of the fibrotic condition. In some embodiments, the fibrotic condition is exacerbated by the cancer. In some embodiments, the cancer present is each and several of those described in detail herein, whether as a comorbid, causative or exacerbating condition.

In some embodiments, the fibrosis to be treated is present with a viral infection. In some embodiments the viral infection is comorbid with the fibrotic condition. In some embodiments, the viral infection is a cause of the fibrotic condition. In some embodiments, the fibrotic condition is exacerbated by the viral infection. In some embodiments, the viral infection present is each and several of the viral infections mentioned herein.

In some embodiments, treatment of a fibrotic disease, which can be alone or present with another condition (which can be comorbid, exacerbating or causative of the fibrosis) selected from each and several of a viral infection, a cancer, or an inflammatory condition, for example, each and several of those described herein, is carried out by administering a compound described herein, for example, one or more ALK-5 inhibitor compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease (with or without a concomitant condition), for example, one or more of those described herein, is carried out by administering two or more compounds described herein, for example, two or more compounds of Formula (I) (II), (III), or (IV), or Table 1 or Table 4, for example, two or more of Ex-10, Ex-11, Ex-12, Ex-13, Ex-33, Ex-34, Ex-57, or Ex-58, or a pharmaceutically acceptable salt of the foregoing. In some embodiments, treatment of a fibrotic disease (with or without a concomitant condition), for example, one or more of those described herein, is carried out by administering a combination of therapeutic agents comprising one or more compounds described herein (for example, one or more of the exemplified compounds, or a pharmaceutically acceptable salt thereof), in combination with one or more additional therapeutic agents (e.g., at least one compound described herein, and at least one additional therapeutic agent, one or more compounds described herein with one or two or more additional therapeutic agents). In some embodiments, combination treatment is provided by administering one compound of the disclosure, for example, a compound of Formula (I) (II), (III), or (IV), or Table 1 or Table 4, for example, compound Ex-10, Ex-11, Ex-12, Ex-13, Ex-33, Ex-34, Ex-57, or Ex-58, or a pharmaceutically acceptable salt of any thereof, and one or more additional therapeutic agents. In some embodiments, the combination of therapeutic agents comprises one compound described herein and more than one additional therapeutic agent.

In some embodiments, fibrosis treatment using at least one compound described herein, alone or in a combination with one or more additional therapeutic agents, is administered during a single stage of the fibrotic disease (e.g., Stage 1, Stage 2, Stage 3). In some embodiments, fibrosis treatment comprises administration of a combination therapy divided across multiple stages of the disease. As a non-limiting example, a compound described herein (for example, one or more of the exemplified compounds, or a pharmaceutically acceptable salt thereof) can be administered during Stage 1, Stage 2, or Stage 3 of the disease, while one or more additional therapeutic agents can be administered during a different stage of the disease than the compound described herein. For example, in some embodiments, treatment of a fibrotic disease (as described in detail herein) is accomplished by administering a compound of the disclosure, for example, one or more of the compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing. In some embodiments, where a combination is used to treat a proliferative disease, the combination is one or more of the compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing, and an IO agent. In some embodiments, the compound described herein and the additional therapeutic agents comprising the combination therapy are administered during all stages of the fibrosis. In some embodiments, the compound of the disclosure is administered during some stages and not others. In some embodiments, wherein a combination therapy is employed, the compound of the disclosure is administered during all stages of the disease and the additional therapeutic agents with which it is combined are administered during some stages of the disease and not others.

In some embodiments, compounds described herein are administered to a subject in need thereof in an amount effective to treat a fibrotic disease, for example, administration of an amount of a compound described hereinto slow down or stop the progression of a disease or condition (e.g., idiopathic pulmonary fibrosis, acute exacerbation of IPF, cardiac disease, liver fibrosis, liver cirrhosis, nonalcoholic steatohepatitis, Peyronie's, Dupuytren's contracture, cystic fibrosis, beta thalassemia, actinic keratosis, hypertension, general inflammatory disorders, dry eye, ulcers, corneal fibrosis, wet age-related macular degeneration, psoriasis, wound closure, chronic kidney disease, renal fibrosis, systemic sclerosis, and chronic Chagas' heart disease), increase the survival time of a subject suffering with a disease or condition (e.g., by at least 10%, 20%, 30%, 40%, 50%, 60%, 70%, 80%, 90%, or 100%, when compared with a subject that was not administered the compound described herein), increase the survival rate in a subject population (e.g., survival after being admitted to the intensive care unit increase by at least 10%, 20%, 30%, 40%, 50%, 60%, 70%, 80%, 90%, or 100% when compared with a subject population that was not administered the compound described herein), reduce the risk of a subject developing a fibrotic condition (e.g., pulmonary fibrosis or IPF) when compared with a subject that was not administered the compound described herein, preserve organ function (e.g., lung function or liver function) when compared with a subject that was not administered the compound described herein, and/or prevent or reduce the risk of acute exacerbation of a condition when compared with a subject that was not administered the compound described herein.

In some embodiments, provided are methods of inhibiting fibrosis in a tissue comprising administering an ALK-5 inhibitor a compound described herein. In some embodiments of the methods described herein, the method involves contacting the tissue with a compound described herein, or a pharmaceutically acceptable salt thereof, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing, in an amount sufficient to decrease or inhibit fibrosis. In some embodiments of the methods described herein, the methods can include inhibiting the formation or deposition of tissue fibrosis, and/or reducing the size, cellularity, composition, cellular or collagen content of a fibrotic lesion. In some embodiments, the fibrotic lesion is in a subject (e.g., human subject). In some embodiments, the method of inhibiting is applied to a subject which has present a concomitant condition, for example, cancer, inflammation, or viral infection, which is comorbid with, causative of, or exacerbating said fibrosis.

In some embodiments, provided are methods of treating fibrosis in a tissue comprising administering a compound described herein, for example, one or more of the compounds of Formula (I) (II), (III), or (IV), or Table 1 or Table 4), for example, one or more of Ex-10, Ex-11, Ex-12, Ex-13, Ex-33, Ex-34, Ex-57, or Ex-58, or a pharmaceutically acceptable salt of the foregoing. In some embodiments of the methods described herein, the method involves contacting the tissue with a compound described herein in an amount sufficient to reverse the progression or eliminate fibrosis. In some embodiments of the methods described herein, the methods can include reversing or eliminating the formation or deposition of tissue fibrosis, and/or reducing the size, cellularity, composition, cellular or collagen content of a fibrotic lesion. In some embodiments, the fibrotic lesion is in a subject (e.g., human subject). In some embodiments, the method of treating is applied to a subject which has present a concomitant condition, for example, cancer, inflammation, or viral infection, which is comorbid with, causative, or exacerbating said fibrosis.

In some embodiments, treatment, amelioration, or prevention (e.g. prophylactic treatment) of a fibrotic condition (e.g., pulmonary fibrosis) which is present with (comorbid, caused by, and/or exacerbated by) a cancer, is provided by administering one or more compounds described herein, for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing.

In some embodiments, treatment, amelioration, or prevention of a fibrotic condition, for example, acute exacerbation of idiopathic pulmonary fibrosis, which is present with a cancerous condition is carried out by administering one or more compounds described herein, for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing.

In some embodiments, treatment, amelioration, or prevention (e.g. prophylactic treatment) of a fibrotic condition (e.g., pulmonary fibrosis) which is comorbid with, caused by, and/or exacerbated by, a cancer, for example, each and several of those described herein, is carried out by administering two or more compounds described herein, for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing.

In some embodiments, treatment of a fibrotic disease which is present with a cancer, for example, one or more of those described herein, is carried out by administering a combination of therapeutic agents comprising one or more compounds described herein, for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing, in combination with one or more additional therapeutic agents (e.g., at least one compound described herein and at least one additional therapeutic agent, one or more compounds described herein with one or two or more additional therapeutic agents). In some embodiments, combination treatment of fibrosis present with a cancer is provided by administering two or more compounds of the disclosure, for example, two or more compounds of Formula (I) (II), (III), or (IV), or Table 1 or Table 4, for example, two or more of Ex-10, Ex-11, Ex-12, Ex-13, Ex-33, Ex-34, Ex-57, or Ex-58, or a pharmaceutically acceptable salt of the foregoing, and one or more additional therapeutic agents.

In some embodiments, treatment, amelioration, or prevention (e.g., prophylactic treatment) of fibrosis which is comorbid with a viral infection (i.e., present with a viral infection) is carried out by administering one or more compounds of the disclosure, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of the foregoing. In some embodiments, treatment of a fibrotic disease present with a viral infection, for example, one or more of those described herein, is carried out by administering two or more compounds of the disclosure, for example, two or more compounds of Formula (I) (II), (III), or (IV), or Table 1 or Table 4, for example, two or more of Ex-10, Ex-11, Ex-12, Ex-13, Ex-33, Ex-34, Ex-57, or Ex-58, or a pharmaceutically acceptable salt of any of the foregoing.

In some embodiments, treatment of a fibrotic disease present with a viral infection, for example, one or more of those described herein, is carried out by administering a combination of therapeutic agents comprising one or more compounds of the disclosure, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing, in combination with one or more additional therapeutic agents (e.g., at least one compound described herein and at least one additional therapeutic agent, one or more compounds described herein with one or two or more additional therapeutic agents).

In some embodiments, treatment, amelioration, or prevention of a fibrotic condition present with a viral infection, for example, acute exacerbation of idiopathic pulmonary fibrosis, is carried out by administering one or more compounds of the disclosure, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing.

In some embodiments, treatment, amelioration, or prevention (e.g., prophylactic treatment) of a fibrotic condition (e.g., pulmonary fibrosis) which is comorbid with, caused by, and/or exacerbated by, an inflammatory condition, is provided by administering one or more compounds of the disclosure, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment, amelioration, or prevention (e.g., prophylactic treatment) of a fibrotic condition (e.g., pulmonary fibrosis) which is present with an inflammatory condition, for example, each and several of those described herein, is carried out by administering two or more compounds described herein, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing.

In some embodiments, treatment, amelioration, or prevention (e.g., prophylactic treatment) of a fibrotic condition (e.g., pulmonary fibrosis) which is comorbid with, caused by, and/or exacerbated by an inflammatory condition, for example, each and several of those described herein, is carried out by administering a combination of therapeutic agents comprising one or more compounds of the disclosure, for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing, in combination with one or more additional therapeutic agents (e.g., at least one compound of the disclosure and at least one additional therapeutic agent, one or more compounds of the disclosure with one or two or more additional therapeutic agents). In some embodiments, combination treatment is provided by administering two or more compounds of the disclosure, for example, two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing, and one or more additional therapeutic agents. In some embodiments, treatment, amelioration, or prevention of a fibrotic condition which is present with an inflammatory condition, for example, acute exacerbation of idiopathic pulmonary fibrosis, is carried out by administering one or more compounds of the disclosure, for example, compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing.

In some embodiments, a fibrotic condition (e.g., pulmonary fibrosis) is present with one or more additional conditions (a concomitant condition), e.g., an inflammatory condition, a cancer, and/or a viral infection. A concomitant condition may be a cause of, or an exacerbation of, the fibrotic condition, or they may be a comorbidity with the fibrotic condition. In some embodiments, the concomitant condition is a viral infection; in some embodiments, the concomitant condition is cancer; in some embodiments, the concomitant condition is an inflammatory condition of any of those mentioned herein. In some embodiments, where treatment, amelioration, or prevention (e.g., prophylactic treatment) of a fibrotic condition (e.g., pulmonary fibrosis) which is present with, caused by, and/or exacerbated by, a cancer, viral infection, or an inflammatory condition is provided, the fibrotic condition is pulmonary fibrosis. In some embodiments, the fibrotic condition is idiopathic pulmonary fibrosis. In some embodiments, the fibrotic condition is an acute exacerbation of idiopathic pulmonary fibrosis.

In some embodiments, a fibrotic condition for which treatment is administered (e.g., pulmonary fibrosis) is present without a concomitant disease state. In some embodiments, treatment of a fibrotic condition present without a concomitant disease state is provided by administering a compound described herein, for example, a compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic condition present without a concomitant disease state is provided by administering a therapeutically effective amount of a compound described herein, for example, a compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment, amelioration, or prevention (e.g., prophylactic treatment) of a fibrotic condition (e.g., pulmonary fibrosis) which is not present with a concomitant cancer, viral infection, or an inflammatory condition is provided. In some embodiments, the fibrotic condition is pulmonary fibrosis. In some embodiments, the fibrotic condition is idiopathic pulmonary fibrosis. In some embodiments, the fibrotic condition is an acute exacerbation of idiopathic pulmonary fibrosis.

In some embodiments, a fibrotic condition which is treated in accordance with the methods described here by administration of a compound described herein (alone or as part of a combination therapy), for example, individually or in combinations of two or more of the compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing, is, for example, but not limited to, a lung fibrosis, commonly known as "scarring of the lungs" (e.g., pulmonary fibrosis, for example, an idiopathic pulmonary fibrosis, an acute exacerbation of an idiopathic pulmonary fibrosis, or a familial pulmonary fibrosis), a liver fibrosis (hepatic fibrosis, e.g., keloids, scleroderma, or nephrogenic systemic fibrosis, a bile duct fibrosis (biliary fibrosis), liver cirrhosis, for example, primary biliary cholangitis (biliary cirrhosis), primary sclerosing cholangitis), fibrosis in the heart tissue (a cardiac fibrosis), a vascular fibrosis, a kidney fibrosis (renal fibrosis), a skin fibrosis (a cutaneous fibrosis or endometrial fibrosis, e.g., keloids, scleroderma, or nephrogenic systemic fibrosis), a gastrointestinal fibrosis (e.g., Crohn's disease), a bone marrow fibrosis (also called myelofibrosis), an athrofibrosis (e.g., of the knee, of the shoulder, or of another joint), Dupuytren's contracture, a mediastinal fibrosis, Peyronie's disease, a retroperitoneal fibrosis, a systemic sclerosis, autoimmune hepatitis, or two or more thereof.

In some embodiments, the fibrotic condition to be treated is pulmonary fibrosis. In some embodiments, the fibrotic condition to be treated is liver fibrosis. In some embodiments, the fibrotic condition to be treated is liver cirrhosis. In some embodiments, the fibrotic condition to be treated is nonalcoholic steatohepatitis. In some embodiments, the fibrotic condition to be treated is Peyronie's disease. In some embodiments, the fibrotic condition to be treated is cystic fibrosis. In some embodiments, the fibrotic condition to be treated is beta-thalassemia. In some embodiments, the fibrotic condition to be treated is actinic keratosis. In some embodiments, the fibrotic condition to be treated is hypertension. In some embodiments, the fibrotic condition to be treated is a chronic kidney disease, for example, renal fibrosis. In some embodiments, the fibrotic condition to be treated is chronic Chagas' heart disease.

In some embodiments, the fibrotic condition to be treated is dry eye, ulcers, corneal fibrosis, wet age-related macular degeneration, chronic wound (failure to heal) or systemic sclerosis. In some embodiments, the fibrotic condition to be treated is psoriasis. In some embodiments, the fibrotic condition is idiopathic pulmonary fibrosis, liver fibrosis, liver cirrhosis, nonalcoholic steatohepatitis, Peyronie's, cystic fibrosis, beta thalassemia, actinic keratosis, hypertension, general inflammatory disorders, dry eye, ulcers, corneal fibrosis, wet age-related macular degeneration, psoriasis, wound closure, chronic kidney disease, renal fibrosis, systemic sclerosis, or chronic Chagas' heart disease. In some embodiments, the fibrotic condition is cardiac fibrosis or a condition associated with cardiac fibrosis, for example, valvular disease, arrhythmia (e.g., atrial fibrillation), myocardial remodeling (e.g., after infarction), cardiomyopathy (e.g., dilated, ischaemic or hypertrophic cardiomyopathy), restenosis (e.g. in-stent restenosis, post-angioplasty restenosis). In some embodiments, the fibrotic condition is Dupuytren's contracture.

In some embodiments, a fibrotic condition (e.g., pulmonary fibrosis) may be present with, may be caused by, and/or may be exacerbated by, a viral infection (concomitant with a viral infection). In some embodiments, the viral infection present may be an Orthomyxoviridae viral infection (e.g., an Influenza A viral infection or an Influenza B viral infection), a Pneumoviridae viral infection (e.g., a metapneumovirus viral infection (e.g., human metapneumovirus (HMPV) infection) or an orthopneumovirus infection (e.g., a respiratory syncytial virus (RSV) (e.g., a human respiratory syncytial virus (HRSV) infection (e.g., a human respiratory syncytial virus A2 (HRSV-A2) infection or a human respiratory syncytial virus B1 (HRSV-B1) infection)))), a Orthohepadnavirus viral infection (e.g., a Hepatitis B virus infection), Hepacivirus viral infection (e.g., a Hepatitis C virus infection), a Paramyxoviridae viral infection (e.g., a Respirovirus infection (e.g., a human parainfluenza virus type 1 (HPIV-1) infection or a human parainfluenza type 3 (HPIV-3) infection) or a Rubulavirus viral infection (e.g., a human parainfluenza virus type 2 (HPIV-2) infection or a human parainfluenza type 4 (HPIV-4) infection)), an Adenoviridae viral infection (e.g., a Mastadenovirus infection (e.g., a human adenovirus B (HAdV-B) infection or a human adenovirus C (HAdV-C) infection)), an Enterovirus viral infection (e.g., a Rhinovirus A infection, a Rhinovirus B infection, or a Rhinovirus C infection).

In some embodiments, treatment is provided for each and several of the fibrosis conditions described herein where each and several of the aforementioned viral infections is present as a comorbid condition, the treatment comprising administering one or more compounds described herein, for example, one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease, for example, each and several of those described herein, is carried out by administering two or more compounds described herein, for example, two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease comorbid with a viral infection, for example, each and several of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compounds described herein with one or two or more additional therapeutic agents). In some embodiments, combination treatment is provided by administering one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, treatment is provided for each and several of the fibrosis conditions described herein where each and several of these viral infections is present as an exacerbating condition, the treatment comprising administering one or more compounds described herein, for example, one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease present with an exacerbating viral infection, for example, each and several of those described herein, is carried out by administering two or more compounds described herein, for example, two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease present with an exacerbating viral infection, for example, one or more of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compounds described herein with one or two or more additional therapeutic agents). In some embodiments, combination treatment is provided by administering one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, treatment is provided for fibrosis present with each and several of these viral infections as a cause of the fibrosis, the treatment comprising administering one or more compounds described herein, for example, one ALK-5 inhibitor compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease present with a causative viral infection, for example, each and several of those described herein, is carried out by administering two or more compounds described herein, for example, two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease present with a causative viral infection, for example, one or more of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compounds described herein with one or two or more additional therapeutic agents). In some embodiments, combination treatment is provided by administering one ALK-5 inhibitor compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, a fibrotic condition (e.g., pulmonary fibrosis) may be present with, may be caused by, and/or may be exacerbated by, an inflammatory condition. As used herein, the terms "inflammatory disease", "inflammatory condition", and "inflammatory disease and/or condition" refer to disease or condition in a subject involving the response of one or more body tissues to stimuli recognized as harmful by the body. In some embodiments, an inflammatory condition is an autoimmune condition. Exemplary inflammatory conditions include non-alcoholic fatty liver disease (NAFLD), alcoholic steatohepatitis (ASH), non-alcoholic steatohepatitis (NASH), primary biliary cholangitis (PBC), primary sclerosing cholangitis, and autoimmune hepatitis. NAFLD is a condition in which fat is deposited in the liver due to causes other than excessive alcohol use, and NASH is an advanced form of NAFLD, wherein the liver is both enflamed and damaged. Aberrant damage repair in NASH can lead to cirrhosis. ASH is a condition in which the liver is enflamed and damaged associated with alcohol use, and it can include liver fibrosis and/or cirrhosis. PBC is an autoimmune disease of the liver, and aberrant repair of liver damage can lead to scarring, fibrosis, and/or cirrhosis. Primary sclerosing cholangitis can be characterized by inflammation and scarring of the bile ducts, which can lead to fibrosis and/or cirrhosis. Autoimmune hepatitis can cause inflammation of the liver, aberrant repair of which can lead to fibrosis and/or cirrhosis.

In some embodiments, treatment is provided for fibrosis present with each and several of these inflammatory conditions present as a comorbid condition of fibrosis, the treatment comprising administering one or more compounds described herein, for example, one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease comorbid with an inflammatory condition, for example, each and several of those described herein, is carried out by administering two or more compounds described herein, for example, two or more ALK-5 inhibitor compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease comorbid with an inflammatory condition, for example, one or more of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compounds described herein with one or two or more additional therapeutic agents). In some embodiments, combination treatment is provided by administering one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, treatment is provided for each of these inflammatory conditions present as an exacerbating condition of fibrosis, the treatment comprising administering one or more compounds described herein, for example, one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease present with an exacerbating inflammatory condition, for example, each and several of those described herein, is carried out by administering two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease present with an exacerbating inflammatory condition, for example, one or more of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compound described herein with one or two or more additional therapeutic agents). In some embodiments, combination treatment is provided by administering one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, treatment is provided for each of these inflammatory conditions present as a cause of the fibrosis, the treatment comprising administering one or more compounds described herein, for example, one ALK-5 inhibitor compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof. In some embodiments, treatment of a fibrotic disease present with a causative inflammatory condition, for example, each and several of those described herein, is carried out by administering two or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing. In some embodiments, treatment of a fibrotic disease present with a causative inflammatory condition, for example, one or more of those described herein, is carried out by administering a combination of therapeutic agents comprising one or more compounds described herein (for example, one or more compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any of the foregoing), in combination with one or more additional therapeutic agents (e.g., at least one compound described herein and at least one additional therapeutic agent, one or more compounds described herein with one or two or more additional therapeutic agents). In some embodiments, combination treatment is provided by administering one compound of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt thereof, and one or more additional therapeutic agents.

In some embodiments, the fibrotic condition is a fibrotic cancer.

Fibrotic cancers are also treatable according to the methods described herein. As used herein, a "fibrotic cancer" is a cancer associated with fibrosis. Fibrosis may precede (e.g., be causative of) or follow (e.g., be caused by) the cancer or treatment of the cancer in fibrotic cancers. Fibrosis may also or alternatively be present with the cancer in fibrotic cancers. Non-limiting examples of fibrotic cancers include myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans), gastric cancer, esophageal cancer, head and neck cancer, cervical cancer, vulvar cancer and hepatocellular cancer (e.g., hepatocellular carcinoma). In some embodiments, the fibrotic cancer is a solid tumor cancer (e.g., kidney, liver, lung, breast, ovarian, endometrial, uterine, and/or pancreatic cancer). In some embodiments, the fibrotic cancer is carcinoma of an internal organ (e.g., pancreas, lung, kidney, liver).

In some embodiments, the disease or condition is a fibrotic condition.

In some embodiments, the fibrotic condition is one or more of idiopathic pulmonary fibrosis, liver fibrosis, liver cirrhosis, nonalcoholic steatohepatitis, Peyronie's, cystic fibrosis, beta thalassemia, actinic keratosis, hypertension, general inflammatory disorders, dry eye, ulcers, corneal fibrosis, wet age-related macular degeneration, psoriasis, wound closure, chronic kidney disease, renal fibrosis, systemic sclerosis, and chronic Chagas' heart disease.

In some embodiments, the condition is idiopathic pulmonary fibrosis.

In some embodiments, the fibrotic condition is cardiac fibrosis or a condition associated with cardiac fibrosis, for example, valvular disease, arrhythmia (e.g., atrial fibrillation), myocardial remodeling (e.g., after infarction), cardiomyopathy (e.g., dilated, ischaemic or hypertrophic cardiomyopathy), restenosis (e.g., in-stent restenosis, post-angioplasty restenosis).

In some embodiments, the fibrotic condition is Dupuytren's contracture.

In pulmonary fibrosis, the fibrotic process is commonly considered the result of a recurrent injury to the alveolar epithelium followed by an uncontrolled proliferation of fibroblasts. In general, fibrosis progresses in three stages (illustrated for pulmonary fibrosis, but common across many fibrotic conditions): the injury stage ("Stage 1"), the epithelial-fibroblastic interaction stage ("Stage 2"), and the aberrant repair and fibrosis stage ("Stage 3"). In Stage 1, generally, the epithelium is damaged, and one or more of the following events can occur: epithelial damage, endothelial damage, for example, in pulmonary fibrosis, destruction of an alveolar capillary basilar membrane, vascular leak, platelet activation, and fibrin clot activation. In Stage 2, generally, fibroblasts begin to interact with the damaged epithelium, and one or more of the following events can occur: release of profibrotic cytokines, (myo)fibroblast recruitment, proliferation, and differentiation, provisional matrix formation, angiogenesis, and defective re-epithelialization. In Stage 3, generally, the epithelial damage is aberrantly repaired resulting in fibrosis, and one or more of the following events can occur: exaggerated extracellular matrix (ECM) accumulation, lack of matrix degradation, for example, in pulmonary fibrosis, progressive lung remodeling and honeycomb changes (in pulmonary fibrosis, the lung tissue comes to resemble a honeycomb).

Non-limiting examples of fibrotic diseases, disorders and conditions include cancer-associated fibrosis; lung fibrosis, commonly known as "scarring of the lungs" (e.g., pulmonary fibrosis, for example, idiopathic pulmonary fibrosis, acute exacerbation of idiopathic pulmonary fibrosis or familial pulmonary fibrosis); liver fibrosis (hepatic fibrosis, e.g., keloids, scleroderma, nephrogenic systemic fibrosis, bile duct fibrosis (biliary fibrosis), liver cirrhosis, for example, primary biliary cholangitis (biliary cirrhosis), primary sclerosing cholangitis); cardiac disease; cardiac fibrosis or restenosis (e.g., in-stent restenosis, post-angioplasty restenosis); vascular fibrosis; kidney fibrosis (renal fibrosis); skin fibrosis (cutaneous fibrosis or endometrial fibrosis, e.g., keloids, scleroderma, or nephrogenic systemic fibrosis); gastrointestinal fibrosis (e.g., Crohn's disease); bone marrow fibrosis (myelofibrosis); athrofibrosis (e.g., of the knee, the shoulder or another joint); Dupuytren's contracture; mediastinal fibrosis; Peyronie's disease; retroperitoneal fibrosis; systemic sclerosis; autoimmune hepatitis; nonalcoholic steatohepatitis; cystic fibrosis; beta-thalassemia; actinic keratosis; hypertension; chronic kidney disease; Chagas' heart disease; dry eye; ulcer; corneal fibrosis; wet age-related macular degeneration; chronic wound (failure to heal, close); psoriasis. In some embodiments, the fibrotic disease, disorder or condition is lung fibrosis, for example, pulmonary fibrosis, such as idiopathic pulmonary fibrosis, acute exacerbation of idiopathic pulmonary fibrosis or familial pulmonary fibrosis. In some embodiments, the fibrotic disease, disorder or condition is a cardiac disease, or cardiac fibrosis or restenosis, for example, in-stent restenosis, post-angioplasty restenosis.

Fibrosis may be associated with another disease, disorder or condition (e.g., inflammation, an inflammatory disease, disorder or condition, such as psoriasis, a proliferative disease, such as cancer, a viral or bacterial infection or the like) or may occur independently. For example, fibrosis may precede (e.g., be causative of) or follow (e.g., be caused by) another disease, disorder or condition. Fibrosis may also or alternatively be present, whether associated or not, with another disease, disorder or condition (e.g., inflammation, an inflammatory disease, disorder or condition, such as psoriasis, a proliferative disease, such as cancer, a viral or bacterial infection or the like), or may be present without a concomitant disease, disorder or condition (e.g., associated disease, disorder or condition). In some embodiments, the fibrosis is present without an associated disease, disorder or condition. In some embodiments, the fibrosis is present with an associated disease, disorder or condition.

Although the occurrence of fibrosis associated with another disease, disorder or condition is not uncommon, for example, the presence of cancer-associated fibrosis, the etiology of fibrosis is not well understood and fibrosis occurs also independently from and/or in the absence of other diseases, disorders or conditions. However, it is believed that similar mechanisms and signaling pathways are present in both fibrosis and many associated diseases, disorders or conditions affecting organs or tissues in which fibrosis is also present, for example, the presence of IPF with lung cancer. For example, it is believed that fibrosis along with many diseases with which it is often present, progress via the TGFβ protein and the signaling cascade implicated by overexpression of it, see for example, Ballester, B; et al., Idiopathic Pulmonary Fibrosis and lung Cancer: Mechanisms and Molecular targets, Int. J. Mol. Sci. 2019, 20, 593; doi:10.3390/ijms20030593.

Fibrosis can be comorbid with, caused by and/or exacerbated by an associated disease, disorder or condition (e.g., an infection, such as an infection described herein, such as a viral or bacterial infection; an inflammatory disease, disorder or condition, such as an inflammatory disease, disorder or condition described herein, such as psoriasis; or a proliferative disease, such as a proliferative disease described herein, such as cancer, in particular, fibrotic cancer). Thus, in some embodiments, a disease, disorder or condition associated with fibrosis is a comorbid, causative and/or exacerbating disease, disorder or condition. In some embodiments, the fibrosis is comorbid with the associated disease, disorder or condition. For example, fibrosis can be comorbid with an infection, for example, a viral or bacterial infection; an inflammatory disease, disorder or condition, such as an inflammatory disease, disorder or condition described herein, such as psoriasis; or a proliferative disease, such as a proliferative disease described herein, such as cancer, in particular, fibrotic cancer. In some embodiments, the fibrosis is caused by the associated disease, disorder or condition (e.g., the fibrosis is caused by an infection, for example, a viral or bacterial infection; an inflammatory disease, disorder or condition, such as an inflammatory disease, disorder or condition described herein, such as psoriasis; or a proliferative disease, such as a proliferative disease described herein, such as cancer). In some embodiments, the fibrosis is comorbid with and/or caused by the associated disease, disorder or condition (e.g., an infection, for example, a viral or bacterial infection; an inflammatory disease, disorder or condition, such as an inflammatory disease, disorder or condition described herein, such as psoriasis; or a proliferative disease, such as a proliferative disease described herein, such as cancer, in particular, fibrotic cancer). In some embodiments, the fibrosis is exacerbated by the associated disease, disorder or condition. For example, fibrosis can be exacerbated by an infection, for example, a viral or bacterial infection; an inflammatory disease, disorder or condition, such as an inflammatory disease, disorder or condition described herein, such as psoriasis; or a proliferative disease, such as a proliferative disease described herein, such as cancer, in particular, fibrotic cancer.

In some embodiments, the disease, disorder or condition associated with fibrosis is an infection (e.g., viral infection, bacterial infection). In further embodiments, the infection is a viral infection (concomitant with a viral infection). Non-limiting examples of viral infections include Orthomyxoviridae viral infection (e.g., an influenza A viral infection or an influenza B viral infection), a Pneumoviridae viral infection (e.g., a metapneumovirus viral infection, such as human metapneumovirus (HMPV) infection, or an orthopneumovirus infection, such as respiratory syncytial virus (RSV) (e.g., human respiratory syncytial virus (HRSV) infection, such as human respiratory syncytial virus A2 (HRSV-A2) infection or human respiratory syncytial virus B1 (HRSV-B1) infection)), a Orthohepadnavirus viral infection (e.g., a Hepatitis B viral infection), a Hepacivirus viral infection (e.g., a Hepatitis C virus infection), a Paramyxoviridae viral infection (e.g., a Respirovirus infection, such as a human parainfluenza virus type 1 (HPIV-1) infection or a human parainfluenza type 3 (HPIV-3) infection, or a Rubulavirus viral infection, such as a human parainfluenza virus type 2 (HPIV-2) infection or a human parainfluenza type 4 (HPIV-4) infection), an Adenoviridae viral infection (e.g., a Mastadenovirus infection, such as a human adenovirus B (HAdV-B) infection or a human adenovirus C (HAdV-C) infection) and an Enterovirus viral infection (e.g., a Rhinovirus A infection, a Rhinovirus B infection or a Rhinovirus C infection). The infection associated with fibrosis can be a comorbid, causative and/or exacerbating infection.

In some embodiments, the disease, disorder or condition associated with fibrosis is an inflammatory disease, disorder or condition. As used herein, "inflammatory disease, disorder or condition" refers to disease, disorder or condition involving the response of one or more of a subject's body tissues to stimuli recognized as harmful by the body. Non-limiting examples of inflammatory diseases, disorders or conditions include non-alcoholic fatty liver disease (NAFLD), alcoholic steatohepatitis (ASH), non-alcoholic steatohepatitis (NASH), primary biliary cholangitis (PBC), primary sclerosing cholangitis, autoimmune hepatitis, skin inflammation and psoriasis. The inflammatory disease, disorder or condition associated with fibrosis can be a comorbid, causative and/or exacerbating disease, disorder or condition.

In some embodiments, an inflammatory disease, disorder or condition is an autoimmune disease, disorder or condition, such as osteoarthritis, rheumatoid arthritis, pain, inflammatory bowel disease, a respiratory disorder or a skin disorder. In some embodiments, the inflammatory disease, disorder or condition is an inflammatory bowel disease, e.g., Crohn's disease, ulcerative colitis or irritable bowel syndrome. In some embodiments, the inflammatory disease, disorder or condition is a respiratory disorder, e.g., asthma, rhinitis, chronic obstructive pulmonary disease, bronchitis, nasal polyposis, nasal congestion, farmer's lung fibroid lung or cough. In some embodiments, the inflammatory disease, disorder or condition is a skin disorder, e.g., dermatitis, cutaneous eosinophilias, Lichen planus, urticaria, psoriasis, pruritus, angiodermas, corneal ulcer, chronic skin ulcer, conjunctivitis, vaculitides, uveitis or erythema.

In some embodiments, the disease, disorder or condition associated with fibrosis is a cancer, such as any of the cancers described herein, in particular, a fibrotic cancer. Stated otherwise, in some embodiments, the fibrosis is cancer-associated fibrosis. The cancer can be a comorbid, causative and/or exacerbating cancer. Alternatively, in some embodiments, the fibrosis is not associated with a cancer.

It will be appreciated that some fibroses can be associated with cancer (e.g., fibrotic cancer), but can also occur independently from and/or in the absence of the associated cancer. For example, IPF can be associated with lung cancer, but can also occur independently from and/or in the absence of lung cancer. Accordingly, in some embodiments, the fibrosis is present in the absence of cancer (e.g., a fibrotic cancer), for example, IPF is present in the absence of lung cancer.

Some embodiments comprise identifying a subject who has fibrosis or who is at risk of developing a fibrosis (e.g., due to an associated disease, disorder or condition, such as a comorbid, causative, or exacerbating disease, disorder or condition), and administering to the subject an effective amount (e.g., a therapeutically effective amount, prophylactically effective amount) of a compound of the present disclosure.

Administration of a compound of the present disclosure, alone or in combination with one or more additional therapeutic agents, including any of those described herein, can occur during a single stage of fibrosis (e.g., Stage 1, Stage 2, Stage 3), or can be divided across multiple stages of fibrosis (e.g., two stages, three stages). For example, a compound of the present disclosure can be administered during Stage 1, Stage 2 or Stage 3 of fibrosis, while one or more additional therapeutic agents can be administered during a different stage of the fibrosis. Alternatively, a compound of the present disclosure and one or more additional therapeutic agent(s) can be administered during all stages of the fibrosis.

In various embodiments, an amount effective to treat a fibrotic disease, disorder or condition is an amount effective to slow down or stop the progression of the fibrotic disease, disorder or condition, increase the survival time of a subject suffering with the fibrotic disease, disorder or condition (e.g., by at least 10%, 20%, 30%, 40%, 50%, 60%, 70%, 80%, 90%, or 100%, when compared with a subject not administered the therapy), increase the survival rate in a subject population (e.g., survival after being admitted to the intensive care unit increases by at least 10%, 20%, 30%, 40%, 50%, 60%, 70%, 80%, 90%, or 100% when compared with a subject population that was not administered the therapy), reduce the risk of a subject developing the fibrotic disease, disorder or condition when compared with a subject that was not administered the therapy, preserve organ function (e.g., lung function, liver function) when compared with a subject that was not administered the therapy, and/or prevent or reduce the risk of acute exacerbation of the fibrotic disease, disorder or condition when compared with a subject that was not administered the therapy.

Also provided herein are methods of inhibiting fibrosis in a tissue, comprising contacting the tissue (e.g., in vitro, ex vivo, in vivo) with a compound of the present disclosure (e.g., an effective amount of a compound of the present disclosure). In various embodiments, an effective amount is an amount effective to inhibit the formation or deposition of tissue fibrosis, and/or reduce the size, cellularity, composition, cellular or collagen content of a fibrotic lesion. In some embodiments, the tissue is in a subject (e.g., a human).

In some embodiments, a proliferative disease, such as cancer, is treated by targeting a tumor stromal cell (e.g., in a tumor microenvironment), such as a cancer-associated fibroblast (CAF), stellate cell or myofibroblast, and/or an immune cell, such as a tumor-associated immune cell (e.g., in the tumor-immune microenvironment), for example, to thereby modulate the tumor-stroma microenvironment and/or the tumor-immune microenvironment.

Cachexia is linked to chronic illness and manifests in involuntary weight loss (e.g., greater than 5% of pre-illness weight) resulting from the atrophy of skeletal muscle and adipose tissues. This condition is distinct from other conditions, like anorexia, where fat stores are depleted but muscle mass remains largely intact. Cachexia affects over half of cancer patients resulting in poor quality of life (fatigue and weakness) and can sometimes even compromise treatment strategies in some individuals. Myostatin, a transforming growth factor-beta (TGF-beta) super-family member, has been well characterized as a negative regulator of muscle growth and development. Without wishing to be bound by any particular theory, it is believed that blocking this pathway would potentially benefit cancer patients, specifically patients with late stage disease and metastasis where cachexia is prominent. Thus, in some embodiments, the disease or condition is cachexia (e.g. cancer cachexia).

Additionally, provided herein are methods of inhibiting tumor growth in a subject (e.g., a subject in need thereof), the methods comprising administering to the subject a therapeutically effective amount of a compound of Formula (I), or a pharmaceutically acceptable salt thereof, or a pharmaceutical composition thereof. Also provided herein are compounds of Formula (I), or a pharmaceutically acceptable salt thereof, and pharmaceutical compositions thereof, for use in inhibiting tumor growth. Also provided herein are uses of compounds of Formula (I), or a pharmaceutically acceptable salt thereof, and pharmaceutical compositions thereof, for the manufacture of a medicament for inhibiting tumor growth.

Also provided herein are methods for inhibiting activin receptor-like kinase (e.g., ALK-5) activity in vivo or in vitro, the methods comprising contacting the activin receptor-like kinase (e.g., ALK-5) with a compound of the disclosure, for example, one or more compounds of Formula (I) (II), (III), or (IV), or Table 1 or Table 4, or a pharmaceutically acceptable salt thereof, or a pharmaceutical composition thereof. Also provided herein are compounds of Formula (I) (II), (III), or (IV), or Table 1 or Table 4, or a pharmaceutically acceptable salt thereof, and pharmaceutical compositions thereof, for use in inhibiting activin receptor-like kinase (e.g., ALK-5) activity in vivo or in vitro. Also provided herein are uses of compounds of Formula (I) (II), (III), or (IV), or Table 1 or Table 4, or a pharmaceutically acceptable salt thereof, and pharmaceutical compositions thereof, for the manufacture of a medicament for inhibiting activin receptor-like kinase (e.g., ALK-5) activity in vitro or in vivo. In certain embodiments, inhibiting occurs in vivo in a subject. In certain embodiments, inhibiting occurs in vitro (e.g., in a cell line or biological sample). In certain embodiments, the methods and uses are for inhibiting ALK-5. In certain embodiments, inhibiting is selective for ALK-5, i.e., selective for ALK-5 over one or more other kinases (e.g., selective for ALK-5 over other activin receptor-like kinases). In certain embodiments, inhibiting is selective for ALK-5 over ALK-2.

The tumor microenvironment often favors tumor growth and survival by favoring cancer biology over healthy cellular function. In particular, "excluded" or "desert" phenotypes create optimal microenvironments for cancer cells to avoid immune surveillance, for the microenvironment to have high acidity and hypoxia, and for there to be high interstitial pressure. This tumor microenvironment prevents the beneficial effects of, for example, immunooncology agents, while poor perfusion and interstitial pressure hinder drug delivery.

"Desert phenotype," as used herein to describe a cancer, refers to an immune phenotype of a tumor characterized by absence or substantial absence of T cells within the tumor and at its margin(s). This phenotype may be caused by factors including, but not limited to, insufficient priming, defects in antigen presentation, and/or lack of antigen.

"Excluded phenotype" as used herein to describe a cancer, refers to an immune phenotype of a tumor characterized by T cells located only or substantially only at the margin(s) of the tumor. In an "excluded phenotype," T cells are absent or substantially absent from the tumor bed. This phenotype may be caused by factors including, but not limited to, stromal barriers, aberrant vasculature, lack of chemokines, oncogenic pathways, and/or hypoxia.

The tumor microenvironment can be beneficially modulated by promoting an infiltrated phenotype. "Infiltrated phenotype" and "immune-inflamed phenotype," as used herein to refer to a cancer, refer to an immune phenotype of a tumor characterized by T cells located throughout or substantially throughout the tumor bed. Promotion of this desirable phenotype may be affected, for example, by inhibiting TGFβ, increasing vascularization (e.g., angiogenesis), decreasing tumor induration, increasing antigen presentation, de-activating cancer-associated fibroblasts, increasing T cell infiltration into a tumor bed, or any combination thereof.

It has now been shown that compounds of the disclosure can modulate the tumor microenvironment (e.g., tumor-stroma microenvironment and/or tumor-immune microenvironment) as, for example, by promoting an infiltrated phenotype. Accordingly, in some embodiments, provided herein is a method for modulating (e.g., normalizing) a tumor microenvironment (e.g., tumor-stroma microenvironment and/or tumor-immune microenvironment) in vitro or in vivo (e.g., in a subject, such as a subject having a tumor), the method comprising contacting the tumor and/or the tumor microenvironment with an effective amount of a compound of the disclosure, for example, one or more compounds of Formula (I) (II), (III), or (IV), or Table 1 or Table 4, or a pharmaceutically acceptable salt thereof, or a pharmaceutical composition thereof. In some embodiments wherein modulating occurs in vivo in a subject in need thereof, the method comprises administering to the subject a therapeutically effective amount of the compound of the disclosure or the pharmaceutical composition thereof.

Also provided is a method for promoting immune infiltration (e.g., immune cell, such as T-cell, infiltration) into a tumor in vitro or in vivo (e.g., in a subject, such as a subject having a tumor), the method comprising contacting the tumor with an effective amount of a compound of the disclosure, for example, one or more compounds of Formula (I) (II), (III), or (IV), or Table 1 or Table 4, or a pharmaceutically acceptable salt thereof, or a pharmaceutical composition thereof. In some embodiments wherein the method occurs in vivo in a subject in need thereof, the method comprises administering to the subject a therapeutically effective amount of the compound of the disclosure or the pharmaceutical composition thereof.

Also provided herein are methods for targeting a tumor stromal cell or immune cell (e.g., tumor-associated immune cell), and/or (e.g., and thereby) modulating (e.g., normalizing) tumor microenvironment (e.g., tumor-stroma microenvironment and/or tumor-immune microenvironment) in vivo or in vitro, the methods comprising contacting a tumor stromal cell or an immune cell (e.g., a tumor-associated immune cell) with a compound of the disclosure, for example, one or more compounds of Formula (I) (II), (III), or (IV), or Table 1 or Table 4, or a pharmaceutically acceptable salt thereof, or a pharmaceutical composition thereof. Also provided herein are compounds of Formula (I) (II), (III), or (IV), or Table 1 or Table 4, or a pharmaceutically acceptable salt thereof, and pharmaceutical compositions thereof for use in targeting a tumor stromal cell or immune cell (e.g., tumor-associated immune cell), and/or (e.g., and thereby) modulating (e.g., normalizing) tumor microenvironment (e.g., tumor-stroma microenvironment and/or tumor-immune microenvironment) in vivo or in vitro. Also provided herein are uses of compounds of Formula (I) (II), (III), or (IV), or Table 1 or Table 4, or a pharmaceutically acceptable salt thereof, and pharmaceutical compositions thereof, for the manufacture of a medicament for targeting a tumor stromal cell or immune cell (e.g., tumor-associated immune cell), and/or (e.g., and thereby) modulating (e.g. normalizing) tumor microenvironment (e.g., tumor-stroma microenvironment and/or tumor-immune microenvironment) in vivo or in vitro. In certain embodiments, modulating occurs in vivo in a subject. In certain embodiments, modulating occurs in vitro (e.g., in a cell line or biological sample). In certain embodiments, the tumor stromal cell is a cancer-associated fibroblast (CAF), a stellate cell or a myofibroblast.

Also provided is a method for promoting tumor vascularization (e.g., angiogenesis) in vitro or in vivo (e.g., in a subject, such as a subject having a tumor), the method comprising contacting the tumor with an effective amount of a compound of the disclosure, for example, one or more compounds of Formula (I) (II), (III), or (IV), or Table 1 or Table 4, or a pharmaceutically acceptable salt thereof, or a pharmaceutical composition thereof. In some embodiments wherein the method occurs in vivo in a subject in need thereof, the method comprises administering to the subject a therapeutically effective amount of the compound of the disclosure or the pharmaceutical composition thereof.

In some embodiments, provided herein is a method for inhibiting metastasis of a cancer, the method comprising administering to the subject a compound as described herein, or a pharmaceutically acceptable salt thereof, or a pharmaceutical composition thereof.

Provided herein is a method of treating a fibrotic, inflammatory or proliferative disease or condition which is susceptible to inhibition of the TGFβ signaling pathway, the method comprising administering to a subject suffering from said fibrotic, inflammatory or proliferative disease or condition an amount of a compound, or a pharmaceutically acceptable salt form thereof, or a pharmaceutical composition thereof, as described herein, effective to inhibit TGFβ signaling.

Also provided herein is a method of suppressing TGFβ signaling in a subject suffering from a disease or condition which is promoted by TGFβ signaling, in particular TGF-β1 signaling, comprising administering an amount of at least one compound, or a pharmaceutically acceptable salt thereof, or a pharmaceutical composition thereof, as described herein, effective to sufficiently suppress said TGFβ signaling to alter the course of the disease or condition.

In some embodiments, provided herein is a method of treating a cancer, fibrotic disease, disorder or condition, inflammatory disease, disorder or condition, or proliferative disease, disorder or condition that is driven by, and/or utilizes the TGF-β signaling pathway for disease progression (e.g., driven by), the method comprising administering to the subject a compound as described herein, or a pharmaceutically acceptable salt thereof, or a pharmaceutical composition thereof.

In some embodiments, provided herein is a method of treating a cancer, fibrotic disease, disorder or condition, inflammatory disease, disorder or condition, or proliferative disease, disorder or condition that expresses or has mutant forkhead box L2 (FOXL2) and/or FOXL2, the method comprising administering to the subject a compound as described herein, or a pharmaceutically acceptable salt thereof, or a pharmaceutical composition thereof.

The FOXL2 gene encodes Forkhead box protein L2, which belongs to the FOX superfamily, and plays an important role in ovarian development and function. In postnatal ovaries FOXL2 regulates granulosa cell differentiation and supports growth of the pre-ovulatory follicies during adult life. A missense mutation in the FOXL2 gene, C134W, is found in adult granulosa cell tumors.

In some embodiments, provided herein is a method of treating a cancer, fibrotic disease, disorder or condition, inflammatory disease, disorder or condition, or proliferative disease, disorder or condition that is associated with an elevated level of phosphorylated SMAD 2 (pSMAD2) or alpha smooth muscle actin (α-SMA), the method comprising administering to the subject a compound as described herein, or a pharmaceutically acceptable salt thereof, or a pharmaceutical composition thereof.

Smads (or SMADs) comprise a family of structurally similar proteins that are the main signal transducers for receptors of the transforming growth factor beta (TGFβ) superfamily, which are critically important for regulating cell development and growth. Defects in Smad signaling can result in TGF-β resistance, causing dysregulation of cell growth. Deregulation of TGF-β signaling has been implicated in many cancer types, including pancreatic, colon, breast, lung, and prostate cancer. In some instances, low levels of CD31 are an indicator of deregulated TGF-β signaling pathway.

In some embodiments, the cancers described herein exhibit an excluded or desert phenotype.

Also provided herein is a method of enhancing the activity of one or more therapeutic agents for treating cancer in a subject, the method comprising administering to the subject a compound as described herein, or a pharmaceutically acceptable salt thereof, or a pharmaceutical composition thereof. In some embodiments, the method further comprises administering one or more additional therapeutic agents to the subject. In some embodiments, at least one of the additional therapeutic agents is an anti-cancer agent. In some embodiments, at least one of the additional therapeutic agents is a PD-1 or PD-L1 inhibitor. In some embodiments, at least one of the additional therapeutic agent is an immune checkpoint inhibitor.

Without wishing to be bound by any particular theory, it is believed that compounds of the disclosure, including the exemplified compounds, can normalize the tumor microenvironment and thereby improve blood vessel perfusion and drug delivery. Enhanced drug delivery is expected, in turn, to enhance the efficacy of a drug, such as an immunomodulator (e.g., immunooncology agent) or anti-cancer agent, including any immunomodulators or anti-cancer agents described herein.

In some embodiments, the ALK-5 inhibitor compounds described herein can be used to increase tumor vasculature. Accordingly, in other embodiments, the combination of the ALK-5 inhibitor compounds described herein can be used to increase the activity of other therapeutic agents. Without wishing to be bound by a particular theory, the ALK-5 inhibitor compounds described herein may improve blood flow to the tumor. In some embodiments, the combination described herein may have an additive effect. In yet other embodiments, the combination may have synergistic effects. In some embodiments, the ALK-5 inhibitor compounds described herein may be used to increase tumor vasculature, and are used in combination with one or more additional therapeutic agents. In an embodiment, this combination improves the efficacy of the therapeutic agent. In an embodiment, the therapeutic agent is an anti-cancer drug. In another embodiment, the anti-cancer drug is selected from any anti-cancer drug described herein. In an embodiment, the anti-cancer drug is selected from the taxane family. In an embodiment, the anti-cancer drug is taxol or abraxane. In some embodiments, the ALK-5 inhibitor being administered is selected from the compounds described in Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any thereof.

Accordingly, also provided herein are methods for modulating (e.g., normalizing) tumor microenvironment (e.g., tumor-stroma microenvironment and/or tumor-immune microenvironment) in vivo or in vitro, the methods comprising contacting a tumor with one or more of the exemplified compounds, for example, one or more compounds of Formula (I) (II), (III), or (IV), or Table 1 or Table 4, or a pharmaceutically acceptable salt thereof, or a pharmaceutical composition of the foregoing. Also provided herein are compounds of compounds of Formula (I) (II), (III), or (IV), or Table 1 or Table 4, and pharmaceutically acceptable salts thereof, and pharmaceutical compositions of the foregoing, for use in modulating (e.g., normalizing) tumor microenvironment (e.g., tumor-stroma microenvironment and/or tumor-immune microenvironment) in vivo or in vitro. Also provided herein are uses of compounds of Formula (I) (II), (III), or (IV), or Table 1 or Table 4, and pharmaceutically acceptable salts thereof, and pharmaceutical compositions of the foregoing, for the manufacture of a medicament for modulating (e.g., normalizing) tumor microenvironment (e.g., tumor-stroma microenvironment and/or tumor-immune microenvironment) in vivo or in vitro. In certain embodiments, the inhibition occurs in vivo in a subject. In certain embodiments, the inhibition occurs in vitro (e.g., in a cell line or biological sample).

Accordingly, in some embodiments, ALK-5 inhibitor compounds described herein can be used to modulate the tumor-immune microenviroment and increase CD8+ T cells, as, for example, by promoting an infiltrated phenotype. In other embodiments, the administration of the ALK-5 inhibitor compounds described herein can be used in combination with an immunomodulator (e.g., a CAR-T therapy, an immune checkpoint inhibitor, such as a PD-1, PD-L1 or CTLA4 inhibitor). In some embodiments, the immunomodulator is a CAR-T therapy, including any of the CAR-T therapies described herein. In some embodiments, the immunomodulator is an immune checkpoint inhibitor, for example, a PD-1, PD-L1 or CTLA4 inhibitor, including any of the immune checkpoint inhibitors described herein. In some embodiments, treatment comprises administering an immunomodulator and a therapeutically effective amount of one or more ALK-5 inhibitor compounds described herein, for example one or more ALK-5 inhibitor compounds of Formula (I) (II), (III), or (IV), or Table 1 or Table 4, for example, one or more of Ex-10, Ex-11, Ex-12, Ex-13, Ex-33, Ex-34, Ex-57, or Ex-58, or a pharmaceutically acceptable salt of any thereof.

Also provided herein are methods for increasing tumor vasculature or blood flow to a tumor or both, comprising contacting a tumor with a compound of the disclosure, for example, one or more compounds of Formula (I) (II), (III), or (IV), or Table 1 or Table 4, or a pharmaceutically acceptable salt thereof, or a pharmaceutical composition thereof. Also provided herein are compounds of Formula (I) (II), (III), or (IV), or Table 1 or Table 4, or a pharmaceutically acceptable salt thereof, and pharmaceutical compositions thereof, for use in increasing tumor vasculature or blood flow to a tumor or both. Also provided herein are uses of compounds of Formula (I) (II), (III), or (IV), or Table 1 or Table 4, or a pharmaceutically acceptable salt thereof, and pharmaceutical compositions thereof, for increasing tumor vasculature or blood flow or both. In certain embodiments, the tumor is in a subject. In certain embodiments, the tumor is ex vivo.

Therapeutic agents (e.g., compounds of the disclosure) and pharmaceutical compositions thereof can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen. In some embodiments, a therapeutic agent (e.g., a compound of the disclosure) is administered orally. In some embodiments, a therapeutic agent (e.g., compound of the disclosure) is administered intravenously. Therapeutic agents (e.g., compounds of the disclosure) can be administered in any of the dosages described herein.

Combination Therapies

The compounds of the disclosure can be administered as a monotherapy. Besides administration as monotherapy, the compounds of the disclosure, including the exemplified compounds and pharmaceutically acceptable salts thereof, and pharmaceutical compositions thereof, can be administered in combination with other therapeutic agents and/or treatment modalities. Accordingly, in some embodiments, the methods further comprise administering to the subject one or more additional therapies (e.g., therapeutic agents). Suitable additional therapies (e.g., therapeutic agents) for use in the methods, compositions and combinations disclosed herein include those discussed herein.

The term "combination therapy" refers to the administration of two or more therapeutic agents to treat a disease, disorder or condition described herein. Such administration encompasses co-administration of the therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Such administration also encompasses use of each type of therapeutic agent in a sequential manner, either at approximately the same time or at different times. A compound of the disclosure, such as an exemplified compound, or a pharmaceutically acceptable salt thereof, or a composition thereof, and an additional therapeutic agent(s) can be administered via the same administration route or via different administration routes. Powders and/or liquids may be reconstituted or diluted to a desired dose prior to administration. Typically, the treatment regimen will provide beneficial effects of the drug combination in treating the diseases, conditions or disorders described herein.

In some embodiments, the compound of the disclosure and the additional therapy(ies) are co-administered, e.g., in a simultaneous or substantially simultaneous manner. In some embodiments, the compound of the disclosure and the additional therapy(ies) are administered sequentially, either at approximately the same time or at different times. For example, the compound of the disclosure can be administered before the additional therapy(ies). Or, the compound of the disclosure can be administered after the additional therapy(ies).

In some embodiments, a therapy for use in combination with a compound of the disclosure provides an agent known to modulate other pathway(s) than is(are) modulated by the compound of the disclosure, or other component(s) (e.g., enzymes) of the same pathway(s), as is (are) modulated by the compound of the disclosure. The compounds of Formula (I) (II), (III), or (IV), or Table 1 or Table 4, or a pharmaceutically acceptable salt thereof, or a composition thereof, can be administered in combination with one or more additional therapies (e.g., therapeutic agents), for example, that improve the activity, potency and/or efficacy in treating a disease in a subject in need thereof, in preventing a disease in a subject in need thereof, in reducing the risk to develop a disease in a subject in need thereof, and/or in inhibiting the activity of a protein kinase in a subject or cell; improve bioavailability; improve safety; reduce drug resistance; reduce and/or modify metabolism; inhibit excretion; and/or modify distribution in a subject or cell of the compounds of Formula (I) (II), (III), or (IV), or Table 1 or Table 4, or a pharmaceutically acceptable salt thereof, or a composition thereof. It will also be appreciated that the additional therapy(ies) employed may achieve a desired effect for the same disorder, and/or it may achieve different effects. In one aspect, a combination therapy includes but is not limited to a combination of a compound described herein and a chemotherapeutic agent(s), therapeutic antibody(ies), and/or radiation treatment, for example, to provide a synergistic or additive therapeutic effect.

When administered in combination with another therapy, a compound of the disclosure, such as an exemplified compound, or a pharmaceutically acceptable salt thereof, or a composition thereof, can be administered before, after or concurrently with the other therapy (e.g., an additional therapeutic agent(s)). When two or more therapeutic agents are co-administered simultaneously (e.g., concurrently), the compound of the disclosure, such as an exemplified compound, or a pharmaceutically acceptable salt thereof, and other therapeutic agent(s) can be in separate formulations or the same formulation. Alternatively, the compound of the disclosure, such as an exemplified compound, or a pharmaceutically acceptable salt thereof, or a composition thereof, and other therapy can be administered sequentially (e.g., as separate compositions) within an appropriate time frame as determined by a skilled clinician (e.g., a time sufficient to allow an overlap of the pharmaceutical effects of the compound of the disclosure, such as the exemplified compound, or a pharmaceutically acceptable salt thereof, or a composition thereof, and the other therapy).

Additional therapeutic agents include therapeutically active agents. Therapeutic agents also include prophylactically active agents. Therapeutic agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional therapeutic agent may be administered at a dose and/or on a time schedule determined for that therapeutic agent. The additional therapeutic agents may also be administered together with each other and/or with the compound or composition described herein in a single dose or administered separately in different doses. The particular combination to employ in a regimen will take into account, for example, compatibility of the compound described herein with the additional therapeutic agent(s) and/or the desired therapeutic and/or prophylactic effect to be achieved. In general, it is expected that the additional therapeutic agent(s)

in combination be utilized at levels that do not exceed the levels at which they are utilized individually. In some embodiments, the levels utilized in combination will be lower than those utilized individually.

In certain embodiments, the additional therapeutic agent is selected from the group consisting of anti-metabolites, DNA-fragmenting agents, DNA-crosslinking agents, intercalating agents, protein synthesis inhibitors, topoisomerase I poisons, (e.g., camptothecin or topotecan), topoisomerase II poisons, microtubule-directed agents, kinase inhibitors, hormones, and hormone antagonists.

In some embodiments, treatment of a proliferative disease, for example, a cancer, is carried out using invention compound of the disclosure, for example, one or more compounds of Formula (I) (II), (III), or (IV), or Table 1 or Table 4, or a pharmaceutically acceptable salt thereof, for example, one or more of Ex-10, Ex-11, Ex-12, Ex-13, Ex-33, Ex-34, Ex-57, or Ex-58, or a pharmaceutically acceptable salt thereof, and one or more immunooncology (IO) agents.

Examples of therapies for use in combination with a compound of the present disclosure (e.g., in combination therapy, in a pharmaceutical combination) include standard of care therapies and/or regimens (e.g., standard of care agents), such as first-line standard of care therapies (e.g., chemotherapies) or last-line standard of care therapies (e.g., chemotherapies). Standard of care therapies are therapies that a clinician should use for a certain type of patient, illness and/or clinical circumstance. Often, organizations such as National Comprehensive Cancer Network (NCCN) publish guidelines and/or treatment algorithms setting forth best practices for treatment of certain patients, illnesses and/or clinical circumstances. See nccn.org. These guidelines often establish, set forth and/or summarize standard of care therapies.

In some embodiments, a compound of the disclosure is administered in combination with a standard of care therapy for fibrosis and/or symptoms of fibrosis. Non-limiting examples of standard of care therapies for fibrosis include nintedanib, pirfenidone and oxygen therapy. In some embodiments, a compound of the disclosure is administered in combination with nintedanib or pirfenidone, or a pharmaceutically acceptable salt thereof. In some embodiments, a compound of the disclosure is administered in combination with oxygen therapy.

In some embodiments, a compound of the disclosure is administered in combination with a standard of care therapy for ovarian cancer. For example, non-limiting examples of standard of care therapies for ovarian cancer include a platinum analogue (e.g., cisplatin, paclitaxel, carboplatin) or a combination including a platinum analogue (e.g., docetaxel and carboplatin; paclitaxel and carboplatin; carboplatin and liposomal doxorubicin (dox); paclitaxel, carboplatin and bevacizumab (bev); carboplatin and gemcitabine (gem)/ (bev); carboplatin, liposomal dox and bev; carboplatin, paclitaxel and bev; cisplatin and gemcitabine; oxaliplatin); altretamine; capecitabine; ifosfamide; irinotecan; melphalan; paclitaxel (e.g., albumin-bound paclitaxel); pemetrexed; or vinorelbine. Non-limiting examples of standard of care therapies for ovarian cancer also include a targeted therapy, such as an antibody therapy (e.g., bevacizumab); a PARP inhibitor (e.g., olaparib, rucaparib, niraparib, veliparib, talazoparib); a tyrosine kinase inhibitor (TKI) (e.g, pazopanib); an immunotherapy; an immune checkpoint inhibitor (e.g., PD-1 or PD-L1 inhibitor); pembrolizumab; or a hormone therapy (e.g., tamoxifen, anastrozole, exemestane, letrozole, an LHIRH agonist, such as leuprolide acetate, megestrol acetate). Non-limiting examples of standard of care therapies for ovarian cancer further include a hormone therapy (e.g., anastrozole, exemestane, letrozole, leuprolide acetate, megestrol acetate, tamoxifen). Non-limiting examples of standard of care therapies for ovarian cancer additionally include cyclophosphamide; etoposide; sorafenib; or vinorelbine.

In some embodiments, a compound of the disclosure is administered in combination with a standard of care therapy for pancreatic cancer. Non-limiting examples of standard of care therapies for pancreatic cancer include FOLFIRINOX (a chemotherapy regimen made up of folinic acid, bolus fluorouracil, irinotecan and oxaliplatin); modified FOLFIRINOX regimen (a chemotherapy regimen made up of folinic acid, continuous infusion fluorouracil, irinotecan and oxaliplatin); gemcitabine and nab-paclitaxel; gemcitabine and capecitabine; olaparib; gemcitabine and erlotinib; gemcitabine, docetaxel and capecitabine; larotrectinib; pembrolizumab; gemcitabine; and the triple combination of nab-paclitaxel, gemcitabine and cisplatin.

In some embodiments, a compound of the disclosure is administered in combination with a standard of care therapy for prostate cancer, including castration resistant prostrate cancer. Non-limiting examples of standard of care therapies for prostate cancer include PARP inhibitors (e.g., olaparib, rucaparib, niraparib, veliparib, talazoparib), LHRH agonists (e.g., goserelin acetate, histrelin acetate, leuprolide acetate, and triptorelin pamoate); LHRH antagonists (e.g., degarelix); anti-androgen receptors (e.g., bicalutamide, flutamide, nilutamide, enzalutamide, apalutamide, darolutamide); corticosteroids (e.g., prednisone, methylprednisolone, hydrocortisone, dexamethasone); estrogens (e.g., diethylstilbestrol); androgen synthesis inhibitors (e.g., ketoconazole, abiraterone acetate); and androgen deprivation therapies.

In some embodiments, a compound of the disclosure is administered in combination with a standard of care therapy for multiple myeloma. Non-limiting examples of standard of care therapies for multiple myeloma include proteasome inhibitors such as bortezomib, carfilzomib and marizomib.

In some embodiments, a compound of the disclosure is administered in combination with radiation therapy. Non-limiting examples of radiation therapy include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At211, I131, I125, Y90, Re186, Re188, Sm153, Bi212, P32, and radioactive isotopes of Lu). Suitable radiation sources for use as a cell conditioner include both solids and liquids. By way of non-limiting example, the radiation source can be a radionuclide, such as I125, I131, Yb169, Ir192 as a solid source, I125 as a solid source, or other radionuclides that emit photons, beta particles, gamma radiation, or other therapeutic rays. The radioactive material can also be a fluid made from any solution of radionuclide(s), e.g., a solution of I125 or I131, or a radioactive fluid can be produced using a slurry of a suitable fluid containing small particles of solid radionuclides, such as Au198, Y90. Moreover, the radionuclide(s) can be embodied in a gel or radioactive microspheres.

Without being limited by any theory, a compound of the disclosure can render abnormal cells more sensitive to treatment with radiation for purposes of killing and/or inhibiting the growth of such cells. Accordingly, some embodiments include a method for sensitizing abnormal cells in a mammal to treatment with radiation which comprises administering to the mammal an amount of a compound as described herein, which amount is effective in sensitizing abnormal cells to treatment with radiation. The amount of a compound of the disclosure in this method can be determined according to the means for ascertaining effective amounts of such compounds described herein.

In some embodiments, standard of care therapy includes radiation therapy.

DNA damaging agents can also be used in combination with a compound of the present disclosure. Non-limiting examples of DNA damaging agents include radiation, topoisomerase inhibitors, PARP inhibitors, DNA crosslinking agents and standard of care agents that induce DNA damage, such as DNA crosslinking agents. Particular non-limiting examples of DNA damaging agents include abraxane, gemcitabine, paclitaxel and temozolomide. As used herein, "DNA damaging agent" refers to any agent that directly or indirectly damages DNA in such a way that homologous recombination could repair the damage. Non-limiting examples of DNA damaging agents are DNA damaging chemicals, chemotherapeutic agents, radiochemotherapy and ionizing or ultraviolet radiation. Non-limiting examples of DNA damaging chemotherapeutic agents include alkylating agents, nitrosoureas, anti-metabolites, plant alkaloids, plant extracts and radioisotopes. Non-limiting examples of DNA damaging chemotherapeutic agents also include DNA-damaging drugs, for example, 5-fluorouracil (5-FU), capecitabine, gemcitabine, temozolomide, S-1 (Tegafur, 5-chloro-2,4-dihydroxypyridine and oxonic acid), 5-ethynyluracil, arabinosylcytosine (ara-C), 5-azacytidine (5-AC), 2',2'-difluoro-2'-deoxycytidine (dFdC), purine antimetabolites (e.g., mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinomycin D, topoisomerase inhibitors (e.g., non-intercalating topoisomerase inhibitors such as epipodophyllotoxins (etoposide or VP16, teniposide or VM-26)), PARP inhibitors, podophylotoxin, bleomycin (Blea), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Radiation, e.g., ultraviolet (UV), infrared (IR), or α-, β-, or γ-radiation, is also a DNA damaging agent.

In some embodiments, standard of care therapy includes a DNA damaging agent, such as a DNA crosslinking agent.

Agents that induce endoplasmic reticulum (ER) stress can also be used in combination with a compound of the present disclosure. Non-limiting examples of agents that induce ER stress include agents that increase levels of reactive oxygen species (ROS) (e.g., napabucasin), chaperone inhibitors, HSP90 inhibitors, HSP70 inhibitors, PDI inhibitors and proteasome inhibitors. Further non-limiting examples of agents that induce ER stress include GSK2606414, GSK2656157, STF-083010, tyrosine kinase inhibitor (e.g., sorafenib), phosphor-eif2α phosphatase (e.g., Sal003), diindolylmethane derivatives, proteasome inhibitors (e.g., bortezomib), levistolide A, andrographolide, tolfenamic acid, cantharidin, carnosic acid, casticin, cryptotanshinone, curcumin, flavokawain B, fucoidan, 2-3,4-dihydroxyphenylethanol, 7-dimethoxyflavone, SMIP004 (N-(4-butyl-2-methyl-phenylacetamide), licochalcone A, neferine, paeonol, pardaxin, parthenolide, piperine, polyphenon E, polyphyllin D, resveratrol, dehydrocostuslactone, γ-tocotrienol, Ω-hydroxyundec-9-enoic acid, ampelopsin, ardisianone, genistein, guttiferone H, guggulsterone, marchantin M, sarsasapogenin, saxifragifolin, prodigiosin, quercetin, honokiol, brefeldin A, A-tocopheryl succinate, verrucarin A, vitamin E succinate, ultrafine and zerumbone. See, for example, Walczak, A., et al. *Oxidative Medicine and Cellular Longevity Volume* 2019, Article ID 5729710, the entire content of which is incorporated herein by reference.

In certain embodiments, a compound as described herein is administered to a subject in need thereof in combination with a B-cell receptor signaling antagonist (e.g., a Bruton's tyrosine kinase (BTK) inhibitor, such as Ibrutinib). Accordingly, methods of the present disclosure include methods for treating cancer comprising administering an effective amount of a compound as described herein and a Bruton's tyrosine kinase (BTK) inhibitor to a subject in need thereof. The administration may be before, concurrently or after administration of the B-cell receptor signaling antagonist (e.g., the BTK inhibitor).

In some embodiments, a compound as described herein and BTK inhibitor are co-administered. In other embodiments, a compound as described herein is administered after the BTK inhibitor. In still different embodiments, a compound as described herein is administered before the BTK inhibitor.

In various embodiments, the BTK inhibitor is Ibrutinib. In some particular embodiments, the cancer is chronic lymphocytic leukemia (CLL), small lymphocytic lymphoma (SLL), or both. In some embodiments, the subject has received a prior treatment regimen for CLL, SLL, or both. In some embodiments, the subject was refractory after the prior treatment regimen, the subject has relapsed CLL, SLL, or both after a response to the prior treatment regimen, or the subject has detectable minimal residual disease (MRD).

In another embodiment, a compound as described herein, is administered to a subject in need thereof in combination with a Bcl-2 inhibitor, such as venetoclax. The administration may be before, concurrently or after administration of the Bcl-2 inhibitor. In certain embodiments the subject is insensitive to treatment with a Bcl-2 inhibitor, is ineligible for treatment with a Bcl-2 inhibitor or has relapsed after treatment with a Bcl-2 inhibitor. In one specific embodiment, a compound as described herein is administered to a subject in need thereof in combination with a Bcl-2 inhibitor, such as venetoclax for treatment of leukemia (e.g., CLL, SLL, or both).

Immunomodulators of particular interest for use in combination with compounds of the present disclosure include: afutuzumab (available from ROCHE®); pegfilgrastim (NEULASTA®); lenalidomide (CC-5013, REVLIMID®); thalidomide (THALOMID®); actimid (CC4047); and IRX-2 (mixture of human cytokines including interleukin 1, interleukin 2, and interferon γ, CAS 951209-71-5, available from IRX Therapeutics).

Chimeric Antigen Receptor T-Cell (CAR-T) therapies of particular interest for use in combination with compounds of the present disclosure include: Tisagenlecleucel (Novartis), Axicabtagene ciloleucel (Kite), and Tocilizumab and Atlizumab (Roche).

In another embodiment, a compound as described herein is administered to a subject in need thereof in combination with an immunomodulator (e.g., a CAR-T therapy, an immune checkpoint inhibitor, such as a PD-1, PD-L1 or CTLA4 inhibitor). In some embodiments, the immunomodulator is a CAR-T therapy, including any of the CAR-T therapies described herein. In some embodiments, the immunomodulator is an immune checkpoint inhibitor, for example, a PD-1, PD-L1 or CTLA4 inhibitor, including any of the immune checkpoint inhibitors described herein. Without wishing to be bound by any particular theory, it is believed that compounds of the disclosure, such as the exemplified compounds, can improve blood vessel perfusion to a tumor and thereby enhance drug delivery to the tumor. Enhanced drug delivery is expected, in turn, to enhance the efficacy of a drug, such as an immunomodulator (e.g., immunooncology agent), including any immunomodulators described herein, for example, by making the tumor more susceptible to circulating drug.

In still another embodiment, a compound described herein, is administered to a subject in need thereof in combination with an immune checkpoint inhibitor (e.g., a PD-1 inhibitor (such as Pembrolizumab or Nivolumab), a PD-L1 inhibitor (such as Atezolizumab, Avelumab, or Durvalumab), a CTLA-4 inhibitor, a LAG-3 inhibitor, or a Tim-3 inhibitor). Accordingly, methods of the present disclosure include methods for treating cancer comprising administering an effective amount of a compound described herein and an immune checkpoint inhibitor to a subject in need thereof. The administration of a compound described herein may be before, concurrently or after administration of the immune checkpoint inhibitor (e.g., a PD-1 inhibitor (such as pembrolizumab or nivolumab), a PD-L1 inhibitor (such as atezolizumab, avelumab, or durvalumab), a CTLA-4 inhibitor, a LAG-3 inhibitor, or a Tim-3 inhibitor).

In some embodiments, a compound described herein and an immune checkpoint inhibitor are co-administered. In other embodiments, a compound described herein is administered after the immune checkpoint inhibitor. In still different embodiments, a compound described herein is administered before the immune checkpoint inhibitor.

Immune checkpoint inhibitors of interest for use in combination with compounds of the present disclosure include: PD-1 inhibitors, such as pembrolizumab (KEYTRUDA®), Pembrolizumab (also known as Lambrolizumab, MK-3475, MK03475, SCH-900475, or KEYTRUDA®). Pembrolizumab and other anti-PD-1 antibodies are disclosed in Hamid, O. et al. (2013) New England Journal of Medicine 369 (2): 134-44, U.S. Pat. No. 8,354,509, and WO 2009/114335, incorporated by reference in their entirety. nivolumab (OPDIVO®), Nivolumab (also known as MDX-1106, MDX-1106-04, ONO-4538, BMS-936558, or OPDIVO®). Nivolumab (clone 5C4) and other anti-PD-1 antibodies are disclosed in U.S. Pat. No. 8,008,449 and WO 2006/121168, incorporated by reference in their entirety.

Immune checkpoint inhibitors of interest for use in combination with compounds of the present disclosure also include PD-1 inhibitors, such as cemiplimab (LIBTAYO®), spartalizumab (PDR001), Pidilizumab (CureTech), MEDI0680 (Medimmune), cemiplimab (REGN2810), dostarlimab (TSR-042), PF-06801591 (Pfizer), tislelizumab (BGB-A317), camrelizumab (INCSHR1210, SHR-1210), and AMP-224 (Amplimmune); AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZM009 (Livzon), HLX-10 (Henlius Biotech), MEDI0680 (Medimmune), PDF001 (Novartis), PF-06801591 (Pfizer), Pidilizumab (CureTech), REGN2810 (Regeneron), TSR-042 (Tesaro) also known as ANBO11, or CS1003 (CStone Pharmaceuticals). MEDI0680 (Medimmune), is also known as AMP-514. MEDI0680 and other anti-PD-1 antibodies are disclosed in U.S. Pat. No. 9,205,148 and WO 2012/145493, incorporated by reference in their entirety. Pidilizumab is also known as CT-011. Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entirety. Other examples of PD-1 inhibitors include pembrolizumab (also known as Lambrolizumab, MK-3475, MK03475, SCH-900475, or KEYTRUDA®) and other anti-PD-1 antibodies (as disclosed in Hamid, O. et al. (2013) New England Journal of Medicine 369 (2): 134-44, U.S. Pat. No. 8,354,509, and WO 2009/114335, incorporated by reference in their entirety), nivolumab (also known as MDX-1106, MDX-1106-04, ONO-4538, BMS-936558, or OPDIVO®) and other anti-PD-1 antibodies (as disclosed in U.S. Pat. No. 8,008,449 and WO 2006/121168, incorporated by reference in their entirety), cemiplimab (LIBTAYO®), spartalizumab (PDR001), pidilizumab (CureTech), MEDI0680 (Medimmune), cemiplimab (REGN2810), dostarlimab (TSR-042), PF-06801591 (Pfizer), sinitilimab, toripalimab, tislelizumab (BGB-A317), camrelizumab (INCSHR1210, SHR-1210), AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZM009 (Livzon), HLX-10 (Henlius Biotech), MEDI0680 (Medimmune), PDF001 (Novartis), PF-06801591 (Pfizer), Pidilizumab (CureTech) also known as CT-011 and other anti-PD-1 antibodies (as disclosed in Rosenblatt, J. et al. (2011) J Immunotherapy 34(5): 409-18, U.S. Pat. Nos. 7,695,715, 7,332,582, and 8,686,119, incorporated by reference in their entirety), REGN2810 (Regeneron), TSR-042 (Tesaro) also known as ANBO11, or CS1003 (CStone Pharmaceuticals). MEDI0680 (Medimmune), is also known as AMP-514. MEDI0680 and other anti-PD-1 antibodies are disclosed in U.S. Pat. No. 9,205,148 and WO 2012/145493, incorporated by reference in their entirety. Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety. In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

PD-L1 inhibitors, such as atezolizumab (TECENTRIQ®), avelumab (BAVENCIO®), durvalumab (IMFINZI®), FAZ053 (Novartis), and BMS-936559 (Bristol-Myers Squibb); and drugs that target CTLA-4, such as ipilimumab (YERVOY®). PD-L1 inhibitors, such as atezolizumab (also known as MPDL3280A, RG7446, R05541267, YW243.55.570, or TECENTRIQ®) and other anti-PD-L1 antibodies as disclosed in U.S. Pat. No. 8,217,149, incorporated by reference in its entirety, avelumab (BAVENCIO® also known as MSB0010718C) and other anti-PD-L1 antibodies as disclosed in WO 2013/079174, incorporated by reference in its entirety, durvalumab (IMFINZI® or MEDI4736) and other anti-PD-L1 antibodies as disclosed in U.S. Pat. No. 8,779,108, incorporated by reference in its entirety), FAZ053 (Novartis), and BMS-936559 (Bristol-Myers Squibb). In certain embodiments, the PD-L1 inhibitor is KN035 (Alphamab; 3DMed; Ascletis Pharma), Envafolimab (TRACON Pharmaceuticals), BMS 936559 (Bristol-Myers Squibb), CS1001 (CStone Pharmaceuticals, Ligand Pharmaceuticals), CX-072 (CytomX Therapeutics), FAZ053 (Novartis), SHR-1316 (Hengrui Medicine), TQB2450 (Chiatai Tianqing), STI-A1014 (Zhaoke Pharm; Lee's Pharm, Lonza, Sorrento Therapeutics, NantWorks), LYN00102 (Lynkcell), A167 (Harbour BioMed, Kelun Group), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety. In certain embodiments, the PD-L1 inhibitor is Cosibelimab (Fortress Biotech), LY3300054 or Iodapolimab (Eli Lilly), GS-4224 (Gilead Sciences), STI-A1015 (Yuhan, Sorrento Therapeutics), BCD-135 (BIOCAD), Cosibelimab (Dana-Farber Cancer Institute, TG Therapeutics), APL-502 (Apollomics), AK106 (Akeso Biopharma), MSB2311 (Transcenta Holding), TG-1501 (TG Therapeutics), FAZ053 (Novartis). In certain embodiments, the PD-L1 inhibitor is MT-6035 (Molecular Templates), Icaritin and ZKAB001 (Lonza, Lee's Pharmaceutical Holdings, Sorrento Therapeutics, Shenogen Pharma Group), TRIDENT Antibody (MacroGenics, Zai Lab), YBL-007 (Anh-Gook Pharmaceutical, Y-Biologics), HTI-1316 (Hengrui Therapeutics), PD-L1 Oncology Project (Weizmann Institute of Sciences), JS003 (Shanghai Junshi Biosciences), ND021 (Numab Therapeutics, CStone Pharmaceuticals), Toca 521 (Tocagen), STT01 (STCube). In certain embodiments, the PD-L1 inhibitor is DB004 (DotBio), MT-5050 (Molecular Templates), KD036 (Kadmon). In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

In some embodiments, the immune checkpoint inhibitor is a cytotoxic T-lymphocyte-associated modulator. In some embodiments, the immune checkpoint inhibitor targets CTLA-4, such as ipilimumab (YERVOY®), tremelimumab, ALPN-202 (Alpine Immune Sciences), RP2 (Replimune), BMS-986249 (Bristol-Myers Squibb), BMS-986218 (Bristol-Myers Squibb), zalifrelimab (Agenus, Ludwig Institute for Cancer Research, UroGen Pharma, Recepta Biopharma), BCD-217 (BIOCAD), Onc-392 (Pfizer, OncoImmune), IBI310 (Innovent Biologics), KN046 (Alphamab), MK-1308 (Merck & Co), REGN4659 (Regeneron Pharmaceuticals), XmAb20717 (Xencor), XmAb22841 (Xencor), Anti-CTLA-4 NF (Bristol-Myers Squibb), MEDI5752 (AstraZeneca), AGEN1181 (Agenus), MGD019 (MacroGenics), ATOR-1015 (Alligator Bioscience), BCD-145 (BIOCAD), PSB205 (Sound Biologics), CS1002 (CStone Pharmaceuticals), ADU-1604 (Aduro Biotech), PF-06753512 (Pfizer), BioInvent-Transgene Research Program (Transgene), AGEN2041 (Agenus, Recepta Biopharam), ATOR-1144 (Alligator Bioscience), CTLA-4 Research Project (Sorrento Therapeutics), PD-L1/CTLA-4 Research Project (Sorrento Therapeutics), HLX13 (Shanghai Henlius Biotech), ISA203 (ISA Pharmaceuticals), PRS-300 Series A (Pieris Pharmaceuticals), BA3071 (BioAtla), CTLA4 Cancer Research Program (Biosortia Pharmaceuticals), RP3 (Replimune), CG0161 (Cold Genesys), APL-509 (Apollomics, JSR), AGEN2041 (Ludwig Institute for Cancer Research), APC 101 (Advanced Proteome), CTLA-4 Inhibitor (Advanced Proteome), BA3071 (BeiGene), BPI-002 (BeyondSpring Pharmaceuticals), CTLA-4 Antibody (Tikcro Technologies), Immuno-Oncology Research Program II (OliPass), PBP1701 (Prestige BioPharma), DB002 (DotBio), DB003 (DotBio), OR-2299 (OncoResponse), NK044 (Alphamab). In certain embodiments, the CTLA-4 inhibitor is ipilimumab. In other embodiments, the CTLA4 inhibitor is tremelimumab.

Immune checkpoint inhibitors of interest for use in combination with compounds described herein also include: LAG-3 inhibitors. In some embodiments, the LAG-3 inhibitor is chosen from LAG525 (Novartis), BMS-986016 (Bristol-Myers Squibb), or TSR-033 (Tesaro). In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420. In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule is IMP761 (Prima BioMed). Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety. In one embodiment, the anti-LAG-3 inhibitor is a soluble LAG-3 protein, e.g., IMP321 (Prima BioMed), e.g., as disclosed in WO 2009/044273, incorporated by reference in its entirety.

Immune checkpoint inhibitors of interest for use in combination with compounds described herein also include: Tim-3 inhibitors. In some embodiments, the TIM-3 inhibitor is MGB453 (Novartis) or TSR-022 (Tesaro). In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274. In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2. Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In various embodiments, the immune checkpoint inhibitor is a PD-1 inhibitor. In specific embodiments, the PD-1 inhibitor is Pembrolizumab, Nivolumab, or a combination thereof. In one embodiment, the anti-PD-1 antibody molecule is Cemiplimab. In one embodiment, the anti-PD-1 antibody molecule is Sintilimab. In one embodiment, the anti-PD-1 antibody molecule is Toripalimab. In one embodiment, the anti-PD-1 antibody molecule is Camrelizumab.

Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

In some embodiments, the immune checkpoint inhibitor is a PD-L1 inhibitor. In some such embodiments, the PD-L1 inhibitor is Avelumab, or a combination thereof. In particular embodiments, the PD-L1 inhibitor is Atezolizumab also known as MPDL3280A, RG7446, R05541267, YW243.55.570, or TECENTRIQ™. Atezolizumab and other anti-PD-L1 antibodies are disclosed in U.S. Pat. No. 8,217,149, incorporated by reference in its entirety. In particular embodiments, the PD-L1 inhibitor is Avelumab also known as MSB0010718C. Avelumab and other anti-PD-L1 antibodies are disclosed in WO 2013/079174, incorporated by reference in its entirety. In particular embodiments, the PD-L1 inhibitor is Durvalumab also known as MEDI4736. Durvalumab and other anti-PD-L1 antibodies are disclosed in U.S. Pat. No. 8,779,108, incorporated by reference in its entirety. In certain embodiments, the PD-L1 inhibitor is KN035 (Alphamab; 3DMed; Ascletis Pharma), Envafolimab (TRACON Pharmaceuticals), BMS 936559 (Bristol-Myers Squibb), CS1001 (CStone Pharmaceuticals, Ligand Pharmaceuticals), CX-072 (CytomX Therapeutics), FAZ053 (Novartis), SHR-1316 (Hengrui Medicine), TQB2450 (Chiatai Tianqing), STI-A1014 (Zhaoke Pharm; Lee's Pharm, Lonza, Sorrento Therapeutics, NantWorks), LYN00102 (Lynkcell), A167 (Harbour BioMed, Kelun Group), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety. In some embodiments, the PD-L1 inhibitor is a monoclonal antibody (e.g., as made by Hisun Pharm and applying for clinical trials as of this filing).

In certain embodiments, the PD-L1 inhibitor is Cosibelimab (Fortress Biotech), LY3300054 or Iodapolimab (Eli Lilly), GS-4224 (Gilead Sciences), STI-A1015 (Yuhan, Sorrento Therapeutics), BCD-135 (BIOCAD), Cosibelimab (Dana-Farber Cancer Institute, TG Therapeutics), APL-502 (Apollomics), AK106 (Akeso Biopharma), MSB2311 (Transcenta Holding), TG-1501 (TG Therapeutics), FAZ053 (Novartis).

In certain embodiments, the PD-L1 inhibitor is MT-6035 (Molecular Templates), Icaritin and ZKAB001 (Lonza, Lee's Pharmaceutical Holdings, Sorrento Therapeutics, Shenogen Pharma Group), TRIDENT Antibody (MacroGenics, Zai Lab), YBL-007 (Anh-Gook Pharmaceutical, Y-Biologics), HTI-1316 (Hengrui Therapeutics), PD-L1 Oncology Project (Weizmann Institute of Sciences), JS003 (Shanghai Junshi Biosciences), ND021 (Numab Therapeutics, CStone Pharmaceuticals), Toca 521 (Tocagen), STT01 (STCube).

In certain embodiments, the PD-L1 inhibitor is DB004 (DotBio), MT-5050 (Molecular Templates), or KD036 (Kadmon).

In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

In some embodiments, the immune checkpoint inhibitor is a cytotoxic T-lymphocyte-associated modulator. In some embodiments, the immune checkpoint inhibitor is a CTLA-4 inhibitor. In certain embodiments, the CTLA-4 inhibitor is ipilimumab, tremelimumab, ALPN-202 (Alpine Immune Sciences), RP2 (Replimune), BMS-986249 (Bristol-Myers Squibb), BMS-986218 (Bristol-Myers Squibb), zalifrelimab (Agenus, Ludwig Institute for Cancer Research, UroGen Pharma, Recepta Biopharma), BCD-217 (BIOCAD), Onc-392 (Pfizer, OncoImmune), IBI310 (Innovent Biologics), KN046 (Alphamab), MK-1308 (Merck & Co), REGN4659 (Regeneron Pharmaceuticals), XmAb20717 (Xencor), XmAb22841 (Xencor), Anti-CTLA-4 NF (Bristol-Myers Squibb), MEDI5752 (AstraZeneca), AGEN1181 (Agenus), MGD019 (MacroGenics), ATOR-1015 (Alligator Bioscience), BCD-145 (BIOCAD), PSB205 (Sound Biologics), CS1002 (CStone Pharmaceuticals), ADU-1604 (Aduro Biotech), PF-06753512 (Pfizer), BioInvent-Transgene Research Program (Transgene), AGEN2041 (Agenus, Recepta Biopharam), ATOR-1144 (Alligator Bioscience), CTLA-4 Research Project (Sorrento Therapeutics), PD-L1/CTLA-4 Research Project (Sorrento Therapeutics), HLX13 (Shanghai Henlius Biotech), ISA203 (ISA Pharmaceuticals), PRS-300 Series A (*Pieris* Pharmaceuticals), BA3071 (BioAtla), CTLA4 Cancer Research Program (Biosortia Pharmaceuticals), RP3 (Replimune), CG0161 (Cold Genesys), APL-509 (Apollomics, JSR), AGEN2041 (Ludwig Institute for Cancer Research), APC 101 (Advanced Proteome), CTLA-4 Inhibitor (Advanced Proteome), BA3071 (BeiGene), BPI-002 (BeyondSpring Pharmaceuticals), CTLA-4 Antibody (Tikcro Technologies), Immuno-Oncology Research Program II (OliPass), PBP1701 (Prestige BioPharma), DB002 (DotBio), DB003 (DotBio), OR-2299 (OncoResponse), NK044 (Alphamab). In certain embodiments, the CTLA-4 inhibitor is ipilimumab. In other embodiments, the CTLA4 inhibitor is tremelimumab.

In some embodiments, the immune checkpoint inhibitor is a LAG-3 inhibitor. In some embodiments, the LAG-3 inhibitor is chosen from LAG525 (Novartis), BMS-986016 (Bristol-Myers Squibb), or TSR-033 (Tesaro).

In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule is IMP761 (Prima BioMed).

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety.

In one embodiment, the anti-LAG-3 inhibitor is a soluble LAG-3 protein, e.g., IMP321 (Prima BioMed), e.g., as disclosed in WO 2009/044273, incorporated by reference in its entirety.

In some embodiments, the immune checkpoint inhibitor is a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In embodiments, a compound as described herein, is administered to a subject in need thereof in combination with a bromodomain inhibitor, a histone deacetylase (HDAC), or both.

A bromodomain inhibitor inhibits at least one bromodomain protein, such as Brd2, Brd3, Brd4 and/or BrdT, for example Brd4. In some of these embodiments, the bromodomain inhibitor is JQ-1 (Nature 2010 Dec. 23; 468(7327): 1067-73), BI2536 (ACS Chem. Biol. 2014 May 16; 9(5): 1160-71; Boehringer Ingelheim), TG101209 (ACS Chem. Biol. 2014 May 16; 9(5):1160-71), OTX015 (Mol. Cancer Ther. Nov. 2013 12; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8): 2968-72; GlaxoSmithKline), PFI-1 (J. Med. Chem. 2012 Nov. 26; 55(22):9831-7; Cancer Res. 2013 Jun. 1; 73(11): 3336-46; Structural Genomics Consortium) of CPI-0610 (Constellation Pharmaceuticals). In some embodiments, the bromodomain inhibitor is TG101209, BI2536, OTX015, C244, IBET762, IBET151, or PFI-1.

A HDAC inhibitor inhibits at least one HDAC protein. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the HDAC inhibitor is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3): 106771) or valproic acid (EMBO J. 2001 Dec. 17; 20(24): 6969-78). For example, in some embodiments the HDAC inhibitor is panobinostat, vorinostat, MS275, belinostat, or LBH589. In some embodiments, the HDAC inhibitor is panobinostat or SAHA.

In some embodiments, methods of the present disclosure further comprise administering radiation therapy to the subject.

Some patients may experience allergic reactions to compounds of the present disclosure and/or other therapeutic agent(s) (e.g., anti-cancer agent(s)) during or after administration. Therefore, anti-allergic agents can be administered in combination with compounds of the present disclosure and/or other therapeutic agent(s) (e.g., anti-cancer agent(s)) to minimize the risk of an allergic reaction. Suitable anti-allergic agents include corticosteroids (Knutson, S., et al., *PLoS One, DOI:*10.1371/journal.pone.0111840 (2014)), such as dexamethasone (e.g., DECADRON®), beclomethasone (e.g., BECLOVENT®), hydrocortisone (also known as cortisone, hydrocortisone sodium succinate, hydrocortisone sodium phosphate, sold under the tradenames ALA-CORT®, hydrocortisone phosphate, SOLU-CORTEF®, HYDROCORT ACETATE® and LANACORT®), prednisolone (sold under the tradenames DELTA-CORTEL®, ORAPRED®, PEDIAPRED® and PRELONE®), prednisone (sold under the tradenames DELTASONE®, LIQUID RED®, METICORTEN® and ORASONE®), methylprednisolone (also known as 6-methylprednisolone, methylprednisolone acetate, methylprednisolone sodium succinate, sold under the tradenames DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

Some patients may experience nausea during and after administration of the compounds described herein and/or other therapeutic agent(s) (e.g., anti-cancer agent(s)). Therefore, anti-emetics can be used in combination with compounds of the present disclosure and/or other therapeutic agent(s) (e.g., anti-cancer agent(s)) to prevent nausea (upper stomach) and vomiting. Suitable anti-emetics include aprepitant (EMEND®), ondansetron (ZOFRAN®), granisetron HCl (KYTRIL®), lorazepam (ATIVAN®, dexamethasone (DECADRON®), prochlorperazine (COMPAZINE®), casopitant (REZONIC® and ZUNRISA®), and combinations thereof.

Medication to alleviate the pain experienced during the treatment period is often prescribed to make the patient more comfortable. Common over-the-counter analgesics, such TYLENOL®, can also be used in combination with compounds of the present disclosure and/or other therapeutic agent(s) (e.g., anti-cancer agent(s)). Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) can be useful for moderate or severe pain, and can be used in combination with compounds of the present disclosure and/or other therapeutic agent(s) (e.g., anti-cancer agent(s)).

In some of the foregoing embodiments, the method is for treating liver cancer, refractory cancers (e.g., non-small cell lung cancer), lung cancer, esophageal cancer, Hodgkin's lymphoma, NK/T-cell lymphoma, or melanoma. In some specific embodiments, the method is for treating esophageal squamous cell carcinoma, gastric cancer, lung cancer, nasopharyngeal carcinoma, bladder cancer, soft tissue sarcoma, diffuse large B-cell lymphoma, head and neck squamous cell carcinomas, kidney cancer, urothelial carcinoma, ovarian cancer, uterine cancer, or pancreatic cancer. In some embodiments, the method is for treating bile duct cancer.

Many chemotherapeutics are presently known in the art and can be used in combination with a compound as described herein. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples of therapeutic agents that can be used in combinations with a compound as described herein are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel, in any form (for example, protein-bound paclitaxel, e.g. ABRAXANE, Celgene, and for example TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

Further examples of chemotherapeutic agents for use in combination with a compound of the present disclosure (e.g., in combination therapy, in a pharmaceutical combination) include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®). A further example is bortezomib. Yet further examples include gemcitabine, nab-paclitaxel (Abraxane®), erlotinib, fluorouracil and FOLFIRINOX (a chemotherapy regimen made up of folinic acid, fluorouracil, irinotecan and oxaliplatin), or any combination of two or more of the foregoing, e.g., to treat pancreatic cancer (e.g., advanced pancreatic cancer, pancreatic ductal adenocarcinoma).

Anti-cancer agents of particular interest for use in combination with the compounds of the present disclosure include:

Topoisomerase inhibitors, including Type I topoisomerase inhibitors, such as irinotecan, topotecan, and camptothecin, and Type 2 topoisomerase inhibitors, such as etoposide, doxorubicin, and epirubicin.

Poly(ADP-ribose) polymerase (PARP) inhibitors, such as olaparib, rucaparib, niraparib, talazoparib, veliparib, pamiparib and iniparib.

DNA crosslinking agents, such as cisplatin, carboplatin and oxaliplatin.

Agents that increase levels of reactive oxygen species (ROS), such as napabucasin.

PARP inhibitors such as olaparib, rucaparib, niraparib, veliparib and talazoparib.

Purine antimetabolites and/or inhibitors of de novo purine synthesis: pemetrexed (Alimta®), gemcitabine (Gemzar®), 5-fluorouracil (Adrucil®, Carac® and Efudex®), methotrexate (Trexall®), capecitabine (Xeloda®), floxuridine (FUDR®), decitabine (Dacogen®), azacitidine (Vidaza® and Azadine®), 6-mercaptopurine (Purinethol®), cladribine (Leustatin®, Litak® and Movectro®), fludarabine (Fludara®), pentostatin (Nipent®), nelarabine (Arranon®), clofarabine (Clolar® and Evoltra®), and cytarabine (Cytosar®).

Anti-angiogenesis agents include, for example, MMP-2 (matrix-metalloproteinase 2) inhibitors, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Embodiments of MMP-2 and MMP-9 inhibitors include those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in some embodiments are AG-3340, RO 323555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In other embodiments, agents useful in methods for combination therapy with a compound as described herein include, but are not limited to: erlotinib, afatinib, Iressa (gefitinib), GDC0941, MLN1117, BYL719 (alpelisib), BKM120 (buparlisib), CYT387, GLPG0634, baricitinib, lestaurtinib, momelotinib, pacritinib, ruxolitinib, TG101348, crizotinib, tivantinib, AMG337, cabozantinib, foretinib, onartuzumab, NVP-AEW541, dasatinib, ponatinib, saracatinib, bosutinib, trametinib, selumetinib, cobimetinib, PD0325901, RO5126766, axitinib, bevacizumab, bostutinib, cetuximab, fostamatinib, imatinib, lapatinib, lenvatinib, ibrutinib, nilotinib, panitumumab, pazopanib, pegaptanib, ranibizumab, sorafenib, sunitinib, SU6656, trastuzumab, tofacitinib, vandetanib, vemurafenib, irinotecan, Taxol, docetaxel, rapamycin or MLN0128.

B-cell receptor signaling antagonists (e.g., a Bruton's tyrosine kinase (BTK) inhibitors): ibrutinib.

Bromodomain inhibitors. A bromodomain inhibitor inhibits at least one bromodomain protein, such as Brd2, Brd3, Brd4 and/or BrdT, for example Brd4. In some of these embodiments, the bromodomain inhibitor is JQ-1 (Nature 2010 Dec. 23; 468(7327):1067-73), BI2536 (ACS Chem. Biol. 2014 May 16; 9(5):1160-71; Boehringer Ingelheim), TG101209 (ACS Chem. Biol. 2014 May 16; 9(5):1160-71), OTX015 (Mol. Cancer Ther. Nov. 2013 12; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium) of CPI-0610 (Constellation Pharmaceuticals). In some embodiments, the bromodomain inhibitor is TG101209, BI2536, OTX015, C244, IBET762, IBET151, or PFI-1.

Histone deacetylase (HDAC) inhibitors. A HDAC inhibitor inhibits at least one HDAC protein. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the HDAC inhibitor is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):106771) or valproic acid (EMBO J. 2001 Dec. 17; 20(24):6969-78). For example, in some embodiments the HDAC inhibitor is panobinostat, vorinostat, MS275, belinostat, or LBH589. In some embodiments, the HDAC inhibitor is panobinostat or SAHA.

In embodiments, a compound as described herein is administered in combination with an epidermal growth factor receptor tyrosine kinase (EGFR) inhibitor. Examples of EGFR inhibitors include erlotinib, osimertinib, cetuximab, gefitinib, necitumumab, lapatinib, neratinib, panitumumab, vandetanib, and necitumumab. A combination of a compound as described herein and an EGFR inhibitor may be useful, for example, in the treatment of cancers that are related to EGFR dysregulation, such as non-small-cell lung cancer (NSCLC), pancreatic cancer, breast cancer, and colon cancer. EGFR may be dysregulated, for example, due to activating mutations in exons 18, 19, 20, or 21. In particular embodiments, the EGFR inhibitor is erlotinib or osimertinib. In particular embodiments, the combination of a compound as described herein and an EGFR inhibitor is used to treat EGFR-mutated NSCLC. In particular embodiments, the combination of a compound as described herein and an EGFR inhibitor is used to treat an EGFR inhibitor-resistant cancer, and the compound as described herein sensitized the cancer to the EGFR inhibitor.

EGFR antibodies: cetuximab (Erbitux®), necitumumab, panitumumab (e.g. cetuximab).

MTAP inhibitors: (3R,4S)-1-((4-amino-5H-pyrrolo[3,2-d]pyrimidin-7-yl)methyl)-4-((methylthio)methyl)pyrrolidin-3-ol (MT-DADMe-Immucillin-A, CAS 653592-04-2).

Methylthioadenosine: ((2R,3R,4S,5S)-2-(6-amino-9H-purin-9-yl)-5-((methylthio)methyl)tetrahydrofuran-3,4-diol, CAS 2457-80-9).

MET inhibitors: capmatinib (INC280, CAS 1029712-80-8).

Platelet-derived growth factor (PDGF) receptor inhibitors: imatinib (Gleevec®); linifanib (N-[4-(3-amino-1H-indazol-4-yl)phenyl]-N'-(2-fluoro-5-methylphenyl)urea, also known as ABT 869, available from Genentech); sunitinib malate (Sutent®); quizartinib (AC220, CAS 950769-58-1); pazopanib (Votrient®); axitinib (Inlyta®); sorafenib (Nexavar®); vargatef (BIBF1120, CAS 928326-83-4); telatinib (BAY57-9352, CAS 332012-40-5); vatalanib dihydrochloride (PTK787, CAS 212141-51-0); and motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

Phosphoinositide 3-kinase (PI3K) inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO 2007/084786); alpelisib (BYL719): (5Z)-5-[[4-(4-Pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7) and everolimus (AFINITOR®).

Cyclin-dependent kinase (CDK) inhibitors: ribociclib (LEE011, CAS 1211441-98-3); aloisine A; alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); crizotinib (PF-02341066, CAS 877399-52-5); 2-(2-chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); indisulam (E7070); roscovitine (CYC202); 6-acetyl-8-cyclopentyl-5-methyl-2-(5-piperazin-1-yl-pyridin-2-ylamino)-8H-pyrido[2,3-d]pyrimidin-7-one, hydrochloride (PD0332991); dinaciclib (SCH727965); N-[5-[[(5-tert-butyloxazol-2-yl)methyl]thio]thiazol-2-yl]piperidine-4-carboxamide (BMS 387032, CAS 345627-80-7); 4-[[9-chloro-7-(2,6-difluorophenyl)-5H-pyrimido[5,4-d][2]benzazepin-2-yl]amino]-benzoic acid (MLN8054, CAS 869363-13-3); 5-[3-(4,6-difluoro-1H-benzimidazol-2-yl)-1H-indazol-5-yl]-N-ethyl-4-methyl-3-pyridinemethanamine (AG-024322, CAS 837364-57-5); 4-(2,6-dichlorobenzoylamino)-1H-pyrazole-3-carboxylic acid N-(piperidin-4-yl)amide (AT7519, CAS 844442-38-2); 4-[2-methyl-1-(1-methylethyl)-1H-imidazol-5-yl]-N-[4-(methylsulfonyl)phenyl]-2-pyrimidinamine (AZD5438, CAS 602306-29-6); palbociclib (PD-0332991); and (2R,3R)-3-[[2-[[3-[[S(R)]-S-cyclopropylsulfonimidoyl]-phenyl]amino]-5-(trifluoromethyl)-4-pyrimidinyl]oxy]-2-butanol (BAY 10000394).

p53-MDM2 inhibitors: (S)-1-(4-chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RG7112), 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid (RG7388), SAR299155, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232), {(3R,5R,6S)-5-(3-chlorophenyl)-6-(4-chlorophenyl)-1-[(2S,3S)-2-hydroxy-3-pentanyl]-3-methyl-2-oxo-3-piperidinyl}acetic acid (AM-8553), (±)-4-[4,5-bis(4-chlorophenyl)-2-(2-isopropoxy-4-methoxy-phenyl)-4,5-dihydro-imidazole-1-carbonyl]-piperazin-2-one (Nutlin-3), 2-methyl-7-[phenyl(phenylamino)methyl]-8-quinolinol (NSC 66811), 1-N-[2-(1H-indol-3-yl)ethyl]-4-N— pyridin-4-ylbenzene-1,4-diamine (JNJ-26854165), 4-[4,5-bis(3,4-chlorophenyl)-2-(2-isopropoxy-4-methoxy-phenyl)-4,5-dihydro-imidazole-1-carboxyl]-piperazin-2-one (Caylin-1), 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2), 5-[[3-dimethylamino)propyl]amino]-3,10-dimethylpyrimido[4,5-b]quinoline-2,4(3H,10H)-dione dihydrochloride (HLI373) and trans-4-iodo-4'-boranyl-chalcone (SC204072).

Mitogen-activated protein kinase (MEK) inhibitors: XL-518 (also known as GDC-0973, CAS No. 1029872-29-4, available from ACC Corp.); selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO 2003/077914); 2-[(2-chloro-4-iodophenyl)amino]-N-(cyclopropylmethoxy)-3,4-difluoro-benzamide (also known as CI-1040 or PD184352 and described in PCT Publication No. WO 2000/035436); N-[(2R)-2,3-dihydroxypropoxy]-3,4-difluoro-2-[(2-fluoro-4-iodophenyl)amino]-benzamide (also known as PD0325901 and described in PCT Publication No. WO 2002/006213); 2,3-bis[amino[(2-aminophenyl)thio]methylene]-butanedinitrile (also known as U0126 and described in U.S. Pat. No. 2,779,780); N-[3,4-difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO 2007/014011); (3S,4R,5Z,8S,9S,11E)-14-(ethylamino)-8,9,16-trihydroxy-3,4-dimethyl-3,4,9; 19-tetrahydro-1H-2-benzoxacyclotetradecine-1,7(8H)-dione] (also known as E6201 and described in PCT Publication No. WO 2003/076424); 2'-amino-3'-methoxyflavone (also known as PD98059 available from Biaffin GmbH & Co., KG, Germany); (R)-3-(2,3-dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); trametinib dimethyl sulfoxide (GSK-1120212, CAS 1204531-25-80); 2-(2-fluoro-4-iodophenylamino)-N-(2-hydroxyethoxy)-1,5-dimethyl-6-oxo-1,6-dihydropyridine-3-carboxamide (AZD 8330); 3,4-difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655); and 5-[(4-bromo-2-fluorophenyl)amino]-4-fluoro-N-(2-hydroxyethoxy)-1-methyl-1H-benzimidazole-6-carboxamide (MEK162).

B-RAF inhibitors: regorafenib (BAY73-4506, CAS 755037-03-7); tuvizanib (AV951, CAS 475108-18-0); vemurafenib (ZELBORAF®, PLX-4032, CAS 918504-65-1); encorafenib (also known as LGX818); 1-methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-hydroxyethyl)-3-(pyridin-4-yl)-1H-pyrazol-4-yl]-2,3-dihydroinden-1-one oxime (GDC-0879, CAS 905281-76-7); 5-[2-[4-[2-(dimethylamino)ethoxy]phenyl]-5-(4-pyridinyl)-1H-imidazol-4-yl]-2,3-dihydro-1H-inden-1-one oxime (GSK2118436 or SB590885); (+/−)-methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662), dabrafenib (TAFINLAR®), and N-(3-(5-chloro-1H-pyrrolo[2,3-b]pyridine-3-carbonyl)-2,4-difluorophenyl)propane-1-sulfonamide (also known as PLX4720).

ALK inhibitors: crizotinib (XALKORI®).

PIM kinase inhibitors such as:

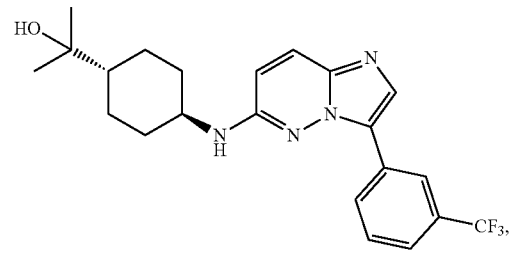 [SMILES: CC(C)(O)[C@H]1CC[C@H](Nc2ccc3ncc(-c4cccc(C(F)(F)F)c4)n3n2)CC1]

or a pharmaceutically acceptable salt thereof.

Proteasome inhibitors: bortezomib (VELCADE®), N-5-benzyloxycarbonyl-Ile-Glu(O-tert-butyl)-Ala-leucinal (PSI), carfilzomib and ixazomib (e.g., bortezomib), marizomib (NPI-0052), delanzomib (CEP-18770), 0-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912). A RNAi screen identified TNK1 as a potential modulator of proteasome inhibitor sensitivity in myeloma. Zhu et al., Blood (2011) 117 (14): 3847-3857. In some embodiments, a compound of the present disclosure (e.g., a compound of Formula I, or a subformula thereof, or a pharmaceutically acceptable salt of the foregoing) is administered in combination with a proteasome inhibitor described herein, e.g., for the treatment of multiple myeloma.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin;

xeloda; ibandronate; camptothecin-11 (CPT-11); topoisomeRASe inhibitor RFS 2000; difluoromethylornithine (DMFO).

Non-limiting examples of therapeutic agents that can be used in combinations with a compound as described herein are mTOR inhibitors. Examples of mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo [30.3.1.049] hexatriaconta-16,24,26,28-tetraen-12-yl] propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (µF04691502, CAS 1013101-36-4); and $N^2$-[1,4-dioxo-4-[[4-(4-oxo-8-phenyl-4H-1-benzopyran-2-yl)morpholinium-4-yl] methoxy]butyl]-L-arginylglycyl-L-α-aspartylL-serine-inner salt (SEQ ID NO: 1482) (SF1126, CAS 936487-67-1), and XL765.

A host of chemotherapeutic agents can be used in combination with the compound of the present disclosure. In some embodiments, the chemotherapeutic agent is selected from the group consisting of mitotic inhibitors (e.g., paclitaxel, nab-paclitaxel), alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples of chemotherapeutic agents for use in combination with a compound of the present disclosure (e.g., in combination therapy, in a pharmaceutical combination) include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.), docetaxel (TAXOTERE™, Rhone-Poulenc Rorer, Antony, France) and cabazitaxel (JEVTANA, Sanofi Genzyme); retinoic acid; esperamicins; capecitabine; and pharmaceutically acceptable salts, acids or derivatives of any of the above. Further non-limiting examples of chemotherapeutic agents for use in combination with a compound of the present disclosure (e.g., in combination therapy, in a pharmaceutical combination) include bortezomib, capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), erlotinib, fludarabine phosphate (Fludara®), 5-fluorouracil (Adrucil®, Efudex®), FOLFIRINOX, gemcitabine (difluorodeoxycitidine), irinotecan (Camptosar®), L-asparaginase (ELSPAR®), 6-mercaptopurine (Purinethol®), methotrexate (Folex®), nabpaclitaxel, pentostatin, 6-thioguanine, thiotepa, and topotecan hydrochloride for injection (Hycamptin®). Yet further non-limiting examples of chemotherapeutic agents for use in combination with a compound of the present disclosure (e.g., in combination therapy, in a pharmaceutical combination) include erlotinib, afatinib, gefitinib, GDC0941, MLN1117, BYL719 (alpelisib), BKM120 (buparlisib), CYT387, GLPG0634, baricitinib, lestaurtinib, momelotinib, pacritinib, ruxolitinib, TG101348, crizotinib, tivantinib, AMG337, cabozantinib, foretinib, onartuzumab, NVP-AEW541, dasatinib, ponatinib, saracatinib, bosutinib, trametinib, selumetinib, cobimetinib, PD0325901, RO5126766, axitinib, bevacizumab, cetuximab, fostamatinib, imatinib, lapatinib, lenvatinib, ibrutinib, nilotinib, panitumumab, pazopanib, pegaptanib, ranibizumab, sorafenib, sunitinib, SU6656, trastuzumab, tofacitinib, vandetanib, vemurafenib, irinotecan, Taxol, docetaxel, rapamycin and MHLN0128. More non-limiting examples of chemotherapeutic agents for use in combination with a compound of the present disclosure (e.g., in combination therapy, in a pharmaceutical combination) include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®).

Commonly prescribed anti-cancer drugs can also be used in combination with a compound of the present disclosure. Non-limiting examples of commonly prescribed anti-cancer drugs include Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Where desired, the compound described herein or a pharmaceutical composition thereof can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

In one embodiment, a compound as described herein, is administered to a subject in need thereof in combination with a CDK9 inhibitor, such as Alvocidib. In a related embodiment, a pharmaceutically acceptable salt of a compound as described herein is administered to a subject in need thereof in combination with a CDK9 inhibitor, such as Alvocidib. The administration may be before, concurrently or after administration of the CDK9 inhibitor. In one specific embodiment, a compound as described herein is administered to a subject in need thereof in combination with a CDK9 inhibitor, such as Alvocidib for treatment of pancreatic cancer. In a related specific embodiment, a pharmaceutically acceptable salt of a compound as described herein is administered to a subject in need thereof in combination with a CDK9 inhibitor, such as Alvocidib for treatment of pancreatic cancer. In some of the foregoing embodiments, the salt is a tartrate salt. In some of the foregoing embodiments, the CDK9 inhibitor is Alvocidib. In some embodiments, the salt is a tartrate salt and the CDK9 inhibitor is Alvocidib.

In certain other embodiments, a method for treating cancer is provided, the method comprising administering an effective amount of a compound as described herein and a CDK inhibitor to a subject in need thereof. A compound as described herein and CDK inhibitor may be any of the AXL kinase or CDK inhibitors known in the art.

In embodiments, the CDK inhibitor is a CDK2, CDK4, CDK6, CDK7, CDK8, CDK9, CDK10, and/or CDK11 inhibitor. In some embodiments, the CDK inhibitor is a CDK7, CDK9 inhibitor, or both. In some embodiments, the CDK inhibitor is dinaciclib (ACS Med. Chem. Lett. 2010 May 17; 1(5):204-8; Mol. Cancer Ther. 2010 August; 9(8):2344-53; Merck, Sharp and Dohme), AT7519 (J. Med. Chem. 2008 Aug. 28; 51(16):4986-99; Astex Pharmaceutical) or palbociclib (J. Med. Chem. 2005 Apr. 7; 48(7):2388-406; Pfizer). In certain embodiments, the CDK inhibitor is a CDK9 inhibitor, such as alvocidib. The alvocidib may be administered as the free bases, as a pharmaceutically acceptable salt or as a prodrug. In certain embodiments, the CDK9 inhibitor is alvocidib. In other embodiments, the CDK9 inhibitor is a pharmaceutically acceptable salt of alvocidib. In other embodiments, the CDK9 inhibitor is a prodrug of alvocidib. Prodrugs of alvocidib include those disclosed in WO 2016/187316, the full disclosure of which is hereby incorporated by reference in its entirety.

Various different cancers can be treated with the combination of a compound as described herein and CDK inhibitor. In some embodiments, the cancer is a hematologic cancer or solid tumor, for example any of the hematologic cancers or solid tumors disclosed herein or known in the art.

In some specific embodiments, the cancer is a hematologic cancer, such as multiple myeloma, myelodysplastic syndrome (MDS), acute myelogenous leukemia (AML), acute lymphoblastic leukemia (ALL), acute lymphocytic leukemia, chronic lymphogenous leukemia, chronic lymphocytic leukemia (CLL), mantle cell lymphoma, diffuse large B-cell lymphoma, follicular lymphoma, or non-Hodgkin's lymphoma. In some specific embodiments, the hematologic cancer is CLL, SLL, or both. In some specific embodiments, the hematologic cancer is CLL. In some specific embodiments, the hematologic cancer is SLL.

In some other specific embodiments, the cancer treated by the combination of a compound as described herein and a CDK inhibitor is a solid tumor, such as a pancreatic, colon or lung cancer.

Embodiments further relate to a method of administering a compound as described herein to a subject in need thereof in combination with a BTK inhibitor (e.g., Ibrutinib) or a CDK9 inhibitor (e.g., Alvocidib) provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of a pharmaceutically acceptable salt of a compound as described herein in this combination therapy can be determined as described herein.

In one embodiment, a compound as described herein is administered to a subject in need thereof in combination with an ATR inhibitor, such as AZD6738 or VX-970. The administration may be before, concurrently or after administration of the ATR inhibitor. In one specific embodiment, a compound as described herein is administered to a subject in need thereof in combination with an ATR inhibitor, such as AZD6738 or VX-970 for treatment of non-small cell lung cancer. In a related specific embodiment, a pharmaceutically acceptable salt of a compound as described herein is administered to a subject in need thereof in combination with an ATR inhibitor, such as AZD6738 or VX-970 for treatment of non-small cell lung cancer. In some of the foregoing embodiments, the salt is a tartrate salt. In some of the foregoing embodiments, the ATR inhibitor is AZD6738. In some of the foregoing embodiments, the ATR inhibitor is VX-970. In some embodiments, the salt is a tartrate salt and the ATR inhibitor is AZD6738. In some embodiments, the salt is a tartrate salt and the ATR inhibitor is VX-970. In some of the foregoing embodiments, the ATR inhibitor is a combination of AZD6738 and VX-970.

In some of the foregoing embodiments, the non-small cell lung cancer comprises TCGA lung adenocarcinoma, one or more LUAD tumors, TCGA lung squamous cell carcinoma, one or more LUSC tumors, one or more MDACC PROSPECT tumors, one or more MDACC BATTLE1 tumors, one or more BATTLE2 tumors, or combinations thereof. In some embodiments, the non-small cell lung cancer comprises TCGA LUAD tumors, for example, tumors enriched in ALK translocations. In some embodiments, the non-small cell lung cancer comprises TCGA LUAD tumors, for example, tumors comprising one or more EGFR mutations.

In one embodiment, a compound as described herein is administered to a subject in need thereof thereby sensitizing the subject to administration of an ATR inhibitor, such as AZD6738 or VX-970. In a related embodiment, a pharmaceutically acceptable salt of a compound as described herein is administered to a subject in need thereof thereby sensitizing the subject to administration of an ATR inhibitor, such as AZD6738 or VX-970. In one specific embodiment, a compound as described herein is administered to a subject in need thereof thereby sensitizing the subject to administration of an ATR inhibitor, such as AZD6738 or VX-970 for treatment of non-small cell lung cancer. In a related specific embodiment, a pharmaceutically acceptable salt of a compound as described herein is administered to a subject in need thereof thereby sensitizing the subject to administration of an ATR inhibitor, such as AZD6738 or VX-970 for treatment of non-small cell lung cancer. In some of the foregoing embodiments, the salt is a tartrate salt. In some of the foregoing embodiments, the ATR inhibitor is AZD6738. In some of the foregoing embodiments, the ATR inhibitor is VX-970. In some embodiments, the salt is a tartrate salt and the ATR inhibitor is AZD6738. In some embodiments, the salt is a tartrate salt and the ATR inhibitor is VX-970. In some of the foregoing embodiments, the ATR inhibitor is a combination of AZD6738 and VX-970.

Radiation therapy can be administered in combination with a compound as described herein in some embodiments. Exemplary radiation therapies include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At211, I131, I125, Y90, Re186, Re188, Sm153, Bi212, P32, and radioactive isotopes of Lu). Suitable radiation sources for use as a cell conditioner of the present invention include both solids and liquids. By way of non-limiting example, the radiation source can be a radionuclide, such as I125, I131, Yb169, Ir192 as a solid source, I125 as a solid source, or other radionuclides that emit photons, beta particles, gamma radiation, or other therapeutic rays. The radioactive material can also be a fluid made from any solution of radionuclide(s), e.g., a solution of I125 or I131, or a radioactive fluid can be produced using a slurry of a suitable fluid containing small particles of solid radionuclides, such as Au198, Y90. Moreover, the radionuclide(s) can be embodied in a gel or radioactive micro spheres.

Without being limited by any theory, a compound as described herein can render abnormal cells more sensitive to treatment with radiation for purposes of killing and/or inhibiting the growth of such cells. Accordingly, some embodiments include a method for sensitizing abnormal cells in a mammal to treatment with radiation which comprises administering to the mammal an amount of a compound as described herein, which amount is effective is sensitizing abnormal cells to treatment with radiation. The amount of a compound as described herein in this method can be determined according to the means for ascertaining effective amounts of such compounds and salts described herein.

The compound as described herein can also be used in combination with an amount of one or more substances selected from anti-angiogenesis agents, signal transduction inhibitors, antiproliferative agents, glycolysis inhibitors, or autophagy inhibitors.

Anti-angiogenesis agents include, for example, MMP-2 (matrix-metalloproteinase 2) inhibitors, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Embodiments of MMP-2 and MMP-9 inhibitors include those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in some embodiments are AG-3340, RO 323555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In other embodiments, agents useful in methods for combination therapy with a compound as described herein include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, RO5126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

In embodiments, a compound as described herein is administered in combination with an epidermal growth factor receptor tyrosine kinase (EGFR) inhibitor. Examples of EGFR inhibitors include erlotinib, osimertinib, cetuximab, gefitinib, necitumumab, lapatinib, neratinib, panitumumab, vandetanib, and necitumumab. A combination of a compound as described herein and an EGFR inhibitor may be useful, for example, in the treatment of cancers that are related to EGFR dysregulation, such as non-small-cell lung cancer (NSCLC), pancreatic cancer, breast cancer, and colon cancer. EGFR may be dysregulated, for example, due to activating mutations in exons 18, 19, 20, or 21. In particular embodiments, the EGFR inhibitor is erlotinib or osimertinib. In particular embodiments, the combination of a compound as described herein and an EGFR inhibitor is used to treat EGFR-mutated NSCLC. In particular embodiments, the combination of a compound as described herein and an EGFR inhibitor is used to treat an EGFR inhibitor-resistant cancer, and the compound as described herein sensitized the cancer to the EGFR inhibitor. In certain embodiments, the EGFR antibody is cetuximab (Erbitux®).

In certain embodiments, a compound as described herein is administered in combination with Erlotinib. In some embodiments, such a combination is used to treat pancreatic cancer. In other embodiments, such a combination is used to treat lung cancer. In further embodiments, the lung cancer is non-small cell lung cancer.

In certain embodiments, a compound as described herein is administered in combination with osimertinib. In some embodiments, such a combination is used to treat lung cancer. In further embodiments, the lung cancer has an EGFR mutation.

Doses, dosing schedules and regimens, and/or routes of administration of additional therapeutic agents in a combination therapy described herein can be determined by a person skilled in the art and, in some embodiments, are as described herein with respect to compositions.

NUMBERED EMBODIMENTS

1. A compound of Formula (I):

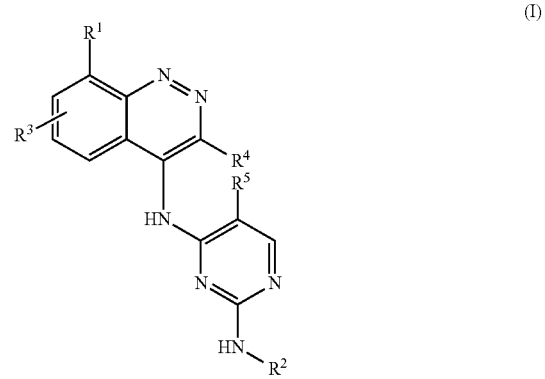

or a pharmaceutically acceptable salt thereof, wherein:
$R^1$ is a $C_1$-$C_5$ alkyl or $C_3$-$C_5$ carbocycle, or a halogen;
$R^3$ is —H, —F or —Cl;
$R^4$ is —H or a halogen, or a $C_1$-$C_3$ alkyl or cyclopropyl, each of which is optionally substituted with one or more —F;
$R^5$ is —H or —F, or a $C_1$-$C_3$ alkyl or cyclopropyl, each of which is optionally substituted with one or more —F; and
$R^2$ is an aryl of at least 6 carbon atoms or nitrogen-containing heteroaryl of at least 6 atoms, each of which is optionally substituted with:
(i) one or more halogens;
(ii) a moiety which is $C_1$-$C_6$ alkyl or $C_3$-$C_6$ carbocycle optionally substituted with a hydroxyl or one or more halogen; and wherein, when selected to be an alkyl larger than $C_3$ or a carbocycle larger than cyclopropyl, said moiety is present at a position on the aryl or heteroaryl of $R^2$ which is meta- or para- to the amino bond to the aryl or heteroaryl of $R^2$;
(iii) a sulfonamide;
(iv) a monocyclic, bicyclic, or spiro-cyclic carbocycle which is optionally substituted with one or more linear, branched, or cyclic alkyl moieties of up to 6 carbon atoms which are optionally substituted with hydroxy or one or more halogen, and wherein, when present, said carbocycle is at a position on the aryl or heteroaryl of $R^2$ which is meta- or para- to the amino bond to the aryl or heteroaryl of $R^2$;
(v) a monocyclic, bicyclic or spiro-cyclic heterocycle which may contain up to 3 heteroatoms which are selected independently from N and O and which is optionally and independently substituted with one or more $C_1$-$C_6$ alkyl or $C_3$-$C_6$ carbocycle which are optionally substituted with hydroxy or one or more halogen, and wherein, when present, said heterocycle is at a position on the aryl of $R^2$ which is meta- or para- to the amino bond to said aryl;
(vi) a moiety of the formula:

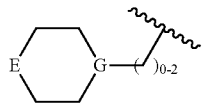

wherein:
G is >N— or >C(H)—; and
E is —O— or >C(H)—$R^{13}$, wherein $R^{13}$ is —H or a $C_1$-$C_6$ alkyl or $C_3$-$C_6$ carbocycle, each of which is optionally substituted with hydroxy or one or more halogen; or (vii) a moiety of the formula:

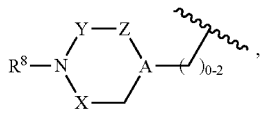

wherein:
- $R^8$ is —H or a $C_1$-$C_6$ alkyl or $C_3$-$C_6$ carbocycle which is optionally substituted with hydroxyl or one or more halogen;
- A is >N— or >C(H)—; and
- X, Y and Z are defined as follows:
  Z is >$CH_2$ and X and Y are independently >$CH_2$ or >C($CH_3$)$_2$, or both X and Y are >CH— and are bonded together through a methylene or ethylene bridge; or Y is >$CH_2$ or >C($CH_3$)$_2$, and X and Z are both >CH— and are bonded together through a methylene or ethylene bridge.

2. The compound of embodiment 1, wherein $R^1$ is a $C_1$-$C_5$ alkyl or $C_3$-$C_5$ carbocycle.
3. The compound of embodiment 2, wherein $R^1$ is —$CH_3$.
4. The compound of embodiment 2, wherein $R^1$ is cyclopropyl.
5. The compound of embodiment 1, wherein $R^1$ is —Cl or —F.
6. The compound of any one of embodiments 1 to 5, wherein $R^3$ is —H.
7. The compound of any one of embodiments 1 to 5 wherein $R^3$ is —F or —Cl.
8. The compound of any one of embodiments 1 to 5, wherein $R^3$ is —F.
9. The compound of any one of embodiments 1 to 5, wherein $R^3$ is —Cl.
10. The compound of any one of embodiments 1 to 9, wherein $R^4$ is a $C_1$-$C_3$ alkyl or cyclopropyl, each of which is optionally substituted with one or more —F.
11. The compound of any one of embodiments 1 to 9, wherein $R^4$ is halogen.
12. The compound of any one of embodiments 1 to 9, wherein $R^4$ is —$CF_3$.
13. The compound of any one of embodiments 1 to 9, wherein $R^4$ is —$CH_3$.
14. The compound of any one of embodiments 1 to 9, wherein $R^4$ is —H.
15. The compound of any one of embodiments 1 to 9, wherein $R^4$ is —Cl.
16. The compound of any one of embodiments 1 to 9, wherein $R^4$ is —F.
17. The compound of any one of embodiments 1 to 16, wherein $R^5$ is a $C_1$-$C_3$ alkyl or cyclopropyl, each of which is optionally substituted with one or more —F.
18. The compound of any one of embodiments 1 to 16, wherein $R^5$ is —H.
19. The compound of any one of embodiments 1 to 16, wherein $R^5$ is —$CH_3$.
20. The compound of any one of embodiments 1 to 16, wherein $R^5$ is —$CF_3$.
21 The compound of any one of embodiments 1 to 16, wherein $R^5$ is —F.
22. The compound of any one of embodiments 1 to 21, wherein $R^2$ is a moiety of the formula:

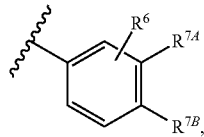

wherein,
- $R^6$ is: —H, —F, —Cl, or a $C_1$-$C_3$ alkyl or cyclopropyl which is optionally and independently substituted with one or more halogen;
- one of $R^{7A}$ and $R^{7B}$ is —H, and the other is:
  (i) a halogen;
  (ii) —$SO_2NR^{7F}{}_2$, wherein each $R^{7F}$ is independently —H or a linear or branched alkyl of up to 4 carbon atoms;
  (iii) a $C_1$-$C_6$ alkyl or $C_3$-$C_6$ carbocycle which is optionally substituted with one or more halogen;
  (iv) a moiety of the formula:

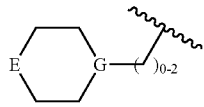

wherein:
- G is >N— or >C(H)—; and
- E is —O— or >C(H)—$R^{13}$, wherein $R^{13}$ is —H or a $C_1$-$C_6$ alkyl or $C_3$-$C_6$ carbocycle, each of which is optionally substituted with hydroxy or one or more halogen; or (v) a moiety of the formula:

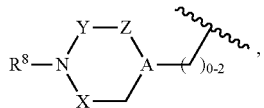

wherein:
- $R^8$ is —H or a $C_1$-$C_6$ alkyl or $C_3$-$C_6$ carbocycle which is optionally substituted with hydroxyl or one or more halogen;
- A is >N— or >C(H)—; and
- X, Y and Z are defined as follows:
  Z is >$CH_2$ and X and Y are independently >$CH_2$ or >C($CH_3$)$_2$, or both X and Y are >CH— and are bonded together through a methylene or ethylene bridge; or
  Y is >$CH_2$ or >C($CH_3$)$_2$, and X and Z are both >CH— and are bonded together through a methylene or ethylene bridge.

23. The compound of embodiment 22 wherein, one of $R^{7A}$ and $R^{7B}$ is —H, and the other is:
(i) a moiety of the structure:

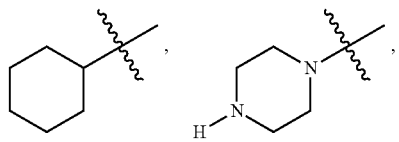

-continued

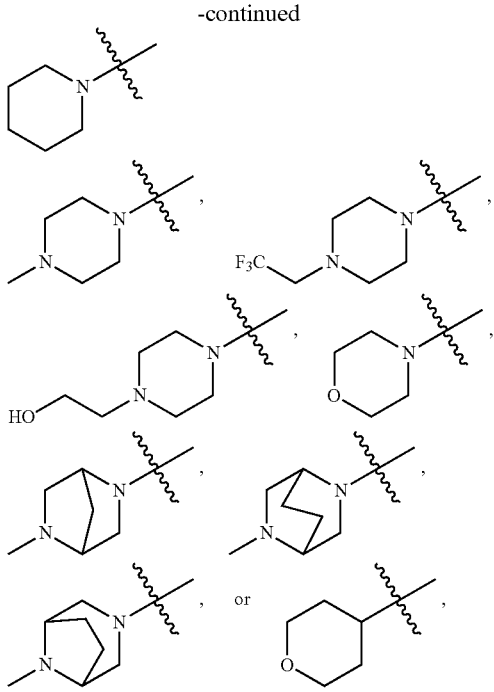

each of which is optionally substituted on one or more carbon atoms thereof with a substituent independently selected from halogen, or $C_1$-$C_4$ alkyl or $C_3$-$C_4$ carbocycle which is optionally substituted with hydroxy or one or more halogen; or (ii) —$SO_2N(R^{7F})_2$.

24. The compound of embodiment 22 or 23, wherein $R^1$ is methyl.
25. The compound of embodiment 22 or 23, wherein $R^1$ is —Cl.
26. The compound of embodiment 22 or 23, wherein $R^1$ is cyclopropyl.
27. The compound of any one of embodiments 24 to 26, wherein $R^3$ is —H.
28. The compound of any one of embodiments 1 to 21, wherein $R^2$ is a heteroaryl moiety of Formula AB, AC, or AD:

Formula AB

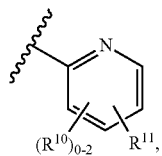

Formula AC

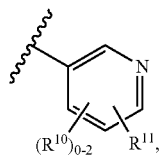

Formula AD

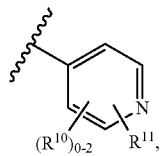

wherein:
each $R^{10}$ is independently —H, —F, —Cl, or s $C_1$-$C_3$ alkyl or cyclopropyl, each of which is optionally substituted with one or more halogen; and
$R^{11}$ is bonded in a position that is meta or para to the amino bond to said heteroaryl moiety and is:
(i) —$SO_2N(R^{10F})_2$, wherein each $R^{10F}$ is independently —H or a $C_1$-$C_4$ alkyl;
(ii) a $C_1$-$C_6$ alkyl or $C_3$-$C_6$ carbocycle, each of which is optionally substituted with one or more halogen;
(iii) a moiety of the formula:

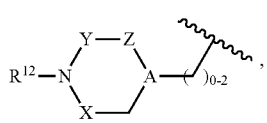

wherein
$R^{12}$ is —H or a $C_1$-$C_6$ alkyl or $C_3$-$C_6$ carbocycle, each of which is optionally substituted with hydroxy or one or more halogen;
A is >N— or >C(H)—; and
X, Y and Z are defined as follows:
Z is >$CH_2$ and X and Y are independently >$CH_2$ or >$C(CH_3)_2$, or X and Y are both >CH— and are bonded together through a methylene or ethylene bridge; or
Y is >$CH_2$ or >$C(CH_3)_2$, and X and Z are both >CH— and are bonded together through a methylene or ethylene bridge; or
(iv) a moiety of the formula:

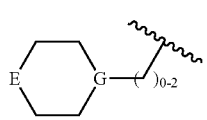

wherein,
G is >N— or >C(H)—; and
E is —O— or >C(H)—$R^{13}$, wherein $R^{13}$ is —H or a $C_1$-$C_6$ alkyl or $C_3$-$C_6$ carbocycle, each of which is optionally substituted with hydroxy or one or more halogen.

29. The compound of embodiment 28 wherein, $R^{11}$ is:
(i) a moiety of the structure:

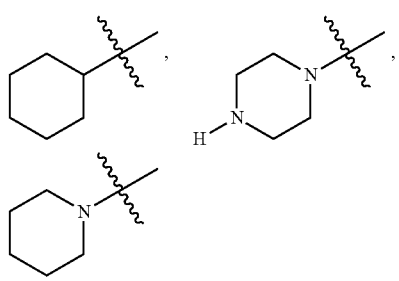

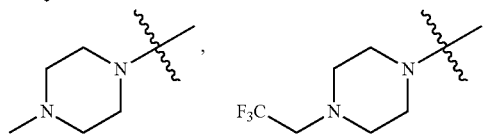

-continued

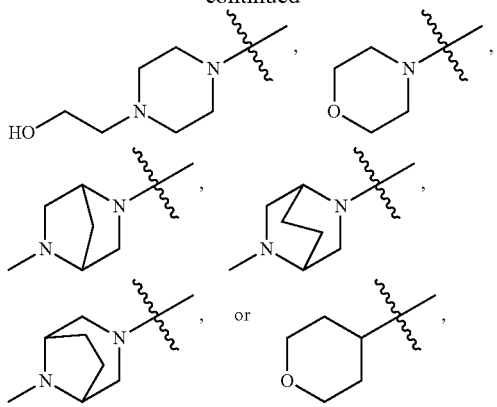

each of which is optionally substituted on one or more carbon atoms thereof with a halogen or with a moiety which is $C_1$-$C_4$ alkyl or $C_3$-$C_4$ carbocycle, each of which is optionally substituted on one or more carbon atoms thereof with: a halogen; or with a moiety which is $C_1$-$C_4$ alkyl or $C_3$-$C_4$ carbocycle, each of which is optionally substituted with hydroxyl or one or more halogen; or (ii) —$SO_2N(R^{10F})_2$.

30. A compound of Formula (II):

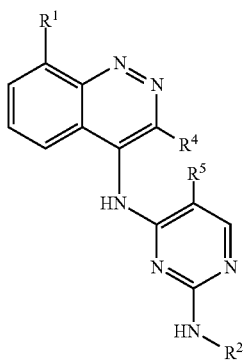

(II)

or a pharmaceutically acceptable salt thereof, wherein:
$R^1$ is: —$CH_3$ or —Cl;
$R^4$ is —H or —$CH_3$;
$R^5$ is —H or —F; and
$R^2$ is:
 d) a moiety of the formula:

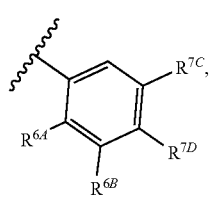

wherein,
 one of $R^{6A}$ and $R^{6B}$ is —H and the other is: —H, —F, —Cl, —$CH_3$, or $CF_3$;
 one of $R^{7C}$ and $R^{7D}$ is —H and the other is:
  (i) —F;
  (ii) —Cl;
  (iii) —$SO_2NH_2$;
  (iv) Cyclohexyl;
  (v) t-butyl; or (vi) a moiety of the formula:

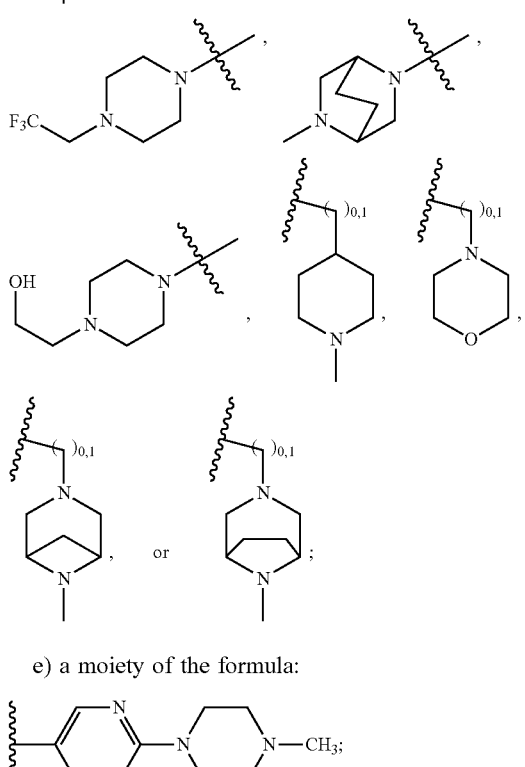

e) a moiety of the formula:

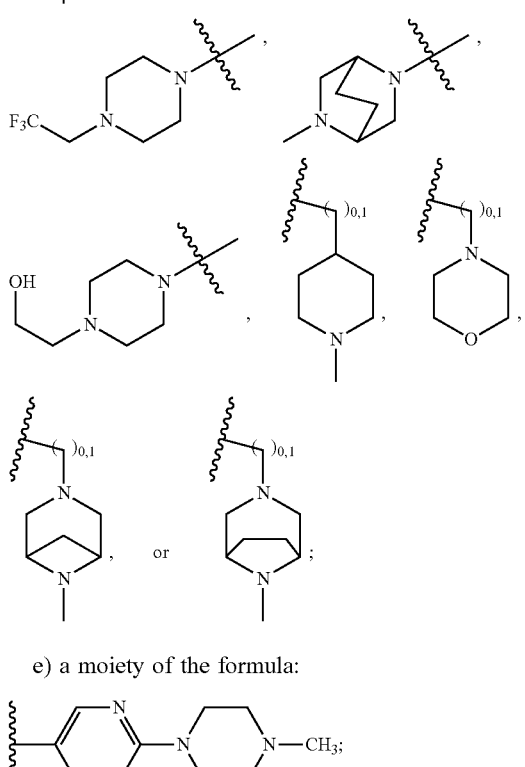

f) a moiety of the formula:

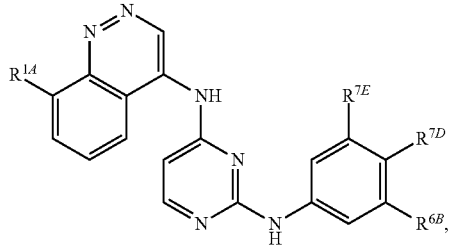

31. The compound of embodiment 1 having the structure of Formula (III):

(III)

or a pharmaceutically acceptable salt thereof, wherein:
$R^{1A}$ is methyl or cyclopropyl;
$R^{6B}$ is —H, —F, or —Cl; and one of $R^{7D}$ and $R^{7E}$ is —H and the other is a heterocycle of the formula:

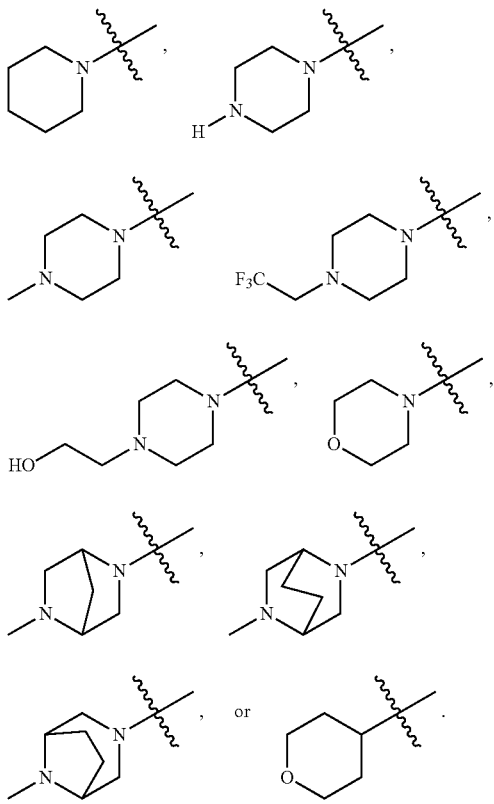

32. The compound of embodiment 31 wherein one of $R^{7D}$ and $R^{7E}$ is —H and the other is a moiety of the formula:

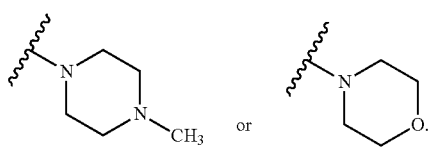

33. A compound of Formula (IV):

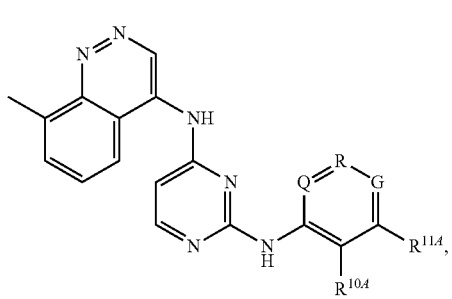

(IV)

or a pharmaceutically acceptable salt thereof, wherein one of Q, R, or G is =N—, and when Q is not selected to be N, it is C—$R^{10A}$ when R is not selected to be N, it is C—$R^{11A}$ when G is not selected to be N, it is C—$R^{11A}$, and wherein $R^{10A}$ is selected independently for each occurrence from —H, —F, —Cl, or a $C_1$-$C_3$ alkyl or cyclopropyl, each of which is optionally substituted with one or more halogen;

$R^{11A}$ is selected independently for each occurrence from:

(i) —H;

(ii) —F or —Cl;

(iii) a $C_1$-$C_3$ alkyl or cyclopropyl, each of which is optionally substituted with one or more halogen;

(iv) —$SO_2N(R^{10F})_2$, wherein each $R^{10F}$ is independently —H or a $C_1$-$C_4$ alkyl;

(v) a $C_1$-$C_6$ alkyl or $C_3$-$C_6$ carbocycle;

(vi) a moiety of the formula:

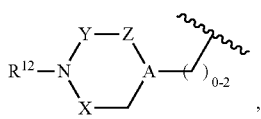

wherein:

$R^{12}$ is —H or a $C_1$-$C_6$ alkyl or $C_3$-$C_6$ carbocycle which is optionally substituted with hydroxy or one or more halogen;

A is >N— or >C(H)—; and

X, Y and Z are defined as follows:

Z is >$CH_2$ and X and Y are independently >$CH_2$ or >$C(CH_3)_2$, or X and Y are both >CH— and are bonded together through a methylene or ethylene bridge; or Y is >$CH_2$ or >$C(CH_3)_2$, and X and Z are both >CH— and are bonded together through a methylene or ethylene bridge; or (vii) a moiety of the formula:

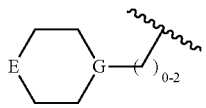

wherein:

G is >N— or >C(H)—; and

E is —O— or >C(H)—$R^{13}$, wherein $R^{13}$ is —H or a $C_1$-$C_6$ alkyl or $C_3$-$C_6$ carbocycle which is optionally substituted with hydroxy or one or more halogen, provided that one of $R^{11A}$ present is not selected to be —H, —F, —Cl, or a $C_1$-$C_3$ alkyl or $C_3$ carbocycle which is optionally substituted at one or more positions with a halogen.

34. A compound of any of Formula (I), (II), (III), or (IV), is selected from the compounds recited in Table 1 (infra), for example, the exemplary compounds Ex-10, Ex-11, Ex-12, Ex-13, Ex-33, Ex-34, Ex-57, or Ex-58, or any of these in the form of a pharmaceutically acceptable salt.

35. The compound of embodiment 31, wherein the compound is of the following formula:

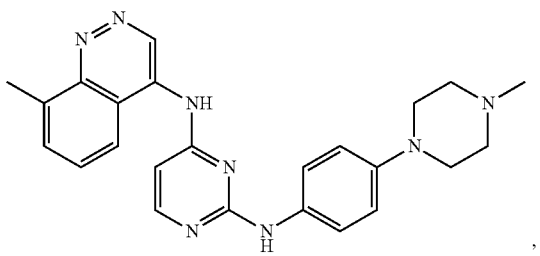

or a pharmaceutically acceptable salt thereof.

36. The compound of embodiment 31, wherein the compound is of the following formula:

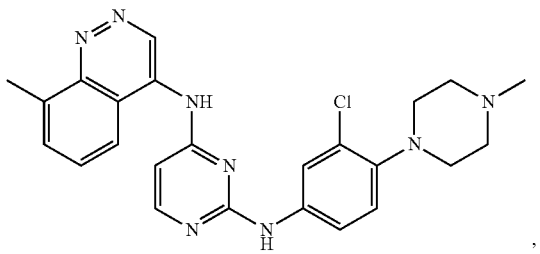

or a pharmaceutically acceptable salt thereof.

37. The compound of embodiment 31, wherein the compound is of the following formula:

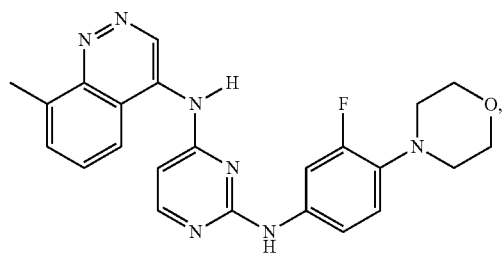

or a pharmaceutically acceptable salt thereof.

38. The compound of embodiment 31, wherein the compound is of the following formula:

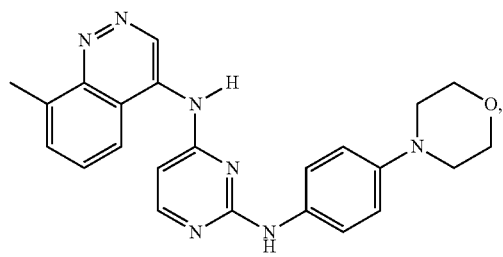 [SMILES: Cc1cccc2c(Nc3ccnc(Nc4ccc(N5CCOCC5)cc4)n3)cnnc12]

or a pharmaceutically acceptable salt thereof.

39. The compound of embodiment 31, wherein the compound is of the following formula:

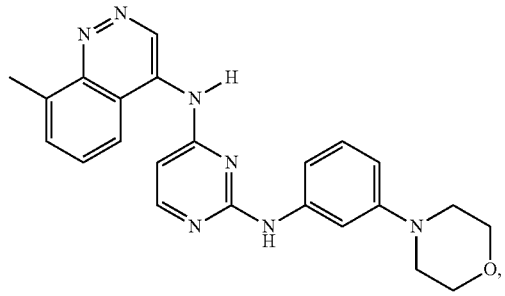 [SMILES: Cc1cccc2c(Nc3ccnc(Nc4cccc(N5CCOCC5)c4)n3)cnnc12]

or a pharmaceutically acceptable salt thereof.

40. The compound of embodiment 31, wherein the compound is of the following formula:

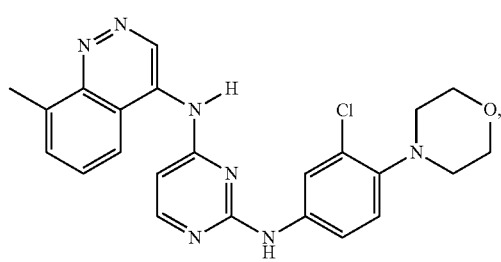 [SMILES: Cc1cccc2c(Nc3ccnc(Nc4ccc(N5CCOCC5)c(Cl)c4)n3)cnnc12]

or a pharmaceutically acceptable salt thereof.

41. The compound of embodiment 31, wherein the compound is of the following formula:

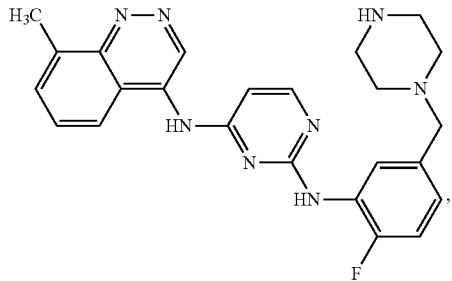 [SMILES: Cc1cccc2c(Nc3ccnc(Nc4cc(CN5CCNCC5)ccc4F)n3)cnnc12]

or a pharmaceutically acceptable salt thereof.

42. The compound of embodiment 31, wherein the compound is of the following formula:

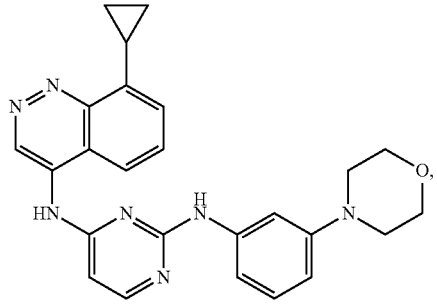 [SMILES: c1cc(Nc2nccc(Nc3cnnc4c(C5CC5)cccc34)n2)cc(N2CCOCC2)c1]

or a pharmaceutically acceptable salt thereof.

43. The compound of embodiment 31, wherein the compound is of the following formula:

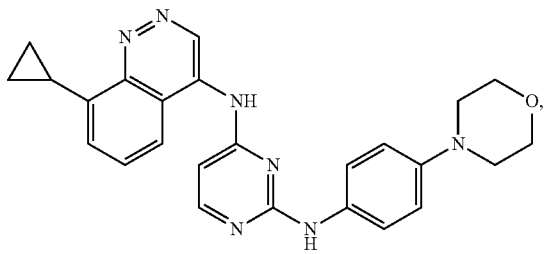 [SMILES: c1cc(C2CC2)c2nncc(Nc3ccnc(Nc4ccc(N5CCOCC5)cc4)n3)c2c1]

or a pharmaceutically acceptable salt thereof.
44. A pharmaceutical composition comprising a compound of any one of embodiments 1-43 and embodiments 96-108, or said compound in the form of a pharmaceutically acceptable salt, and at least one pharmaceutically acceptable excipient.
45. A method of treating a proliferative disease in a subject, the method comprising administering to the subject a compound of any one of embodiments 1-43 and embodiments 96-108, or said compound in the form of a pharmaceutically acceptable salt, or a pharmaceutical composition of embodiment 44.
46. The method of embodiment 45, wherein the proliferative disease is cancer.
47. The method of embodiment 46, wherein the cancer is: lung cancer, brain cancer, thyroid cancer, anaplastic astrocytoma, liver cancer, pancreatic cancer, skin cancer, melanoma, metastatic melanoma, colorectal cancer, breast cancer, prostate cancer, renal cancer, hepatocellular cancer, ovarian cancer, an HPV-associated cancer, multiple myeloma, myelodysplastic syndrome, a hematological cancer, or myelofibrosis.
48. The method of embodiment 47, wherein the cancer is non-small cell lung cancer (NSCLC).
49. The method of embodiment 47, wherein the cancer is neuroblastoma or glioblastoma.
50. The method of embodiment 47, wherein the cancer is anaplastic thyroid cancer (ATC).
51. The method of embodiment 47, wherein the cancer is colon carcinoma.
52. The method of embodiment 47, wherein the cancer is hepatocellular carcinoma (HCC).
53. The method of embodiment 47, wherein the cancer is pancreatic carcinoma.
54. The method of embodiment 47, wherein the cancer is anaplastic large cell lymphoma (ALCL) or myelodysplastic syndrome.
55. The method of embodiment 47, wherein the cancer is anaplastic astrocytoma.
56. The method of embodiment 47, wherein the cancer is pancreatic ductal adenocarcinoma.
57. The method of embodiment 47, wherein the cancer is an associated CAF cancer, metastatic melanoma, colorectal cancer, breast cancer, prostate cancer, renal cancer, hepatocellular cancer, ovarian cancer, an HPV-associated cancer, multiple myeloma, myelodysplastic syndrome, or myelofibrosis.
58. The method of embodiment 47, wherein the HPV-associated cancer is selected from: cervical cancer, oropharyngeal cancer, anal cancer, vulvar/vaginal cancer, or penile cancer.
59. The method of any one of embodiments 47-58, wherein said cancer is driven by TGF-β signaling.
60. The method of embodiment 45, wherein the proliferative disease is a fibrotic condition.
61. The method of embodiment 60, wherein the fibrotic condition is idiopathic pulmonary fibrosis, liver fibrosis, liver cirrhosis, nonalcoholic steatohepatitis, Peyronie's, cystic fibrosis, beta thalassemia, actinic keratosis, hypertension, a general inflammatory disorder, dry eye, ulcer, corneal, wet age-related macular degeneration, psoriasis, wound closure, chronic kidney disease, renal fibrosis, systemic sclerosis, or chronic Chagas' heart disease.
62. A method of inhibiting tumor growth in a subject, the method comprising administering to the subject a compound of any one of embodiments 1-43, or a pharmaceutically acceptable salt thereof, or a pharmaceutical composition of embodiment 44.
63. The method of any one of embodiments 45-62, further comprising administering one or more additional therapeutic agents to the subject.
64. The method of embodiment 63, wherein at least one of the additional therapeutic agents is an anti-cancer agent.
65. The method of embodiment 63 or 64, wherein at least one of the additional therapeutic agents is a PD-1 or PD-L1 inhibitor.
66. The method of any one of embodiments 45-62, further comprising treating the subject with radiation therapy or surgery.
67. A method of inhibiting ALK-5 activity in vivo or in vitro, the method comprising contacting ALK-5 with a compound of any one of embodiments 1-43 and 96-108, or a pharmaceutically acceptable salt thereof, or a pharmaceutical composition of embodiment 44.
68. The method of embodiment 67, wherein the inhibiting occurs in vivo in a subject.
69. The method of embodiment 67, wherein the inhibiting occurs in vitro.
70. The method of any one of embodiments 45-66 and 68, wherein the subject is a human.
71. A method of treating a fibrotic, inflammatory or proliferative disease or condition which is susceptible to inhibition of the TGFβ signaling pathway, the method comprising administering to a subject suffering from said fibrotic, inflammatory or proliferative disease or condition a compound of any one of embodiments 1-43 and 96-108, or a pharmaceutically acceptable salt form thereof, or a pharmaceutical formulation of embodiment 44, in an amount effective to inhibit TGFβ signaling.
72. The method of embodiment 71, wherein said compound, or pharmaceutically acceptable salt form of said compound, is a compound, or a compound in the form of a pharmaceutically acceptable salt, of any one of embodiments 34 to 43.
73. The method of embodiment 71, wherein said compound, or pharmaceutically acceptable salt form of said compound, is a compound of embodiment 34, or a pharmaceutically acceptable salt form thereof.
74. The method of embodiment 71, wherein said compound, or pharmaceutically acceptable salt form of said compound, is the compound of embodiment 35, or a pharmaceutically acceptable salt form thereof.
75. The method of embodiment 71, wherein said compound, or pharmaceutically acceptable salt form of said compound, is the compound of embodiment 36, or a pharmaceutically acceptable salt form thereof.

76. The method of embodiment 71, wherein said compound, or pharmaceutically acceptable salt form of said compound, is the compound of embodiment 37, or a pharmaceutically acceptable salt form thereof.

77. The method of embodiment 71, wherein said compound, or pharmaceutically acceptable salt form of said compound, is the compound of embodiment 38, or a pharmaceutically acceptable salt form thereof.

78. The method of embodiment 71, wherein said compound, or pharmaceutically acceptable salt form of said compound, is the compound of embodiment 39, or a pharmaceutically acceptable salt form thereof.

79. The method of embodiment 71, wherein said compound, or pharmaceutically acceptable salt form of said compound, is the compound of embodiment 40, or a pharmaceutically acceptable salt form thereof.

80. The method of embodiment 71, wherein said compound, or pharmaceutically acceptable salt form of said compound, is the compound of embodiment 41, or a pharmaceutically acceptable salt form thereof.

81. The method of embodiment 71, wherein said compound, or pharmaceutically acceptable salt form of said compound, is the compound of embodiment 42, or a pharmaceutically acceptable salt form thereof.

82. The method embodiment 71, wherein said compound, or pharmaceutically acceptable salt form of said compound, is the compound of embodiment 43, or a pharmaceutically acceptable salt form thereof.

83. The method of any one of embodiments 71-82, wherein said disease or condition is a fibrotic disease or condition.

84. The method of any one of embodiments 71-82, wherein said disease or condition is an inflammatory disease or condition.

85. The method of embodiment 83, wherein said fibrotic disease or condition is selected from idiopathic pulmonary fibrosis, liver fibrosis, liver cirrhosis, nonalcoholic steatohepatitis, Peyronie's, cystic fibrosis, beta thalassemia, actinic keratosis, hypertension, general inflammatory disorders, dry eye, ulcers, corneal, wet age-related macular degeneration, psoriasis, wound closure, chronic kidney disease, renal fibrosis, systemic sclerosis, or chronic Chagas' heart disease.

86. The method of embodiment 85, wherein said fibrotic disease or condition is idiopathic pulmonary fibrosis.

87. The method of any one of embodiments 71-82, wherein the disease or condition is a proliferative disease or condition selected from anaplastic astrocytoma, pancreatic cancer, metastatic melanoma, colorectal cancer, breast cancer, prostate cancer, renal cancer, hepatocellular cancer, ovarian cancer, an HPV-associated cancer, cervical cancer, oropharyngeal cancer, anal cancer, vulvar/vaginal cancer, penile cancer, multiple myeloma, myelodysplastic syndrome, or myelofibrosis.

88. A method of suppressing TGFβ signaling in a subject suffering from a disease or condition which is promoted by TGFβ-signaling, comprising administering an amount of at least one compound, or a pharmaceutically acceptable salt thereof, of any one of embodiments 1-43 and 96-108, or a pharmaceutical composition of embodiment 44 effective to sufficiently suppress TGFβ signaling to alter the course of the disease or condition.

89. A compound of Formula Int-A5:

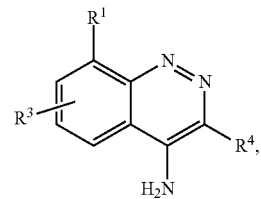

Int-A5 or a salt thereof, wherein:
$R^1$ is a $C_1$-$C_5$ alkyl or $C_3$-$C_5$ carbocycle, or a halogen;
$R^3$ is —H, —F, or —Cl; and
$R^4$ is —H, a halogen, or a $C_1$-$C_3$ alkyl or cyclopropyl, each of which is optionally substituted with one or more —F.

90. A compound of Formula Int-B2:

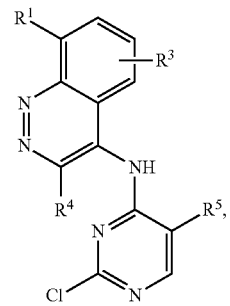

Int-B2 or a salt thereof, wherein:
$R^1$ is a $C_1$-$C_5$ alkyl or $C_3$-$C_5$ carbocycle, or a halogen;
$R^3$ is —H, —F, or —Cl;
$R^4$ is —H, a halogen, or a $C_1$-$C_3$ alkyl or cyclopropyl, each of which is optionally substituted with one or more —F; and
$R^5$ is —H, —F, or a $C_1$-$C_3$ alkyl or cyclopropyl, each of which is optionally substituted with one or more —F.

91. A process for preparing the compound of embodiment 89, or a salt thereof, comprising:
(a) providing a compound of Formula IntA-4:

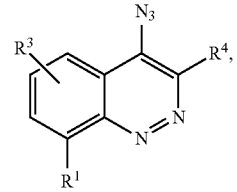

Int-A4 and reducing the azide functional group to an amino functional group using a palladium-catalyzed reduction,
wherein:
$R^1$ is a $C_1$-$C_5$ alkyl or $C_3$-$C_5$ carbocycle, or a halogen;
$R^3$ is —H, —F, or —Cl; and
$R^4$ is —H, a halogen, or a $C_1$-$C_3$ alkyl or $C_3$ carbocycle, each of which is optionally substituted with one or more —F.

92. The process of embodiment 91, further comprising preparing the compound of Formula Int-A4 by treating the compound of Formula Int-A3:

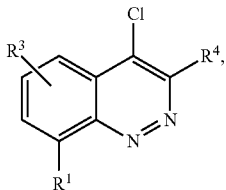

Int-A3 with sodium azide, wherein $R^1$, $R^3$ and $R^4$ are as defined for the compound of Formula Int-A4.

93. The process of embodiment 92, further comprising preparing the compound of Formula Int-A3 by treating the compound of Formula Int-A2:

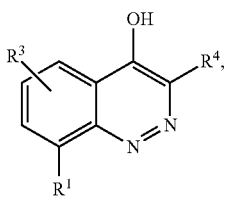

Int-A2 with phosphorousoxytrichloride, wherein $R^1$, $R^3$ and $R^4$ are as defined for the compound of Formula Int-A4.

94. The process of embodiment 93, further comprising preparing the compound Int-A2 by treating the compound of Formula Int-A1:

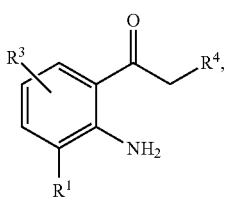

Int-A1 or a salt thereof, with sodium nitrite in an acid solution, wherein $R^1$, $R^3$ and $R^4$ are as defined for the compound of Formula Int-A4.

95. A process for preparing the compound of embodiment 90, or a salt thereof, comprising:

(a) providing a compound of Formula IntB-1:

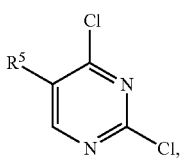

Int-B1 and reacting it with a compound of Formula Int-A5:

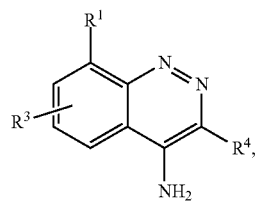

Int-A5 in the presence of a palladium coupling catalyst, wherein:

$R^1$ is a $C_1$-$C_5$ alkyl or $C_3$-$C_5$ carbocycle, or a halogen;

$R^3$ is —H, —F, or —Cl;

$R^4$ is —H, a halogen, or a $C_1$-$C_3$ alkyl or cyclopropyl, each of which is optionally substituted with one or more —F; and $R^5$ is —H, —F, or a $C_1$-$C_3$ alkyl or cyclopropyl, each of which is optionally substituted with one or more —F.

96. The compound of any one of embodiments 24 to 26, wherein $R^3$ is —F, $R^4$ is —H or —$CH_3$, $R^5$ is —H, and $R^6$ is —H.

97. The compound of embodiment 27, wherein $R^4$ is —H, —Cl, —F, —$CF_3$, or —$CH_3$, $R^5$ is —H, —$CH_3$, —$CF_3$, —Cl, or —F, and $R^6$ is —H, —F, —Cl, —$CH_3$, or —$CF_3$.

98. The compound of embodiment 97, wherein $R^4$ is —H or —$CH_3$, $R^5$ is —H or —F, and $R^6$ is —H, —F, —Cl, or —$CF_3$.

99. The compound of any one of embodiments 24 to 27 and 96 to 98, wherein one of $R^{7A}$ and $R^{7B}$ is hydrogen and the other is $C_1$-$C_6$ alkyl or $C_3$-$C_6$ carbocycle, each of which is optionally substituted with one or more halogen.

100. The compound of embodiment 28 or embodiment 29, wherein $R^1$ is —Cl.

101. The compound of embodiment 28 or embodiment 29, wherein $R^1$ is —$CH_3$.

102. The compound of embodiment 28 or embodiment 29, wherein $R^1$ is cyclopropyl.

103. The compound of embodiment 28 or embodiment 29, wherein $R^1$ is —$CF_3$.

104. The compound of any one of embodiments 100 to 103, wherein $R^3$ is —H or —F.

105. The compound of any one of embodiments 100 to 104, wherein $R^4$ is —H, —Cl, or $CH_3$.

106. The compound of any one of embodiments 100 to 105, wherein $R^5$ is —H or —F.

107. The compound of any one of embodiments 28, 29, and 100 to 106, wherein each $R^{10}$ is independently $C_1$-$C_3$ alkyl or cyclopropyl, each of which is optionally and independently substituted with one or more halogen.

108. The compound of any one of embodiments 28, 29, and 100 to 106, wherein each $R^{10}$ is independently —H, —$CH_3$, —$CF_3$, —Cl, or —F.

EXAMPLES

Synthetic Schemes for Intermediates

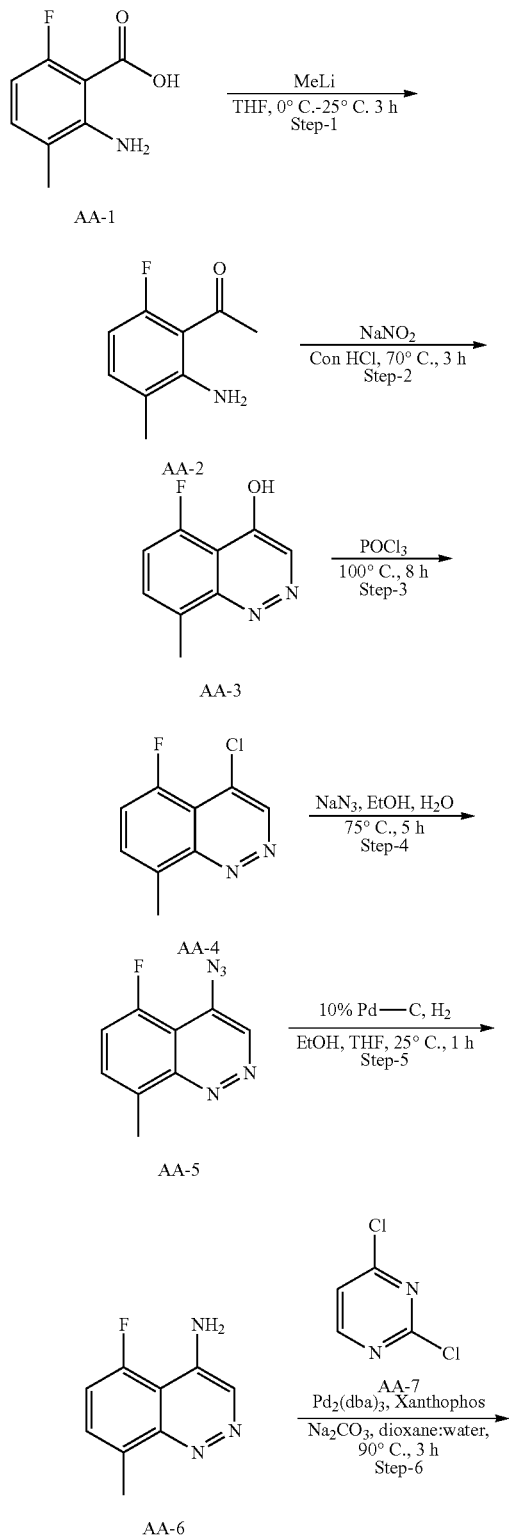

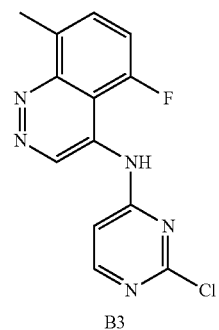

Synthesis of 1-(2-amino-6-fluoro-3-methylphenyl)ethan-1-one (AA-2)

To a suspension 2-amino-6-fluoro-3-methylbenzoic acid (AA-1) (10 g, 59.10 mmol) in tetrahydrofuran (50 mL) was added MeLi (1.6 M in diethyl ether) (129.43 mL, 207.1 mmol), at 0° C. and the resulting mixture was stirred at 0° C. temperature for 3 h. The reaction mixture was quenched with ammonium chloride solution (100 mL) and extracted with EtOAc (2×100 mL). The combined organic layers were washed with brine (50 mL), dried over sodium sulfate and concentrated under reduced pressure to afford the crude compound which was triturated with n-pentane (2×25 mL) yielding AA-2. LCMS (M+H): 168.3.

Synthesis of 5-fluoro-8-methylcinnolin-4-ol (AA-3)

To a stirred solution of 1-(2-amino-6-fluoro-3-methylphenyl)ethan-1-one (AA-2) (4.0 g, 23.92 mmol) in conc. HCl (32 mL) was added drop wise NaNO$_2$ in water (10 mL) (1.81 g, 68.99 mmol) at −5° C. and was stirred for 3 h at 70° C. The reaction mixture was filtered, washed with diethyl ether (20 mL). The filtrate was neutralized with Sat sodium bicarbonate up to $P^H=7$, the solid precipitated was filtered and dried to afford (AA-3). LCMS (M+H): 179.07.

Synthesis of 4-chloro-5-fluoro-8-methylcinnoline (AA-4)

POCl$_3$ (21 mL) was added to the compound 5-fluoro-8-methylcinnolin-4-ol (AA-3) (2.1 g, 11.79 mmol) at room temperature and allowed to stir at 100° C. for 8 h. The reaction mixture was cooled to room temperature and POCl$_3$ was distilled off. The residue was poured in to ice water (75 mL) and basified with sat sodium bi carbonate up to $P^H=7$. The precipitated solid was filtered and dried under vacuum to afford (AA-4). LCMS (M+H): 197.0.

Synthesis of 4-azido-5-fluoro-8-methylcinnoline (AA-5)

To a stirred solution of 4-chloro-5-fluoro-8-methylcinnoline (AA-4) (1.6 g, 8.16 mmol) in ethanol and water (80 mL, 1:1) was added NaN$_3$ (2.62 g, 40.8 mmol) and stirred for 4 h at 90° C. The reaction mixture was cooled to room temperature and concentrated under vacuum. The residue was diluted with water (100 mL) and the precipitated solid was filtered and dried under vacuum to afford (AA-5): LCMS (M+H): 204.10.

Synthesis of 5-fluoro-8-methylcinnolin-4-amine (AA-6)

To a stirred solution of 4-azido-5-fluoro-8-methylcinnoline (AA-5) (1.4 g, 6.89 mmol) in ethanol and THF (75 mL, 25 mL) was added 10% Pd/C (50% moisture) (0.4 g) and the reaction mixture was stirred under hydrogen par apparatuses for 1 h. The reaction mixture was filtered through a celite pad and washed with methanol (100 L). The filtrate was concentrated under vacuum and co-distilled with toluene (10 mL) to afford crude compound which was triturated ether (10 mL) to afford (AA-6). LCMS (M+H): 178.06.

Synthesis of N-(2-chloropyrimidin-4-yl)-5-fluoro-8-methylcinnolin-4-amine (B3)

A mixture of 5-fluoro-8-methylcinnolin-4-amine (AA-6) (1 g, 5.64 mmol), 2,4 dichloro pyrimidine (AA-7) (1.25 g 8.47 mmol) and $Na_2CO_3$ (1.79 g, 16.94 mmol) in 1,4 dioxane (40 mL), water (10 mL) was degassed for 20 min and added $Pd_2(dba)_3$ (0.51 g, 0.564 mmol), Xantphos (0.32 g, 0.564 mmol), the resulting reaction mixture was stirred for 3 h at 90° C. The reaction mixture was cooled to room temperature and concentrated under vacuum. The residue was diluted with water (100 mL) and the precipitated solid was filtered and triturated with ethyl acetate (200 mL) to afford (B3). LCMS (M+H): 290.10.

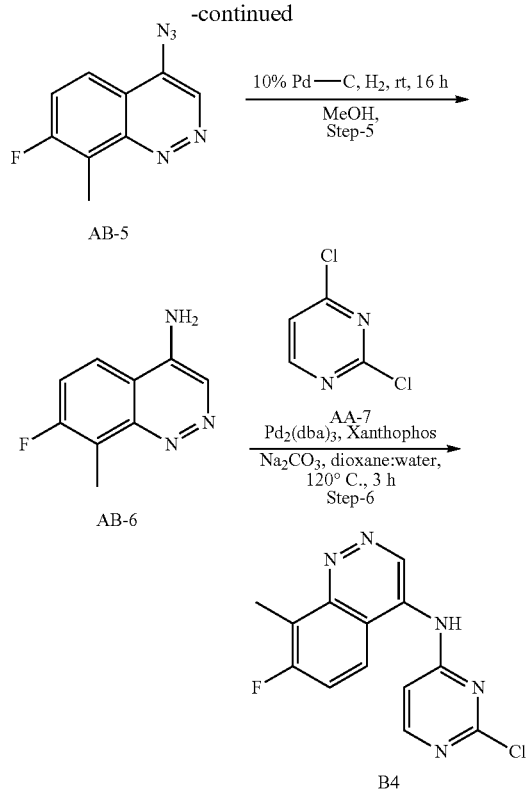

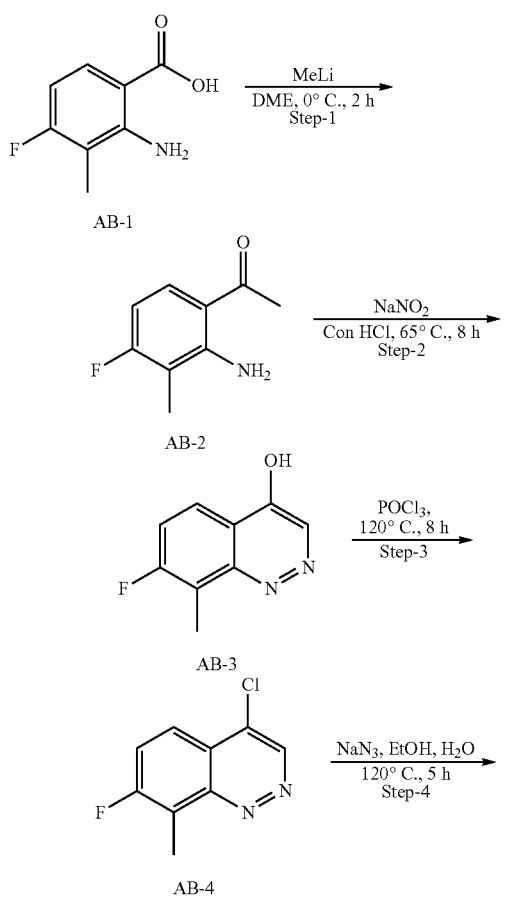

1-(2-amino-4-fluoro-3-methylphenyl)ethan-1-one (AB-2)

To a suspension 2-amino-4-fluoro-3-methylbenzoic acid (AB-1) (3.0 g, 59.17 mmol) in tetrahydrofuran (200 mL) was added MeLi (1.6 M in diethyl ether, 45 mL, 236.68 mmol) at 0° C. and the resulting reaction mixture was stirred to at 25° C. for 5 h. Reaction mixture was slowly quenched with ammonium chloride solution (50 mL), extracted with ethyl acetate (2×200 mL). Combined organic layers was washed with water (100 mL), brine (100 mL), dried over sodium sulfate and concentrated under vacuum to afford crude compound which was purified by flash column chromatography on silica gel (100-200 mesh) using 30% ethyl acetate and hexanes as a eluent to afford AB-2. LCMS (M+H): 168.1

Synthesis of 4-chloro-7-fluoro-8-methylcinnoline (AB-4)

$POCl_3$ (30 mL) was added to the compound 7-fluoro-8-methylcinnolin-4-ol (AB-3) (2.5 g, 14.97 mmol) at room temperature and allowed to stir at 100° C. for 6 h. The reaction mixture was distilled off under reduced pressure, residue was poured in to ice water (50 mL) and basified with sat sodium bicarbonate solution up to $p^H$=7. The precipitated solid was filtered and dried under vacuum to afford (AB-4). $^1H$ NMR $CDCl_3$, 400 MHz): δ 9.36 (s, 1H), 8.10-8.06 (m, 1H), 7.64 (t, J=9.2 Hz, 1H), 2.94 (s, 3H). LCMS (M+H): 197.0

Synthesis of 4-azido-7-fluoro-8-methylcinnoline (AB-5)

To a stirred solution of 4-chloro-7-fluoro-8-methylcinnoline (AB-4) (2.0 g, 10.20 mmol) in ethanol (30 mL), water (5 mL) was added NaN₃ (2.0 g, 30.61 mmol) and the resulting reaction mixture was stirred for 6 h at 75° C. The reaction mixture was cooled to room temperature and concentrated under vacuum. The residue was diluted with water (50 mL) and the precipitated solid was filtered and dried under vacuum to afford (AB-5). ¹H NMR (CDCl₃, 400 MHz): δ 9.23 (s, 1H), 7.94-7.90 (m, 1H) 7.50 (t, J=9.2 Hz, 1H), 2.90 (s, 3H). LCMS (M+H): 204.1

Synthesis of 7-fluoro-8-methylcinnolin-4-amine (AB-6)

To a stirred solution of 4-azido-7-fluoro-8-methylcinnoline (AB-5) (1.9 g, 9.35 mmol) in ethanol, (50 mL) was added 10% Pd/C (50% moisture) (0.5 g) and stirred under hydrogen gas in par apparatuses for 16 h. The reaction mixture was filtered through a celite pad and the residue was washed with methanol (2×100 mL). The filtrate was concentrated under reduced pressure and co-distilled with toluene (2×25 mL) to give crude compound which was and triturated with ether (2×25 mL) to afford (AB-6). (1H NMR (CDCl₃, 500 MHz): δ 8.77 (s, 1H), 7.63-7.60 (m, 1H) 7.38 (t, J=11.0 Hz, 1H), 4.72 (bs, 2H), 2.84 (s, 3H). LCMS (M+H): 178.10

Synthesis of N-(2-chloropyrimidin-4-yl)-7-fluoro-8-methylcinnolin-4-amine (B4)

A mixture of 7-fluoro-8-methylcinnolin-4-amine (AB-6) (1.2 g, 6.77 mmol), 2,4 dichloro pyrimidine (7) (1.5 g 10.15 mmol) and Na₂CO₃ (2.15 g 20.31 mmol) in 1,4 dioxane (50 mL), water (10 mL) was degassed for 20 min and added Pd₂(dba)₃ (0.620 g, 0.677 mmol), Xantphos (0.392 g, 0.677 mmol), the resulting reaction mixture was stirred for 6 h at 90° C. The reaction mixture was cooled to room temperature and concentrated under vacuum, the residue was diluted with water (50 mL) and the precipitated solid was filtered and washed with ethyl acetate (2×20 mL) to afford (B4). ¹H NMR DMSO-d₆, 400 MHz): δ 10.53 (s, 1H), 10.13 (s, 1H), 8.44 (d, J=6.0 Hz, 1H), 8.37-8.34 (m, 1H), 7.85-7.78 (m, 1H), 7.25 (d, J=6.0 Hz, 1H) 2.90 (s, 3H), LCMS (M+H): 290.12

Scheme-3

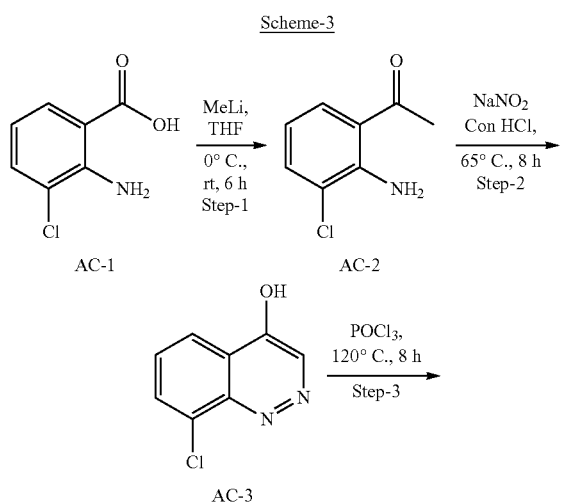

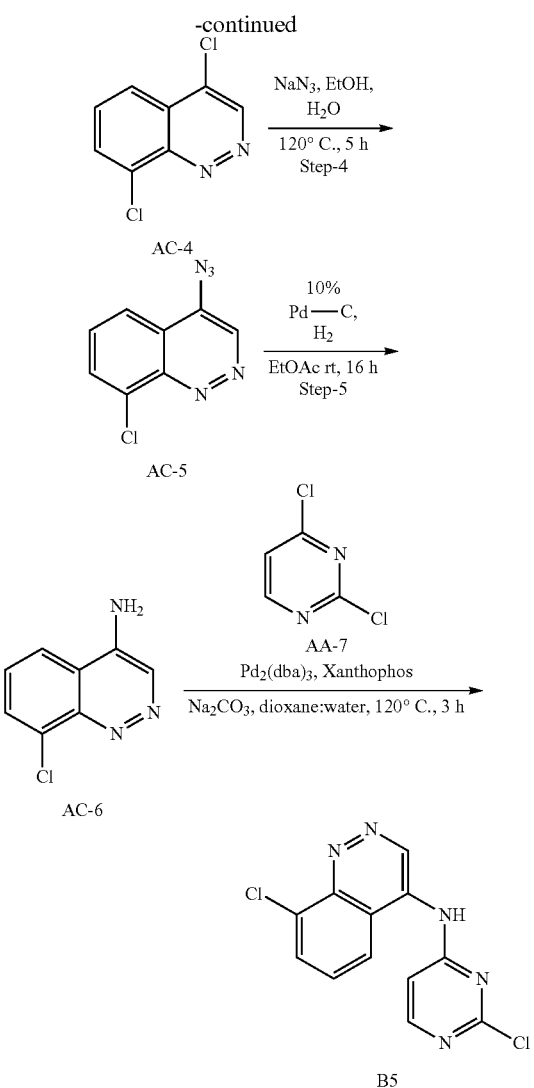

1-(2-amino-3-chlorophenyl)ethan-1-one (AC-2)

To a suspension 2-amino-3-chlorobenzoic acid (AC-1) (20.0 g, 116.95 mmol) in tetrahydrofuran (300 mL) was added MeLi (1.6 M in diethyl ether, 293 mL, 467.83 mmol) at 0° C. and the resulting reaction mixture was stirred at 25° C. temperature for 2 h. The reaction mixture was quenched with saturated ammonium chloride solution (50 mL) and extracted with ethyl acetate (2×200 mL). The combined organic layers were washed with water (100 mL), brine (100 mL), dried over sodium sulfate and concentrated under vacuum to afford the crude product which was purified by flash column chromatography on silica gel (100-200 mesh) using 30% ethyl acetate and hexanes to afford (AC-2). LCMS (M+H): 170.06

Synthesis of 8-chlorocinnolin-4-ol (AC-3)

To a stirred solution of 1-(2-amino-3-chlorophenyl)ethan-1-one (AC-2) (15.0 g, 88.75 mmol) in conc HCl (100 mL) was added a solution of NaNO₂ (7.40 g 106.50 mmol) in water (25 mL) drop wise at −5° C. and the resulting reaction mixture was stirred for 3 h at 70° C. The reaction mixture was cooled to room temperature and filtered, the residue was washed with diethyl ether (1.5 L) and the filtrate was neutralized with Sat sodium bicarbonate up to $p^H=7$ the precipitated solid was filtered and dried under vacuum to afford (AC-3): (1H NMR CDCl$_3$, 300 MHz): δ 10.40 (bs, 1H), 8.18 (d, J=6.0 Hz, 1H), 7.88 (s, 1H), 7.77-7.74 (m, 1H), 7.34 (t, J=8.1 Hz, 1H). LCMS (M−H): 181.7.

Synthesis of 4, 8-dichlorocinnoline (AC-4)

POCl$_3$ (50 mL) was added to the compound 8-chlorocinnolin-4-ol (AC-3) (4.5 g, 25.0 mmol) at room temperature and allowed to stir at 100° C. for 8 h. The reaction mixture was cooled to room temperature and excess of POCl$_3$ was distilled off. The residue was poured in to ice water (50 mL) and basified with sat sodium bicarbonate solution up to $p^H=7$, the precipitated solid was filtered and dried under vacuum to afford (AC-4): $^1$H NMR CDCl$_3$, 400 MHz): δ 9.46 (s, 1H), 8.17-8.13 (m, 1H), 8.02-8.00 (m, 1H), 7.81-7.34 (m, 1H). LCMS (M+H): 198.97

Synthesis of 4-azido-8-chlorocinnoline (AC-5)

To a stirred solution 4,8-dichlorocinnoline (AC-4) (4.3 g, 21.82 mmol) in ethanol (50 mL), water (5 mL), was added NaN$_3$ (7.10 g, 109.13 mmol) and stirred for 6 h at 75° C. The reaction mixture was cooled to room temperature and concentrated under vacuum. The residue was diluted with water (50 mL) and the precipitated solid was filtered and dried under vacuum to afford (5). $^1$H NMR (CDCl$_3$, 400 MHz): δ 9.31 (s, 1H), 7.99-7.95 (m, 2H) 7.68-7.63 (m, 1H). LCMS (M+H): 205.95

Synthesis of 8-chlorocinnolin-4-amine (AC-6)

To a stirred solution of 4-azido-8-chlorocinnoline (AC-5) (4.0 g, 19.51 mmol) in Ethyl acetate (100 mL) was added 10% Pd/C (50% moisture) (0.5 g) and stirred under hydrogen par apparatuses at 20 PSI for 16 h. The reaction mixture was filtered through a celite and washed with methanol (2×100 mL), the filtrate was concentrated under reduced pressure and co-distilled with toluene (2×25 mL) and washed with ether (2×25 mL) to afford AC-6. (1H NMR (CDCl$_3$, 300 MHz): δ 8.71 (s, 1H), 8.18 (dd J=7.8 Hz, 1.2 Hz, 1H) 7.91 (dd J=6.6 Hz, 6.0 Hz, 1H) 7.56-7.51 (m, 1H), 7.45 (bs, 2H). LCMS (M+H): 180.11

Synthesis of 8-chloro-N-(2-chloropyrimidin-4-yl) cinnolin-4-amine (B5)

A solution of 8-chlorocinnolin-4-amine (AC-6) (1.0 g, 5.58 mmol), 2,4 dichloro pyrimidine (AA-7) (1.0 g 6.70 mmol) and Na$_2$CO$_3$ (1.78 g 16.74 mmol) in 1,4 dioxane (50 mL), water (5 mL), was degassed for 20 min and added Pd$_2$(dba)$_3$ (0.510 g, 0.558 mmol), Xantphos (0.323 g, 0.558 mmol), the resulting reaction mixture was stirred for 6 h at 90° C. The reaction mixture was cooled to room temperature and concentrated under vacuum, the residue was diluted with water (50 mL), the precipitated solid was filtered, washed with ethyl acetate (2×20 mL) and dried under vacuum to afford (B5). LCMS (M+H): 292.01

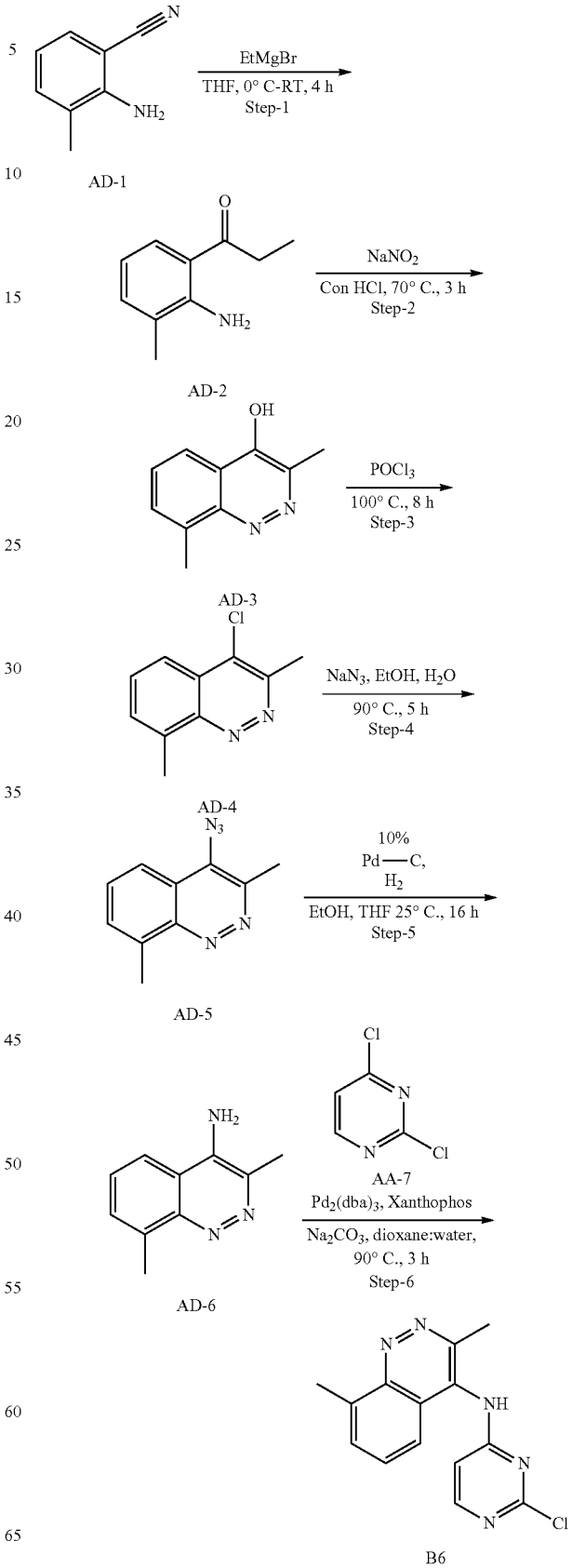

Scheme-4

1-(2-amino-3-methylphenyl)propan-1-one (AD-2)

To a suspension 2-amino-3-methylbenzonitrile (AD-1) (20 g, 151.51 mmol) in tetrahydrofuran (400 mL) was added EtMgBr (1 M in diethyl ether, 760 mL, 757.55 mmol) at 0° C. and the resulting reaction mixture was stirred at RT for 4 h. The reaction mixture was quenched with saturated ammonium chloride solution (400 mL) and extracted with EtOAc (2×500 mL). The combined organic layers were washed with brine (300 mL), dried over sodium sulfate and concentrated under vacuum to afford to crude compound which was triturated with n-pentane (2×200 mL) to afford (AD-2). $^1$H NMR (CDCl$_3$, 400 MHz): δ 7.67 (dd, J=8.4, 0.8 Hz, 1H), 7.18 (dd, J=7.2, 0.8 Hz, 1H), 6.61-6.57 (m, 1H), 2.99 (q, J=7.2 Hz, 2H), 2.16 (s, 3H), 1.22 (t, J=7.2 Hz, 3H): LCMS (M+H): 164.08

Synthesis of 3,8-dimethylcinnolin-4-ol (AD-3)

To a stirred solution of 1-(2-amino-3-methylphenyl)propan-1-one (AD-2) (18 g, 110.42 mmol), in conc. HCl (290 mL) was added a solution of NaNO$_2$ (11.49 g 165.64 mmol) in water (40 mL) drop wise at −5° C. and stirred for 3 h at 70° C. The reaction mixture was cooled to room temperature, filtered, and the residue was washed with diethyl ether (500 mL). The filtrate was neutralized with Sat sodium bicarbonate solution up to p$^H$=7 and the precipitated solid was filtered and dried under vacuum to afford (AD-3). $^1$H NMR (CDCl$_3$, 400 MHz): δ 9.94 (br s, 1H), 8.15 (dd, J=8.4, 0.8 Hz, 1H), 7.48 (d, J=7.2 Hz, 1H), 7.27-7.23 (m, 1H), 2.52 (s, 3H), 2.43 (s, 3H). LCMS (M+H): 175.1

Synthesis of 4-chloro-3,8-dimethylcinnoline (AD-4)

POCl$_3$ (65 mL) was added to the compound 3,8-dimethylcinnolin-4-ol (AD-3) (4.5 g, 25.86 mmol) at room temperature and allowed to stir at 100° C. for 8 h. The reaction mixture was cooled to room temperature and excess POCl$_3$ was distilled off. The residue was poured in to ice water (100 mL) and basified with sat sodium bicarbonate solution up to p$^H$=7, the precipitated solid was filtered and dried under vacuum to afford (AD-4). $^1$H NMR CDCl$_3$, 400 MHz): δ 8.0 (d, J=8.8 Hz, 1H), 7.71-7.69 (m, 1H), 7.62-7.60 (m, 1H), 3.04 (s, 3H), 3.01 (s, 3H). LCMS (M+H): 193.06.

Synthesis of 4-azido-3,8-dimethylcinnoline (AD-5)

To a stirred solution of 4-chloro-3,8-dimethylcinnoline (AD-4) (4.5 g, 23.43 mmol) in ethanol (60 mL), water (10 mL), was added NaN$_3$ (4.57 g, 70.31 mmol) and the resulting reaction mixture was stirred for 5 h at 90° C. The reaction mixture was cooled to room temperature and concentrated under vacuum. The residue was diluted with water (50 mL), the precipitated solid was filtered and dried under vacuum to afford (AD-5). $^1$H NMR (CDCl$_3$, 400 MHz): 7.96-7.93 (m, 1H), 7.67-7.57 (m, 2H), 3.07 (s, 3H), 2.98 (s, 3H). LCMS (M+H): 200.08

Synthesis of 3, 8-methylcinnolin-4-amine (AD-6)

To a stirred solution of 4-azido-3,8-dimethylcinnoline (AD-5) (4 g, 20.10 mmol) in Ethanol (40 mL) was added 10% Pd/C (2 g) and stirred under hydrogen par apparatuses for 16 h. The reaction mixture was filtered through a celite and washed with ethanol (20 mL). The filtrate was concentrated under vacuum to give crude which was triturated with diethyl ether (2×20 mL) to afford AD-6. (1H NMR (DMSO-d$_6$, 400 MHz): δ 8.01 (d, J=8.4 Hz, 1H), 7.56 (d, J=6.8 Hz, 1H), 7.45 (t, J=8.0 Hz, 1H), 7.08 (bs, 2H), 3.1 (s, 3H), 2.76 (s, 3H) LCMS (M+H): 174.09.

Synthesis of N-(2-chloropyrimidin-4-yl)-3,8-dimethylcinnolin-4-amine (B6)

A mixture of 3, 8-methylcinnolin-4-amine (AD-6) (2 g, 11.56 mmol), 2,4 dichloro pyrimidine (7) (2.58 g 17.34 mmol) and Na$_2$CO$_3$ (3.67 g 34.68 mmol) in 1,4-Dioxnae (40 mL), water (10 mL) was degassed for 20 min and added Pd$_2$(dba)$_3$ (1.05 g, 1.15 mmol), Xantphos (0.8 g, 1.38 mmol), the resulting reaction mixture was stirred for 3 h at 90° C. The reaction mixture was cooled to room temperature and concentrated under vacuum, the residue was diluted with water (50 mL), the precipitated solid was filtered and triturated with ethyl acetate (2×50 mL) to afford (B6). LCMS (M+H): 286.14.

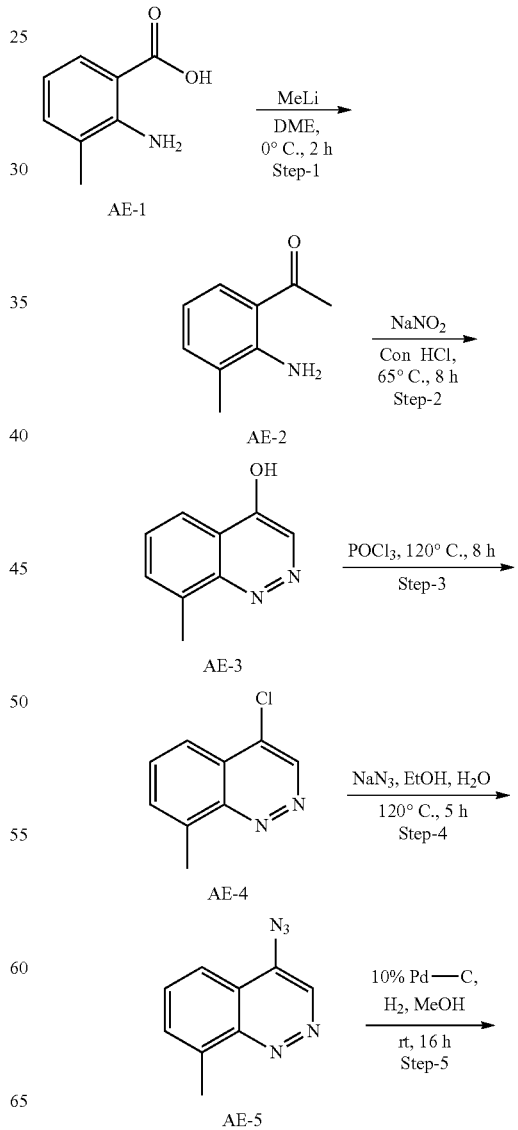

Scheme 5

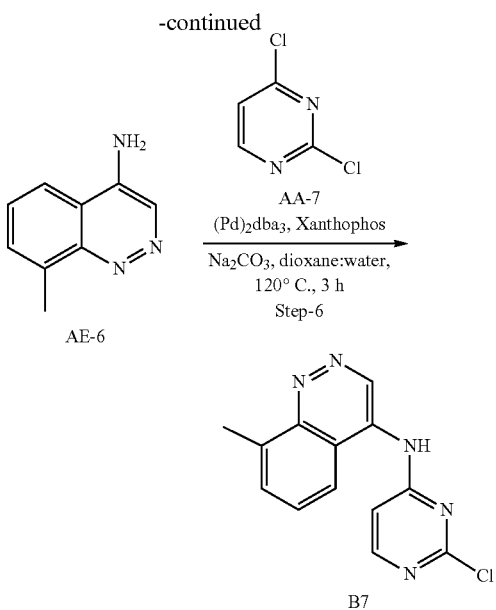

Step 1: 1-(2-amino-3-methylphenyl)ethan-1-one (AE-2)

To a suspension 2-amino-3-methylbenzoic acid (65 g, 430.46 mmol) (AE-1) in dimethoxyethane (DME) (1.5 L) was added MeLi (3.1 M in DME) (0.972 mL, 33013.22 mmol), at 0° C. and the resulting mixture was stirred to 0° C. temperature for 3 h. The reaction mixture was quenched with ammonium chloride solution (200 mL). Solvent was evaporated under vacuum and the resulting residue was washed with water and extracted with EtOAc (2×200 mL). The combined organic layers were washed with water (100 mL), brine (100 mL), dried over sodium sulphate, filtered and concentrated under reduced pressure and the residue was purified by flash column chromatography on silica gel (100-200 mesh) using 3% ethyl acetate/hexane to afford AE-2: $^1$H NMR (CDCl$_3$, 400 MHz): δ 7.65 (d, J=8.4 Hz, 1H), 7.21 (d, J=6.8 Hz, 1H), 6.59 (t, J=8.0 Hz, 1H), 6.41 (bs, 2H), 2.16 (s, 3H): LCMS (M+H): 150.1

Step 2: Synthesis of 8-methylcinnolin-4-ol (AE-3)

To a stirred solution of 1-(2-amino-3-methylphenyl) ethan-1-one (50 g, 0.335 mmol) (AE-2) and conc. HCl (275 mL) was added drop wise NaNO$_2$ in water (75 mL) (25.469 g 369.12 mmol) at −5° C. and stirred at 70° C. for 3 h. The reaction mixture was filtered, washed with ether (50 mL). The filtrate was neutralized with Sat sodium bicarbonate (pH=7) and the precipitated solid was filtered and dried under reduced pressure to afford AE-3; ($^1$H NMR CDCl$_3$, 500 MHz): δ 10.06 (bs, 1H), 8.14 (d, J=8.0 Hz, 1H), 7.87 (s, 1H), 7.54 (d, J=7.0 Hz, 1H), 7.32-7.29 (m, 1H), 2.56 (s, 3H). LCMS (M+H): 161.1

Step 3: Synthesis of 4-chloro-8-methylcinnoline (AE-4)

POCl$_3$ (220 mL) was added to the compound 8-methyl-cinnolin-4-ol (10.5 g, 65.62 mmol) (AE-3) at room temperature and allowed to stir at 100° C. for 8 h, the reaction mixture was cooled to room temperature and concentrated under reduced pressure. The residue was diluted with water (50 mL), basified with sat sodium bi carbonate (pH=7) and extracted twice with EtOAc (2×200 mL). The combined organic layers were washed with water (120 mL), brine (120 mL), dried over sodium sulphate, filtered and concentrated under vacuum to afford AE-4; $^1$H NMR (CDCl$_3$, 400 MHz): δ 9.35 (s, 1H), 8.05 (d, J=7.6 Hz, 1H), 7.77-7.71 (m, 2H), 3.05 (s, 3H) LCMS (M+H): 179.1

Step 4: Synthesis of 4-azido-8-methylcinnoline (AE-5)

To a stirred solution of 4-chloro-8-methylcinnoline (8.0 g, 48.48 mmol) (AE-4) in ethanol (100 mL), water (25 mL), was added NaN$_3$ (9.5 g, 145.45 mmole) and stirred for 5 h at 80° C. The reaction mixture was cooled to room temperature and concentrated under reduced pressure. The residue was diluted with water (50 mL) and the precipitated solid was filtered and dried under vacuum to afford AE-5: $^1$H NMR (CDCl3, 400 MHz): δ 9.23 (s, 1H), 7.89 (d, J=8.4 Hz, 1H), 7.69-7.61 (m, 2H), 3.02 (s, 3H). LCMS (M+H): 186.1

Step 5: Synthesis of 8-methylcinnolin-4-amine (AE-6)

To a stirred solution of 4-azido-8-methylcinnoline (6.0 g, 32.43 mmol) (AE-5) in ethanol (100 mL) was added 10% Pd/C (50% moisture) (3.4 g) and stirred for 24 h under hydrogen balloon pressure. The reaction mixture was filtered through celite pad and the residue was washed with methanol (2×50 mL). The filtrate was concentrated under reduced pressure to afford AE-6. $^1$H NMR (DMSO-d6, 400 MHz): δ 8.63 (s, 1H), 8.01 (d, J=8.4 Hz, 1H), 7.56 (d, J=6.8 Hz, 1H), 7.45 (t, J=8.0 Hz, 1H), 7.08 (bs, 2H), 2.76 (s, 3H). LCMS (M+H): 160.1

Step 6: Synthesis of N-(2-chloropyrimidin-4-yl)-8-methylcinnolin-4-amine (8)

To a stirred solution of 8-methylcinnolin-4-amine (3.0 g, 48.48 mmol) (AE-6), 2,4 dichloro pyrimidine (5.62 g 37.73 mmole) (AA-7) and Na$_2$CO$_3$ (6.0 g 56.58 mmol) in 1,4 dioxane (75 mL), water (15 mL), was degassed for 20 min and added Pd$_2$(dba)$_3$ (1.72 g, 1.886 mmol), Xantphos (1.09 g, 1.886 mmol) and stirred at 120° C. for 5 h. The reaction mixture was cooled to room temperature and concentrated under reduced pressure. The residue was diluted with water (50 mL) and precipitated solid was filtered, washed with ethyl acetate (50 mL) and dried under reduced pressure to afford B7: 1H NMR (DMSO-d6, 400 MHz): δ 10.50 (s, 1H), 10.03 (s, 1H), 8.36 (d, J=6.0 Hz, 1H), 8.26 (d, J=9.6 Hz, 1H), 7.75-7.73 (m, 2H), 7.19 (d, J=5.6 Hz, 1H) 2.90 (s, 3H), LCMS (M+H): 272.0

Scheme-6

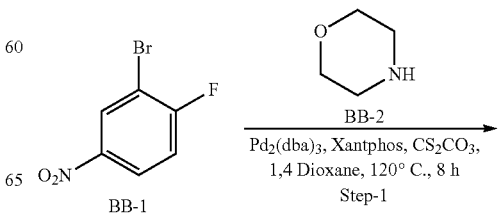

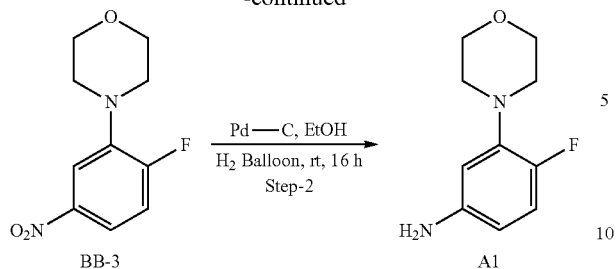

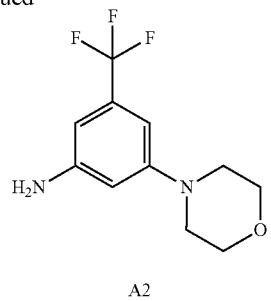

Synthesis of 4-(2-fluoro-5-nitrophenyl)morpholine (BB-3)

To a stirred solution of 2-bromo-1-fluoro-4-nitrobenzene (BB-1) (2.0 g, 9.0 mmol) in 1,4-dioxane (50 mL) was added morpholine (2) (0.79 g 9.0 mmol) and Cs$_2$CO$_3$ (8.78 g 2.70 mmol) and degassed for 15 min then added Pd$_2$(dba)$_3$ (0.82 g, 0.90 mmol), Xantphos (0.520 g, 0.90 mmol) and resulting reaction mixture was stirred for 16 h at 120° C. The reaction mixture was cooled to room temperature and diluted with water (20 mL) and extracted with ethyl acetate (2×40 mL). The combined organic layers were washed with brine (25 mL), dried over sodium sulfate and concentrated under vacuum to get crude compound which was purified by flash column chromatography on silica gel (100-200 mesh) using 5-10% ethyl acetate and hexanes as a eluent to afford (BB-3). LCMS (M+H): 227.18

Synthesis of 4-fluoro-3-morpholinoaniline (A1)

To a stirred solution of 4-(2-fluoro-5-nitrophenyl) morpholine (BB-3) (0.5 g, 15.76 mmol) in methanol was added 10% Pd/C (0.250 g) (50 mL) and stirred under hydrogen balloon pressure for 16 h at 25° C. The reaction mixture was filtered through celite pad and washed with methanol (100 mL), the filtrate was concentrated under vacuum to afford (A1). ($^1$H NMR CDCl$_3$, 400 MHz): δ 6.84-6.79 (m, 1H), 6.27-622 (m, 2H), 3.85 (t, J=4.4 Hz, 4H), 3.57 (bs, 2H), 3.05-3.03 (m, 4H). LCMS (M+H): 197.20.

Synthesis of 4-(3-nitro-5-(trifluoromethyl) phenyl) morpholine (BC-3)

A mixture of 1-fluoro-3-nitro-5-(trifluoromethyl) benzene (BC-1) (2.0 g, 9.56 mmol), morpholine (BB-2) (1.5 mL 14.35 mmol) was stirred for 5 h at 100° C. The reaction mixture was cooled to room temperature, diluted with water (20 mL) and the precipitated solid was filtered and dried to get crude compound which was purified by flash column chromatography on silica gel (100-200 mesh) using 5-10% ethyl acetate and hexane as a eluent to afford (BC-3): (1H NMR CDCl$_3$, 400 MHz): δ 7.90 (s, 1H), 7.85 (t, J=2.0 Hz, 1H) 7.35 (s, 1H), 3.91-388 (m, 4H), 3.33-3.30 (m, 4H). LCMS (M+H): 277.03.

Synthesis of 3-morpholino-5-(trifluoromethyl) aniline (A2)

To a stirred solution of 4-(3-nitro-5-(trifluoromethyl) phenyl) morpholine (BC-3) (1.5 g, 5.43 mmol) in methanol (50 mL) was added 10% Pd/C (0.5 g) and stirred under hydrogen balloon pressure for 16 h at 25° C. The reaction mixture was filtered through celite pad and washed with methanol (100 mL), filtrate was concentrated under vacuum to afford (A2). LCMS (M+H): 247.16

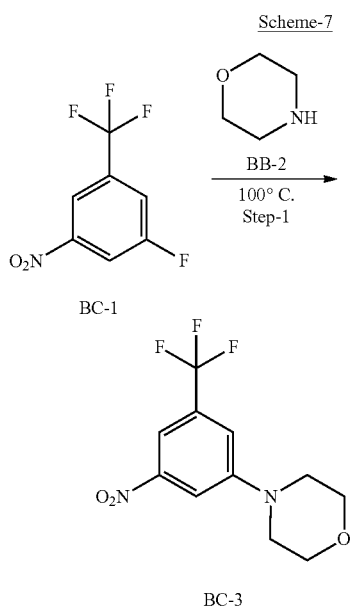

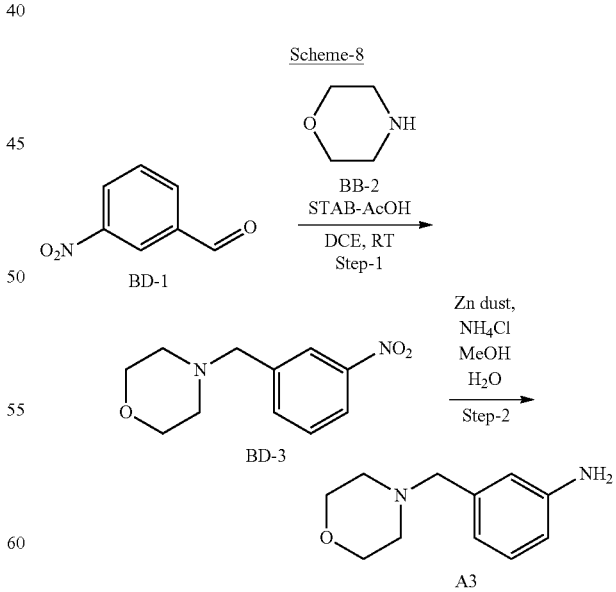

Synthesis of 4-(3-nitrobenzyl) morpholine (BD-3)

To a stirred solution of 23-nitrobenzaldehyde (BD-1) (1.0 g, 6.221 mmol) in in DCE (20 mL) was added morpholine (0576 mL 6.221 mmol) and Na(OAc)₃BH (4.192 g 19.86 mmol), cat amount of acetic acid, the resulting reaction mixture was stirred for 16 h at 25° C. The reaction mixture was diluted with water (25 mL) and extracted with dichloromethane (2×100 mL). The combined organic layers were washed with brine (25 mL), dried over sodium sulfate and concentrated under reduced pressure to afford the crude compound which was purified by flash column chromatography on silica gel (100-200 mesh) using 5-10% ethyl acetate and hexanes as an eluent to afford (BD-3): LCMS (M+H): 223.1

Synthesis of 3-(morpholinomethyl)aniline (A3)

To a stirred solution of 4-(3-nitrobenzyl)morpholine (BD-3) (1.0 g, 4.50 mmol)) in methanol (10 mL), water (2.0 mL) was added Zn dust (2.0 g 45.04 mmol) and ammonium chloride (2.3 g, 45.04 mmol) and the resulting reaction mixture was stirred for 3 h at 25° C. The reaction mixture was filtered through celite pad and washed with methanol (100 mL), the filtrate was concentrated under vacuum and diluted with water (20 mL) and was extracted with ethyl acetate (2×100 mL). The combined organic layers were washed with brine (25 mL), dried over sodium sulfate and concentrated under vacuum to afford the crude compound which was purified by flash column chromatography on silica gel (100-200 mesh) using 30-40% ethyl acetate and hexane as a eluent to afford (A3): LCMS (M+H): 193.1.

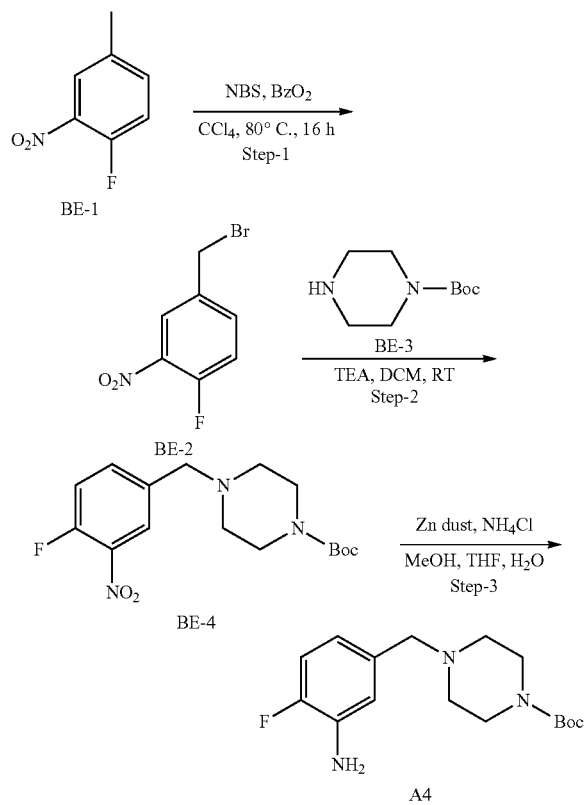

Scheme-9

Synthesis of 4-(bromomethyl)-1-fluoro-2-nitrobenzene (BE-2)

To a stirred solution of 1-fluoro-4-methyl-2-nitrobenzene (BE-1) (5.0 g, 32.23 mmol) in CCl₄ (100 mL) was added NBS (6.0 g 38.68 mmol) and benzyl peroxide (0.780 g, 3.223 mmol) and the resulting reaction mixture was stirred for 16 h at 80° C. The reaction mixture was diluted with water (25 mL) and extracted with dichloromethane (2×250 mL). The combined organic layers were washed with brine (50 mL), dried over sodium sulfate and concentrated under vacuum to get crude compound which was purified by flash column chromatography on silica gel (100-200 mesh) using 2-5% thyl acetate and hexanes as a eluent to afford (BE-2). LCMS (M+H): 339.1.

Synthesis of tert-butyl 4-(4-fluoro-3-nitrobenzyl)piperazine-1-carboxylate (BE-4)

To a stirred solution of 4-(bromomethyl)-1-fluoro-2-nitrobenzene (BE-2) (1.56 g, 6.410 mmol) in DCM (20 mL) was added tert-butyl piperazine-1-carboxylate (BE-3) (1.19 g 10.30 mmol) and triethylamine (1.94 mL, 19.23 mmol) and the resulting reaction mixture was stirred for 16 h at 25° C. The reaction mixture was diluted with water (25 mL) and extracted with dichloromethane (2×100 mL). The combined organic layers were washed with brine (25 mL), dried over sodium sulfate and concentrated under vacuum to afford the crude compound which was purified by flash column chromatography on silica gel (100-200 mesh) using 5-10% thyl acetate and hexanes as a eluent to afford (BE-4). LCMS (M+H): 340.1

Synthesis of tert-butyl 4-(3-amino-4-fluorobenzyl)piperazine-1-carboxylate (A4)

To a stirred solution of tert-butyl 4-(4-fluoro-3-nitrobenzyl)piperazine-1-carboxylate (BE-4) (1.12 g, 2.94 mmol) in methanol (20 mL), water (5 mL) was added Zn dust (1.91 g 29.49 mmol) and ammonium chloride (1.56 g, 29.49 mmol) and the resulting reaction mixture was stirred for 2 h at 25° C. The reaction mixture was filtered through celite pad and washed with methanol (100 mL), filtrate was concentrated under vacuum, diluted with water (20 mL) and extracted t with ethyl acetate (2×100 mL). The combined organic layers were washed with brine (25 mL), dried over sodium sulfate and concentrated under reduced pressure to get crude compound which was purified by flash column chromatography on silica gel (100-200 mesh) using 20-30% ethyl acetate and hexanes to afford (A4). LCMS (M+H): 310.2.

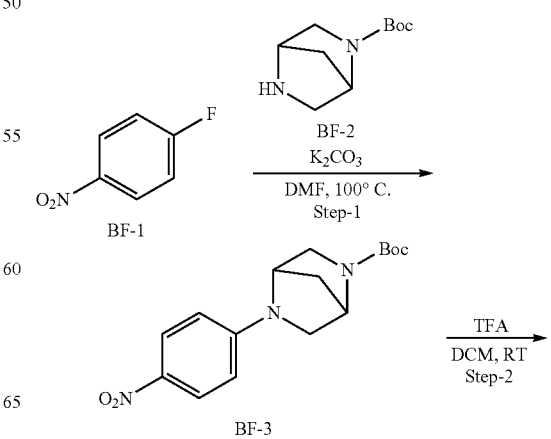

Scheme-10

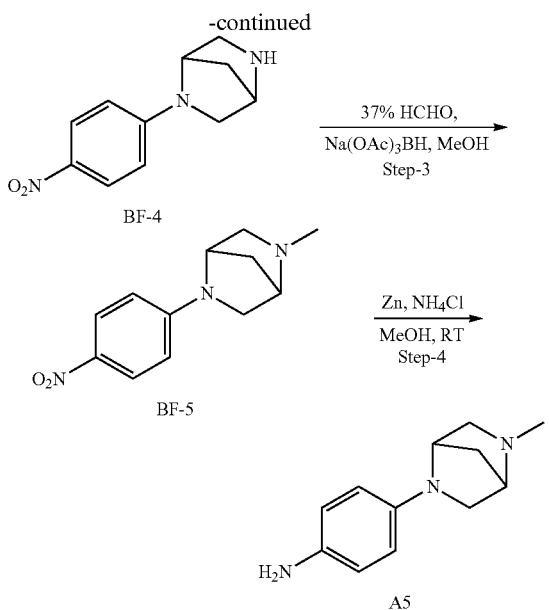

Synthesis of tert-butyl 5-(4-nitrophenyl)-2,5-diazabicyclo[2.2.1]heptane-2-carboxylate (BF-3)

To a stirred solution of 1-fluoro-4-nitrobenzene (BF-1) (0.5 g, 3.546 mmol) in DMF (5 mL) was added tert-butyl 2,5-diazabicyclo[2.2.1]heptane-2-carboxylate (BF-2) (0.702 g 3.546 mmol) and $K_2CO_3$ (1.468 g 10.63), the resulting reaction mixture was stirred for 16 h at 80° C. The reaction mixture was cooled to RT, diluted with water (20 mL) and the precipitated solid was filtered and dried under vacuum to afford (BF-3). (1H NMR $CDCl_3$, 400 MHz): δ 8.12 (d, J=8.8 Hz, 2H), 6.49 (d, J=9.2 Hz, 2H) 4.71-4.53 (m, 2H), 3.60-3.26 (m, 4H), 2.0 (s, 2H), 1.42 (s, 9H). LCMS (M+H): 320.25

Synthesis of 2-(4-nitrophenyl)-2,5-diazabicyclo[2.2.1]heptane (BF-4)

To a stirred solution of tert-butyl 5-(4-nitrophenyl)-2,5-diazabicyclo[2.2.1]heptane-2-carboxylate (BF-3) (1.0 g, 3.125 mmol) in DCM (10 mL) was added TFA (2.0 mL) and the resulting reaction mixture was stirred for 3 h at RT. The reaction mixture was concentrated under vacuum, diluted with water (25 mL), neutralized with saturated sodium bicarbonate solution and extracted twice with ethyl acetate (2×100 mL). The combined organic layers were washed with brine (125 mL), dried over sodium sulfate and concentrated under reduced pressure to afford the crude compound which was purified by flash column chromatography on silica gel (100-200 mesh) using 20-30% ethyl acetate and hexanes as a eluent to afford (BF-4). ($^1$H NMR $CDCl_3$, 300 MHz): δ 8.11 (d, J=9.0 Hz, 2H), 6.47 (d, J=9.6 Hz, 2H), 4.45 (s, 1H), 3.89 (s, 1H), 3.66-3.62 (m, 1H), 3.14-3.03 (m, 3H), 1.95-1.91 (m, 2H). LCMS (M+H): 220.11.

Synthesis of 2-methyl-5-(4-nitrophenyl)-2,5-diazabicyclo[2.2.1]heptane (BF-5)

To a stirred solution of 2-(4-nitrophenyl)-2,5-diazabicyclo[2.2.1]heptane (BF-4) (0.45 g, 3.125 mmol) in MeOH (8 mL) was added 37% HCHO (0.307 mL 10.22 mmol) and Na(OAc)$_3$BH (1.2 g 6.135 mmol) and the resulting reaction mixture was stirred for 16 h at 25° C. The reaction mixture was concentrated under vacuum, diluted with water (25 mL) and neutralize with saturated sodium bicarbonate solution, the solid precipitated was filtered and dried under vacuum to afford (BF-5).

(1H NMR $CDCl_3$, 400 MHz): δ 8.12-8.10 (m, 2H), 6.49-6.46 (m, 2H) 4.75 (s, 1H), 3.60 (s, 1H), 3.60-3.40 (m, 2H), 3.02-2.99 (m, 1H), 266-2.64 (m, 1H), 2.42 (s, 3H), 2.09-2.03 (m, 1H), 1.92-1.90 (m, 1H). LCMS (M+H): 234.17.

Synthesis of 4-(5-methyl-2,5-diazabicyclo[2.2.1]heptan-2-yl)aniline (A5)

To a stirred solution of 2-methyl-5-(4-nitrophenyl)-2,5-diazabicyclo[2.2.1]heptane (BF-5) (0.48 g, 2.051 mmol) in methanol (50 mL) and water (2.5 mL) was added Zn dust (1.33 g 20.512 mmol) and ammonium chloride (1.087 g, 20.152 mmol) and the resulting reaction mixture was stirred for 2 h at 25° C. The reaction mixture was filter through celite pad and washed with methanol (100 mL), the filtrate was concentrated under vacuum, diluted with water (20 mL) and extracted with ethyl acetate (2×100 mL). The combined organic layers were washed with brine (25 mL), dried over sodium sulfate and concentrated under reduced pressure to afford the crude compound which was purified by flash column chromatography on silica gel (100-200 mesh) using 50-60% ethyl acetate and hexanes as a eluent to afford (A5). LCMS (M+H): 204.18.

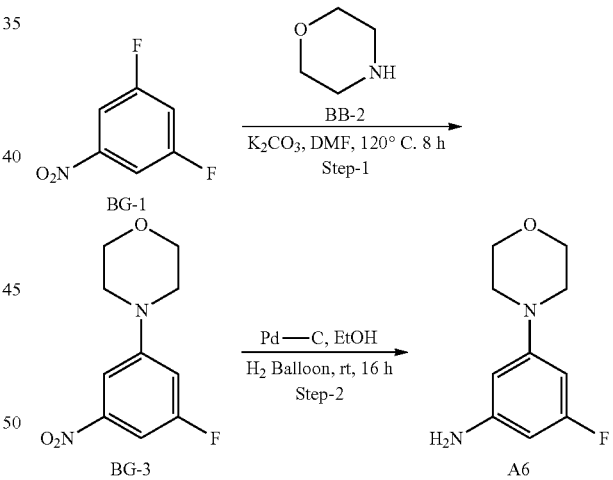

Scheme-11

Synthesis of 4-(3-fluoro-5-nitrophenyl) morpholine (BG-3)

To a stirred solution of 1, 3-difluoro-5-nitrobenzene (BG-1) (5.0 g, 31.44 mmol) in DMF (15 mL) was added morpholine (BB-2) (2.73 g 31.44 mmol) and $K_2CO_3$ (26.03 g 18.86) and the resulting reaction mixture was stirred for 16 h at 120° C. The reaction mixture was cooled to room temperature, diluted with water (25 mL) and extracted twice with ethyl acetate (2×100 mL). The combined organic layers were washed with brine (125 mL), dried over sodium sulfate and concentrated under reduced pressure to afford the crude compound which was purified by flash column chromatography on silica gel (100-200 mesh) using 10-20% ethyl acetate and hexanes as a eluent to afford (BG-3). (LCMS (M+H): 227.18.

Synthesis of 3-fluoro-5-morpholinoaniline (A6)

To a stirred solution of 4-(3-fluoro-5-nitrophenyl) morpholine (BG-3) (2.7 g, 11.94 mmol) in Ethanol (30 mL) was added 10% Pd/C (50% moisture) (1.5 g) and the resulting reaction mixture was stirred under hydrogen gas in par apparatuses for 16 h. The reaction mixture was filtered through a celite pad and washed with methanol (2×100 mL). The filtrate was concentrated under reduced pressure, co-distilled with toluene (2×25 mL) and triturated with diethyl ether (2×25 mL) to afford (A6). LCMS (M+H): 197.08 were washed with brine (125 mL), dried over sodium sulfate and concentrated under reduced pressure to afford crude compound which was purified by flash column chromatography on silica gel (100-200 mesh) using 1-2% ethyl acetate and hexanes to afford (BH-2). $^1$H NMR CDCl$_3$, 400 MHz): δ 8.08 (s, 1H), 7.92-7.86 (m, 1H) 7.48-7.45 (m, 1H), 4.50 (s, 2H). GCMS (M): 232.1

1-(3-fluoro-5-nitrobenzyl)-4-methylpiperazine (BH-4)

To a stirred solution of 1-(bromomethyl)-3-fluoro-5-nitrobenzene (BH-2) (2.0 g, 8.58 mmol) in DCM (20 mL) was added 1-methylpiperazine (BH-3) (1.03 g 10.30 mmol) and triethylamine (3.8 mL, 25.75 mmol) and the resulting reaction mixture was stirred for 16 h at 25° C. The reaction mixture was diluted with water (25 mL) and extracted twice with dichloromethane (2×100 mL). The combined organic layers were washed with brine (25 mL), dried over sodium sulfate, and concentrated under vacuum to afford the crude material which was purified by flash column chromatography on silica gel (100-200 mesh) using 10-20% ethyl acetate and hexanes to afford (BH-4). LCMS (M+H): 254.18.

3-fluoro-5-((4-methylpiperazin-1-yl) methyl) aniline (A7)

To a stirred solution of 1-(3-fluoro-5-nitrobenzyl)-4-methylpiperazine (BH-4) (1.6 g, 6.32 mmol) in methanol (50 mL), sodium borohydride (2.3 g 63.24 mmol) and NiCl$_2$.6H$_2$O (0.45 g, 1.89 mmol)) was added at 0° C. and the resulting reaction mixture was stirred at RT for 3 h. The reaction mixture was filtered through celite and washed with methanol (100 mL), the filtrate was concentrated under vacuum, diluted with water (20 mL) and extracted with dichloromethane (2×100 mL). The combined organic layers were washed with brine (25 mL), dried over sodium sulfate and concentrated under reduced to afford (A7): (1H NMR DMSO-d$_6$, 400 MHz): δ 6.91 (d, J=8.0 Hz, 2H), 6.49 (d, J=8.4 Hz, 1H), 4.95 (s, 2H), 3.53 (t, J=4.4 Hz, 4H), 3.25 (s, 3H), 2.29-2.26 (m, 4H). LCMS (M+H): 224.18.

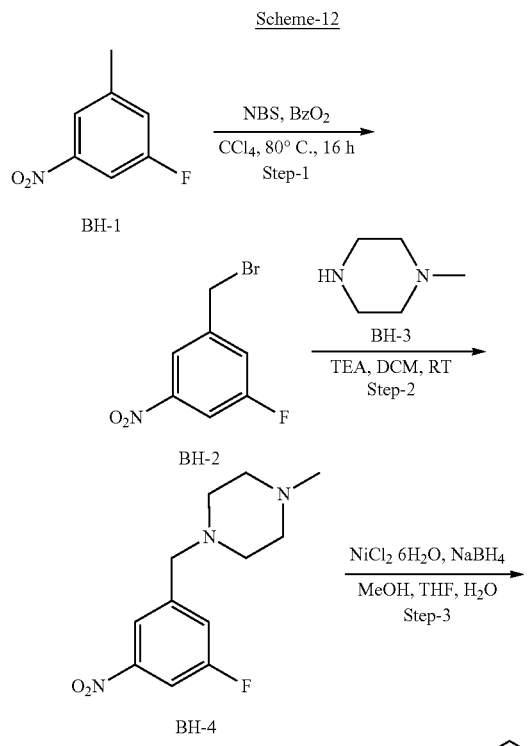

Scheme-12

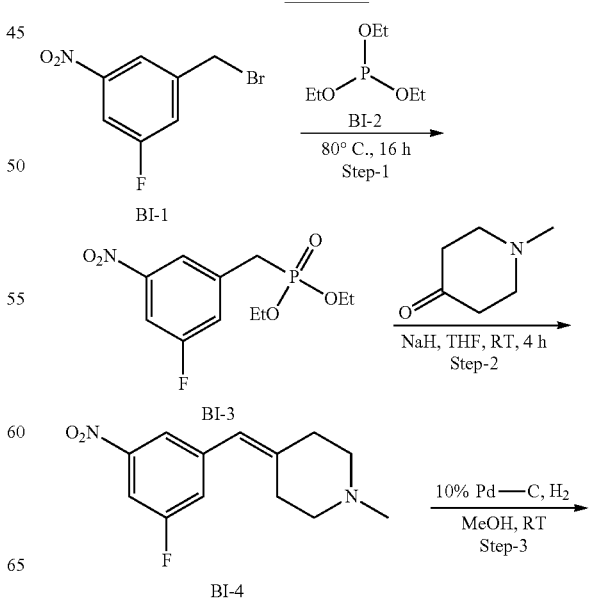

Scheme-13

Synthesis of 1-(bromomethyl)-3-fluoro-5-nitrobenzene (BH-2)

To a stirred solution of 1-fluoro-3-methyl-5-nitrobenzene (BH-1) (10.0 g, 64.47 mmol) in CCl$_4$ (1000 mL) was added NBS (9.1 g 51.57 mmol) and benzyl peroxide (1.56 g, 6.44 mmol) and the resulting reaction mixture was stirred for 16 h at 80° C. The reaction mixture was cooled to room temperature, diluted with water (25 mL) and extracted with dichloromethane (2×250 mL). The combined organic layers

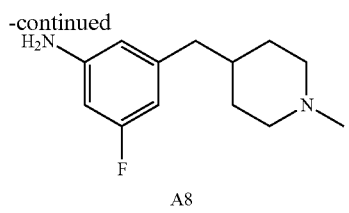

A8

Synthesis of diethyl (3-fluoro-5-nitrobenzyl) phosphonate (BI-3)

To a stirred solution of 1-(bromomethyl)-3-fluoro-5-nitrobenzene (BI-1) (2.0 g, 8.58 mmol), triethyl phosphate (1.4 g 8.58 mmol) was added and the resulting reaction mixture was stirred for 3 h at 80° C. The reaction was cooled to room temperature, diluted with water (25 mL) and extracted with dichloromethane (2×100 mL). The combined organic layers were washed with brine (125 mL), dried over sodium sulfate, filtered and concentrated under reduced pressure to afford the crude compound which was purified by flash column chromatography on silica gel (100-200 mesh) using 10% ethyl acetate and hexanes as a eluent to afford (BI-3). 1H NMR CDCl$_3$, 400 MHz): δ 7.98 (s, 1H), 7.985-7.81 (m, 1H) 7.42-7.38 (m, 1H), 4.15-4.05 (m, 4H), 3.25 (s, 1H), 3.20 (s, 1H), 136-1.27 (m, 6H). LCMS (M+H): 292.17.

Synthesis of 4-(3-fluoro-5-nitrobenzylidene)-1-methylpiperidine (BI-4)

To suspension of sodium hydride (0.26 g, 9.14 mmol) in tetrahydrofuran (20 mL) was added a solution of diethyl (3-fluoro-5-nitrobenzyl) phosphonate (BI-2) (1.9 g, 6.52 mmol) and 1-methylpiperidin-4-one (BI-3) (0.73 g, 6.52 mmol) at 0° C., the resulting reaction mixture was stirred at room temperature for 3 h. The reaction mixture diluted with cold water (20 mL), extracted with ethyl acetate (2×100 mL). The combined organic layers were washed with brine (25 mL), dried over sodium sulfate and concentrated under vacuum to afford the crude compound which purified by flash column chromatography on silica gel (100-200 mesh) using ethyl acetate and hexanes as a eluent to afford (BI-4). LCMS (M+H): 340.27

3-fluoro-5-((4-methylpiperazin-1-yl) methyl) aniline (A8)

To a stirred solution of 1-(3-fluoro-5-nitrobenzyl)-4-methylpiperazine (BI-4) (1.2 g, 4.8 mmol) in methanol (50 mL) Sodium borohydride (1.8 g 63.24 mmol) and NiCl$_2$.6H$_2$O (0.340 g, 1.89 mmol)) was added at 0° C. and the resulting reaction mixture was filtered through celite and washed with methanol (100 mL), filtrate was concentrated under reduced pressure, diluted with water (20 mL) and extracted with dichloromethane (2×100 mL). The combined organic layers were washed with brine (25 mL), dried over sodium sulfate and concentrated under vacuum to afford (A8). (LCMS (M+H): 223.24

Scheme-14

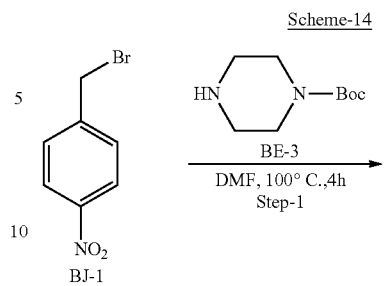

Step1: Synthesis of tert-butyl 4-(4-nitrobenzyl) piperazine-1-carboxylate (BJ-3)

To a stirred solution of 1-(bromomethyl)-4-nitrobenzene (BJ-1) (2.0 g, 9.34 mmol), tert-butyl piperazine-1-carboxylate (BE-3) (1.72 g, 9.34 mmol) in DMF (10 mL) was added K$_2$CO$_3$ (3.87 g, 28.02 mmol) and the resulting reaction mixture was stirred for 4 h at 100° C. The reaction mixture was cooled to room temperature and diluted with water (750 mL), the precipitated solid was filtered and dried under vacuum to afford (BJ-3).

Step2: Synthesis of tert-butyl 4-(4-aminobenzyl) piperazine-1-carboxylate (A9)

To a stirred solution of tert-butyl 4-(4-nitrobenzyl) piperazine-1-carboxylate (BJ-3) (1.2 g, 3.73 mmol) in ethanol (5 mL), water (5 mL) was added Fe (1.04 g 18.67 mmol) and ammonium chloride (0.4 g, 7.46 mmol) and the resulting reaction mixture was stirred for 5 h at 100° C. The reaction mixture was cooled to room temperature and filtered through celite pad and washed with methanol (100 mL), filtrate was concentrated under reduced pressure and diluted with water (20 mL), extracted with ethyl acetate (2×100 mL). The combined organic layers were washed with brine (25 mL), dried over sodium sulfate, concentrated under reduced pressure to get crude compound which was purified by flash column chromate grapy on silica gel (100-200 mesh) using 60-70% ethyl acetate in hexanes as a eluent to afford (A9): LCMS (M+H): 292.20

Scheme-15

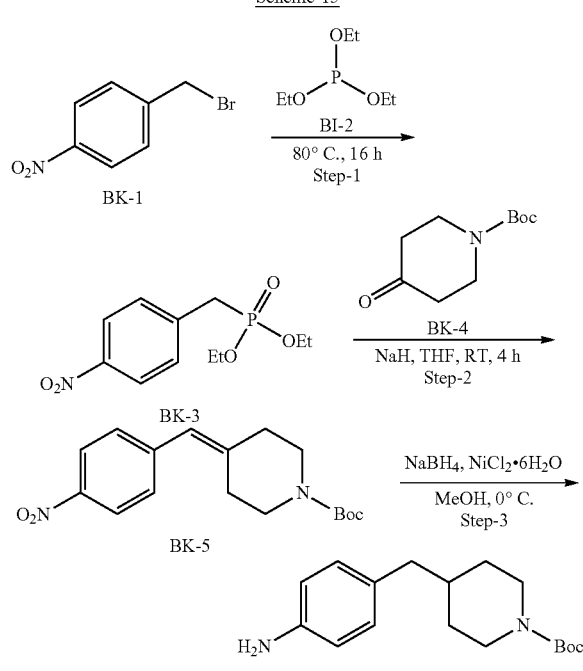

Synthesis of diethyl (4-nitrobenzyl)phosphonate (BK-3)

A mixture of 1-(bromomethyl)-4-nitrobenzene (BK-1) (5.0 g, 23.14 mmol), triethyl phosphate (BI-2) (3.8 g, 23.14 mmol) was for 3 h at 80° C. The reaction was cooled to room temperature, diluted with water (50 mL) and extracted with dichloromethane (2×100 mL). The combined organic layers were washed with brine (20 mL), dried over sodium sulfate and concentrated under reduced pressure to afford the crude compound which was purified by flash column chromatography on silica gel (100-200 mesh) using 10% ethyl acetate and hexanes as a eluent to afford (BK-3): LCMS (M+H): 274.10

Synthesis of tert-butyl 4-(4-nitrobenzylidene)piperidine-1-carboxylate (BK-5)

To suspension of sodium hydride (0.8 g, 21.97 mmol) in tetrahydrofuran (40 mL) was added a solution of diethyl (4-nitrobenzyl) phosphonate (BK-3) (4.0 g, 14.65 mmol) and tert-butyl 4-oxopiperidine-1-carboxylate (BK-4) (2.9 g, 14.65 mmol) at 0° C., the resulting reaction mixture was stirred at room temperature for 3 h. The reaction mixture was diluted with cold water (20 mL), extracted with ethyl acetate (2×100 mL). The combined organic layers were washed with brine (25 mL), dried over sodium sulfate and concentrated under vacuum to afford the crude compound which purified by flash column chromatography on silica gel (100-200 mesh) using 20% ethyl acetate and hexanes as a eluent to afford (BK-5). LCMS (M+H): 263.0 [M-58]

Synthesis of tert-butyl 4-(4-aminobenzyl)piperidine-1-carboxylate (A10)

To a stirred solution of tert-butyl 4-(4-nitrobenzylidene) piperidine-1-carboxylate (BK-5) (2.5 g, 7.86 mmol) in methanol (25 mL) Sodium borohydride (4.4 g, 78.61 mmol) and $NiCl_2 \cdot 6H_2O$ (1.86 g, 7.86 mmol)) was added at 0° C. and the resulting reaction mixture was stirred for 1 h at RT. Reaction mixture was filtered through celite and washed with methanol (100 mL), filtrate was concentrated under reduced pressure, diluted with water (20 mL) and extracted with dichloromethane (2×100 mL). The combined organic layers were washed with brine (25 mL), dried over sodium sulfate and concentrated under vacuum to afford (A10). (LCMS (M+H): 235.1 [M-58]

Scheme-16

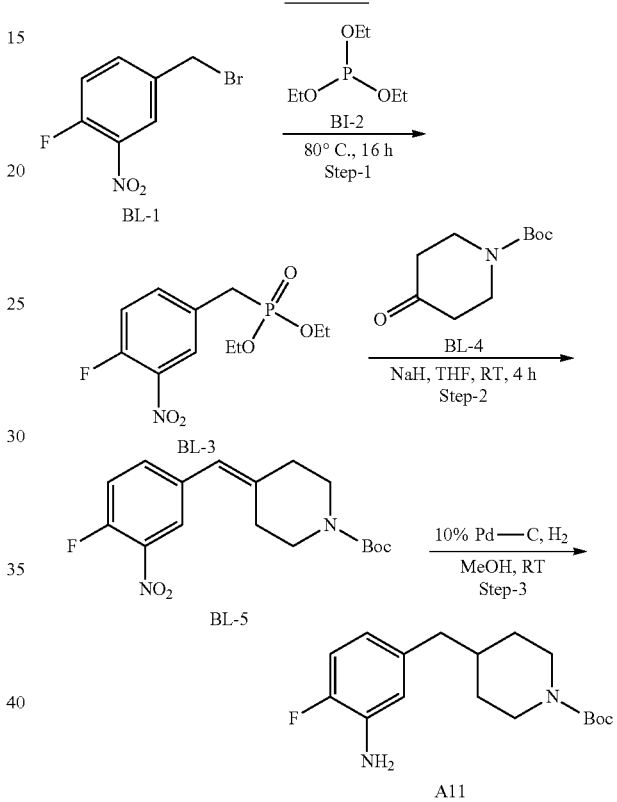

Synthesis of diethyl (4-fluoro-3-nitrobenzyl)phosphonate (BL-3)

To a stirred solution of 4-(bromomethyl)-1-fluoro-2-nitrobenzene (BL-1) (5.0 g, 21.36 mmol), triethyl phosphate (BI-2) (5.01 g, 30.16 mmol) was added and the resulting reaction mixture was stirred for 3 h at 80° C. The reaction was cooled to room temperature, diluted with water (50 mL) and extracted with dichloromethane (2×100 mL). The combined organic layers were washed with brine (20 mL), dried over sodium sulfate, filtered and concentrated under reduced pressure to afford the crude compound which was purified by flash column chromatography on silica gel (100-200 mesh) using 10% ethyl acetate and hexanes as a eluent to afford (BL-3). LCMS (M+H): 292.0

Synthesis of tert-butyl 4-(4-fluoro-3-nitrobenzylidene)piperidine-1-carboxylate (BL-5)

To a suspension of sodium hydride (0.82 g, 20.60 mmol) in tetrahydrofuran (40 mL) was added a solution of diethyl (4-fluoro-3-nitrobenzyl) phosphonate (BL-3) (4.0 g, 13.73 mmol) and tert-butyl 4-oxopiperidine-1-carboxylate (BL-4) (2.73 g, 13.73 mmol) at 0° C., the resulting reaction mixture was stirred at room temperature for 3 h. The reaction mixture diluted with cold water (20 mL), extracted with ethyl acetate (2×100 mL). The combined organic layers were washed with brine (25 mL), dried over sodium sulfate and concentrated under vacuum to afford the crude compound which purified by flash column chromatography on silica gel (100-200 mesh) using 20% ethyl acetate and hexanes as a eluent to afford (BL-5). LCMS (M+H): 281.1 [M-58]

Synthesis of tert-butyl 4-(3-amino-4-fluorobenzyl) piperidine-1-carboxylate (A11)

To a stirred solution of tert-butyl 4-(4-fluoro-3-nitrobenzylidene)piperidine-1-carboxylate (BL-5) (1.2 g, 2.97 mmol) in methanol (30 mL):THF (5 mL) was added 10% Pd/C (50% moisture) (0.82 g) and the resulting reaction mixture was stirred under 60 psi hydrogen pressure for 16 h. The reaction mixture was filtered through a celite pad and washed with methanol (100 L). The filtrate was concentrated under reduced pressure, co distilled with toluene (10 mL) and washed with ether (10 mL) to afford A11. (LCMS (M+H): 209.1 [M-100]

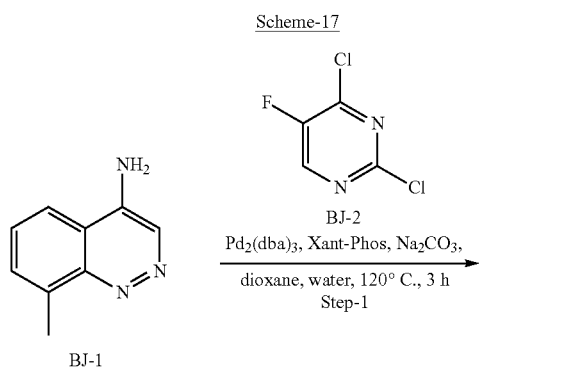

Synthesis of N-(2-chloro-5-fluoropyrimidin-4-yl)-8-methylcinnolin-4-amine (BJ-3)

A mixture of 8-methylcinnolin-4-amine (BJ-1) 0.5 g, 3.14 mmol), 2,4-dichloro-5-fluoropyrimidine (BJ-2) (1.55 g 9.42 mmol), K$_2$CO$_3$ (0.87 g 6.28 mmol) in 1,4 dioxane (50 mL) and water (5 mL) was degassed for 5 min and added Pd$_2$(dba)$_3$ (0.145 g, 0.14 mmol), Xantphos (0.080 g, 0.314 mmol) and resulting reaction mixture was stirred for 1 h at 100° C. The reaction mixture was cooled to room temperature, diluted with water (20 mL) and extracted with ethyl acetate (2×100 mL). Combined organic layers were washed with brine (25 mL), dried over sodium sulfate and concentrated under vacuum to afford crude compound which was purified by flash column by using 30% ethyl acetate and hexanes on 100-200 silica gel to afford (BJ-3). LCMS (M−H): 288.0 b) Synthesis of Example Compounds

The compound according to the present invention can be produced by the methods described in Examples below. However, these examples are only for illustrative purposes, and the compound according to the present invention is not limited to the specific examples mentioned below in any way.

General Synthetic Procedure

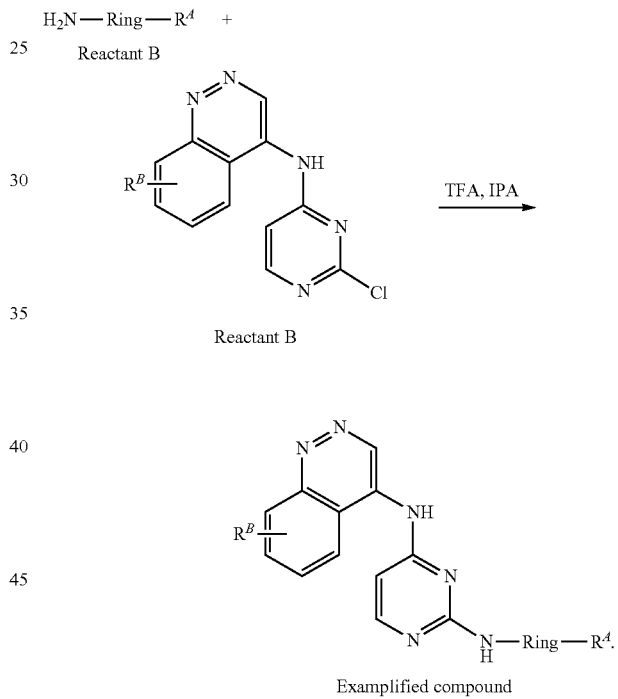

Using the above-described general synthetic schemes and analogs of the general and specific synthetic schemes described here, and with appropriate selection of the reagent designated as "reactant A" in the general synthetic scheme above, for example, one of the following:

4-(4-methylpiperazin-1-yl)aniline; tert-butyl 4-(4-aminophenyl)piperazine-1-carboxylate; tert-butyl 4-(3-amino-4-fluorobenzyl)piperazine-1-carboxylate; 3-((4-methylpiperazin-1-yl)methyl)aniline; tert-butyl 4-(4-aminobenzyl)piperidine-1-carboxylate; tert-butyl 4-(3-amino-5-fluorobenzyl)piperazine-1-carboxylate; 4-(4-methylpiperazin-1-yl)aniline; tert-butyl 4-(4-amino-2-fluorophenyl)piperazine-1-carboxylate; tert-butyl 4-(4-aminophenyl)piperazine-1-carboxylate;
4-morpholinoaniline; 3-morpholinoaniline; 3-chloro-4- morpholinoaniline; 3-fluoro-4-morpholinoaniline; tert-butyl 4-(4-aminophenyl)piperazine-1-carboxylate; tert-butyl 4-(3-amino-4-fluorobenzyl)piperidine-1-carboxylate; 4-(4-(2,2,2-trifluoroethyl)piperazin-1-yl)aniline; tert-butyl 4-(4-aminobenzyl)piperazine-1-carboxylate; 2-fluoro-4-(4-methylpiperazin-1-yl)aniline; tert-butyl 4-(4-amino-3-fluorophenyl)piperazine-1-carboxylate; 6-(4-methylpiperazin-1-yl)pyridin-3-amine; 4-(4-methylpiperazin-1-yl)aniline; 4-(morpholinomethyl)aniline; 4-((4-methylpiperazin-1-yl)methyl)aniline; 4-(8-methyl-3,8-diazabicyclo[3.2.1]octan-3-yl)aniline; 4-((4-methylpiperazin-1-yl)methyl)-3-(trifluoromethyl)aniline; 4-chloroaniline; tert-butyl 4-(3-aminobenzyl)piperazine-1-carboxylate; 4-(4-methylpiperazin-1-yl)aniline; 4-(4-methylpiperazin-1-yl)aniline; 3-chloro-4-(4-methylpiperazin-1-yl)aniline; 3-aminobenzenesulfonamide; tert-butyl 4-(3-aminophenyl)piperidine-1-carboxylate; 2-(4-(4-aminophenyl)piperazin-1-yl)ethan-1-ol; 4-fluoro-3-morpholinoaniline; 3-morpholino-5-(trifluoromethyl)aniline; 3-morpholinoaniline; 4-morpholinoaniline; 3-fluoro-5-((4-methylpiperazin-1-yl) methyl) aniline; 3-fluoro-5-((4-methylpiperazin-1-yl) methyl) aniline; 3-fluoro-5-morpholinoaniline; 4-(5-methyl-2,5-diazabicyclo[2.2.1]heptan-2-yl)aniline; 4-(tetrahydro-2H-pyran-4-yl)aniline; 3-(morpholinomethyl)aniline; tert-butyl 4-(4-aminophenyl)piperazine-1-carboxylate; 4-(4-methylpiperazin-1-yl)aniline; tert-butyl 4-(4-aminophenyl)piperazine-1-carboxylate; 3-morpholinoaniline; 4-morpholinoaniline; 3-fluoro-4-(4-methylpiperazin-1-yl)aniline; or 4-(tert-butyl)aniline; 4-(piperidin-1-yl)aniline; 4-cyclohexylaniline, the example compounds listed in Table 1 were prepared and characterized as shown:

TABLE 1

Example Compounds of the invention:

| EXP No. | Structure | Structure Name | NMR/LC-MS |
| --- | --- | --- | --- |
| EX-01 | 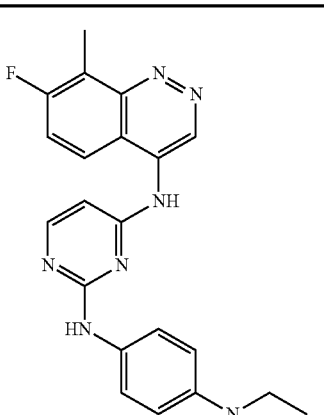 | N4-(7-fluoro-8-methylcinnolin-4-yl)-N2-(4-(4-methyl-piperazin-1-yl)-phenyl)-pyrimidine-2,4-diamine | (1H NMR DMSO-d$_6$, 400 MHz): δ 10.59 (s, 1H), 9.77 (s, 1H), 9.32 (s, 1H), 8.48-8.44 (m, 1H), 8.21 (d, J = 5.6 Hz, 1H), 7.79 (t, J = 9.2 Hz, 1H), 7.55 (d, J = 8.8 Hz, 2H), 6.86 (d, J = 9.2 Hz, 2H), 6.67 (d, J = 5.6 Hz, 1H), 3.06 (t, J = 4.4 Hz, 4H), 2.79 (s, 3H) 2.45 (t, J = 4.8 Hz, 4H), 2.22 (s, 3H). LCMS (M + H): 445.2, HPLC Purity: 97.77%. |
| EX-02 | 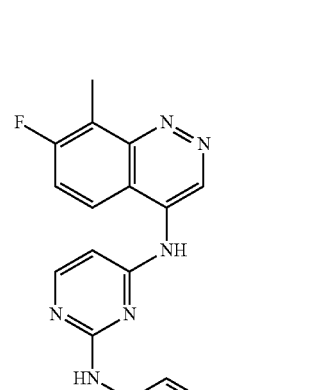 | N4-(7-fluoro-8-methylcinnolin-4-yl)-N2-(4-(piperazin-1-yl)phenyl)-pyrimidine-2,4-diamine | (1H NMR DMSO-d$_6$, 400 MHz): δ 10.56 (s, 1H), 9.77 (s, 1H), 9.29 (s, 1H), 8.48-8.44 (m, 1H), 8.20 (d, J = 5.6 Hz, 1H), 7.77 (t, J = 9.2 Hz, 1H), 7.54 (d, J = 8.4 Hz, 2H), 6.84 (d, J = 9.2 Hz, 2H), 6.66 (d, J = 5.6 Hz, 1H), 2.96 (t, J = 4.4 Hz, 4H), 2.84-2.83 (m, 4H), 2.79 (s, 3H). LCMS (M + H): 431.20, HPLC: 97.34%. |

TABLE 1-continued

Example Compounds of the invention:

| EXP No. | Structure | Structure Name | NMR/LC-MS |
|---|---|---|---|
| EX-03 | 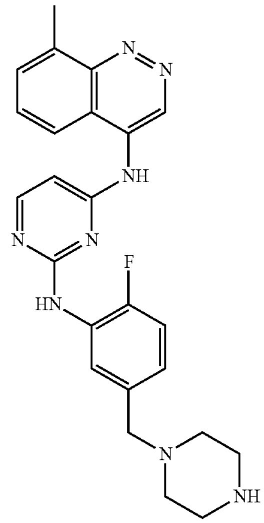 [SMILES: Cc1cccc2c(Nc3ccnc(Nc4cc(CN5CCNCC5)ccc4F)n3)cnnc12] | N2-(2-fluoro-5-(piperazin-1-yl-methyl)phenyl)-N4-(8-methyl-cinnolin-4-yl)-pyrimidine-2,4-diamine | (1H NMR DMSO-$d_6$, 400 MHz): δ 10.24 (s, 1H), 9.77 (s, 1H), 8.80 (s, 1H), 8.32 (d, J = 8.4 Hz, 1H), 8.12 (s, 1H), 7.76 (d, J = 6.8 Hz, 1H), 7.66-7.63 (m, 2H), 7.17-7.12 (m, 1H), 7.02-6.99 (m, 1H), 6.65-6.63 (m, 1H), 3.39-3.36 (m, 3H), 3.17-3.14 (m, 1H), 2.86 (s, 3H), 2.59-2.57 (m, 3H), 2.23-2.20 (m, 4H). LCMS (M − H): 443.2, HPLC: 97.92%. |
| EX-04 | 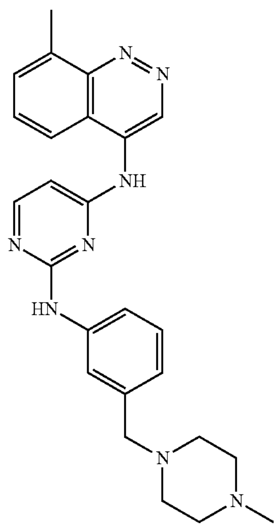 [SMILES: Cc1cccc2c(Nc3ccnc(Nc4cccc(CN5CCN(C)CC5)c4)n3)cnnc12] | N4-(8-methyl-cinnolin-4-yl)-N2-(3-((4-methyl-piperazin-1-yl)methyl)phenyl)pyrimidine-2,4-diamine | (1H NMR DMSO-$d_6$, 500 MHz): δ 10.23 (s, 1H), 9.77 (s, 1H), 9.20 (s, 1H), 8.30 (d, J = 9.0 Hz, 1H), 8.08 (s, 1H), 7.69-7.55 (m, 4H), 7.14 (t, J = 7.5 Hz, 1H), 6.80 (d, J = 7.5 Hz, 1H), 6.50 (s, 1H), 3.37 (s, 2H), 2.84 (s, 3H), 2.36-2.30 (m, 8H), 2.10 (s, 3H). LCMS (M + H): 441.20, HPLC: 99.55%. |
| EX-05 | 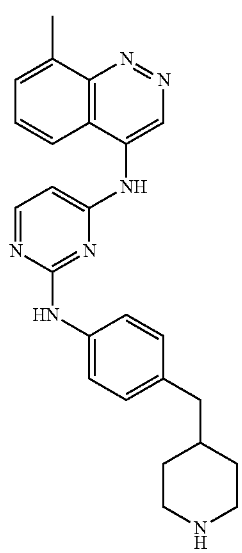 [SMILES: Cc1cccc2c(Nc3ccnc(Nc4ccc(CC5CCNCC5)cc4)n3)cnnc12] | N4-(8-methylcinnolin-4-yl)-N2-(4-(piperidin-4-ylmethyl)pheny)pyrimidine-2,4-diamine | (1H NMR DMSO-$d_6$, 500 MHz δ 10.32 (s, 1H), 9.84 (s, 1H), 9.26 (s, 1H), 8.32 (d, J = 9.0 Hz, 1H), 8.14-8.11 (m, 1H), 7.65-7.63 (m, 4H), 7.00 (d, J = 7.0 Hz, 2H), 6.58-6.56 (m, 1H), 4.00-3.98 (m, 1H), 2.87 (s, 5H), 2.40-2.33 (m, 4H), 1.50-1.48 (m, 3H), 1.02-0.99 (m, 2H). LCMS (M + H): 426.2, HPLC: 97.18%. |

TABLE 1-continued

Example Compounds of the invention:

| EXP No. | Structure | Structure Name | NMR/LC-MS |
|---|---|---|---|
| EX-06 | 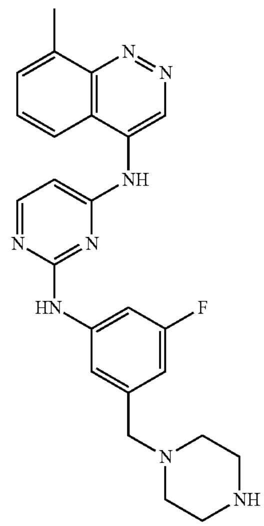 [SMILES: Cc1cccc2c(Nc3ccnc(Nc4cc(F)cc(CN5CCNCC5)c4)n3)cnnc12] | N2-(3-fluoro-5-(piperazin-1-ylmethyl)phenyl)-N4-(8-methyl-cinnolin-4-yl)pyrimidine-2,4-diamine | (1H NMR DMSO-d$_6$, 400 MHz): δ 10.52 (s, 1H), 9.82 (s, 1H), 9.76 (s, 1H), 8.35-8.29 (m, 2H), 7.76-7.73 (m, 2H), 7.67 (d, J = 11.6 Hz, 1H), 7.44 (s, 1H), 6.80 (d, J = 5.6 Hz, 1H), 6.68 (d, J = 9.6 Hz, 1H), 5.95 (bs, 1H), 3.42 (s, 2H), 2.92 (s, 3H), 2.83-2.81 (m, 4H), 2.40-2.36 (m, 4H). LCMS (M + H): 445.2, HPLC Purity: 98.99%. |
| EX-07 | 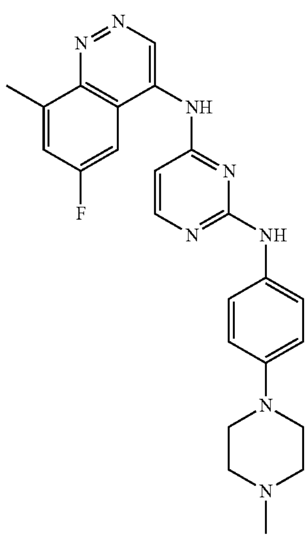 [SMILES: Cc1cc(F)cc2c(Nc3ccnc(Nc4ccc(N5CCN(C)CC5)cc4)n3)cnnc12] | N4-(6-fluoro-8-methylcinnolin-4-yl)-N2-(4-(4-methylpiperazin-1-yl)phenyl)pyrimidine-2,4-diamine | (1H NMR DMSO-d$_6$, 400 MHz): δ 10.50 (s, 1H), 9.53 (s, 1H), 9.35 (s, 1H), 8.22-8.17 (m, 1H), 7.72 (d, J = 6.4 Hz, 1H), 7.58 (d, J = 7.2 Hz, 2H), 6.90 (d, J = 7.2 Hz, 2H), 6.67 (d, J = 4.4 Hz, 1H), 3.17 (bs, 4H), 2.85 (bs, 7H), 2.49 (s, 3H), LCMS (M + H): 445.1, HPLC: 97.84%. |
| EX-08 | 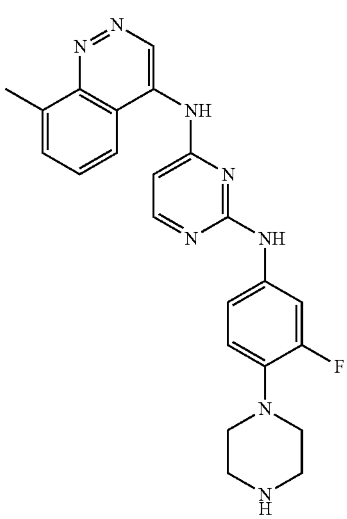 [SMILES: Cc1cccc2c(Nc3ccnc(Nc4ccc(N5CCNCC5)c(F)c4)n3)cnnc12] | N2-(3-fluoro-4-(piperazin-1-yl)phenyl)-N4-(8-methylcinnolin-4-yl)pyrimidine-2,4-diamine | (1H NMR DMSO-d$_6$, 500 MHz): δ 10.54 (s, 1H), 9.76 (s, 1H), 9.55 (s, 1H), 8.36-8.33 (m, 1H), 8.26 (d, J = 5.5 Hz, 1H), 7.76-7.68 (m, 3H), 7.38-7.35 (m, 1H), 6.94 (t, J = 9.5 Hz, 1H), 6.75 (d, J = 5.5 Hz, 1H), 2.92 (s, 3H), 2.85-2.83 (m, 8H). LCMS (M − H): 429.2, HPLC: 97.24%, |

TABLE 1-continued

Example Compounds of the invention:

| EXP No. | Structure | Structure Name | NMR/LC-MS |
|---|---|---|---|
| EX-09 | 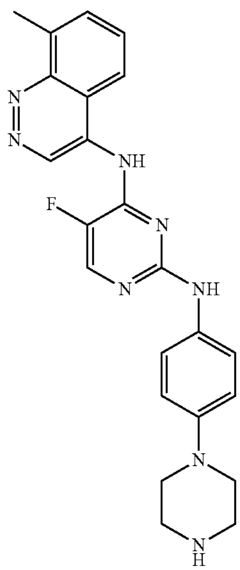 [SMILES: Cc1cccc2c(Nc3nc(Nc4ccc(N5CCNCC5)cc4)ncc3F)cnnc12] | 5-fluoro-N4-(8-methyl-cinnolin-4-yl)-N2-(4-(piperazin-1-yl)phenyl)pyrimidine-2,4-diamine | (1H NMR (DMSO-$d_6$, 500 MHz): δ 9.65 (s, 1H), 9.07 (s, 1H), 8.22 (d, J = 4.0 Hz, 1H), 8.11 (d, J = 9.0 Hz, 1H), 7.72 (d, J = 6.5 Hz, 1H), 7.64 (s, 1H), 7.33 (d, J = 9.0 Hz, 2H), 6.68 (d, J = 9.0 Hz, 2H), 2.91 (s, 3H) 2.90-2.82 (m, 8H). LCMS (M + H): 431.3 HPLC: 99.28% |
| EX-10 | 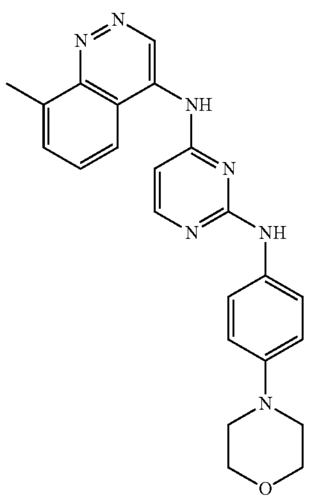 [SMILES: Cc1cccc2c(Nc3ccnc(Nc4ccc(N5CCOCC5)cc4)n3)cnnc12] | N4-(8-methylcinnolin-4-yl)-N2-(4-morpholino-phenyl)-pyrimidine-2,4-diamine | 1H NMR (DMSO-$d_6$, 400 MHz): δ 10.56 (s, 1H), 9.68 (s, 1H), 9.32 (s, 1H), 8.36 (t, J = 5.2 Hz, 1H), 8.21 (d, J = 5.6 Hz, 1H), 7.76-7.73 (m, 2H), 7.59 (d, J = 8.8 Hz, 2H), 6.88 (d, J = 9.2 Hz, 2H), 6.70 (d, J = 5.6 Hz, 1H), 3.76 (t, J = 4.4 Hz, 4H), 3.05 (t, J = 4.4 Hz, 4H), 2.91 (s, 3H). LCMS (M + H): 414.21, HPLC: 98.73%. |
| EX-11 | 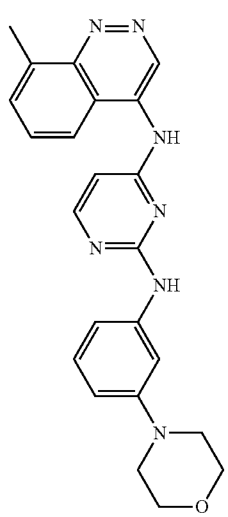 [SMILES: Cc1cccc2c(Nc3ccnc(Nc4cccc(N5CCOCC5)c4)n3)cnnc12] | N4-(8-methylcinnolin-4-yl)-N2-(3-morpholinophenyl)pyrimidine-2,4-diamine | (1H NMR DMSO-$d_6$, 400 MHz): δ 10.51 (s, 1H), 9.75 (s, 1H), 9.40 (s, 1H), 8.35 (t, J = 5.2 Hz, 1H), 8.27 (d, J = 5.6 Hz, 1H), 7.75-7.72 (m, 2H), 7.34 (s, 1H), 7.27 (d, J = 8.0 Hz, 1H), 7.11 (t, J = 8.0 Hz, 1H), 6.70 (d, J = 5.6 Hz, 1H), 6.56 (dd, $J_1$ = 2.0 Hz, $J_2$ = 8.0 Hz, 1H), 3.67 (t, J = 4.8 Hz, 4H), 2.98 (t, J = 4.4 Hz, 4H), 2.91 (s, 3H), LCMS (M + H): 414.23, HPLC: 98.87%. |

TABLE 1-continued

Example Compounds of the invention:

| EXP No. | Structure Name | NMR/LC-MS |
|---|---|---|
| EX-12 | N2-(3-chloro-4-morpholino-phenyl)-N4-(8-methyl-cinnolin-4-yl)-pyrimidine-2,4-diamine | (1H NMR DMSO-d$_6$, 400 MHz): δ 10.55 (s, 1H), 9.76 (s, 1H), 9.60 (s, 1H), 8.35 (t, J = 5.2 Hz, 1H), 8.28 (d, J = 6.0 Hz, 1H), 7.95 (s, 1H), 7.75-7.74 (m, 2H), 7.63 (dd, J$_1$ = 2.4 Hz, J$_2$ = 2.4 Hz, 1H), 7.10 (d, J = 8.8 Hz, 1H), 6.77 (d, J = 5.6 Hz, 1H), 3.74 (t, J = 4.8 Hz, 4H), 2.92-2.91 (m, 4H), 2.90 (s, 3H), LCMS (M + H): 448.18, HPLC: 97.58%. |
| EX-13 | N2-(3-fluoro-4-morpholino-phenyl)-N4-(8-methylcinnolin-4-yl)-pyrimidine-2,4-diamine | (1H NMR DMSO-d$_6$, 400 MHz): δ 10.54 (s, 1H), 9.76 (s, 1H), 9.58 (s, 1H), 8.35 (t, J = 5.2 Hz, 1H), 8.27 (d, J = 5.6 Hz, 1H), 7.76-7.72 (m, 3H), 7.39 (dd, J$_1$ = 2.0 Hz, J$_2$ = 1.6 Hz 1H), 6.98 (t, J = 9.2 Hz, 1H), 6.76 (d, J = 6.0 Hz, 1H), 3.74 (t, J = 5.2 Hz, 4H), 2.95-2.94 (m, 4H), 2.92 (s, 3H), LCMS (M + H): 432.23, HPLC: 96.01%. |
| EX-15 | N4-(6-fluoro-8-methyl-cinnolin-4-yl)-N2-(4-(piperazin-1-yl)phenyl)-pyrimidine-2,4-diamine | (1H NMR DMSO-d$_6$, 400 MHz): δ 10.59 (s, 1H), 9.51 (s, 1H), 9.31 (s, 1H), 8.22-8.16 (m, 2H), 7.72 (d, J = 9.2 Hz, 1H), 7.55 (t, J = 8.8 Hz, 2H), 6.85 (d, J = 8.8 Hz, 2H), 6.66 (d, J = 5.6 Hz, 1H), 3.40 (bs, 1H), 2.98-2.96 (m, 4H), 2.93 (s, 3H), 2.85-2.84 (m, 4H). LCMS (M + H): 431.32, HPLC: 99.72%. |

TABLE 1-continued

Example Compounds of the invention:

| EXP No. | Structure | Structure Name | NMR/LC-MS |
|---|---|---|---|
| EX-16 | 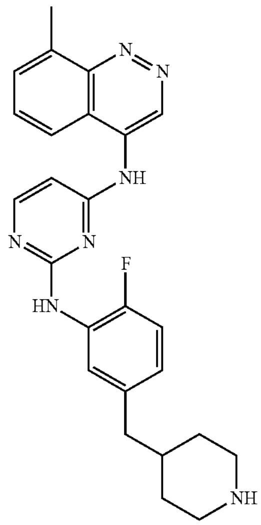 [SMILES: Cc1cccc2c(Nc3ccnc(Nc4cc(CC5CCNCC5)ccc4F)n3)cnnc12] | N2-(2-fluoro-5-(piperidin-4-ylmethyl)-phenyl)-N4-(8-methyl-cinnolin-4-yl)-pyrimidine-2,4-diamine | (1H NMR DMSO-$d_6$, 400 MHz): δ 10.34 (s, 1H), 9.72 (s, 1H), 8.93 (s, 1H), 8.33-8.30 (m, 1H), 8.19 (d, J = 5.6 Hz, 1H), 7.72-7.68 (m, 2H), 7.56 (d, J = 7.2 Hz, 1H), 7.14-7.09 (m, 1H), 6.90-6.87 (m, 1H), 6.70 (d, J = 5.6 Hz, 1H), 2.88 (s, 3H), 2.80 (d, J = 11.2 Hz, 2H), 2.42 (d, J = 6.4 Hz, 2H), 2.26 (t, J = 10.8 Hz, 2H), 1.43 (d, J = 12.4 Hz, 3H), 0.99-0.93 (m, 2H). LCMS (M + H): 442.10, HPLC: 98.42%. |
| EX-17 | 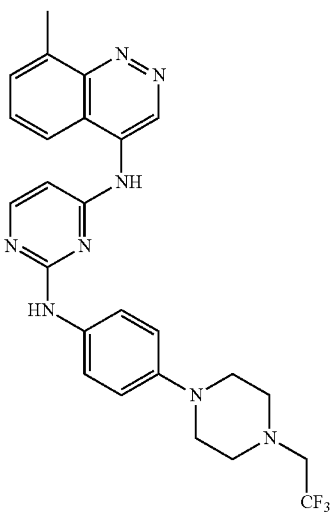 | N4-(8-methyl-cinnolin-4-yl)-N2-(4-(4-(2,2,2-trifluoroethyl)-piperazin-1-yl)phenyl)-pyrimidine-2,4-diamine | (1H NMR DMSO-$d_6$, 400 MHz): δ 10.54 (s, 1H), 9.67 (s, 1H), 9.31 (s, 1H), 8.35 (t, J = 5.2 Hz, 1H), 8.20 (d, J = 5.6 Hz, 1H), 7.75-7.71 (m, 2H), 7.56 (d, J = 8.8 Hz, 2H), 6.86 (d, J = 9.2 Hz, 2H), 6.69 (d, J = 5.6 Hz, 1H), 3.27-3.19 (m, 2H), 3.08-3.06 (m, 4H), 2.78-2.75 (m, 4H), 2.91 (s, 3H). LCMS (M + H): 431.20, HPLC: 96.87%. |
| EX-20 | 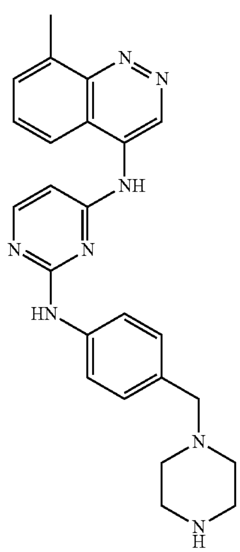 [SMILES: Cc1cccc2c(Nc3ccnc(Nc4ccc(CN5CCNCC5)cc4)n3)cnnc12] | N4-(8-methyl-cinnolin-4-yl)-N2-(4-(piperazin-1-yl-methyl)phenyl)pyrimidine-2,4-diamine | (1H NMR DMSO-$d_6$, 400 MHz): δ 10.48 (s, 1H), 9.78 (s, 1H), 9.46 (s, 1H), 8.35-8.31 (m, 1H), 8.22 (d, J = 4.4 Hz, 1H), 7.72-7.67 (m, 4H), 7.14 (d, J = 6.8 Hz, 2H), 6.70 (d, J = 4 Hz, 1H), 3.34 (s, 2H), 2.91 (s, 3H), 2.66 (t, J = 3.6 Hz, 4H), 2.22 (bs, 4H). LCMS (M + H): 427.2, HPLC: 99.16%. |

TABLE 1-continued

Example Compounds of the invention:

| EXP No. | Structure | Structure Name | NMR/LC-MS |
|---|---|---|---|
| EX-21 | 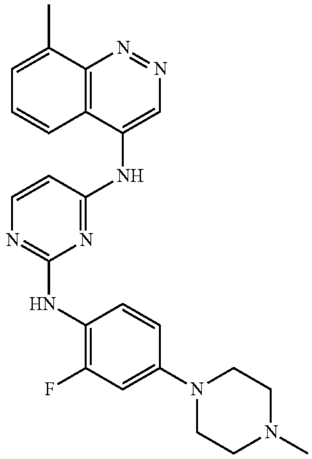 [SMILES: Cc1cccc2c(Nc3ccnc(Nc4ccc(N5CCN(C)CC5)cc4F)n3)cnnc12] | N2-(2-fluoro-4-(4-methyl-piperazin-1-yl)phenyl)-N4-(8-methyl-cinnolin-4-yl)-pyrimidine-2,4-diamine | (1H NMR DMSO-$d_6$, 400 MHz): δ 10.43 (s, 1H), 9.62 (s, 1H), 8.82 (s, 1H), 8.33 (t, J = 6 Hz, 1H), 8.12 (d, J = 5.6 Hz, 1H), 7.71 (d, J = 4.0 Hz, 2H), 7.38 (t, J = 9.2 Hz, 1H), 6.82 (dd, $J_1$ = 11.2 Hz, $J_2$ = 2.8 Hz 1H), 6.73-6.62 (m, 2H), 3.14 (t, J = 5.2 Hz, 4H), 2.88 (s, 3H), 2.47-2.44 (m, 4H), 2.23 (s, 3H). LCMS (M + H): 445.30, HPLC: 95.96%. |
| EX-22 | 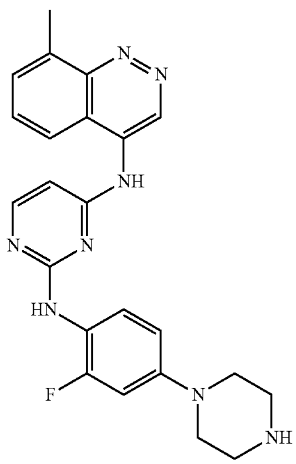 [SMILES: Cc1cccc2c(Nc3ccnc(Nc4ccc(N5CCNCC5)cc4F)n3)cnnc12] | N2-(2-fluoro-4-(piperazin-1-yl)phenyl)-N4-(8-methylcinnolin-4-yl)pyrimidine-2,4-diamine | (1H NMR DMSO-$d_6$, 400 MHz): δ 10.45 (s, 1H), 9.62 (s, 1H), 8.83 (s, 1H), 8.34 (t, J = 4.8 Hz, 1H), 8.13 (d, J = 5.6 Hz, 1H), 7.72 (d, J = 5.2 Hz, 2H), 7.36 (t, J = 9.2 Hz, 1H), 6.81 (dd, $J_1$ = 12 Hz, $J_2$ = 2.4 Hz 1H), 6.72-6.67 (m, 2H), 3.04 (t, J = 5.2 Hz, 4H), 2.89 (s, 3H), 2.83 (t, J = 4.8 Hz, 4H). LCMS (M + H): 431.1, HPLC: 96.66%. |
| EX-23 | 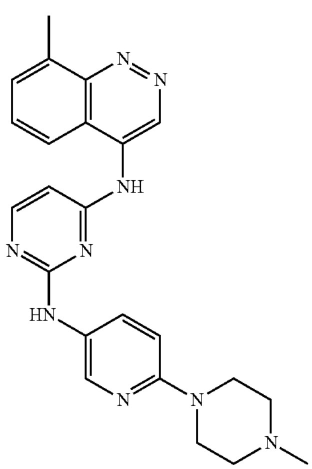 [SMILES: Cc1cccc2c(Nc3ccnc(Nc4ccc(N5CCN(C)CC5)nc4)n3)cnnc12] | N4-(8-methylcinnolin-4-yl)-N2-(6-(4-methylpiperazin-1-yl)pyridin-3-yl)pyrimidine-2,4-diamine | (1H NMR DMSO-$d_6$, 400 MHz): δ 10.54 (s, 1H), 9.70 (s, 1H), 9.28 (s, 1H), 8.38-8.33 (m, 2H), 8.19 (t, J = 5.6 Hz, 1H), 7.90 (d, J = 7.6 Hz, 1H), 7.74-7.73 (m, 2H), 6.78 (d, J = 9.2 Hz, 1H), 6.69 (d, J = 5.2 Hz 1H), 3.39 (t, J = 4.4 Hz, 4H), 2.90 (s, 3H), 2.40 (t, J = 4.8 Hz, 4H), 2.21 (s, 3H). LCMS (M + H): 428.27, HPLC: 97.60%. |

TABLE 1-continued

Example Compounds of the invention:

| EXP No. | Structure | Structure Name | NMR/LC-MS |
|---|---|---|---|
| EX-24 | 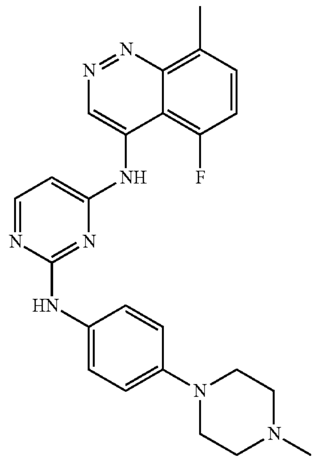 | N4-(5-fluoro-8-methylcinnolin-4-yl)-N2-(4-(4-methylpiperazin-1-yl)phenyl)pyrimidine-2,4-diamine | (1H NMR DMSO-$d_6$, 400 MHz): δ 10.56 (s, 1H), 9.68 (s, 1H), 9.32 (s, 1H), 8.36 (t, J = 5.2 Hz, 1H), 8.21 (d, J = 5.6 Hz, 1H), 7.76-7.73 (m, 2H), 7.59 (d, J = 8.8 Hz, 2H), 6.88 (d, J = 9.2 Hz, 2H), 6.70 (d, J = 5.6 Hz, 1H), 3.76 (t, J = 4.4 Hz, 4H), 3.05 (t, J = 4.4 Hz, 4H), 2.91 (s, 3H), LCMS (M + H): 414.21, HPLC Purity: 98.73%. |
| EX-25 | 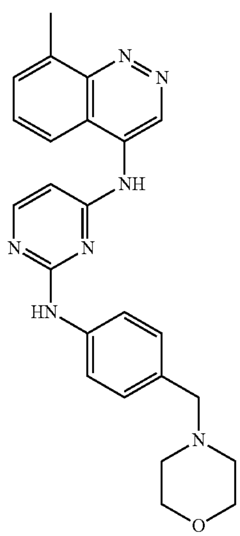 [SMILES: Cc1cccc2c(Nc3ccnc(Nc4ccc(CN5CCOCC5)cc4)n3)cnnc12] | N4-(8-methylcinnolin-4-yl)-N2-(4-(morpholinomethyl)phenyl)pyrimidine-2,4-diamine | 1H NMR DMSO-$d_6$, 500 MHz): δ 10.53 (s, 1H), 9.75 (s, 1H), 9.53 (s, 1H), 8.34 (t, J = 5.0 Hz, 1H), 8.24 (d, J = 5.5 Hz, 1H), 7.75 (d, J = 5.0 Hz, 2H), 7.68 (d, J = 8.5 Hz, 2H), 7.17 (d, J = 8.5 Hz, 2H), 6.74 (d, J = 5.5 Hz, 1H), 3.57 (t, J = 4.5 Hz, 4H) 3.39 (s, 2H), 2.92 (s, 3H), 2.32-2.36 (m, 4H). LCMS (M − H): 426.2 HPLC: 95.35% |
| EX-26 | 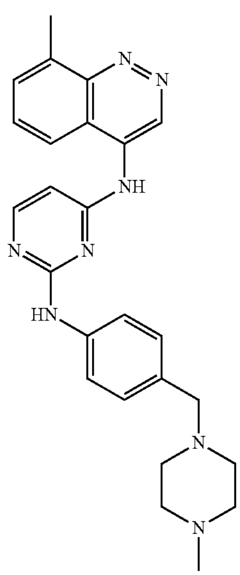 [SMILES: Cc1cccc2c(Nc3ccnc(Nc4ccc(CN5CCN(C)CC5)cc4)n3)cnnc12] | N4-(8-methylcinnolin-4-yl)-N2-(4-((4-methylpiperazin-1-yl)methyl)phenyl)pyrimidine-2,4-diamine | (1H NMR DMSO-$d_6$, 500 MHz): δ 10.49 (s, 1H), 9.75 (s, 1H), 9.47 (s, 1H), 8.33 (d, J = 7.5 Hz, 1H), 8.23 (d, J = 5.0 Hz, 1H), 7.72-7.67 (m, 4H), 7.14 (d, J = 8.5 Hz, 2H), 6.70 (d, J = 3.5 Hz, 1H), 3.37 (s, 2H), 2.91 (s, 3H), 2.36-2.33 (m, 8H), 2.14 (s, 3H), LCMS (M − H): 439.2, HPLC: 99.25%. |

TABLE 1-continued

Example Compounds of the invention:

| EXP No. | Structure | Structure Name | NMR/LC-MS |
|---|---|---|---|
| EX-27 | 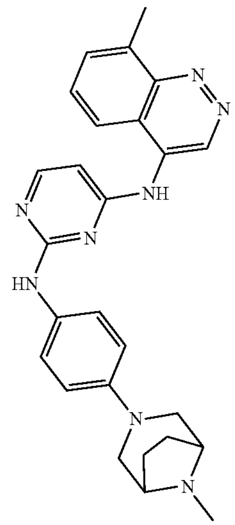 [SMILES: Cc1cccc2c(Nc3ccnc(Nc4ccc(N5CC6CCC(C5)N6C)cc4)n3)cnnc12] | N2-(4-(8-methyl-3,8-diazabicyclo[3.2.1]octan-3-yl)phenyl)-N4-(8-methylcinnolin-4-yl)pyrimidine-2,4-diamine | (1H NMR DMSO-$d_6$, 400 MHz): δ 10.56 (s, 1H), 9.65 (s, 1H), 9.23 (s, 1H), 8.37-8.34 (m, 1H), 8.19 (d, J = 5.6 Hz, 1H), 7.75-7.71 (m, 2H), 7.51 (d, J = 8.8 Hz, 2H), 6.73 (d, J = 9.2 Hz, 2H), 6.67 (d, J = 5.6 Hz, 1H), 3.30-3.26 (m, 2H), 3.22-3.18 (m, 2H), 2.91 (s, 3H), 2.79-2.76 (m, 2H), 2.22 (s, 3H), 1.96-1.93 (m, 2H), 1.66-1.63 (m, 2H). LCMS (M + H): 453.37, HPLC: 99.00%, |
| EX-28 | 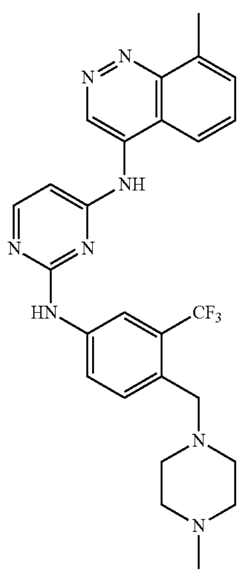 [SMILES: Cc1cccc2c(Nc3ccnc(Nc4ccc(CN5CCN(C)CC5)c(C(F)(F)F)c4)n3)cnnc12] | N4-(8-methylcinnolin-4-yl)-N2-(4-((4-methylpiperazin-1-yl)methyl)-3-(trifluoromethyl)phenyl)pyrimidine-2,4-diamine | (1H NMR DMSO-$d_6$, 400 MHz): δ 10.55 (s, 1H), 9.83 (d, J = 9.2 Hz, 2H), 8.36-8.29 (m, 2H), 8.13 (s, 1H), 8.03 (d, J = 8.4 Hz, 1H), 7.76 (d, J = 5.6 Hz, 2H), 7.57 (d, J = 8.4 Hz, 1H), 6.81 (d, J = 6.0 Hz, 1H), 3.52 (s, 2H), 2.92 (s, 3H), 2.39-2.32 (m, 8H), 2.15 (s, 3H). 2.15 (s, 3H). LCMS (M + H): 509.15, HPLC: 95.32%, |
| EX-29 | 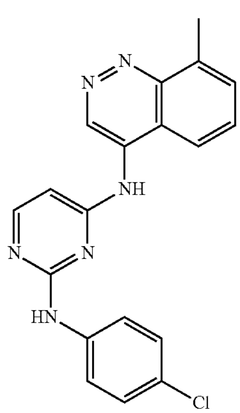 [SMILES: Cc1cccc2c(Nc3ccnc(Nc4ccc(Cl)cc4)n3)cnnc12] | N2-(4-chlorophenyl)-N4-(8-methylcinnolin-4-yl)pyrimidine-2,4-diamine | (1H NMR DMSO-$d_6$, 400 MHz): δ 10.28 (s, 1H), 9.84 (s, 1H), 9.44 6561 (s, 1H), 8.31 (d, J = 8.0 Hz, 1H), 8.14 (d, J = 4.4 Hz, 1H), 7.81 (d, J = 8.8 Hz, 2H), 7.66-7.59 (m, 2H), 7.25 (d, J = 8.8 Hz, 2H), 6.60-6.59 (m, 1H), 2.86 (s, 3H). LCMS (M + H): 363.18, HPLC: 97.78%, |

TABLE 1-continued

Example Compounds of the invention:

| EXP No. | Structure | Structure Name | NMR/LC-MS |
|---|---|---|---|
| EX-31 | 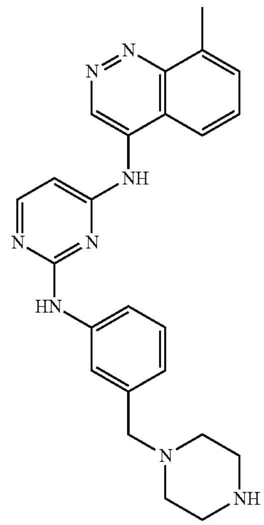 [SMILES: Cc1cccc2c(Nc3ccnc(Nc4cccc(CN5CCNCC5)c4)n3)cnnc12] | N4-(8-methylcinnolin-4-yl)-N2-(3-(piperazin-1-ylmethyl)phenyl)pyrimidine-2,4-diamine | (1H NMR DMSO-$d_6$, 500 MHz): δ 10.54 (s, 1H), 9.75 (s, 1H), 9.54 (s, 1H), 8.34 (t, J = 8.0 Hz, 1H), 8.26 (d, J = 5.5 Hz, 1H), 7.75-7.72 (m, 2H), 7.66 (s, 2H), 7.18 (t, J = 9.0 Hz, 1H), 6.86 (d, J = 7.0 Hz, 1H), 6.74 (d, J = 6.0 Hz, 1H), 3.36 (s, 2H), 2.91 (s, 3H), 2.61-2.62 (m, 4H), 2.23-2.26 (m, 4H). LCMS (M + H): 427.3, HPLC: 95.47%. |
| EX-32 | 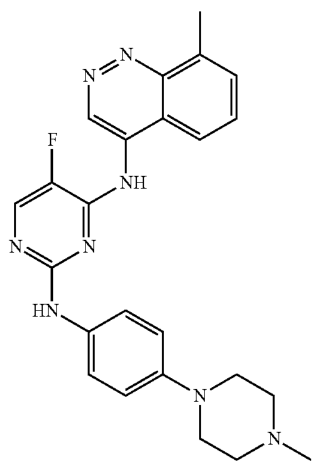 [SMILES: Cc1cccc2c(Nc3nc(Nc4ccc(N5CCN(C)CC5)cc4)ncc3F)cnnc12] | 5-fluoro-N4-(8-methylcinnolin-4-yl)-N2-(4-(4-methylpiperazin-1-yl)phenyl)pyrimidine-2,4-diamine | (1H NMR DMSO-$d_6$, 500 MHz): ): δ 9.85 (s, 1H), 9.78 (s, 1H), 9.09 (s, 1H), 8.24 (d, J = 3.5 Hz, 1H), 8.11 (d, J = 9.0 Hz, 1H), 7.72-7.67 (m, 2H), 7.32 (s, 2H), 6.69 (d, J = 6.5 Hz, 2H), 2.99 (t, J = 5.0 Hz, 4H), 2.90 (s, 3H), 2.43 (t, J = 5.5 Hz, 4H), 2.21 (s, 3H). LCMS (M + H): 445.2, HPLC: 98.32%. |
| EX-33 | 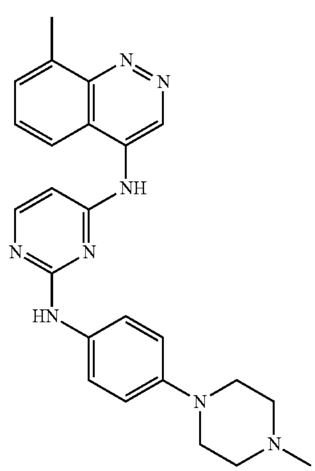 [SMILES: Cc1cccc2c(Nc3ccnc(Nc4ccc(N5CCN(C)CC5)cc4)n3)cnnc12] | N4-(8-methylcinnolin-4-yl)-N2-(4-(4-methylpiperazin-1-yl)phenyl)pyrimidine-2,4-diamine | (1H NMR DMSO-d6, 500 MHz): δ 10.35 (s, 1H), 9.69 (bs, 1H), 9.07 (bs, 1H), 8.33 (d, J = 8.0 Hz, 1H), 8.10 (d, J = 5.0 Hz, 1H), 7.64-7.57 (m, 4H), 6.84 (d, J = 8.0 Hz, 2H), 6.53 (s, 1H), 3.05 (t, J = 4.5 Hz, 4H), 2.86 (s, 3H), 2.45 (t, J = 5.0 Hz, 4H), 2.20 (s, 3H). LCMS (M − H): 425.2, HPLC Purity: 99.36% |

TABLE 1-continued

Example Compounds of the invention:

| EXP No. | Structure | Structure Name | NMR/LC-MS |
|---|---|---|---|
| EX-34 | 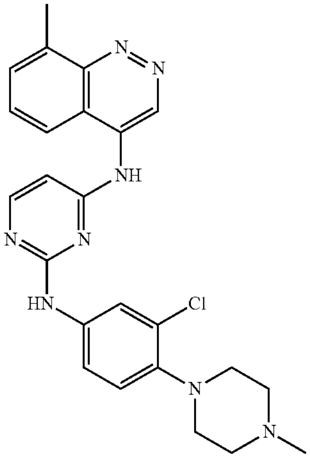 [SMILES: Cc1cccc2c(Nc3ccnc(Nc4ccc(N5CCN(C)CC5)c(Cl)c4)n3)cnnc12] | N2-(3-chloro-4-(4-methyl-piperazin-1-yl)-phenyl)-N4-(8-methylcinnolin-4-yl)pyrimidine-2,4-diamine | 1H NMR DMSO-d6, 400 MHz): δ 10.14 (s, 1H), 10.11 (bs, 1H), 9.11 (bs, 1H), 8.29 (d, J = 8.4 Hz, 1H), 8.01 (s, 1H), 7.96 (d, J = 2.4 Hz, 1H), 7.66-7.63 (m, 1H), 7.63-7.47 (m, 2H), 7.03 (d, J = 8.8 Hz, 1H), 6.42 (s, 1H), 2.89-2.87 (m, 4H), 2.81 (s, 3H), 2.49-2.46 (m, 4H), 2.22 (s, 3H). LCMS: [M − H]+, 459. HPLC: 95.21% |
| EX-35 | 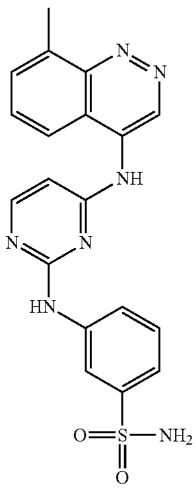 [SMILES: Cc1cccc2c(Nc3ccnc(Nc4cccc(S(N)(=O)=O)c4)n3)cnnc12] | 3-((4-((8-methylcinnolin-4-yl)amino)-pyrimidin-2-yl)amino)benzenesulfonamide | (1H NMR DMSO-d6, 500 MHz): δ 10.64 (s, 1H), 9.91 (s, 1H), 9.81 (s, 1H), 8.39-8.37 (m, 1H), 8.32-8.30 (m, 2H), 7.98 (d, J = 8.5 Hz, 1H), 7.77-7.76 (m, 2H), 7.47-7.41 (m, 4H), 6.85 (d, J = 5.5 Hz, 1H), 2.92 (s, 3H), LCMS (M + H): 408.1, HPLC: 98.03%. |
| EX-36 | 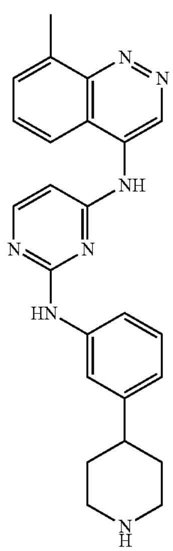 [SMILES: Cc1cccc2c(Nc3ccnc(Nc4cccc(C5CCNCC5)c4)n3)cnnc12] | N4-(8-methylcinnolin-4-yl)-N2-(3-(piperidin-4-yl)phenyl)pyrimidine-2,4-diamine | (1H NMR DMSO-d6, 400 MHz): δ 10.49 (s, 1H), 9.79 (bs, 1H), 9.47 (s, 1H), 8.36-8.33 (m, 1H), 8.26 (d, J = 5.6 Hz, 1H), 7.75-7.72 (m, 2H), 7.61-7.56 (m, 2H), 7.16 (t, J = 7.6 Hz, 1H), 6.80 (d, J = 7.2 Hz,1H) 6.73 (d, J = 5.6 Hz, 1H), 2.96-2.91 (m, 2H), 2.89 (s, 3H), 2.53-2.49 (m, 4H), 1.64-1.61 (m, 2H), 1.46-1.40 (m, 2H), LCMS (M − H): 410.3, HPLC: 95.43%. |

TABLE 1-continued

Example Compounds of the invention:

| EXP No. | Structure | Structure Name | NMR/LC-MS |
|---|---|---|---|
| EX-37 | 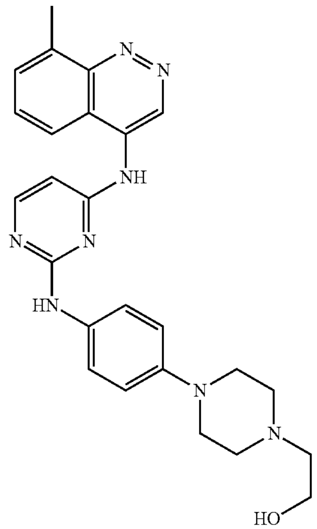 [SMILES: Cc1cccc2c(Nc3ccnc(Nc4ccc(N5CCN(CCO)CC5)cc4)n3)cnnc12] | 2-(4-(4-((4-((8-methylcinnolin-4-yl)amino)pyrimidin-2-yl)amino)phenyl)piperazin-1-yl)ethan-1-ol | (1H NMR DMSO-$d_6$, 400 MHz): δ 10.47 (s, 1H), 9.68 (bs, 1H), 9.21 (s, 1H), 8.35-8.33 (m, 1H), 8.16 (d, J = 5.6 Hz, 1H), 7.70-7.66 (m, 2H), 7.56 (d, J = 8.8 Hz, 2H), 6.84 (d, J = 9.2 Hz, 2H) 6.63 (d, J = 5.6 Hz, 1H), 4.42 (s, 1H), 3.54-3.53 (m, 2H), 3.05 (t, J = 4.4 Hz, 4H), 2.89 (s, 3H), 2.57-2.54 (m, 4H), 2.49-2.42 (m, 2H), LCMS (M + H): 457.34, HPLC: 97.82%. |
| EX-38 | 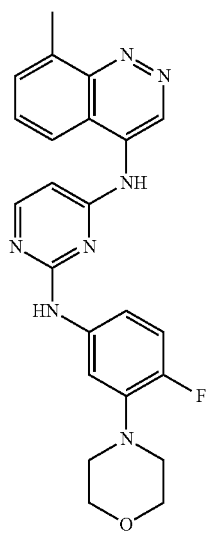 [SMILES: Cc1cccc2c(Nc3ccnc(Nc4ccc(F)c(N5CCOCC5)c4)n3)cnnc12] | N2-(4-fluoro-3-morpholinophenyl)-N4-(8-methylcinnolin-4-yl)pyrimidine-2,4-diamine | (1H NMR DMSO-$d_6$, 400 MHz): δ 10.49 (s, 1H), 9.76 (s, 1H), 9.47 (s, 1H), 8.34 (t, J = 5.2 Hz, 1H), 8.26 (d, J = 5.6 Hz, 1H), 7.76-7.72 (m, 2H), 7.40-7.38 (m, 2H), 7.04-6.99 (m, 1H), 6.74 (d, J = 5.2 Hz, 1H), 3.65-3.64 (m, 4H), 2.91 (s, 3H) 2.88-2.72 (m, 4H), LCMS (M + H): 432.14, HPLC: 97.80% |
| EX-39 | 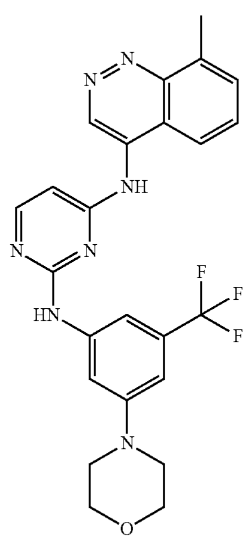 [SMILES: Cc1cccc2c(Nc3ccnc(Nc4cc(N5CCOCC5)cc(C(F)(F)F)c4)n3)cnnc12] | N4-(8-methylcinnolin-4-yl)-N2-(3-morpholino-5-(trifluoromethyl)phenyl)pyrimidine-2,4-diamine | (1H NMR DMSO-$d_6$, 400 MHz): δ 10.52 (s, 1H), 9.82 (s, 1H), 9.71 (s, 1H), 8.35-8.31 (m, 2H), 7.74 (d, J = 5.6 Hz, 2H), 7.67 (s, 1H), 7.62 (s, 1H), 6.80-6.78 (m, 2H), 3.67 (t, J = 4.4 Hz, 4H), 3.04-3.03 (m, 4H), 2.92 (s, 3H). LCMS (M + H): 482.16, HPLC: 97.12%. |

TABLE 1-continued

Example Compounds of the invention:

| EXP No. | Structure | Structure Name | NMR/LC-MS |
|---|---|---|---|
| EX-40 | 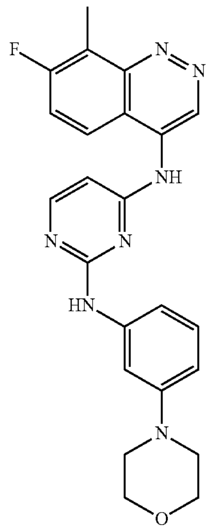 [SMILES: Cc1c(F)ccc2c(Nc3ccnc(Nc4cccc(N5CCOCC5)c4)n3)cnnc12] | N4-(7-fluoro-8-methylcinnolin-4-yl)-N2-(3-morpholinophenyl)pyrimidine-2,4-diamine | (1H NMR DMSO-$d_6$, 400 MHz): δ 10.55 (s, 1H), 9.85 (s, 1H), 9.42 (s, 1H), 8.48-8.44 (m, 1H), 8.27 (d, J = 5.6 Hz, 1H), 7.80 (t, J = 9.2 Hz, 1H), 7.33 (s, 1H), 7.26 (d, J = 8.4 Hz, 1H), 7.10 (t, J = 8.0 Hz, 1H), 6.72 (d, J = 5.6 Hz, 1H), 6.57-6.54 (m, 1H), 3.66 (t, J = 4.8 Hz, 4H), 2.98 (t, J = 4.8 Hz, 4H), 2.79 (s, 3H). LCMS (M + H): 432.32, HPLC: 98.02%. |
| EX-41 | 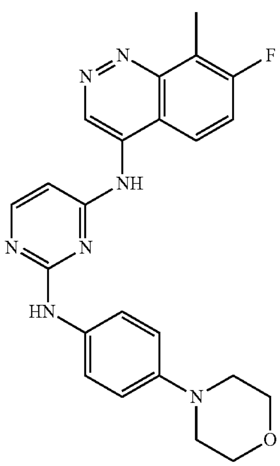 [SMILES: Cc1c(F)ccc2c(Nc3ccnc(Nc4ccc(N5CCOCC5)cc4)n3)cnnc12] | N4-(7-fluoro-8-methylcinnolin-4-yl)-N2-(4-morpholinophenyl)pyrimidine-2,4-diamine | (1H NMR DMSO-$d_6$, 400 MHz): δ 10.58 (s, 1H), 9.78 (s, 1H), 9.33 (s, 1H), 8.48-8.44 (m, 1H), 8.21 (d, J = 5.2 Hz, 1H), 7.78 (t, J = 9.2 Hz, 1H), 7.57 (d, J = 8.8 Hz, 2H), 6.87 (d, J = 8.0 Hz, 2H), 6.67 (d, J = 5.6 Hz, 1H), 3.74 (t, J = 4.4 Hz, 4H), 3.07 (t, J = 4.4 Hz, 4H), 2.79 (s, 3H). LCMS (M + H): 432.39, HPLC: 95.36%. |
| EX-42 | 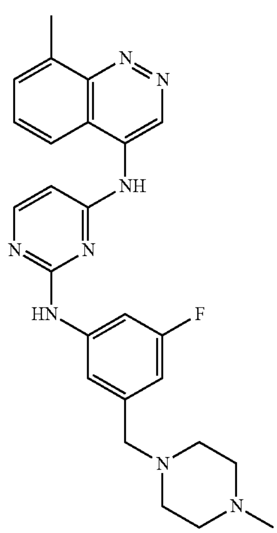 | N2-(3-fluoro-5-((4-methylpiperazin-1-yl)methyl)phenyl)-N4-(8-methylcinnolin-4-yl)pyrimidine-2,4-diamine | (1H NMR DMSO-$d_6$, 500 MHz δ 10.51 (s, 1H), 9.81 (s, 1H), 9.74 (s, 1H), 8.35-8.28 (m, 2H), 7.74-7.67 (m, 3H), 7.43 (s, 1H), 6.77 (d, J = 5.2 Hz, 1H), 6.64 (d, J = 9.2 Hz, 1H), 3.38 (s, 2H), 2.91 (s, 3H), 2.33-2.32 (m, 8H), 2.12 (s, 3H), LCMS (M + H): 459.27, HPLC: 96.41%. |

TABLE 1-continued

Example Compounds of the invention:

| EXP No. | Structure | Structure Name | NMR/LC-MS |
|---|---|---|---|
| EX-43 | 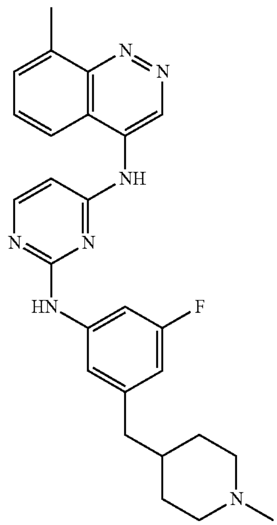 [SMILES: Cc1cccc2c(Nc3ccnc(Nc4cc(F)cc(CN5CCN(C)CC5)c4)n3)cnnc12] | N2-(3-fluoro-5-((1-methylpiperidin-4-yl)methyl)phenyl)-N4-(8-methylcinnolin-4-yl)pyrimidine-2,4-diamine | (1H NMR DMSO-$d_6$, 400 MHz): δ 10.48 (s, 1H), 9.83 (s, 1H), 9.69 (s, 1H), 8.34-8.29 (m, 2H), 7.75 (d, J = 5.2 Hz, 2H), 7.56 (d, J = 12.4 Hz, 1H), 7.34 (s, 1H), 6.77 (d, J = 5.6 Hz, 1H), 6.54 (d, J = 8.8 Hz, 1H), 2.92 (s, 3H), 2.68-2.67 (m, 2H), 2.43-2.41 (m, 2H), 2.10 (s, 3H), 1.70-1.72 (m, 2H), 1.50-1.47 (m, 2H), 133-1.23 (m, 1H), 1.17-1.11 (m, 2H). LCMS (M + H): 458.39, HPLC Purity: 98.45%. |
| EX-44 | 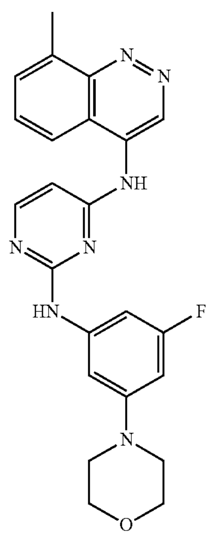 [SMILES: Cc1cccc2c(Nc3ccnc(Nc4cc(F)cc(N5CCOCC5)c4)n3)cnnc12] | N2-(3-fluoro-5-morpholinophenyl)-N4-(8-methylcinnolin-4-yl)pyrimidine-2,4-diamine | (1H NMR DMSO-$d_6$, 400 MHz): δ 10.27 (s, 1H), 10.25 (s, 1H), 9.82 (s, 1H), 8.30 (d, J = 8.0 Hz, 1H), 8.15 (s, 1H), 7.64-7.61 (m, 2H), 7.22 (d, J = 12.0 Hz, 1H), 7.15 (s, 1H), 6.61-6.59 (m, 1H), 6.31 (d, J = 12.4 Hz, 1H), 3.63-3.62 (m, 4H), 2.98-2.96 (m, 4H), 2.86 (s, 3H). LCMS (M + H): 432.1, HPLC: 96.27%. |
| EX-45 | 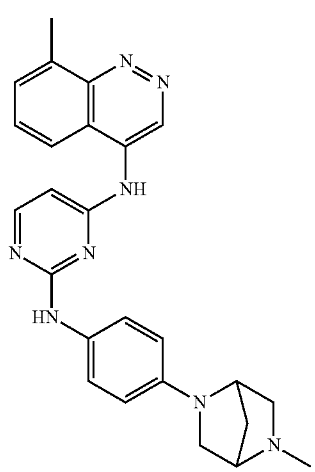 [SMILES: Cc1cccc2c(Nc3ccnc(Nc4ccc(N5CC6CC5CN6C)cc4)n3)cnnc12] | N2-(4-(5-methyl-2,5-diazabicyclo[2.2.1]heptan-2-yl)phenyl)-N4-(8-methylcinnolin-4-yl)pyrimidine-2,4-diamine | (1H NMR DMSO-$d_6$, 400 MHz): δ 10.46 (s, 1H), 9.64 (s, 1H), 9.04 (s, 1H), 8.33 (d, J = 9.2 Hz, 1H), 8.12 (d, J = 4.8 Hz, 1H), 7.69-7.67 (m, 2H), 7.46 (d, J = 8.4 Hz, 2H), 6.57 (s, 1H), 6.49 (d, J = 9.2 Hz, 2H), 3.37 (s, 1H), 3.29 (s, 1H), 3.10 (d, J = 8.8 Hz, 1H), 2.88 (s, 3H), 2.76-2.73 (m, 1H), 2.50-2.49 (m, 1H), 2.23 (s, 3H), 1.85-1.82 (m, 1H), 1.76-1.73 (m, 1H). LCMS (M + H): 439.38, HPLC: 95.02%. |

TABLE 1-continued

Example Compounds of the invention:

| EXP No. | Structure | Structure Name | NMR/LC-MS |
|---|---|---|---|
| EX-46 | 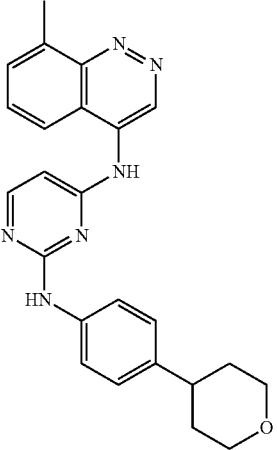 [SMILES: Cc1cccc2c(Nc3ccnc(Nc4ccc(C5CCOCC5)cc4)n3)cnnc12] | N4-(8-methylcinnolin-4-yl)-N2-(4-(tetrahydro-2H-pyran-4-yl)phenyl)pyrimidine-2,4-diamine | (1H NMR DMSO-$d_6$, 400 MHz): δ 10.56 (s, 1H), 9.73 (s, 1H), 9.48 (s, 1H), 8.35 (t, J = 5.2 Hz, 1H), 8.24 (d, J = 5.6 Hz, 1H), 7.74 (d, J = 5.6 Hz, 2H), 7.66 (d, J = 8.4 Hz, 2H), 7.13 (d, J = 8.4 Hz, 2H), 6.73 (d, J = 5.6 Hz, 1H), 3.96-3.93 (m, 2H), 3.46-3.39 (m, 2H), 2.92 (s, 3H), 2.71-2.66 (m, 1H), 1.68-1.62 (m, 4H). LCMS (M + H): 413.26, HPLC: 98.96%. |
| EX-47 | 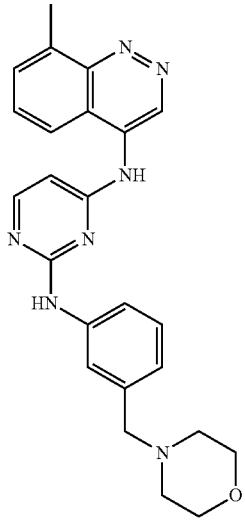 [SMILES: Cc1cccc2c(Nc3ccnc(Nc4cccc(CN5CCOCC5)c4)n3)cnnc12] | N4-(8-methylcinnolin-4-yl)-N2-(3-(morpholinomethyl)phenyl)pyrimidine-2,4-diamine | (1H NMR DMSO-$d_6$, 400 MHz): δ 10.39 (s, 1H), 9.77 (s, 1H), 9.39 (s, 1H), 8.32 (d, J = 8.4 Hz, 1H), 8.18 (m, 1H), 7.72-7.64 (m, 4H), 7.17 (t, J = 8.0 Hz, 1H), 6.85 (d, J = 7.6 Hz, 1H), 6.64-6.62 (m, 1H), 3.50 (t, J = 4.4 Hz, 4H), 3.39 (s, 2H), 2.88 (s, 3H), 2.32-2.30 (m, 4H), LCMS (M + H): 428.2, HPLC: 96.47%. |
| EX-48 | 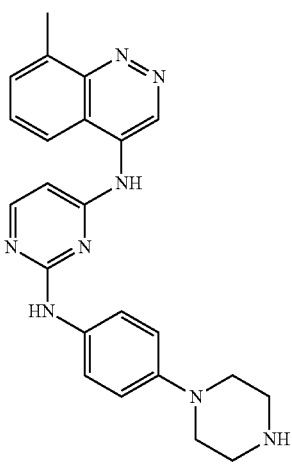 [SMILES: Cc1cccc2c(Nc3ccnc(Nc4ccc(N5CCNCC5)cc4)n3)cnnc12] | N4-(8-methylcinnolin-4-yl)-N2-(4-(piperazin-1-yl)phenyl)pyrimidine-2,4-diamine | (1H NMR DMSO-$d_6$, 400 MHz): δ 10.36 (s, 1H), 9.73 (s, 1H), 9.04 (s, 1H), 8.32 (d, J = 6.6 Hz, 1H), 8.06 (d, J = 6.0 Hz, 1H), 7.62-7.57 (m, 4H), 6.82 (t, J = 6.8 Hz, 2H), 6.52 (d, J = 8.4 Hz, 1H), 3.36-3.20 (m, 2H), 2.95-2.93 (m, 2H), 2.87-2.85 (m, 2H), 2.83 (s, 3H), 2.82-2.81 (m, 2H). LCMS (M − H): 411.2, HPLC: 98.03%. |

TABLE 1-continued

Example Compounds of the invention:

| EXP No. | Structure | Structure Name | NMR/LC-MS |
|---|---|---|---|
| EX-49 | 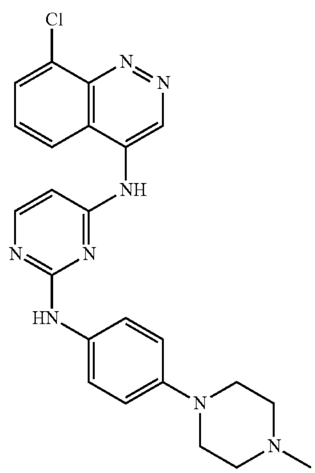 [SMILES: CN1CCN(c2ccc(Nc3nccc(Nc4cnnc5c(Cl)cccc45)n3)cc2)CC1] | N4-(8-chlorocinnolin-4-yl)-N2-(4-(4-methylpiperazin-1-yl)phenyl)pyrimidine-2,4-diamine | (1H NMR DMSO-$d_6$, 500 MHz): δ 10.69 (s, 1H), 9.84 (s, 1H), 9.35 (s, 1H), 8.51 (d, J = 3.5 Hz, 1H), 8.23 (d, J = 5.5 Hz, 1H), 8.09 (d, J = 6.0 Hz, 1H), 7.81 (J = 8.5 Hz, 1H), 7.54 (d, J = 8.5 Hz, 2H), 6.87 (d, J = 9.0 Hz, 2H), 6.70 (d, J = 5.5 Hz, 1H), 3.06 (t, J = 4.5 Hz, 4H), 2.46 (t, J = 5.5 Hz, 4H), 2.22 (s, 3H). LCMS (M + H): 447.2, HPLC: 95.47%. |
| EX-50 | 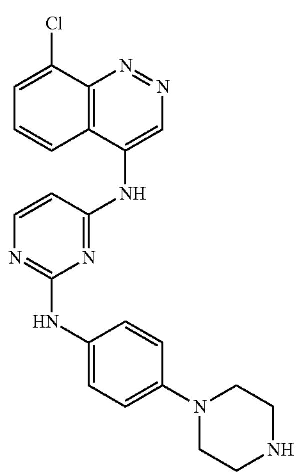 [SMILES: Clc1cccc2c(Nc3ccnc(Nc4ccc(N5CCNCC5)cc4)n3)cnnc12] | N4-(8-chlorocinnolin-4-yl)-N2-(4-(piperazin-1-yl)phenyl)pyrimidine-2,4-diamine | (1H NMR DMSO-$d_6$, 500 MHz): δ 10.66 (s, 1H), 9.88 (s, 1H), 9.33 (s, 1H), 8.52 (t, J = 4.0 Hz, 1H), 8.22 (d, J = 5.5 Hz, 1H), 8.08 (d, J = 7.0 Hz, 1H), 7.80 (t J = 9.0 Hz, 1H), 7.54 (d, J = 8.5 Hz, 2H), 6.85 (d, J = 9.0 Hz, 2H), 6.69 (d, J = 6.0 Hz, 1H), 2.97 (t, J = 4.5 Hz, 4H), 2.83 (t, J = 4.0 Hz, 4H). LCMS (M + H): 433.1, HPLC: 95.29%. |
| EX-51 | 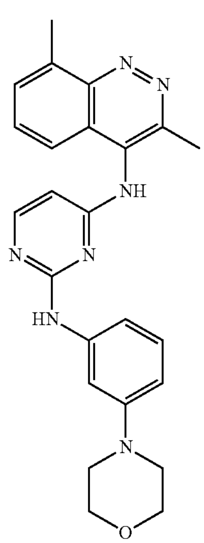 [SMILES: Cc1nnc2c(C)cccc2c1Nc1ccnc(Nc2cccc(N3CCOCC3)c2)n1] | N4-(3,8-dimethylcinnolin-4-yl)-N2-(3-morpholinophenyl)pyrimidine-2,4-diamine | ($^1$H NMR DMSO-d6, 400 MHz): δ 9.65 (s, 1H), 8.87 (s, 1H), 8.09 (d, J = 5.6 Hz, 1H), 7.86-7.83 (m, 1H), 7.71-7.66 (m, 2H), 7.02 (br s, 1H), 6.82-6.74 (m, 2H), 6.37 (d, J = 6.8 Hz, 1H), 6.32 (d, J = 5.6 Hz, 1H), 3.58 (t, J = 4.8 Hz, 4H), 2.95 (s, 3H), 2.75-2.71 (m, 7H). LCMS: m/z: 428.18 [M + H]$^+$, RT: 1.4 min; HPLC: 98.15% |

TABLE 1-continued

Example Compounds of the invention:

| EXP No. | Structure | Structure Name | NMR/LC-MS |
|---------|-----------|----------------|-----------|
| EX-52 | 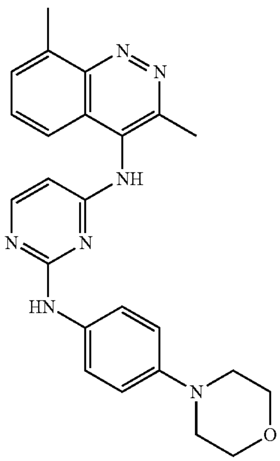 [SMILES: Cc1nnc2c(C)cccc2c1Nc1ccnc(Nc2ccc(N3CCOCC3)cc2)n1] | N4-(3,8-dimethylcinnolin-4-yl)-N2-(4-morpholinophenyl)pyrimidine-2,4-diamine | (1H NMR DMSO-d6, 400 MHz): δ 9.54 (s, 1H), 8.78 (s, 1H), 8.04 (d, J = 8.4 Hz, 1H), 7.81-7.77 (m, 1H), 7.69-7.64 (m, 2H), 7.09 (br s, 2H), 6.50 (d, J = 8 Hz, 2H), 6.25 (d, J = 5.6 Hz, 1H), 3.70 (t, J = 4.4 Hz, 4H), 2.96 (s, 3H), 2.91 (t, J = 4.4 Hz, 4H), 2.74 (s, 3H). LCMS: m/z: 428.19 [M + H]+, RT: 1.36 min; HPLC: 96.45% |
| EX-53 | 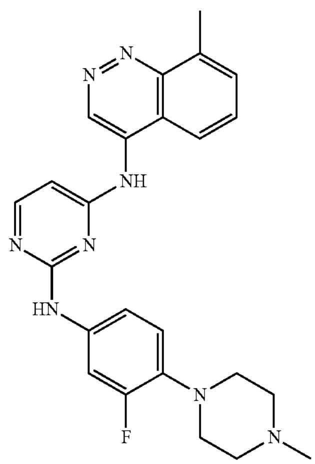 [SMILES: Cc1cccc2c(Nc3ccnc(Nc4ccc(N5CCN(C)CC5)c(F)c4)n3)cnnc12] | N2-(3-fluoro-4-(4-methylpiperazin-1-yl)phenyl)-N4-(8-methylcinnolin-4-yl)pyrimidine-2,4-diamine | (1H NMR DMSO-d$_6$, 500 MHz): δ 10.56 (s, 1H), 9.76 (s, 1H), 9.56 (s, 1H), 8.36-8.33 (m, 1H), 8.26 (t, J = 5.5 Hz, 1H), 7.76-7.70 (m, 3H), 7.36 (d, J = 8.5, 2.0 Hz, 1H), 6.94 (t, J = 9.5 Hz, 1H), 6.75 (d, J = 6.0 Hz, 1H), 2.95-2.93 (m, 4H), 2.92 (s, 3H), 2.50-2.46 (m, 4H), 2.92 (s, 3H), LCMS (M + H): 445.2, HPLC: 96.02% |
| EX-54 | 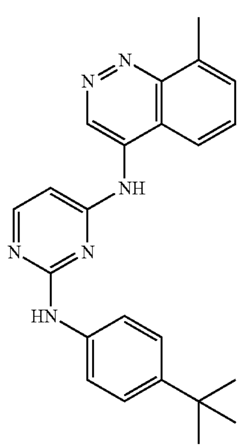 | N2-(4-(tert-butyl)phenyl)-N4-(8-methylcinnolin-4-yl)pyrimidine-2,4-diamine | (1H NMR DMSO-d$_6$, 500 MHz): δ 10.48 (s, 1H), 10.07 (s, 1H), 9.68 (s, 1H), 8.36-8.33 (m, 1H), 8.24 (d, J = 5.6 Hz, 1H), 7.79 (s, 2H), 7.58 (d, J = 8.0 Hz, 2H), 7.28 (d, J = 8.0 Hz, 2H), 6.77 (d, J = 5.6 Hz, 1H), 2.92 (s, 3H), 1.27 (s, 9H). LCMS (M − H): 429.2, HPLC: 96.28% |

TABLE 1-continued

Example Compounds of the invention:

| EXP No. | Structure | Structure Name | NMR/LC-MS |
|---|---|---|---|
| EX-55 | 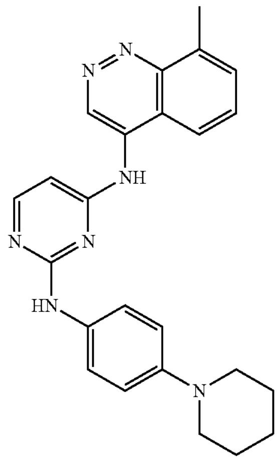 [SMILES: Cc1cccc2c(Nc3ccnc(Nc4ccc(N5CCCCC5)cc4)n3)cnnc12] | N4-(8-methylcinnolin-4-yl)-N2-(4-(piperidin-1-yl)phenyl)pyrimidine-2,4-diamine | (1H NMR DMSO-$d_6$, 400 MHz): δ 10.55 (s, 1H), 9.67 (s, 1H), 9.27 (s, 1H), 8.36-8.33 (m, 1H), 8.20 (d, J = 5.6 Hz, 1H), 7.75-7.71 (m, 2H), 7.54 (d, J = 8.8 Hz, 2H), 6.85 (d, J = 9.2 Hz, 2H), 6.68 (d, J = 5.6 Hz, 1H), 3.06-0283 (m, 4H), 2.91 (s, 3H), 1.67-1.60 (m, 4H), 1.55-1.49 (m, 2H). LCMS (M + H): 412.31, HPLC P: 93.28% |
| EX-56 | 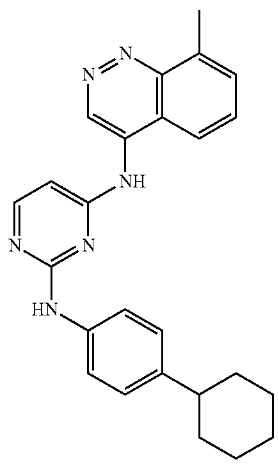 [SMILES: Cc1cccc2c(Nc3ccnc(Nc4ccc(C5CCCCC5)cc4)n3)cnnc12] | N2-(4-cyclohexylphenyl)-N4-(8-methylcinnolin-4-yl)pyrimidine-2,4-diamine | (1H NMR DMSO-$d_6$, 400 MHz): δ 10.56 (s, 1H), 9.72 (s, 1H), 9.45 (s, 1H), 8.36-8.33 (m, 1H), 8.24 (d, J = 5.6 Hz, 1H), 7.76-7.74 (m, 2H), 7.63 (d, J = 8.4 Hz, 2H), 7.10 (d, J = 8.4 Hz, 2H), 6.73 (d, J = 5.6 Hz, 1H), 2.9 (s, 3H), 2.44-2.32 (m, 1H), 1.80-1.68 (m, 5H), 1.42-1.23 (m, 5H). LCMS (M + H): 411.12, HPLC: 98.16%, yield: 8%. |
| EX-57 | 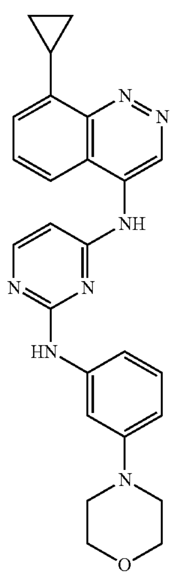 [SMILES: c1cc(Nc2nccc(Nc3cnnc4c(C5CC5)cccc34)n2)cc(N2CCOCC2)c1] | N4-(8-cyclopropylcinnolin-4-yl)-N2-(3-morpholinophenyl)pyrimidine-2,4-diamine | (1H NMR DMSO-$d_6$, 400 MHz): δ 6 10.50 (s, 1H), 9.73 (s, 1H), 9.39 (s, 1H), 8.28-8.25 (m, 2H), 7.74 (t, J = 7.6 Hz, 1H), 7.38-7.35 (m, 2H), 7.25 (d, J = 8.8 Hz, 1H), 7.10 (t, J = 8.0 Hz, 1H), 6.72 (d, J = 5.6 Hz, 1H), 6.28 (s, 1H), 3.67 (t, J = 4.0 Hz, 4H), 3.48-3.45 (m, 1H), 2.98-2.97 (m, 4H), 1.23-1.18 (m, 2H), 0.97-0.94 (m, 2H). LCMS 440.45, (M + H): HPLC: 97.15%. |

TABLE 1-continued
Example Compounds of the invention:
| EXP No. | Structure | Structure Name | NMR/LC-MS |
|---|---|---|---|
| EX-58 | 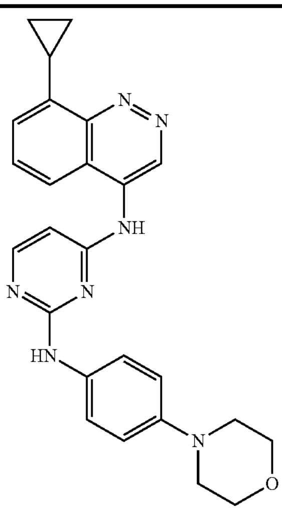 | N4-(8-cyclopropylcinnolin-4-yl)-N2-(4-morpholinophenyl)pyrimidine-2,4-diamine | (1H NMR DMSO-$d_6$, 400 MHz): δ 6 10.25 (s, 1H), 9.69 (s, 1H), 9.01 (s, 1H), 8.24 (d, J = 4.4 Hz, 1H), 8.05 (d, J = 4.4 Hz, 1H), 7.61-7.55 (m, 3H), 7.23 (d, J = 6.4 Hz, 1H), 6.83 (d, J = 9.2 Hz, 2H), 6.47 (s, 1H), 3.73 (t, J = 4.4 Hz, 4H), 3.43-3.39 (m, 1H), 3.01 (t, J = 4.4 Hz, 4H), 1.16-1.13 (m, 2H), 0.90-.088 (m, 2H) LCMS (M + H): 440.46 HPLC: 98.98%. |
Synthesis of Certain Example Compounds
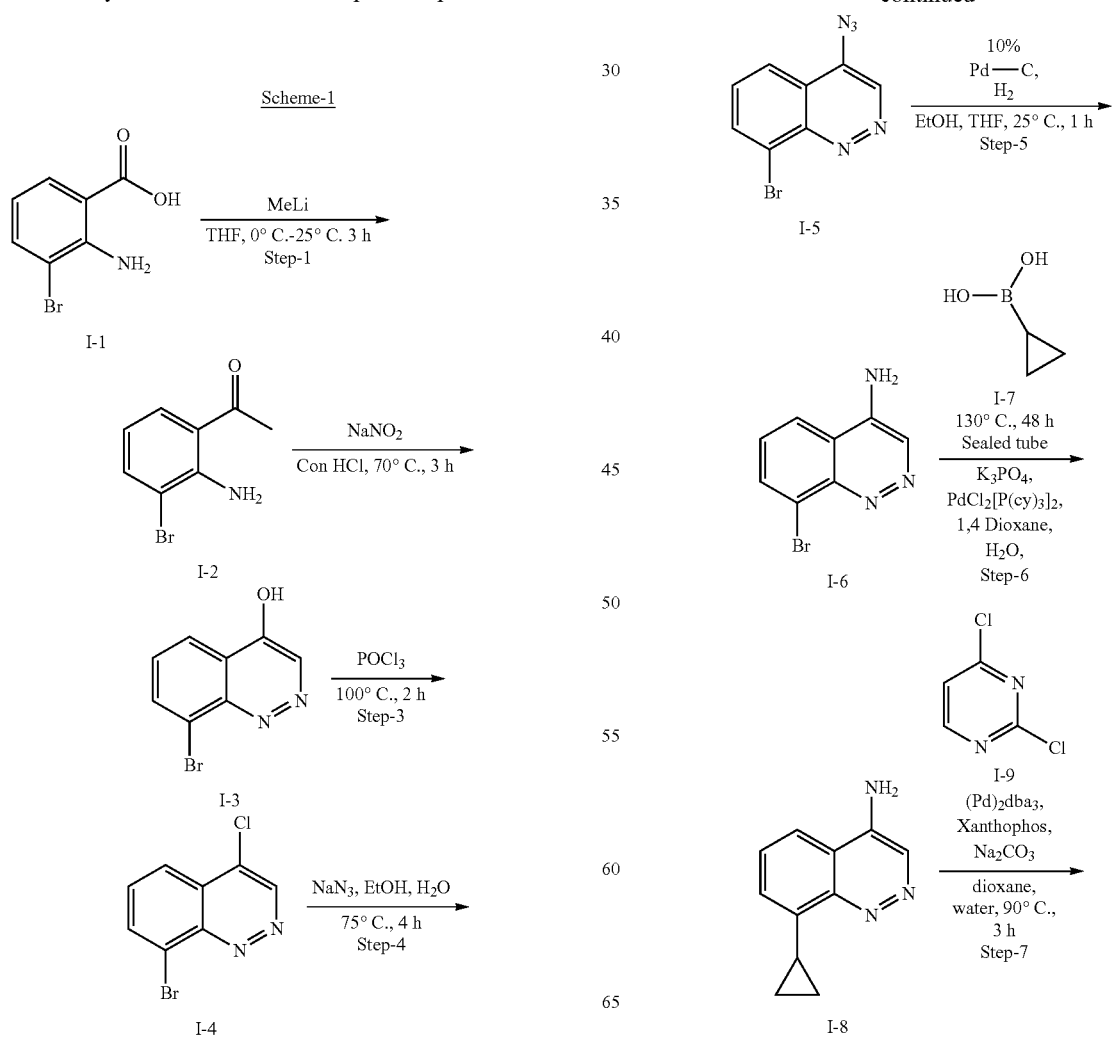

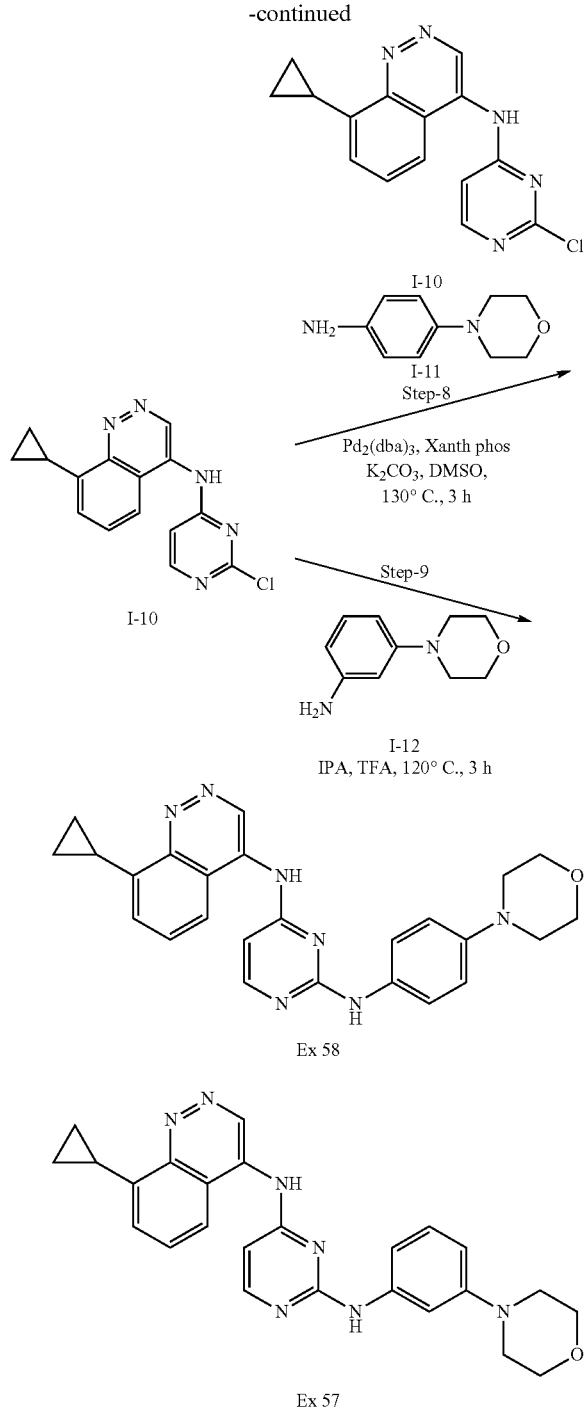

under vacuum to afford crude compound which was triturated with n-pentane (2×100 mL) to afford compound (I-2), which was characterized by LCMS (M+1): 214.

2) Synthesis of 8-bromocinnolin-4-ol (1-3)

To a stirred solution of 1-(2-amino-3-bromophenyl)ethan-1-one (2) (14 g, 93.9 mmol) in conc. HCl (140 mL) was added drop wise a solution of NaNO$_2$ (7.77 g 112.68 mmol) in water (10.5 mL) at −5° C. and was stirred for 3 h at 70° C. The reaction mixture was cooled to room temperature, filtered and the residue was washed with diethyl ether (100 mL). The filtrate was neutralized with Sat sodium bicarbonate up to p$^H$=7 and solid precipitated was filtered and dried under vacuum to afford the compound (I-3) which was characterized by LCMS (M+H): 224.88.

3) Synthesis of 8-bromo-4-chlorocinnoline (I-4)

The compound 8-bromocinnolin-4-ol (I-3) (10.5 g, 46.69 mmol) was taken into 250 ml two neck RBF and added POCl$_3$ (100 mL) drop wise at RT and allowed to stir at 100° C. for 2 h. The reaction mixture was cooled to RT and the excess POCl$_3$ was distilled out, residue was poured into ice water (250 mL) and neutralized with sat sodium bicarbonate solution up to p$^H$=7, the precipitated solid was filtered off and dried under vacuum to afford the compound (I-4) which was characterized by LCMS (M+H): 243.25.

4) Synthesis of 4-azido-8-bromocinnoline (I-5)

To a stirred solution of 8-bromo-4-chlorocinnoline (4) (8 g, 32.6 mmol) in ethanol (80 mL), water (16 mL), was added NaN$_3$ (4.50 g, 65.3 mmol) and stirred at 75° C. for 4 h. The reaction mixture was cooled to room temperature and concentrated under vacuum. The residue was diluted with water (100 mL), the precipitated solid was filtered off and dried under vacuum to afford the compound (I-5) which was characterized by LCMS (M+2H): 252.02.

5) Synthesis of 8-bromocinnolin-4-amine (I-6)

To a stirred solution of 4-azido-8-bromocinnoline (I-5) (2.5 g, 9.96 mmol) in Ethanol, THF (50, 100 mL) was added 10% Pd/C (50% moisture) (0.400 g) and reaction was allowed to stir under hydrogen gas for 1 h. The reaction mixture was filtered through a celite, the residue was washed with methanol (2×200 mL). The filtrate was concentrated under reduced pressure, co-distilled with toluene (2×500 mL) and triturated with ether (2×50 mL) to afford compound (I-6) which was characterized by LCMS (M+2H): 226.10.

6) Synthesis of 8-cyclopropylcinnolin-4-amine (I-8)

A mixture of 8-bromocinnolin-4-amine (I-6) (1.5 g, 6.72 mmol), cyclopropylboronic acid (I-7) (0.867 g 10.08 mmol) and K$_3$PO$_4$ (4.98 g 23.52 mmol) in 1, 4 dioxane (50 mL), water (15 mL) was degassed for 10 min and added PdCl$_2$[P(cy)$_3$]$_2$ (2.5 g, 3.36 mmol). The resulting reaction mixture was stirred at 130° C. for 48 h in sealed tube. The reaction mixture was cooled to room temperature, concentrated under vacuum and diluted with water (50 mL), the solid precipitated was filtered and dried under vacuum to afford the title compound (8) which was characterized by LCMS (M+H): 186.07.

1) Synthesis of 1-(2-amino-3-bromophenyl)ethan-1-one (1-2)

To a suspension 2-amino-3-bromobenzoic acid (1) (20 g, 93 mmol) in THF (400 mL) was added MeLi (1.6 M in diethyl ether) (203 mL, 325.58 mmol) at 0° C., the resulting reaction mixture was stirred at 25° C. temperature for 3 h, then quenched with saturated ammonium chloride solution (2000 mL) and extracted with EtOAc (2×500 mL). The organic layers were combined, washed with water (150 mL), brine (150 mL), dried over sodium sulfate and concentrated

7) Synthesis of N-(2-chloropyrimidin-4-yl)-8-cyclopropylcinnolin-4-amine (I-10)

A mixture of 8-cyclopropylcinnolin-4-amine (I-8) (1.5 g, 10.2 mmol), 2,4 dichloride pyrimidine (I-9) (1.92 g 10.2 mmol) and Na$_2$CO$_3$ (2.16 g 20.4 mmol) in 1,4 dioxane (45 mL), water (5 mL) was degassed for 10 min and added Pd$_2$(dba)$_3$ (0.933 g, 1.02 mmol Xantphos (0.59 g, 1.02 mmol), the resulting reaction mixture was stirred at 90° C. for 3 h. The reaction mixture was cooled to room temperature, concentrated under vacuum and diluted with water (50 mL), the solid precipitated was filtered, washed with ethyl acetate (2×50 mL) and dried under vacuum to afford the compound (I-10) which was characterized by LCMS (M+H): 298.20. The crude thus obtained was used for next step without purification.

Synthesis of N4-(8-cyclopropylcinnolin-4-yl)-N2-(4-morpholinophenyl)pyrimidine-2,4-diamine (Ex-58)

Into a mixture of N-(2-chloropyrimidin-4-yl)-8-cyclopropylcinnolin-4-amine (0.5 g, 1.68 mmol (I-10), 4-morpholinoaniline (I-11) (0.3 g 1.68 mmol) and potassium carbonate (0.695 g, 5.04 mmol) in degassed (10 min.) DMSO (10 mL) was added Pd$_2$(dba)$_3$ (0.103 g, 0.168 mmol) and Xantphos (0.1 g, 0.168 mmol) and the resulting reaction mixture was stirred for 3 h at 130° C. The reaction mixture was then cooled to room temperature and diluted with water (50 mL), the precipitated solid was filtered and dried under vacuum to afford crude compound which was purified by prep HPLC to give the compound (Ex-58) which was characterized with the following:

(1H NMR DMSO-d$_6$, 400 MHz): δ 10.25 (s, 1H), 9.69 (s, 1H), 9.01 (s, 1H), 8.24 (d, J=4.4 Hz, 1H), 8.05 (d, J=4.4 Hz, 1H), 7.61-7.55 (m, 3H), 7.23 (d, J=6.4 Hz, 1H), 6.83 (d, J=9.2 Hz, 2H), 6.47 (s, 1H), 3.73 (t, J=4.4 Hz, 4H), 3.43-3.39 (m, 1H), 3.01 (t, J=4.4 Hz, 4H), 1.16-1.13 (m, 2H), 0.90-0.088 (m, 2H); LCMS (M+H): 440.46; HPLC: 98.98%.

Preparation of N4-(8-methylcinnolin-4-yl)-N2-(3-morpholinophenyl) pyrimidine-2, 4-diamine (Ex-57)

To a stirred solution of N-(2-chloropyrimidin-4-yl)-8-cyclopropylcinnolin-4-amine (I-10) (0.2 g, 0.673 mmol), 3-morpholinoaniline (I-12) (0.119 g, 0.673 mmol) in IPA (10 mL) was added TFA (0.518 mL, 6.73 mmol) and resulting reaction mixture was stirred for 3 h at 120° C. The reaction mixture was cooled to room temperature, concentrated under vacuum and the solid precipitated was purified by prep HPLC to give the compound (Ex-57) which was characterized as follows:

(1H NMR DMSO-d$_6$, 400 MHz): δ 10.50 (s, 1H), 9.73 (s, 1H), 9.39 (s, 1H), 8.28-8.25 (m, 2H), 7.74 (t, J=7.6 Hz, 1H), 7.38-7.35 (m, 2H), 7.25 (d, J=8.8 Hz, 1H), 7.10 (t, J=8.0 Hz, 1H), 6.72 (d, J=5.6 Hz, 1H), 6.28 (s, 1H), 3.67 (t, J=4.0 Hz, 4H), 3.48-3.45 (m, 1H), 2.98-2.97 (m, 4H), 1.23-1.18 (m, 2H), 0.97-0.94 (m, 2H); LCMS (M+H): 440.45; HPLC: 97.15%.

Synthesis of N4-(8-methylcinnolin-4-yl)-N2-(4-morpholinophenyl)pyrimidine-2,4-diamine (Ex-10)

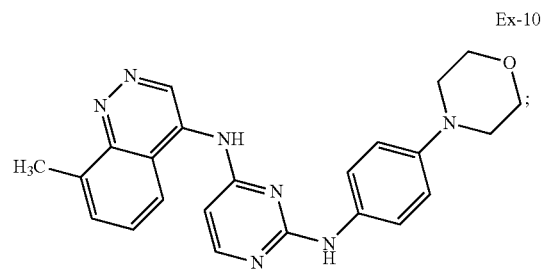 [SMILES: Cc1cccc2c(Nc3ccnc(Nc4ccc(N5CCOCC5)cc4)n3)cnnc12]

To a stirred solution of N-(2-chloropyrimidin-4-yl)-8-methylcinnolin-4-amine (B7) (20 g, 73.80 mmol), 4-morpholinoaniline (13.13 g 73.80 mmole) and potassium carbonate (30.55 g, 221.40 mmol) in DMSO (250 mL) was degassed for 20 min then added Pd$_2$(dba)$_3$ (6.75 g, 7.380 mmole), Xantphos (4.26 g, 7.380 mmole) was stirred for 3 h at 130° C. The reaction mixture was cooled and the residue was diluted with water (750 mL). The resulting precipitated solid was filtered dried under reduced pressure and purified by flash column chromatography by using methanol and dichloromethane to afford the compound Ex-10, which was triturated with a (1:1)ether (2×250 mL): DCM (2×250 mL), ACN (2×250 mL, Pentane (2×250 mL) and Hexane (2×250 mL), then dried. The purified material was analyzed to yield the following data:

(1H NMR DMSO-d$_6$, 400 MHz): δ 10.56 (s, 1H), 9.68 (s, 1H), 9.32 (s, 1H), 8.36 (t, J=5.2 Hz, 1H), 8.21 (d, J=5.6 Hz, 1H), 7.76-7.73 (m, 2H), 7.59 (d, J=8.8 Hz, 2H), 6.88 (d, J=9.2 Hz, 2H), 6.70 (d, J=5.6 Hz, 1H), 3.76 (t, J=4.4 Hz, 4H), 3.05 (t, J=4.4 Hz, 4H), 2.91 (s, 3H), LCMS (M+H): 414.21, HPLC Purity: 98.73%.

Synthesis of N4-(8-methylcinnolin-4-yl)-N2-(3-morpholinophenyl)pyrimidine-2,4-diamine (Ex-11)

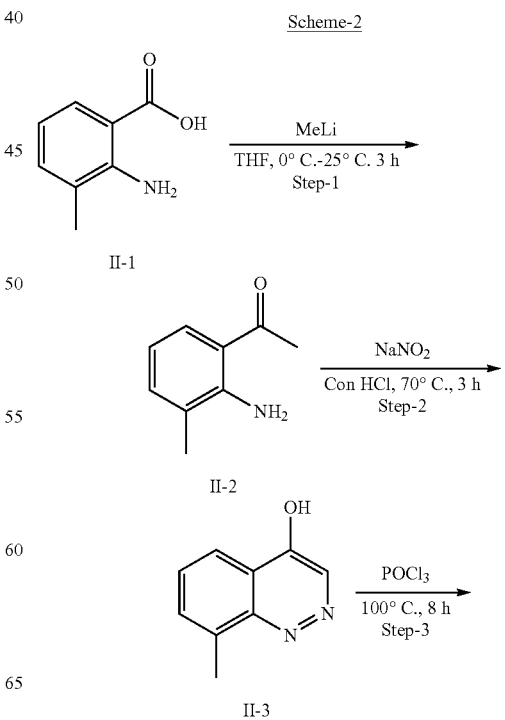

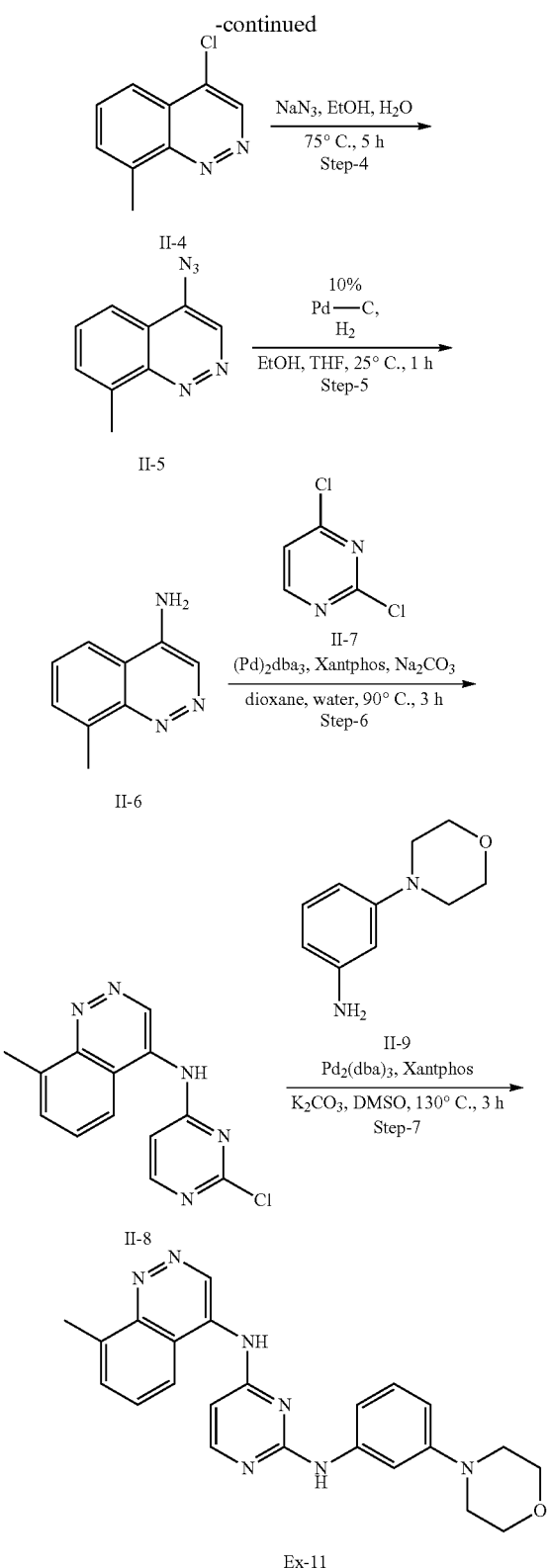

1) Synthesis of 1-(2-amino-3-methylphenyl)ethan-1-one (II-2)

MeLi (1.6 M in diethyl ether) (2.48 L, 3973.5 mmol) was added to a suspension of 2-amino-3-methylbenzoic acid (II-1) (150 g, 993.37 mmol) in THF (2.5 L) at 0° C. and the reaction mixture was stirred at 25° C. for 3 h. The reaction mixture was quenched with saturated ammonium chloride solution (2000 mL) and extracted twice with EtOAc (2×10 L). The combined organic layers were washed with water (1.0 L) and brine (1.0 L), dried over sodium sulphate and concentrated under vacuum to afford the crude compound which was triturated with n-pentane (2×500 mL) to afford title compound (II-2). $^1$H NMR (CDCl$_3$, 400 MHz): δ 7.65 (d, J=8.4 Hz, 1H), 7.21 (d, J=6.8 Hz, 1H), 6.59 (t, J=8.0 Hz, 1H), 6.41 (bs, 2H), 2.59 (s, 3H), 2.16 (s, 3H). LCMS (M+H): 150.1.

2) Synthesis of 8-methylcinnolin-4-ol (11-3)

NaNO$_2$ (70 g, 1014.7 mmol) in water (95 mL) was added dropwise to a stirred solution of 1-(2-amino-3-methylphenyl) ethan-1-one (II-2) (126 g, 845.6 mmol) in concentrated HCl (1.26 L) at −5° C. and the reaction mixture was stirred for 3 h at 70° C. The reaction mixture was cooled to room temperature, filtered and the residue was washed with diethyl ether (1.5 L). The filtrate was neutralized with saturated sodium bicarbonate (to pH=7) and the precipitated solid was filtered and dried under vacuum to afford the title compound (11-3). (1H NMR CDCl$_3$, 500 MHz): δ 10.06 (bs, 1H), 8.14 (d, J=8.0 Hz, 1H), 7.87 (s, 1H), 7.54 (d, J=7.0 Hz, 1H), 7.32-7.29 (m, 1H), 2.56 (s, 3H). LCMS (M+H): 161.1.

3) Synthesis of 4-chloro-8-methylcinnoline (II-4)

POCl$_3$ (380 mL) was added to compound (11-3) (38 g, 187.0 mmol) at room temperature and allowed to stir at 100° C. for 8 h. The reaction mixture was cooled to room temperature and the excess POCl$_3$ was distilled off. The residue was poured into ice water (750 mL) and neutralized with saturated sodium bicarbonate (to pH=7). The precipitated solid was filtered off and dried under vacuum to afford the title compound (11-4). $^1$H NMR CDCl$_3$, 400 MHz): δ 9.35 (s, 1H), 8.05 (d, J=7.6 Hz, 1H), 7.77-7.71 (m, 2H), 3.05 (s, 3H). LCMS (M+H): 179.1.

4) Synthesis of 4-azido-8-methylcinnoline (II-5)

NaN$_3$ (54.77 g, 842.69 mmol) was added to a stirred solution of compound (II-4) (30 g, 168.5 mmol) in ethanol (400 mL) and water (100 mL) and the reaction mixture was stirred at 75° C. for 5 h. The reaction mixture was cooled to room temperature and concentrated under vacuum. The residue was diluted with water (500 mL) and the precipitated solid was filtered off and dried under vacuum to afford the title compound (II-5). $^1$H NMR (CDCl$_3$, 400 MHz): δ 9.23 (s, 1H), 7.89 (d, J=8.4 Hz, 1H), 7.69-7.61 (m, 2H), 3.02 (s, 3H). LCMS (M+H): 186.1.

5) Synthesis of 8-methylcinnolin-4-amine (II-6)

10% Pd/C (50% moisture) (5.0 g) was added to a stirred solution of 4-azido-8-methylcinnoline (II-5) (25 g, 135.13 mmol) in ethanol (750 mL) and THF (500 mL) and the reaction mixture was allowed to stir under hydrogen for 1 h. The reaction mixture was filtered through a celite plug and the residue washed with methanol (2×1.0 L). The filtrate was concentrated under vacuum, co-distilled with toluene (2×500 mL) and triturated with ether (2×500 mL) to afford the title compound II-6. 1H NMR (DMSO-d$_6$, 400 MHz): δ

8.63 (s, 1H), 8.01 (d, J=8.4 Hz, 1H), 7.56 (d, J=6.8 Hz, 1H), 7.45 (t, J=8.0 Hz, 1H), 7.08 (bs, 2H), 2.76 (s, 3H). LCMS (M+H): 160.1.

6) Synthesis of N-(2-chloropyrimidin-4-yl)-8-methylcinnolin-4-amine (11-8)

A mixture of 8-methylcinnolin-4-amine (11-6) (21 g, 132.02 mmol), 2,4-dichloropyrimidine (II-7) (14.66 g 199.05 mmol) and Na$_2$CO$_3$ (42.80 g 396.60 mmol) in 1,4-dioxane (800 mL) and water (200 mL) was degassed for 20 min. Pd$_2$(dba)$_3$ (12.0 g, 13.20 mmol) and Xantphos (7.64 g, 13.202 mmol) were added to the reaction mixture which was then stirred at 90° C. for 3 h. The reaction mixture was cooled to room temperature, concentrated under vacuum and diluted with water (500 mL). The precipitated solid was filtered, washed with ethyl acetate (2×750 mL) and dried under vacuum to afford the title compound (II-8). $^1$H NMR (DMSO-d$_6$, 400 MHz): δ 10.50 (s, 1H), 10.03 (s, 1H), 8.36 (d, J=6.0 Hz, 1H), 8.26 (d, J=9.6 Hz, 1H), 7.75-7.73 (m, 2H), 7.19 (d, J=5.6 Hz, 1H) 2.90 (s, 3H). LCMS (M+H): 272.0.

7) N4-(8-methylcinnolin-4-yl)-N2-(3-morpholinophenyl)pyrimidine-2,4-diamine (Ex-11)

A mixture of N-(2-chloropyrimidin-4-yl)-8-methylcinnolin-4-amine (II-8) (15.0 g, 55.35 mmol) 3-morpholinoaniline (11-9) (10.85 g, 55.35 mmol) (13.13 g 73.80 mmol) and potassium carbonate (23.0 g, 166.05 mmol) in DMSO (250 mL) was degassed for 20 min. Pd$_2$(dba)$_3$ (5.10 g, 5.535 mmol) and Xantphos (2.95 g, 5.535 mmol) were added to the reaction mixture which was then stirred for 3 h at 130° C. The reaction mixture was cooled to room temperature and diluted with water (500 mL). The precipitated solid was filtered and dried under vacuum to afford the crude product which was purified by flash column chromatography (100-200 silica mesh) using 1-5% methanol/dichloromethane as eluent to give the title compound Ex-11. (1H NMR DMSO-d$_6$, 400 MHz): δ 10.51 (s, 1H), 9.75 (s, 1H), 9.40 (s, 1H), 8.35 (t, J=5.2 Hz, 1H), 8.27 (d, J=5.6 Hz, 1H), 7.75-7.72 (m, 2H), 7.34 (s, 1H), 7.27 (d, J=8.0 Hz, 1H), 7.11 (t, J=8.0 Hz, 1H), 6.70 (d, J=5.6 Hz, 1H), 6.56 (dd, J$_1$=2.0 Hz, J$_2$=8.0 Hz, 1H), 3.67 (t, J=4.8 Hz, 4H), 2.98 (t, J=4.4 Hz, 4H), 2.91 (s, 3H). LCMS (M+H): 414.23. HPLC: 98.87%.

Synthesis of N2-(3-chloro-4-morpholino-phenyl)-N4-(8-methyl-cinnolin-4-yl)-pyrimidine-2,4-diamine (Ex-12)

Scheme-3

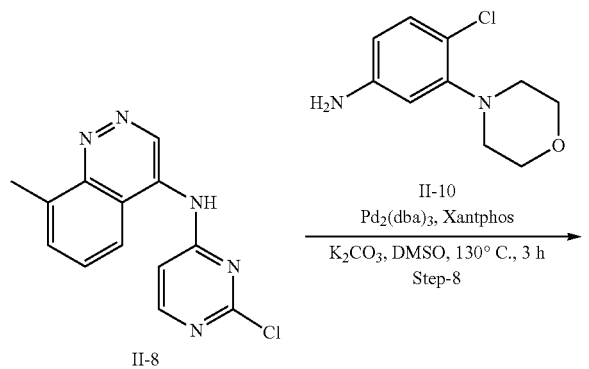

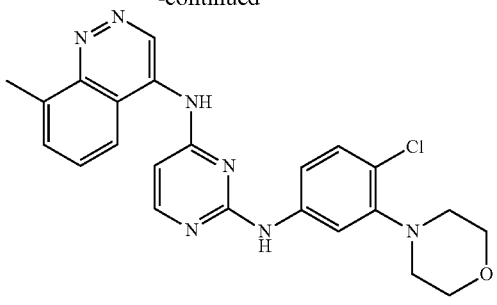

Ex-12

A mixture of N-(2-chloropyrimidin-4-yl)-8-methylcinnolin-4-amine (II-8) (15.0 g, 55.35 mmol), 4-chloro-3-morpholinoaniline (II-10) (11.7 g, 55.35 mmol)) and potassium carbonate (23.0 g, 166.05 mmol) in DMSO (250 mL) was degassed for 20 min. Pd$_2$(dba)$_3$ (5.10 g, 5.535 mmol) and Xantphos (2.95 g, 5.54 mmol) were added to the reaction mixture which was then stirred for 3 h at 130° C. The reaction mixture was cooled to room temperature and diluted with water (500 mL). The precipitated solid was filtered and dried under vacuum to afford the crude product which was purified by flash column chromatography (100-200 silica mesh) using 1-5% methanol/dichloromethane as eluent to give the title compound (Ex-12). ($^1$H NMR DMSO-d$_6$, 400 MHz): δ 10.55 (s, 1H), 9.76 (s, 1H), 9.60 (s, 1H), 8.35 (t, J=5.2 Hz, 1H), 8.28 (d, J=6.0 Hz, 1H), 7.95 (s, 1H), 7.75-7.74 (m, 2H), 7.63 (dd, J$_1$=2.4 Hz, J$_2$=2.4 Hz, 1H), 7.10 (d, J=8.8 Hz, 1H), 6.77 (d, J=5.6 Hz, 1H), 3.74 (t, J=4.8 Hz, 4H), 2.92-2.91 (m, 4H), 2.90 (s, 3H). LCMS (M+H): 448.18. HPLC: 97.58%.

Synthesis of N2-(3-fluoro-4-morpholino-phenyl)-N4-(8-methylcinnolin-4-yl)-pyrimidine-2,4-diamine (Ex-13)

Scheme-4

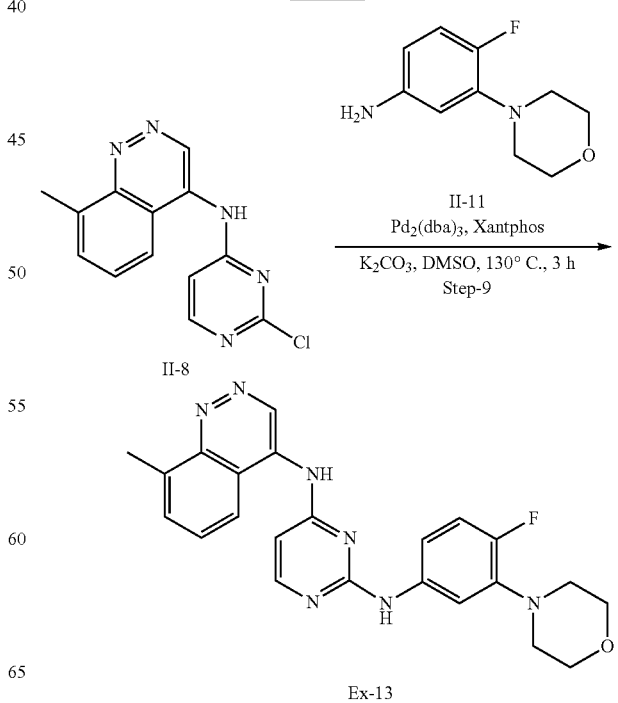

A mixture of N-(2-chloropyrimidin-4-yl)-8-methylcinnolin-4-amine (II-8) (15.0 g, 55.35 mmol) with 3-floro-4-morpholinoaniline (II-11) (10.8 g, 55.35 mmol) and potassium carbonate (23.0 g, 166.05 mmol) in DMSO (250 mL) was degassed for 20 min. Pd$_2$(dba)$_3$ (5.10 g, 5.535 mmol) and Xantphos (2.95 g, 5.535 mmol) were added to the reaction mixture which was then stirred for 3 h at 130° C. The reaction mixture was cooled to room temperature and diluted with water (500 mL). The precipitated solid was filtered and dried under vacuum to afford the crude product which was purified by flash column chromatography (100-200 silica mesh) using 5-10% methanol/dichloromethane as eluent to give the title compound (Ex-13). (1H NMR DMSO-d$_6$, 400 MHz): δ 10.54 (s, 1H), 9.76 (s, 1H), 9.58 (s, 1H), 8.35 (t, J=5.2 Hz, 1H), 8.27 (d, J=5.6 Hz, 1H), 7.76-7.72 (m, 3H), 7.39 (dd, J$_1$=2.0 Hz, J$_2$=1.6 Hz 1H), 6.98 (t, J=9.2 Hz, 1H), 6.76 (d, J=6.0 Hz, 1H), 3.74 (t, J=5.2 Hz, 4H), 2.95-2.94 (m, 4H), 2.92 (s, 3H). LCMS (M+H): 432.23. HPLC: 96.01%.

Synthesis of N$^4$-(8-methylcinnolin-4-yl)-N$^2$-(4-(4-methylpiperazin-1-yl)phenyl)pyrimidine-2,4-diamine (Ex-33)

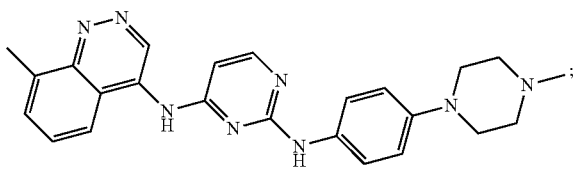

Ex-33

To a stirred solution of N-(2-chloropyrimidin-4-yl)-8-methylcinnolin-4-amine (1.0 g, 3.69 mmol) (B7), 4-(4-methylpiperazin-1-yl)aniline (0.705 g 3.69 mmole) in IPA (40 mL), was added TFA (1.68 mL, 11.07 mmole) and the mixture stirred at 120° C. for 16 h. The reaction mixture was then cooled to room temperature and concentrated under reduced pressure. The solid thus formed was filtered and washed with ether (25 mL) and dried under reduced pressure to afford the crude compound which was then purified by prep HPLC to provide the compound Ex-33, which was analyzed: $^1$H NMR (DMSO-d6, 500 MHz): δ 10.35 (s, 1H), 9.69 (bs, 1H), 9.07 (bs, 1H), 8.33 (d, J=8.0 Hz, 1H), 8.10 (d, J=5.0 Hz, 1H), 7.64-7.57 (m, 4H), 6.84 (d, J=9.0 Hz, 1H), 6.53 (s, 1H), 3.05 (t, J=4.5 Hz, 4H), 2.86 (s, 3H), 2.45 (t, J=5.0 Hz, 4H), 2.20 (s, 3H), LCMS: m/z: 425.2 [M−H]+, RT: 1.895 min, HPLC Purity: 99.36%.

Prep HPLC methodology used in the foregoing synthesis
Mobile Phase A: 0.1% FA in H2O (Aq), Mobile Phase B: ACN,
Column: X-SELECT-C18 (150×30)
Method: 0/5, 1/5, 8/40, 10/50, 10.1/98, 13/98, 13.1/5, 16/5.
Flow Rate: 22 ml/min Diluent:
Solubility: ACN+THF+Water+MEOH and Temp: Ambient Synthesis of N2-(3-chloro-4-(4-methylpiperazin-1-yl)phenyl)-N4-(8-methylcinnolin-4-yl)pyrimidine-2,4-diamine_(Ex-34)

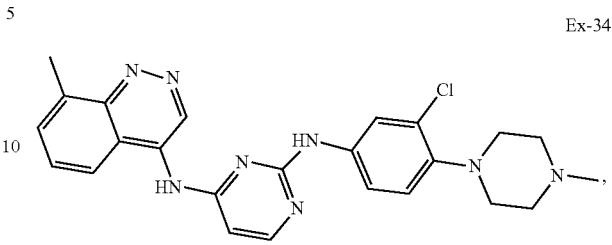

Ex-34

To a stirred solution of N-(2-chloropyrimidin-4-yl)-8-methylcinnolin-4-amine (0.2 g, 0.74 mmol) (B7), 3-chloro-4-(4-methylpiperazin-1-yl)aniline (0.168 g, 0.740 mmol) in IPA (10 mL), was added TFA (0.26 mL, 2.22 mmol) and the resulting mixture was stirred at 120° C. for 16 h. The reaction mixture was then cooled to room temperature and concentrated under reduced pressure. The precipitated solid thus obtained was filtered, washed with ether (25 mL) and dried under reduced pressure to afford crude compound which was purified by prep HPLC to afford the compound Ex-34, which was analyzed by NMR, LC/MS and HPLC to yield the following data: $^1$H NMR (DMSO-d6, 400 MHz): δ 10.14 (s, 1H), 10.11 (bs, 1H), 9.11 (bs, 1H), 8.29 (d, J=8.4 Hz, 1H), 8.01 (s, 1H), 7.96 (d, J=2.4 Hz, 1H), 7.66-7.63 (m, 1H), 7.63-7.47 (m, 3H), 7.03 (d, J=8.8 Hz, 1H), 6.42 (s, 1H), 2.89-2.87 (m, 4H), 2.81 (s, 3H), 2.49-2.46 (m, 4H), 2.22 (s, 3H), LCMS: m/z: 459.1 [M−H]+, RT: 1.58 min, HPLC Purity: 95.21%.

Prep HPLC method used in the foregoing synthesis:
Mobile Phase A: 0.1% FA in H$_2$O (Aq), Mobile Phase B: ACN,
Column: KROMOSIL-C18 (150×25 MM)
Method: 0/10, /33, 7.1/98, 9/98, 9.1/10, 11/10
Flow Rate: 20 ml/min
Solubility: ACN+THF+Water+MEOH and Temp: Ambient Assay Procedures Selected compounds of the invention were assayed for activity.

Activity determinations and selectivity were conducted by Thermo Fisher Scientific "SelectScreen™ Biochemical Kinase Profiling Service" using their "LanthaScreen™ Eu Kinase Binding Assay Screening" (www.thermofisher.com/selectscreen).

Assay Theory

Figure 4:
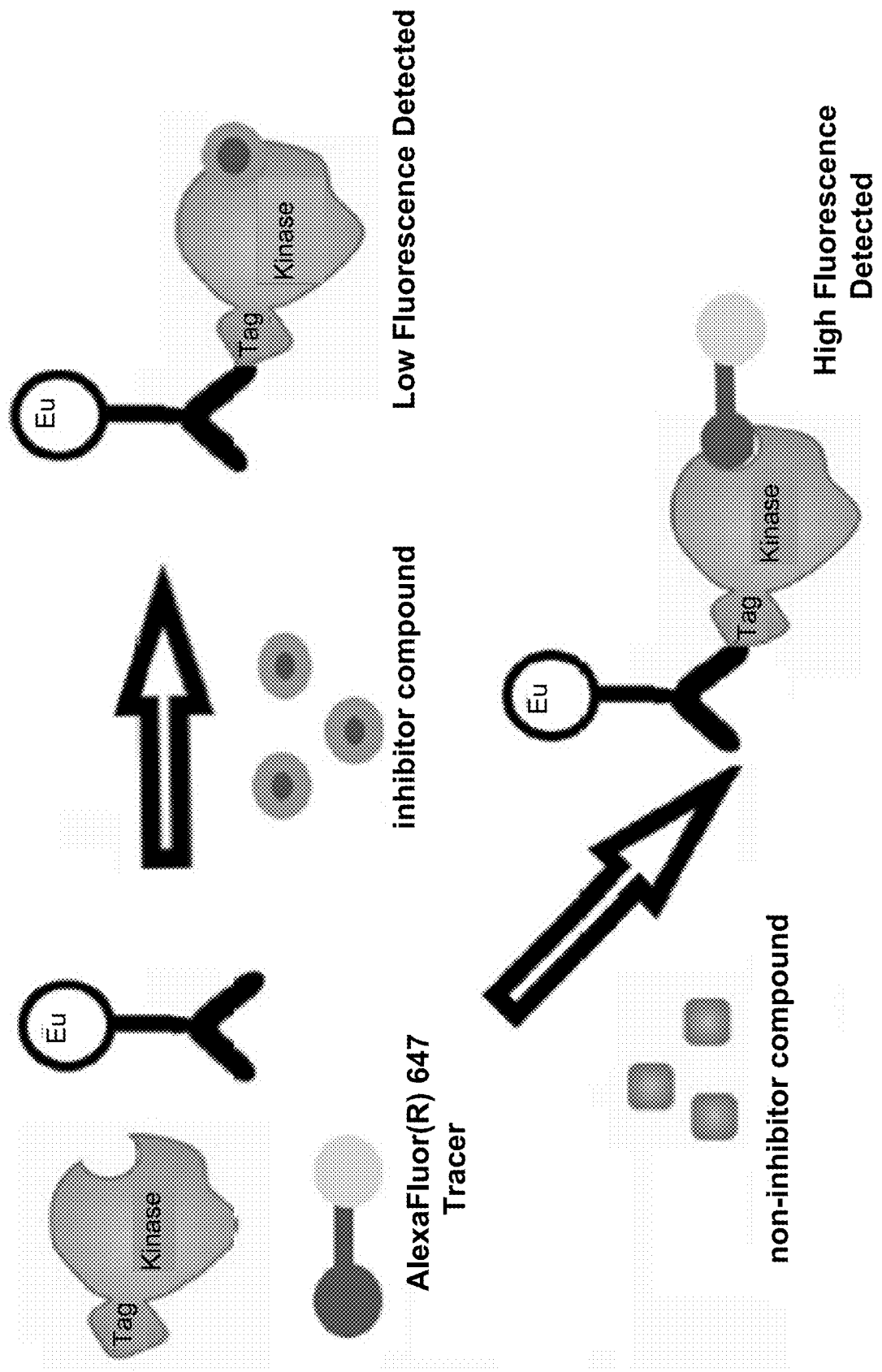
FIG. 4 shows a schematic of LanthaScreen Eu Kinase Binding Assay procedure.

The principle of the LanthaScreen Eu Kinase Binding Assay is shown in FIG. 4. Binding of an Alexa Fluor™ conjugate or "tracer" to a kinase is detected by addition of a Eu-labeled anti-tag antibody. Binding of the tracer and antibody to a kinase results in a high degree of FRET, whereas displacement of the tracer with a kinase inhibitor results in a loss of FRET. This assay is carried out by mixing the compound tested with the reagents and reading, no development step is required.

Life Technologies' Kinase Tracers are based on ATP-competitive kinase inhibitors, making them suitable for detection of any compounds that bind to the ATP site. Inhibitors that bind the ATP site include both Type I kinase inhibitors, which bind solely to the ATP site, and Type II inhibitors (e.g., Gleevec®/Imatinib, Sorafenib, BIRB-796), which bind to both the ATP site and a second site often referred to as the allosteric site.

The following protocol is used to carry out this assay:
The Test Compounds are screened in 1% DMSO (final) in the well. For 10 point titrations, 3-fold serial dilutions are conducted from the starting concentration (see Table 2 below).

TABLE 2

Kinase assay protocol details:

| Kinase | Kinase Conc nM | Antibody | Antibody Conc nM | Tracer* | Tracer Conc nM | Tracer Kd nM | Known inhibitor | IC 50 nM |
|---|---|---|---|---|---|---|---|---|
| TGF-β1 (ALK-5) | 5 | EU-anti-GST | 2 | Tracer 178 | 10 | 30 | Dasatinib | 36.8 |
| ACVR1 (ALK-2) | 5 | EU-anti-GST | 2 | Tracer 236 | 100 | 76 | Staurosporine | 48.1 |
| ACVR1 (ALK-2) R206H | 5 | EU-anti-GST | 2 | Tracer 236 | 100 | 44 | Staurosporine | 33.8 |

*Tracers are sourced from ThermoFisher

All Kinase/Antibody Mixtures are diluted to a 2× working concentration in the specified kinase buffer. The 4× AlexaFluor labeled Tracer is prepared in Kinase Buffer.

Assay Protocol

Bar-coded, low volume, white 384-well plate (Greiner Cat. #784207)
1. 160 nL—100× Test Compound in 100% DMSO
2. 3.84 µL—Kinase Buffer
3. 8.0 µL—2× Kinase/Antibody Mixture
4. 4.0 µL—4× Tracer
5. 30-second plate shake
6. 60-minute incubation at room temperature
7. Read on fluorescence plate reader and analyze the data The following controls are made for each individual kinase and are located on the same plate as the kinase:

0% Displacement Control: the maximum Emission Ratio is established by the 0% Displacement Control wells, which do not contain known inhibitor in the reaction and therefore exhibits no displacement of the tracer.

100% Displacement Control: the minimum Emission Ratio is established by the 100% Displacement Control wells, which contain the highest concentration of the known inhibitor used in that assay.

Known Inhibitor Control Protocol: a known inhibitor control standard curve, 10 point titration, is run for each individual kinase on the same plate as the kinase to ensure the inhibitor is displaced within an expected IC50 range previously determined.

The LanthaScreen Eu Kinase Binding Assay data is analyzed using the equations in Table 3 for each set of data points.

TABLE 3

The following equations are used for each set of data points:

| Value | Equation |
|---|---|
| Emission Ratio (ER) | $\dfrac{AF647\ \text{Emission (665 nm)}}{\text{Europium Emission (615 nm)}}$ |
| % Displacement | $\left\{ \dfrac{ER_{0\%\ Disp\ Control} - ER_{Sample}}{ER_{0\%\ Disp\ Control} - ER_{100\%\ Disp\ Control}} \right\} \times 100$ |
| Difference Between Data Points (single point only) | $\|\%\ \text{Displacement}_{Point\ 1} - \%\ \text{Displacement}_{Point\ 2}\|$ |
| Test Compound Interference | For each emission wavelength, fluorescence interference is flagged for a compound well that is more than 20% outside the range of the controls |

TABLE 3-continued

The following equations are used for each set of data points:

| Value | Equation |
|---|---|
| Z (using ER values) | $1 - \left\{ \dfrac{3 * Stdev_{0\%\ Disp\ Ctrl} + 3 * Stdev_{100\%\ Disp\ Ctrl}}{Mean_{0\%\ Disp\ Ctrl} - Mean_{100\%\ Disp\ Ctrl}} \right\}$ |

Data generated were plotted using the graphing software XLfit from IDBS. The dose response curve is curve fit to model number 205. If the bottom of the curve does not fit between −20% & 20% inhibition, it is set to 0% inhibition. If the top of the curve does not fit between 70% and 130% inhibition, it is set to 100% inhibition.

TGF-beta (also referred to as TGF-β1) is a multifunctional, highly conserved cytokine with many key functions in development, cell growth, apoptosis, as well as playing a key role in the tissue repair response and functioning as a potent immune modulator. TGF-β signaling is triggered when the activated TGF-β homodimer binds to the TGF-β receptor 2, which in turn leads to the recruitment and phosphorylation of TGF-β receptor 1 (ALK5). Activated TGF-β receptor 1 phosphorylates the signal transduction molecules SMAD2 and SMAD3. These bind to common mediator SMAD4 and translocate to the nucleus where they bind to short conserved DNA sequences called the SMAD binding element and induce the transcription of various target genes. A stable cellular reporter was generated to test the ability of compounds of the invention to inhibit the canonical TGF-β1 induced SMAD signaling pathway in a cellular context was performed using the following protocol.

Certain example compounds were also or alternatively assayed using the RDSR Cellular Reporter Assay.

Overview and Design: The RD SMAD reporter (RDSR) cell line was generated by stably integrating the SMAD cellular reporter plasmid (Promega, pGL4.48[luc2P/SBE/Hygro]) into the human rhabdomyosarcoma cell line RD (ATCC, CCL-136). Once SMAD signaling is triggered, with, for example, the addition of TGF-β 1, receptor activated SMADs bind the SMAD binding elements (SBEs) leading to the expression of intracellular luciferase. To determine the potency of compounds at inhibiting TGF-beta induced SMAD signaling, the RDSR reporter system was utilized.

Methods:

The rhabdomyosarcoma line RD (ATCC, CCL-136) was transfected with a SMAD reporter vector (Promega, E3671) and a polyclonal stable cell line was selected using hygromycin B. The transfected vector contains three copies of a SMAD-binding element (SBE) that drive transcription of the luciferase reporter gene luc2P (Photinus pyralis). luc2P is a synthetically-derived luciferase sequence with humanized codon optimization that is designed for high expression and reduced anomalous transcription. The luc2P gene contains hPEST, a protein destabilization sequence, which allows luc2P protein levels to respond more quickly than those of luc2 to induction of transcription. The intracellular luciferase is quantified by the addition of equal volume (100 µl) of ONE-GLO substrate (Promega, E6120) and read within ten minutes on the Envision plate reader. The stable RDSR cell line was tested by evaluating the response to human TGF-β1 (R&D Systems, 7754-BH-005) as well as human myostatin (R&D Systems, 788-G8-010/CF) in a concentration dependent manner after twenty-four hours of stimulation. Human IL-1 was used as a negative control and showed no response (data not shown). For compound evaluation, the tool drugs Galunisertib and Vactosertib were included as positive controls. The tool drugs and the compounds of the invention being tested were all incubated with cells for one hour at 37° C. before stimulation with 200 pg/ml rhTGF-beta1 for twenty-four hours. The activity of the reporter was determined with the addition of ONE-GLO (Promega) substrate and luminescence counts collected on the Envision plate reader (Perkin Elmer). Using this method, it was determined that the Vactosertib control compound had activity of about 7.9 nM and the Galunisertib control compound had an activity of about 365 nM. The activity of compounds of the invention as determined using this method are reported in the third column of Table 1, below. Compounds of the invention generally had activity within the range between Galunisertib and Vactosertib.

Using the procedures above, selected compounds of the invention were assayed for activity and selectivity. In vitro kinase inhibition data for ALK-5 and ALK-2 is shown below in Table 4. Inhibiton data is expressed as $IC_{50}$ (nM). Compounds disclosed herein are selective inhibitors of ALK-5. Selectivity for ALK-5 is expressed as ALK2 $IC_{50}$/ALK5 $IC_{50}$.

Key for activity reported in Table 4:

ALK5 $IC_{50}$ Activity (nM):

≤10=[+++]; 10<Alk 5 $IC_{50}$ (nM)<100=[++]; 100≤Alk 5 $IC_{50}$ (nM)=[+]

Selectivity (nM) ALK2/ALK5

≤10=[+]; 10<ALK2/ALK5<100=[++]; 100≤ALK2/ALK5=[+++]

TGFβ-R1 inhibition (RD-SMAD activity, nM):

≤100=[+++]; 100<RD-SMAD activity <1000=[++]; 1000≤RD-SMAD activity=[+]

TABLE 4

Assay Data for Selected Compounds of the Invention

| Exp Cmpd No | Kinase Inhibition: ALK5 $IC_{50}$ (nM) | Kinase Selectivity: ALK2 IC50/ ALK5 IC50 | RD-SMAD reporter activity (nM) |
|---|---|---|---|
| EX-01 | (+++) | (++) | (+++) |
| EX-02 | (+++) | (++) | (+++) |
| EX-03 | (+++) | (++) | (++) |
| EX-04 | (+++) | (+) | (+++) |
| EX-05 | (+++) | (++) | (++) |
| EX-06 | (+++) | (+) | (+++) |
| EX-07 | (+++) | (++) | (+++) |
| EX-08 | (+++) | (++) | (+++) |
| EX-09 | (++) | (+) | (++) |
| EX-10 | (+++) | (++) | (+++) |
| EX-11 | (+++) | (++) | (+++) |
| EX-12 | (+++) | (++) | (+++) |
| EX-13 | (+++) | (++) | (+++) |
| EX-15 | (+++) | (++) | (+++) |
| EX-16 | (++) | (++) | (++) |
| EX-17 | (+++) | (++) | (+++) |
| EX-20 | (+++) | (++) | (+++) |
| EX-21 | (++) | (++) | (++) |
| EX-22 | (+++) | (+++) | (+++) |
| EX-23 | (+++) | (++) | (+++) |
| EX-24 | (+++) | (++) | (+++) |
| EX-25 | (+++) | (++) | (+++) |
| EX-26 | (+++) | (++) | (+++) |
| EX-27 | (+++) | (++) | (+++) |
| EX-28 | (+++) | (++) | (+++) |
| EX-33 | (+++) | (++) | (+++) |
| EX-34 | (+++) | (++) | (+++) |
| EX-35 | (+++) | (+) | (+++) |
| EX-36 | (+++) | (+) | (+++) |
| EX-37 | (+++) | (++) | (+++) |
| EX-38 | (++) | (++) | (+++) |
| EX-39 | (+++) | (+) | (++) |
| EX-40 | (+++) | (++) | (+++) |
| EX-41 | (+++) | (++) | (+++) |
| EX-42 | (+++) | (+) | (++) |
| EX-43 | (+++) | (+) | (++) |
| EX-44 | (+++) | (++) | (+++) |
| EX-45 | (+++) | (++) | (+++) |
| EX-46 | (+++) | (++) | (+++) |
| EX-47 | (+++) | (++) | (+++) |
| EX-48 | (+++) | (++) | (+++) |
| EX-49 | (+++) | (++) | (+++) |
| EX-50 | (+++) | (++) | (++) |
| EX-51 | (+++) | (+) | (++) |
| EX-52 | (+++) | (+) | (++) |
| EX-53 | (+++) | (++) | (++) |
| EX-54 | (++) | (++) | (++) |
| EX-55 | (+++) | (++) | (+++) |
| EX-56 | (+++) | (+++) | (++) |
| EX-29 | (+++) | (++) | (+++) |
| EX-31 | (+++) | (+) | (+++) |
| EX-32 | (++) | (++) | (++) |
| EX-57 | (+++) | (++) | (+++) |
| EX-58 | (+++) | (++) | (+++) |

The following examples, which are offered as comparison to the compounds of the invention, were synthesized using the procedures described and assayed in accordance with the procedures described herein.

TABLE 5

Selected Assay Results for Comparator Compounds

| Comparator Compound Identifier | Structure | ALK-2 IC50 nM | Sel over ALK-5 | RD-SMAD reporter activity (nM) |
|---|---|---|---|---|
| Cf-A | [structure: 8-methyl-cinnoline with 4-HN linked to pyrimidine-2-NH-phenyl(F)-piperazine-N-CH3] | (+) | (+) | (+) |
| Cf-B | [structure: 8-methyl-cinnoline with 4-HN linked to pyrimidine-2-NH-phenyl(F)-piperazine-NH] | (+) | (+) | (+) |

USE OF SELECTED COMPOUNDS OF THE INVENTION

Example A—Fibroblast Tissue Studies—Fibroblast to Myofibroblast Transformation (FMT) Assay Idiopathic pulmonary fibrosis (IPF) is a respiratory disease characterized by abnormal fibroblast activation and progressive fibrotic remodelling of the lungs. Though the exact pathophysiological mechanisms of IPF remain unknown, TGF-β1 is thought to act as a main driver of the disease by mediating fibroblast-to-myofibroblast transformation (FMT). TGF-β1 induced myofibroblasts are thought to play a major role in fibrosis due to excessive deposition of extracellular matrix. To test the ability of compounds of the invention to inhibit the TGF-β1 dependent transition of fibroblasts to myofibroblasts in a relevant disease model of IPF, a study was carried out using an FMT assay employing lung fibroblasts from IPF patients. In this model the transition of fibroblasts to myofibroblasts is determined by the expression of the biomarker alpha smooth muscle actin (SMA).

Procedure: The overall assay procedure is illustrated in FIG. 1, which depicts a routine commercial assay of this type performed by Charles River laboratories. Primary human bronchial fibroblasts derived from IPF patients (3 cell lines, Donor 1, IPF05, Donor 2, IPF06 and Donor 3, IPF08) were seeded on day zero and the media refreshed on day two. On day five, aliquots of Example Compounds EX-10 and EX-11, and controls Galunisertib, Vactosertib and Nintedanib were added at various dilutions (See FIG. 3, response curves generated by an eight-point concentration semi-log dilutions, starting at 10 µM). Each drug concentration condition was evaluated in biological duplicates. One hour after compound addition, cells were stimulated with 1.25 ng/ml of TGF-01 and cultured for 72 hours thereafter.

At the end of 72 hours cells were fixed using formaldehyde. The results were generated using high content imaging after staining cells using the nuclear stain DAPI as well as evaluation of the expression of alpha SMA. The following controls were run alongside of the determinations made using Compounds EX-10 and EX-11: 1 µM of the selective ALK5 inhibitor SB525334 (available from Sigma-Aldrich) as well as the approved IPF drug Nintedanib (eight point semi log curve, 10 µM starting concentration). As a negative control 0.1% DMSO was used matching the DMSO concentration in treated wells. The following calculations used to determine cell number as well as percent inhibition of alpha SMA expression are presented in Table 6 below:

TABLE 6

Calculations used in assay of fibrosis inhibition

| Value | Equation |
|---|---|
| Data normalization of raw αSMA (DxA) to percentage inhibition (PIN) values, on a plate-to-plate basis | $PIN = 100 - \dfrac{\mu_p - X_I}{\mu_p - \mu_\eta} \times 100$<br><br>µp is the average αSMA value of the positive control (TGF-β1 + 1 µM SB525334)<br>µn is the average of αSMA value of the vehicle control (TGF-β1 + 0.1% DMSO)<br>Xi is the compound αSMA value |
| Analysis of % remaining cells | $\% \text{ remaining cells} = \dfrac{X_i}{\mu_\eta} \times 100$<br><br>µn is the average numbers of nuclei of the vehicle control (TGF-β1 + 0.1% DMSO)<br>Xi is the compound number of nuclei<br>DAPI fluorescence applied for HCA-based quantification of the number of imaged cells, on a plate-to-plate basis |

Figure 3:
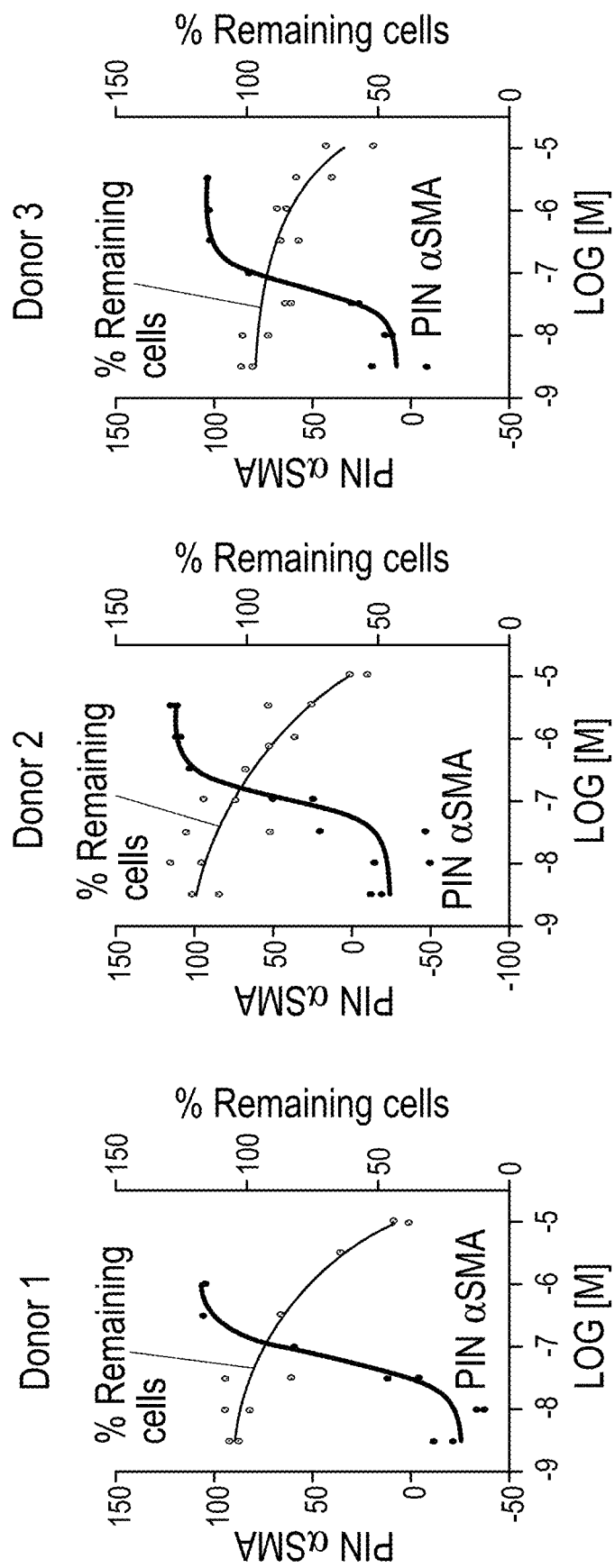
FIG. 3 shows normalized data for percentage of inhibition (PIN) of αSMA and percentage of remaining cells for EX-11 from the assay described in Example A.

The results from these assays are shown in Table 7, below, and selected normalized data from Ex 11 is shown in FIG. 3 (see above for normalization calculations). Tested compounds EX-10 and EX-11 showed a high efficiency by inducing a full inhibition (max PIN greater than 75) of TGF-β1 mediated alpha-SMA expression, in at least two donors. One of the compounds (Ex-11) showed a full concentration-dependent inhibition of TGF-β-mediated alpha-SMA expression in all three donors (presented graphically as normalized data for percentage of inhibition (PIN) and remaining cells (%) in FIG. 3). This data indicates that the compounds tested block FMT, which has been implicated in disease pathogenesis, and therefore have the potential to be used as a therapeutic in IPF.

TABLE 7

Results of IPF growth study

| Compound | LogM IC50αSMA | Max PIN (%) | potentially toxic (>25% loss of nuclei) | Spearman Rank correlation | Assay window |
|---|---|---|---|---|---|
| IPF05 | | | | | |
| EX-10 | −6.8 | 106.4 | >−5.5 | 0.9 | 12.6 |
| EX-11 | −7.2 | 107.2 | >−6.0 | | |
| Galunisertib | −5.7 | 100.8 | — | | |
| Vactosertib | −7.4 | 32.7 | >−7.0 | | |
| Nintedanib | −6.5 | 92.1 | >−6.0 | | |
| IPF06 | | | | | |
| EX-10 | −6.7 | 110.3 | — | 0.9 | 6.7 |
| EX-11 | −7.0 | 112.9 | >−5.5 | | |
| Galunisertib | −5.9 | 104.4 | >−5.5 | | |
| Vactosertib | −7.0 | 112.1 | >−6.0 | | |
| Nintedanib | −6.3 | 86.8 | >−5.5 | | |
| IPF08 | | | | | |
| EX-10 | −7.0 | 100.3 | >−5.5 | 0.9 | 27.2 |
| EX-11 | −7.3 | 103.7 | >−6.0 | | |
| Galunisertib | −5.9 | 99.6 | — | | |
| Vactosertib | −7.1 | 104.0 | >−6.5 | | |
| Nintedanib | −6.4 | 88.2 | >−5.5 | | |

Example B—A549 Xenograft Study

To test compounds for in vivo on-target activity (ALK5/TGF-βR1 inhibition), a study was completed using an A549 murine xenograft model. This model was utilized since an ALK5 inhibitor is expected to reduce the amount of the key TGF-β signaling molecule phosphoSMAD2 in the A549 xenograft cells. The TGF-β mediated phosphorylation in A549 cells takes place at amino acid residue four hundred and sixty-five and four hundred and sixty-seven (both are serine residues).

Eight-week old, female athymic nude mice (Charles River) were injected with approximately four million A549 cells (ATCC, CCL-185). The cells employed were harvested and resuspended in plain RPMI media (no phenol red added) and matrigel (Fisher Scientific) at a one to one ratio. Injection comprised a two-hundred microliter sample injected into the right hind flank of each mouse. Resulting tumors were measured every three days by caliper and as tumors reached an average of one hundred and thirty millimeters cubed, mice were randomized in groups of three.

All compounds were resuspended in 1-Methyl-2-pyrrolidinone (10%) plus 20% Solutol in water (90%). Galunisertib was included as a positive control and given at seventy-five milligram per kilogram to three mice. The drug suspensions were sonicated for fifteen minutes to generate a fine particle suspension before being administered to a subject. Mice were dosed (per oral gavage) at dose levels of one hundred mg/Kg, seventy-five mg/Kg, fifty mg/Kg and ten mg/Kg with three mice in each group. A vehicle control group with three mice was used to establish the baseline level of phospho SMAD2 in the tumor xenograft. Three hours after drug administration, tumors were harvested and stored at negative eighty degrees Celsius until further processing. The phospho SMAD2 levels were determined using the BioPlex Pro anti phospho-SMAD2 (Ser 465/467) beads from Biorad and this signal was normalized using GAPDH levels from each sample (Milliplex MAP GAPDH beads, Sigma/Millipore). Tumors were processed according to kit instructions and beads analyzed using the MagPix instrument by Luminex.

All compounds tested (Ex-10, Ex-11, Ex-12, and Ex-13) reduced the phopho SMAD2 levels (p-SMAD2) in a dose dependent fashion. All of the pSMAD2 levels reported were normalized to GAPDH detection.

Figure 2A:
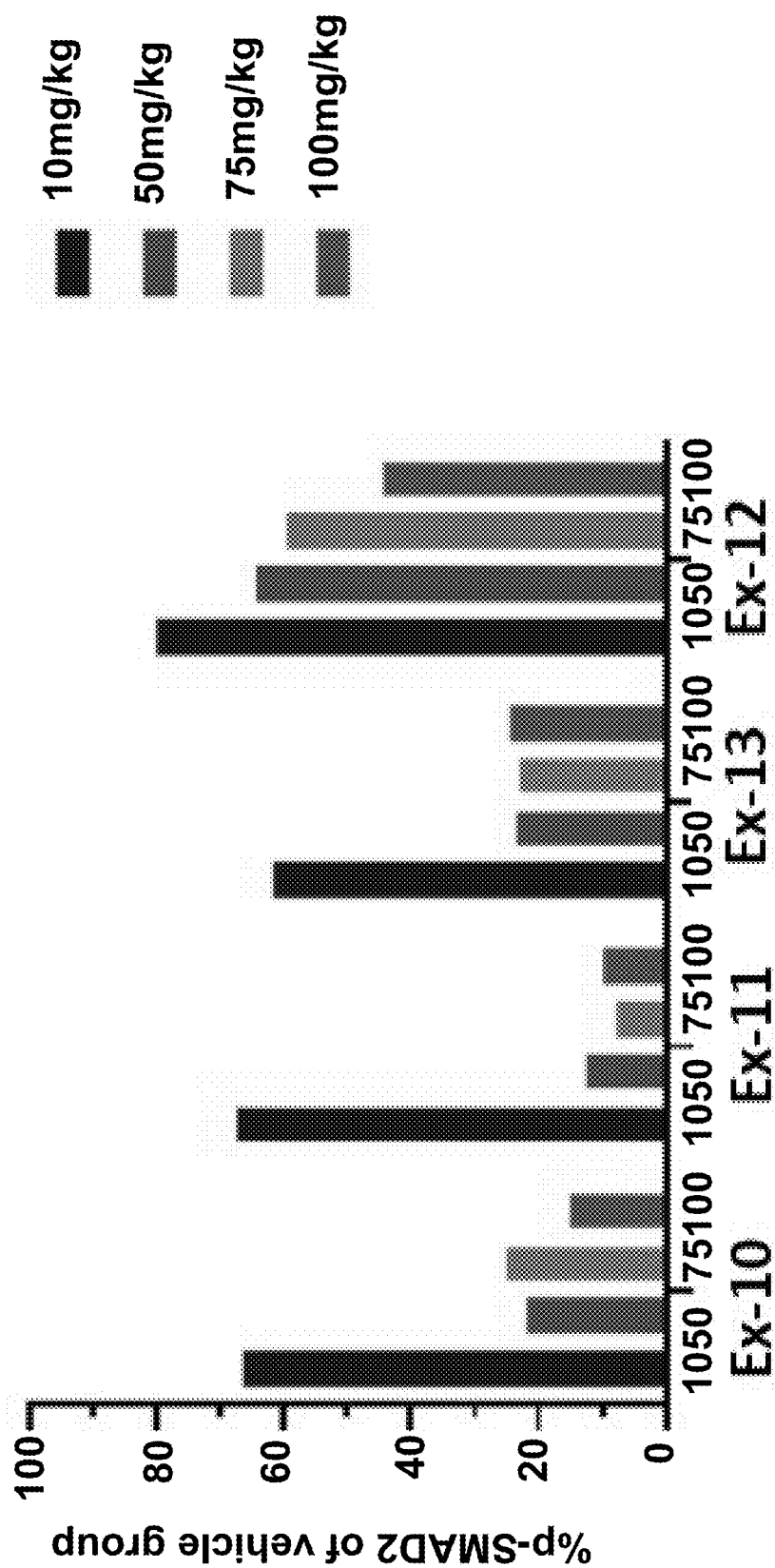
FIG. 2A shows a dose-dependent reduction in percent p-SMAD2 inhibition observed in treated mice compared to the group receiving only vehicle in the study described in Example B.

FIG. 2A shows the amount of p-SMAD2 observed in treated samples expressed as percent of the levels of p-SMAD2 observed with vehicle-only group. Table 8, below, expresses the amount of p-SMAD2 inhibition as a percentage of the level of p-SMAD2 observed with vehicle group, e.g., an observation of p-SMAD2 at a level of 80% of what is observed with vehicle equals 20% p-SMAD2 inhibition. With reference to Table 8, as can be seen, samples dosed with seventy-five milligrams per kilogram (75 mg/Kg) Ex-11 exhibited 92.5% inhibition based upon the average p-SMAD2 levels observed in the vehicle-only control group, e.g., with reference to FIG. 2A, the observed level of p-SMAD2 in the 75 mg/Kg Ex-11 dosed group was 7.5% of the p-SMAD2 levels observed in the vehicle-only group. With reference to Table 8 again, in the group dosed with Ex-12 at a level of 100 mg/Kg, p-SMAD2 levels were inhibited by 55.5%, e.g., with reference to FIG. 2A, the amount of p-SMAD2 observed was 45.5% of p-SMAD2 levels observed in the vehicle group.

TABLE 8

Percent of p-SMAD2 Inhibition Compared to Vehicle Control (100% inhibition yields 0 p-SMAD2 observed relative to vehicle)

| Amount of Example Cmpd Tested | 10 mg/Kg | 50 mg/Kg | 75 mg/Kg | 100 mg/Kg |
|---|---|---|---|---|
| Ex-10 | 33.5% | 78.3% | 74.8% | 84.8% |
| Ex-11 | 32.6% | 87.6% | 92.5% | 90.1% |
| Ex-12 | 19.9% | 35.8% | 40.1% | 55.5% |
| Ex-13 | 37.9% | 76.3% | 76.8% | 75.7% |

As can be seen from the data presented in Table 8 and FIG. 2A, administration of selected compounds of the disclosure suppressed expression of p-SMAD2 in the xenograph tumors, which is believed to be indicative of a suppression of TGFβ-R1 signaling therein, indicating the compounds will be useful in the treatment of disease.

Figure 2B:
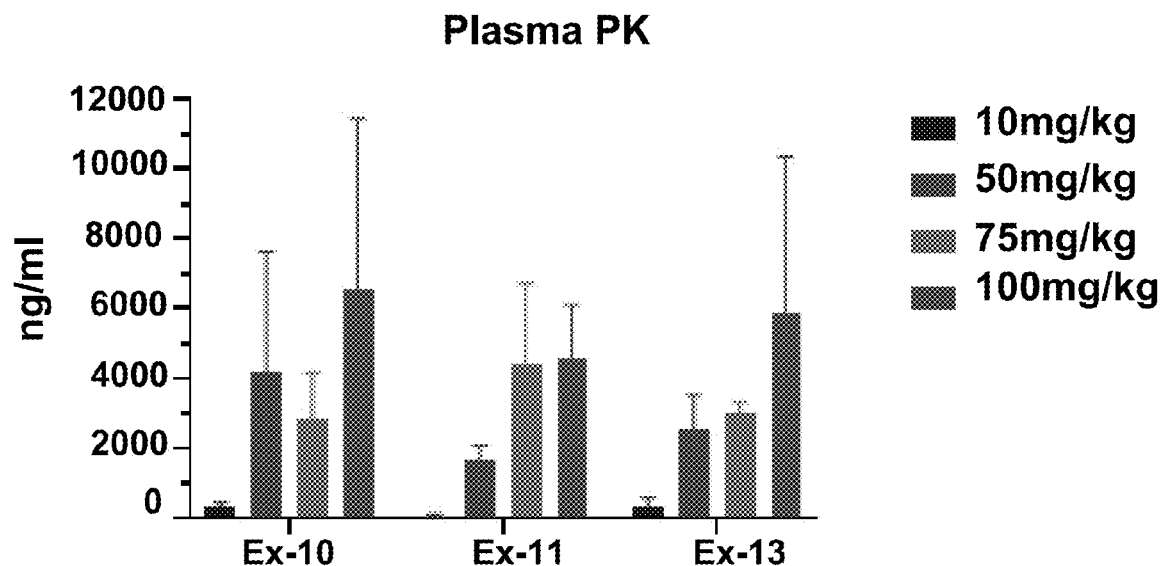
FIG. 2B shows plasma PK of mice from Example B.
Figure 2C:
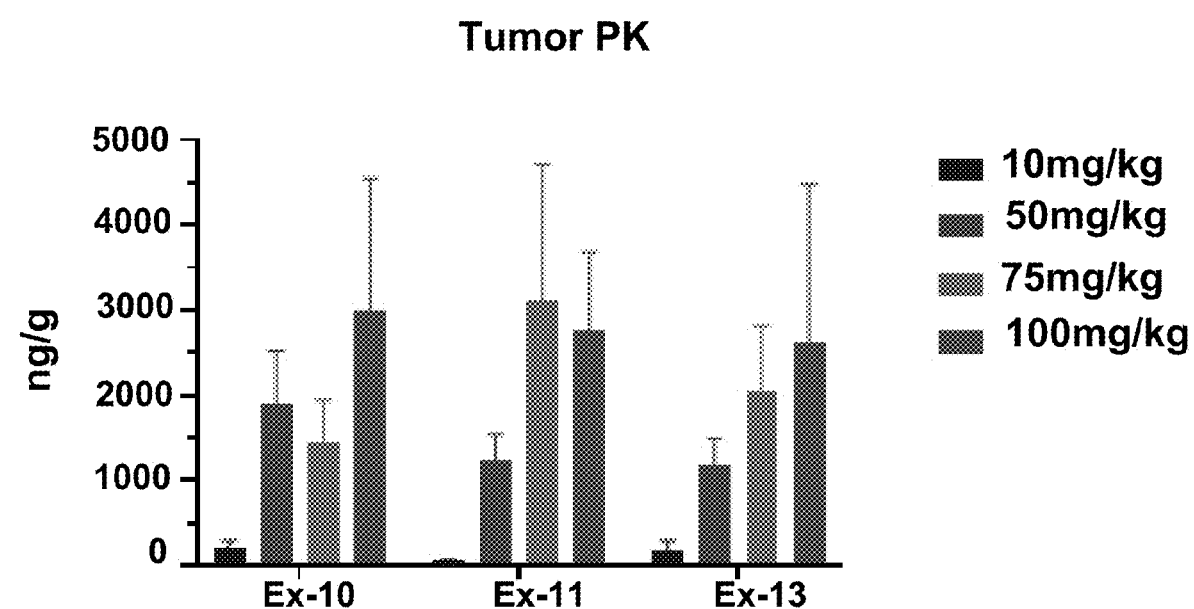
FIG. 2C shows tumor PK of mice from Example B.

FIGS. 2B and 2C show the concentration of each compound at different dosages in plasma (FIG. 2B) and in tumor (FIG. 2C), respectively. All compounds show an overall trend of dose-dependent increase in measured concentration with respect to increased dosage. Drug concentrations in plasma and tumor also correlate with each other well.

Figure 2D:
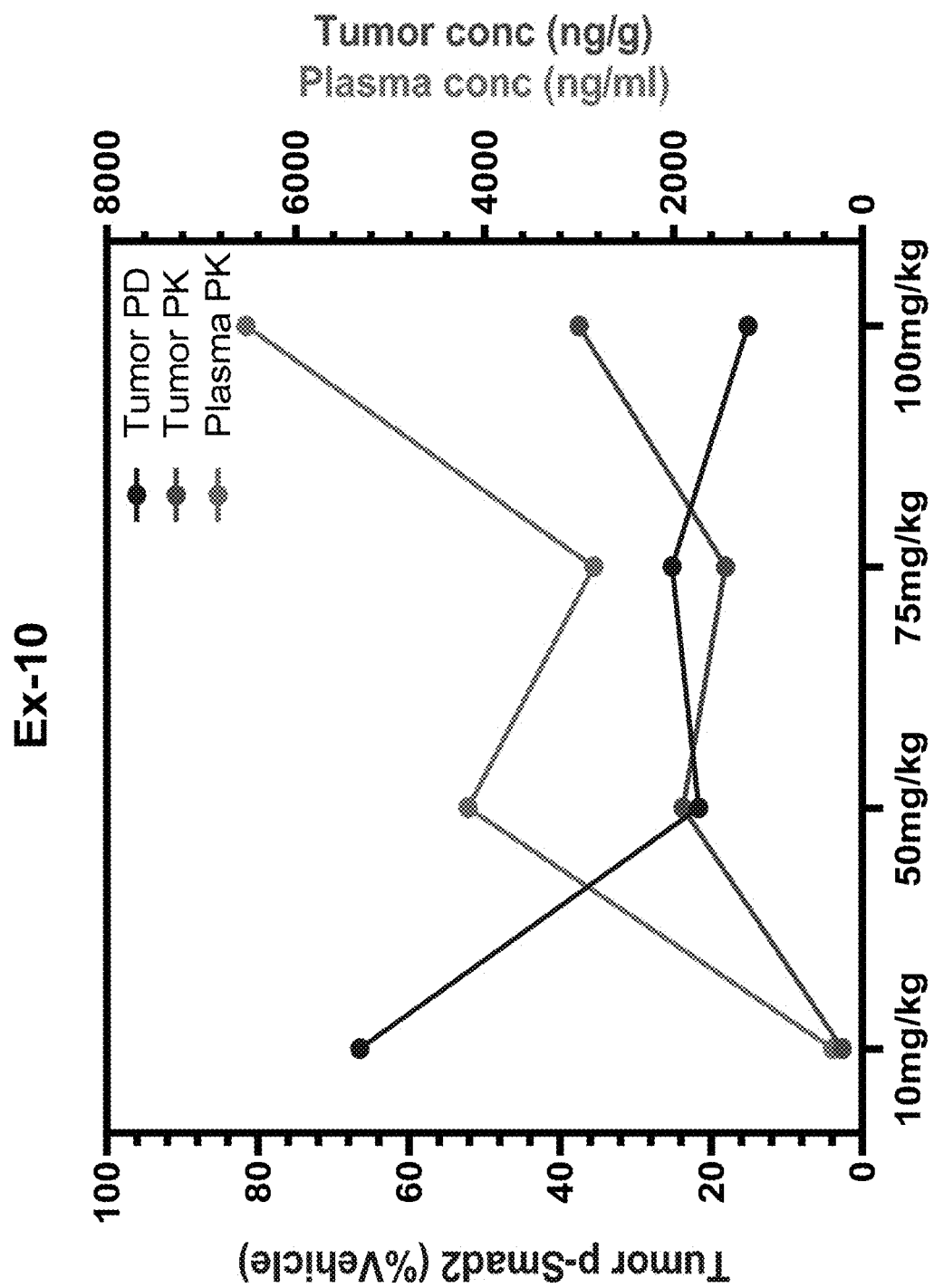
FIG. 2D shows plasma PK, tumor PK, and tumor PD of mice from Example B treated with EX-10.
Figure 2E:
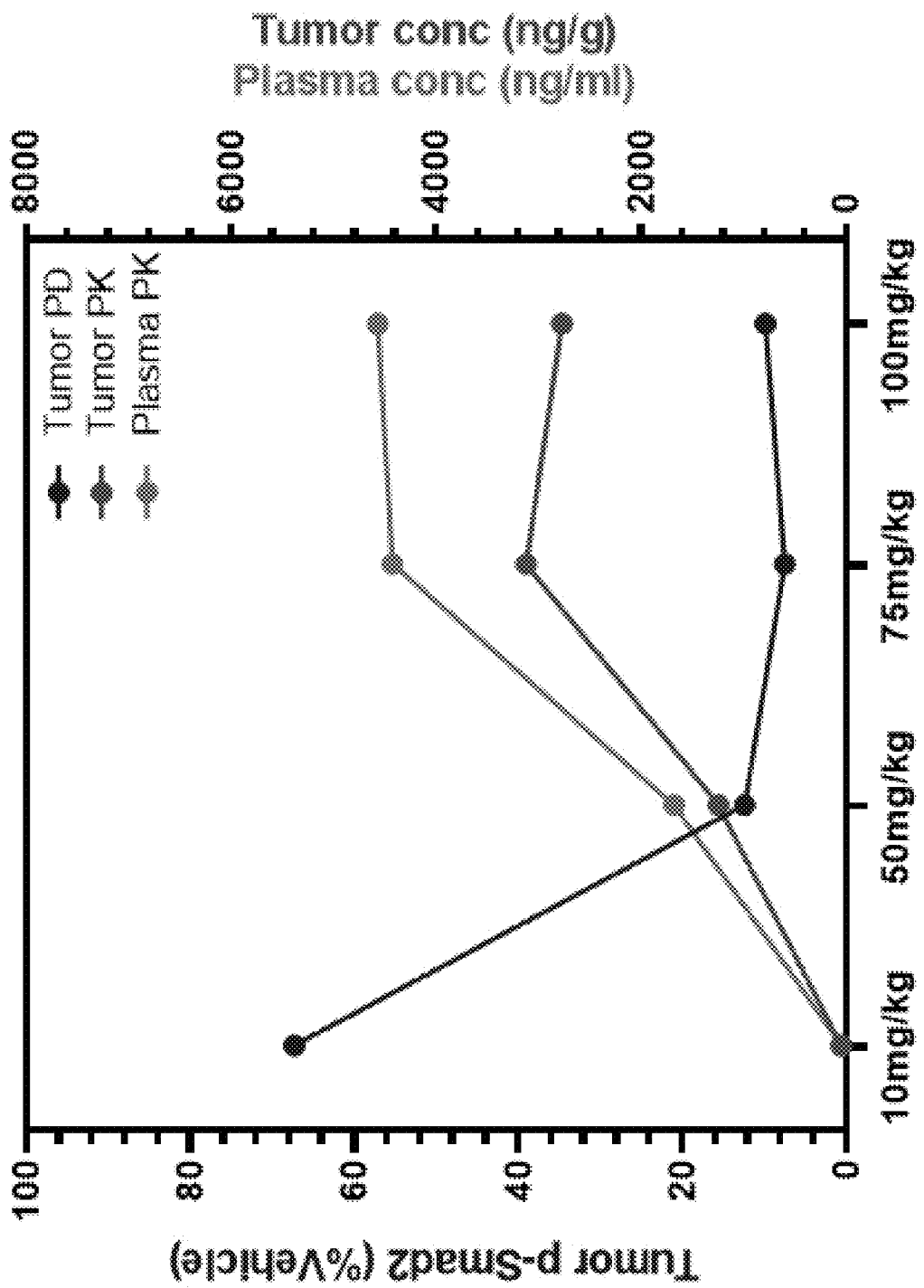
FIG. 2E shows plasma PK, tumor PK, and tumor PD of mice from Example B treated with EX-11.
Figure 2F:
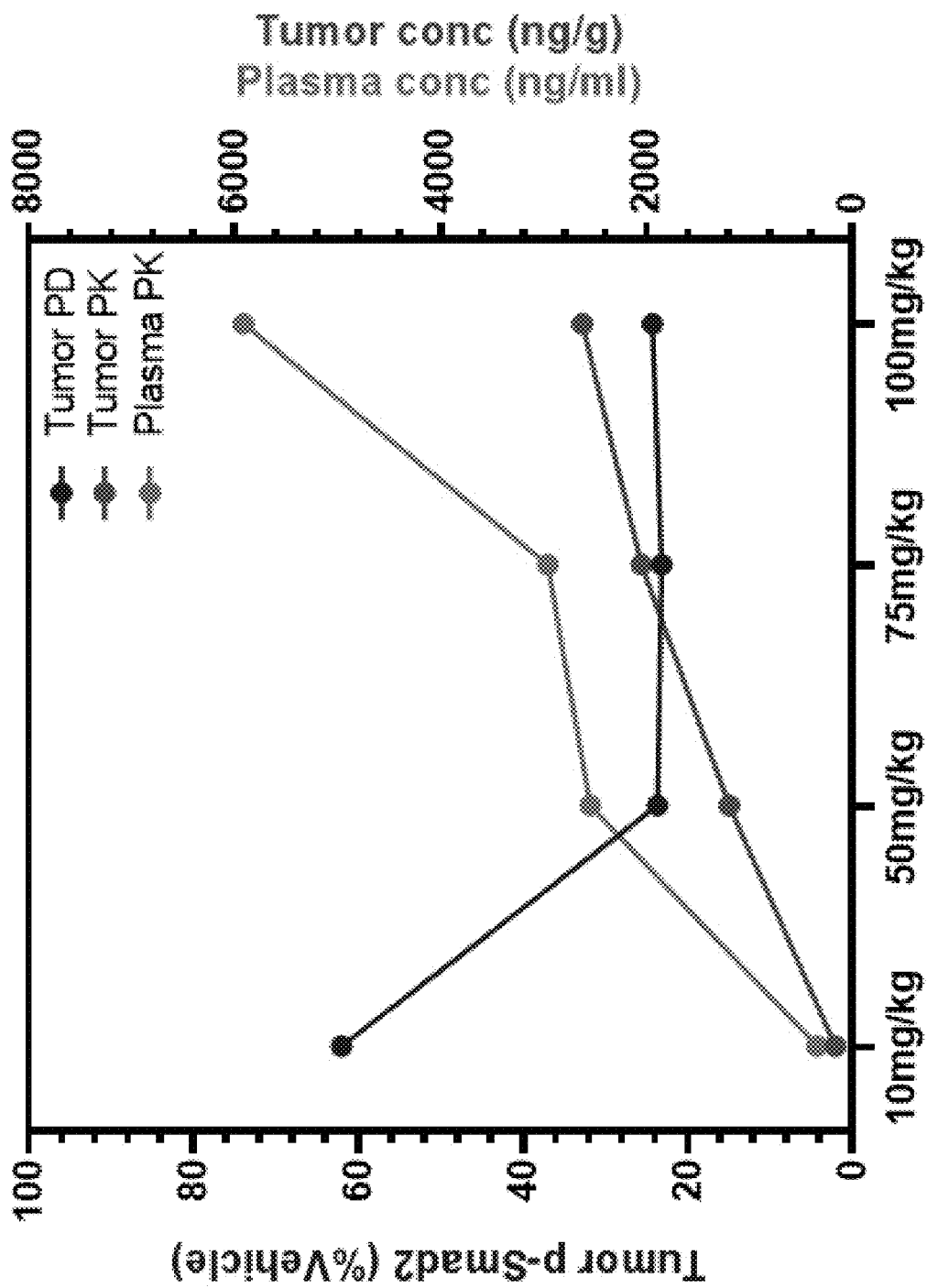
FIG. 2F shows plasma PK, tumor PK, and tumor PD of mice from Example B treated with EX-13.

FIGS. 2D-F show the PK/PD relationship for Ex-10 (FIG. 2D), Ex-11 (FIG. 2E), and Ex-13 (FIG. 2F), respectively. Overall, plasma PK and tumor PK mirror each other, and PK and Tumor PD (p-SMAD2 levels) are reversely correlated.

Example C—In Vitro T$_{reg}$ Differentiation Study

The effect of EX-11 on Treg differentiation was evaluated using human CD4$^+$CD45RA$^+$ naïve T cells from Lonza. CD4$^+$/CD45RA$^+$ naïve T cells were treated with EX-11, CD3/CD28 (STEMCELL Technologies) and 10 ng/ml of IL-2 (Thermo Fisher Scientific) with or without 5 ng/ml TGFβ (R&D Systems) in ImmunoCult™-XF T cell expansion medium for 5 days. Flow cytometry was performed using anti-human FoxP3 staining kit (BD biosciences) to evaluate the frequency of CD4$^+$CD25$^+$Foxp3$^+$ Treg cells.

Figure 5:
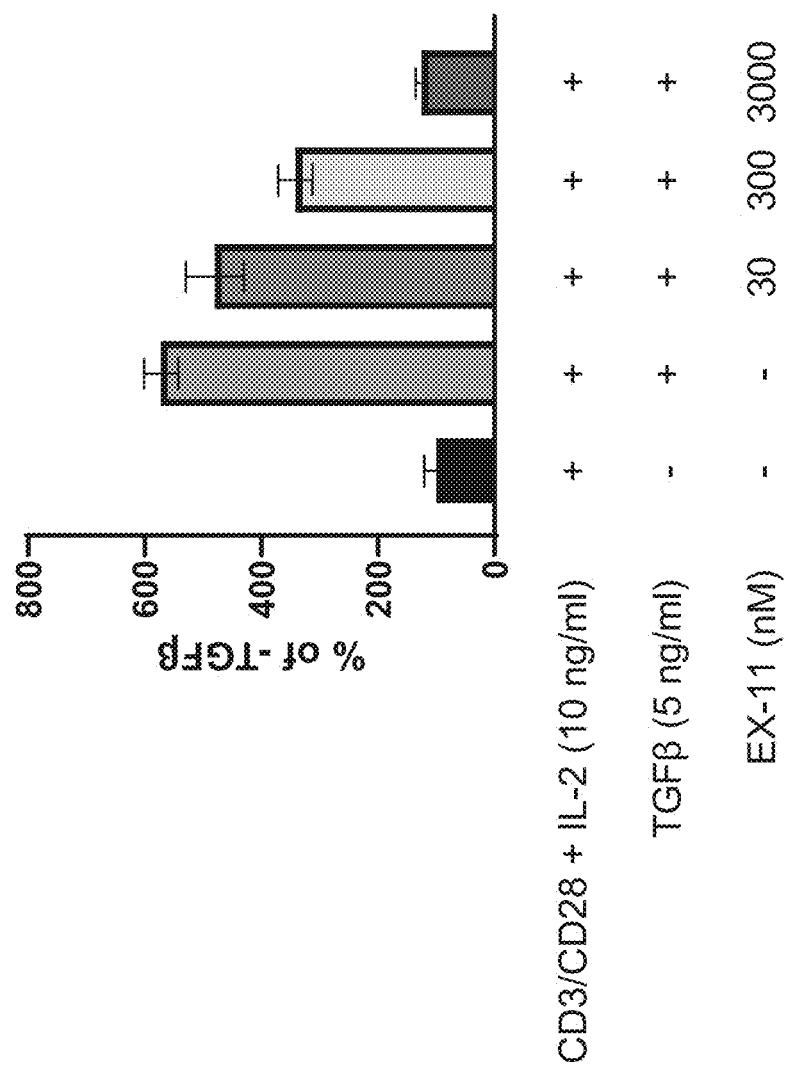
FIG. 5 shows $CD4^+CD25^+Foxp3^+$ Treg cells as a percentage of $CD4^+CD25^+Foxp3^+$ Treg cells not treated with TGFβ in $CD4^+CD45RA^+$ naïve T cells stimulated with CD3/CD28+IL2+TGFβ and treated with vehicle or 30 nM, 300 nM, or 3,000 nM EX-11 as described in Example C.

TGFβ-treated CD4$^+$CD45RA$^+$ naïve T cells showed 573% increase of Treg frequency compared to TGFβ-untreated cells. FIG. 5 shows that EX-11 suppressed the Treg frequency in a dose dependent manner (by 480, 342 and 126% at 30, 300 and 3000 nM, respectively; FIG. 5).

Example D—Longitudinal PK/PD Analysis of p-SMAD2 in A549 Xenograft Mouse Model The ability of EX-10 and EX-11 to suppress TGF-beta signaling over time was demonstrated using a xenograft study carried out in a manner similar to that described in Example B. Accordingly, a longitudinal, twenty-four-hour, one-dose study was performed using Ex-10 and Ex-11 in an A549 xenograft mouse model. In this study, p-SMAD2 (Ser465/Ser467) and a housekeeping gene (GAPDH) were measured at six timepoints from zero (established using vehicle-treated animals) up to twenty-four hours post dose for a single drug dose of seventy-five milligrams per kilogram per subject (three subjects per dosing group).

For this study, xenografts were prepared and implanted in mice as follows. At five weeks of age, female athymic nude mice (purchased from Charles River) were injected with approximately 3.2 million A549 cells (ATCC, CCL-185). Cells were harvested and resuspended in plain RPMI media (no phenol red added) and Matrigel (Corning 356237) at a one-to-one ratio, and two hundred-microliters of the cell suspension were injected into the right hind flank of each mouse. Tumors were measured every three days by caliper, and as tumors reached an average of ninety millimeters cubed, mice were randomized in groups of three. Each of the test compounds (Ex-10 and Ex-11) was resuspended in 1-methyl-2-pyrrolidinone (Sigma, 494496) (10%) plus 20% Solutol (Sigma 42966) in water (90%). The drug suspensions were sonicated for fifteen minutes to generate a fine particle suspension before being given to the test subjects. Subjects were dosed (per oral gavage) with the suspension. A vehicle control group with three mice was used to establish the baseline and timepoint zero of phospho-SMAD-2 in the tumor xenograft. The test compounds were administered to the respective subject groups at seventy-five milligrams per kilogram. Samples were obtained post administration of test compounds at 20 minutes, one hour, two hours, four hours, and twenty-four hours. Tumors were harvested, snap frozen and stored at negative eighty degrees Celsius until further processing. Plasma was collected from all animals by collecting whole blood via cardiac puncture, followed by centrifugation in tubes containing EDTA (BD, microtainer tubes, 365974). A group of three mice receiving vehicle only served as the zero timepoint for both drug groups. The phospho-SMAD-2 levels were determined using the Bio-Plex Pro™ Phospho-Smad2 (Ser465/Ser467) Set (BioRad 171V50019M). The phospho-SMAD-2 levels were normalized to GAPDH (MILLIPLEX MAP GAPDH Total Magnetic Bead MAPmate™, Millipore 46-667MAG) levels from each sample. All analytes were analyzed in a multiplex fashion with the Bio-Plex Pro Cell Signaling Reagent Kit (BioRad 171304006M). Frozen tumor samples (fifteen to thirty milligrams) were lysed in 100 μl lysis buffer, processed in a bead mill tube, and centrifuged. The resulting lysate was used at 1:50 dilution for the assay according to the manufacturer's instructions. Bead suspension was analyzed using the Luminex system (MAGPIX).

Figure 6A:
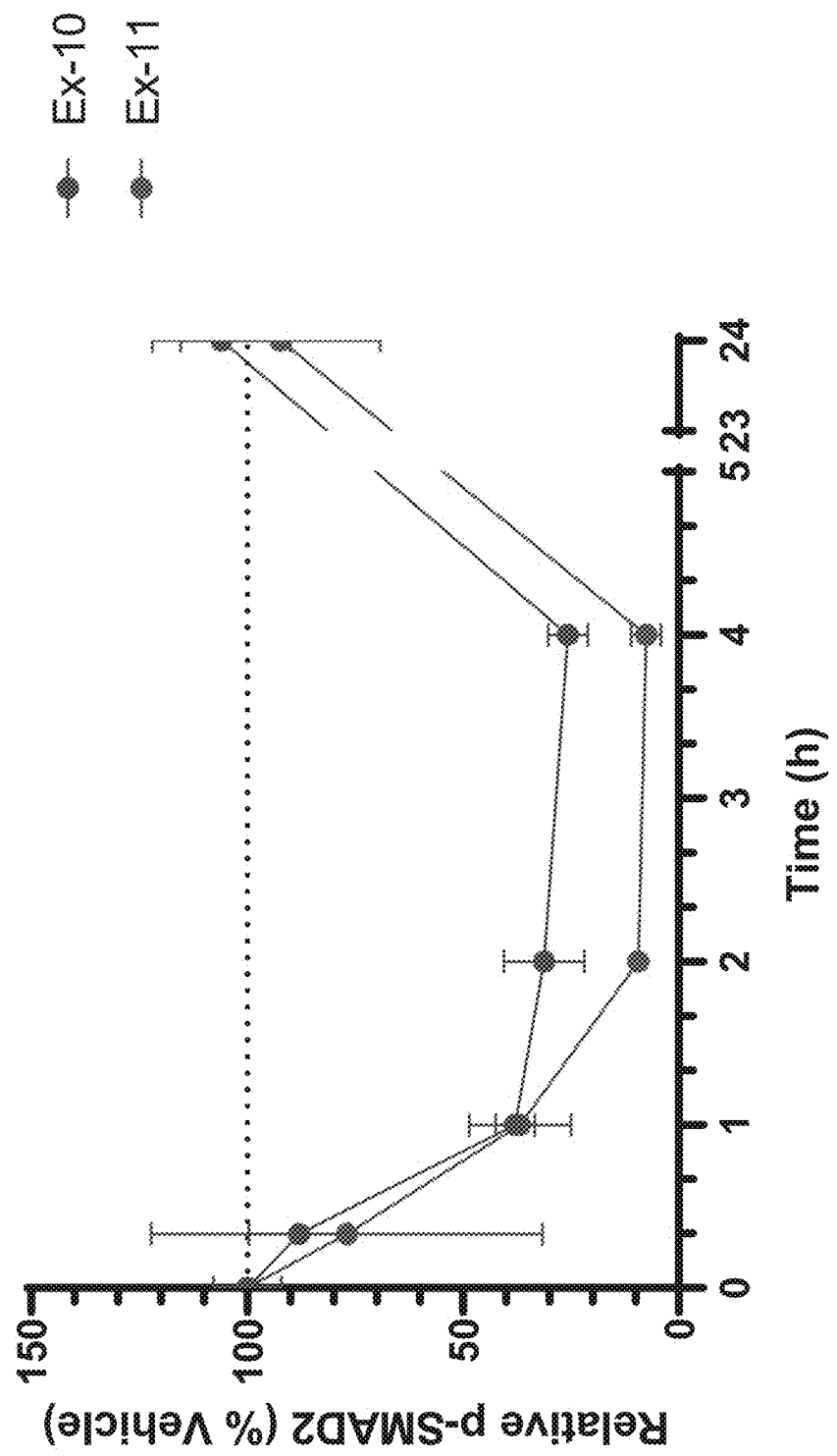
FIG. 6A shows relative pSMAD2 over time in tumor samples from mice from Example D treated with EX-10 or EX-11.

As seen in FIG. 6A, Ex-10 and Ex-11 gradually reduced the p-SMAD2 levels post drug administration and reached maximum inhibition from 2 hours to 4 hours post drug administration. At 4 hours post drug administration, Ex-10 and Ex-11 led to 74.3% and 92.3% inhibition of p-SMAD2 compared to the vehicle group, respectively. At 24 hours post drug administration, p-SMAD2 levels rose back to baseline levels prior to drug administration for both compounds.

Figure 6B:
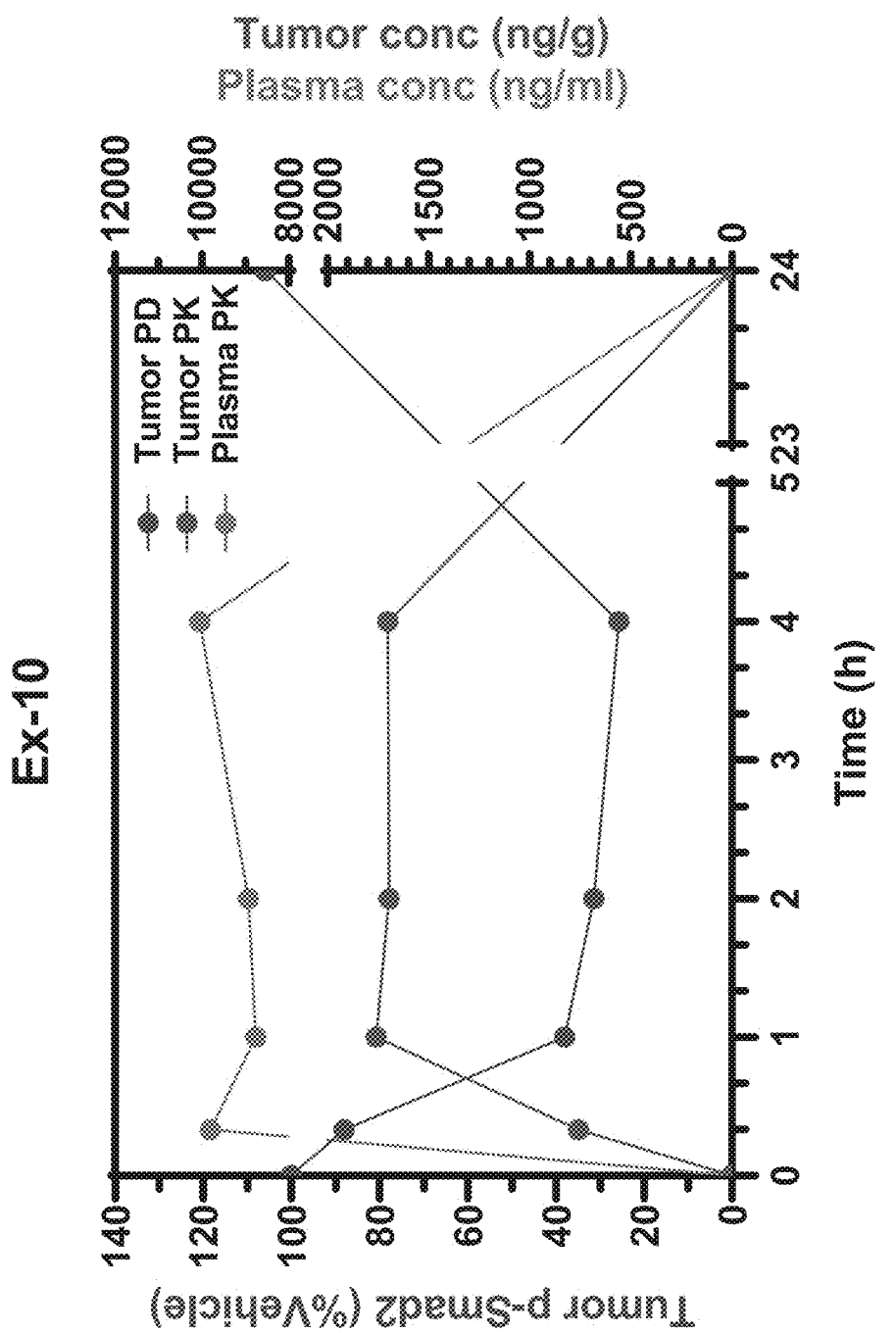
FIG. 6B shows the PK/PD relationship for EX-10 in the Longitudinal PK/PD Analysis of pSMAD2 in Example D.
Figure 6C:
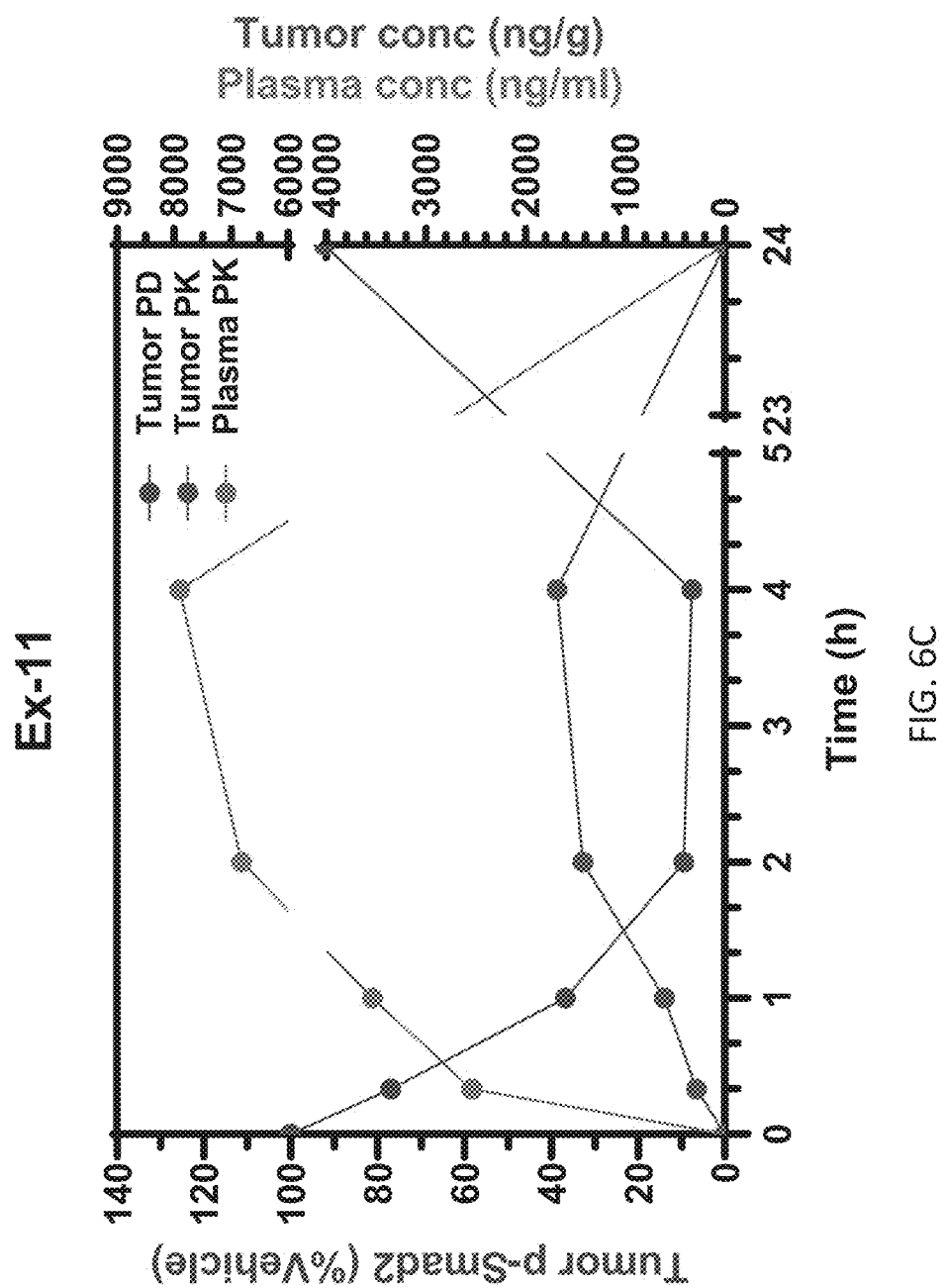
FIG. 6C shows the PK/PD relationship for EX-11 in the Longitudinal PK/PD Analysis of pSMAD2 in Example D.

FIGS. 6B and 6C show the PK/PD relationship for Ex-10 (FIG. 6B) and Ex-11 (FIG. 6C). Overall, plasma PK and tumor PK mirrored one other, and PK and tumor PD (p-SMAD2 levels) were reversely correlated. Ex-10 concentration in plasma and tumor spiked 20 minutes to 1-hour post drug administration and stayed high up to 4 hours post drug administration. These kinetics were consistent with maximum p-SMAD2 inhibition in the tumor during that time frame. At 24 hours post drug administration, Ex-10 was cleared out of the system completely, resulting in tumor p-SMAD2 recovery back to the baseline level (FIG. 6B). Similar trend was observed for Ex-11, where drug concentration in plasma and tumor increased upon drug administration and reached maxima around 4 hours post drug administration. Ex-11 was cleared out of the system at 24-hour post drug administration, resulting in recovery of tumor p-SMAD2 level (FIG. 6C).

Example E—ES-2 Survival Study (Ovarian Cancer Xenouraft)

Ovarian cancer is still associated with poor prognosis and remains among the leading causes of oncology-related deaths in females. High recurrence rates, resistance to chemotherapy and meager outcome highlight the need for improved therapies that stem from understanding the complex and multifactorial etiology of ovarian malignancies. TGF-01 signaling within tumor microenvironment regulates important steps in ovarian cancer progression such as epithelial to mesenchymal transition, dissemination, and metastasis. Inhibition of TGF-01 signaling pathway has shown a potential as a pharmaceutical target in ovarian malignancies. ES-2 ovarian cancer mouse xenograft model was used to test efficacy of EX-11 in ovarian cancer, as measured by improvement in survival.

Sixteen-week-old female athymic nude mice were injected with two million ES-2-luc cells. The cells used were harvested and resuspended in four hundred microliters of PBS and implanted via an i.p. injection. Five days after cell implantation the mice were randomized and enrolled ten animals per group in test or vehicle control group. Randomization was performed based on weight. Bioluminescence was verified in study animals to confirm disease progression before dosing began on day five.

All compounds were dissolved in TWEEN20 (10%) in water and administered via oral gavage. Vactosertib was included as a positive control for TGF-β1 signaling inhibition and for comparative efficacy test of the competitor compound. Vactosertib was given at twenty-five milligram per kilogram once a day, with vehicle administered during second dosing to match BID dosing in vehicle volume and handling of EX-11 group (Table 9). The drug suspensions were sonicated for fifteen minutes to generate a fine particle suspension before administration. Mice were dosed with EX-11 at a level of one hundred and fifty mg/Kg twice a day.

Mortality was recorded for animals found dead in the cage, and for the animals sacrificed based on humane end point based on main three criteria—loss of mobility and response, wasting with pronounced ascites fluid buildup, and palpable drop in body temperature (animals were assessed as cold to touch when handled in gloves).

On study day 22, the remaining surviving animals in the vehicle group were determined moribund, and the study was terminated based on humane end point criteria. Two hours after final drug administration, animals were sacrificed, tissues were harvested and stored at negative eighty degrees Celsius until further processing.

TABLE 9

Study groups and dosing schedule for ES-2 survival study

| Group | No. | Treatment | Dosing event | article | Dosing Volume (mL/kg) | Dosing level (mg/mg) | ROA | Dosing Frequency & Duration |
|---|---|---|---|---|---|---|---|---|
| 1 | 10 | Vehicle | am | Vehicle | 10 | | P.O. | BID × 22 |
| | | | pm | Vehicle | 10 | | P.O. | BID × 22 |
| 2 | 10 | Vactosertib | am | Vactosertib | 10 | 25 mg/kg | P.O. | QD × 22 (5 days/week) |
| | | | pm | Vehicle | 10 | | P.O. | QD × 22 |
| 3 | 10 | EX-11 | 150 | EX-11 | 10 | 150 mg/kg | P.O. | BID × 22 |

Figure 7:
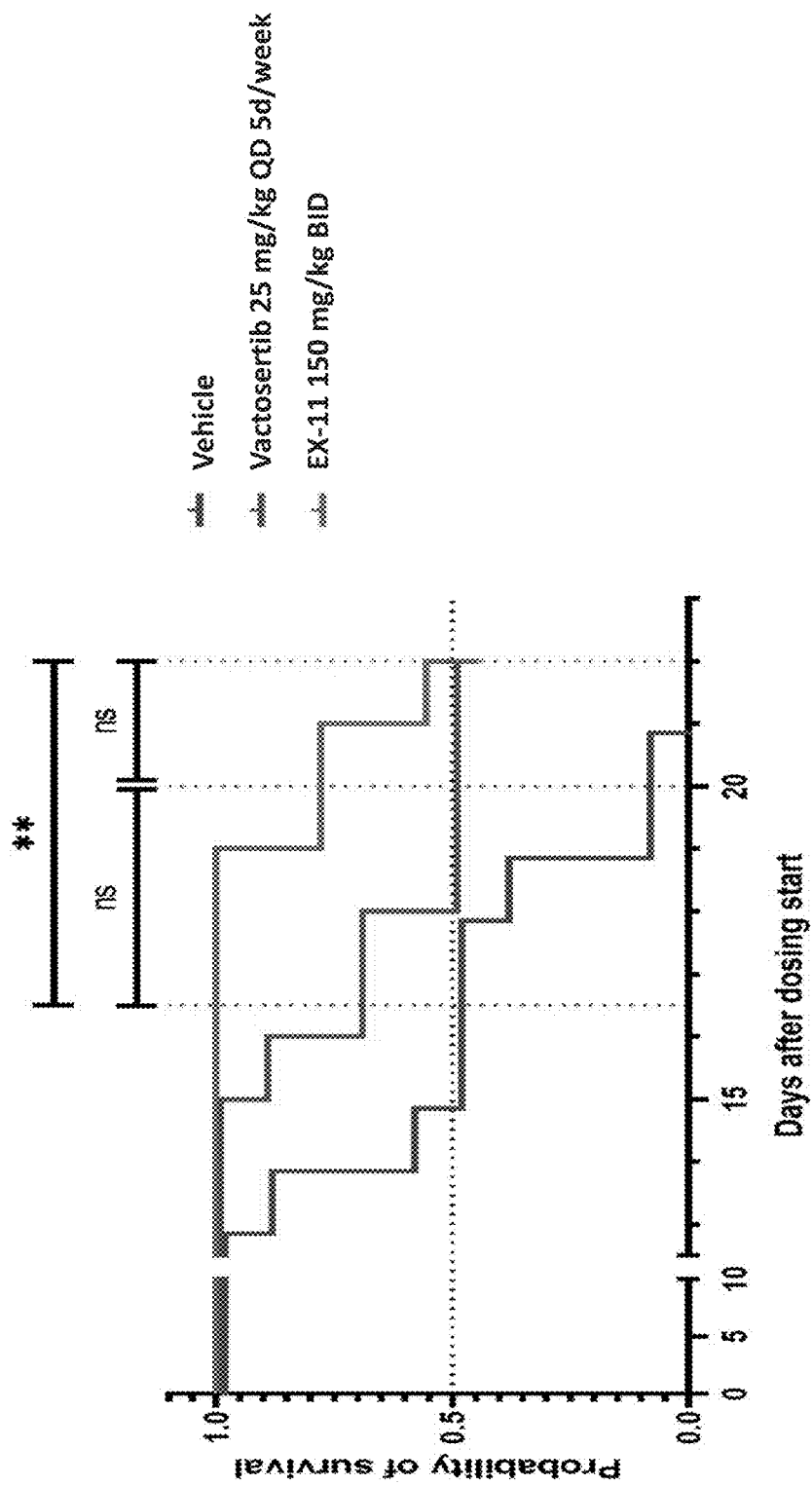
FIG. 7 shows that survival of ES-2-luc tumor-bearing female mice was significantly improved by ALK5 inhibitor EX-11 when administered at 150 mg/Kg twice per day, as described in Example E.

The results of the survival study are summarized in FIG. 7. Overall survival of animals treated with EX-11 was significantly increased when compared with vehicle-treated animals. The effect on survival was associated with delay in visual observation of disease progression, as exhibited in improved mobility and visible wasting of muscle and fat mass.

Example F—FOXL2 Cell Viability Assay

EX-11 was submitted to a cell viability assay in KGN and COV434 cell lines. KGN cells are derived from FOXL2$^{C134W}$ AGCT of a 69-year-old woman with a recurrent metastatic GCT. COV434 cells are derived from FOXL2WT JGCT of a 27-year-old woman with a recurrent metastatic GCT. The cells were seeded in triplicate in 96 well culture plates and treated with nine, 3-fold dilutions of EX-11 or DMSO for 6 days (KGN) or 3 days (Cov434), which represented 3 cell doublings, respectively. Viability was assessed by Cell Titer Glo (Promega).

Figure 8:
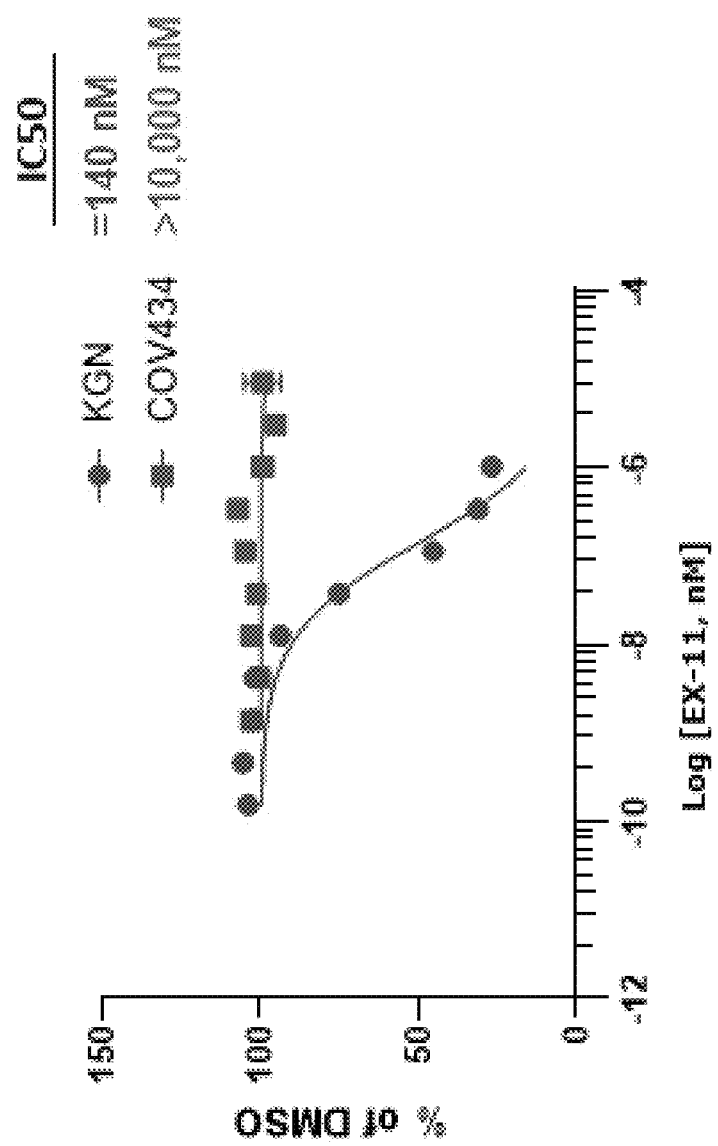
FIG. 8 shows dose response curves for EX-11 in Example F.

FIG. 8 shows that KGN cells expressing FOXL2$^{C134W}$ were >70-fold more sensitive to treatment with EX-11 than COV434 cells expressing wild-type FOXL2. The IC$_{50}$ value of EX-11 in KGN cells was 140 nM, while the IC$_{50}$ value of EX-11 in COV434 cells was greater than 10,000 nM. These data show that EX-11 can inhibit FOXL2$^{C134W}$-driven growth.

Example G—pSmad2 Luminex Assay in KGN Cell Line

KGN cells were incubated with three 10-fold dilutions of EX-11 or DMSO for 2 hours. Cells were harvested and lysed, and protein concentration was quantified by BCA. 10 μg of total protein was added to the assay plate provided in the Milliplex TGFβ 6-plex kit with GAPDH MapMate beads, and the manufacturer's protocol was followed. Data was collected on the MagPix Xmap (Luminex).

Figure 9:
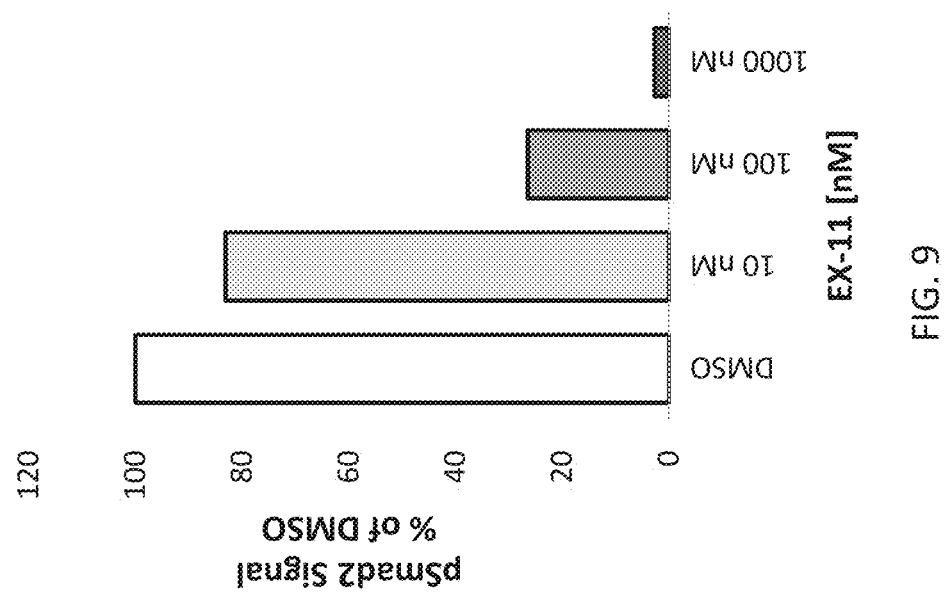
FIG. 9 shows expression of endogenous pSMAD2 in KGN cells treated with EX-11 at 10 nM, 100 nM, or 1,000 nM as described in Example G.

FIG. 9 shows a dose-dependent decrease in pSmad2, with 17, 74, and 97% pathway inhibition observed at 10, 100, and 1,000 nM of EX-11, respectively. These data show on target inhibition by EX-11 and a correlation between TGFβ pathway inhibition and cell death (from Example F, IC50=140 nM).

Example H—TGFβ Induced Proliferation in KGN Cell Line

KGN and COV434 cells were seeded in triplicate in 96 well culture plates and incubated in the presence or absence of TGFβ (1 ng/mL) for 6 or 7 days, respectively. Proliferation was measured by Cell Titer Glo.

Figure 10:
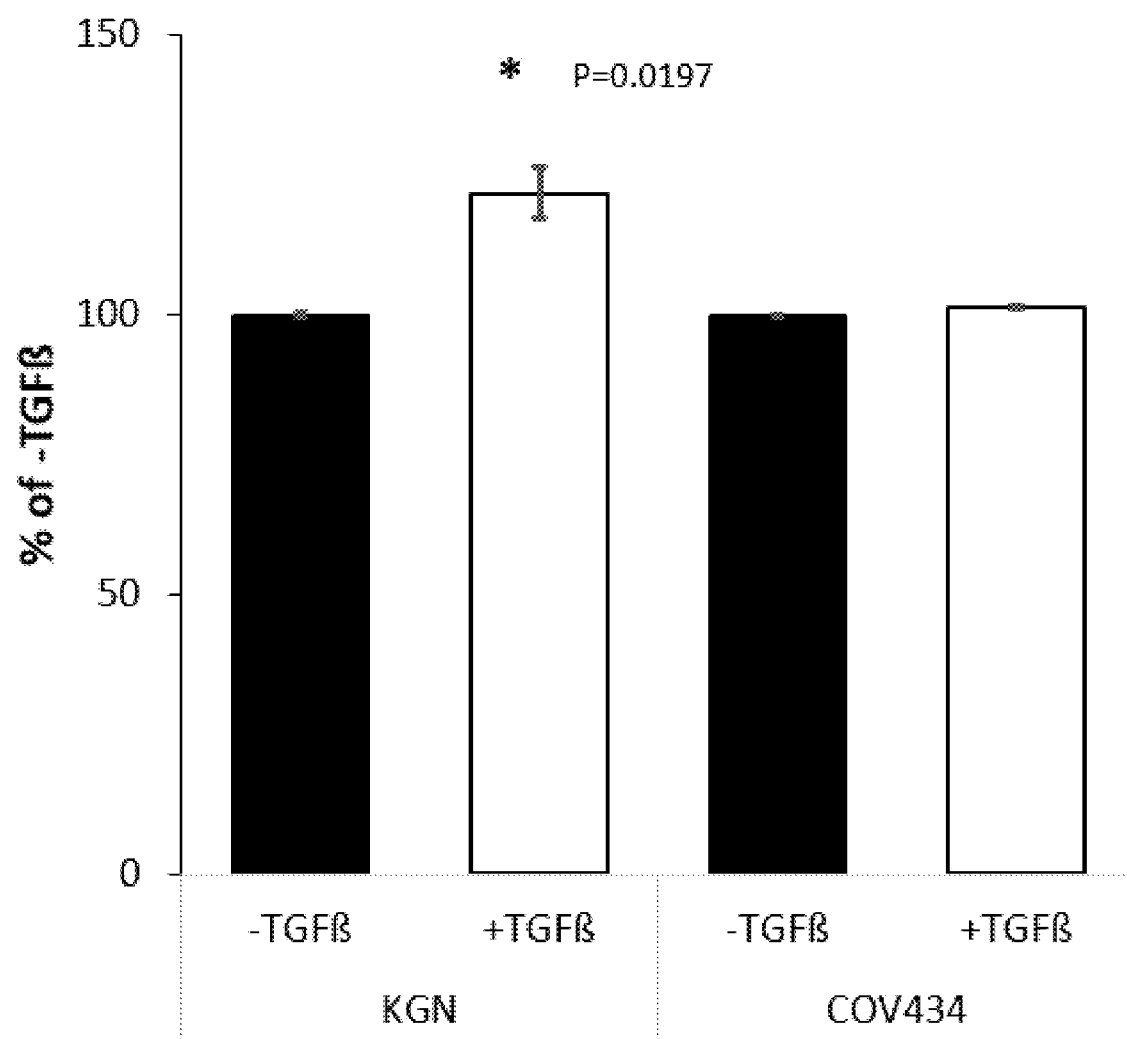
FIG. 10 shows TGF-β levels in KGN and COV434 cell lines from the experiment described in Example H.

FIG. 10 shows that the proliferation of KGN cells (FoxL2 mutant) significantly increased with TGFβ stimulation. There was no change in the FoxL2 wild-type line, COV434. These data suggest that TGFβ pathway signaling increases the oncogenic potential of the FoxL2 C134W mutation, and could benefit from EX-11 intervention.

Example I—TMA Analysis

Five consecutive sections of tissue microarrays of the following indications were purchased: NSCLC (US Biolabs), mesothelioma (US Biolabs), ovarian (US Biolabs and US BioMax), breast (US Biolabs), and pancreatic cancers (US BioMax). Three sections of each indication were baked, dewaxed, and underwent epitope retrieval. Serial sections were then incubated overnight at 4° C. with antibodies to biomarkers of the TGFβ pathway: pSmad2 (CST), αVβ6 (ProteinTech), and SMA (CST). Sections were then washed and stained with AF-647-conjugated secondary antibody for 1 hour at room temperature, washed, stained with DAPI, and cover-slipped. Sections were imaged in the Olympus VS200 slide scanner and MFI of each patient sample was quantified for each target on the CellSens software.

Tables 10 and 11 show the results of the TMA analysis. "X" in Table 10 signifies the marker was overexpressed in the tumor sections compared to the normal tissue in that indication. Breast cancer showed high pSmad2 and αVβ6 in all subtypes suggesting high TGFβ signaling. Gastric and pancreatic cancers showed high αSMA, suggesting a large stromal/fibrotic component to the samples. AGCT showed high pSmad2 and αSMA, as well as the highest correlation ($r^2$) between all three biomarkers, suggesting high TGFβ signaling and high fibrosis.

TABLE 10

Biomarker Signal

| | | pSmad2 | αVβ6 | αSMA |
|---|---|---|---|---|
| Ovarian | Serous | X | X | |
| | Endometrial | | X | |
| | Mucinous | | | |
| | AGCT | X | | X |
| | Other | | | |
| Gastric | Diffuse | | X | X |
| | Intestinal | | | X |
| Breast | ER+ | X | X | |
| | PR+ | X | X | |
| | HER2+ | X | X | |
| | TNBC | X | X | |
| Pancreatic | | | | X |
| Mesothelioma | | X | X | |

TABLE 11

Correlation of Biomarkers

| | | pSmad2/αVβ6 | pSmad2/αSMA | aSMA/αVβ6 |
|---|---|---|---|---|
| Ovarian | Serous | ++ | + | + |
| | Endometrial | ++ | ++ | + |
| | Mucinous | + | ++ | + |
| | AGCT | +++ | ++ | +++ |
| | Other | ++ | + | + |
| Gastric | Diffuse | ++ | ++ | + |
| | Intestinal | ++ | ++ | + |
| Breast | ER+ | ++ | + | + |
| | PR+ | +++ | + | + |
| | HER2+ | + | + | + |
| | TNBC | ++ | ++ | |
| Pancreatic | | ++ | ++ | + |
| Mesothelioma | | ++ | + | + |

("+" is ≤0.1; "++" is >0.1 ≤ 0.5; and "+++" is >0.5)

Example J—CAF Gene Suppression Assay In Primary Lung Fibroblast

Human primary dermal fibroblasts (ATCC) were divided into four groups: DMSO-TGFβ, DMSO+TGFβ (1 ng/mL), 30 nM EX-11+TGFβ (1 ng/mL), and 300 nM EX-11+TGFβ (1 ng/mL). Cells were treated for 24 hours, then mRNA was extracted, quantified, and reverse transcribed. qPCR was run for the following cancer associated fibroblast (CAF) genes: ACTA2, FAP, ITGB1, CD9, TAGLN, ANTXR1, SOC1, Lamp5, Col1A2, and TGFβ1, using the TaqMan system in a Quant Studio.

Figure 11:
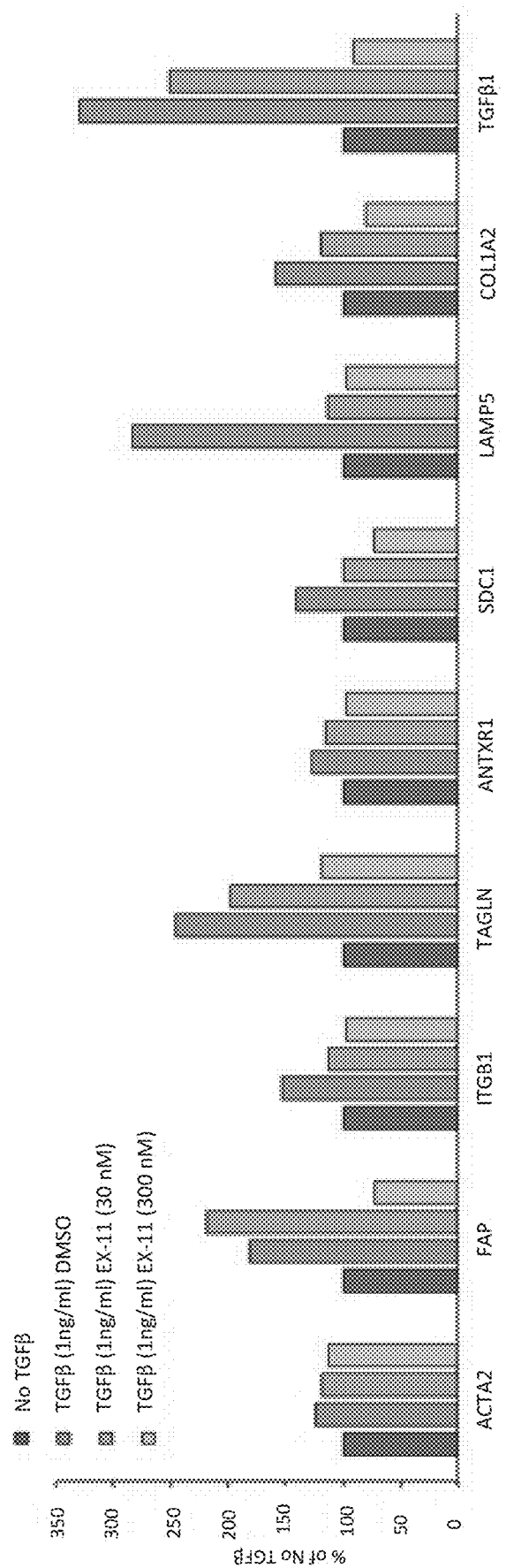
FIG. 11 shows the results of the assay described in Example J.

As shown in FIG. 11, all genes except CD9 followed the same trend. Upregulation of gene expression was observed with TGFβ stimulation, which was dose dependently reversed (and, in some cases, decreased from baseline) by EX-11. TAGLN, Lamp5, and TGFβ1 had the highest fold change expression with TGFβ stimulation (about 2-3 fold); all returned to baseline with 300 nM EX-11. FAP, SDC1 and Col1A2 decreased expression about 20-30% from baseline with 300 nM EX-11.

Example K—EMT6 Syngeneic TNBC Model

The objective of this study was to evaluate preclinically the in vivo therapeutic efficacy of combining EX-11 with anti-PD-L1 and/or anti-PD-1 therapy for the treatment of EMT6 tumors orthotopically implanted in the mammary fat pad of female Balb/C mice.

Balb/C mice (aged 7-9 weeks) were inoculated orthotopically in the right mammary fat pad with EMT6 breast cancer cells ($2.5\times10^5$) in 0.1 ml of PBS. Tumor measurements were performed via digital calipers. Once the mean tumor size reached approximately 85 mm$^3$ (day 11), 120 mice were randomized to 8 treatment arms (15 mice per arm). Mice were treated according to the parameters outlined in Table 12.

TABLE 12

Treatment Parameters for EMT6 Syngeneic TNBC Model

| Group | Treatment | N | Dose Route | *Dosing Frequency & Duration | Dose Level (mg/kg) | Dose Volume (mL/kg) |
|---|---|---|---|---|---|---|
| 1 | Vehicle | 15 | PO | BID × 21 days | n/a | 10 |
| 2 | Anti-PDL-1 | 15 | IP | BIW × 3 weeks | 10 (first dose), 5 (all subsequent doses) | 10 |
| 3 | EX-11 | 15 | PO | BID × 21 days | 75 | 10 |
| 4 | EX-11 | 15 | PO | BID × 21 days | 150 | 10 |
| 5 | Anti-PDL-1 | 15 | IP | BIW × 3 weeks | 10 (first dose), 5 (all subsequent doses) | 10 |
| | EX-11 | | PO | BID × 21 days | 75 | 10 |
| 6 | Anti-PDL-1 | 15 | IP | BIW × 3 weeks | 10 (first dose), 5 (all subsequent doses) | 10 |
| | EX-11 | | PO | BID × 21 days | 150 | 10 |
| 7 | Anti-PD-1 | 15 | IP | BIW × 3 weeks | 10 | 10 |
| 8 | Anti-PD-1 | 15 | IP | BIW × 3 weeks | 10 | 10 |
| | EX-11 | | PO | BID × 21 days | 150 | 10 |

The anti-PD-L1 inhibitor used in this study was a product of BioXcell (Cat #: BE0101, Clone #: 10F.9G2). The vehicle for the anti-PD-L1 inhibitor was PBS. The anti-PD-1 inhibitor used in this study was a product of BioXcell (Cat #: BE0146, Clone #: RMP1-14). The vehicle for the anti-PD-1 inhibitor was PBS. These inhibitors were injected intraperitoneally (i.p.), bi-weekly (BIW) for 3 weeks. The vehicle for EX-11 was NMP (10%)+20% Solutol in WFI (Water for Injection) (90%). The vehicle used for EX-11 was also used for the "Vehicle" arm of the study. EX-11 and the vehicle were delivered via oral gavage (p.o.), bi-daily (BID) for 21 days.

Body weights and tumor volumes were measured twice per week. Tumor volumes were measured in two dimensions using a caliper, and the volume was expressed in mm$^3$ using the formula: $V=(L\times W\times W)/2$, where V is tumor volume, L is tumor length (the longest tumor dimension) and W is tumor width (the longest tumor dimension perpendicular to L). Tumor Growth Inhibition (TGI) reported was TGI at the final study day, and is expressed as Mean % Δ Inhibition and was calculated using the following formula: $[(C-C0)-(T-T0)/(C-C_0)]*100\%$, where C refers to the tumor volume of the vehicle on the final study day, C0 to the tumor volume of the vehicle on the first day of dosing, T to the tumor volume of the treatment on a specific day of dosing and T0 to the tumor volume of the treatment group on the first day of dosing.

The first phase of the study was the dosing phase and was terminated at day 21, where 3 animals were sacrificed, and plasma and tumor samples were collected for biomarker analysis. The remaining 12 animals were monitored without dosing to determine mean survival. Endpoints prior to 50 days were as follows: 1) tumor volume exceeding 3000 mm$^3$, 2) body weight loss over 20% for 3 consecutive days from the first day of treatment, 3) mouse with tumor ulceration of approximately 25% or greater on the surface of the tumor, and 4) severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice.

Figure 12A:
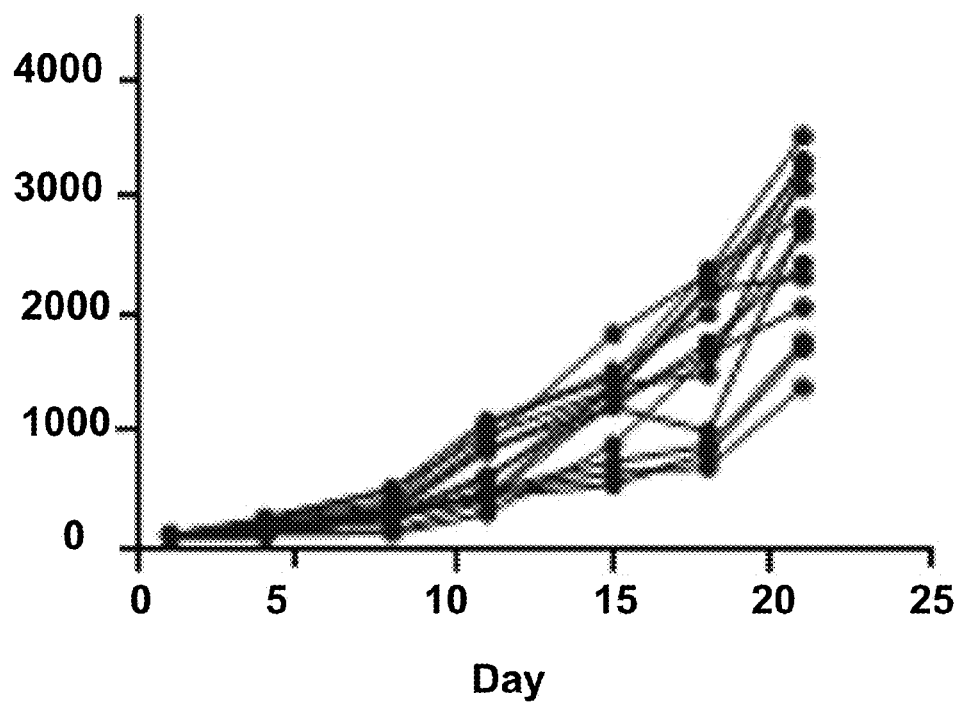
FIG. 12A shows individual tumor volume curves for Group 1 during the dosing phase of Example K.
Figure 12B:
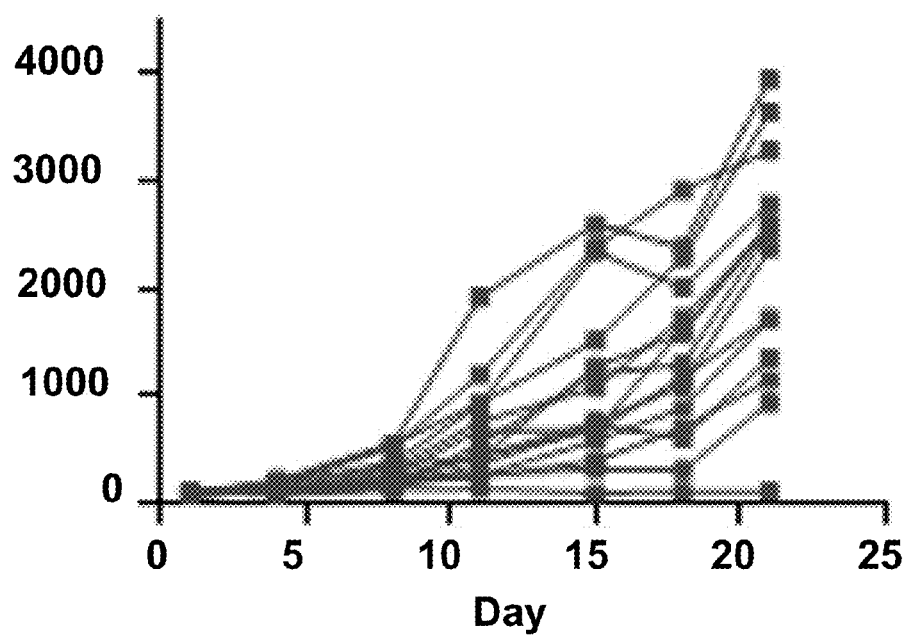
FIG. 12B shows individual tumor volume curves for Group 2 during the dosing phase of Example K.
Figure 12C:
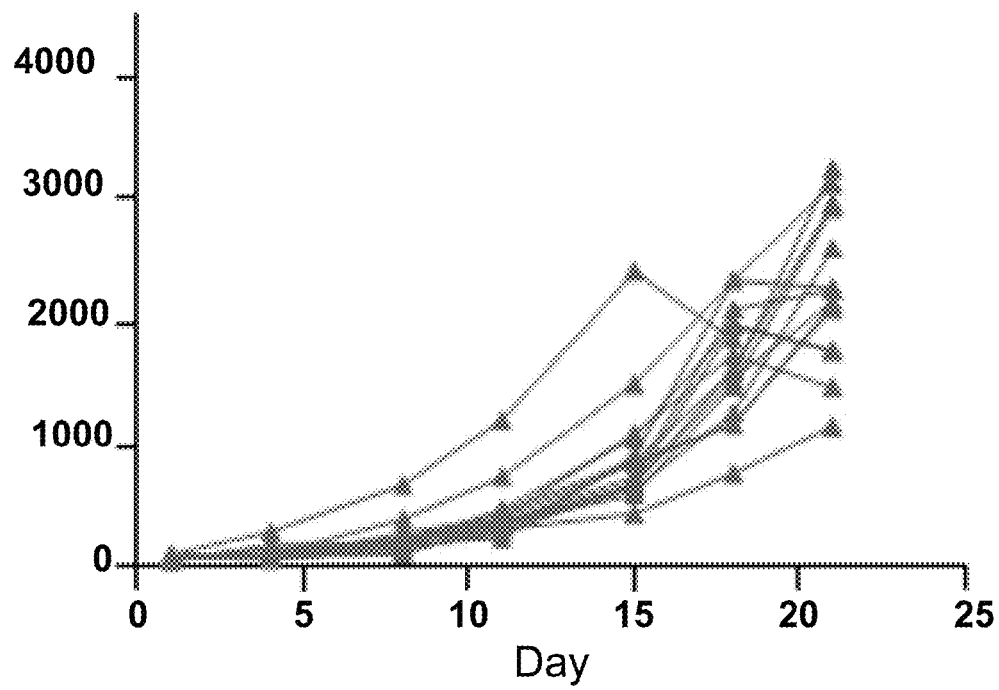
FIG. 12C shows individual tumor volume curves for Group 3 during the dosing phase of Example K.
Figure 12D:
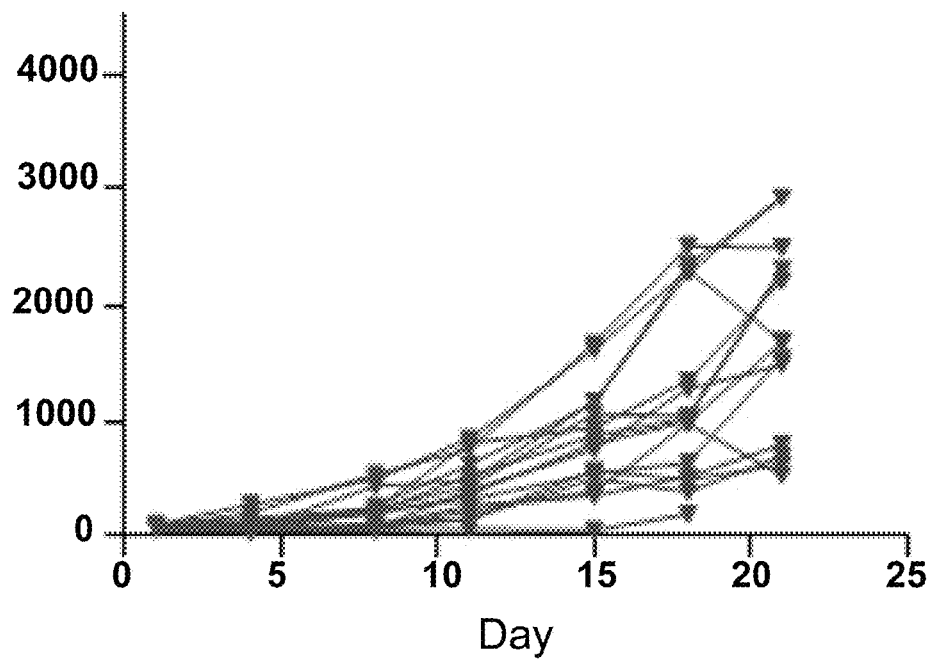
FIG. 12D shows individual tumor volume curves for Group 4 during the dosing phase of Example K.
Figure 12E:
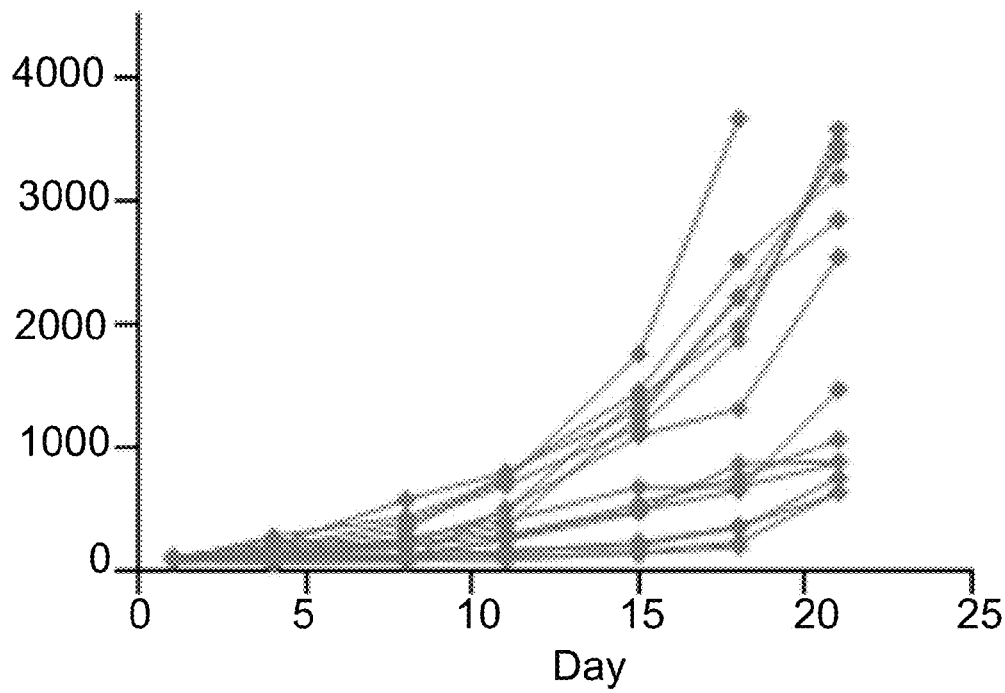
FIG. 12E shows individual tumor volume curves for Group 5 during the dosing phase of Example K.
Figure 12F:
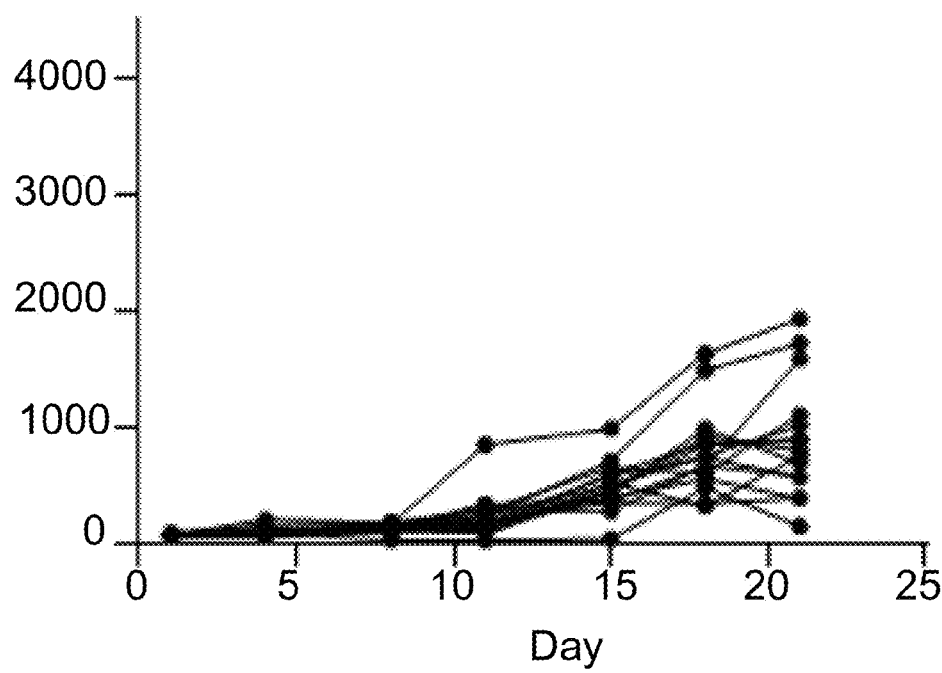
FIG. 12F shows individual tumor volume curves for Group 6 during the dosing phase of Example K.
Figure 12G:
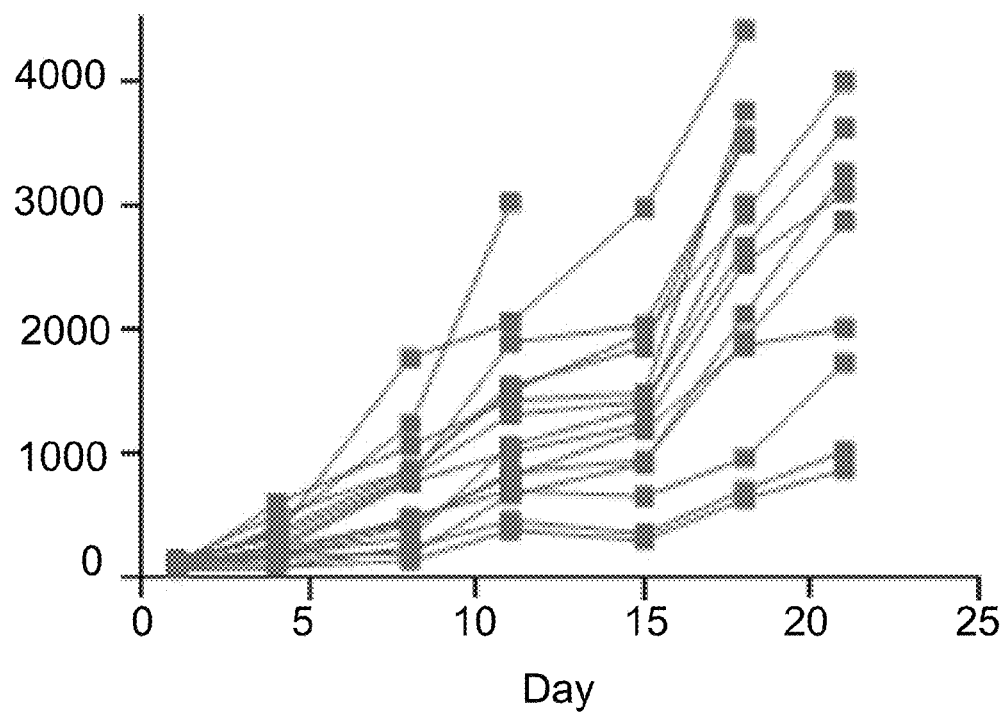
FIG. 12G shows individual tumor volume curves for Group 7 during the dosing phase of Example K.
Figure 12H:
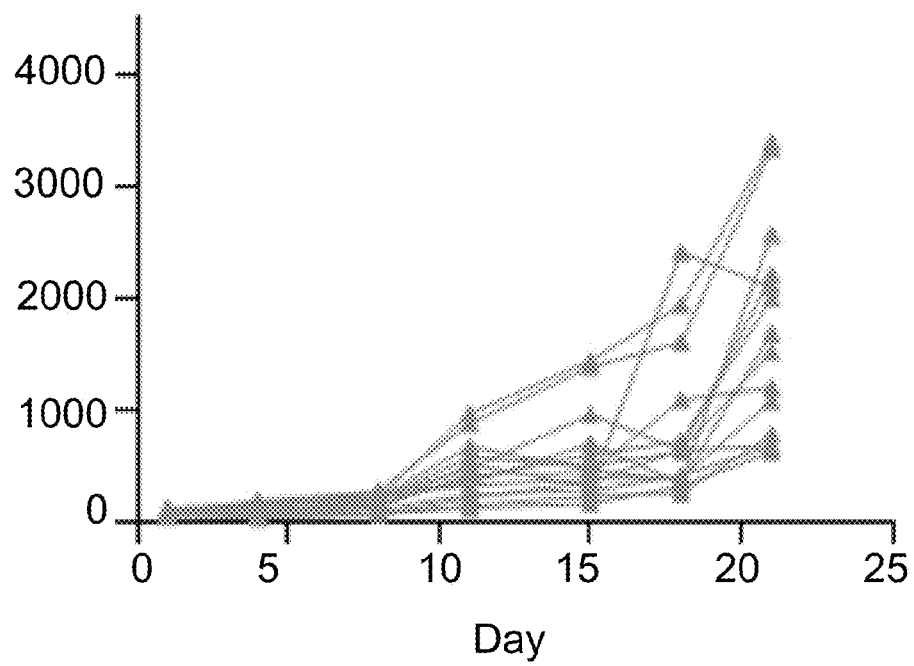
FIG. 12H shows individual tumor volume curves for Group 8 during the dosing phase of Example K.
Figure 12I:
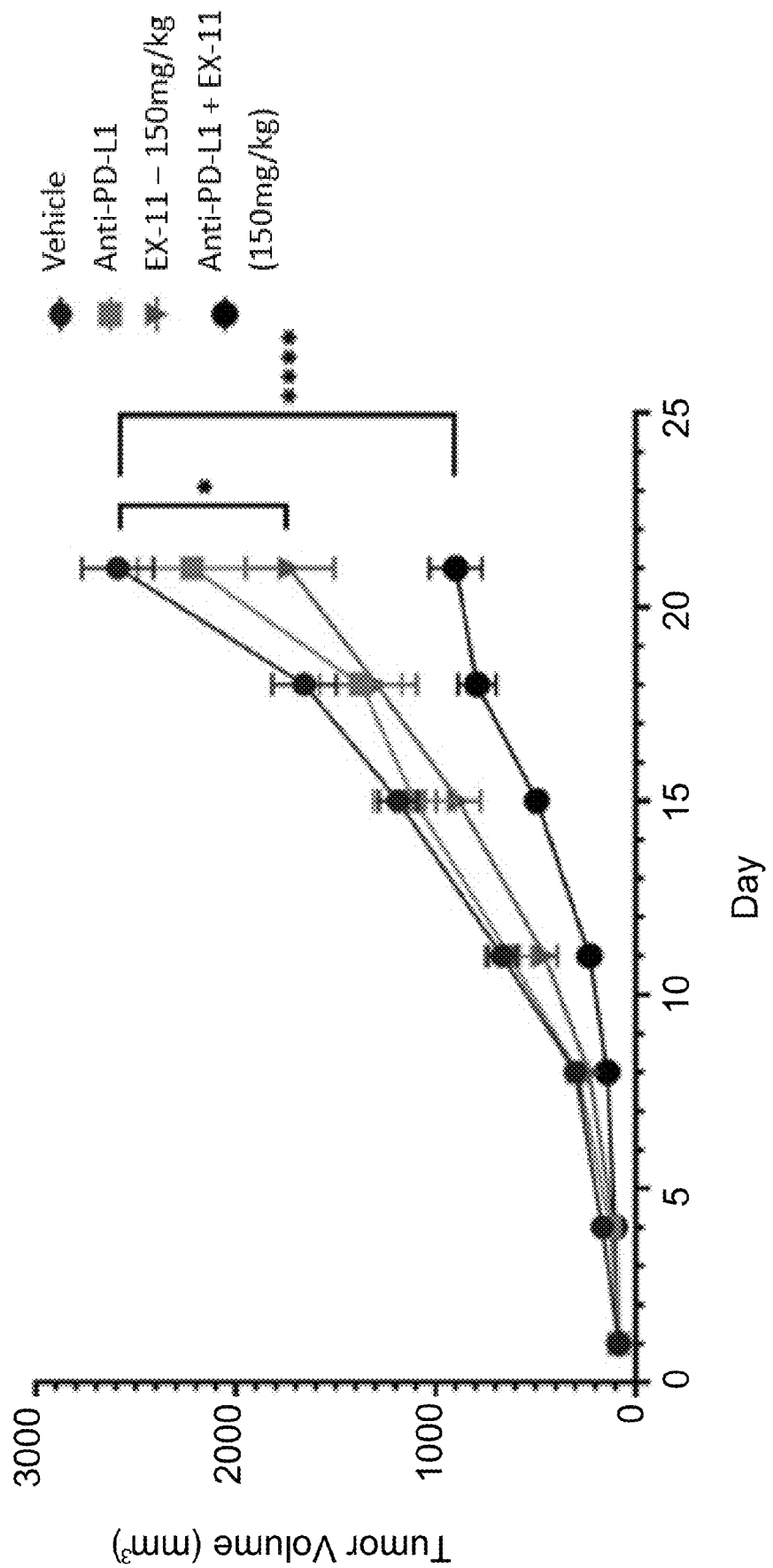
FIG. 12I shows mean tumor volume over dosing period in the groups in Example K that received vehicle, anti-PD-L1, EX-11 150 mg/kg, or a combination of anti-PD-L1+EX-11 150 mg/kg.
Figure 12J:
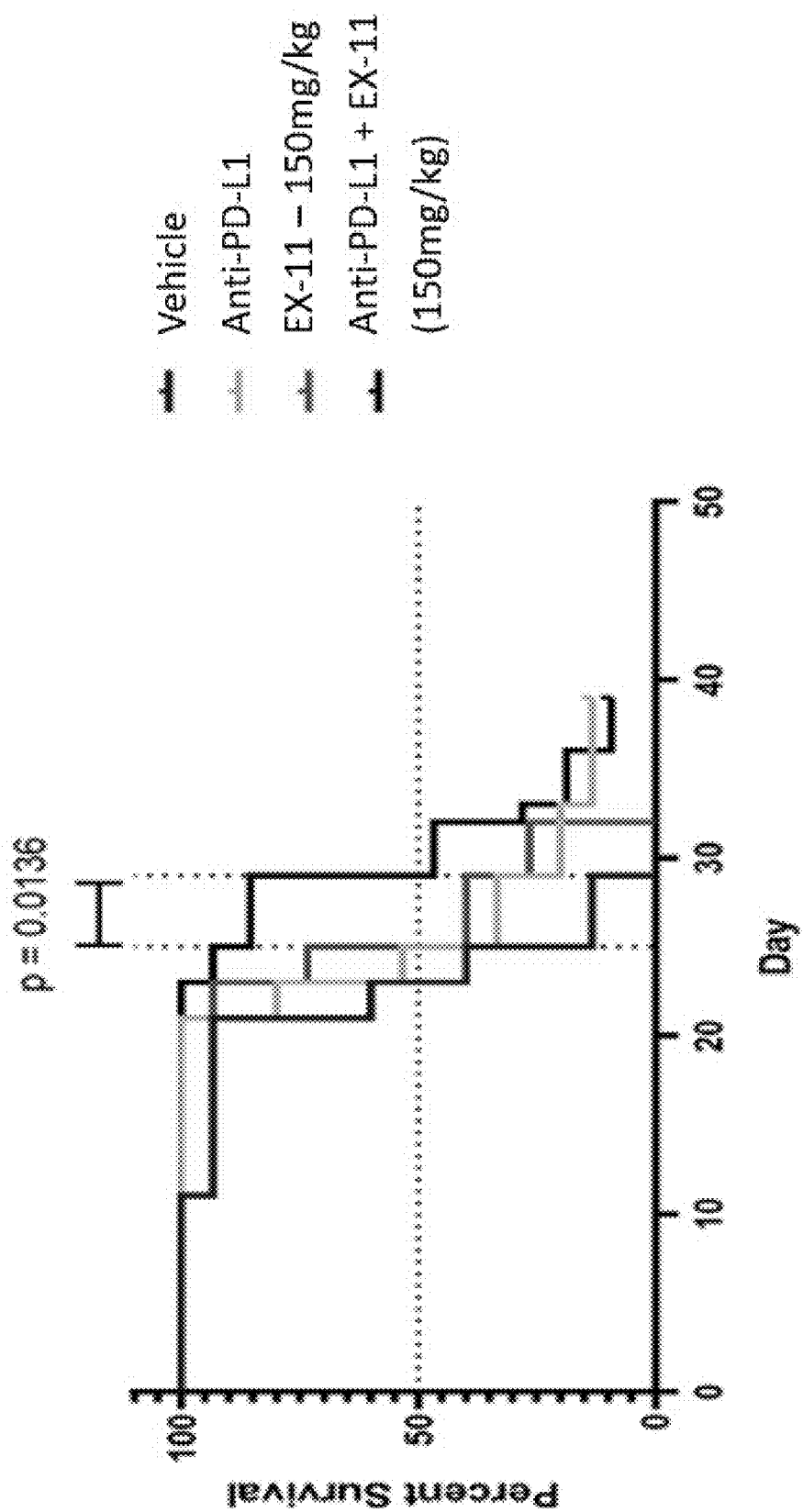
FIG. 12J shows survival curves for the groups in Example K that received vehicle, anti-PD-L1, EX-11 150 mg/kg, or a combination of anti-PD-L1+EX-11 150 mg/kg.
Figure 12K:
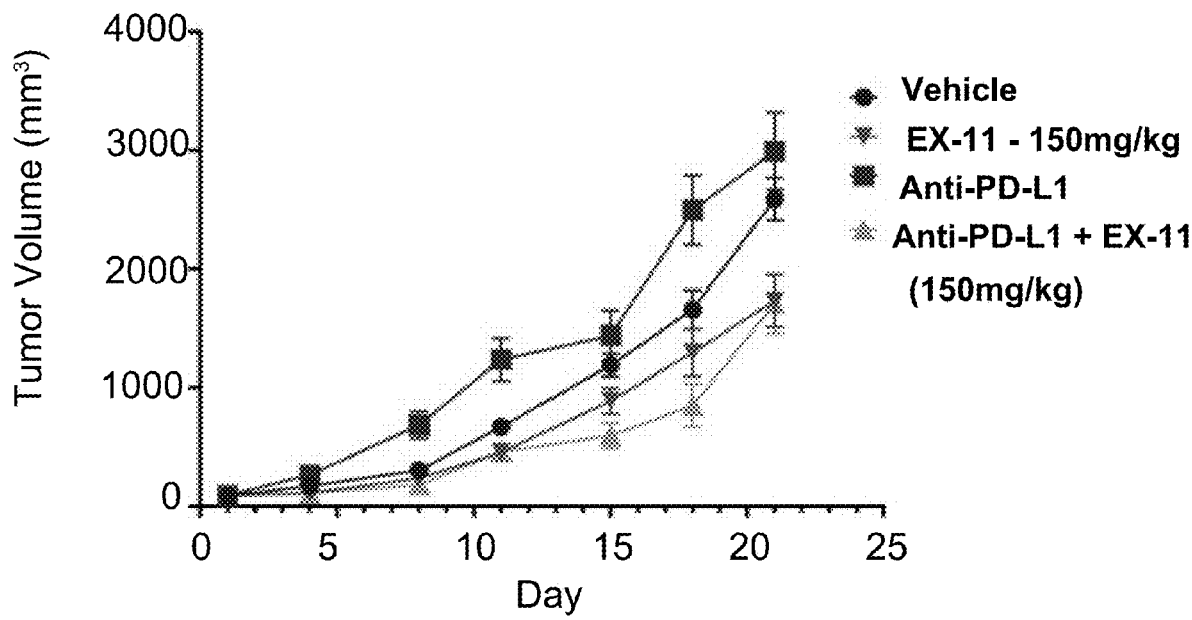
FIG. 12K shows mean tumor volume over dosing period in the groups in Example K that received vehicle, anti-PD-1, EX-11 150 mg/kg, or a combination of anti-PD-1+EX-11 150 mg/kg.
Figure 12L:
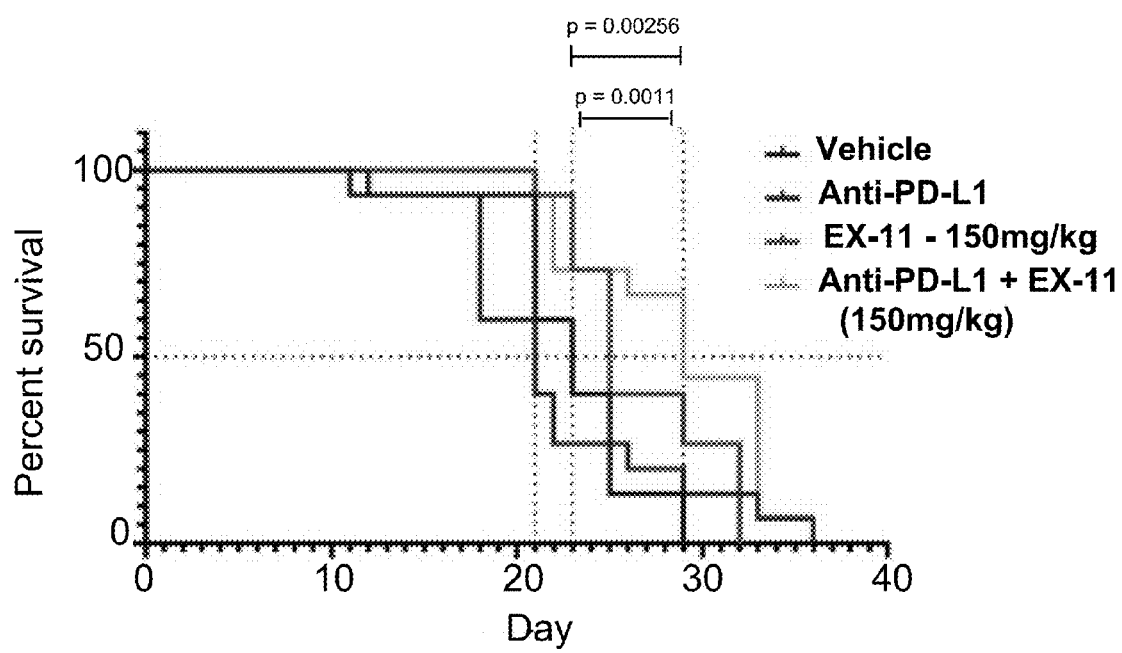
FIG. 12L shows survival curves for the groups in Example K that received vehicle, anti-PD-1, EX-11 150 mg/kg, or a combination of anti-PD-1+EX-11 150 mg/kg.
Figure 12M:
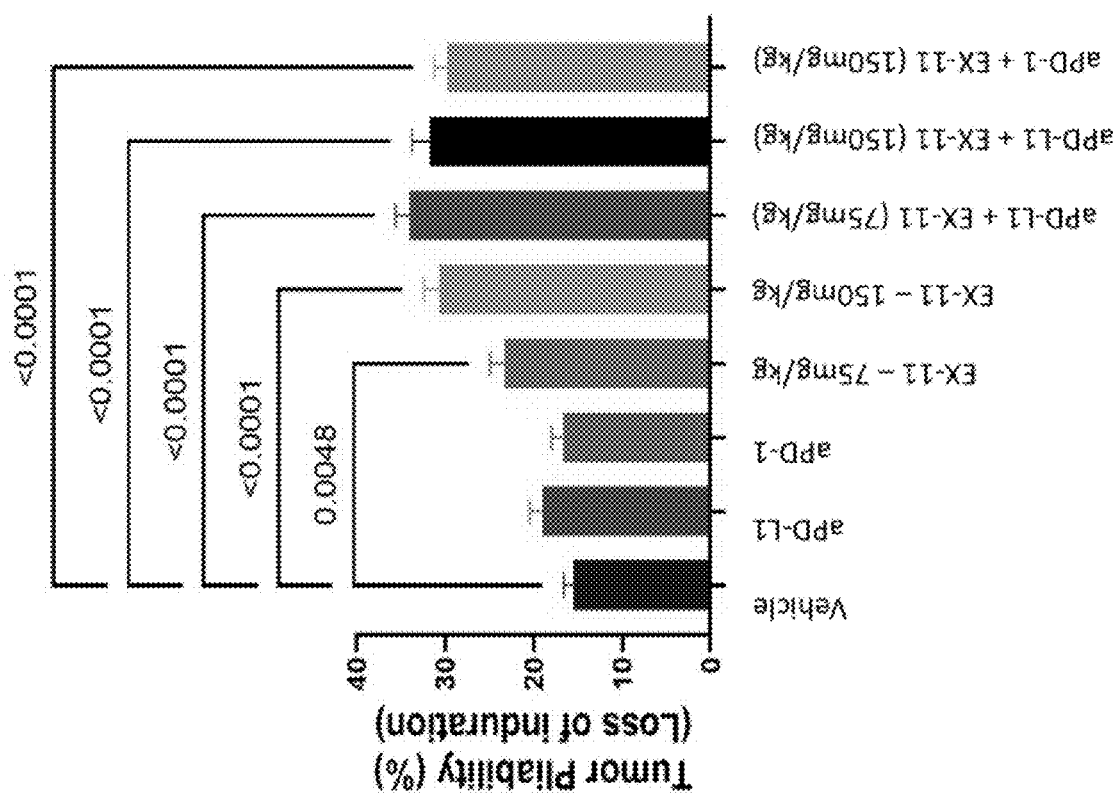
FIG. 12M shows quantification of tumor pliability of tumors from Example K.

Individual tumor growth curves for each treatment group are shown in FIGS. 13A-13H. Single agent treatment with anti-PD-L1 or anti-PD-1 did not result in significant tumor growth inhibition (TGI) compared to vehicle. Single agent treatment with EX-11 at 75 mg/kg did not result in significant TGI, but single agent treatment with 150 mg/kg EX-11 resulted in significant TGI by 37% (p=0.04) (FIG. 12I). The combination of anti-PD-L1 and EX-11 at 75 mg/kg did result in significant TGI, but the combination of anti-PD-L1 and EX-11 at 150 mg/kg resulted in significant tumor growth inhibition of 65% (p<0.0001) (FIG. 12I), and resulted in a significant increase in mean survival versus vehicle by 17% (p=0.0136) (FIG. 12J and Table 13). The combination of anti-PD-1 and EX-11 at 150 mg/kg resulted in significant TGI by 34% versus vehicle (p=0.049) but was not significant in comparison with the EX-11 single agent treatment (FIG. 12K). However, the combination of anti-PD-1 and EX-11 at 150 mg/kg resulted in significant increase in mean survival versus vehicle by 26% (p=0.0011), and versus anti-PD-1 single agent by 38% (p=0.00256), as shown in FIG. 12L and Table 13. Tumors in all groups receiving EX-11 treatment were substantially more pliable than tumors in groups receiving the vehicle, anti-PD-L1 single agent, or anti-PD-1 single agent, suggesting a decrease in intra-tumoral pressure. This was quantified by measuring the amount of tumor compression achievable along the long tumor axis compared to the original uncompressed measurement, as shown in FIG. 12M. Figures were generated in GraphPad Prism.

TABLE 13

Mean Survival Days for Mice in Various Treatment Groups

| Group | Mean survival (days) |
| --- | --- |
| Vehicle | 23 |
| PD-L1 | 25 |
| EX-11 150 mpk | 25 |
| EX-11 + PD-L1 | 29 (16% increase vs aPD-L1) (p = 0.0136) |
| PD-1 | 21 |
| EX-11 150 mpk + PD-1 | 29 (38% increase vs aPD-1) (p = 0.0025) |

Example L—4T1 Syngeneic TNBC Model

The objective of this study was to evaluate preclinically the in vivo therapeutic efficacy of combining EX-II with anti-PD-1 therapy for the treatment of luciferase expressing 4T1 (4T1-luc) tumors orthotopically implanted in the mammary fat pad of female Balb/C mice.

Female, Balb/C mice (aged 6-8 weeks) were inoculated orthotopically in the right mammary fat pad with 4T1 breast cancer cells ($3 \times 10^5$) in 0.1 ml of PBS. Tumor measurements were performed via digital calipers. Once the mean tumor size reached approximately 90 mm³ (day 11), 60 mice were randomized to 6 treatment arms (10 mice per arm). Mice were treated according to the parameters outlined in Table 14.

TABLE 14

Treatment Parameters for 4T1 Syngeneic TNBC Model

| Group | Treatment | N | Dose Route | *Dosing Frequency & Duration | Dose Level (mg/kg) | Dose Volume (mL/kg) |
| --- | --- | --- | --- | --- | --- | --- |
| 1 | Vehicle | 10 | PO | BID × 21 days (12 h apart) | n/a | 10 |
| 2 | Anti-PD1 | 10 | IP | BIW × 3 weeks | 10 | 10 |
| 3 | EX-11 | 10 | PO | BID × 21 days (12 h apart) | 75 | 10 |
| 4 | EX-11 | 10 | PO | BID × 21 days (12 h apart) | 150 | 10 |
| 5 | Anti-PD1 | 10 | IP | BIW × 3 weeks | 10 | 10 |
|   | EX-11 |   | PO | BID × 21 days (12 h apart) | 75 | 10 |
| 6 | Anti-PD1 | 10 | IP | BIW × 3 weeks | 10 | 10 |
|   | EX-11 |   | PO | BID × 21 days (12 h apart) | 150 | 10 |

The anti-PD-1 inhibitor used in this study was a product of BioXcell (Cat #: BE0146, Clone #: RMP1-14). The vehicle for anti-PD-1 inhibitor was PBS. The drug was injected intraperitoneally (i.p.), bi-weekly (BIW) for 3 weeks. The vehicle for EX-11 was NMP (10%)+20% Solutol in WFI (Water for Injection) (90%). The vehicle used for EX-11 was also used for the "Vehicle" arm of the study. EX-11 and the vehicle were delivered via oral gavage (p.o.), bi-daily (BID) for 21 days.

Body weights and tumor volumes were measured twice per week. Tumor volumes were measured in two dimensions using a caliper, and the volume was expressed in mm³ using the formula: $V=(L \times W \times W)/2$, where V is tumor volume, L is tumor length (the longest tumor dimension) and W is tumor width (the longest tumor dimension perpendicular to L). Tumor Growth Inhibition (TGI) reported was as of the final study day and is expressed as Mean % Δ Inhibition, calculated using the following formula: $[(C-C_0)-(T-T0)/(C-C_0)]*100\%$, where C refers to the tumor volume of the vehicle on the final study day, C0 to the tumor volume of the vehicle on the first day of dosing, T to the tumor volume of the treatment on a specific day of dosing and T0 to the tumor volume of the treatment group on the first day of dosing.

The study dosing phase was 21 days. At the end of the study, animals were injected with luciferin, then sacrificed. Ex vivo imaging of the lung and liver tissue was performed to assess metastasis. Endpoints prior to 21 days were as follows: 1) tumor volume exceeding 2000 mm³, 2) body weight loss over 20% for 3 consecutive days from the first day of treatment, 3) mouse with tumor ulceration of approximately 25% or greater on the surface of the tumor, and 4) severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice.

Individual tumor growth curves for each treatment group are shown in FIG. 13A-13F. Single agent treatment with anti-PD-1 did not result in significant tumor growth inhibition (TGI) compared to vehicle. Single agent treatment with EX-11 at 75 mg/kg did not result in significant TGI, but single agent treatment with EX-11 at 150 mg/kg resulted in significant TGI by 38% (p=0.0254). The combination of anti-PD-1 and EX-11 at 75 mg/kg did not result in significant TGI compared to vehicle, but the combination of anti-PD-1 and EX-11 at 150 mg/kg resulted in significant TGI by 50% versus vehicle (p=0.0002).

Figure 13B:
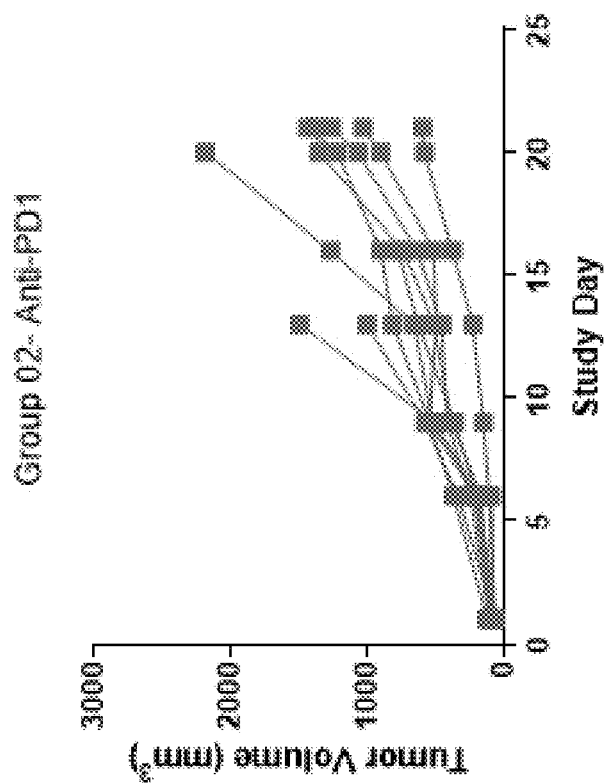
FIG. 13B shows individual tumor volume curves for Group 2 during the dosing phase of Example L.
Figure 13A:
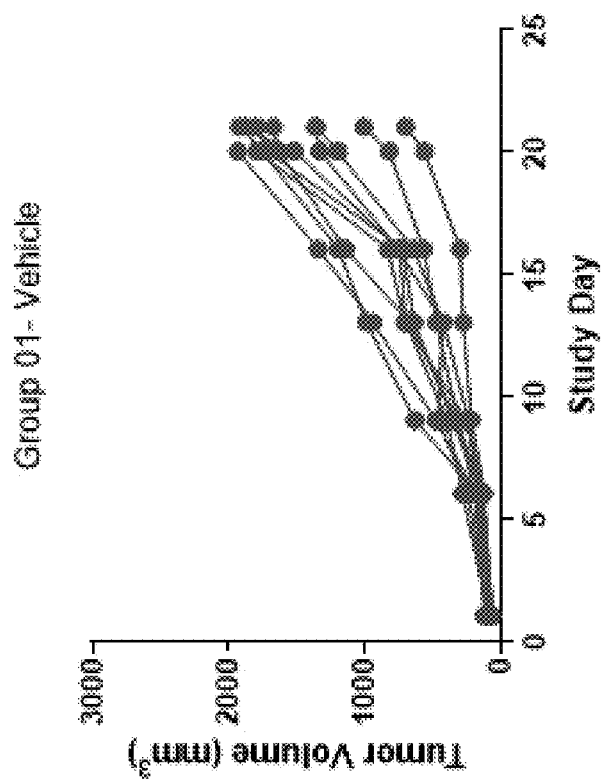
FIG. 13A shows individual tumor volume curves for Group 1 during the dosing phase of Example L.
Figure 13D:
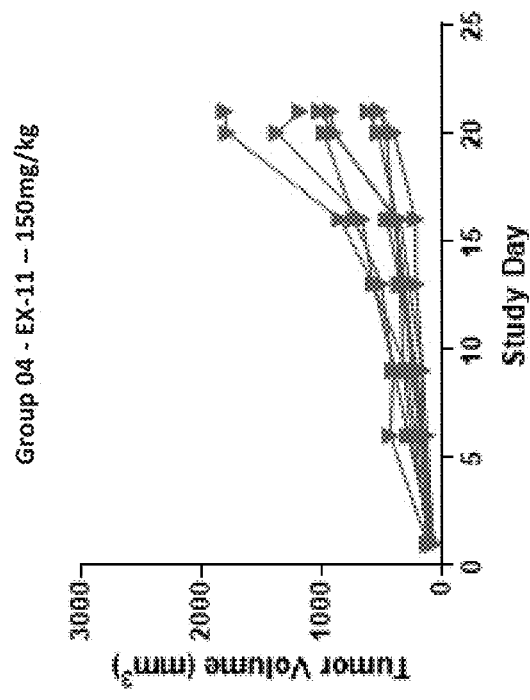
FIG. 13D shows individual tumor volume curves for Group 4 during the dosing phase of Example L.
Figure 13C:
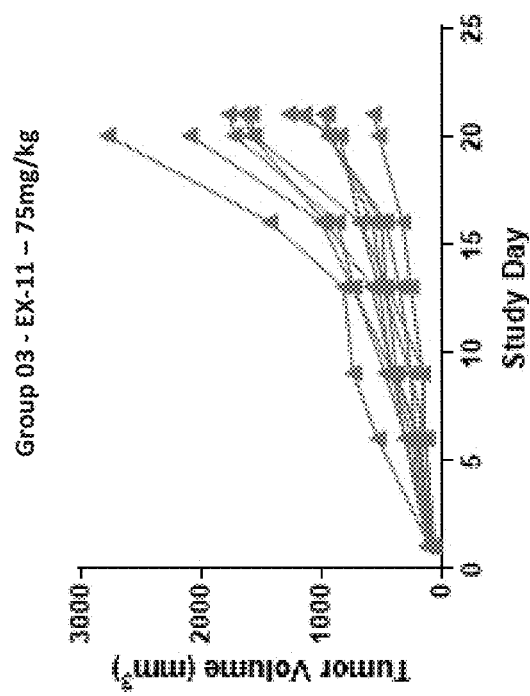
FIG. 13C shows individual tumor volume curves for Group 3 during the dosing phase of Example L.
Figure 13F:
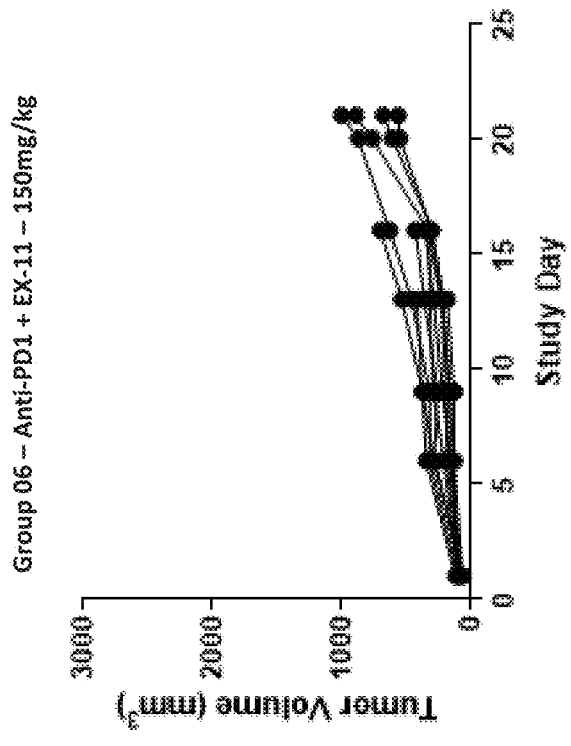
FIG. 13F shows individual tumor volume curves for Group 6 during the dosing phase of Example L.
Figure 13E:
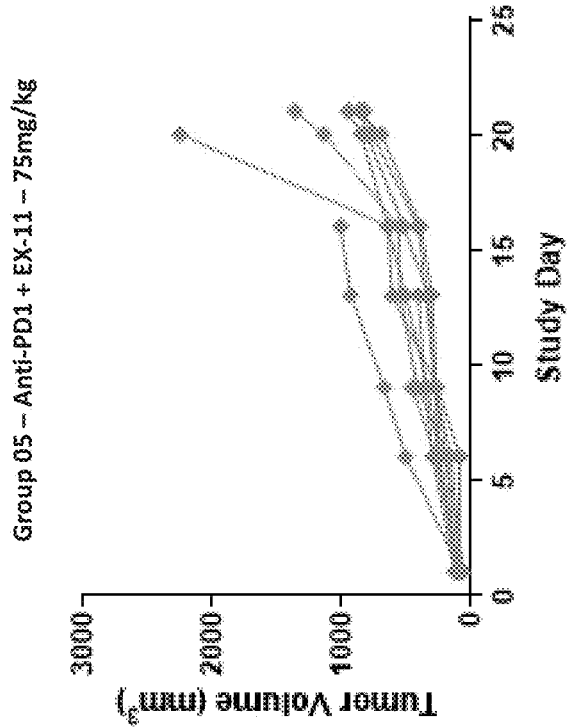
FIG. 13E shows individual tumor volume curves for Group 5 during the dosing phase of Example L.
Figure 13G:
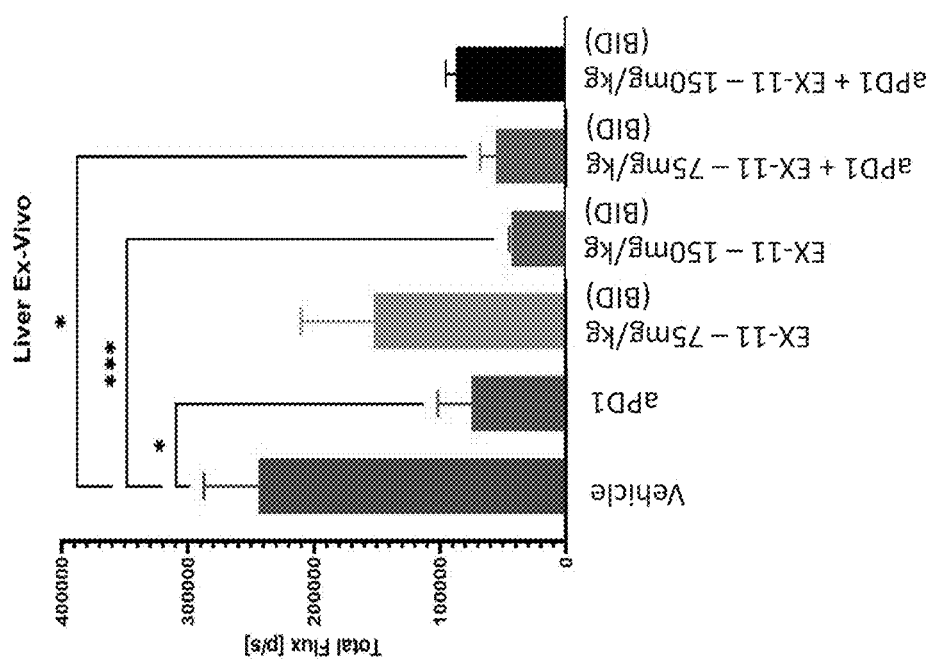
FIG. 13G shows mean luminescence flux values in lung tissue from the groups in Example L that received vehicle, anti-PD-1, EX-11 150 mg/kg, or a combination of anti-PD-1+EX-11 150 mg/kg.
Figure 13H:
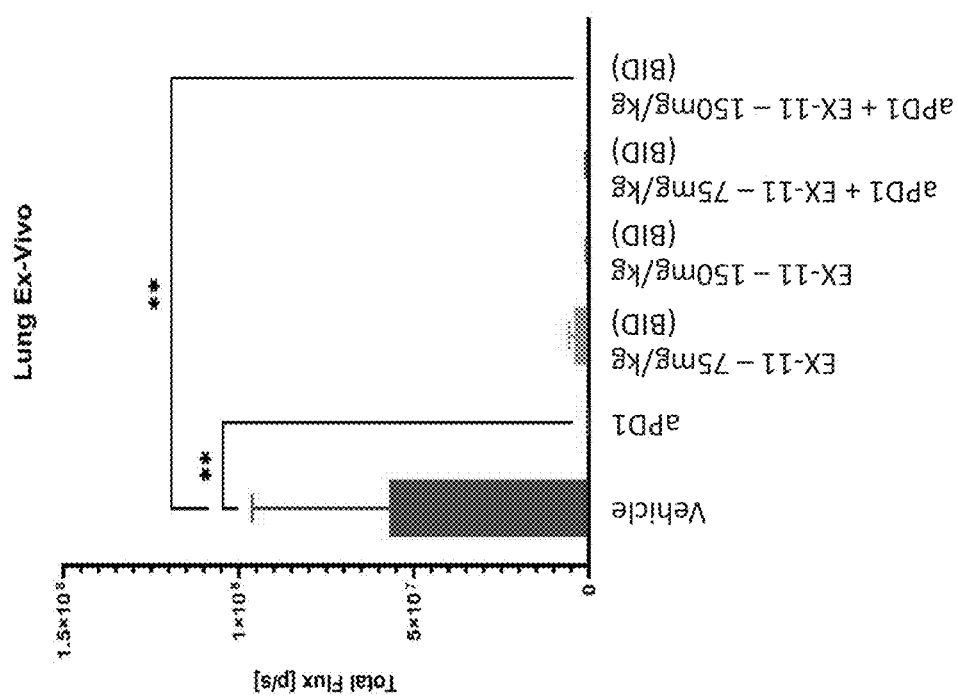
FIG. 13H shows mean luminescence flux values in liver tissue from the groups in Example L that received vehicle, anti-PD-1, EX-11 150 mg/kg, or a combination of anti-PD-1+EX-11 150 mg/kg.

As shown in FIG. 13G, ex vivo analysis of lung showed significant reduction in luminescence compared to vehicle with single agent anti-PD-1 treatment and the combination of anti-PD-1 and EX-11 at 150 mg/kg (p=0.0014 and 0.0056, respectively). As shown in FIG. 13H, ex vivo analysis of liver showed significant reduction in luminescence compared to vehicle with single agent anti-PD-1 treatment (p=0.0322), and stronger reduction in luminescence compared to vehicle with single agent EX-11 at 150 mg/kg (p=0.004). The combination of anti-PD-1 and EX-11 at 75 mg/kg, but not 150 mg/kg, also showed a significant reduction in luminescence compared to vehicle (p=0.0208). Figures were generated in GraphPad Prism.

Example M—Cloudman S91 Melanoma Syngeneic Study

The objective of this study was to evaluate preclinically the in vivo therapeutic efficacy of EX-11+/−anti-PD-1 therapy for the treatment of subcutaneous Cloudman S91 melanoma model in DBA/2 mice.

Female, DBA/2 mice (aged 7-9 weeks) were inoculated subcutaneously in the right flank region with Cloudman S91 melanoma cells ($2 \times 10^5$) in 0.1 ml of PBS. Once the mean tumor size reached approximately 100 mm$^3$ (day 19), 60 mice were randomized to 6 treatment arms (10 mice per arm). Mice were treated according to the parameters outlined in Table 15.

TABLE 15

Treatment Parameters for Cloudman S91 Melanoma Syngeneic Study

| Group | Treatment | N | Dose Route | *Dosing Frequency & Duration | Dose Level (mg/kg) | Dose Volume (mL/kg) | Dose Solution (mg/mL) |
|---|---|---|---|---|---|---|---|
| 1 | Vehicle | 10 | PO | BID × 21 days (12 h apart) | n/a | 10 | 0 |
| 2 | Anti-PD1 | 10 | IP | BIW × 3 weeks | 10 | 10 | 1 |
| 3 | EX-11 | 10 | PO | BID × 21 days (12 h apart) | 75 | 10 | 7.5 |
| 4 | EX-11 | 10 | PO | BID × 21 days (12 h apart) | 150 | 10 | 15 |
| 5 | Anti-PD1 EX-11 | 10 | IP PO | BIW × 3 weeks BID × 21 days (12 h apart) | 10 75 | 10 10 | 1 7.5 |
| 6 | Anti-PD1 EX-11 | 10 | IP PO | BIW × 3 weeks BID × 21 days (12 h apart) | 10 150 | 10 10 | 1 15 |

The anti-PD-1 inhibitor used in this study was a product of Crownbio/OEM (Cat #: CVP033, Lot #: 0920L765). The vehicle for the anti-BD-1 inhibitor was PBS. The drug was injected intraperitoneally (i.p.), bi-weekly (BIW) for 3 weeks. The vehicle for EX-11 was 1000 tween-20, 900% ddH$_2$O. The vehicle used for EX-11 was also used for the "Vehicle" arm of the study. EX-11 and the vehicle were delivered via oral gavage (p.o.), bi-daily (BID) for 21 days.

Body weights and tumor volumes were measured 3 times per week. Tumor volumes were measured in two dimensions using a caliper, and the volume was expressed in mm$^3$ using the formula: V=(L×W×W)/2, where V is tumor volume, L is tumor length (the longest tumor dimension) and W is tumor width (the longest tumor dimension perpendicular to L).

The study was terminated 50 days post-inoculation. Statistical analysis of the difference in mean tumor volume and overall survival among the groups was performed in GraphPad Prism. Endpoints prior to 50 days were as follows: 1) tumor volume exceeding 3000 mm$^3$, 2) body weight loss over 200% for 3 consecutive days from the first day of treatment, 3) mouse with tumor ulceration of approximately 250% or greater on the surface of the tumor, and 4) severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice.

Figure 14A:
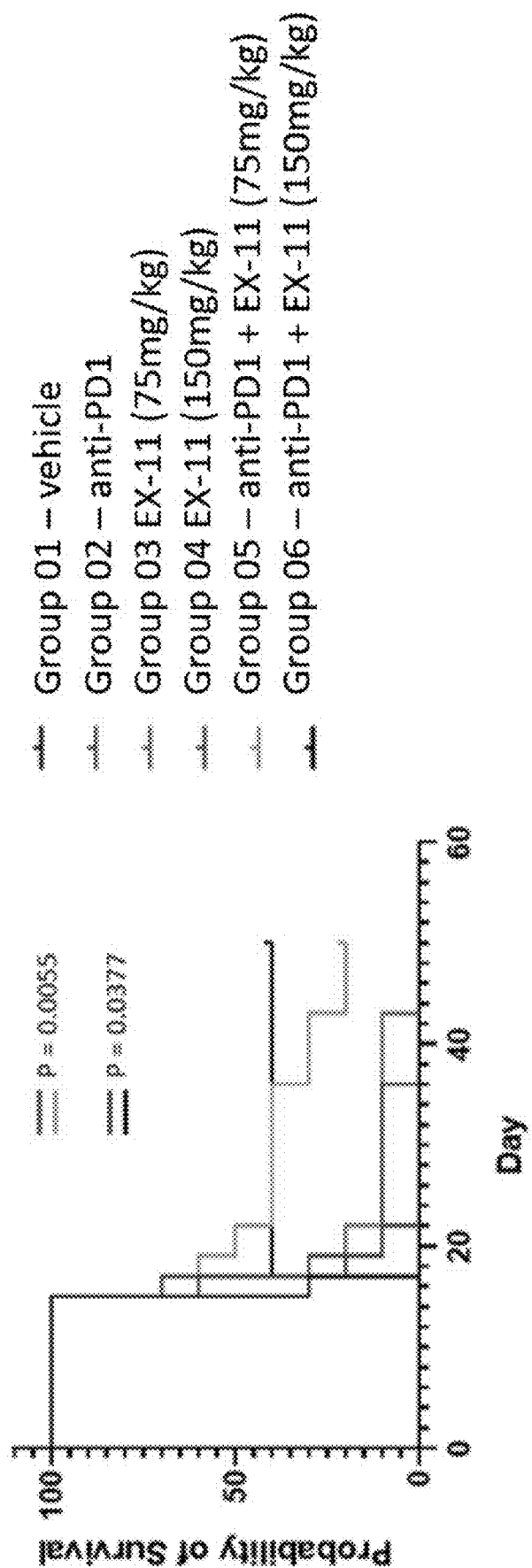
FIG. 14A shows a Kaplan-Meier survival curve for mice treated as described in Example M. A log-rank (Mantel-Cox) test used to calculate significant differences in survival.
Figure 14B:
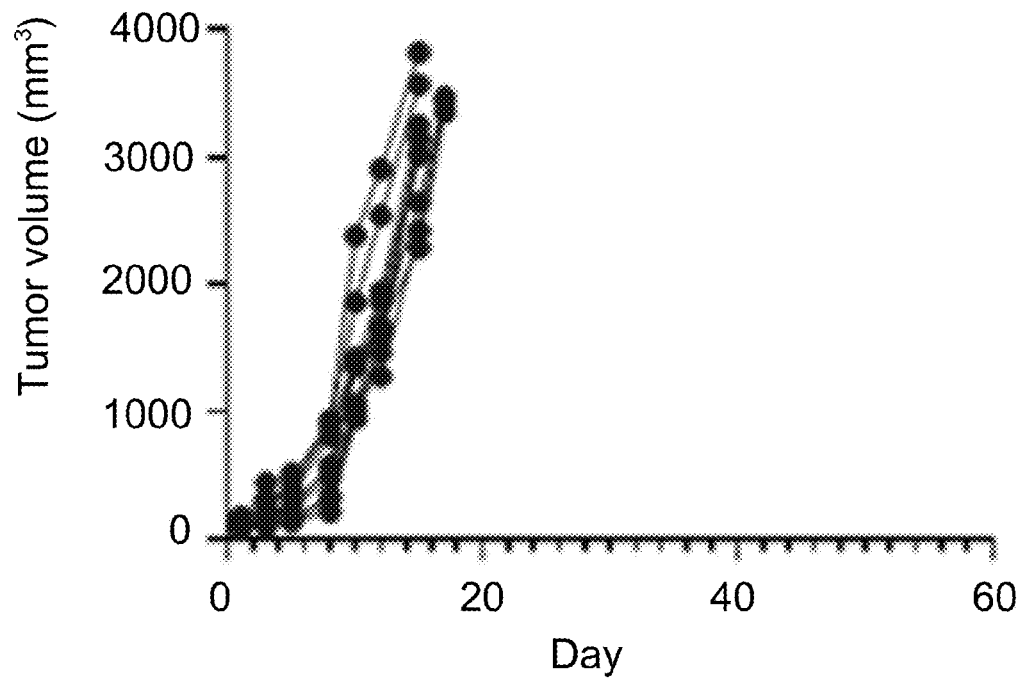
FIG. 14B shows individual tumor volume curves for Group 1 during the dosing phase of Example M.
Figure 14C:
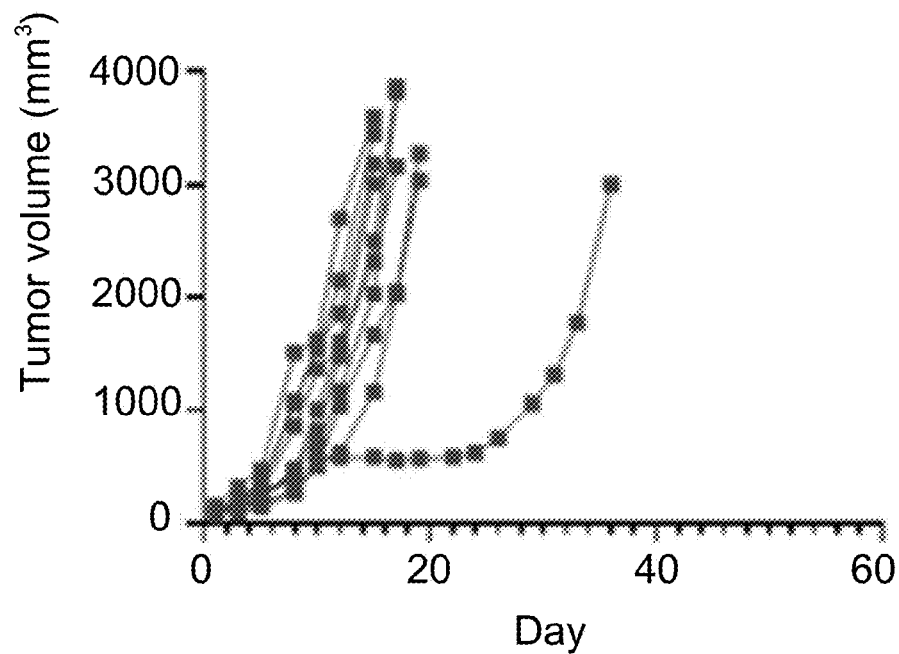
FIG. 14C shows individual tumor volume curves for Group 2 during the dosing phase of Example M.
Figure 14D:
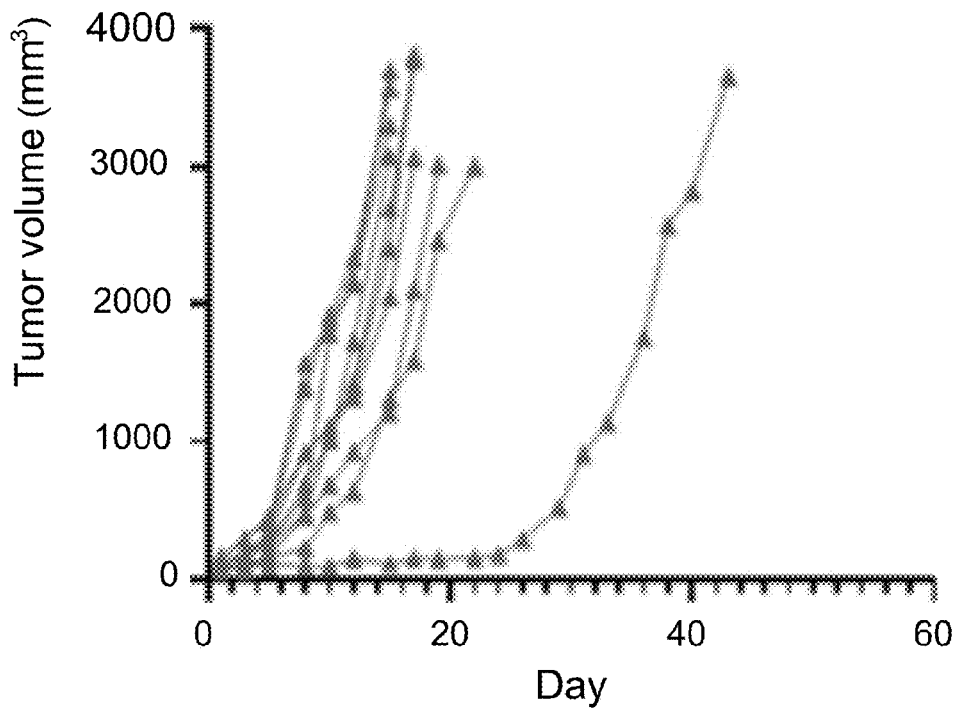
FIG. 14D shows individual tumor volume curves for Group 3 during the dosing phase of Example M.
Figure 14E:
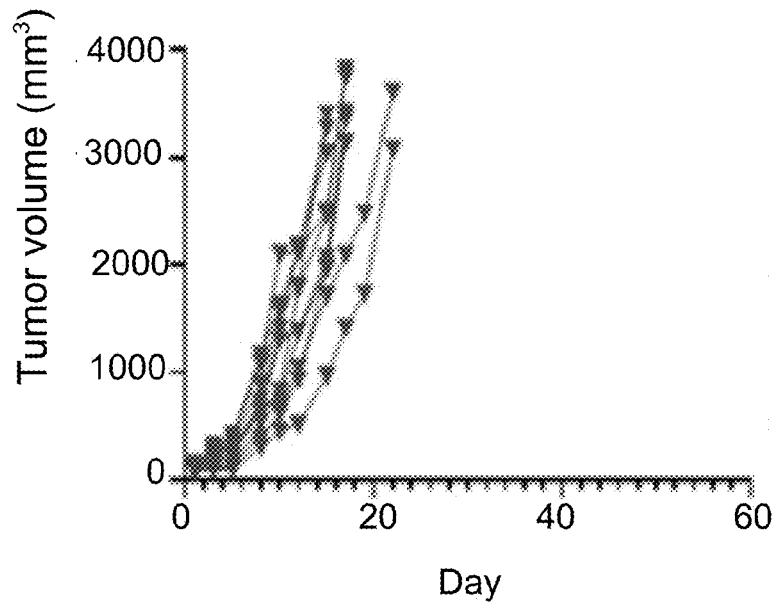
FIG. 14E shows individual tumor volume curves for Group 4 during the dosing phase of Example M.
Figure 14F:
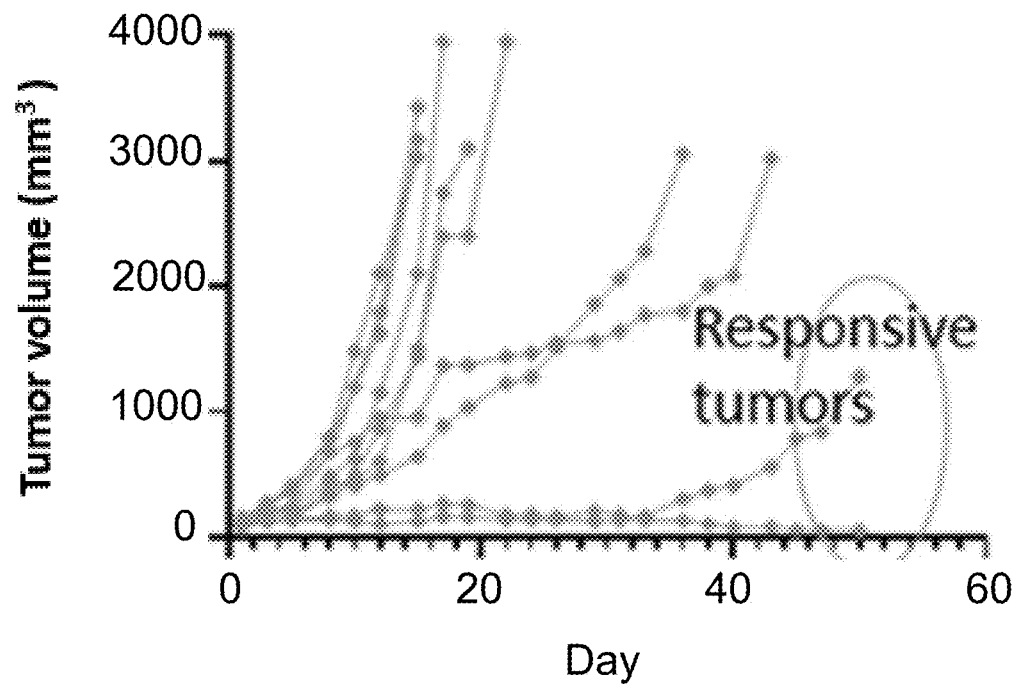
FIG. 14F shows individual tumor volume curves for Group 5 during the dosing phase of Example M.
Figure 14G:
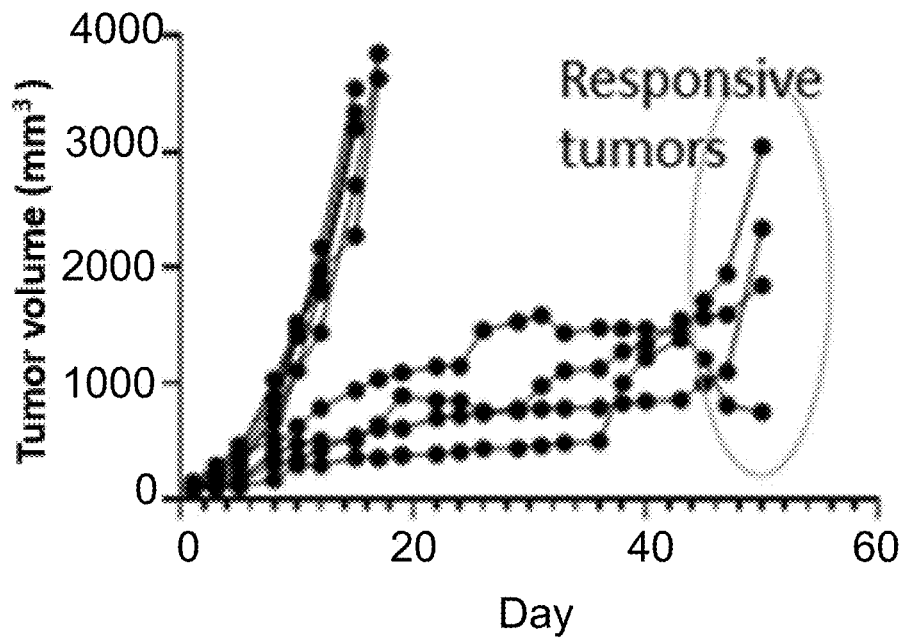
FIG. 14G shows individual tumor volume curves for Group 6 during the dosing phase of Example M.

An increase in survival was found in the EX-11 (75 mg/kg)+anti-PD-1 group compared with the vehicle control (P=0.0055) (FIG. 14A). This was also true for the EX-11 (150 mg/kg)+anti-PD-1 group compared with the vehicle control (P=0.0377). Mice that received either EX-11 alone or anti-PD-1 alone did not exhibit an increase in survival compared with the vehicle control. Consistent with these findings, a subset of mice in the EX-11$^+$ anti-PD-1 groups responded to treatment, as their tumor growth rate was reduced compared to non-responsive mice within the same groups (FIGS. 14F and 14G). The tumor growth rate of non-responsive mice closely resembled the tumor growth rate of tumors in the vehicle, EX-11 alone, and anti-PD-1 alone groups. Figures were generated in GraphPad Prism.

Example N—Cachexia Model

TGF-β1 signaling regulates ovarian cancer progression during initial carcinogenesis, tumor dissemination, and reestablishment of ascites through peritoneal cavity. Clear cell carcinoma is a specifically aggressive and therapy-resistant subtype of epithelial ovarian cancer. ES-2 clear cell carcinoma in vivo model was used to test efficacy of EX-11 in reducing ovarian tumor burden as determined by ascites fluid volume assessment. Because ALK5 signaling can regulate muscle growth and wasting, the efficacy of EX-11 in preventing ovarian cancer-induced cachexia was tested. Muscle health was assessed using histological evaluation of heart muscle tissue, and by comparison of gross weight of hind limb between the different treatment groups.

Sixteen-week-old female athymic nude mice were injected with two million ES-2-luc cells. The cells used were harvested and resuspended in four hundred microliters of PBS and implanted via an i.p. injection. Five days after cell implantation, mice were randomized and enrolled ten animals per group for test or vehicle control group. Randomization was performed based on weight. Bioluminescence was verified in study animals to confirm disease progression before dosing began on day five.

All compounds were dissolved in TWEEN20 (10%) in water and administered via oral gavage. The drug suspensions were sonicated for fifteen minutes to generate a fine particle suspension before administration. Mice were dosed with EX-11 at a level of one hundred and fifty mg/Kg twice a day.

Mortality was recorded for animals found dead in the cage, and for the animals sacrificed based on humane end point based on main three criteria—loss of mobility and response, wasting with pronounced ascites fluid buildup, and palpable drop in body temperature (animals were assessed as cold to touch when handled in gloves).

On study day 22, the remaining surviving animals in the vehicle group were determined moribund, and the study was terminated based on humane end point criteria. Two hours after final drug administration, animals were sacrificed, ascites fluid was collected using 1 mL syringe fitted with 21G needle and dispensed into pre-weighted fifteen milliliter conical tubes for weight assessment. Tissues were harvested and formalin fixed for histological evaluation, and representative samples were also snap frozen and stored at negative eighty degrees Celsius until further processing. The entire right hind limb was detached at hip joint, skin was removed, and samples were frozen and stored for weight analysis. Un-implanted littermates were used for comparison with disease-free tissues such as muscle and heart.

Figure 15A:
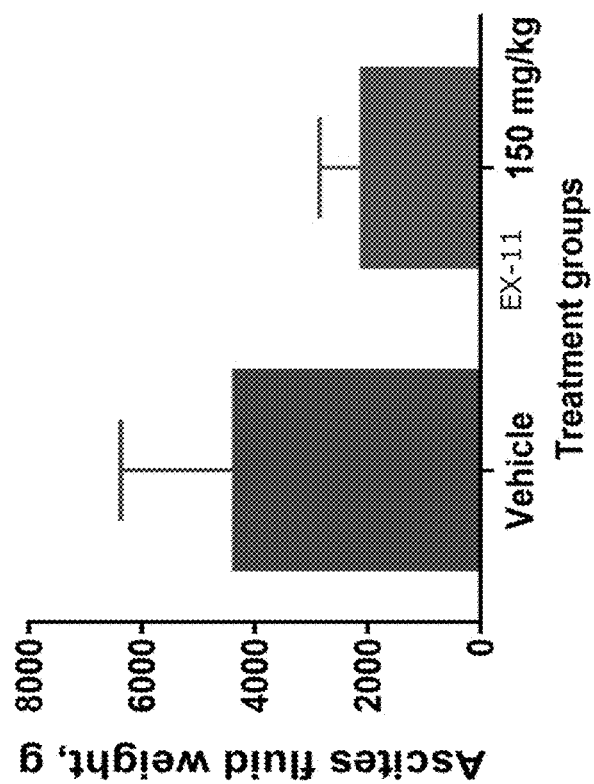
FIG. 15A shows EX-11-treated animals from Example N had reduced ascites fluid volume compared to vehicle-treated group.
Figure 15B:
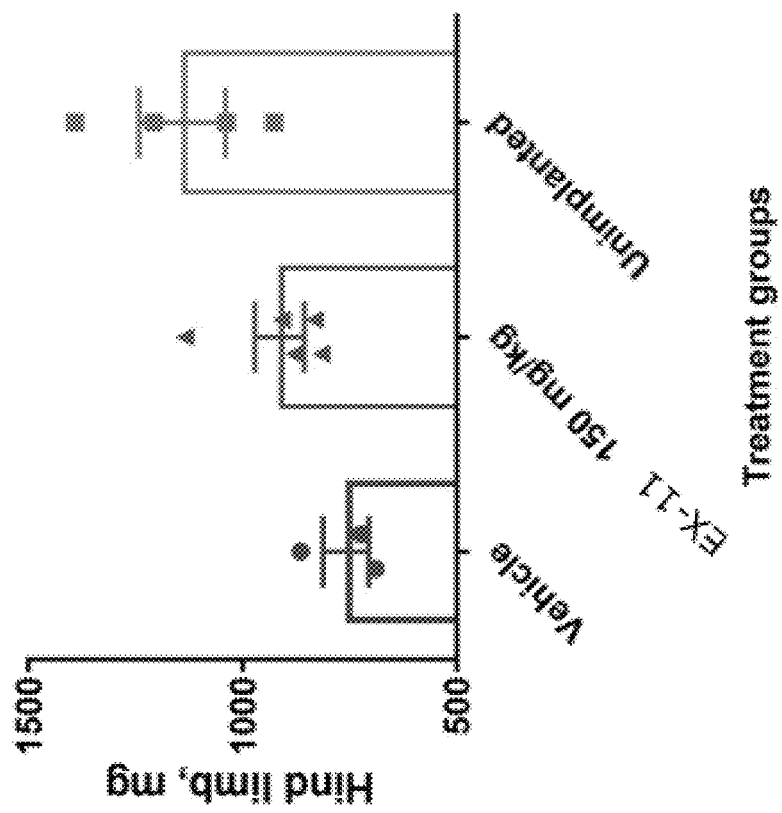
FIG. 15B shows EX-11 BID treatment at 150 mg/Kg, as described in Example N, improved hind limb weight retention compared to vehicle treatment.

FIGS. 15A and 15B summarize results that indicate that EX-11 treatment at 150 mg/Kg can delay disease progression in ovarian clear cell carcinoma model using ES-2-luc cells implanted into athymic nude female mice. Comparison of ascites fluid volume collected from EX-11 and vehicle-treated animals shows reduction in total fluid volume in EX-11-treated group (FIG. 15A). Whole limb weights were recorded higher for the EX-11 treated group compared to vehicle-treated animals (FIG. 15B).

Example O—Tolerability Model

Vactosertib and PF-06952229 are two additional ALK5 small molecule inhibitors that are competitors of EX-11. Both compounds are currently in clinical trials. The objective of this study was to evaluate preclinically the in vivo tolerability of EX-11 compared with vactosertib and PF-06952229 in athymic nude mice, and approximate the safety margin of each drug.

Female, athymic nude mice (aged 6-8 weeks) were randomized to one of 12 study arms (n=3 per arm) (Table 16) and weighed prior to dosing. Mice were dosed via oral gavage either once daily (QD), or bi-daily (BID) for five days. The vehicle for EX-11 and vactosertib (Vacto) was 10% tween-20, 90% ddH$_2$O. The vehicle for PF-06952229 (PF) was 10% DMSO, 40% PEG300, 5% tween-80, 45% saline. For the vehicle alone group in this study, the PF-06952229 vehicle was used. At the end of each day for 10 days, mice were weighed, and symptoms of toxicity (if present) were recorded. A qualitative determination of overall toxicity was made based on the number and severity of symptoms for each cohort. The safety margin was determined at the end of day 10 based on the following equation: (maximum tolerated dose)/(minimum effective dose).

TABLE 16

Study Arms

| Dose | EX-11 (BID) | Vacto (QD) | Vacto (BID) | PF (BID) |
|---|---|---|---|---|
| 1,000 mpk | X | | | |
| 300 mpk | X | X | X | X |
| 150 mpk | | X | X | X |
| 50 mpk | | X | X | X |
| Vehicle | | | | X |

No significant loss of weight was observed in any mouse in any arm except for mouse #3 in the vactosertib 300 mg/kg (BID) cohort. This mouse exhibited dose-limiting-toxicity (DLT) by day 4 with 18% weight loss. The mouse was given a dosing holiday and rebounded to within 5.5% of its original weight by day 10. In EX-11 arms, no detectable toxicity was observed in any mouse at either 300 or 1,000 mg/kg (BID).

The minimum effective dose of EX-11 based on prior studies with EX-11 is 150 mg/kg (BID). This means that the safety margin for EX-11 is greater than or equal to a 6.7-fold increase (1000/150=6.7) from the minimum effective dose (MED) in this model.

In the vactosertib arms, mice fared well at 150 and 300 mg/kg (QD). Mild but tolerable toxicity was observed at 150 mg/kg (BID). Mice experienced DLT at 300 mg/kg (BID). The minimum effective dose of vactosertib based on animal studies ranges from 25-40 mg/kg (QD), although humans are dosed BID in clinical trials at comparable concentrations based on mg/kg. This means that the safety margin for vactosertib likely ranges from between a 3.75 and 6-fold increase (150/40=3.75) (150/25=6) from the MED in this model.

In the PF-06952229 arms, mice experienced DLT at 150 mg/kg (BID) and up. The minimum effective dose has been shown to be 30 mg/kg (BID) in animal studies. Because PF-06952229 was only tolerated at 50 mg/kg (BID) in our study, the data suggest that the safety margin for this drug has approximately a 1.7-fold increase (50/30=1.7) from the MED in this model. No detectable toxicity was observed in the vehicle control arm.

In summary, EX-11 appears to have a larger safety margin than both vactosertib and PF-06952229 over a 5-day dosing window and a 10-day examination period.

Example P—Nanostring Analyses

The objective of this study was to determine the differential gene expression (DGE) patterns of 4T1, EMT6, and S91 tumors treated with EX-11+immune checkpoint inhibitor (ICI), EX-11 alone, ICI alone, or vehicle control. For the purpose of this study, ICI=anti-PD-1 or anti-PD-L1, as indicated.

For NanoString assays, tumors from three syngeneic models of cancer were used:

| Study No. | Cell Line | Mouse Model |
|---|---|---|
| 1 | 4T1 (triple-negative breast cancer [TNBC] | Balb/c mice |
| 2 | EMT6 (TNBC) | C3H mice |
| 3 | S91 (melanoma) | DBA/2 mice |

RNA was isolated from the frozen tumors of ≥3 mice per group using the Direct-Zol RNA Miniprep (Zymo Research). The treatment arms and number of mice/tumors used for downstream applications is outlined in Table 17 (R=Responder, NS=Non-responder).

TABLE 17

Treatment Arms and Number of Mice for each Study

| Study | Group | Mice |
|---|---|---|
| 4T1 | Vehicle | 9 |
| | aPD-1 | 6 |
| | EX-11 | 7 |
| | EX-11 + aPD-1 | 4 |
| EMT6 | Vehicle | 3 |
| | aPD-1 | 3 |
| | EX-11 | 3 |
| | aPD-L1 | 3 |
| | EX-11 + aPD-1 | 3 |
| | EXH + aPD-L1 | 3 |
| S91 | Vehicle | 9 |
| | aPD-1 | 8 |
| | EX-11 | 7 |
| | EX-11 + aPD-1 (NS) | 12 |
| | EX-11 + aPD-1 (R) | 5 |

Equal concentrations of RNA for each tumor within each group were pooled. Two-hundred ng of RNA per group was used for downstream applications. Three separate NanoString nCounter panels were used per protocol: 1) Fibrosis, 2) PanCancer Pathways, 3) Immunology. RCC raw data files were uploaded into nCounter 4.0 software where counts were normalized to housekeeping genes. Gene lists in each panel were combined into a single spreadsheet for downstream analyses. For genes found in ≥1 panel, mean count values were used. RStudio software was used to generate heat maps of DGE signatures within each study for each group. Ingenuity Pathway Analysis (IPA) was used to identify the dysregulated signaling pathways within each study for each group.

For RStudio analyses, heat maps produced noticeable patterns of DGE within each study and between each group. Arguably, the most striking finding was that of S91 EX-11+ anti-PD-1 or anti-PD-L1 (ICI) (Responders) compared to S91 EX-11+ICI (Non-responders). The non-responders clustered closely with the vehicle control group, whereas the responders clustered further from the non-responders and control groups than from all other groups in the study. This suggests that the decreased tumor growth rate of the responders is a result of a differential pattern of gene expression induced by the EX-11+ICI combination—a result not seen in the non-responders for reasons not yet understood.

Figure 16:
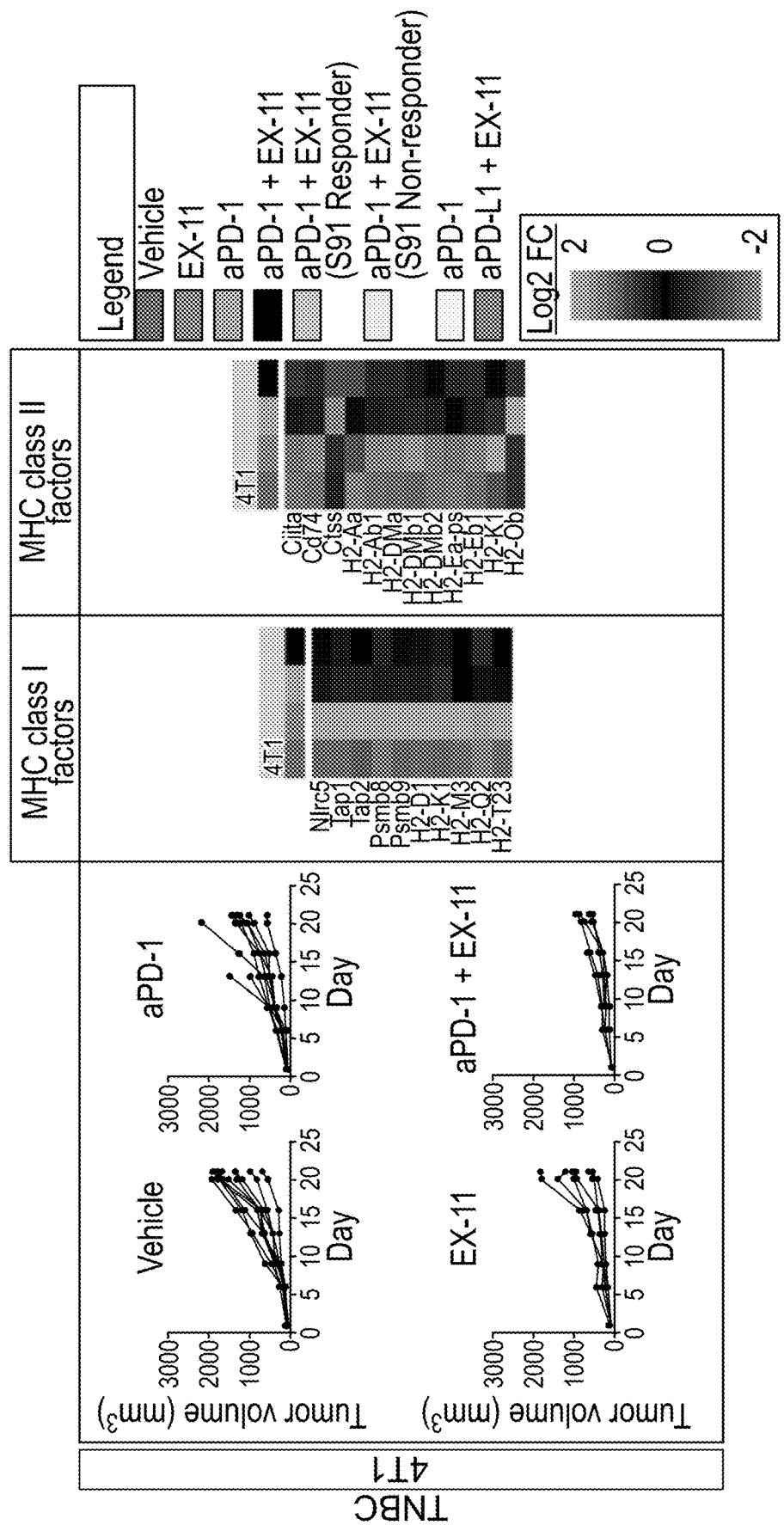
FIG. 16 shows tumor growth curves for all groups in 4T1, EMT6, and S91 studies used in Example P (left-hand portion of the figure), and heat maps of factors involved in MHC class I and class II antigen presentation pathways resulting from the Nanostring analyses described in Example P (right-hand portion of the figure).
Figure 16:
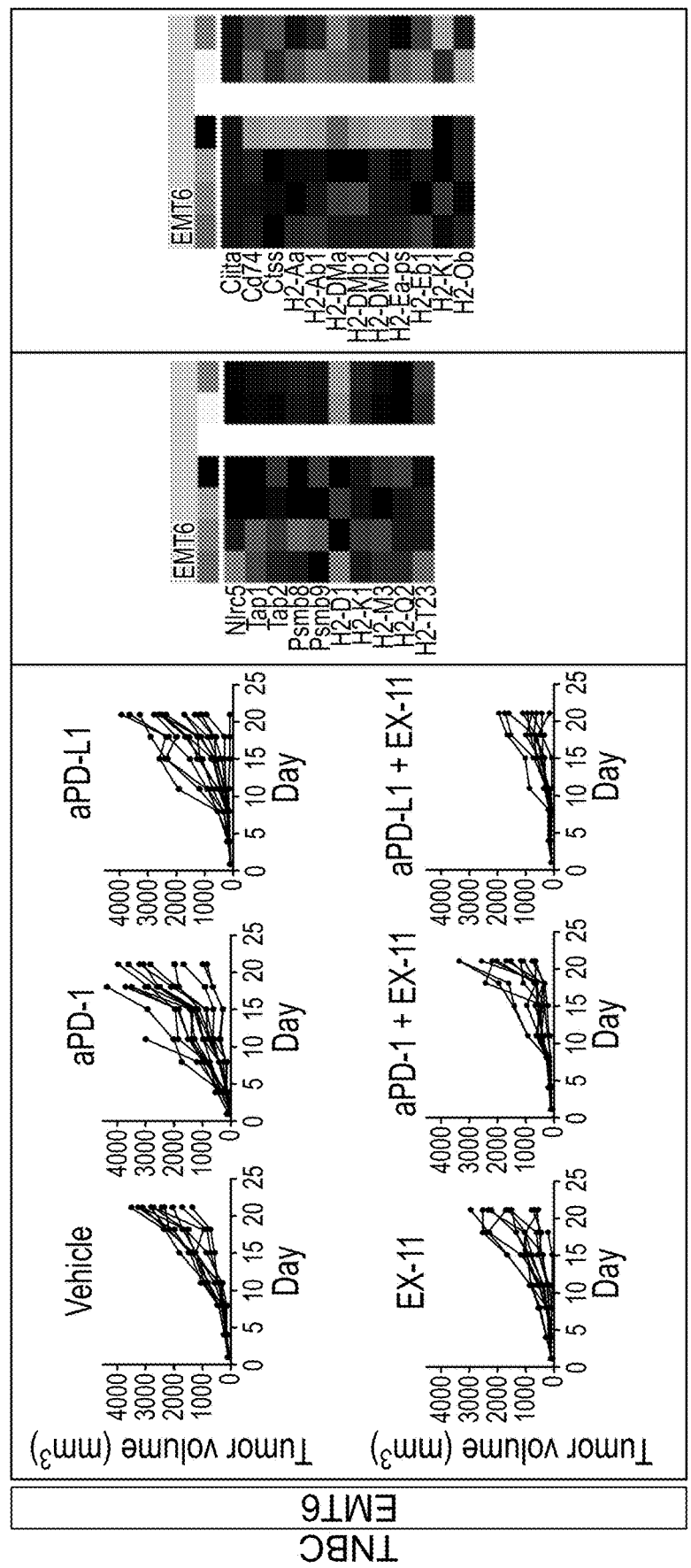
Figure 16:
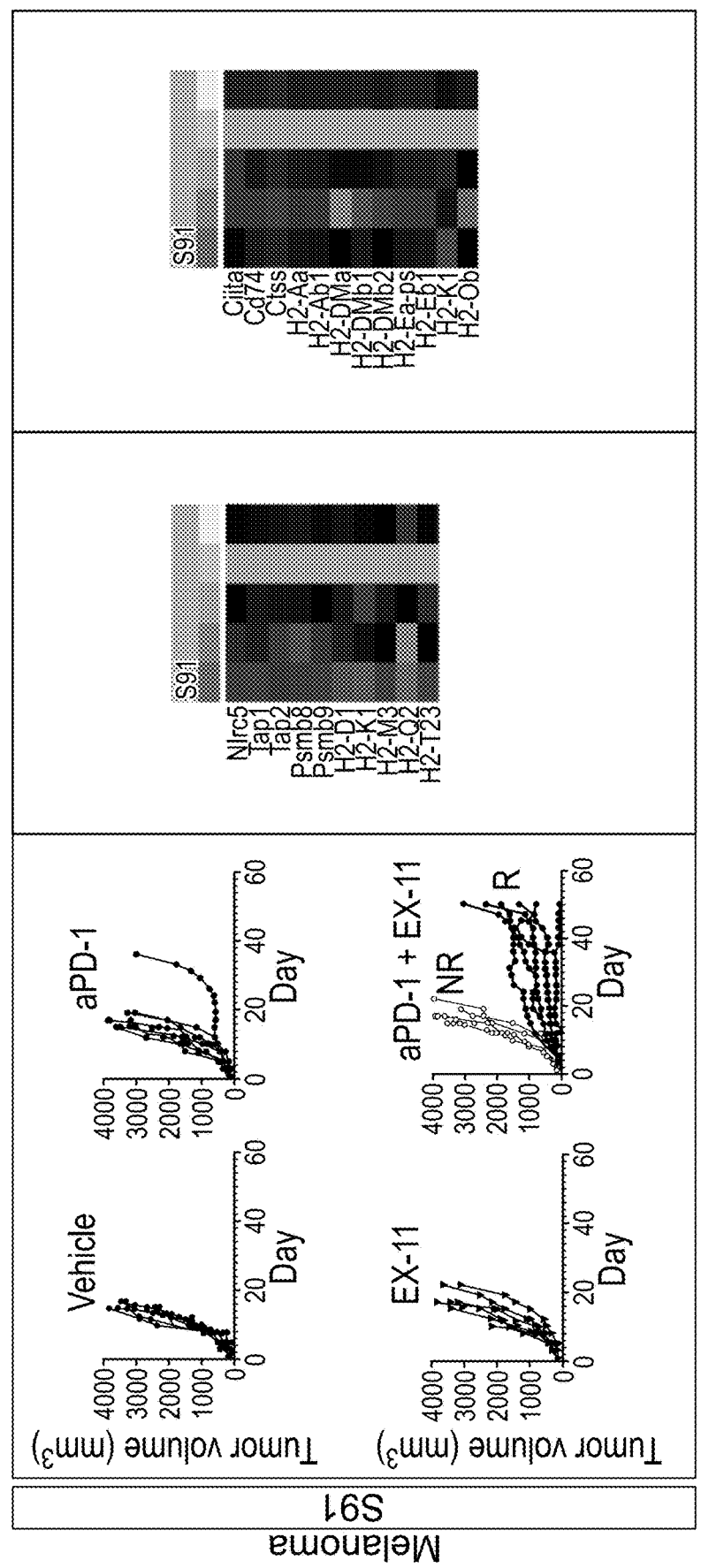

For IPA analyses, the antigen presentation pathway (APP) was determined to be the most highly dysregulated signaling pathway subject to EX-11 alone and/or EX-11+ICI (depending on the study) compared with the vehicle and/or ICI alone groups. This was a common theme among all three studies. These data suggest that EX-11 upregulates the APP in tumors, and that the addition of ICI often enhances this effect (FIG. 16).

In summary, these results have led to the hypothesis that upregulation of the APP by EX-11 sensitizes the ICI response to elicit anti-tumor immunity.

Example Q—Bleomycin-Induced Lung Fibrosis Study

Fibrosis, the formation of excess connective tissue causing stromal hardening and scar formation is a hallmark of cancer. Up to 20% of cancers are linked to chronic, inflammation-related fibrosis, including hepatocellular, gastric, esophageal, head and neck, colon, pancreatic, cervix, and vulvar cancers. The contribution of fibrosis for early cancer development remains unclear; however, in some advanced solid tumors it is believed that fibrotic tissues act like a barrier, preventing therapeutic agents like chemotherapy or biologics from penetrating the tumor tissue. Additionally, strong fibrotic tissue is thought to contribute to excluding immune cells from entering the tumor core, creating immune excluded or immune desert phenotypes. To evaluate the anti-fibrotic properties of Ex-11, a prophylactic model of bleomycin-induced lung fibrosis in male C57BL/6 mice was utilized, and various endpoints evaluated.

All mice in this study were 8-week-old male C57BL/6 mice purchased from Taconic. On Day −2 prior to bleomycin administration, all animals were weighed and distributed into groups with 10 mice each (Table 18) such that each group of animals contained animals of similar body weights.

TABLE 18

Treatment Groups and Parameters for the Study

| Grp | N | Group Name | Treatment (Days −1 to 21) | In-Life Study Parameters | Measurements and Harvest |
|---|---|---|---|---|---|
| 1 | 10 | Naïve | Vehicle | Body weights 3x/week Daily observation | Body weights Lungs inflated and fixed in formalin for H&E and MT staining to assess Ashcroft score, inflammation and fibrosis |
| 2 | 10 | Bleomycin + Vehicle | Vehicle | | |
| 3 | 10 | Bleomycin + Ex-11 75 mg/kg (150 mg/kg per day) | PO, BID | | |
| 4 | 10 | Bleomycin + Pirfenidone 100 mg/kg (200 mg/kg per day) | PO, BID | | |

On day 0, animals were treated with 1.5 U/kg bleomycin (Blenoxane catalog number NDC 61703-323-22, Hospira Pharmaceutical) intratracheally, except Group 1, which was administered normal saline via oropharyngeal route to serve as the healthy naïve control group. Prophylactic treatment was administered from one day prior to bleomycin administration to day 21 post bleomycin administration. On Day 21, only the morning dose was administered. Animals were harvested on day 21 and lung weights were measured. Body weights of all mice was recorded at least three times a week beginning on Day −2 and ending on the day of harvest, Day 21. Pirfenidone was used as positive control compound, as it is an FDA-approved drug for the treatment of idiopathic pulmonary fibrosis (IPF) in humans. All compounds were prepared in 10% Tween-20 in water; a homogenous suspension was formulated using a magnetic stir bar.

Only one animal in the pirfenidone group was lost during the study; all other animals survived. At the end of the study, total lung tissues were weighed and fixed for histological examination, which was conducted by a trained pathologist blinded to the treatment groups. Specifically, whole lungs from each mouse were paraffin-embedded in a single block. Two slides from each block were sectioned to the depth of the mainstem bronchi (near the center of each lobe) and stained with either hematoxylin and eosin (H&E) or Masson's trichrome (MT). Glass slides were evaluated using light microscopy by a board-certified veterinary pathologist. Lung sections were scored according to the methods described below, evaluating five randomly chosen fields in each tissue. Fixed lungs were sectioned, and consecutive tissue sections were stained with H&E or MT. Various pathological scoring parameters were used to determine the average Ashcroft score, as well as average inflammation and collagen deposition indicating fibrosis.

Parameter of scoring formalin fixed lung sections:
Modified Ashcroft Score: H&E-stained lung sections were scored according to the modified Ashcroft scale. Scores for five representative 200× microscopic fields per sample were averaged to obtain a mean score for each animal.
Grade 0=Normal lung
Grade 1=Minimally detectable thickening of alveolar walls Grade 2=Mild thickening of alveolar walls
Grade 3=Moderate contiguous thickening of walls with fibrous nodules
Grade 4=Thickened septa and confluent fibrotic masses totaling less than 10% of the microscopic field
Grade 5=Increased fibrosis with definite damage to lung structure and formation of fibrous bands or small fibrous masses between 10-50% of the microscopic field
Grade 6=Large contiguous fibrotic masses consolidating more than 50% of the microscopic field
Grade 7=Severe distortion of structure and large fibrous areas
Grade 8=Total fibrous obliteration of lung within the microscopic field Inflammation: This feature included infiltration/aggregation of lymphocytes, macrophages, and neutrophils. Inflammatory cell infiltrates were scored in H&E-stained sections and were graded for severity on a 0-5 scale:
0=not present
1=minimal
2=mild
3=moderate
4=marked
5=severe Increased collagen (fibrosis): This feature was scored in MT-stained sections according to extent and based on the abundance of collagen deposition above baseline levels:
0=normal levels of collagen
1=minimally increased (<10% of the lung affected)
2=mildly increased (10-25% of the lung affected)
3=moderately increased (26-50% of the lung affected)
4=markedly increased (51-75% of the lung affected)
5=severely increased (>75% of the lung affected)

All animals reached the end of the study on day 21 except for one animal in group 4 (pirfenidone group). The body weight of all study animals throughout the study is shown in FIG. 19A. No severe weight loss of over 5-10% was reported in any of the treatment groups including when dosing with Ex-11 at 75 mg/kg twice a day in this model. The largest percent change in weight was observed in group 4 on day 9 at an average of −1.2%. Overall, all treatment arms were well tolerated.

Figure 18A:
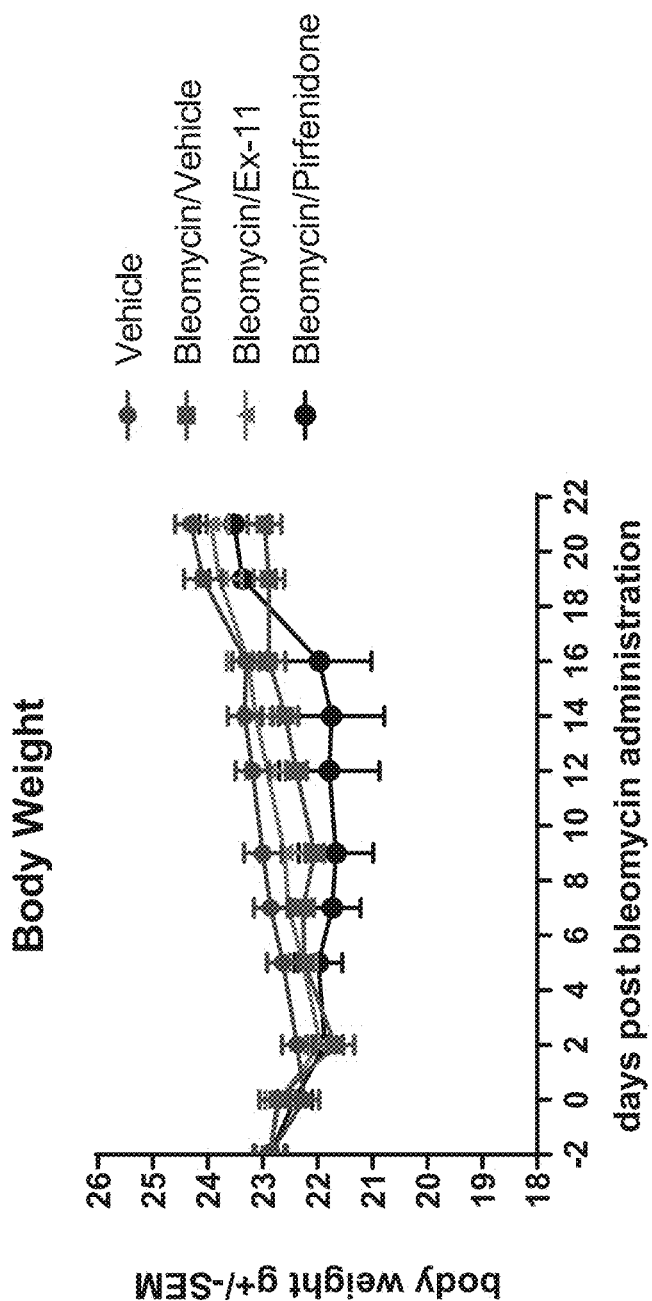
FIG. 18A shows body weight (recorded in grams) of all animals in the study described in Example Q from day 0 to day 21. Each data point represents the average of each group with the error bars indicating the standard error of the mean.
Figure 18B:
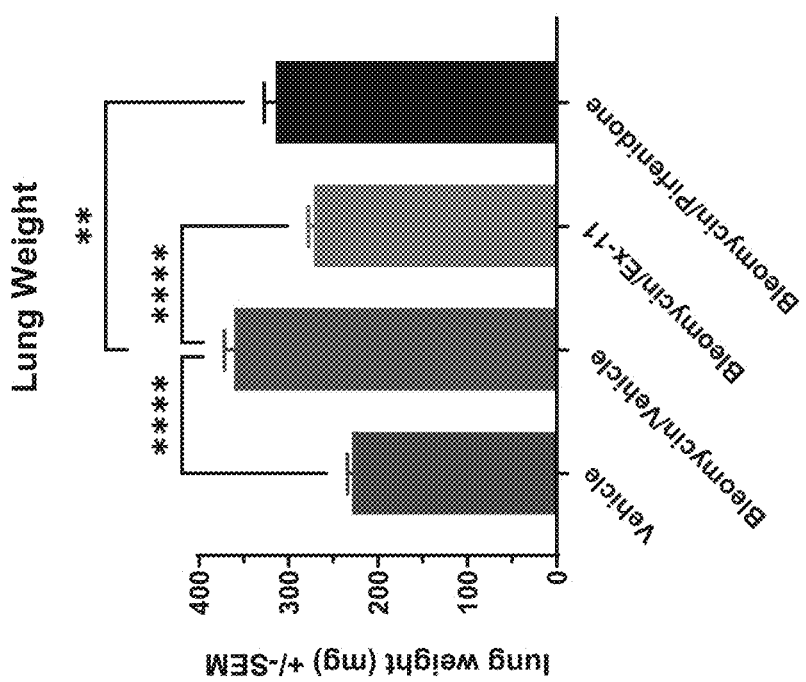
FIG. 18B shows mean lung weights in grams averaged from each group in the study described in Example Q on day 21. Error bars indicate standard error of the mean (SEM). ** adjusted p value <0.0001 and  adjusted p value 0.0037, both by ordinary one-way ANOVA test.
Figure 18C:
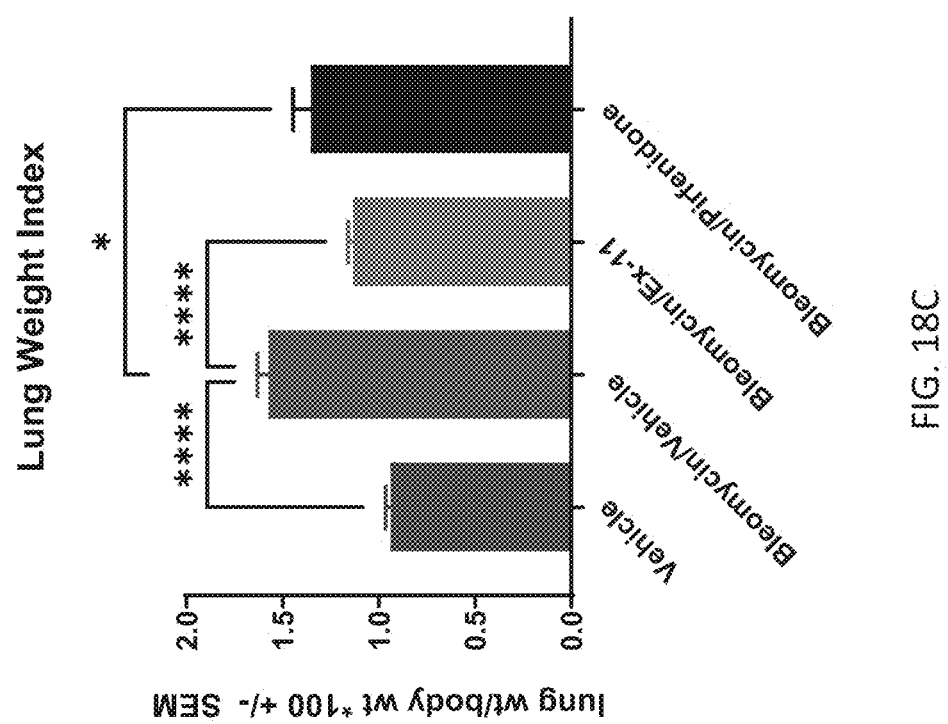
FIG. 18C shows mean lung weights normalized to the weight of each animal averaged from each group in the study described in Example Q on day 21. Error bars indicate standard error of the mean (SEM). **** adjusted p value <0.0001 and * adjusted p value 0.0228, both by ordinary one-way ANOVA test.

Upon study completion, the total lung weight was determined. Diseased lungs weighed significantly more (group 2) and a significant decrease in lung weight was observed when animals were treated with Ex-11 or the comparator compound pirfenidone (FIG. 18B). When normalizing the lung weights to total animal weight (also known as lung weight index), the difference between bleomycin/vehicle and bleomycin/Ex-11 groups was still highly statistically significant (FIG. 18C).

Figure 18D:
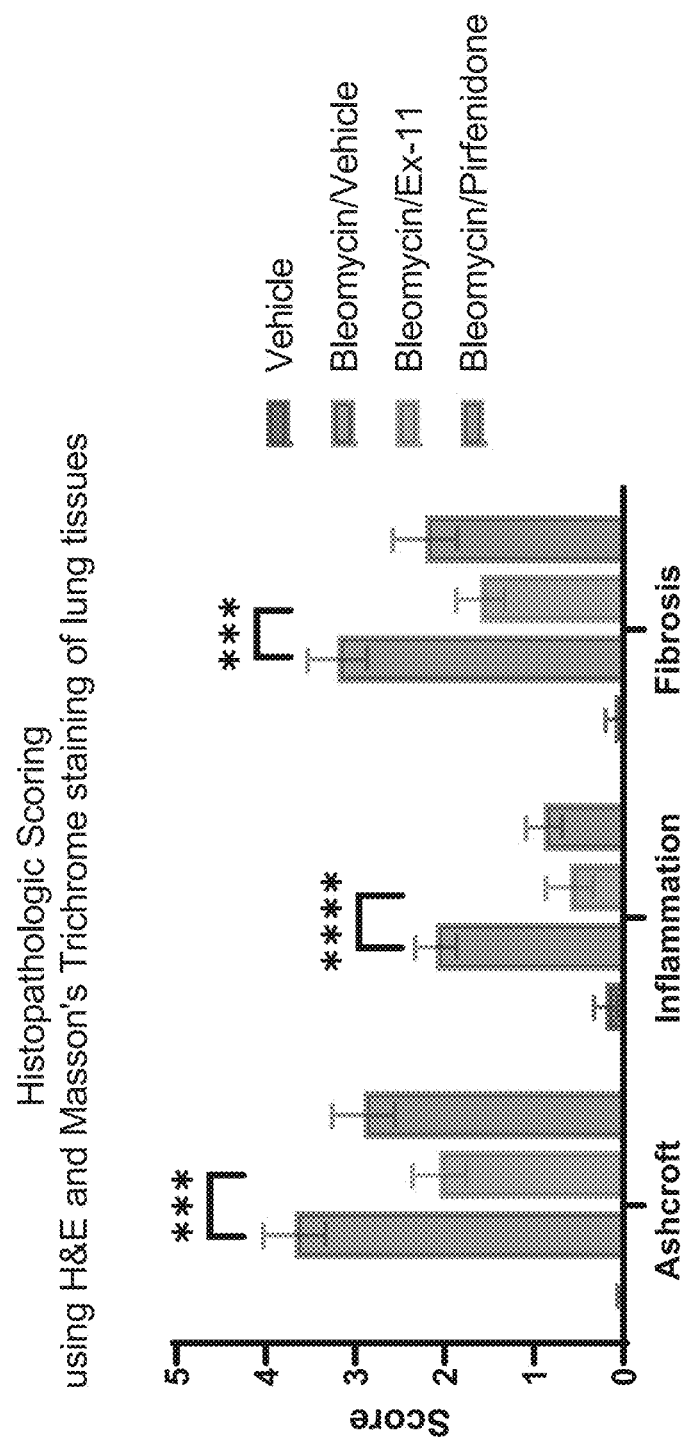
FIG. 18D shows the results of histopathologic scoring using H&E or Masson's trichrome staining of lung tissues from the study described in Example Q.
Figure 18F:
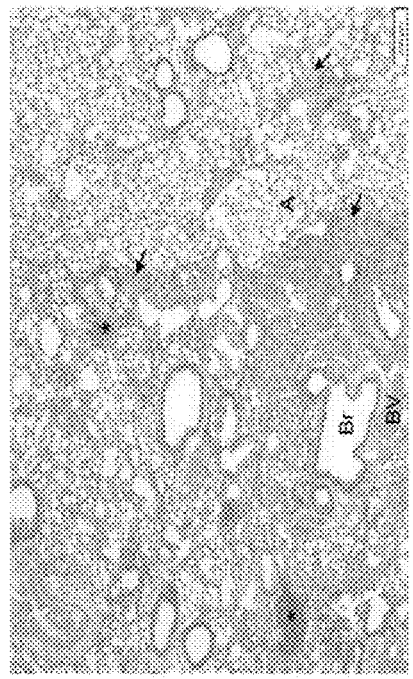
FIG. 18F is a representative H&E image from a bleomycin/vehicle group animal from the study described in Example Q, and shows areas of less affected alveoli (A) are patchy. Foci of mixed cell infiltrates (*) are present in regions of fibrosis. A representative blood vessel (BV) and bronchiole (Br) are indicated.
Figure 18H:
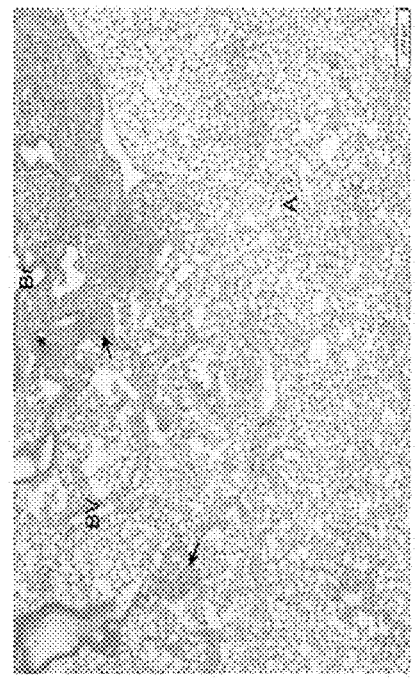
FIG. 18H is a representative H&E image from a bleomycin/pirfenidone animal from the study described in Example Q, and shows regionally extensive fibrotic mass and occasional smaller nodules (arrows) observed within the pulmonary parenchyma. The region of fibrosis contained low numbers of inflammatory cells (*). The majority of alveoli (A) captured in the image were unaffected. A representative blood vessel (BV) and bronchiole (Br) are indicated.
Figure 18E:
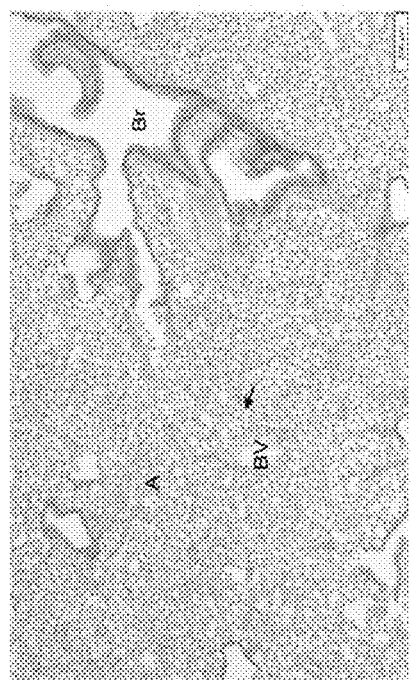
FIG. 18E is a representative H&E image from a naïve animal from the study described in Example Q, and shows alveoli (A) composed of thin-walled septa (arrow) and clear air space. A representative blood vessel (BV) and bronchiole (Br) are also indicated.
Figure 18G:
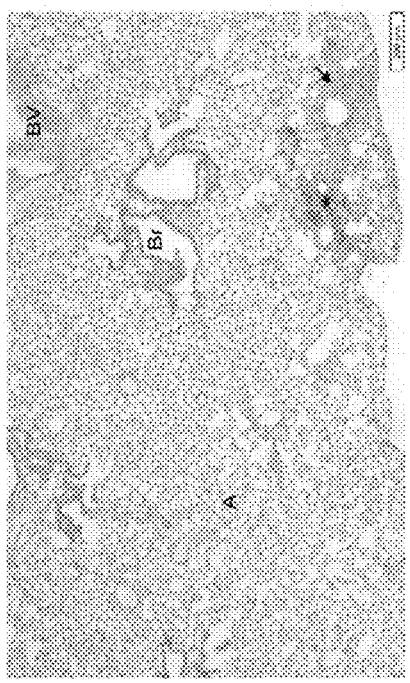
FIG. 18G is a representative H&E image from a bleomycin/EX-11 group animal from the study described in Example Q, and shows a focal fibrotic mass (arrow) observed along the margin of the lung. The region of fibrosis contained a focus of inflammation (*). Remaining alveoli (A) captured in the image are within normal limits. A representative blood vessel (BV) and bronchiole (Br) are indicated.
Figure 18J:
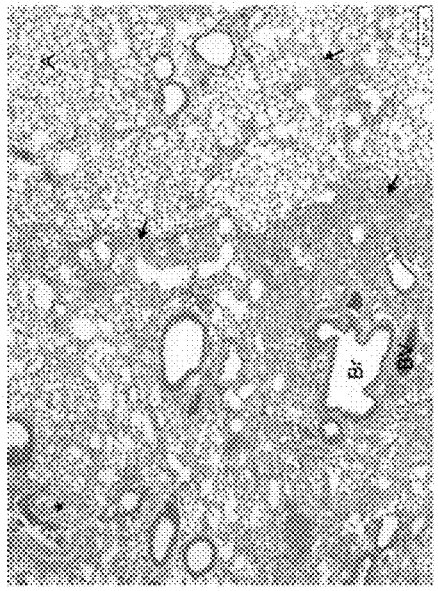
FIG. 18J is a representative Masson's trichrome image from a bleomycin/vehicle group animal from the study described in Example Q, and shows increased collagen (light blue staining) throughout the section and away from bronchioles (Br) and blood vessels (BV), consistent with fibrosis. Resident collagen (*) was restricted to the perivascular/peribronchiolar spaces. The pulmonary parenchyma in a majority of the captured image was replaced by a multifocal to coalescing fibrotic masses (arrows). Areas of less affected alveoli (A) were patchy.
Figure 18L:
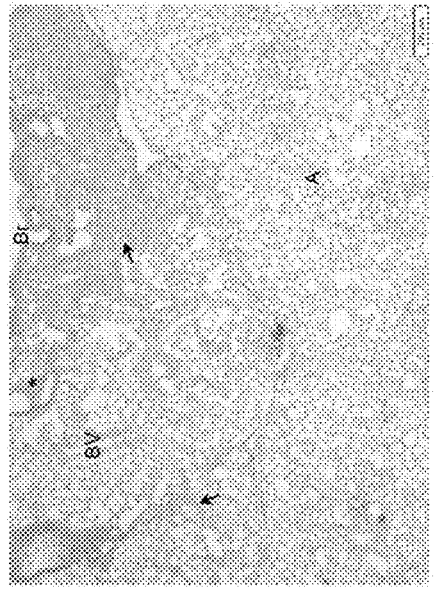
FIG. 18L is a representative Masson's trichrome image from a bleomycin/pirfenidone group animal from the study described in Example Q, and shows areas of increased collagen (fibrosis; arrows) form one larger mass and occasional smaller nodules within the parenchyma. Unaffected alveoli (A) were common and comprised the majority of the captured region. Resident collagen (*) was observed around bronchioles (Br) and blood vessels (BV).
Figure 18I:
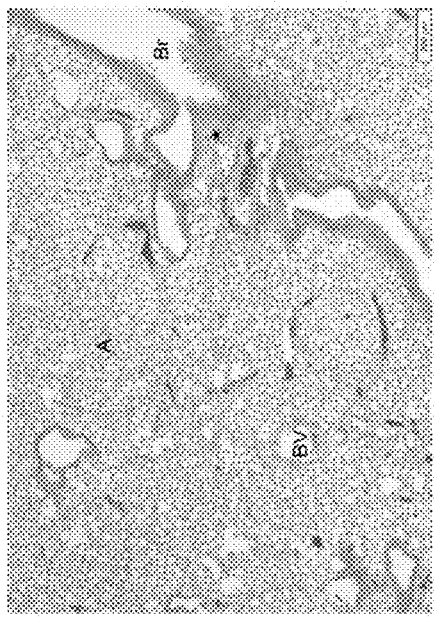
FIG. 18I is a representative Masson's trichrome image from a naïve animal from the study described in Example Q, and shows that in non-lesioned lung, resident supportive collagen (*; bright blue staining) was limited to the areas around blood vessels (BV) and bronchioles (Br). Representative alveoli (A) are indicated.
Figure 18K:
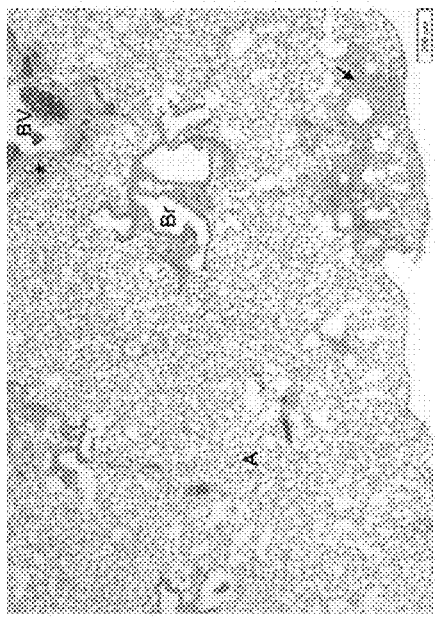
FIG. 18K is a representative Masson's trichrome image from a bleomycin/Ex-11 group animal from the study described in Example Q, and shows fibrosis (arrow) formed a single mass along the lung margin. The remainder of the alveoli (A) in the captured image were normal. Resident collagen (*) was observed around bronchioles (Br) and blood vessels (BV).

FIG. 18D shows the average scores when evaluating all the available lungs from study animals when evaluating five randomly chosen fields of each lung tissue. The trained pathologist determined the Ashcroft score as well as average inflammation using H&E-stained tissue. Average fibrosis/collagen deposition was determined using Masson's Trichrome-stained tissue with red staining for keratin and muscle fibers, blue or green color for collagen, light red or pink for cytoplasm, and dark brown to black cell fornuclei. The difference between group 2 (bleomycin/vehicle) and group 3 (bleomycin/Ex-11) shows a highly statistically significant reduction in the average score when using an ordinary one-way ANOVA test (Ashcroft score: adjusted p-value: 0.0002, Average lung inflammation: adjusted p-value: <0.0001, Average lung fibrosis/collagen deposition: adjusted p-value: 0.0002). FIGS. 19E-L show representative images at 40× magnification for each treatment group when using H&E and MT staining, respectively.

Example R—HLA Expression in KGN Cell Line

KGN cells were treated with 30 nM EX-11, 300 nM EX-11 or DMSO in the absence or presence of 1 ng/mL TGFβ for 72 hours. Cells were then washed, collected and incubated in the dark at 4° C. for 1 hour with a pan HLA class I antibody conjugated to PE (BD Pharmingen cat #560168). The cells were washed and analyzed by flow cytometry on an Attune N×T.

Figure 19:
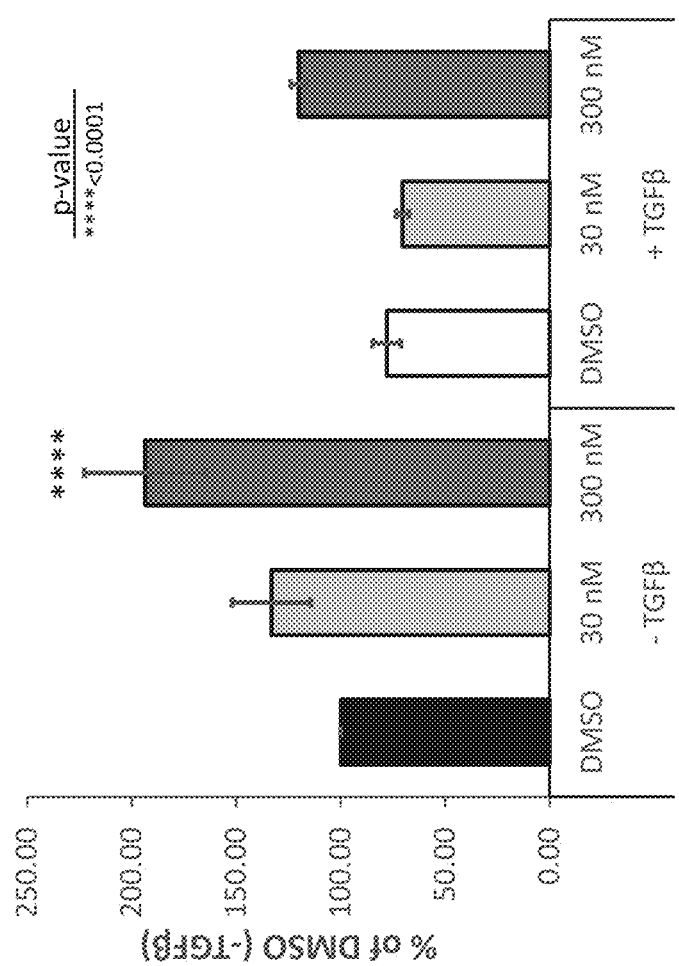
FIG. 19 shows human leukocyte antigen (HLA) Class I expression in KGN cells treated with EX-11 with and without TGFβ stimulation, as described in Example R.

As shown in FIG. 19, HLA class I expression was repressed by TGFβ stimulation, which repression was reversed with EX-11 treatment. In the absence of TGFβ, EX-11 dose-dependently increased HLA class I expression up to 2-fold.

Example S—Immune Phenotyping of TMAs

Five consecutive sections of tissue microarrays of the following indications were purchased: NSCLC (US Biolabs), mesothelioma, ovarian, breast, and pancreatic cancers (US Biomax). One section of each indication was baked, dewaxed, and underwent epitope retrieval. Sections were then dual-stained overnight at 4° C. with the following primary antibodies: CD8 (CST) and αSMA (CST). Sections were washed, stained with AF-647 (CD8)- or AF-488 (αSMA)-conjugated secondary antibodies for 1 hour at room temperature, washed, stained with DAPI, and coverslipped. Sections were imaged in the Olympus VS200 slide scanner and each patient sample was evaluated and grouped into one of four categories: Inflamed (CD8 signal throughout tumor and stromal sections), Excluded (CD8 staining confined to stromal sections), Desert (very little to no CD8 staining), or NA (non-evaluable due to loss of sample or absence of tumor/stromal tissue).

Figure 20:
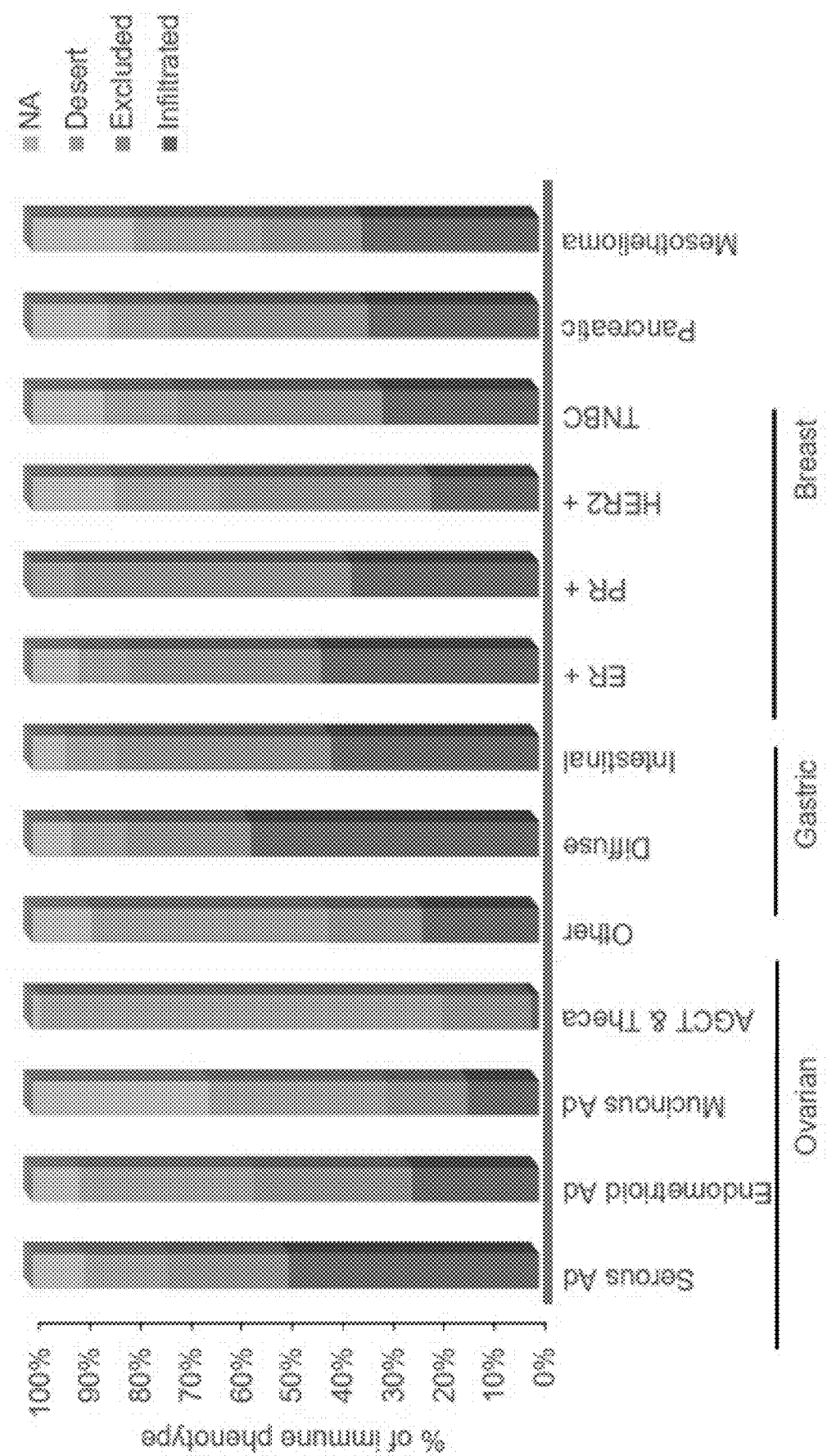
FIG. 20 shows the results of the immune phenotyping of TMAs described in Examples S.

As shown in FIG. 20, AGCT & Theca samples had the strongest desert phenotype (80%) and only a single inflamed sample, suggesting TGFβ pathway inhibition could be beneficial for these indications. Ovarian serous adenocarcinoma and diffuse gastric cancer had the highest percentage of inflamed samples (50-60%). PR+ breast cancer had the highest percentage of excluded cores (50%).

Example T—Double Combination of EX-11 and Abraxane in EMT6 Triple Negative Breast Cancer Syngeneic Model The objective of this study was to evaluate preclinically if combining EX-11 with a chemotherapeutic agent increased tumor growth inhibition.

Female, Balb/C mice (aged 6-8 weeks) were inoculated orthotopically in the left mammary fat pad with EMT6 breast cancer ($1.0 \times 10^6$ cells) in 0.1 ml of PBS. Tumor measurements were performed via digital calipers. Once the mean tumor size reached approximately 77 mm³ (day 6), 32 mice were randomized to 4 treatment arms (8 mice per arm). Mice were treated according to the parameters outlined in Table 19.

TABLE 19

| Group | Treatment | N | Dose Route | *Dosing Frequency & Duration | Dose Level (mg/kg) | Dose Volume (mL/kg) |
|---|---|---|---|---|---|---|
| 1 | Vehicle | 8 | PO | BID × 21 days | n/a | 10 |
| 2 | Abraxane | 8 | IP | Q7d × 3 weeks | 30 | 10 |
| 3 | EX-11 | 8 | PO | BID × 21 days | 150 | 10 |
| 4 | Abraxane | 8 | IP | Q7d × 3 weeks | 30 | 10 |
|   | EX-11 | 8 | PO | BID × 21 days | 150 | 10 |

Abraxane (product of Bristol Myers Squibb) was purchased from St Josef Hospital (Freiburg, Germany). The vehicle for abraxane was 0.9% NaCl. The vehicle for EX-11 was NMP (10%)+20% Solutol in WFI (Water for Injection) (90%). The vehicle used for EX-11 was also used for the "Vehicle" arm of the study. EX-11 and the vehicle were delivered via oral gavage (p.o.), bi-daily (BID) for 21 days.

Body weights and tumor volumes were measured twice per week. Tumor volumes were measured in two dimensions using a caliper, and the volume was expressed in mm$^3$ using the formula: V=(L×W×W)/2, where V is tumor volume, L is tumor length (the longest tumor dimension) and W is tumor width (the longest tumor dimension perpendicular to L).

The first phase of the study was the dosing phase which started at Day 6 and was terminated at day 20, due to excess deaths following the administration of the third dose of abraxane. Endpoints prior to day 20 were as follows: 1) tumor volume exceeding 2000 mm$^3$, 2) body weight loss over 20% for 3 consecutive days from the first day of treatment, 3) mouse with tumor ulceration of approximately 25% or greater on the surface of the tumor, and 4) severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice.

Figure 17A:
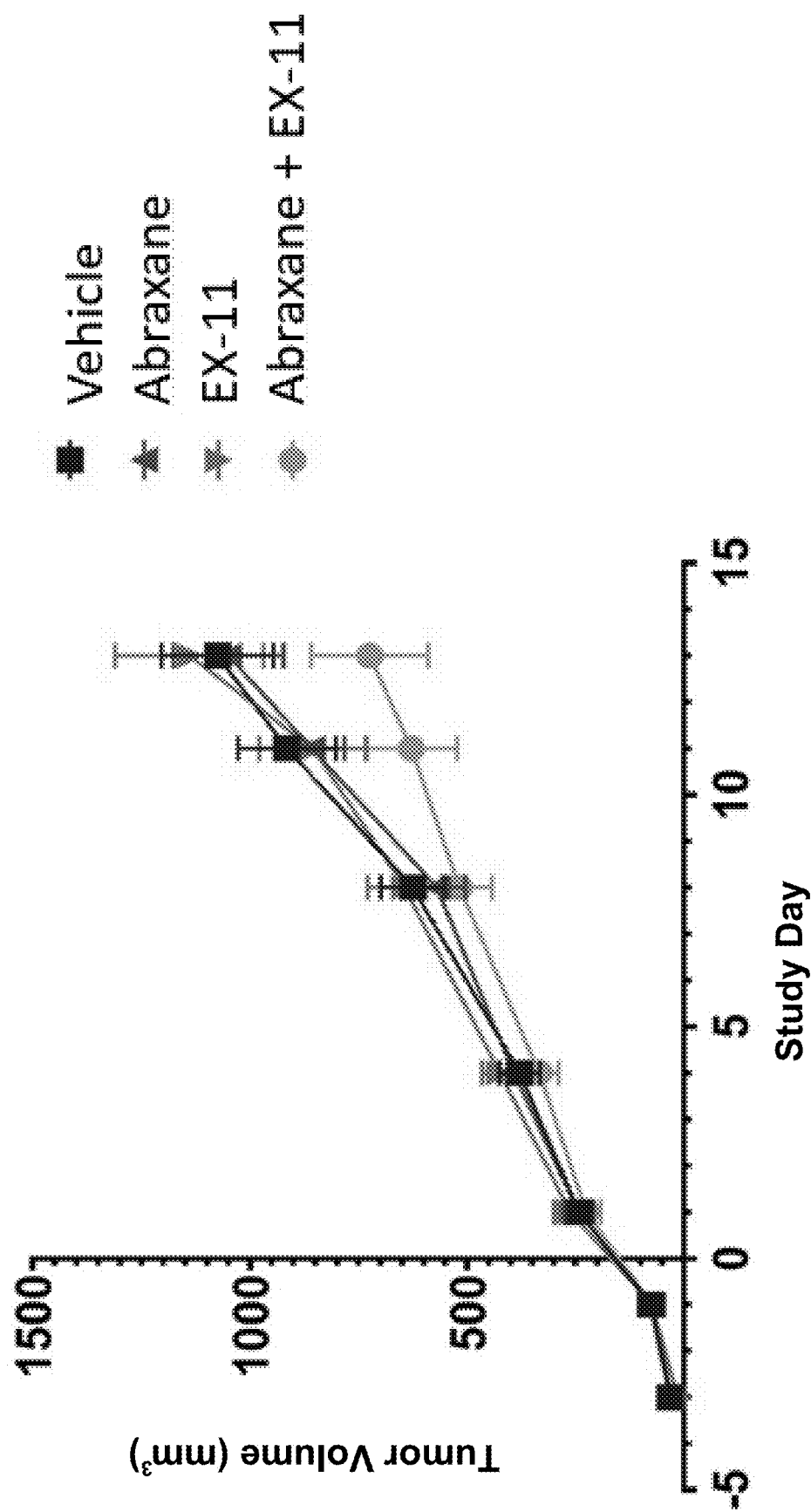
FIG. 17A shows mean tumor volume for vehicle, abraxane, EX-11, and combination abraxane+EX-11 treatment groups from Example T over dosing period (mean±SEM).
Figure 17B:
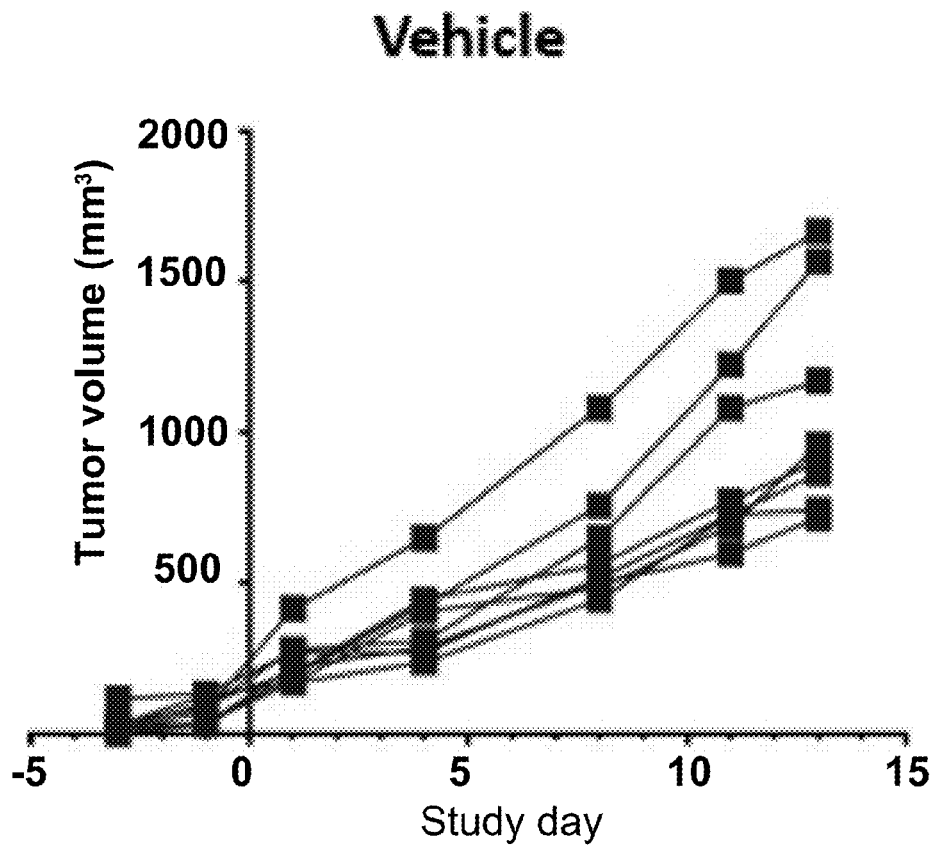
FIG. 17B shows individual tumor volume curves from the vehicle treatment group from Example T over the dosing period.
Figure 17C:
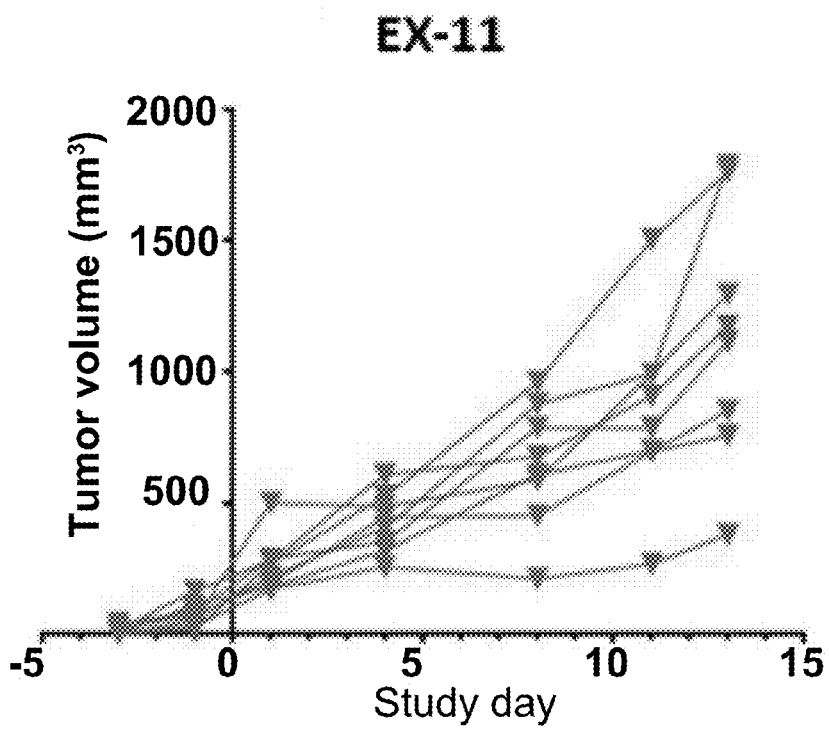
FIG. 17C shows individual tumor volume curves from the EX-11 treatment group from Example T over the dosing period.
Figure 17D:
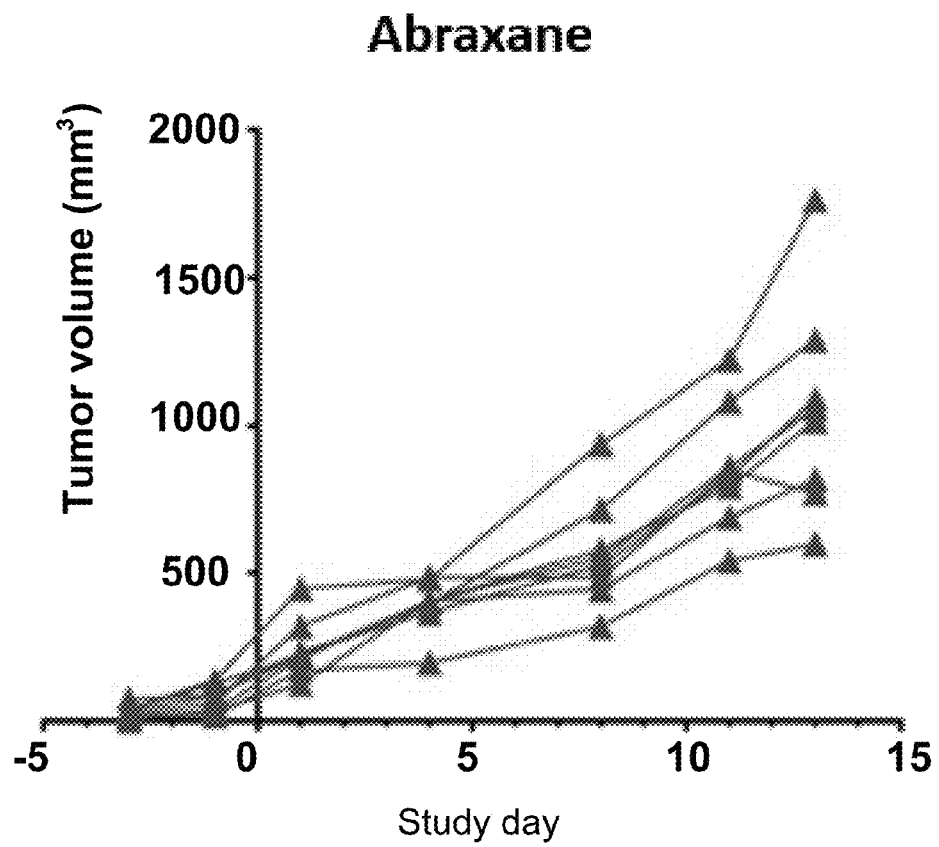
FIG. 17D shows individual tumor volume curves from the abraxane treatment group from Example T over the dosing period.
Figure 17E:
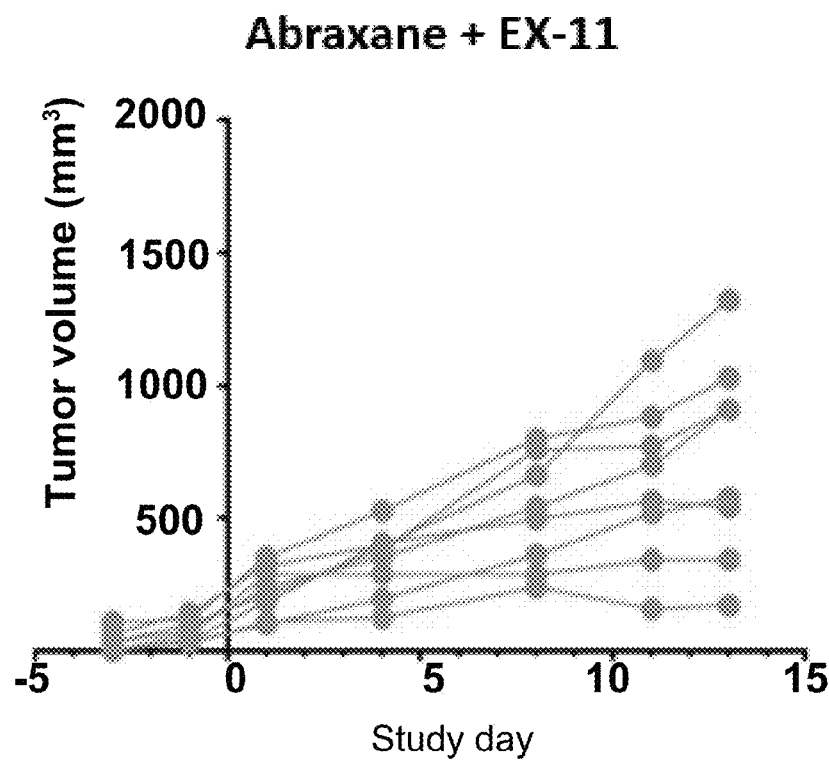
FIG. 17E shows individual tumor volume curves from the abraxane+EX-11 treatment group from Example T over the dosing period.
Figure 17F:
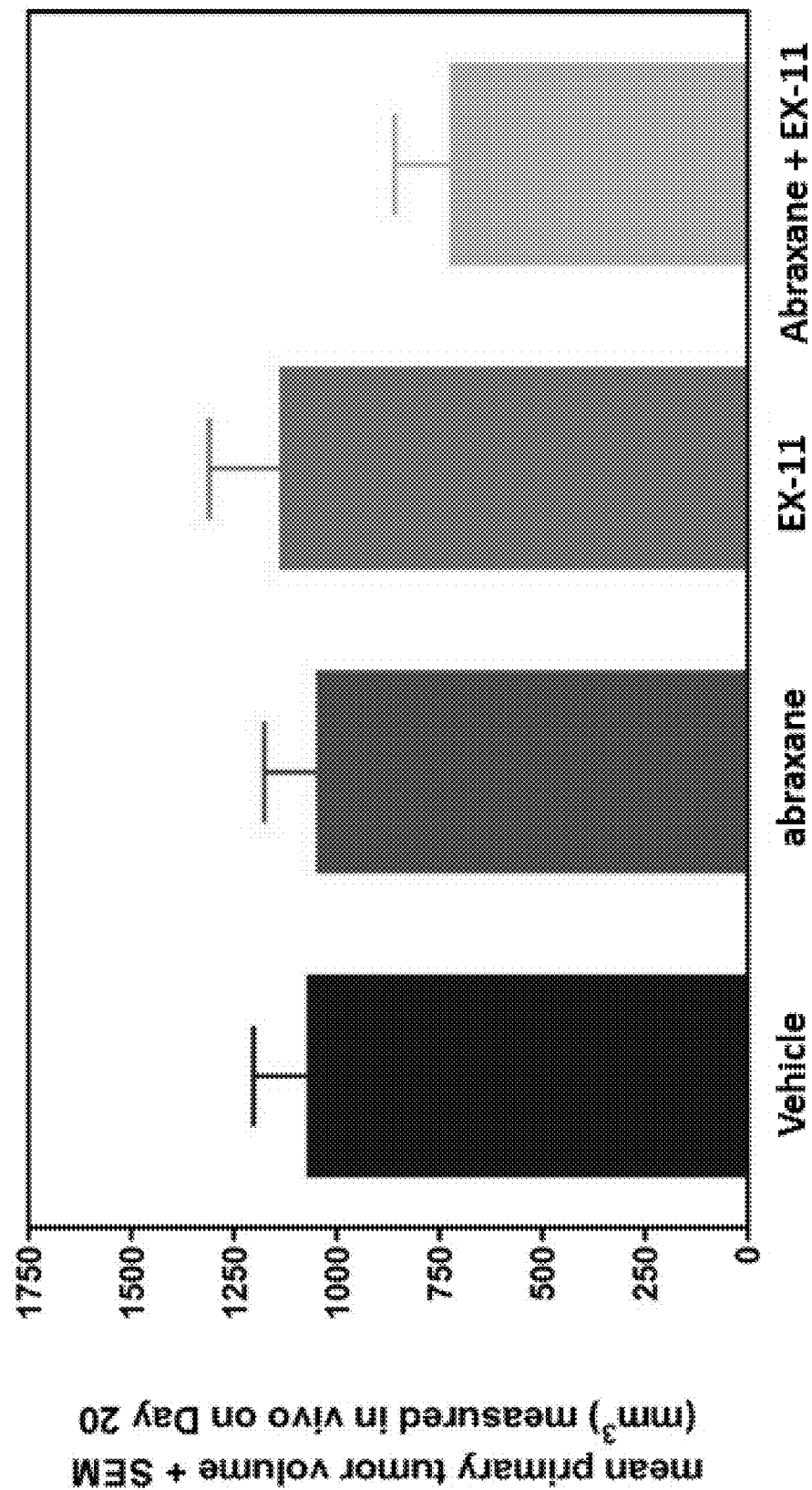
FIG. 17F is a bar graph showing final day mean tumor volume for each treatment group described in Example T.

Individual tumor growth curves for each treatment group are shown in FIGS. 17B-17E. Single agent treatment with abraxane and EX-11 did not show efficacy compared to vehicle, as shown in FIG. 17A. The combination of abraxane and EX-11 resulted in smaller mean tumor volume on the final day, as shown in FIG. 17F. Figures were generated in GraphPad Prism.

This experiment is being repeated using an optimized dose of abraxane to reduce toxicity. It is expected that a significant therapeutic effect will be observed in repeating the experiment using an optimized dosage of abraxane.

Example U—Immunohistochemistry (IHC)

Examples K, L and M demonstrated that EX-11 both prolongs survival and decreases tumor growth rate when combined with an immune checkpoint inhibitor (ICI). EX-11 is an ALK5 inhibitor that has been proposed to affect multiple processes in the tumor microenvironment through downregulation of TGF-β signaling, including vasculature remodeling and leukocyte infiltration. The objective of this study was to compare the levels of CD31 and CD45, subject to different treatment conditions in 4T1, EMT6, and S91 tumors. CD31 is an established marker of vascular differentiation, and CD45 is an established marker of leukocytes.

For IHC analyses, tumors from three syngeneic models of cancer were used:
1) Example L: 4T1 (triple-negative breast cancer [TNBC]); Balb/c mice
2) Example K: EMT6 (TNBC); Balb/C mice
3) Example M: S91 (melanoma); DBA/2 mice Tumors were fixed in formalin for 48 hours, then stored in 7000 EtOH prior to paraffin embedding. Embedded blocks were sectioned at 5 μM and placed on glass slides for IHC staining. Table 20 illustrates the tumors used for IHC staining (R=Responder, NR=Non-responder). Table 21 illustrates the antibodies used for each marker.

TABLE 20

| Tumor | Treatment | n |
|---|---|---|
| 4T1 | Vehicle | 3 |
| 4T1 | EX-11 | 3 |
| 4T1 | Anti-PD-1 | 3 |
| 4T1 | Anti-PD-1 + EX-11 | 3 |
| EMT6 | Vehicle | 3 |
| EMT6 | EX-11 | 3 |
| EMT6 | Anti-PD-1 | 3 |
| EMT6 | Anti-PD-1 + EX-11 | 3 |
| EMT6 | Anti-PD-1 | 3 |
| EMT6 | Anti-PD-1 + EX-11 | 3 |
| S91 | Vehicle | 3 |
| S91 | EX-11 | 3 |
| S91 | Anti-PD-1 | 3 |
| S91 | Anti-PD-1 + EX-11 (R) | 3 |
| S91 | Anti-PD-1 + EX-11 (NR) | 3 |

TABLE 21

| Antibody | Company | Diluent | Dilution Factor |
|---|---|---|---|
| CD31 (PECAM-1)(D8V9E) XP* Rabbit mAb #77699 | CST | PBS, 5% goat serum, 0.2% triton | 200 |
| CD45 (D3F8Q) Rabbit mAb #70257 | CST | PBS, 5% goat serum, 0.2% triton | 400 |

Leica Biosystems Bond Software and Leica Bond Rx Research Stainer were used per protocol to stain tissue sections. The Olympus VS200 ASW software and scanner were used to scan images. Images were manually scored by a pathologist, blinded to treatment information. Scoring was performed using an Olympus OlyVIA virtual image scope. CD45 was scored by calculating the number of CD45-positive cells divided by the total number of viable nucleated cells within the whole tumor region(s). CD31 density was scored by calculating the total number of CD31 positive vessels divided by the whole tumor area (mm$^2$).

Figure 21A:
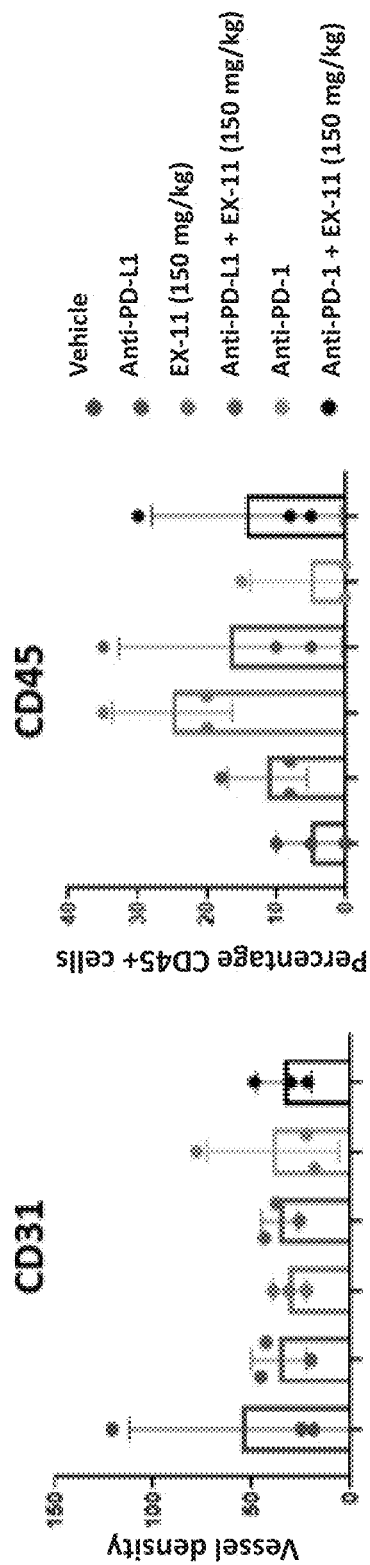
FIG. 21A shows quantification of CD31+ blood vessel density and percentage of CD45+ cells in tumor sections from each of the EMT6 treatment groups described in Example U.
Figure 21B:
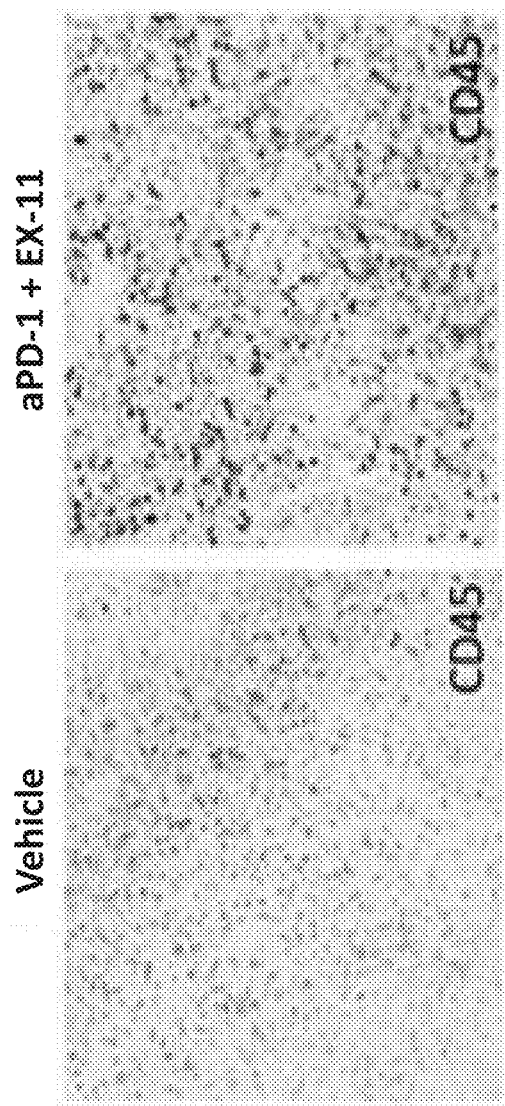
FIG. 21B shows representative micrographs stained for CD45 from the vehicle and aPD-1+EX-11 EMT6 treatment groups described in Example U.
Figure 21C:
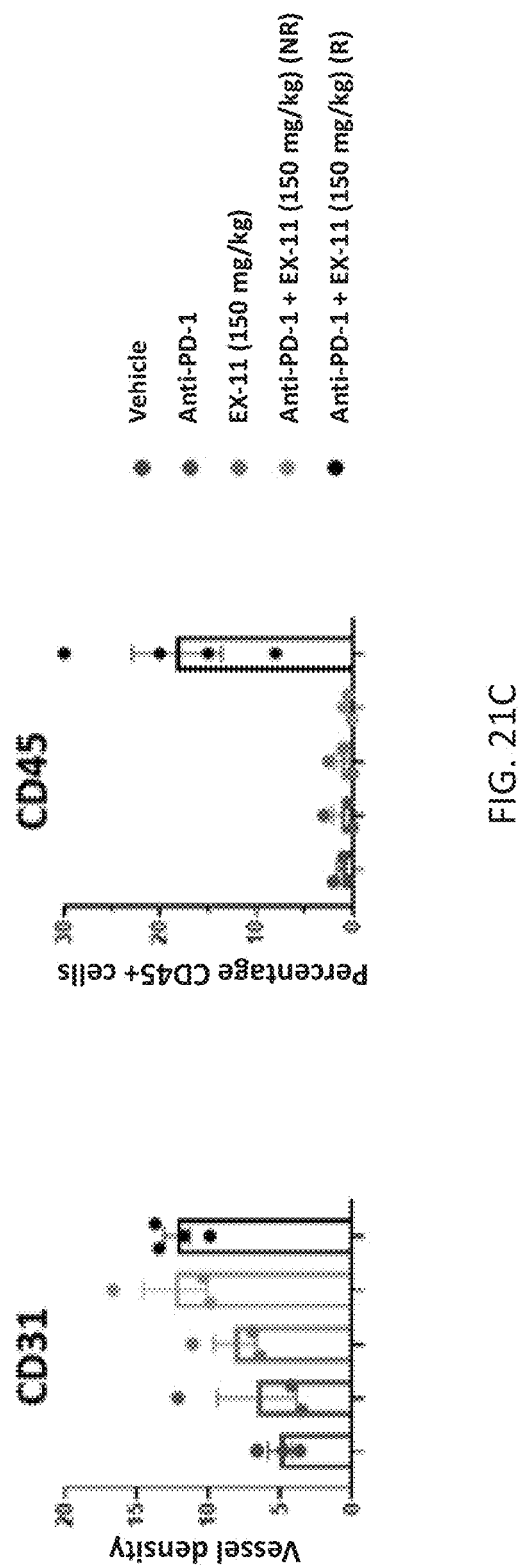
FIG. 21C shows quantification of CD31+ blood vessel density and percentage of CD45+ cells in tumor sections from each of the S91 treatment groups described in Example U.
Figure 21D:
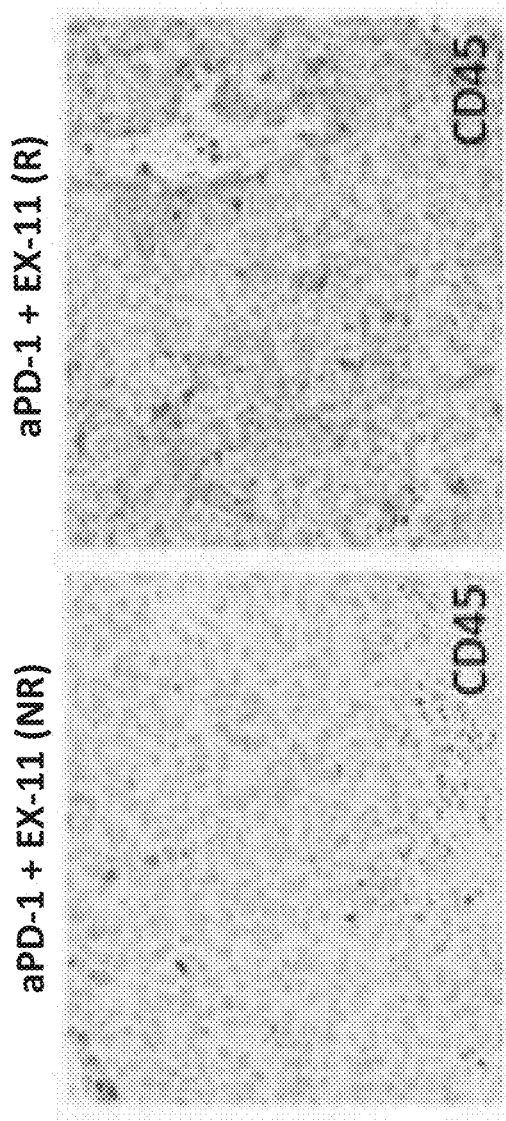
FIG. 21D shows representative micrographs stained for CD45 from the aPD-1+EX-11 (NR) and aPD-1+EX-11 (R) S91 treatment groups described in Example U.

In EMT6 tumors, no difference in CD31 staining was observed between groups (FIG. 21A). However, CD45 was increased in all EX-11 groups compared with anti-PD-1 and vehicle groups (FIG. 21A). In S91 tumors, CD31 was increased in anti-PD-1+EX-11 groups compared with either drug alone or the vehicle control (FIG. 21C). This was independent of response rates within the anti-PD-1+EX-11 cohort. CD45 was drastically increased in anti-PD-1+EX-11 responsive (R) tumors compared with all other groups, including the anti-PD-1+EX-11 non-responsive (NR) tumors (FIG. 21C).

In summary, these data indicate that EX-11 increases CD45 tumor infiltration in the context of the EMT6 model. These data also show that an increase in leucocyte infiltration in anti-PD-1+EX-11 (R) tumors is highly associated with diminished tumor growth and improved survival of mice in the context of the S91 model.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

In Column 248, Claim 16, Line 45, the formula:
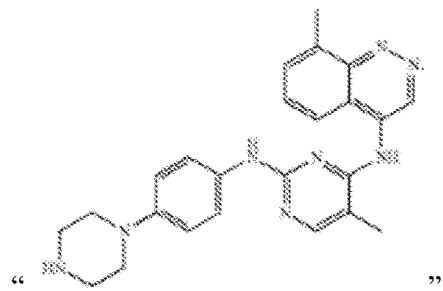
Should appear as follows:
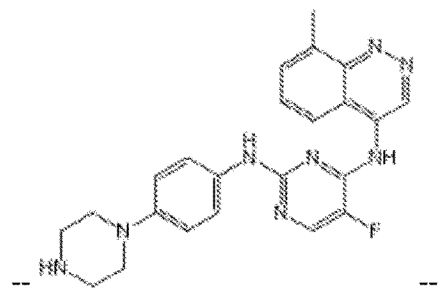

What is claimed is:

1. A compound of Formula (I):

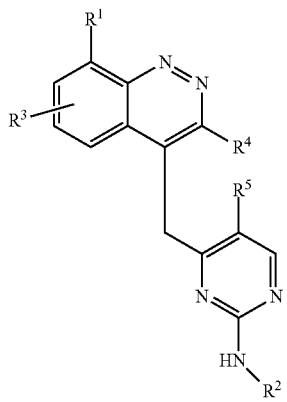

(I)

or a pharmaceutically acceptable salt thereof, wherein:
$R^1$ is a $C_1$-$C_5$ alkyl, $C_3$-$C_5$ carbocycle, or a halogen;
$R^2$ is an aryl of at least 6 carbon atoms or nitrogen-containing heteroaryl of at least 6 atoms, optionally substituted with one or more of:
(i) one or more halogens;
(ii) a $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$;
(iii) a sulfonamide;
(iv) a monocyclic, bicyclic, or spirocyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$; or
(v) a monocyclic, bicyclic or spirocyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of $R^2$ which is meta- or para- to the amino bond to said aryl;
$R^3$ is —H, —F, or —Cl;
$R^4$ is —H, a halogen, or a $C_1$-$C_3$ alkyl or cyclopropyl optionally substituted with one or more —F; and
$R^5$ is —H, —F, or a $C_1$-$C_3$ alkyl or cyclopropyl optionally substituted with one or more —F.

2. The compound of claim 1, wherein $R^1$ is a $C_1$-$C_5$ alkyl or $C_3$-$C_5$ carbocycle.

3. The compound of claim 1, wherein $R^1$ is —$CH_3$, cyclopropyl, —Cl, or —F.

4. The compound of claim 1, wherein $R^2$ is a phenyl or pyridinyl substituted with one or more of:
(i) one or more halogens;
(ii) a $C_1$-$C_6$ alkyl optionally substituted with a hydroxyl or one or more halogen wherein, when selected to be an alkyl larger than $C_3$, the alkyl is present at a position on the aryl or heteroaryl of $R^2$ which is meta- or para- to the amino bond to the aryl or heteroaryl of $R^2$;
(iii) a sulfonamide;
(iv) a monocyclic, bicyclic, or spirocyclic carbocycle which is optionally substituted with a hydroxyl, one or more halogen, or one or more linear, branched, or cyclic alkyl moieties of up to 6 carbon atoms which are optionally substituted with hydroxy or one or more halogen, wherein said carbocycle is attached to the aryl or heteroaryl of $R^2$ by a single bond or a methylene or ethylene linker and wherein, when present and selected to be a carbocycle larger than cyclopropyl, the carbocycle is at a position on the aryl or heteroaryl of $R^2$ which is meta- or para- to the amino bond to the aryl or heteroaryl of $R^2$; or
(v) a monocyclic, bicyclic or spirocyclic heterocycle which may contain up to 3 heteroatoms which are selected independently from N and O, and which is optionally and independently substituted with one or more $C_1$-$C_6$ alkyl or $C_3$-$C_6$ carbocycle which are optionally substituted with hydroxy or one or more halogen, wherein said heterocycle is attached to the aryl or heteroaryl of $R^2$ by a single bond or a methylene or ethylene linker and wherein, when present, said heterocycle is at a position on the aryl of R² which is meta- or para- to the amino bond to said aryl.

5. The compound of claim 1, wherein R² is:

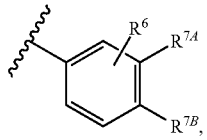

wherein:
R⁶ is —H, —F, —Cl, or a $C_1$-$C_3$ alkyl or cyclopropyl which is optionally and independently substituted with one or more halogen;
one of $R^{7A}$ and $R^{7B}$ is —H, and the other is:
(i) a halogen;
(ii) —$SO_2NR^{7F}{}_2$, wherein each $R^{7F}$ is independently —H or a linear or branched alkyl of up to 4 carbon atoms;
(iii) a $C_1$-$C_6$ alkyl which is optionally substituted with one or more halogen; or

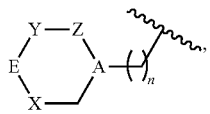 (iv)

wherein:
A is N or C(H);
E is O, N(R⁸), or C(H)(R¹³);
R⁸ is —H or a $C_1$-$C_6$ alkyl or $C_3$-$C_6$ carbocycle which is optionally substituted with hydroxyl or one or more halogen;
R¹³ is —H or a $C_1$-$C_6$ alkyl or $C_3$-$C_6$ carbocycle which is optionally substituted with hydroxy or one or more halogen; and
n is 0, 1, or 2, and
when E is N(R⁸), X, Y, and Z are defined as follows:
Z is C(H)₂ and X and Y are independently C(H)₂ or C(CH₃)₂, or both X and Y are CH) and are bonded together through a methylene or ethylene bridge; or
Y is C(H)₂ or C(CH₃)₂, and X and Z are both C(H) and are bonded together through a methylene or ethylene bridge, and
when E is O or C(H)(R¹³), X, Y, and Z are C(H)₂.

6. The compound of claim 5, wherein R⁶ is —H, —F, —Cl, —CH₃, or —CF₃.

7. The compound of claim 5, wherein one of $R^{7A}$ and $R^{7B}$ is —H, and the other is:

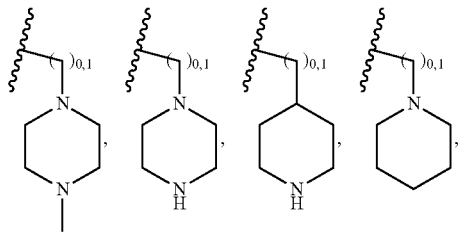

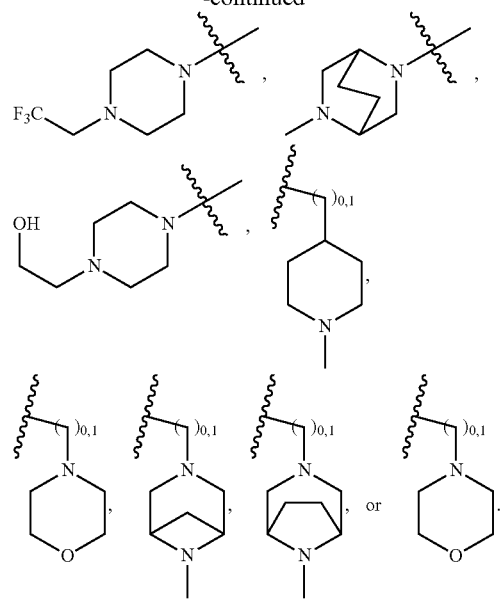

8. The compound of claim 1, wherein R³ is —H.
9. The compound of claim 1, wherein R⁴ is-CF₃,-CH₃, —H, —Cl, or —F.
10. The compound of claim 6, wherein R⁴ is-H.
11. The compound of claim 1, wherein R⁵ is —H,-CH₃,—CF₃ or —F.
12. The compound of claim 11, wherein R⁵ is-H.
13. The compound of claim 1 of Formula (II):

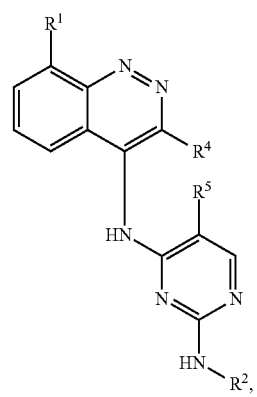 (II)

or a pharmaceutically acceptable salt thereof, wherein:
R¹ is-CH₃ or —Cl;
R² is:

a)

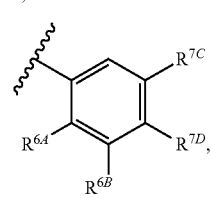

wherein:

one of $R^{6A}$ and $R^{6B}$ is —H, and the other is —H, —F, —Cl,-CH$_3$, or CF$_3$;

one of $R^{7C}$ and $R^{7D}$ is —H, and the other is:

(i) —F;
(ii) —Cl;
(iii) —SO$_2$NH$_2$;
(iv) cyclohexyl;
(v) t-butyl; or
(vi)

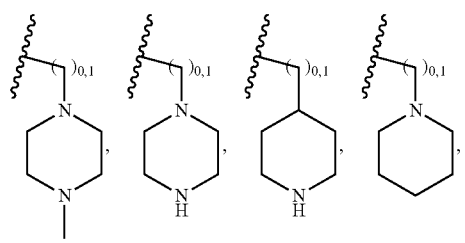

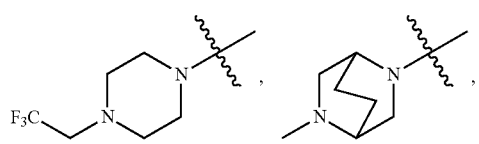

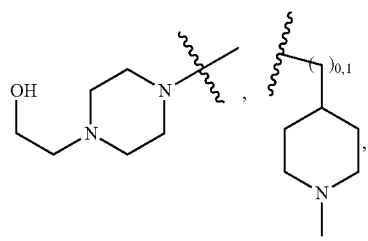

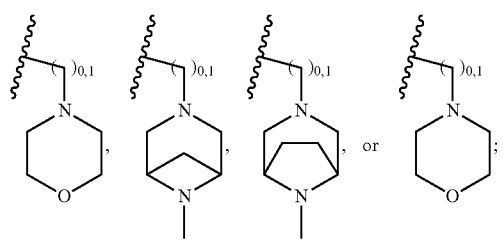

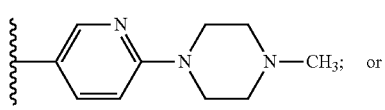

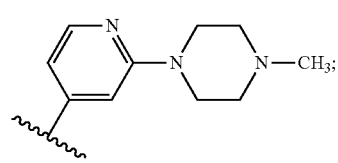

$R^4$ is —H or -CH$_3$; and
$R^5$ is —H or —F.

14. The compound of claim 1 of Formula (III):

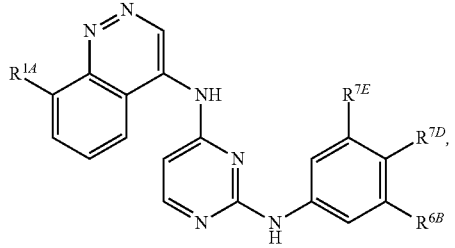

(III)

or a pharmaceutically acceptable salt thereof, wherein:
$R^{1A}$ is -CH$_3$ or cyclopropyl;
$R^{6B}$ is —H, —F, or —Cl; and
one of $R^{7D}$ and $R^{7E}$ is —H, and the other is a heterocycle of the formula:

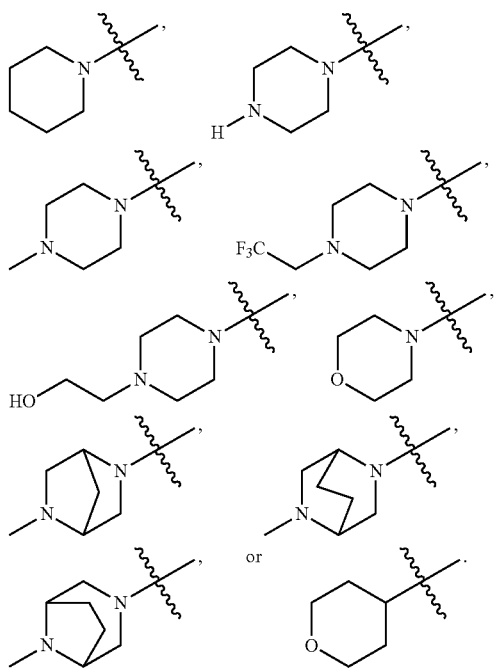

15. The compound of claim 1 having the following structure:

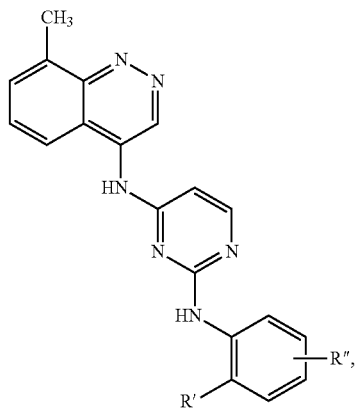

or a pharmaceutically acceptable salt thereof, wherein R' is H or F; and R" is at a position meta or para to the amino bond, and is morpholino or piperazinyl optionally N-substituted with-CH$_3$,-CH$_2$CF$_3$, or -CH$_2$CH$_2$OH.

16. A compound, or a pharmaceutically acceptable salt thereof, selected from:
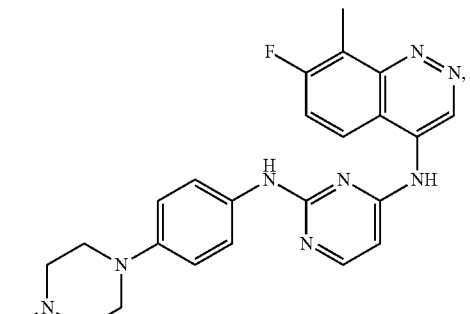
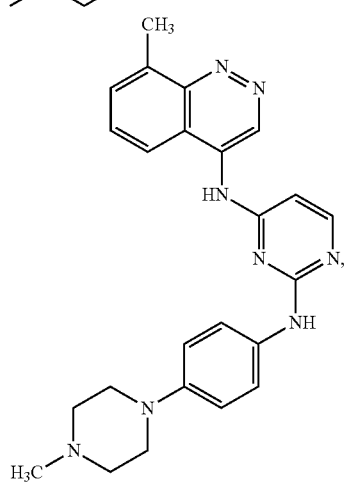
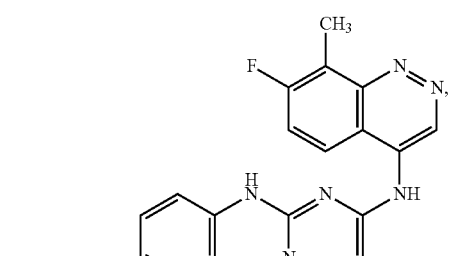
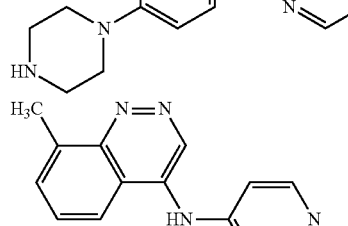
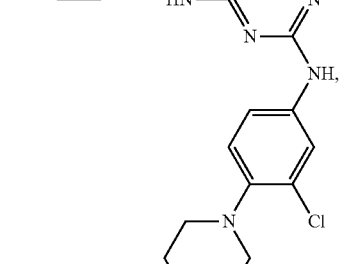
-continued
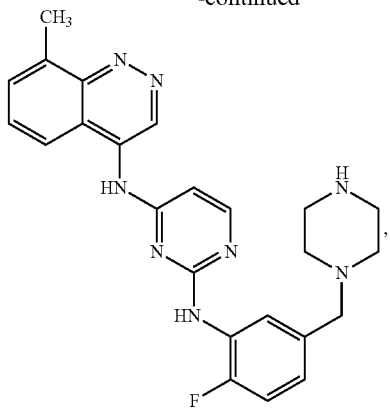
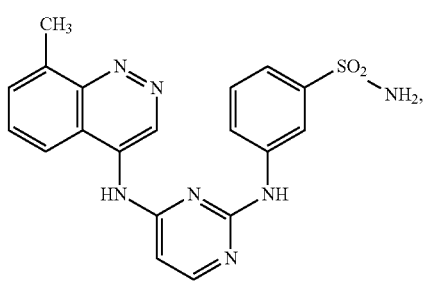
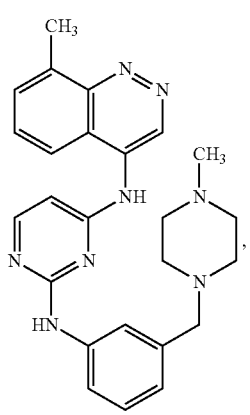
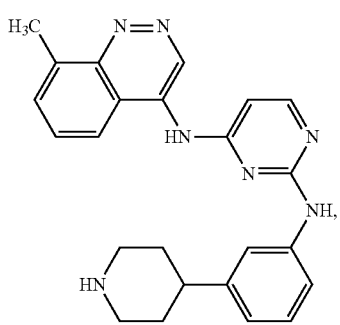

247
-continued
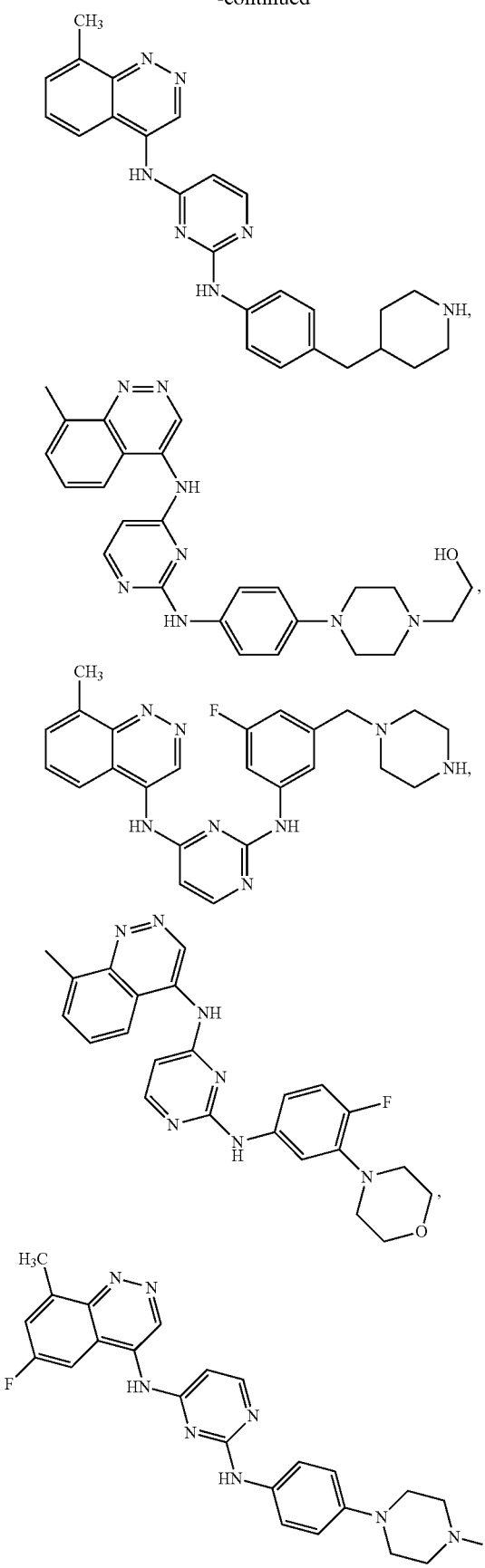
248
-continued
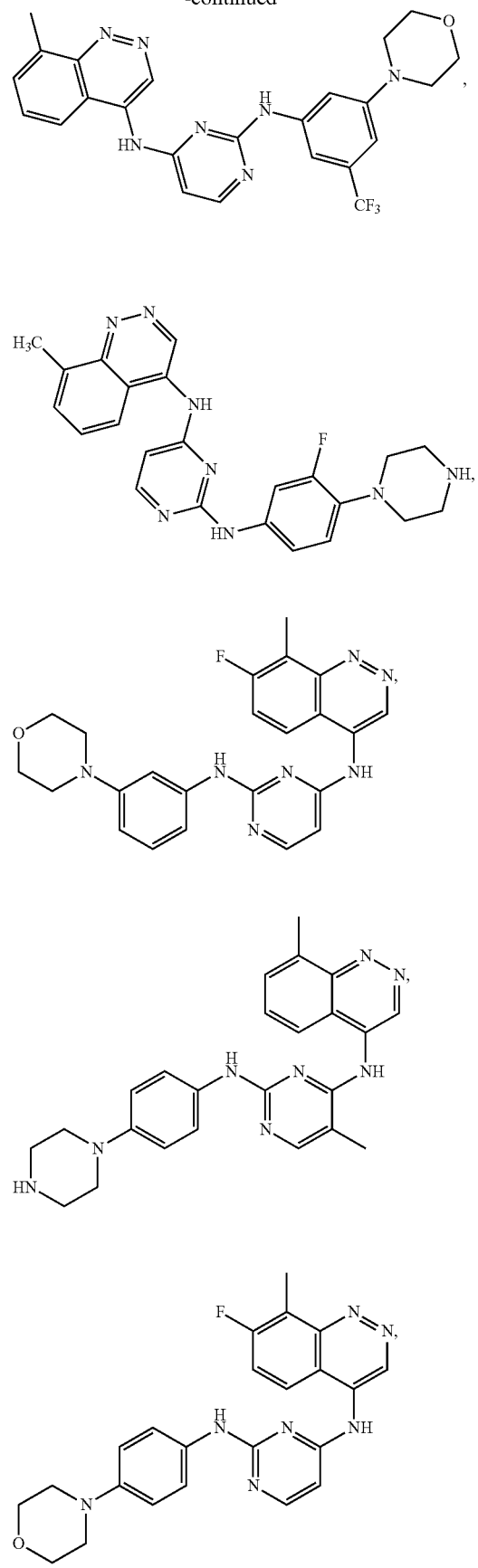

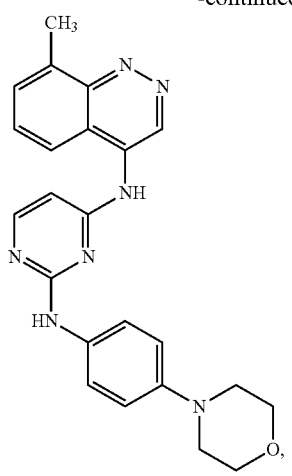
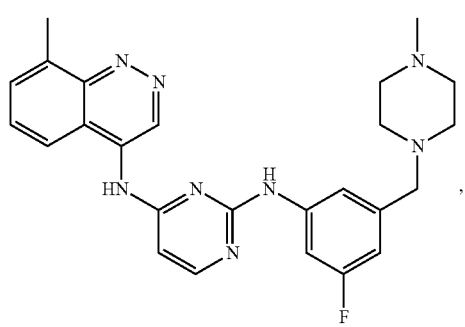
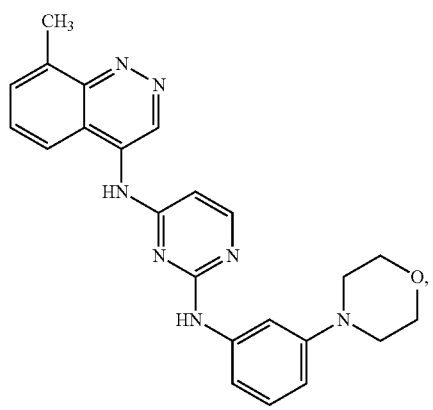
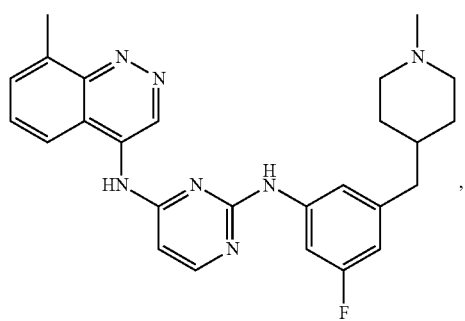
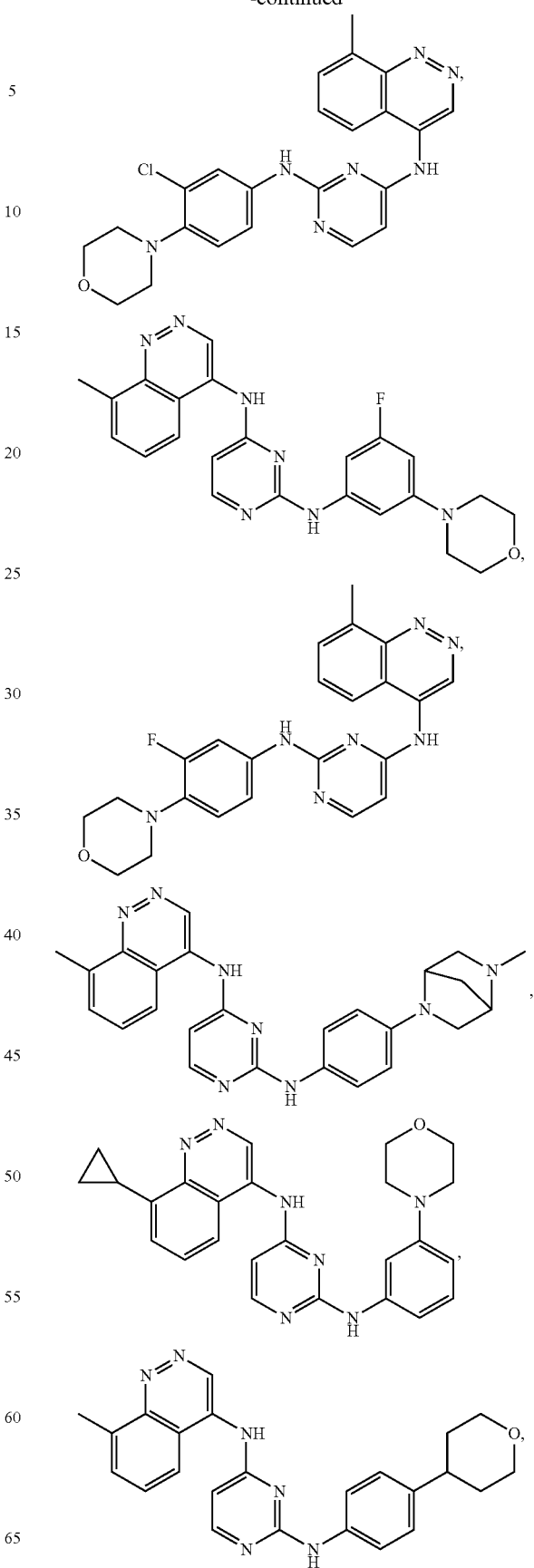

251
-continued
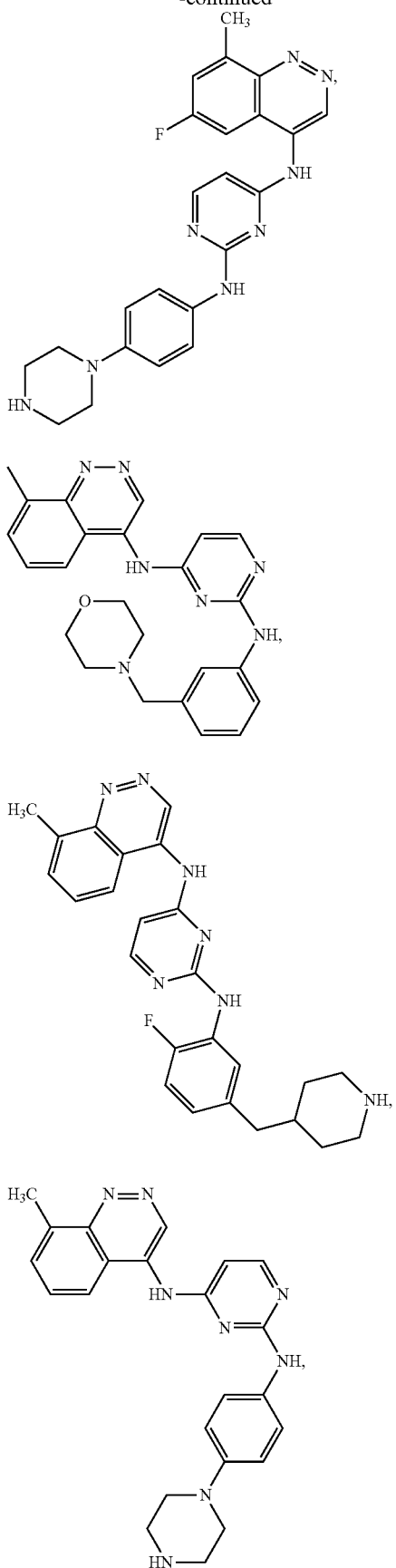
252
-continued
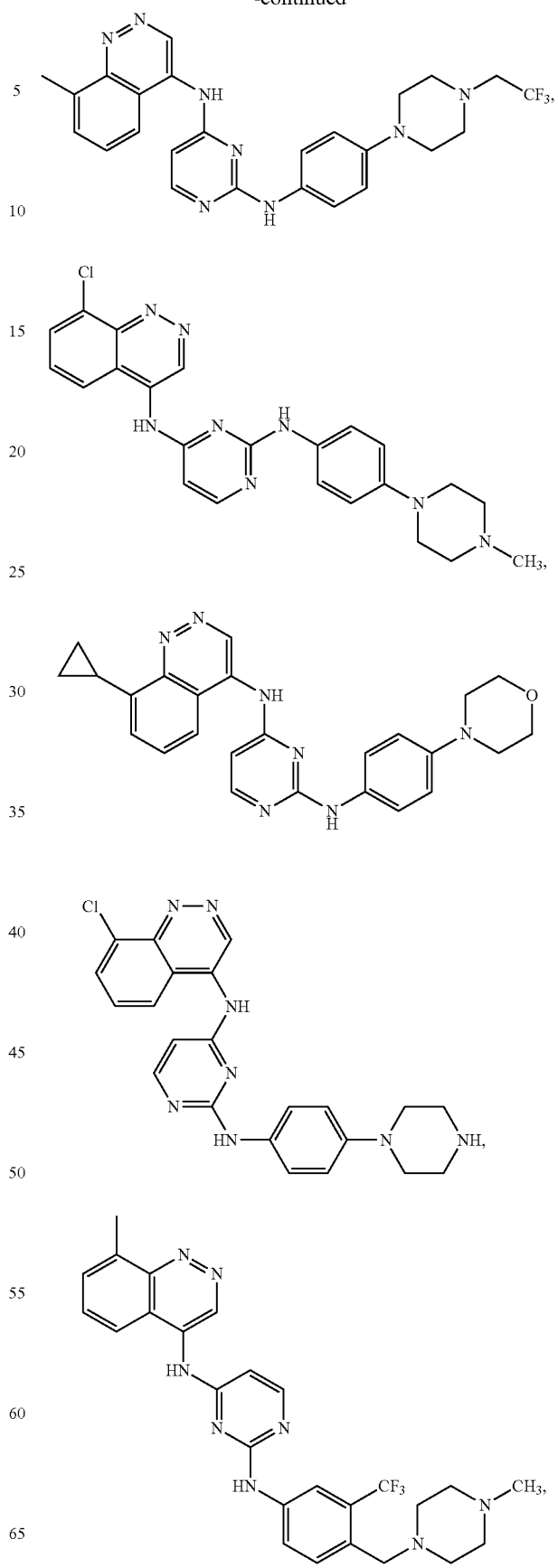

253
-continued
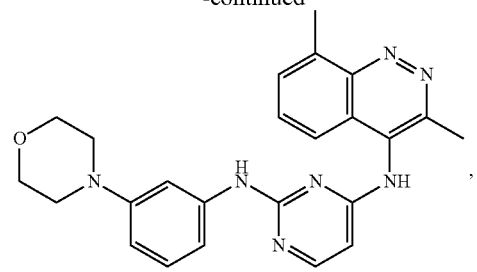
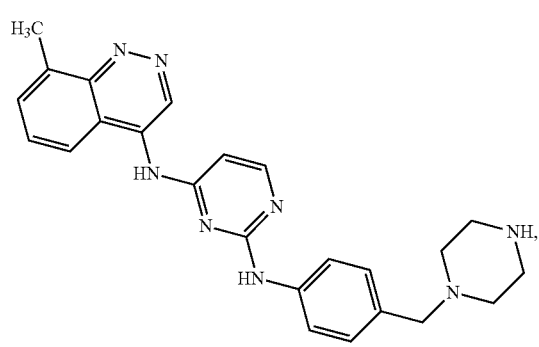
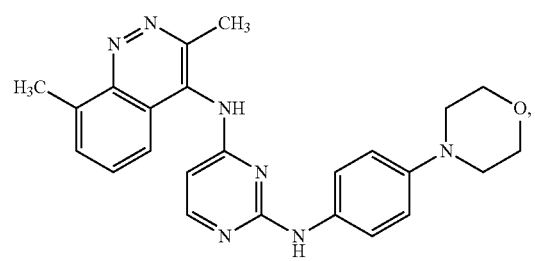
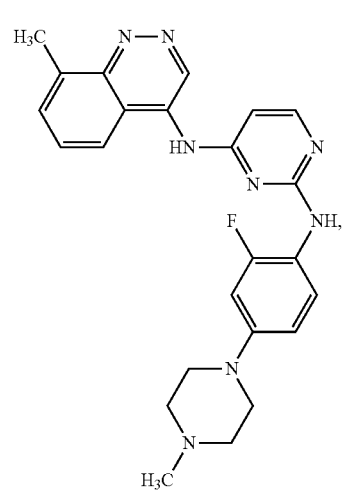
254
-continued
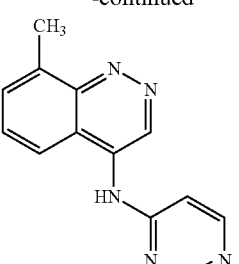
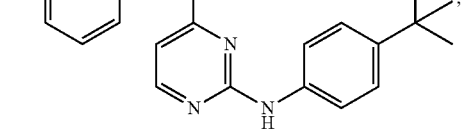
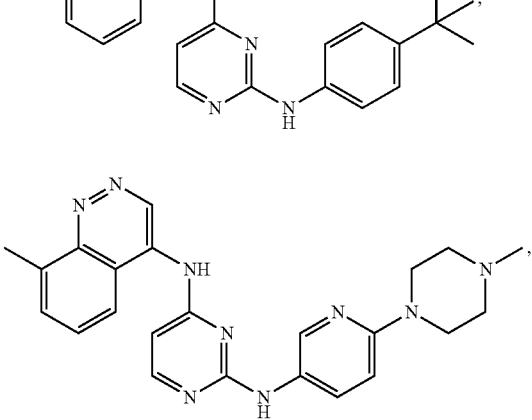
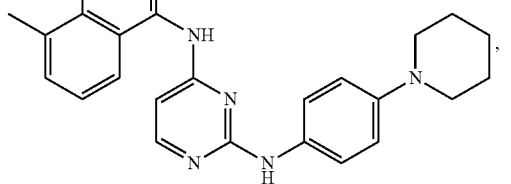

255
-continued
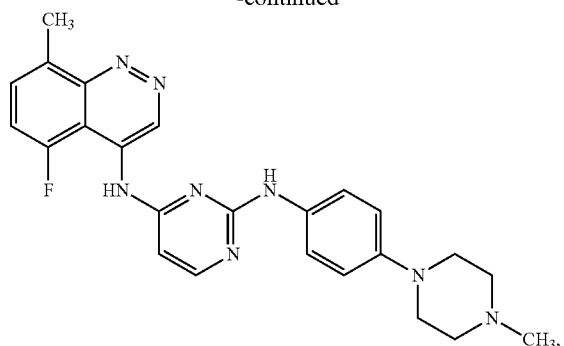
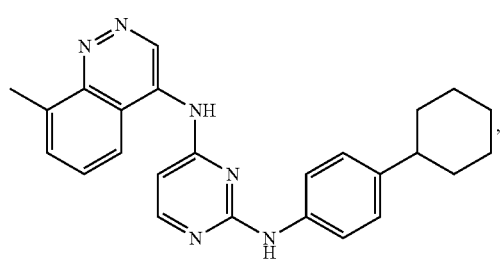
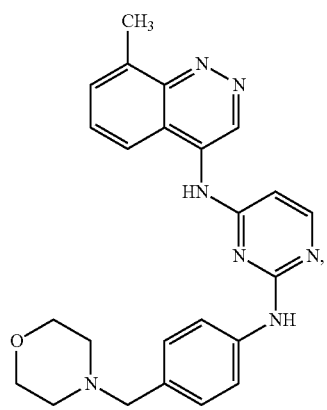
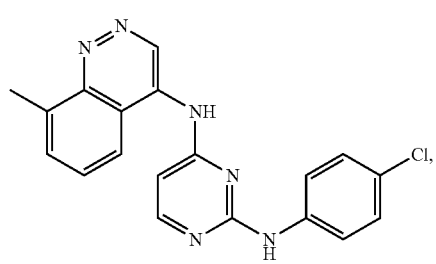
256
-continued
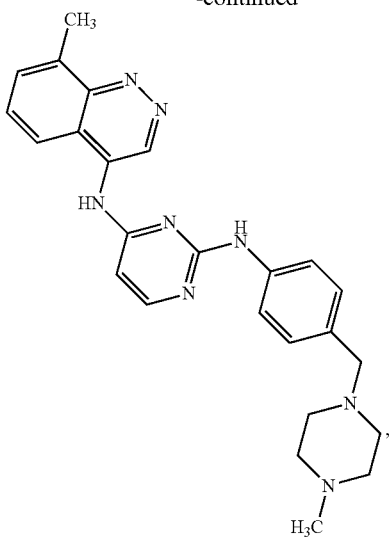
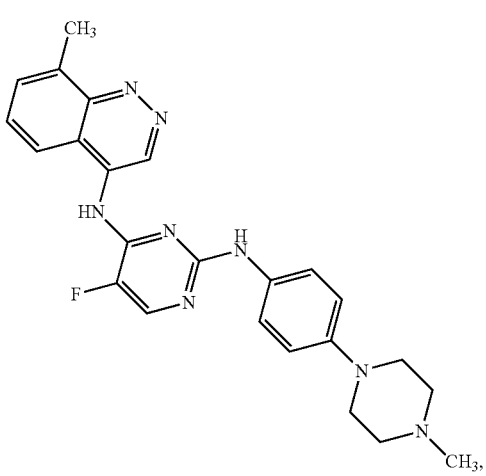
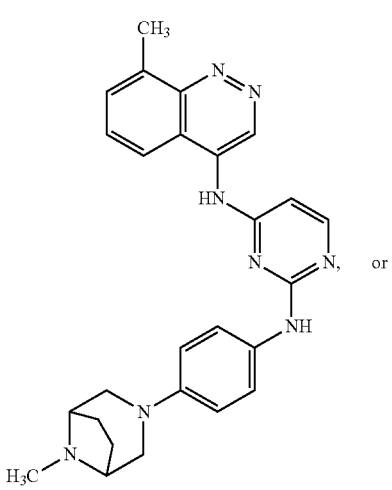
or -continued

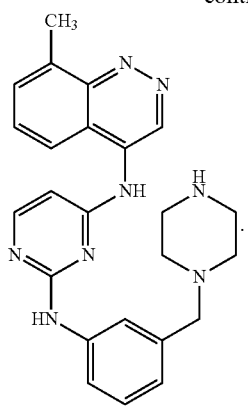

17. The compound of claim 16, wherein the compound is of the following formula:

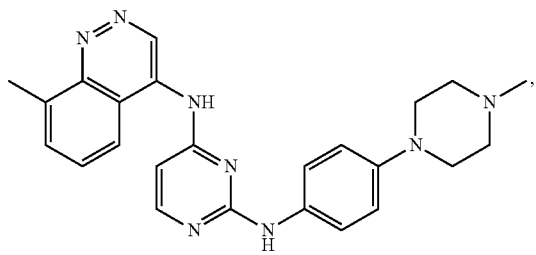

or a pharmaceutically acceptable salt thereof.

18. The compound of claim 16, wherein the compound is of the following formula:

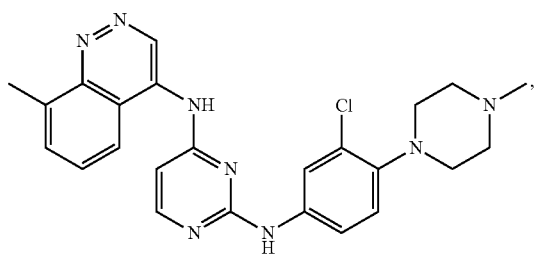

or a pharmaceutically acceptable salt thereof.

19. The compound of claim 16, wherein the compound is of the following formula:

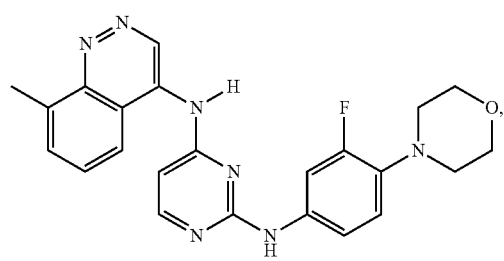

or a pharmaceutically acceptable salt thereof.

20. The compound of claim 16, wherein the compound is of the following formula:

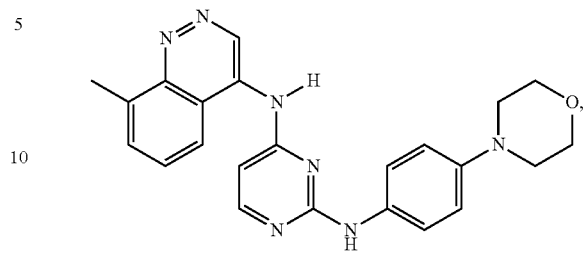

or a pharmaceutically acceptable salt thereof.

21. The compound of claim 16, wherein the compound is of the following formula:

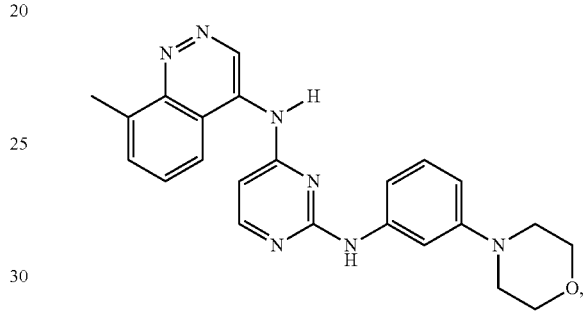

or a pharmaceutically acceptable salt thereof.

22. The compound of claim 16, wherein the compound is of the following formula:

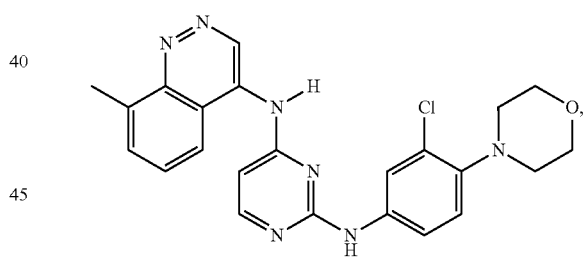

or a pharmaceutically acceptable salt thereof.

23. The compound of claim 16, wherein the compound is of the following formula:

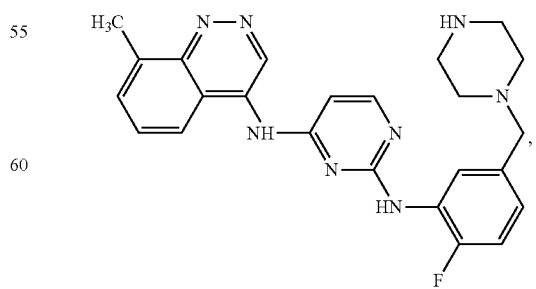

or a pharmaceutically acceptable salt thereof.

24. The compound of claim 16, wherein the compound is of the following formula:

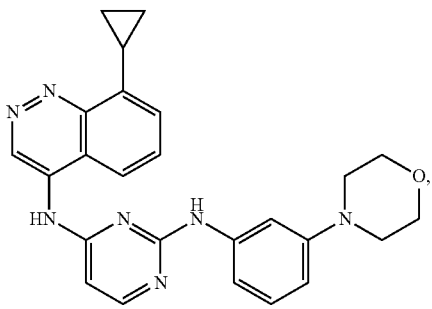 [SMILES: c1cc(Nc2nccc(Nc3cnnc4c(C5CC5)cccc34)n2)cc(N2CCOCC2)c1]

or a pharmaceutically acceptable salt thereof.

25. The compound of claim 16, wherein the compound is of the following formula:

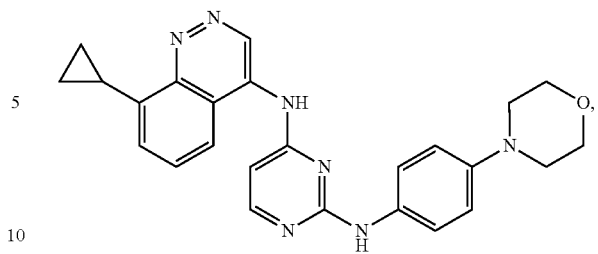

or a pharmaceutically acceptable salt thereof.

26. A pharmaceutical composition comprising a compound of claim 1, or a pharmaceutically acceptable salt thereof, and at least one pharmaceutically acceptable excipient.

27. A method of inhibiting ALK-5 activity in vivo or in vitro, the method comprising contacting ALK-5 with a compound of claim 1, or a pharmaceutically acceptable salt thereof.

* * * * *

UNITED STATES PATENT AND TRADEMARK OFFICE
CERTIFICATE OF CORRECTION

PATENT NO. : 11,746,103 B2
APPLICATION NO. : 17/733650
DATED : September 5, 2023
INVENTOR(S) : Bettina Franz et al.

It is certified that error appears in the above-identified patent and that said Letters Patent is hereby corrected as shown below:

In the Claims

In Column 239, Claim 1, Line 45, after (I), the formula:

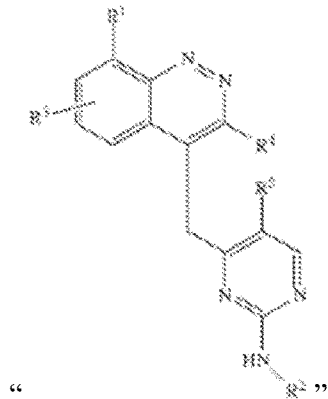

"

Should appear as follows:

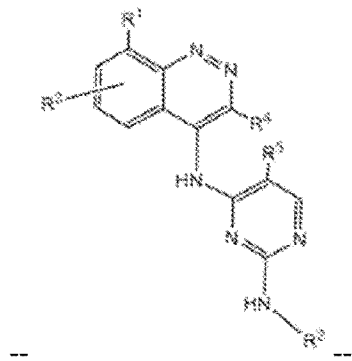

--  --

Signed and Sealed this
Twenty-seventh Day of February, 2024

Katherine Kelly Vidal
*Director of the United States Patent and Trademark Office*

In Column 242, Claim 7, Line 20, delete:
" 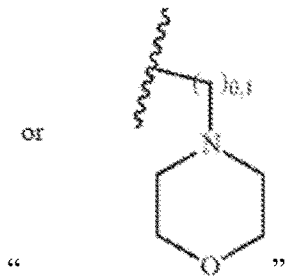 "
And insert:
-- 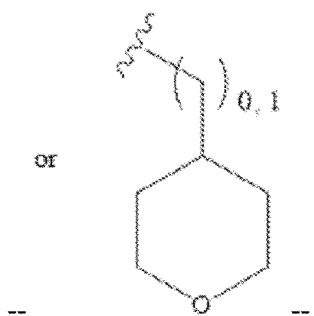 --
In Column 242, Claim 10, Line 29, delete:
"of claim 6"
And insert:
-- of claim 9 --
In Column 243, Claim 13, Line 45, delete:
" 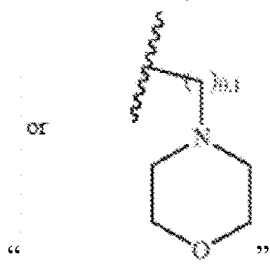 "
And insert:
-- 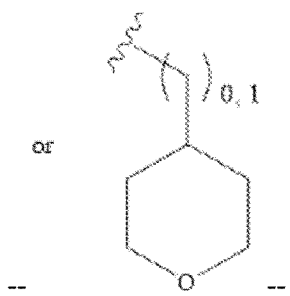 --